US011332746B1

(12) United States Patent
Freier

(10) Patent No.: US 11,332,746 B1
(45) Date of Patent: May 17, 2022

(54) COMPOUNDS AND METHODS FOR REDUCING LRRK2 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 16/972,822

(22) PCT Filed: Jun. 27, 2019

(86) PCT No.: PCT/US2019/039558
§ 371 (c)(1),
(2) Date: Dec. 7, 2020

(87) PCT Pub. No.: WO2020/006267
PCT Pub. Date: Jan. 2, 2020

Related U.S. Application Data

(60) Provisional application No. 62/690,790, filed on Jun. 27, 2018.

(51) Int. Cl.
| C12N 15/11 | (2006.01) |
| C12N 15/113 | (2010.01) |
| A61K 47/02 | (2006.01) |
| A61K 47/46 | (2006.01) |
| A61K 31/7125 | (2006.01) |
| A61P 25/16 | (2006.01) |

(52) U.S. Cl.
CPC ...... *C12N 15/1137* (2013.01); *A61K 31/7125* (2013.01); *A61K 47/02* (2013.01); *A61K 47/46* (2013.01); *A61P 25/16* (2018.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01); *C12N 2310/3525* (2013.01)

(58) Field of Classification Search
None
See application file for complete search history.

(56) References Cited

U.S. PATENT DOCUMENTS

| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |

(Continued)

FOREIGN PATENT DOCUMENTS

| WO | WO 2004/094636 | 11/2004 |
| WO | WO 2006/045392 | 5/2006 |

(Continued)

OTHER PUBLICATIONS

Alegre-Abarrategui et al., LRRK2 regulates autophagic activity and localizes to specific membrane microdomains in a novel human genomic reporter cellular model: Hum Mol Genet (2009) 18(21): 4022-4034.

Atashrazm et al. "LRRK2 Inhibitors and Their Potential in the Treatment of Parkinson's Disease: Current Perspectives" Clin Pharmacol (2016) 177-189.

Bieri et al., "LRRK2 modifies α-syn pathology and spread in mouse models and human neurons" Gitler Lab (2019) 1-41.

Branch et al., "A good antisense molecule is hard to find," TIBS (1998) 23:45-50.

(Continued)

*Primary Examiner* — Ekaterina Poliakova-Georgantas
(74) *Attorney, Agent, or Firm* — McNeill Baur PLLC

(57) ABSTRACT

Provided are compounds, methods, and pharmaceutical compositions for reducing the amount or activity of LRRK2 RNA in a cell or animal, and in certain instances reducing the amount of LRRK2 protein in a cell or animal Such compounds, methods, and pharmaceutical compositions are useful to ameliorate at least 5 one symptom or hallmark of a neurodegenerative disease. Such symptoms and hallmarks include ataxia, neuropathy, and aggregate formation. Such neurodegenerative diseases include Parkinson's disease.

26 Claims, No Drawings

Specification includes a Sequence Listing.

(56) References Cited

U.S. PATENT DOCUMENTS

| | | |
|---|---|---|
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,029,986 B2 | 10/2011 | Meitinger et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,187,811 B2 | 5/2012 | Ericksson et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,669,048 B2 | 3/2014 | Reijo Pera et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,840,710 B2 | 12/2017 | Hastings et al. |
| 10,907,160 B2 | 2/2021 | Zhao et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |

(56) References Cited

U.S. PATENT DOCUMENTS

| | | | |
|---|---|---|---|
| 2012/0135941 | A1 | 5/2012 | Collard et al. |
| 2013/0130378 | A1 | 5/2013 | Manoharan et al. |
| 2014/0107330 | A1 | 4/2014 | Freier et al. |
| 2014/0128322 | A1 | 5/2014 | Chen et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |
| 2012/0052487 | A9 | 11/2015 | Khvorova et al. |
| 2017/0137826 | A1 | 5/2017 | Hastings et al. |
| 2018/0362988 | A1 | 12/2018 | Zhao et al. |
| 2021/0340546 | A1 | 11/2021 | Zhao et al. |

FOREIGN PATENT DOCUMENTS

| | | |
|---|---|---|
| WO | WO 2007/124096 | 11/2007 |
| WO | WO 2008/091799 | 7/2008 |
| WO | WO 2009/099991 | 8/2009 |
| WO | WO 2011/114106 | 9/2011 |
| WO | WO 2013/173635 | 11/2013 |
| WO | WO 2016/097212 | 6/2016 |
| WO | WO 2012/131365 | 3/2017 |
| WO | WO 2017/087282 | 5/2017 |
| WO | WO 2017/120365 | 7/2017 |
| WO | WO 2019/118325 | 6/2019 |
| WO | WO 2020/006267 | 1/2020 |

OTHER PUBLICATIONS

Chan et al., "Rac1 protein rescues neurite retraction caused by G2019S leucine-rich repeat kinase 2 (LRRK2)." J Biol Chem (2011) 286(18):16104-9.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cho et al., "Leucine-rich repeat kinase 2 regulates Sec16A at ER exit sites to allow ER-Golgi export" EMBO J (2014) 33: 2314-2331.

Crooke et al., "Basic Principles of Antisense Therapeutics" Antisense Research and Application (1998) Chapter 1:1-50.

Crooke, ST., et al., "Antisense Drug Technology" Second Edition, CRC Press (2008) Chapters 1-28.

Daher et al., "Abrogation of α-synuclein-mediated dopaminergic neurodegeneration in LRRK2-deficient rats" PNAS (2014) 111: 9289-9294.

Daher et al., "Leucine-rich Repeat Kinase 2 (LRRK2) Pharmacological Inhibition Abates α-synuclein Gene-induced Neurodegeneration" J Biol Chem (2015) 290: 19433-19444.

Daher et al., "Neurodegenerative phenotypes in an A53T α-synuclein transgenic mouse model are independent of LRRK2" Hum Mol Genet (2012) 21: 2420-2431.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Genbank Acc. No. NM_198578.3.

Genbank Acc. No. NT_029419.11.

Gautschi et al., "Activity of a novel bcl-2/bcl-xLbispecific antisense oligonucleotide against tumors of diverse histologic origins" J. Natl. Cancer Inst. (2001) 93:463-471.

Guerreiro et al., "LRRK2 interactions with α-synuclein in Parkingson's disease brains and in cell models" J Mol Med (2013) 91: 513-522.

Henderson et al., "LRRK2 activity does not dramatically alter α-synuclein pathology in primary neurons" Acta Neuropathologica Comm (2018) 6: 1-11.

Herzig et al., "LRRK2 protein levels are determined by kinase function and are crucial for kidney and lung homeostasis in mice" Human Mol Gen (2011) 20(21): 4209-4223.

Herzig et al., "High LRRK2 Levels Fail to Induce or Exacerbate Neuronal Alpha-Synucleinopathy in Mouse Brain" PLoS One (2012) 7(5): 1-14.

Hinkle et al., "LRRK2 knockout mice have an intact dopaminergic system but display alterations in exploratory and motor co-ordination behaviors" Mol Neurodegener (2012) 7: 1-17.

International Search Report for PCT/US17/12374 dated Mar. 23, 2017.

International Search Report for PCT/US19/39558 dated Nov. 14, 2019.

Lin et al., "Leucine-rich repeat kinase 2 regulates the progression of neuropathology induced by Parkinson's-disease-related mutant alpha-synuclein" Neuron (2009) 64: 807-827.

Lloret et al., "Validation of LRRK2 as a Drug Target for Treatment of Parkinson's Disease Using Antisense Technology" Michael J. Fox Foundation Funded Grant Interim Progress Report, (2009) retreived from the internet on Sep. 11, 2018 (https://www.michaeljfox.org/foundation/grant-detail.php?grant_id=542).

Luk et al., "Pathological α-synuclein transmission initiates Parkinson-like neurodegeneration in nontransgenic mice" Science (2012) 338(6109): 949-953.

Maher et al., "Comparative hybrid arrest by tandem antisense oligodeoxy ribonucleotides or oligodeoxyribonucleoside methylpbosphonates in a cell-free system" Nucl. Acid. Res. (1998) 16(8):3341-3358.

New England Biolabs 1998/99 Catalog (cover page and pp. 121 and 284).

Nichols et al., "Substtate specificity and inhibitors of LRRK2, a protein kinase mutated in Parkinson's disease." Biochem J. (2009) 424(1):47-60.

O'Hara et al., "LRRK2 and α-Synuclein: Distinct or Synergistic Players in Parkinson's Disease?" Frontiers in Neuroscience (2020) 14: 1-18.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Sheng et al., "Deletion of the WD40 Domain of LRRK2 in Zebrafish Causes Parkinsonism-Like Loss of Neurons and Locomotive Defect" PloS Genetics (2010) 6(4):e1000914.

Sibley et al., "Identification of allele-specific RNAi effectors targeting genetic forms of Parkinson's disease" PLoS One (2011) 6(10): e26194.

Sibley et al., "Silencing of Parkinson's disease-associated genes with artificial mirtron mimics of miR-1224" Nucleic Acids Res. (2012) 40(19): 9863-9875.

Tong et al., "Loss of leucine-rich repeat kinase 2 causes age-dependent bi-phasic alterations of the autophagy pathway" Mol Neurodegener (2012) 7: 1-16.

Tran et al., "Antisense oligonucleotides to LRRK2 ameliorate alpha-synuclein pathology and behavioral deficit induced by preformed alpha-synuclein fibrils." Abstract from Society for Neuroscience meeting Nov. 15, 2016, retreived from the internet Aug. 15, 2018 http://www.abstractsonline.com/pp8/index.html#!/4071/presentation/14652/.

Volpicelli-Daley et al., "LRRK2 Expression Augments α-Synuclein Sequestration into Inclusions in Neurons" J Neuroscience (2016) 36(28):7415-7427.

Volpicelli-Daley et al., "LRRK2 facilitates formation of alph-synuclein inclusions." abstract from Society for Neuroscience meeting, Nov. 15, 2016, retreived online Aug. 21, 2018 http://www.abstractsonline.com/pp8/index.html#!/4071/presentation/14651.

Volta et al., "Chronic and acute LRRK2 silencing has no long-term behavioral effects, whereas wild-type and mutant LRRK2 overexpression induce motor and cognitive deficits and altered regulation of dopamine release." Parkinsonism anRelat Disord (2015) 21(10):1156-63.

Woolf et al., "Specificity of antisense oligonucleotides in vivo" PNAS (1992) 89: 7305-7309.

Ynigo-Mojado et al., "Efficient allele-specific targeting of LRRK2 R1441 mutations mediated by RNAi" PLoS One (2011) 6: e21352.

(56) References Cited

OTHER PUBLICATIONS

Zhao et al., "Antisense oligonucleotides to LRRK2 ameliorate alpha-synuclein pathology and behavioral deficit induced by pre-formed alpha-sunuclein fibrils" Abstract from American Acadamy of Neurology meeting, Oct. 16, 2012, retreived from the internet Aug. 15, 2018: http://www.abstractsonline.com/pp8/#!/4046/presentation/8588.

Zhao et al., "Antisense Oligonucleotides to LRRK2 Ameliorate alpha-Synuclein Pathology and Behavioral Deficit Induced by Pre-Formed alpha-Synuclein Fibrils." Annals of Neurology (2017) 82(21):S56-S57.

Zhao et al., "Antisense Oligonucleotides to LRRK2 Ameliorate alpha-Synuclein Pathology and Behavioral Deficit Induced by Pre-Formed alpha-Synuclein Fibrils." 13th International Conference on Alzheimer's and Parkinson's diseases, abstract presented Apr. 1, 2017.

Zhao et al., "LRRK2 Antisense Oligonucleotides Ameliorate α-Synuclein Inclusion Formation in a Parkinson's Disease Mouse Model" Mol Ther Nucleic Acids (2017) 8:508-519.

Cole et al., "Antisense Oligonucleotide Therapeutics for the Treatment of Neurodegenerative Diseases" Presentation for Genetic Epidemiology of Parkinson's Disease (GEO-PD) (Sep. 12, 2014).

Hirst "LRRK2 ASO: Path to the Clinic" Abstract for Michael J Fox LRRK2 Summit (Mar. 25-26, 2019).

Swayze "This Is Your Brain on Antisense Oligonucleotides: Distribution, Activity and Application to the Treatment of Severe Neurodegenerative Disease" Abstract for 253rd Meeting of the American Chemical Society (Apr. 2-6, 2017).

Swayze "This Is Your Brain on Antisense Oligonucleotides: Distribution, Activity and Application to the Treatment of Severe Neurodegenerative Disease" Presentation for 253rd Meeting of the American Chemical Society (Apr. 2, 2017).

Tatarnikov et al., "Neurotransmission in LRRK2 and VPS35 mutant mice—rescued by acute LRRK2 knock-down" Presentation for Society for Neuroscience Annual Meeting (Sep. 15, 2016).

Zhao et al., "Antisense oligonucleotides to LRRK2 ameliorate alpha-synuclein pathology and behavioral deficit induced by pre-formed alpha-synuclein fibrils" Presentation for Society for Neuroscience Annual Meeting (Sep. 15, 2016).

Zhao "Inhibitors of Leucine-rich Repeat Kinase 2 (LRRK2): Progress & Promise for the Treatment of Parkinson's Disease" Presentation for World CNS Summit (Feb. 20, 2017).

Zhao et al., "LRRK2 Antisense Oligonucleotides Ameliorate α-Synuclein Inclusion Formation in a Parkinson's Disease Mouse Model" Abstract for 142nd Annual Meeting of the American Neurological Association (Oct. 15-17, 2017).

Zhao et al., "LRRK2 Antisense Oligonucleotides Ameliorate α-Synuclein Inclusion Formation in a Parkinson's Disease Mouse Model" Poster for 142nd Annual Meeting of the American Neurological Association (Oct. 15-17, 2017).

COMPOUNDS AND METHODS FOR REDUCING LRRK2 EXPRESSION

SEQUENCE LISTING

The present application is being filed along with a Sequence Listing in electronic format. The Sequence Listing is provided as a file entitled BIOL0324USASEQ_ST25.txt, created on Dec. 2, 2020, which is 1.12 MB in size. The information in the electronic format of the sequence listing is incorporated herein by reference in its entirety.

FIELD

Provided are compounds, methods, and pharmaceutical compositions for reducing the amount or activity of leucine-rich repeat kinase 2 (LRRK2) RNA in a cell or animal, and in certain instances reducing the amount of LRRK2 protein in a cell or animal Such compounds, methods, and pharmaceutical compositions are useful to ameliorate at least one symptom or hallmark of a neurodegenerative disease. Such symptoms and hallmarks include ataxia, neuropathy, and aggregate formation. Such neurodegenerative diseases include Parkinson's disease.

BACKGROUND

The LRRK2 gene encodes a protein with an armadillo repeat (ARM) region, an ankyrin repeat (ANK) region, a leucine-rich repeat (LRR) domain, a kinase domain, a RAS domain, a GTPase domain, and a WD40 domain. The protein is present largely in the cytoplasm but also associates with the mitochondrial outer membrane. One segment of the LRRK2 protein is enriched with leucine and may be involved in signal transduction and cytoskeleton assembly. Other parts of the LRRK2 protein are also thought to be involved in protein-protein interactions. Additional studies indicate that LRRK2 protein has an enzyme function known as kinase activity, including phosphorylation and GTPase activity. LRRK2 is active in the brain and other tissues throughout the body.

Genomewide association studies have found an association between LRRK2 and Parkinson's disease. Indeed, LRRK2 is the greatest known genetic contributor to Parkinson's disease. Nonetheless, Parkinson's disease has not been considered to be a genetic disease. The majority of Parkinson's disease cases are idiopathic. Approximately 10 percent of Parkinson's disease cases have been linked to a genetic cause. Mutations in the LRRK2 gene are the most common cause of Parkinson's disease in this relatively small group, representing one to two percent of total Parkinson's disease cases.

Currently there is a lack of acceptable options for treating neurodegenerative diseases such as Parkinson's disease, including non-LRRK2 mediated Parkinson's disease. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of LRRK2 RNA, and in certain embodiments reducing the amount of LRRK2 protein in a cell or animal. In certain embodiments, the animal has a neurodegenerative disease. In certain embodiments, the animal has Parkinson's disease. In certain embodiments, compounds useful for reducing expression of LRRK2 RNA are oligomeric compounds. In certain embodiments, compounds useful for reducing expression of LRRK2 RNA are modified oligonucleotides.

Also provided are methods useful for ameliorating at least one symptom or hallmark of a neurodegenerative disease. In certain embodiments, the neurodegenerative disease is Parkinson's disease. In certain embodiments, the Parkinson's disease is either LRRK2 mediated Parkinson's disease or non-LRRK2 mediated Parkinson's disease. In certain embodiments, the symptom or hallmark includes ataxia, neuropathy, and aggregate formation. In certain embodiments, amelioration of these symptoms results in improved motor function, reduced neuropathy, and reduction in number of aggregates.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is ataxia, neuropathy, and aggregate formation. In certain embodiments, amelioration of these symptoms results in improved motor function, reduced neuropathy, and reduction in number of aggregates.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "cEt nucleoside" means a nucleoside comprising cEt modified sugar.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyribosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "MOE" means methoxyethyl. "2'-MOE" or "2'-MOE modified sugar" means a 2'-OCH$_2$CH$_2$OCH$_3$ group in place of the 2'-OH group of a ribosyl sugar moiety. As used herein, "2'-MOE nucleoside" means a nucleoside comprising a 2'-MOE modified sugar.

As used herein, "motif" means the pattern of unmodified and/or modified sugar moieties, nucleobases, and/or internucleoside linkages, in an oligonucleotide.

As used herein, "RNA" means an RNA transcript that encodes a protein and includes pre-mRNA and mature mRNA unless otherwise specified.

As used herein, "neurodegenerative disease" means a condition marked by progressive loss of function or structure, including loss of motor function and death of neurons. In certain embodiments, the neurodegenerative disease is Parkinson's disease. In certain embodiments, the Parkinson's disease may be LRRK2 mediated Parkinson's disease or non-LRRK2 mediated Parkinson's disease.

"Non-LRRK2 mediated Parkinson's Disease" is a diagnosis of Parkinson's disease not associated with a causative LRRK2 genetic mutation. Causative LRRK2 genetic mutations include G2019S, R1441C, R1441G, I2020T, and Y1699C. Diagnosis of Parkinson's disease may be accomplished by any method including evaluating an individual's medical history, observation of signs and symptoms, and standard clinical tests or assessments. Genetic testing for a mutation associated with LRRK2, such as G2019S, R1441C, R1441G, I2020T, and Y1699C, may reveal whether an individual has non-LRRK2 mediated Parkinson's disease. An individual having a diagnosis of Parkinson's disease, but without a causative LRRK2 mutation, has non-LRRK2 mediated Parkinson's disease. "Identifying an animal having non-LRRK2 mediated Parkinson's Disease" means identifying an animal having been diagnosed with Parkinson's Disease or predisposed to develop Parkinson's Disease without a causative LRRK2 mutation.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein "prodrug" means a therapeutic agent in a form outside the body that is converted to a different form within an animal or cells thereof. Typically conversion of a prodrug within the animal is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcripexpression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "siRNA" refers to a ribonucleic acid molecule having a duplex structure including two antiparallel and substantially complementary nucleic acid strands. The two strands forming the duplex structure may be different portions of one larger RNA molecule, or they may be separate RNA molecules. Where the two strands are part of one larger molecule, and therefore are connected by consecutive nucleobases between the 3'-end of one strand and the 5' end of the respective other strand forming the duplex structure, the connecting RNA chain is referred to as a "hairpin loop". The RNA strands may have the same or a different number of nucleotides.

As used herein, "standard cell assay" means the assay described in Example 4 and reasonable variations thereof.

As used herein, "standard in vivo assay" means the experiment described in Example 14 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) ribosyl moiety, as found in RNA (an "unmodified RNA sugar moiety"), or a 2'-H(H) deoxyribosyl moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

Certain Embodiments

The present disclosure provides the following non-limiting numbered embodiments:

Embodiment 1. An oligomeric compound comprising a modified oligonucleotide consisting of 12 to 50 linked nucleosides wherein the nucleobase sequence of the modified oligonucleotide is at least 90% complementary to an equal length portion of a LRRK2 nucleic acid, and wherein the modified oligonucleotide comprises at least one modification selected from a modified sugar, a sugar surrogate, and a modified internucleoside linkage.

Embodiment 2: An oligomeric compound comprising a modified oligonucleotide consisting of 12 to 50 linked nucleosides and having a nucleobase sequence comprising at least 12, at least 13, at least 14, at least 15, at least 16, at least 17, at least 18, at least 19, or at least 20 contiguous nucleobases of any of the nucleobase sequences of SEQ ID NOS: 30-3847.

Embodiment 3: An oligomeric compound comprising a modified oligonucleotide consisting of 12 to 50 linked nucleosides and having a nucleobase sequence comprising a portion of at least 8, at least 9, at least 10, at least 11, at least 12, at least 13, at least 14, at least 15, at least 16, at least 17, at least 18, at least 19, or at least 20 contiguous nucleobases, wherein the portion is complementary to:

an equal length portion of nucleobases 18,633-18,658 of SEQ ID NO: 2;

an equal length portion of nucleobases 21,721-21,755 of SEQ ID NO: 2;

an equal length portion of nucleobases 27,963-28,016 of SEQ ID NO: 2;

an equal length portion of nucleobases 35,415-35,446 of SEQ ID NO: 2;

an equal length portion of nucleobases 77,221-77,264 of SEQ ID NO: 2;

an equal length portion of nucleobases 81,581-81,612 and/or 87,838-87,869 of SEQ ID NO: 2;

an equal length portion of nucleobases 81,627-81,651 of SEQ ID NO: 2;

an equal length portion of nucleobases 82,058-82,081 of SEQ ID NO: 2;

an equal length portion of nucleobases 82,180-82,220 of SEQ ID NO: 2;

an equal length portion of nucleobases 82,500-82,525 of SEQ ID NO: 2;

an equal length portion of nucleobases 91,038-91,067 of SEQ ID NO: 2;

an equal length portion of nucleobases 92,148-92,173 of SEQ ID NO: 2;

am equal length portion of nucleobases 98,186-98,220 of SEQ ID NO: 2;

an equal length portion of nucleobases 98,218-98,242 of SEQ ID NO: 2;

an equal length portion of nucleobases 99,199-99,223 of SEQ ID NO: 2;

an equal length portion of nucleobases 119,903-119,936 of SEQ ID NO: 2; or an equal length portion of nucleobases 4,062-4,086 of SEQ ID NO: 1.

Embodiment 4. The oligomeric compound of any of embodiments 1-3, wherein the modified oligonucleotide has a nucleobase sequence that is at least 80%, 85%, 90%, 95%, or 100% complementary to the nucleobase sequence of SEQ ID NO: 1 or SEQ ID NO: 2, when measured across the entire nucleobase sequence of the modified oligonucleotide.

Embodiment 5. The oligomeric compound of any of embodiments 1-4, wherein the modified oligonucleotide comprises at least one modified nucleoside.

Embodiment 6. The oligomeric compound of embodiment 5, wherein the modified oligonucleotide comprises at least one modified nucleoside comprising a modified sugar moiety.

Embodiment 7. The oligomeric compound of embodiment 6, wherein the modified oligonucleotide comprises at least one modified nucleoside comprising a bicyclic sugar moiety.

Embodiment 8. The oligomeric compound of embodiment 7, wherein the modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 9. The oligomeric compound of any of embodiments 5-8, wherein the modified oligonucleotide comprises at least one modified nucleoside comprising a non-bicyclic modified sugar moiety.

Embodiment 10. The oligomeric compound of embodiment 9, wherein the modified oligonucleotide comprises at least one modified nucleoside comprising a non-bicyclic modified sugar moiety comprising a 2'-MOE modified sugar or 2'-OMe modified sugar.

Embodiment 11. The oligomeric compound of any of embodiments 5-10, wherein the modified oligonucleotide comprises at least one modified nucleoside comprising a sugar surrogate.

Embodiment 12. The oligomeric compound of embodiment 11, wherein the modified oligonucleotide comprises at least one modified nucleoside comprising a sugar surrogate selected from morpholino and PNA.

Embodiment 13. The oligomeric compound of any of embodiments 1-12, wherein the modified oligonucleotide has a sugar motif comprising:

a 5'-region consisting of 1-5 linked 5'-region nucleosides;

a central region consisting of 6-10 linked central region nucleosides; and a 3'-region consisting of 1-5 linked 3'-region nucleosides; wherein each of the 5'-region nucleosides and each of the 3'-region nucleosides comprises a modified sugar moiety and each of the central region nucleosides comprises an unmodified 2'-deoxyribosyl sugar moiety.

Embodiment 14. The oligomeric compound of any of embodiments 1-13, wherein the modified oligonucleotide comprises at least one modified internucleoside linkage.

Embodiment 15. The oligomeric compound of embodiment 14, wherein each internucleoside linkage of the modified oligonucleotide is a modified internucleoside linkage.

Embodiment 16. The oligomeric compound of embodiment 14 or 15 wherein at least one internucleoside linkage is a phosphorothioate internucleoside linkage.

Embodiment 17. The oligomeric compound of embodiment 14 or 16 wherein the modified oligonucleotide comprises at least one phosphodiester internucleoside linkage.

Embodiment 18. The oligomeric compound of any of embodiments 14, 16, or 17, wherein each internucleoside linkage is either a phosphodiester internucleoside linkage or a phosphorothioate internucleoside linkage.

Embodiment 19. The oligomeric compound of any of embodiments 1-18, wherein the modified oligonucleotide comprises at least one modified nucleobase.

Embodiment 20. The oligomeric compound of embodiment 19, wherein the modified nucleobase is a 5-methyl cytosine.

Embodiment 21. The oligomeric compound of any of embodiments 1-20, wherein the modified oligonucleotide consists of 12-30, 12-22, 12-20, 14-20, 15-25, 16-20, 18-22 or 18-20 linked nucleosides.

Embodiment 22. The oligomeric compound of any of embodiments 1-21, wherein the modified oligonucleotide consists of 17 or 20 linked nucleosides.

Embodiment 23. The oligomeric compound of any of embodiments 1-22 consisting of the modified oligonucleotide.

Embodiment 24. The oligomeric compound of any of embodiments 1-22 comprising a conjugate group comprising a conjugate moiety and a conjugate linker.

Embodiment 25. The oligomeric compound of embodiment 24, wherein the conjugate group comprises a GalNAc cluster comprising 1-3 GalNAc ligands.

Embodiment 26. The oligomeric compound of embodiment 24 or 25, wherein the conjugate linker consists of a single bond.

Embodiment 27. The oligomeric compound of embodiment 25, wherein the conjugate linker is cleavable.

Embodiment 28. The oligomeric compound of embodiment 27, wherein the conjugate linker comprises 1-3 linker-nucleosides.

Embodiment 29. The oligomeric compound of any of embodiments 24-28, wherein the conjugate group is attached to the modified oligonucleotide at the 5'-end of the modified oligonucleotide.

Embodiment 30. The oligomeric compound of any of embodiments 24-28, wherein the conjugate group is attached to the modified oligonucleotide at the 3'-end of the modified oligonucleotide.

Embodiment 31. The oligomeric compound of any of embodiments 1-30 comprising a terminal group.

Embodiment 32. The oligomeric compound of any of embodiments 1-31 wherein the oligomeric compound is a singled-stranded oligomeric compound.

Embodiment 33. The oligomeric compound of any of embodiments 1-27 or 29-31, wherein the oligomeric compound does not comprise linker-nucleosides.

Embodiment 34. An oligomeric duplex comprising an oligomeric compound of any of embodiments 1-31 or 33.

Embodiment 35. An antisense compound comprising or consisting of an oligomeric compound of any of embodiments 1-33 or an oligomeric duplex of embodiment 34.

Embodiment 36. A pharmaceutical composition comprising an oligomeric compound of any of embodiments 1-33 or an oligomeric duplex of embodiment 34 and a pharmaceutically acceptable carrier or diluent.

Embodiment 37. A modified oligonucleotide according to the following formula:
(SEQ ID NO: 222)
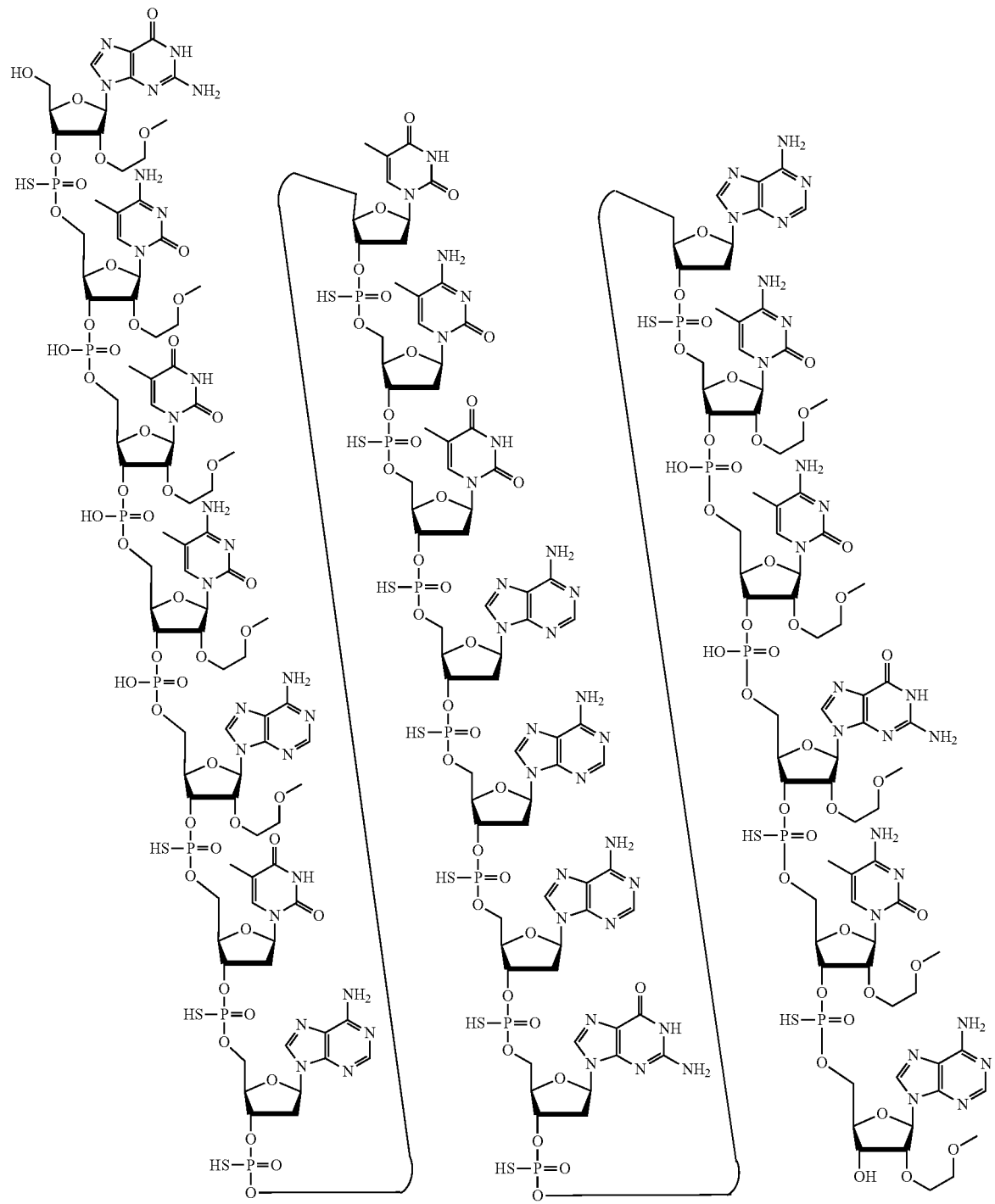
(SEQ ID NO: 222)
or a salt thereof.

Embodiment 38. A modified oligonucleotide according to the following formula:
(SEQ ID NO: 888)
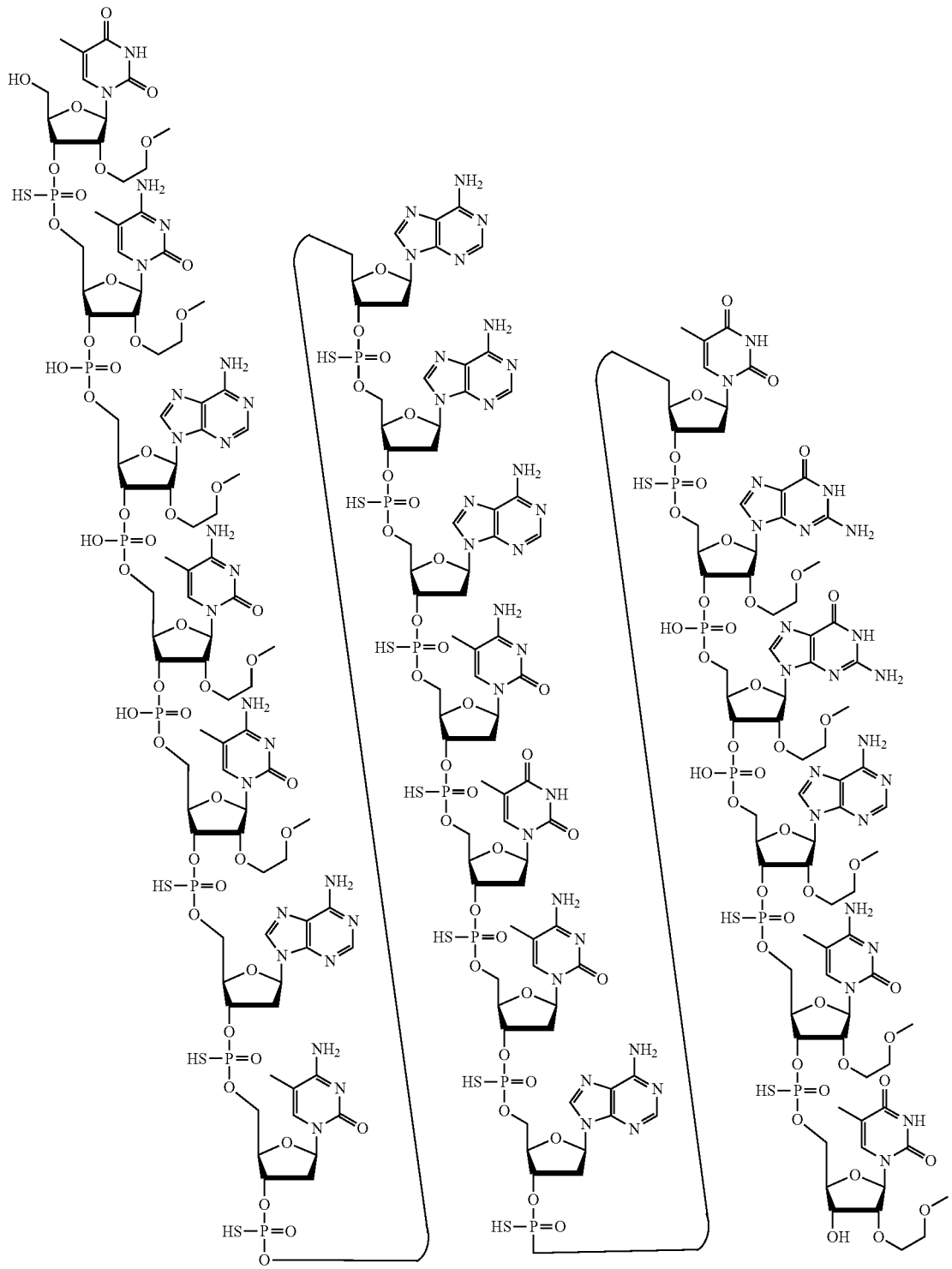
(SEQ ID NO: 888)
or a salt thereof.

Embodiment 39. A modified oligonucleotide according to the following formula:
(SEQ ID NO: 1431)
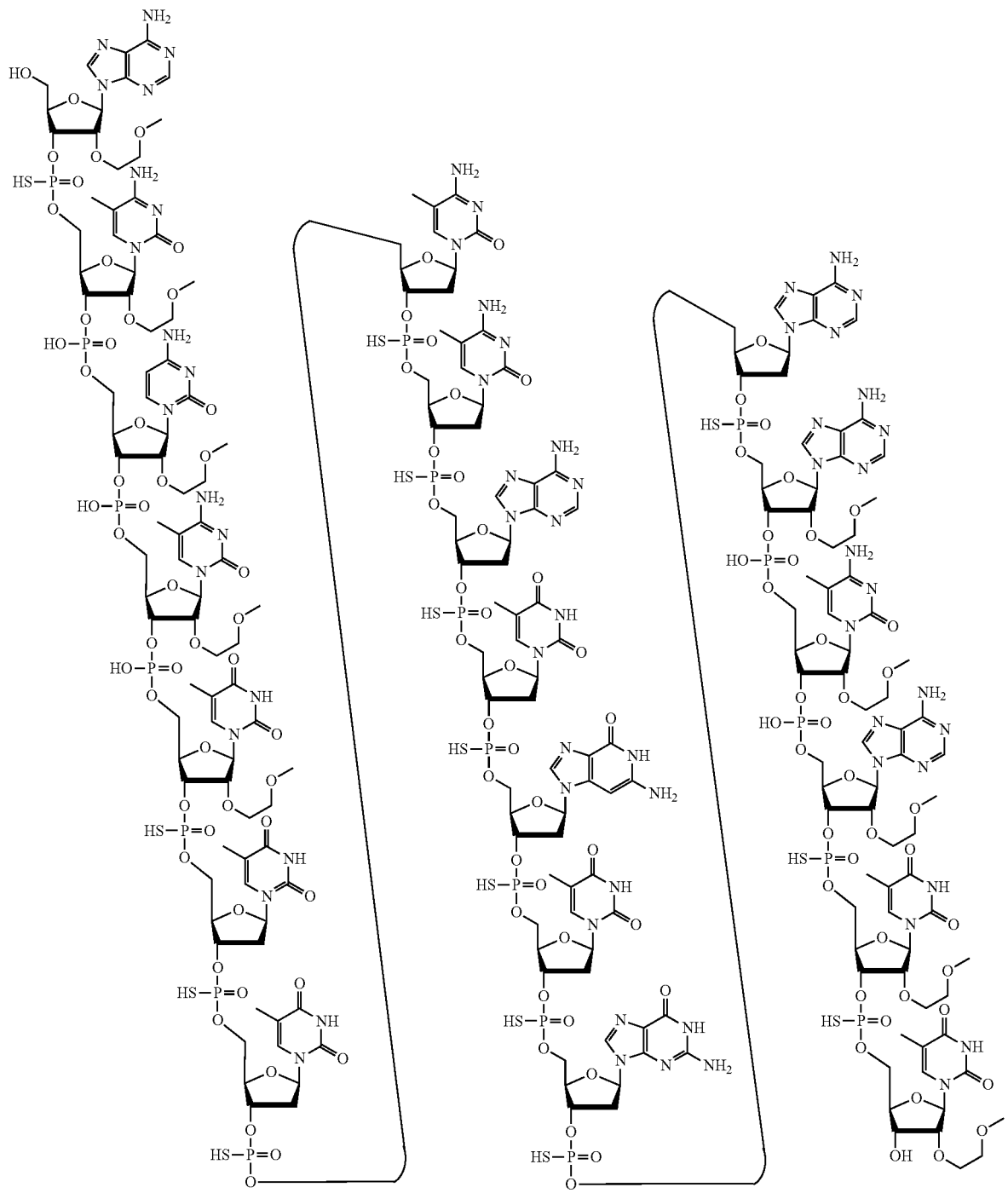
(SEQ ID NO: 1431)
or a salt thereof.

Embodiment 40. A modified oligonucleotide according to the following formula:
(SEQ ID NO: 3590)
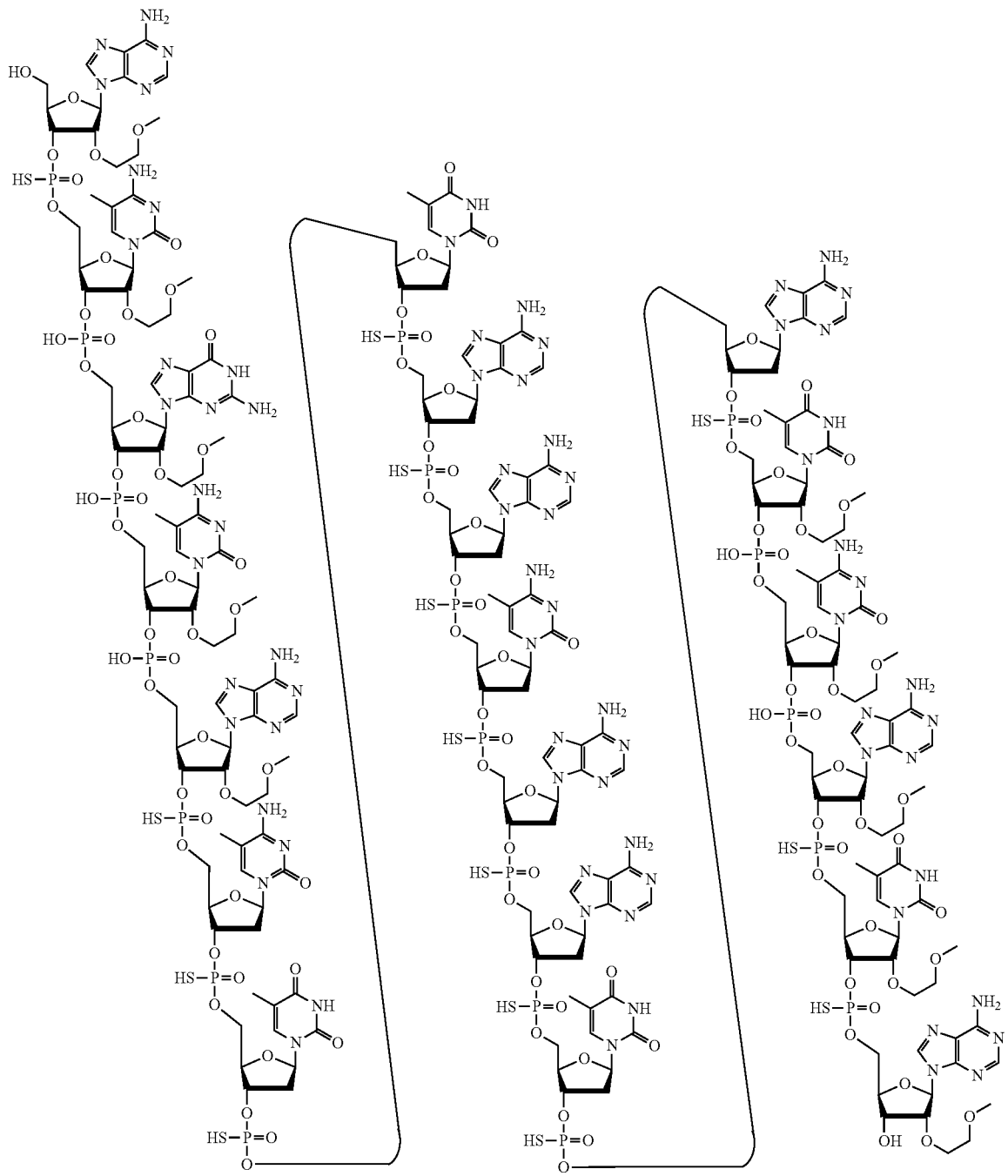
(SEQ ID NO: 3590)
or a salt thereof.

Embodiment 41. A modified oligonucleotide according to the following formula:
(SEQ ID NO: 3385)
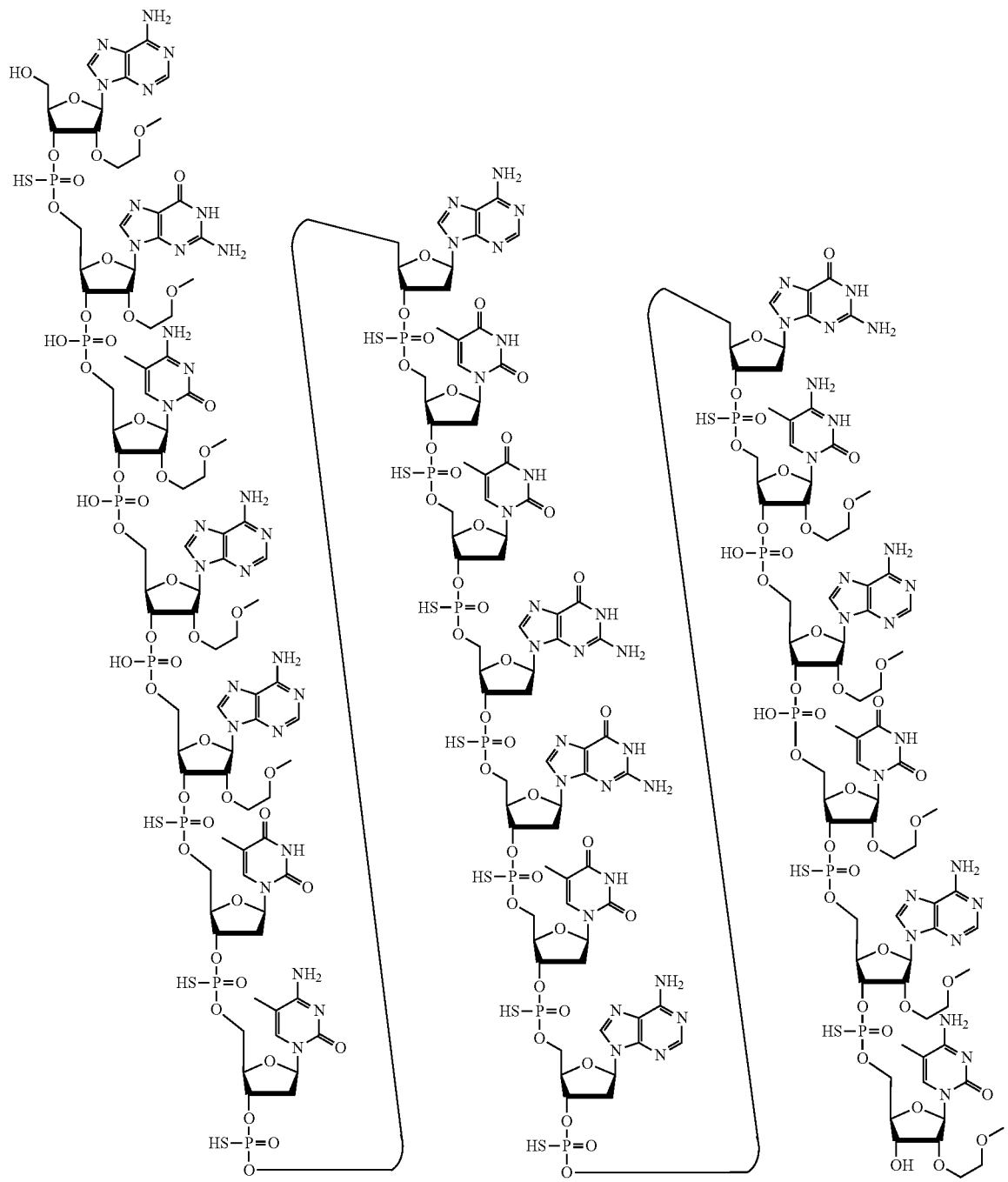
(SEQ ID NO: 3385)
or a salt thereof.

Embodiment 42. A modified oligonucleotide according to the following formula:
(SEQ ID NO: 852)
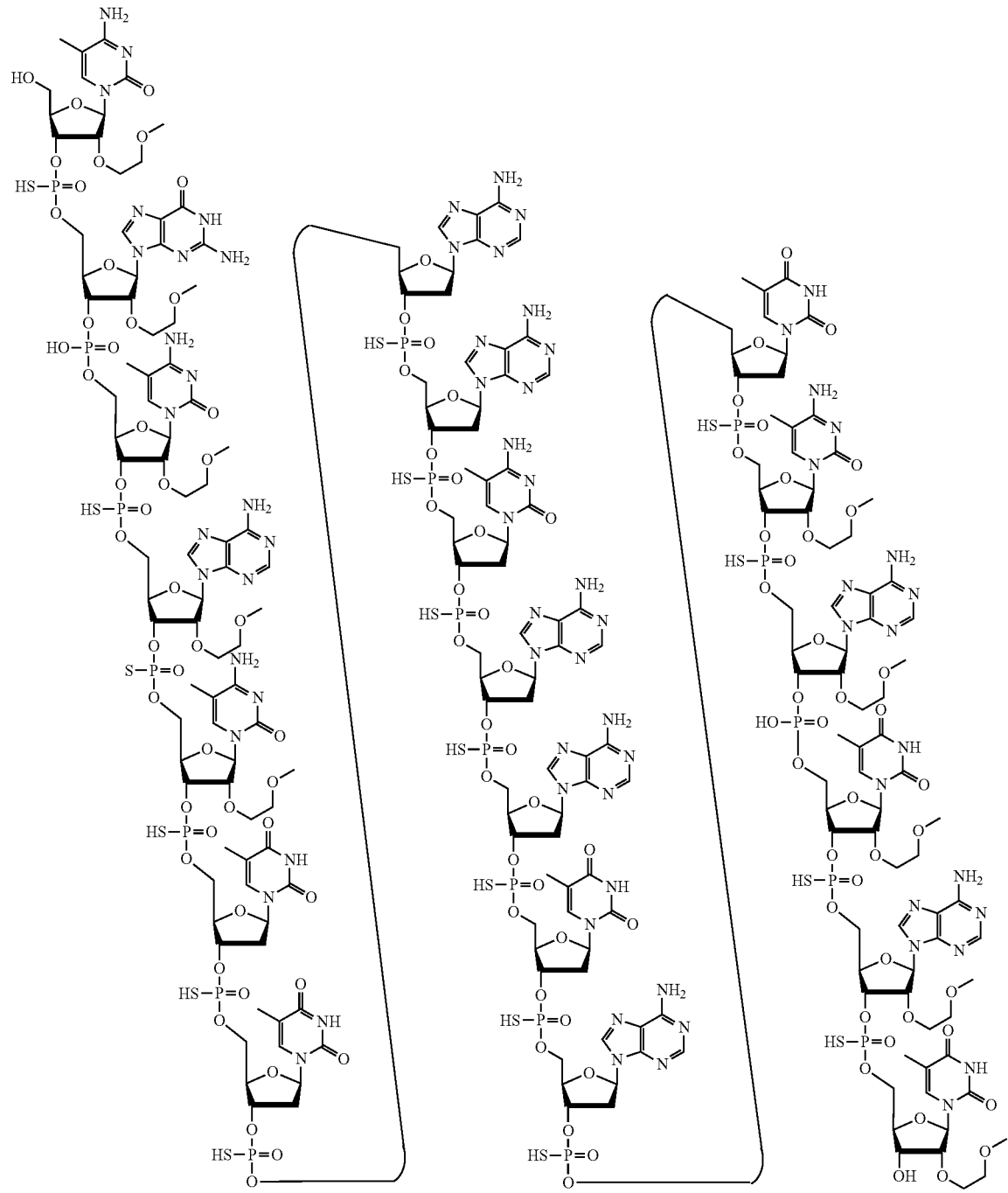
(SEQ ID NO: 852)
or a salt thereof.
Embodiment 43. The modified oligonucleotide of any of embodiments 37-42, which is a sodium salt of the formula.

Embodiment 44. A modified oligonucleotide according to the following formula:
(SEQ ID NO: 222)
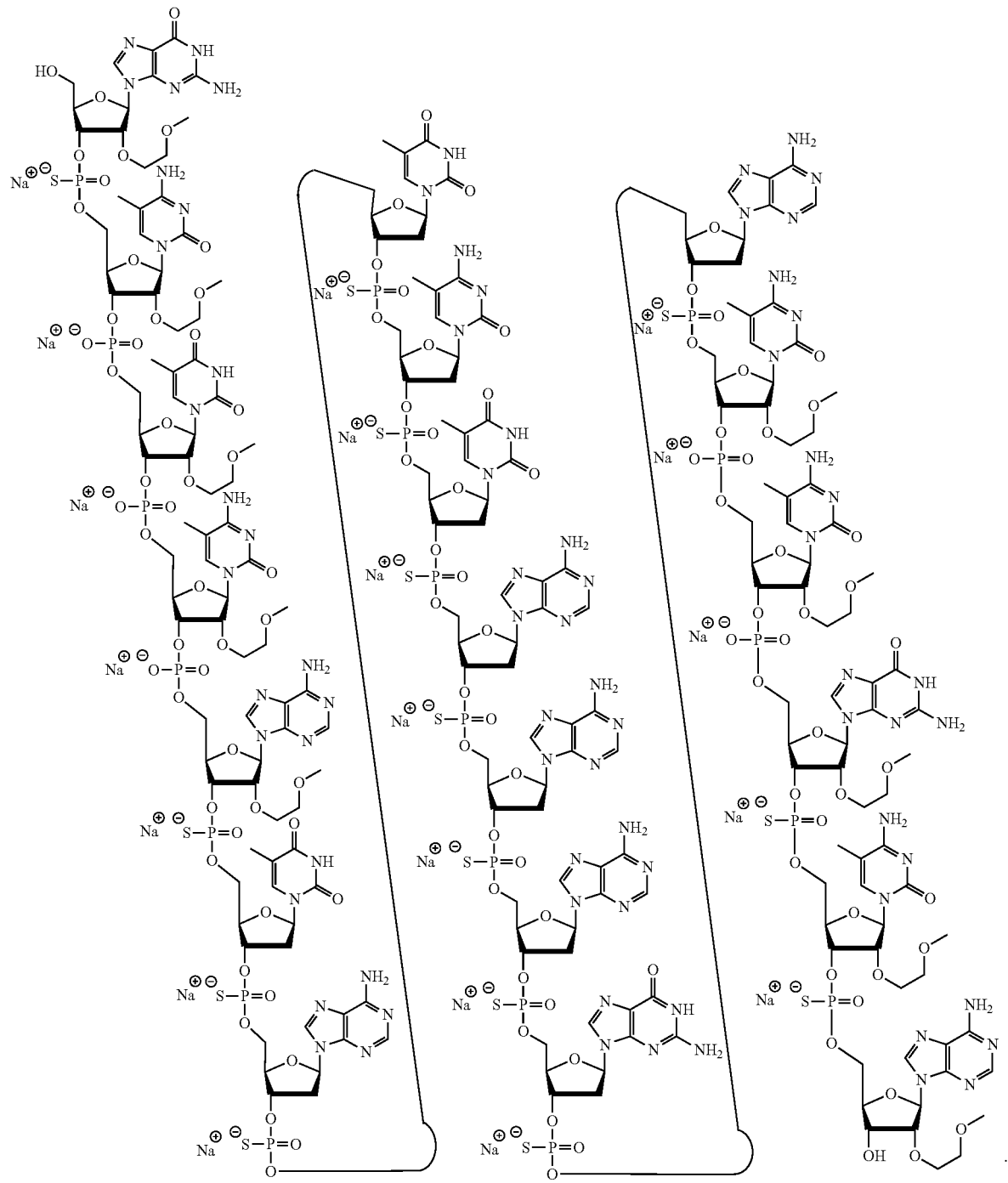
(SEQ ID NO: 222).

Embodiment 45. A modified oligonucleotide according to the following formula:
(SEQ ID NO: 888)
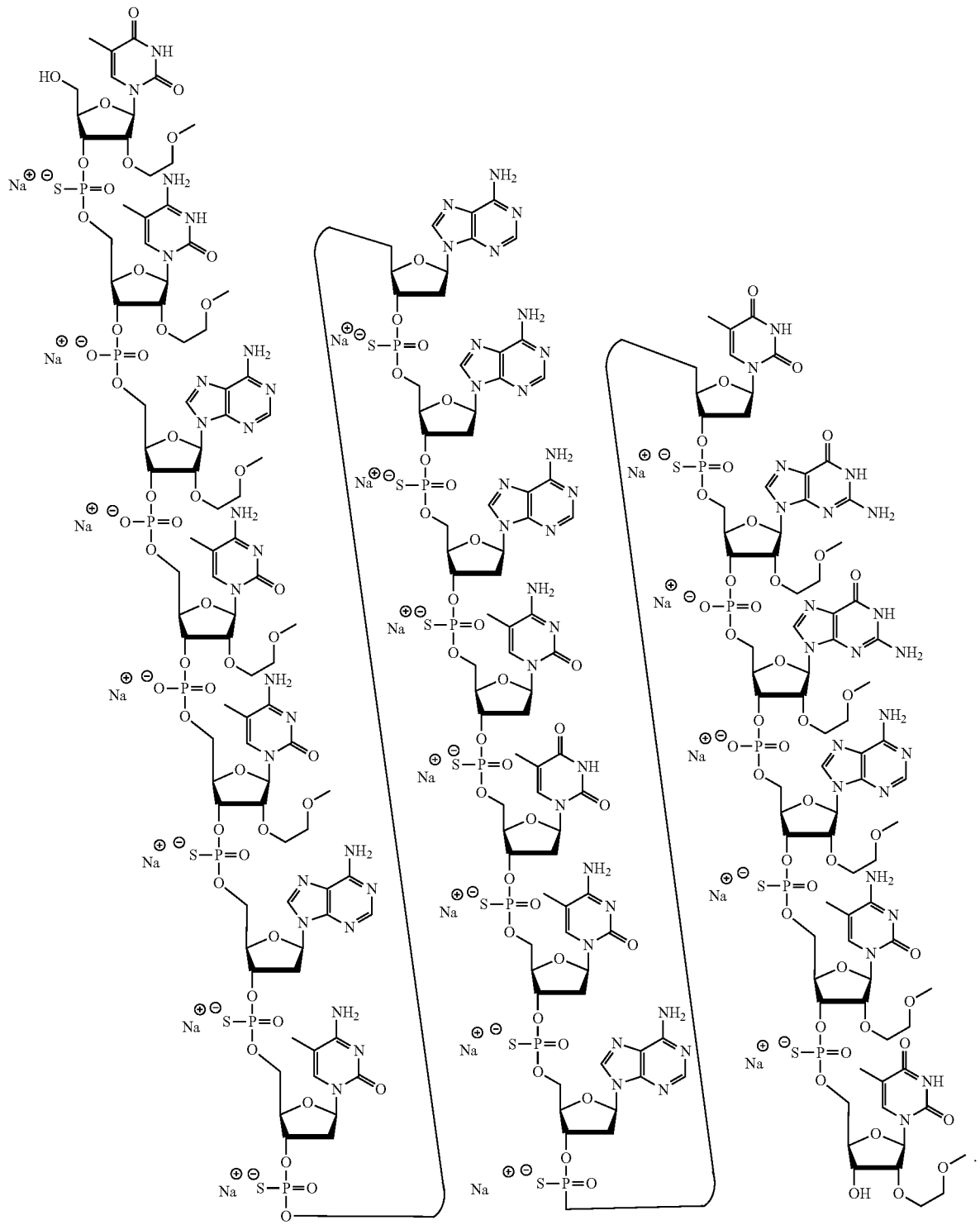
(SEQ ID NO: 888).

Embodiment 46. A modified oligonucleotide according to the following formula:
(SEQ ID NO: 1431)
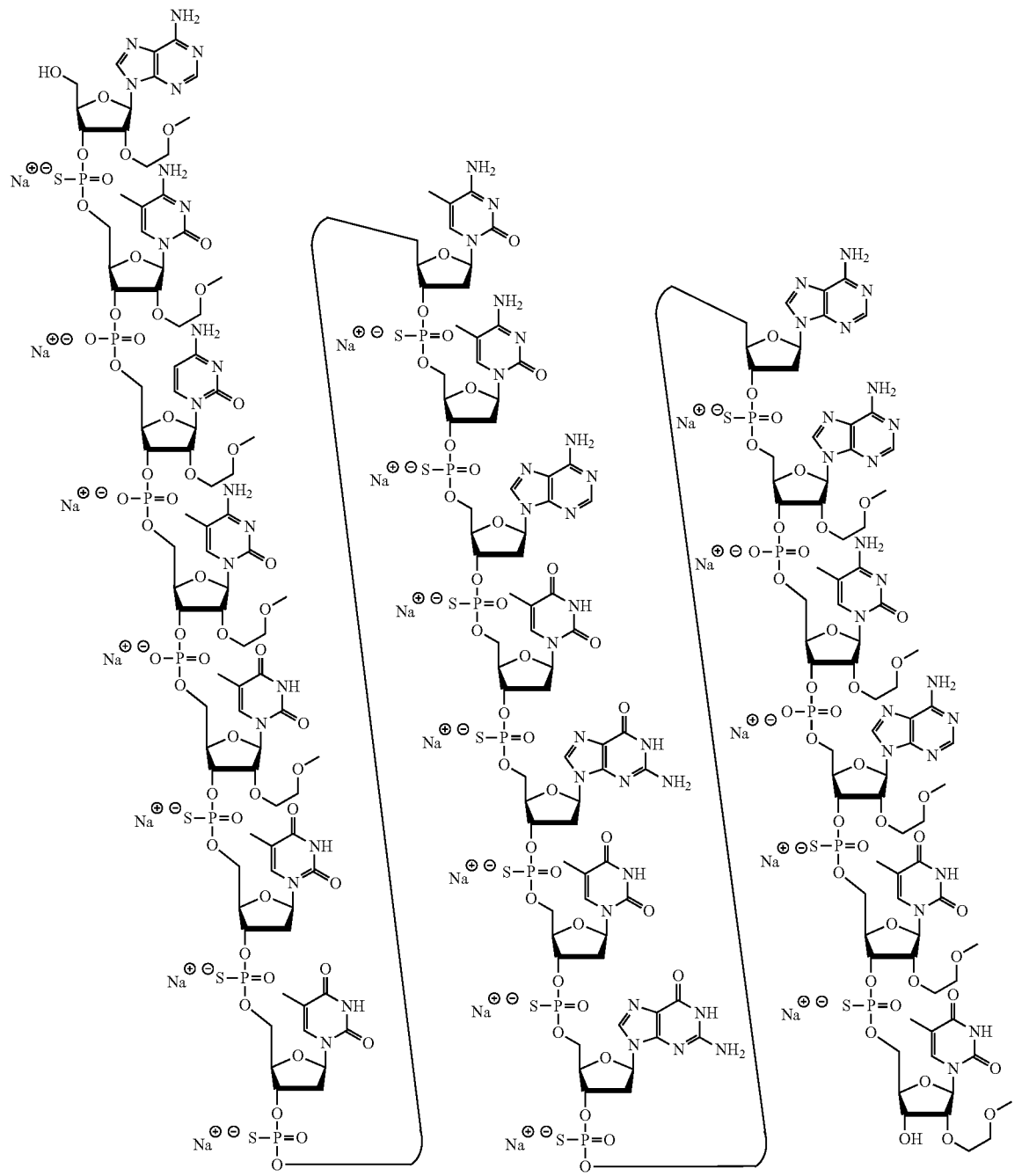
(SEQ ID NO: 1431).

Embodiment 47. A modified oligonucleotide according to the following formula:
(SEQ ID NO: 3590)
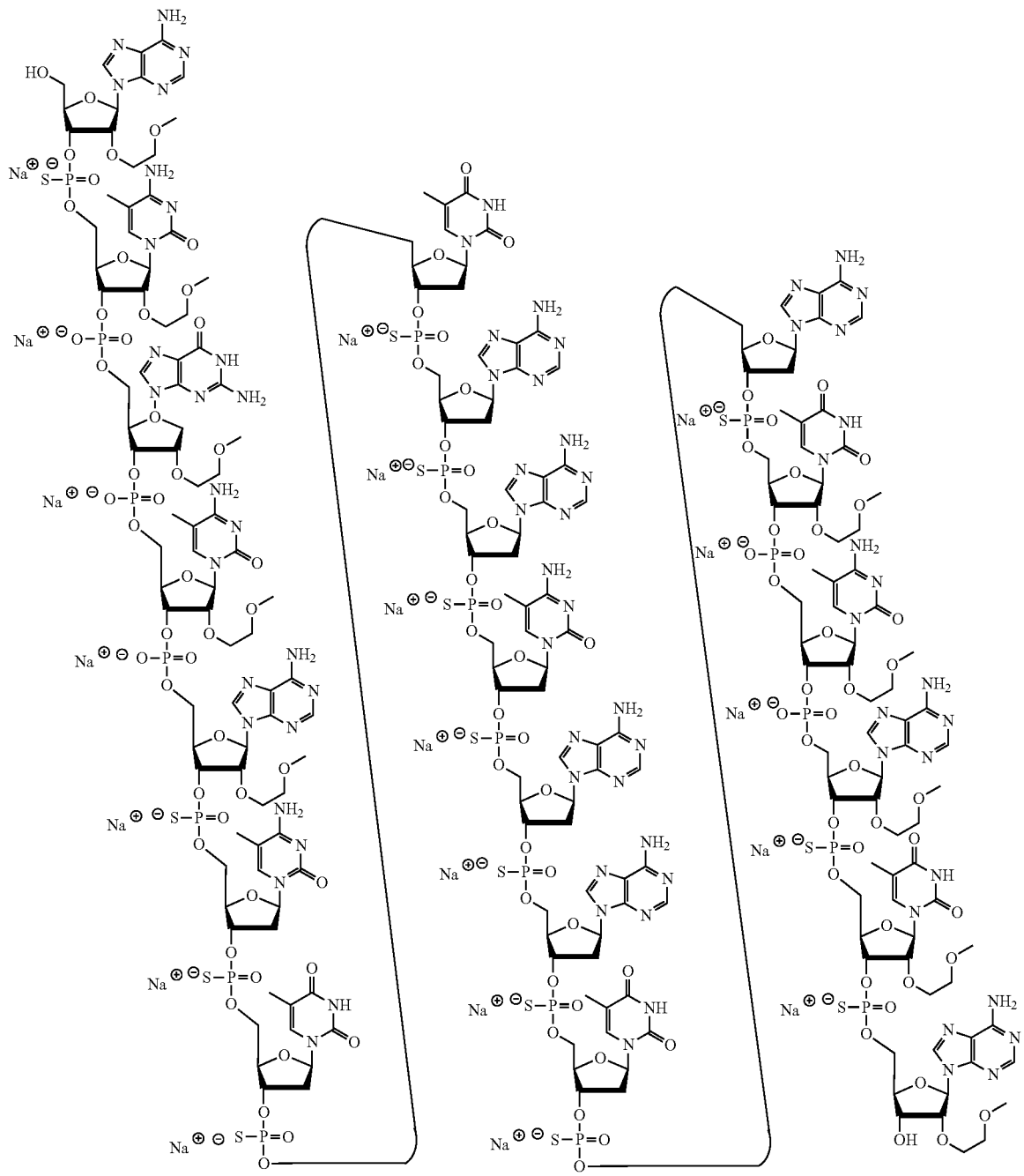
(SEQ ID NO: 3590).

Embodiment 48. A modified oligonucleotide according to the following formula:
(SEQ ID NO: 3385)
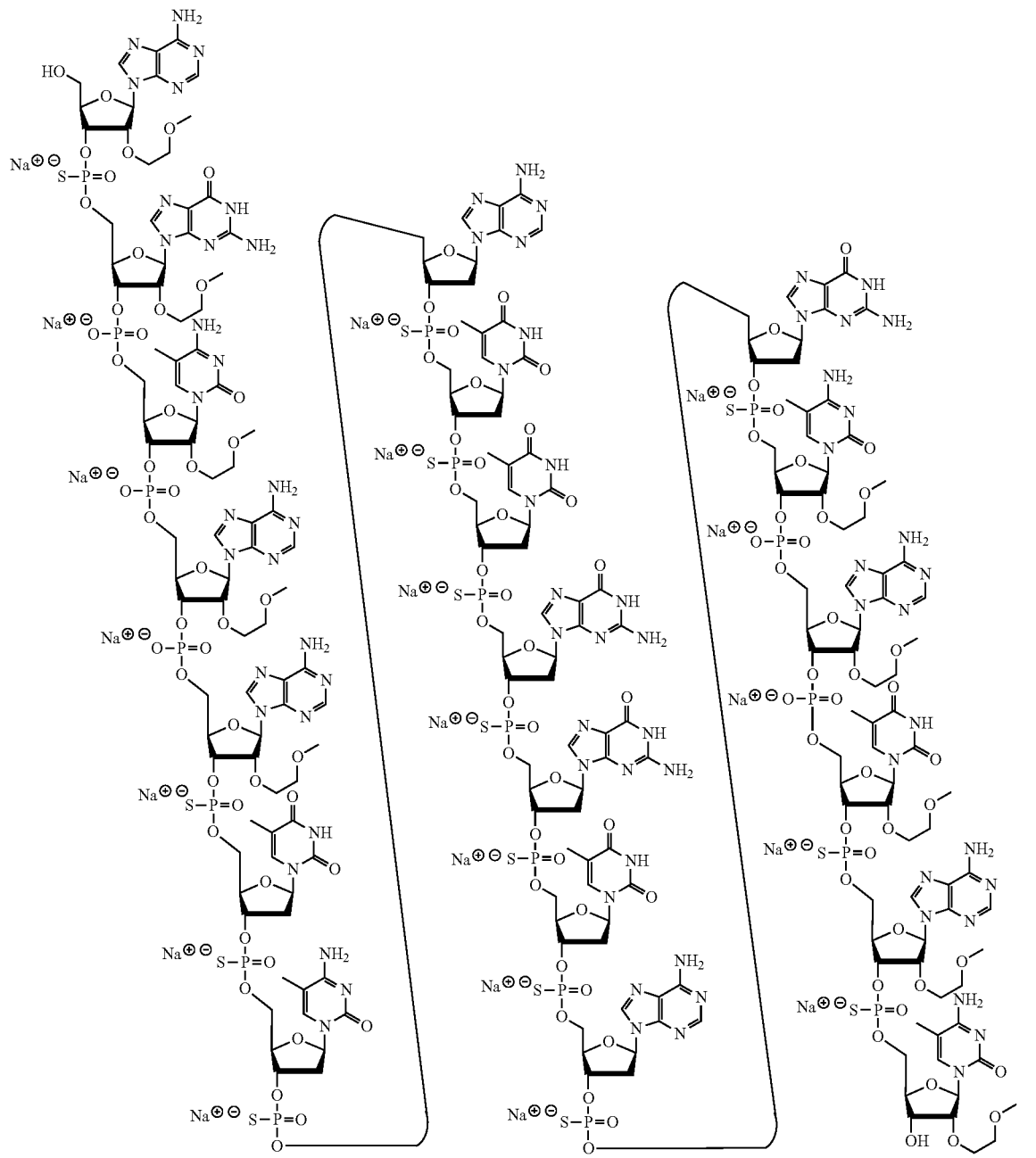
(SEQ ID NO: 3385).

Embodiment 49. A modified oligonucleotide according to the following formula:

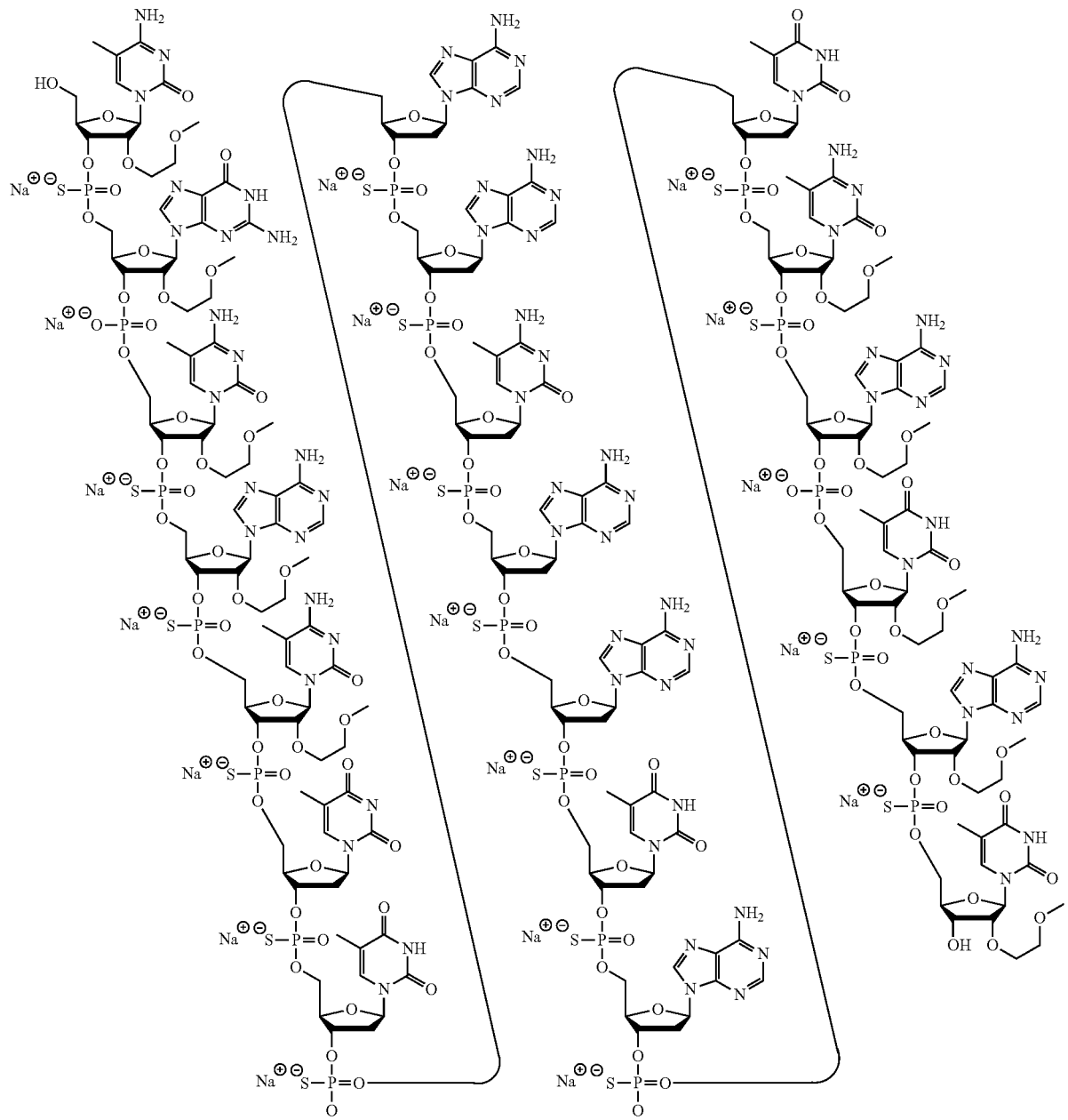

(SEQ ID NO: 852).

Embodiment 50. A chirally enriched population of the modified oligonucleotide of any of embodiments 37-49 wherein the population is enriched for modified oligonucleotides comprising at least one particular phosphorothioate internucleoside linkage having a particular stereochemical configuration.

Embodiment 51. The chirally enriched population of embodiment 50, wherein the population is enriched for a modified oligonucleotide comprising at least one particular phosphorothioate internucleoside linkage having the (Sp) configuration.

Embodiment 52. The chirally enriched population of embodiment 50 or 51, wherein the population is enriched for modified oligonucleotides having at least one particular phosphorothioate internucleoside linkage having the (Rp) configuration.

Embodiment 53. The chirally enriched population of embodiment 50, wherein the population is enriched for modified oligonucleotides having a particular, independently selected stereochemical configuration at each phosphorothioate internucleoside linkage Embodiment 54. The chirally enriched population of embodiment 53, wherein the population is enriched for modified oligonucleotides having the (Sp) configuration at each phosphorothioate internucleoside linkage.

Embodiment 55. The chirally enriched population of embodiment 53, wherein the population is enriched for modified oligonucleotides having the (Rp) configuration at each phosphorothioate internucleoside linkage.

Embodiment 56. The chirally enriched population of embodiment 50 or embodiment 53 wherein the population is enriched for modified oligonucleotides having at least 3 contiguous phosphorothioate internucleoside linkages in the Sp-Sp-Rp configuration, in the 5' to 3' direction.

Embodiment 57. A population of modified oligonucleotides of any of embodiments 37-49, wherein all of the phosphorothioate internucleoside linkages of the modified oligonucleotide are stereorandom.

Embodiment 58. A pharmaceutical composition comprising the modified oligonucleotide of any of embodiments 37-49 and a pharmaceutically acceptable diluent or carrier.

Embodiment 59. The pharmaceutical composition of embodiment 58, wherein the pharmaceutically acceptable diluent is artificial cerebrospinal fluid.

Embodiment 60. The pharmaceutical composition of embodiment 59, wherein the pharmaceutical composition consists essentially of the modified oligonucleotide and artificial cerebrospinal fluid.

Embodiment 61. A method comprising administering to an animal a pharmaceutical composition of any of embodiments 36 or 58-60.

Embodiment 62. A method of treating a disease associated with LRRK2 comprising administering to an individual having or at risk for developing a disease associated with LRRK2 a therapeutically effective amount of a pharmaceutical composition according to any of embodiments 36 or 58-60; and thereby treating the disease associated with LRRK2.

Embodiment 63. The method of embodiment 62, wherein the disease associated with LRRK2 is a neurodegenerative disease.

Embodiment 64. The method of embodiment 63, wherein the neurodegenerative disease is Parkinson's disease.
Embodiment 65. The method of embodiment 64, wherein at least one symptom or hallmark of the neurodegenerative disease is ameliorated.

Embodiment 66. The method of embodiment 65, wherein the symptom or hallmark is any of ataxia, neuropathy, and aggregate formation.

Embodiment 67. An oligomeric compound comprising a modified oligonucleotide according to the following formula:

Ges mCeo Teo mCeo Aes Tds Ads Tds mCds Tds
       Ads Ads Ads Gds Ads mCeo mCeo Ges mCes
       Ae (SEQ ID NO: 222); wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 68. An oligomeric compound comprising a modified oligonucleotide according to the following formula:

Tes mCeo Aeo mCeo mCes Ads mCds Ads Ads Ads
       mCds Tds mCds Ads Tds Geo Geo Aes mCes
       Te (SEQ ID NO: 888); wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 69. An oligomeric compound comprising a modified oligonucleotide according to the following formula:

Aes mCeo mCeo mCeo Tes Tds Tds mCds mCds
       Ads Tds Gds Tds Gds Ads Aeo mCeo Aes Tes
       Te (SEQ ID NO: 1431); wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 70. An oligomeric compound comprising a modified oligonucleotide according to the following formula:

Aes mCeo Geo mCeo Aes mCds Tds Tds Ads Ads
       mCds Ads Ads Tds Ads Teo mCeo Aes Tes Ae
       (SEQ ID NO: 3590); wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 71. An oligomeric compound comprising a modified oligonucleotide according to the following formula: Aes Geo mCeo Aeo Aes Tds mCds Ads Tds Tds Gds Gds Tds Ads Gds mCeo Aeo Tes Aes mCe (SEQ ID NO: 3385); wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 72. An oligomeric compound comprising a modified oligonucleotide according to the following formula: mCes Geo mCes Aes mCes Tds Tds Ads Ads mCds Ads Ads Tds Ads Tds mCes Aeo Tes Aes Te (SEQ ID NO: 852); wherein, A=an adenine nucleobase,
mC=a 5-methyl cytosine nucleobase,
G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.

Embodiment 73. The oligomeric compound of embodiment 3, wherein the modified oligonucleotide is an RNAi compound.

Embodiment 74. The oligomeric compound of embodiment 73, wherein the RNAi compound is an ssRNA or an siRNA.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt"), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O- 2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

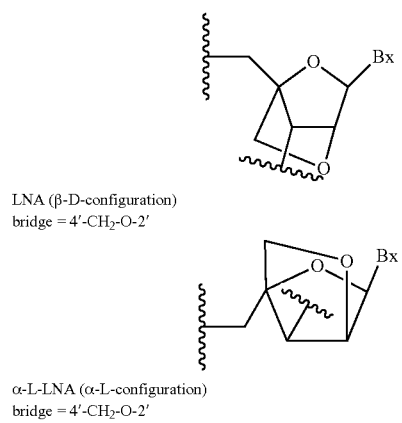

LNA (β-D-configuration)
bridge = 4'-CH$_2$-O-2'

α-L-LNA (α-L-configuration)
bridge = 4'-CH$_2$-O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

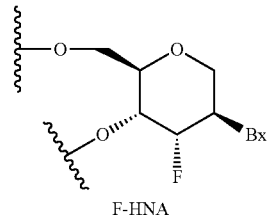

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

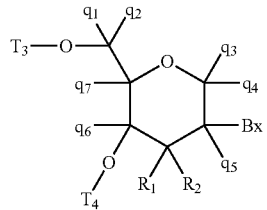

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

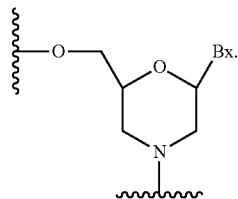

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp) Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

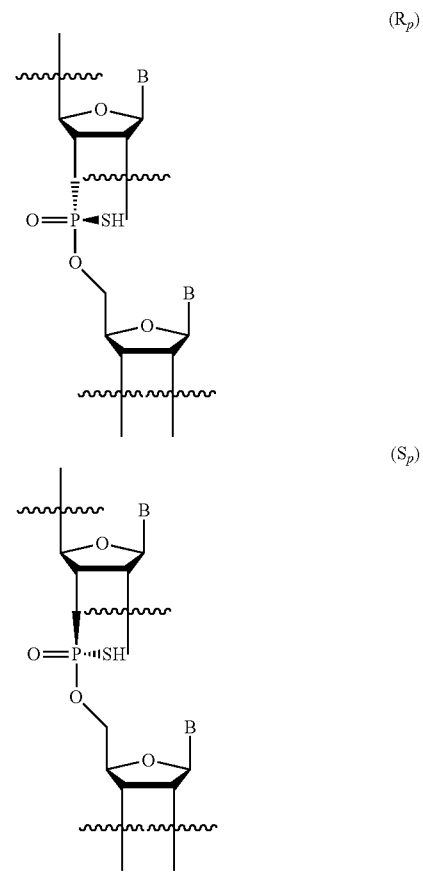

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxy nucleoside. In certain embodiments, at least one nucleoside of the gap of a gapmer is a modified nucleoside.

In certain embodiments, the gapmer is a deoxy gapmer. In certain embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phophate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal V. Certain Target Nucleic Acids In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the mRNA to reduce the expression of both bcl-2 and in vitro and in vivo. Furthermore, this oligonucleotide demonstrated potent antitumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved.

In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. LRRK2

In certain embodiments, oligomeric compounds comprise or consist of an oligonucleotide comprising a region that is complementary to a target nucleic acid, wherein the target nucleic acid is LRRK2. In certain embodiments, LRRK2 nucleic acid has the sequence set forth in SEQ ID NO: 1 (GENBANK Accession No: NM_198578.3) and SEQ ID NO: 2 (GENBANK Accession No: NT_029419.11 truncated from nucleotides 2759000 to 2909000).

In certain embodiments, contacting a cell with an oligomeric compound complementary to SEQ ID NO: 1 or SEQ ID NO: 2 reduces the amount of LRRK2 RNA, and in certain embodiments reduces the amount of LRRK2 protein. In certain embodiments, the oligomeric compound consists of a modified oligonucleotide. In certain embodiments, contacting a cell with an oligomeric compound complementary to SEQ ID NO: 1 or SEQ ID NO: 2 ameliorates one or more symptom or hallmark of a neurodegenerative disease. In certain embodiments, the oligomeric compound consists of a modified oligonucleotide. In certain embodiments, the symptom or hallmark is ataxia, neuropathy, and aggregate formation. In certain embodiments, contacting a cell with a modified oligonucleotide complementary to SEQ ID NO: 1 or SEQ ID NO: 2 results in improved motor function, reduced neuropathy, and reduction in number of aggregates. In certain embodiments, the oligomeric compound consists of a modified oligonucleotide C. Certain Target Nucleic Acids in Certain Tissues In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such tissues include brain tissues, such as, cortex, substantia nigra, striatum, midbrain, and brainstem and spinal cord.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, in ionized (anion) form, or ionized and in association with a cation (salt) form, aqueous solutions of such compounds exist in equilibrium among such forms. For example, a phosphate linkage of an oligonucleotide in aqueous solution exists in equilibrium among free acid, anion, and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or salts thereof" expressly includes all such forms that may be fully or partially protonated/de-protonated/in association with a cation. In certain instances, one or more specific cation is identified.

In certain embodiments, oligomeric compounds disclosed herein are in aqueous solution with sodium. In certain embodiments, oligomeric compounds are in aqueous solution with potassium. In certain embodiments, oligomeric compounds are in acritical CSF. In certain embodiments, oligomeric compounds are in PBS. In certain embodiments, oligomeric compounds are in water. In certain such embodiments, the pH of the solution is adjusted with NaOH and/or HCl to achieve a desired pH.

VII. Certain Compositions

1. Compound No: 780241 Compound No: 780241 may be characterized as a 5-10-5 MOE gapmer having a sequence of (from 5' to 3') GCTCATATCTAAAGACCGCA (incorporated herein as SEQ ID NO: 222), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 780241 may be characterized by the following chemical notation: Ges mCeo Teo mCeo Aes Tds Ads Tds mCds Tds Ads Ads Ads Gds Ads mCeo mCeo Ges mCes Ae; wherein, A=an adenine nucleobase, mC=a 5-methyl cytosine nucleobase, G=a guanine nucleobase, T=a thymine nucleobase, e=a 2'-MOE modified sugar, d=a 2'-deoxyribose sugar, s=a phosphorothioate internucleoside linkage, and o=a phosphodiester internucleoside linkage.

Compound No: 780241 may be represented by the following chemical structure:
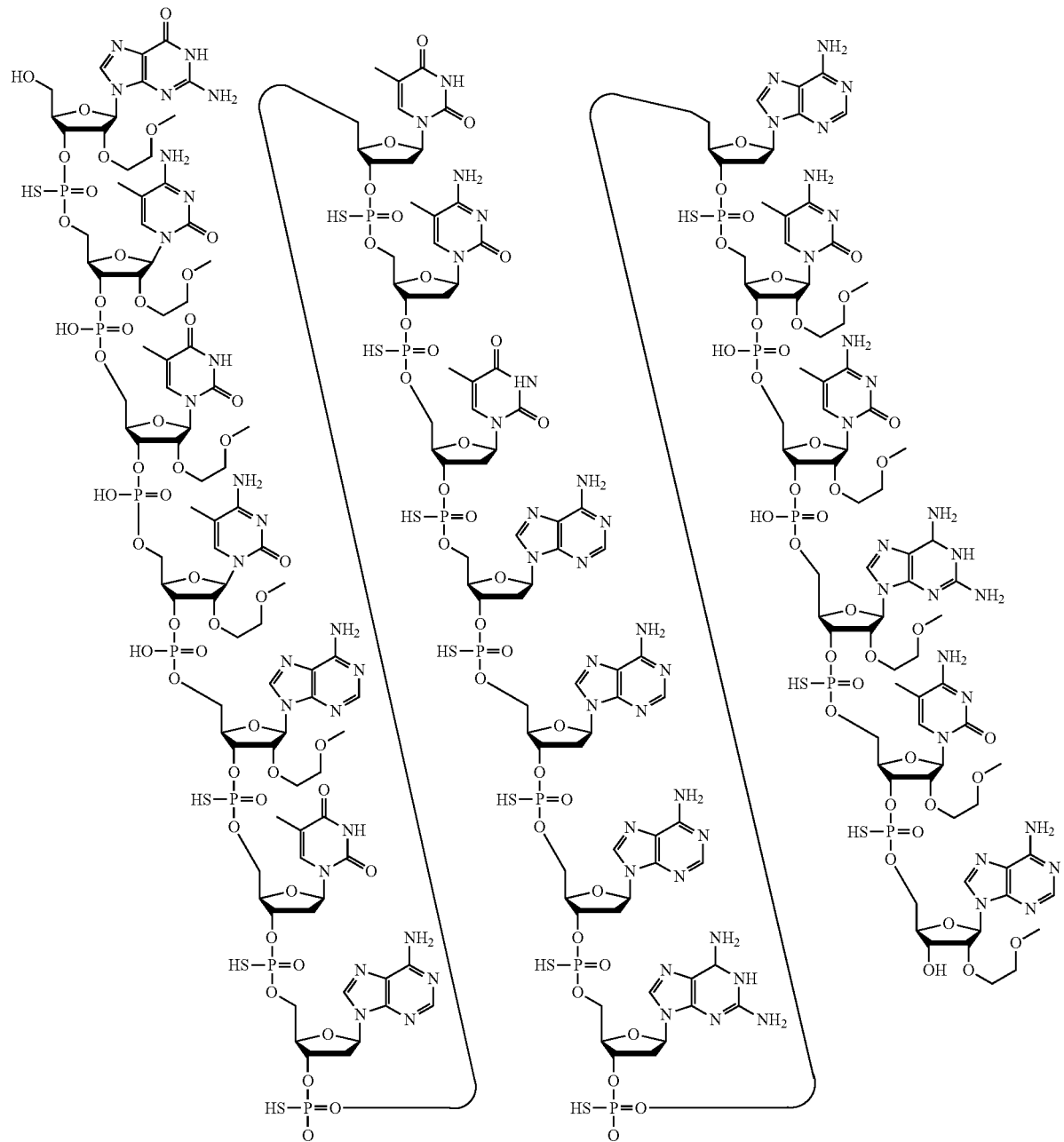

Structure 1. Compound No: 780241 (SEQ ID NO: 222).

Compound No: 780241 may be represented by the following chemical structure:

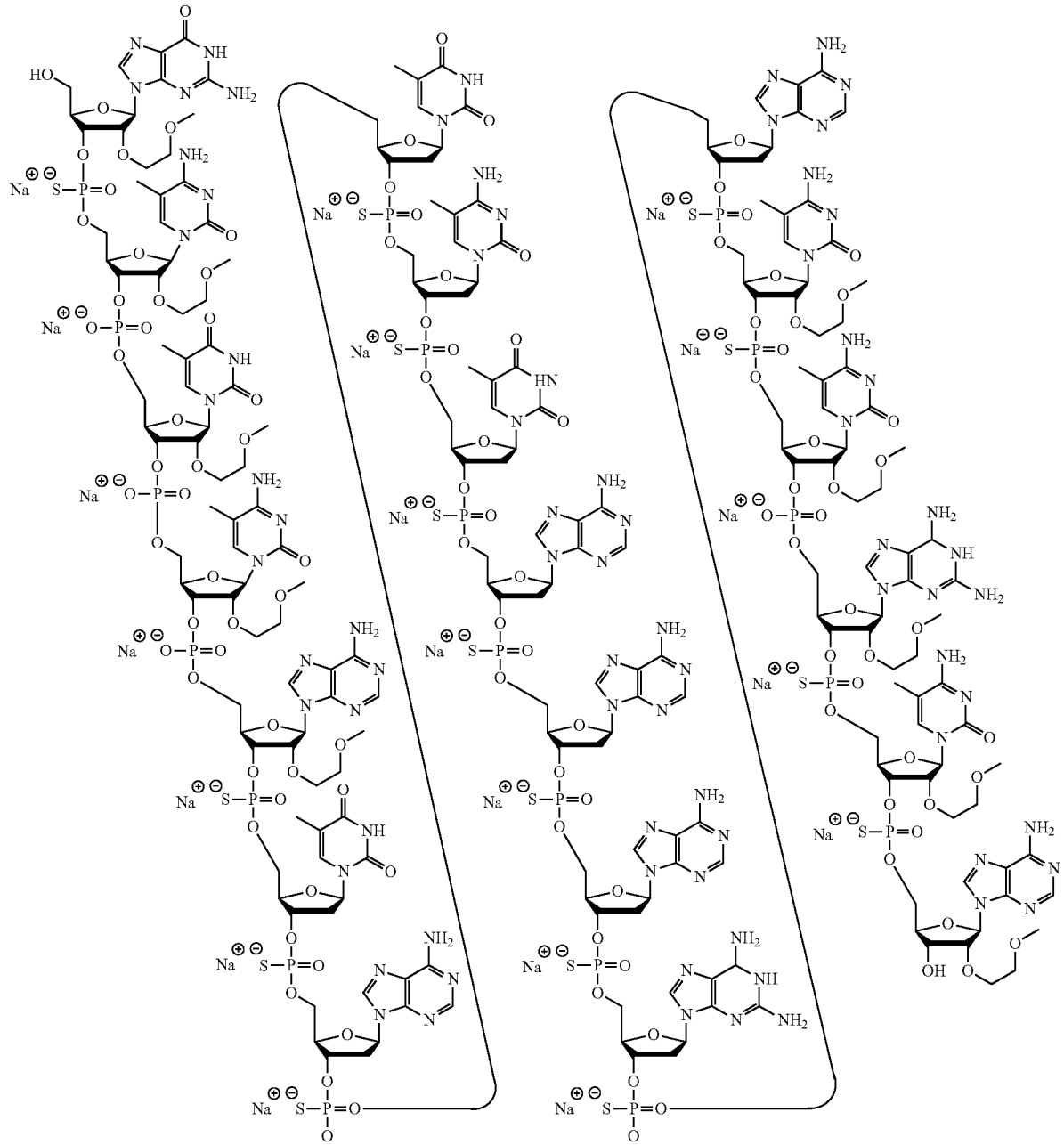

Structure 2. The Sodium salt of Compound No: 780241 (SEQ ID NO: 222).

2. Compound No: 802714

Compound No: 802714 may be characterized as a 5-10-5 MOE gapmer, having a sequence of (from 5' to 3') TCAC-CACAAACTCATGGACT (incorporated herein as SEQ ID NO: 888), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 802714 may be characterized by the following chemical notation: Tes mCeo Aeo mCeo mCes Ads mCds Ads Ads Ads mCds Tds mCds Ads Tds Geo Geo Aes mCes Te; wherein,
  A=an adenine nucleobase,
  mC=a 5-methyl cytosine nucleobase,
  G=a guanine nucleobase,
  T=a thymine nucleobase,
  e=a 2'-MOE modified sugar,
  d=a 2'-deoxyribose sugar,
  s=a phosphorothioate internucleoside linkage, and
  o=a phosphodiester internucleoside linkage.

Compound No: 802714 may be represented by the following chemical structure:

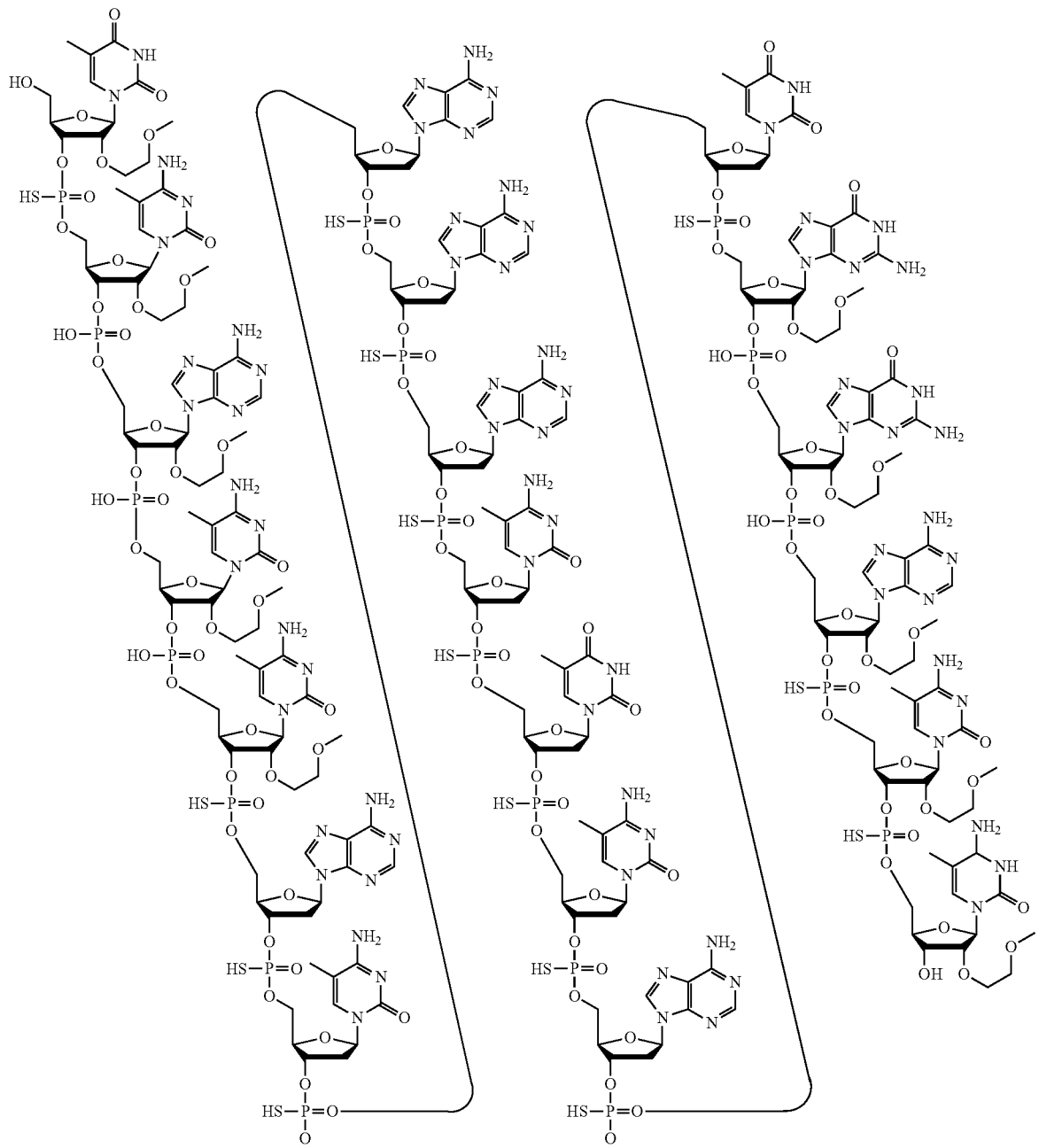

Structure 3. Compound No: 802714 (SEQ ID NO: 888).

Compound No: 802714 may be represented by the following chemical structure:

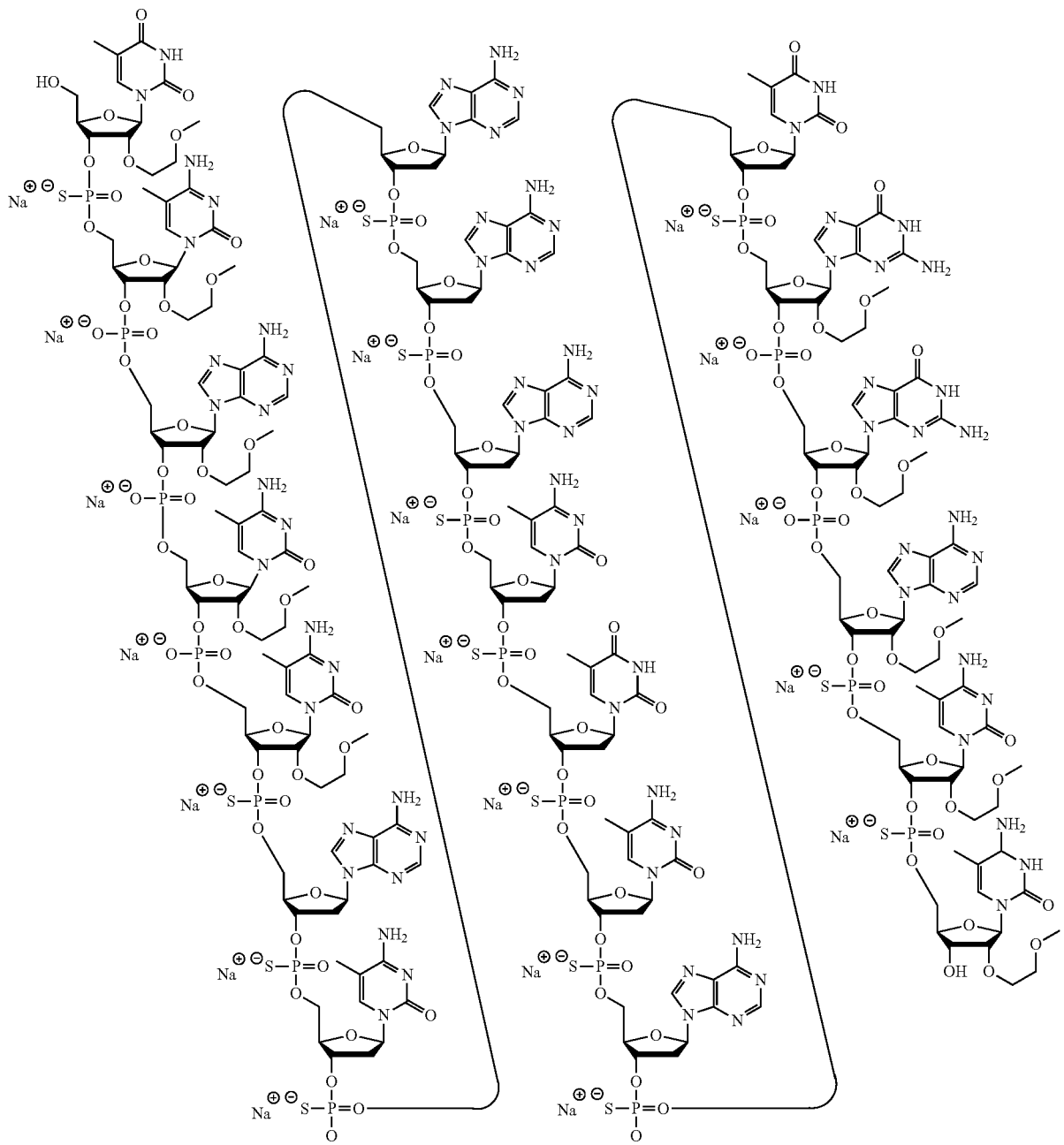

Structure 4. The Sodium salt of Compound No: 802714 (SEQ ID NO: 888).

3. Compound No: 803268

Compound No: 803268 may be characterized as a 5-10-5 MOE gapmer, having a sequence of (from 5' to 3') ACCCTTTCCATGTGAACATT (incorporated herein as SEQ ID NO: 1431), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 803268 may be characterized by the following chemical notation: Aes mCeo mCeo mCeo Tes Tds Tds mCds mCds Ads Tds Gds Tds Gds Ads Aeo mCeo Aes Tes Te; wherein, A=an adenine nucleobase, mC=a 5-methyl cytosine nucleobase, G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.
Compound No: 803268 may be represented by the following chemical structure:
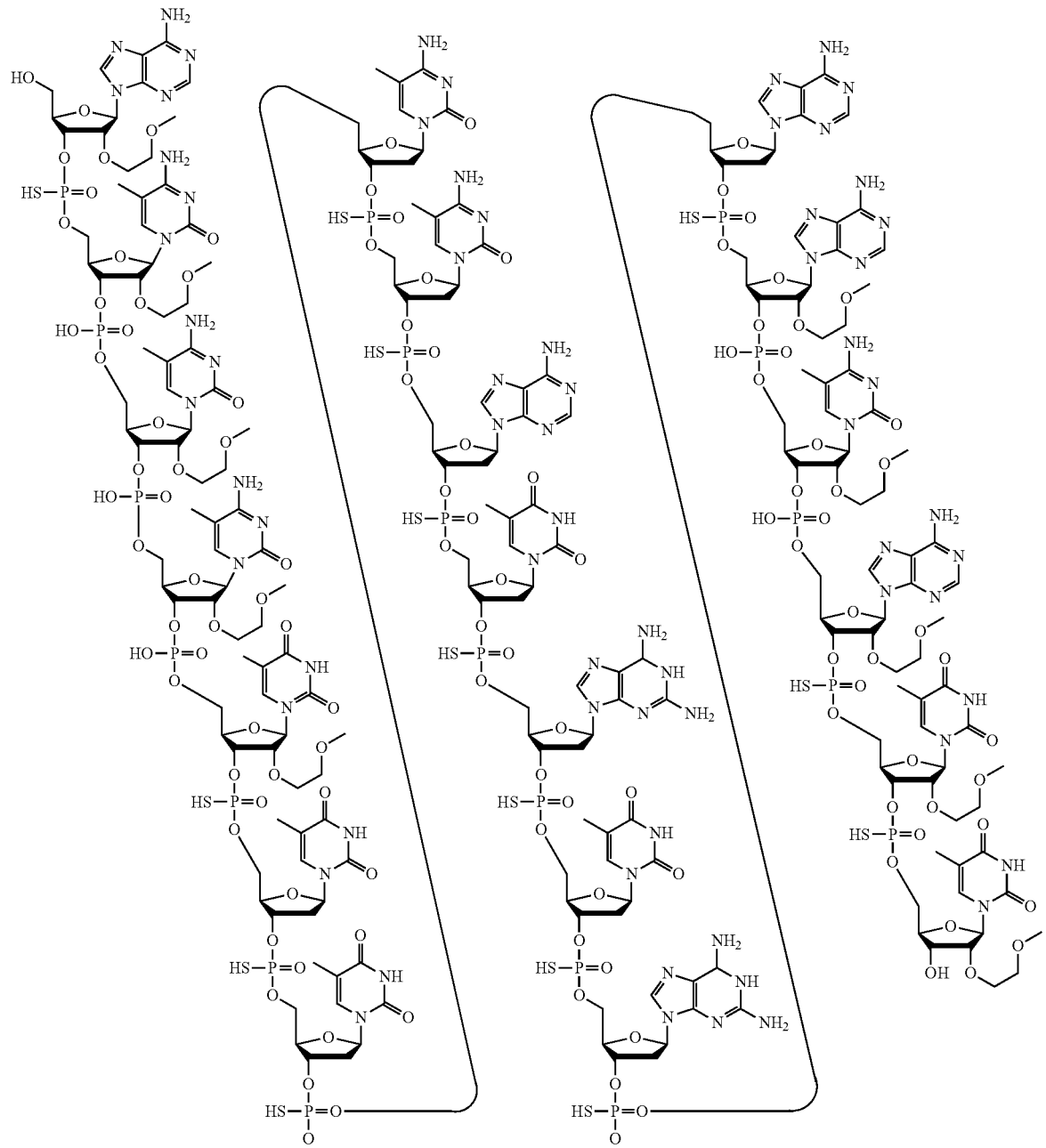

Structure 5. Compound No: 803268 (SEQ ID NO: 1431).

Compound No: 803268 may be represented by the following chemical structure:

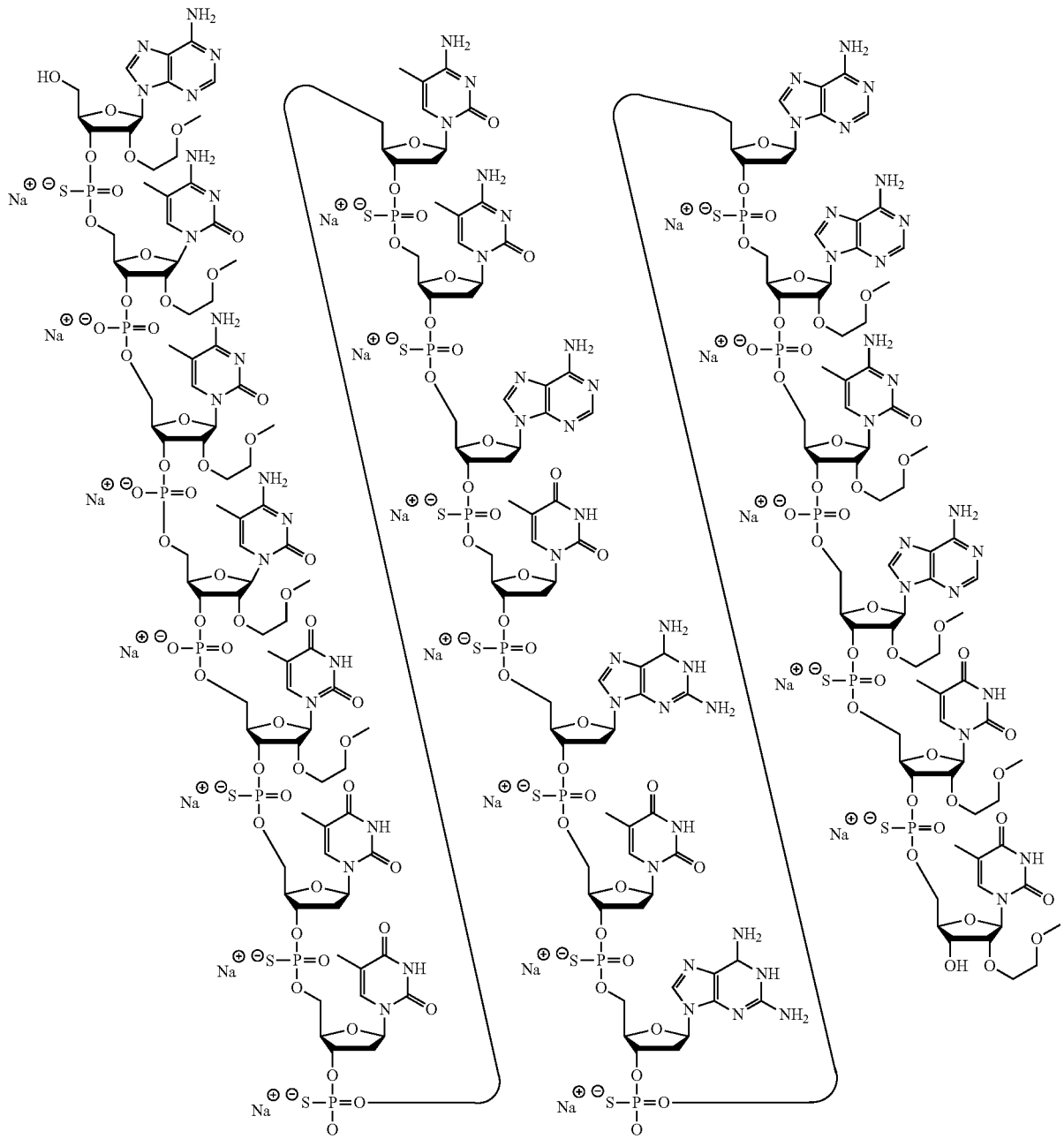

Structure 6. The Sodium salt of Compound No: 803268 (SEQ ID NO: 1431).

4. Compound No: 876031

Compound No: 876031 may be characterized as a 5-10-5 MOE gapmer, having a sequence of (from 5' to 3') ACGCACTTAACAATATCATA (incorporated herein as SEQ ID NO: 3590), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 876031 may be characterized by the following chemical notation: Aes mCeo Geo mCeo Aes mCds Tds Tds Ads Ads mCds Ads Ads Tds Ads Teo mCeo Aes Tes Ae; wherein, A=an adenine nucleobase, mC=a 5-methyl cytosine nucleobase, G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.
Compound No: 876031 may be represented by the following chemical structure:
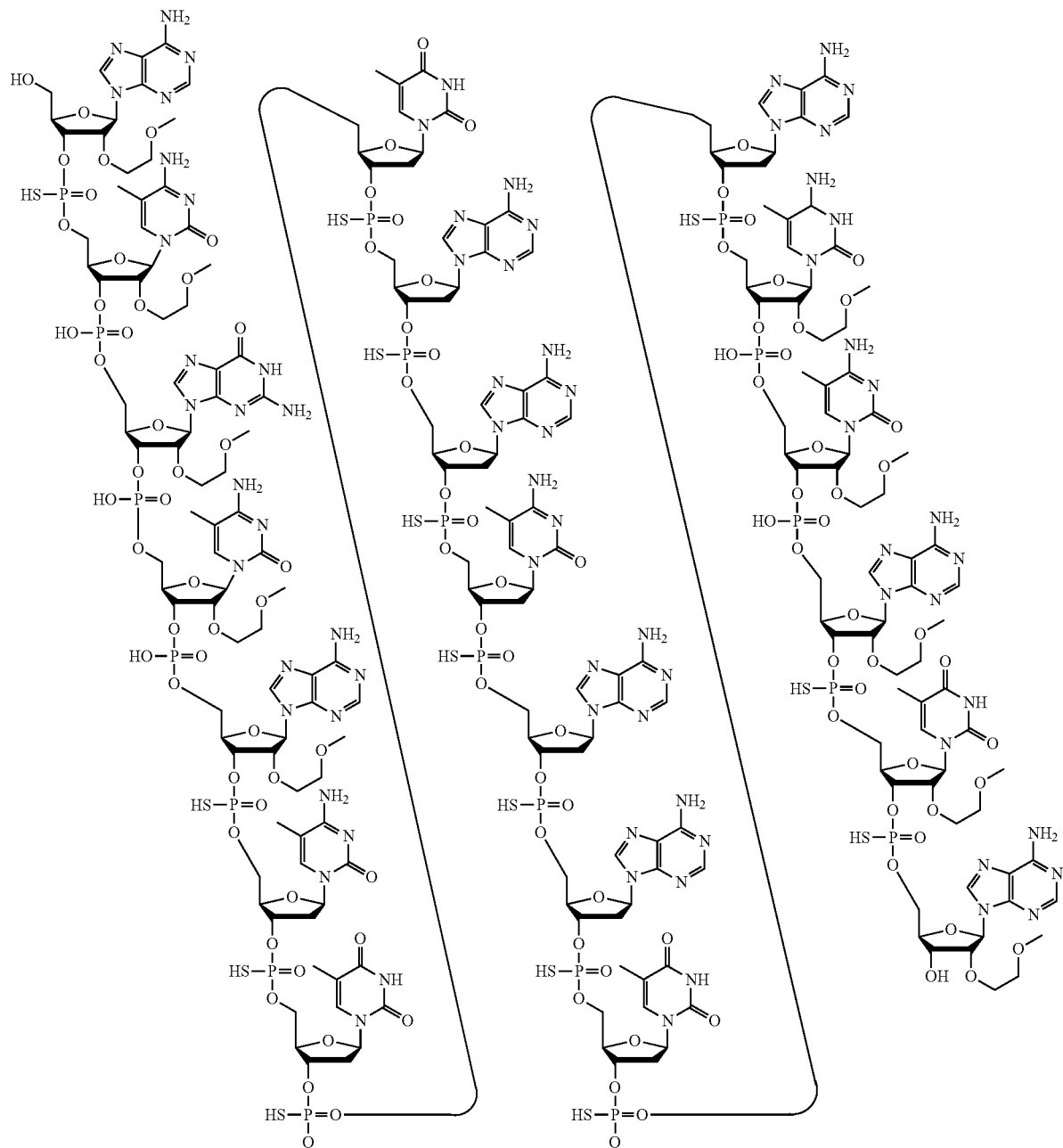

Structure 7. Compound No: 876031 (SEQ ID NO: 3590).

Compound No: 876031 may be represented by the following chemical structure:

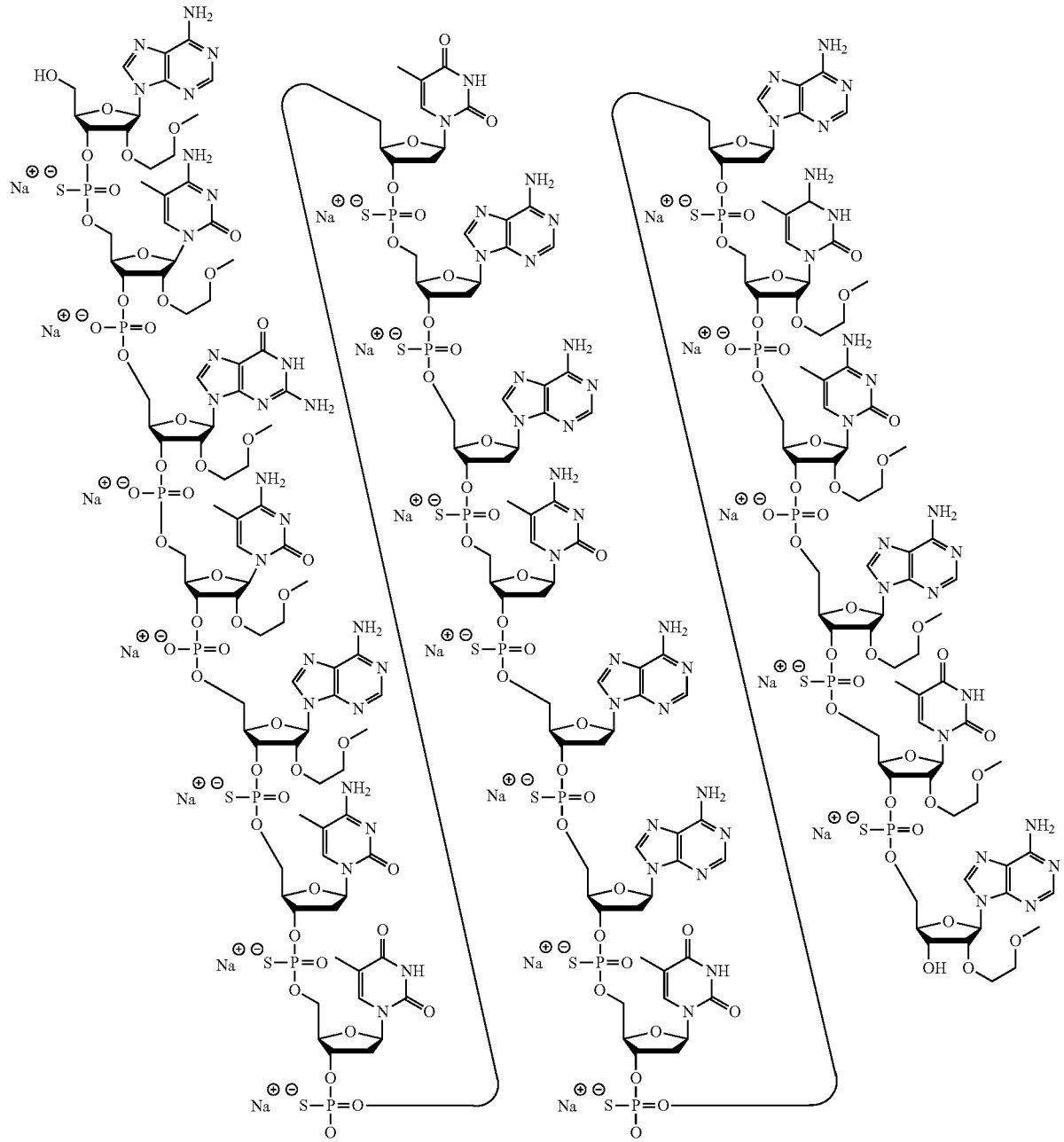

Structure 8. The Sodium salt of Compound No: 876031 (SEQ ID NO: 3590).

5. Compound No: 876604

Compound No: 876604 may be characterized as a 5-10-5 MOE gapmer, having a sequence of (from 5' to 3') AGCAATCATTGGTAGCATAC (incorporated herein as SEQ ID NO: 3385), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methyl cytosine.

Compound No: 876604 may be characterized by the following chemical notation: Aes Geo mCeo Aeo Aes Tds mCds Ads Tds Tds Gds Gds Tds Ads Gds mCeo Aeo Tes Aes mCe; wherein, A=an adenine nucleobase, mC=a 5-methyl cytosine nucleobase, G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.
Compound No: 876604 may be represented by the following chemical structure:
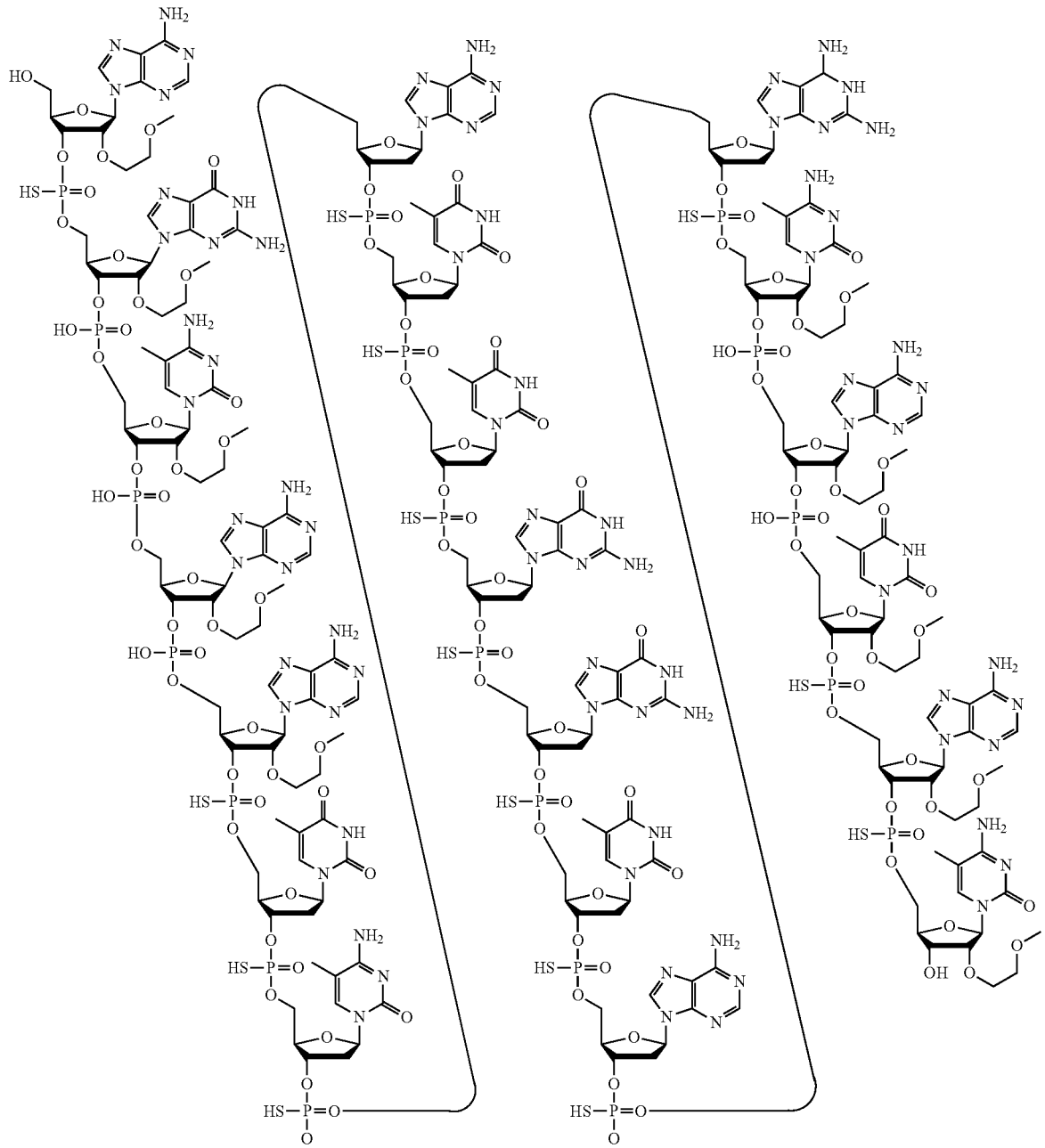

Structure 8. Compound No: 876604 (SEQ ID NO: 3385).

Compound No: 876604 may be represented by the following chemical structure:

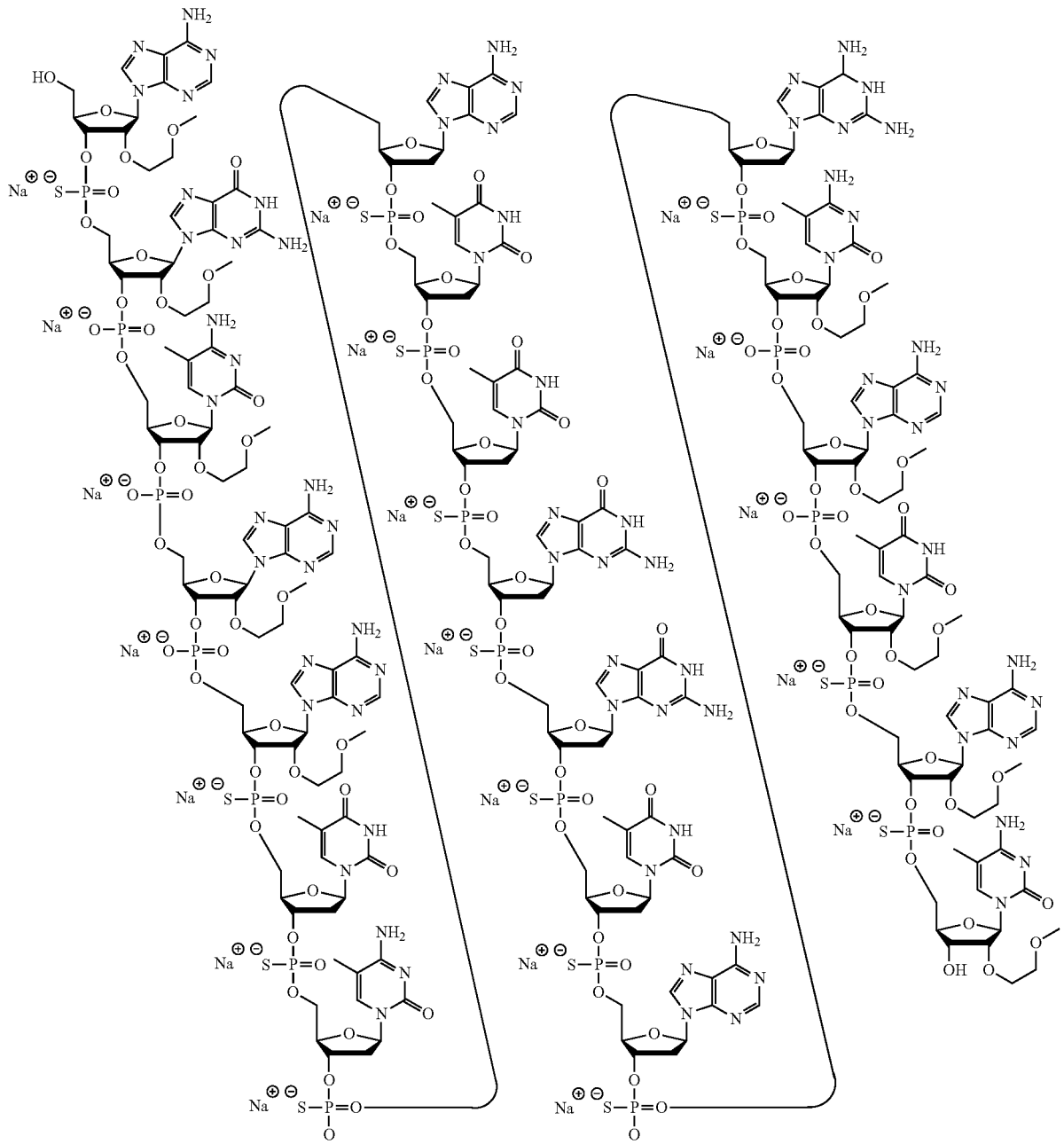

Structure 10. The Sodium Salt of Compound No: 876604 (SEQ ID NO: 3385).

6. Compound No: 934556

Compound No: 934556 may be characterized as a 5-10-5 MOE gapmer, having a sequence of (from 5' to 3') CGCACTTAACAATATCATAT (incorporated herein as SEQ ID NO: 852), wherein each of nucleosides 1-5 and 16-20 (from 5' to 3') comprise a 2'-MOE modification and each of nucleosides 6-15 are 2'-deoxynucleosides, wherein the internucleoside linkages between nucleosides 2 to 3 and 17 to 18 are phosphodiester internucleoside linkages and the internucleoside linkages between nucleosides 1 to 2, 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methyl cytosine.

Compound No: 934556 may be characterized by the following chemical notation: mCes Geo mCes Aes mCes Tds Tds Ads Ads mCds Ads Ads Tds Ads Tds mCes Aeo Tes Aes Te; wherein, A=an adenine nucleobase, mC=a 5-methyl cytosine nucleobase, G=a guanine nucleobase,
T=a thymine nucleobase,
e=a 2'-MOE modified sugar,
d=a 2'-deoxyribose sugar,
s=a phosphorothioate internucleoside linkage, and
o=a phosphodiester internucleoside linkage.
Compound No: 934556 may be represented by the following chemical structure:
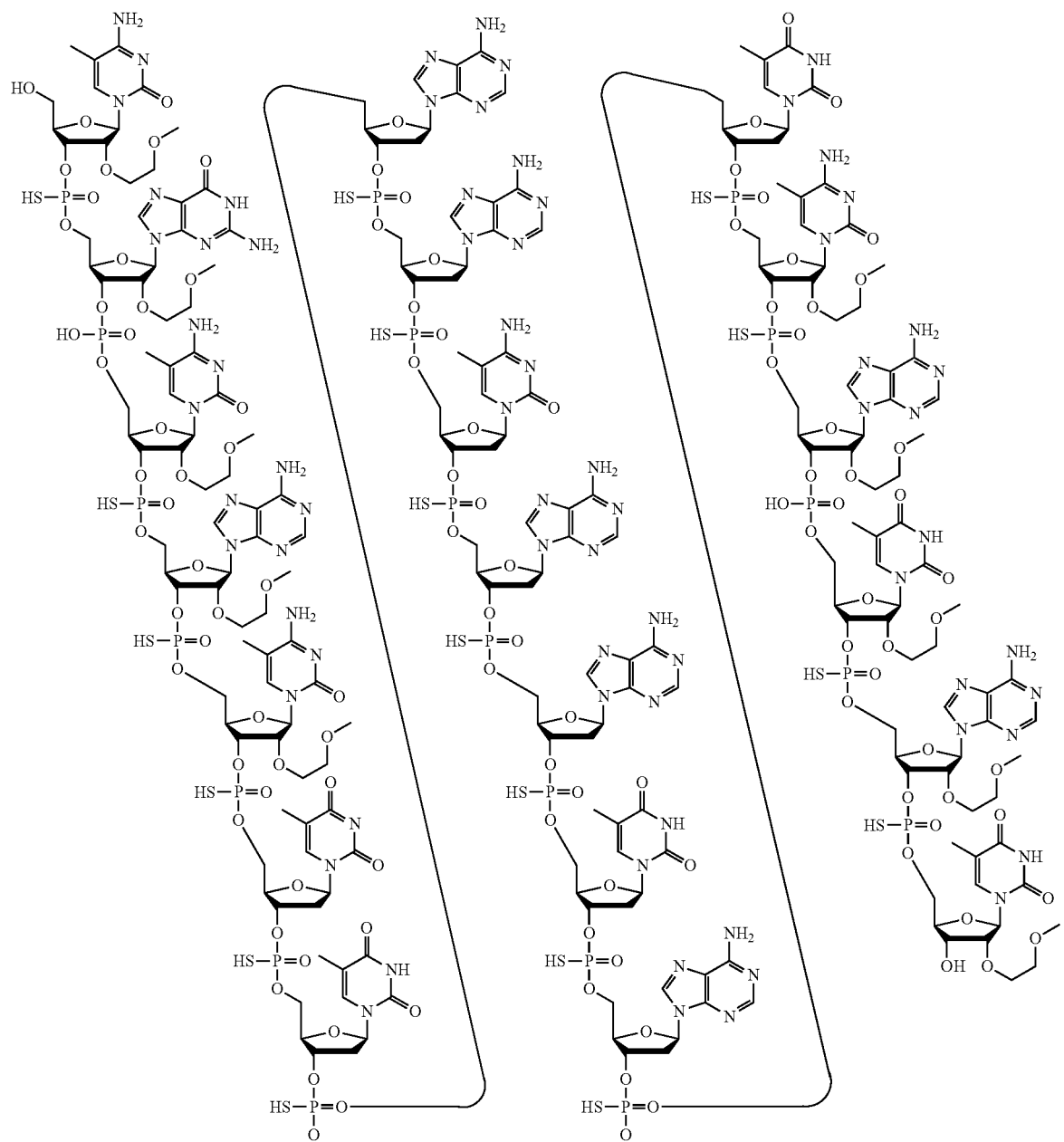

Structure 11. Compound No: 934556 (SEQ ID NO: 852).
Compound No: 934556 may be represented by the following chemical structure:

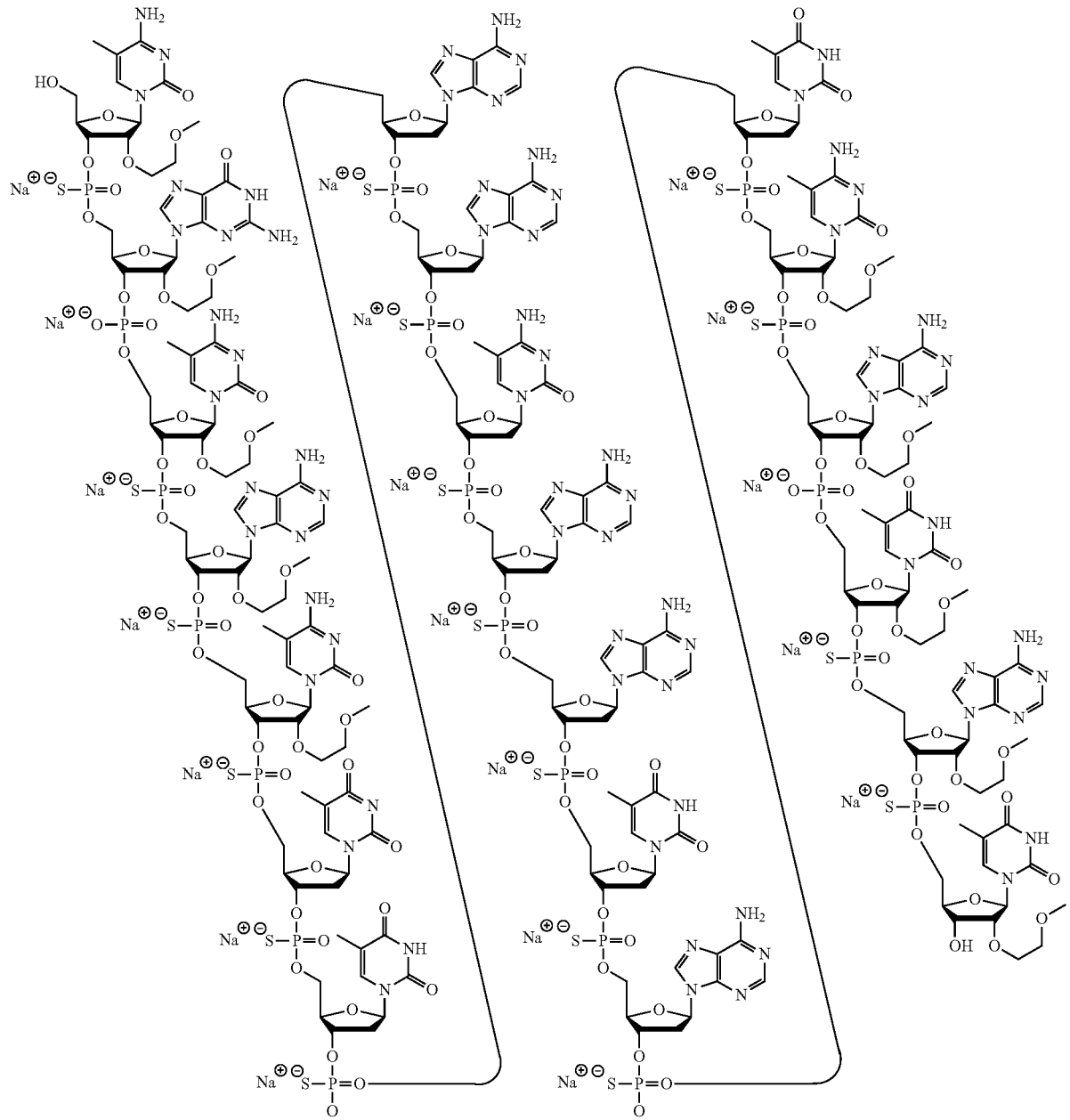

Structure 12. The Sodium salt of Compound No: 934556 (SEQ ID NO: 852).

VIII. Certain Hotspot Regions
1. Nucleobases 18,633-18,658 of SEQ ID NO: 2

In certain embodiments, nucleobases 18,633-18,658 of SEQ ID NO: 2 comprise a hotspot region. In certain embodiments, siRNAs are complementary to nucleobases 18,633-18,658 of SEQ ID NO: 2. In certain embodiments, modified oligonucleotides are complementary to nucleobases 18,633-18,658 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssooss.

The nucleobase sequences of SEQ ID Nos: 852, 1997, 2073, 2148, 3513, and 3590 are complementary to nucleobases 18,633-18,658 of SEQ ID NO: 2.

In certain embodiments, modified oligonucleotides complementary to nucleobases 18,633-18,658 of SEQ ID NO: 2 achieve at least 54% reduction of LRRK2 RNA in vitro in at least one single dose assay.

2. Nucleobases 21,721-21,755 of SEQ ID NO: 2

In certain embodiments, nucleobases 21,721-21,755 of SEQ ID NO: 2 comprise a hotspot region. In certain embodiments, siRNAs are complementary to nucleobases 21,721-21,755 of SEQ ID NO: 2. In certain embodiments, modified oligonucleotides are complementary to nucleobases 21,721-21,755 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooosssssssssssooss.

The nucleobase sequences of SEQ ID Nos: 291, 869, 870, 871, 872, 873, 874, 875, 876, 877, 878, 879, and 880 are complementary to nucleobases 21,721-21,755 of SEQ ID NO: 2.

In certain embodiments, modified oligonucleotides complementary to nucleobases 21,721-21,755 of SEQ ID NO: 2 achieve at least 52% reduction of LRRK2 RNA in vitro in at least one single dose assay.

3. Nucleobases 27,963-28,016 of SEQ ID NO: 2

In certain embodiments, nucleobases 27,963-28,016 of SEQ ID NO: 2 comprise a hotspot region. In certain embodiments, siRNAs are complementary to nucleobases 27,963-28,016 of SEQ ID NO: 2. In certain embodiments, modified oligonucleotides are complementary to nucleobases 27,963-28,016 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 293, 886, 887, 888, 889, 890, 891, 892, 893, and 3745 are complementary to nucleobases 27,963-28,016 of SEQ ID NO: 2.

In certain embodiments, modified oligonucleotides complementary to nucleobases 27,963-28,016 of SEQ ID NO: 2 achieve at least 39% reduction of LRRK2 RNA in vitro in at least one single dose assay.

4. Nucleobases 35,415-35,446 of SEQ ID NO: 2

In certain embodiments, nucleobases 35,415-35,446 of SEQ ID NO: 2 comprise a hotspot region. In certain embodiments, siRNAs are complementary to nucleobases 35,415-35,446 of SEQ ID NO: 2. In certain embodiments, modified oligonucleotides are complementary to nucleobases 35,415-35,446 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooosssssssssssooss.

The nucleobase sequences of SEQ ID Nos: 920, 921, 2378, 2454, 2530, 2606, 2683, 2759, 2835, 3061, 3137, 3212, and 3288 are complementary to nucleobases 35,415-35,446 of SEQ ID NO: 2.

In certain embodiments, modified oligonucleotides complementary to nucleobases 35,415-35,446 of SEQ ID NO: 2 achieve at least 42% reduction of LRRK2 RNA in vitro in at least one single dose assay.

5. Nucleobases 77,221-77,264 of SEQ ID NO: 2

In certain embodiments, nucleobases 77,221-77,264 of SEQ ID NO: 2 comprise a hotspot region. In certain embodiments, siRNAs are complementary to nucleobases 77,221-77,264 of SEQ ID NO: 2. In certain embodiments, modified oligonucleotides are complementary to nucleobases 77,221-77,264 of SEQ ID NO: 2. In certain embodiments, modified oligonucleotides are 20 nucleobases in length. In certain embodiments, modified oligonucleotides are gapmers.

In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 131, 217, 1106, 1107, and 1108 are complementary to nucleobases 77,221-77,264 of SEQ ID NO: 2.

In certain embodiments, modified oligonucleotides complementary to nucleobases 77,221-77,264 of SEQ ID NO: 2 achieve at least 51% reduction of LRRK2 RNA in vitro in at least one single dose assay.

6. Nucleobases 81,581-81,612 and 87,838-87,869 of SEQ ID NO: 2

In certain embodiments, nucleobases 81,581-81,612 and 87,838-87,869 of SEQ ID NO: 2 comprise a hotspot region. In certain embodiments, siRNAs are complementary to nucleobases 81,581-81,612 and 87,838-87,869 of SEQ ID NO: 2. In certain embodiments, modified oligonucleotides are complementary to nucleobases 81,581-81,612 and 87,838-87,869 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooosssssssssssooss.

The nucleobase sequences of SEQ ID Nos: 667, 668, 669, 670, 671, 1785, 1786, 1787, 1788, 1789, 1790, 1791, and 1792 are complementary to nucleobases 81,581-81,612 and 87,838-87,869 of SEQ ID NO: 2.

In certain embodiments, modified oligonucleotides complementary to nucleobases 81,581-81,612 and 87,838-87,869 of SEQ ID NO: 2 achieve at least 38% reduction of LRRK2 RNA in vitro in at least one single dose assay.

7. Nucleobases 81,627-81,651 of SEQ ID NO: 2

In certain embodiments, nucleobases 81,627-81,651 of SEQ ID NO: 2 comprise a hotspot region. In certain embodiments, siRNAs are complementary to nucleobases 81,627-81,651 of SEQ ID NO: 2. In certain embodiments, modified oligonucleotides are complementary to nucleobases 81,627-81,651 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 674, 1799, 1800, 1801, 1802, and 1803 are complementary to nucleobases 81,627-81,651 of SEQ ID NO: 2.

In certain embodiments, modified oligonucleotides complementary to nucleobases 81,627-81,651 of SEQ ID NO: 2 achieve at least 66% reduction of LRRK2 RNA in vitro in at least one single dose assay.

8. Nucleobases 82,058-82,081 of SEQ ID NO: 2

In certain embodiments, nucleobases 82,058-82,081 of SEQ ID NO: 2 comprise a hotspot region. In certain embodiments, siRNAs are complementary to nucleobases 82,058-82,081 of SEQ ID NO: 2. In certain embodiments, modified oligonucleotides are complementary to nucleobases 82,058-82,081 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 222, 1130, 1131, 1132, and 1133 are complementary to nucleobases 82,058-82,081 of SEQ ID NO: 2.

In certain embodiments, modified oligonucleotides complementary to nucleobases 82,058-82,081 of SEQ ID NO: 2 achieve at least 53% reduction of LRRK2 RNA in vitro in at least one single dose assay.

9. Nucleobases 82,180-82,220 of SEQ ID NO: 2

In certain embodiments, nucleobases 82,180-82,220 of SEQ ID NO: 2 comprise a hotspot region. In certain embodiments, siRNAs are complementary to nucleobases 82,180-82,220 of SEQ ID NO: 2. In certain embodiments, modified oligonucleotides are complementary to nucleobases 82,180-82,220 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 225, 1145, 2005, 2840, 3369, 3446, 3521, 3598, and 3674 are complementary to nucleobases 82,180-82,220 of SEQ ID NO: 2.

In certain embodiments, modified oligonucleotides complementary to nucleobases 82,180-82,220 of SEQ ID NO: 2 achieve at least 64% reduction of LRRK2 RNA in vitro in at least one single dose assay.

10. Nucleobases 82,500-82,525 of SEQ ID NO: 2

In certain embodiments, nucleobases 82,500-82,525 of SEQ ID NO: 2 comprise a hotspot region. In certain embodiments, siRNAs are complementary to nucleobases 82,500-82,525 of SEQ ID NO: 2. In certain embodiments, modified oligonucleotides are complementary to nucleobases 82,500-82,525 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 439, 1807, 1808, 1809, 1810, 1811, and 1812 are complementary to nucleobases 82,500-82,525 of SEQ ID NO: 2.

In certain embodiments, modified oligonucleotides complementary to nucleobases 82,500-82,525 of SEQ ID NO: 2 achieve at least 49% reduction of LRRK2 RNA in vitro in at least one single dose assay.

11. Nucleobases 91,038-91,067 of SEQ ID NO: 2

In certain embodiments, nucleobases 91,038-91,067 of SEQ ID NO: 2 comprise a hotspot region. In certain embodiments, siRNAs are complementary to nucleobases 91,038-91,067 of SEQ ID NO: 2. In certain embodiments, modified oligonucleotides are complementary to nucleobases 91,038-91,067 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 692, 1826, 1827, 1828, 1829, 1830, 1831, 1832, 1833, 1834, and 1835 are complementary to nucleobases 91,038-91,067 of SEQ ID NO: 2.

The modified oligonucleotides of Compound Nos: 780642, 803664, 803665, 803666, 803667, 803668, 803669, 803670, 803671, 803672, and 803673 are complementary to nucleobases 91,038-91,067 of SEQ ID NO: 2.

In certain embodiments, modified oligonucleotides complementary to nucleobases 91,038-91,067 of SEQ ID NO: 2 achieve at least 42% reduction of LRRK2 RNA in vitro in at least one single dose assay.

12. Nucleobases 92,148-92,173 of SEQ ID NO: 2

In certain embodiments, nucleobases 92,148-92,173 of SEQ ID NO: 2 comprise a hotspot region. In certain embodiments, siRNAs are complementary to nucleobases 92,148-92,173 of SEQ ID NO: 2. In certain embodiments, modified oligonucleotides are complementary to nucleobases 92,148-92,173 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 1213, 2613, 2690, 3143, 3219, and 3295 are complementary to nucleobases 92,148-92,173 of SEQ ID NO: 2.

In certain embodiments, modified oligonucleotides complementary to nucleobases 92,148-92,173 of SEQ ID NO: 2 achieve at least 59% reduction of LRRK2 RNA in vitro in at least one single dose assay.

13. Nucleobases 98,186-98,220 of SEQ ID NO: 2

In certain embodiments, nucleobases 98,186-98,220 of SEQ ID NO: 2 comprise a hotspot region. In certain embodiments, siRNAs are complementary to nucleobases 98,186-98,220 of SEQ ID NO: 2. In certain embodiments, modified oligonucleotides are complementary to nucleobases 98,186-98,220 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 1231, 1232, 2462, 2538, 2614, 2691, 2767, 3069, 3144, 3220, 3296 are complementary to nucleobases 98,186-98,220 of SEQ ID NO: 2.

In certain embodiments, modified oligonucleotides complementary to nucleobases 98,186-98,220 of SEQ ID NO: 2 achieve at least 55% reduction of LRRK2 RNA in vitro in at least one single dose assay.

14. Nucleobases 98,218-98,242 of SEQ ID NO: 2

In certain embodiments, nucleobases 98,218-98,242 of SEQ ID NO: 2 comprise a hotspot region. In certain embodiments, siRNAs are complementary to nucleobases 98,218-98,242 of SEQ ID NO: 2. In certain embodiments, modified oligonucleotides are complementary to nucleobases 98,218-98,242 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 150, 1233, 2008, 3372, 3449, and 3524 are complementary to nucleobases 98,218-98,242 of SEQ ID NO: 2.

In certain embodiments, modified oligonucleotides complementary to nucleobases 98,218-98,242 of SEQ ID NO: 2 achieve at least 38% reduction of LRRK2 RNA in vitro in at least one single dose assay.

15. Nucleobases 99,199-99,223 of SEQ ID NO: 2

In certain embodiments, nucleobases 99,199-99,223 of SEQ ID NO: 2 comprise a hotspot region. In certain embodiments, siRNAs are complementary to nucleobases 99,199-99,223 of SEQ ID NO: 2. In certain embodiments, modified oligonucleotides are complementary to nucleobases 99,199-99,223 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 1243, 2311, 2387, 2920, 2995, and 3755 are complementary to nucleobases 99,199-99,223 of SEQ ID NO: 2.

In certain embodiments, modified oligonucleotides complementary to nucleobases 99,199-99,223 of SEQ ID NO: 2 achieve at least 52% reduction of LRRK2 RNA in vitro in at least one single dose assay.

16. Nucleobases 119,903-119,936 of SEQ ID NO: 2

In certain embodiments, nucleobases 119,903-119,936 of SEQ ID NO: 2 comprise a hotspot region. In certain embodiments, siRNAs are complementary to nucleobases 119,903-119,936 of SEQ ID NO: 2. In certain embodiments, modified oligonucleotides are complementary to nucleobases 119,903-119,936 of SEQ ID NO: 2. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 750, 1927, 1928, 1929, 1930, 1931, 1932, 1933, 1934, 1935, 2822, 2898, 3351, and 3733 are complementary to nucleobases 119,903-119,936 of SEQ ID NO: 2.

In certain embodiments, modified oligonucleotides complementary to nucleobases 119,903-119,936 of SEQ ID NO: 2 achieve at least 51% reduction of LRRK2 RNA in vitro in at least one single dose assay.

17. Nucleobases 4,062-4,086 of SEQ ID NO: 1

In certain embodiments, nucleobases 4,062-4,086 of SEQ ID NO: 1 comprise a hotspot region. In certain embodiments, siRNAs are complementary to nucleobases 4,062-4,086 of SEQ ID NO: 1. In certain embodiments, modified oligonucleotides are complementary to nucleobases 4,062-4,086 of SEQ ID NO: 1. In certain embodiments, modified oligonucleotides are 20 nucleobases in length. In certain embodiments, modified oligonucleotides are gapmers. In certain embodiments, the gapmers are 5-10-5 MOE gapmers. In certain embodiments, the internucleoside linkages of the modified oligonucleotides are phosphodiester ("o") and phosphorothioate ("s") internucleoside linkages. In certain embodiments, the phosphodiester ("o") and phosphorothioate ("s") internucleoside linkages are arranged in order from 5' to 3': sooossssssssssssooss.

The nucleobase sequences of SEQ ID Nos: 39, 231, 232, 233, 1161, and 1162 are complementary to nucleobases 4,062-4,086 of SEQ ID NO: 1.

In certain embodiments, modified oligonucleotides complementary to nucleobases 4,062-4,086 of SEQ ID NO: 1 achieve at least 56% reduction of LRRK2 RNA in vitro in at least one single dose assay.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "ATmCGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of 5-10-5 MOE Gapmers with Phosphorothioate Internucleoside Linkages on Human LRRK2 RNA Expression In Vitro, Single Dose Modified oligonucleotides complementary to a human LRRK2 nucleic acid were designed and tested for their effect on LRRK2 RNA in vitro.

Cultured SH-SY5Y cells at a density of 20,000 cells per well were transfected using electroporation with 5,000 nM concentration of modified oligonucleotide or no modified oligonucleotide for untreated controls. After approximately 24 hours, RNA was isolated from the cells and LRRK2 RNA levels were measured by quantitative real-time PCR Human primer probe set RTS3133_MGB (forward sequence TTCCACACTTGCGGTCTTTAGA, designated herein as SEQ ID NO: 11; reverse sequence GCGGGACCTGGTAGGTACTG, designated herein as SEQ ID NO: 12; probe sequence ATGAGCAGCAATGAT, designated herein as SEQ ID: 13) was used to measure RNA levels. LRRK2 RNA levels were adjusted according to total RNA content, as measured by RIBOGREEN®. Results are presented in the table below as percent LRRK2 RNA levels relative to untreated control cells. The modified oligonucleotides with percent control values marked with an asterisk (*) target the amplicon region of the primer probe set. Additional assays may be used to measure the potency and efficacy of oligonucleotides targeting the amplicon region.

The modified oligonucleotides on Table 1 are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddeeeee; wherein 'd' represents a 2'-deoxyribose sugar and 'e' represents a 2'-MOE modified sugar. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 1 below is complementary to human LRRK2 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to the sequence of human LRRK2 RNA reduced the amount of human LRRK2 RNA.

TABLE 1

Percent control of human LRRK2 RNA with 5-10-5 MOE gapmers
with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | LRRK2 % control | SEQ ID NO |
|---|---|---|---|---|---|---|---|
| 422420 | 368 | 387 | 10392 | 10411 | ATTAATTTGCACAGAAGTGA | 75 | 30 |
| 422421 | 375 | 394 | 10399 | 10418 | GACTTCTATTAATTTGCACA | 65 | 31 |
| 422425 | 441 | 460 | 10465 | 10484 | ACCAAGGACTTCCCAATCAT | 111 | 32 |
| 422428 | 606 | 625 | 16126 | 16145 | GTGCATGGCATCAAAAATTA | 35 | 33 |
| 422433 | 1791 | 1810 | 52705 | 52724 | TCCACATTTCTGAATCCCAG | 24 | 34 |
| 422435 | 1904 | 1923 | N/A | N/A | TCTTGGTCATCTGGATACAT | 76 | 35 |
| 422436 | 1913 | 1932 | N/A | N/A | CACTGAATTTCTTGGTCATC | 84 | 36 |
| 422437 | 1919 | 1938 | N/A | N/A | CCCAGACACTGAATTTCTTG | 53 | 37 |
| 422450 | 3886 | 3905 | N/A | N/A | GAGGAATCTCTTTCAGTTTA | 58 | 38 |
| 422451 | 4064 | 4083 | 84059 | 84078 | AACCTTATGATGTCTTTGGC | 44 | 39 |
| 422456 | 4472 | 4491 | 88573 | 88592 | GAAACATCCAAATGTGTGCC | 64 | 40 |
| 422457 | 4484 | 4503 | 88585 | 88604 | TGCTTCTCATCAGAAACATC | 66 | 41 |
| 422458 | 4580 | 4599 | 88681 | 88700 | TCCTCGGTGGCATTCACAAA | 96 | 42 |
| 422461 | 4908 | 4927 | 93369 | 93388 | CCACTTGGGTTCCACAAAGT | 39 | 43 |
| 422462 | 4915 | 4934 | 93376 | 93395 | TACAAAGCCACTTGGGTTCC | 57 | 44 |
| 422466 | 5480 | 5499 | 100469 | 100488 | GGAAACCATTCTTCCATGAG | 85 | 45 |
| 422469 | 5702 | 5721 | 101340 | 101359 | TTTCTAGGCAGGTCAGCCAA | 74 | 46 |
| 422470 | 5978 | 5997 | 113175 | 113194 | AGCAGGCGATCCAAGGAACC | 90 | 47 |
| 422472 | 6139 | 6158 | 118472 | 118491 | CAATGATGGCAGCATTGGGA | 72 | 48 |
| 422475 | 6260 | 6279 | 124891 | 124910 | TGTTGGTTATAAATGACATT | 81 | 49 |
| 422477 | 6461 | 6480 | 126577 | 126596 | TGAGGATTTTCTTTCAAACA | 96 | 50 |
| 422479 | 6500 | 6519 | 129645 | 129664 | TTCAAAATGTCAAAGACCTG | 98 | 51 |
| 422480 | 6841 | 6860 | 132551 | 132570 | AAGTGACAGAATCAGTCATC | 83 | 52 |
| 422483 | 7108 | 7127 | 137512 | 137531 | TGAGTTTCTGAATGGTGAAA | 92 | 53 |
| 438386 | 117 | 136 | 3236 | 3255 | GCTGCCACTAGCCATGGTGG | 99 | 54 |
| 438387 | 185 | 204 | 3304 | 3323 | TCCTGGACATTGTTCAGCCT | 48 | 55 |
| 438388 | 381 | 400 | 10405 | 10424 | TGGACAGACTTCTATTAATT | 73 | 56 |
| 438401 | 3944 | 3963 | 83939 | 83958 | AGTTCCAAGTTGTAACTGAC | 71 | 57 |
| 438405 | 4408 | 4427 | 87312 | 87331 | AGAGCCAAGGCTTCATGGCA | 98 | 58 |
| 438408 | 4619 | 4638 | 88720 | 88739 | TTTATGATGGTTTTCCGAAG | 107 | 59 |
| 438410 | 4649 | 4668 | N/A | N/A | TGATCTCGGATCTTGAAATT | 88 | 60 |
| 438429 | 8882 | 8901 | 147051 | 147070 | ATGAATACTGGTCAGGGCCA | 77 | 61 |
| 438432 | N/A | N/A | 4483 | 4502 | AAACTGATTTCAGTTCCCCA | 50 | 62 |
| 438433 | N/A | N/A | 52819 | 52838 | ACCTTGGTCATCTGGATACA | 93 | 63 |
| 438434 | N/A | N/A | 92072 | 92091 | TGATCTCGGATCTATGAAAT | 94 | 64 |
| 438436 | N/A | N/A | 114858 | 114877 | CCCCTGGTGTTCAAAAGCAG | 69 | 65 |

TABLE 1-continued

Percent control of human LRRK2 RNA with 5-10-5 MOE gapmers with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | LRRK2 % control | SEQ ID NO |
|---|---|---|---|---|---|---|---|
| 438437 | N/A | N/A | 129638 | 129657 | TGTCAAAGACCTGAGAAAGT | 116 | 66 |
| 438538 | 171 | 190 | 3290 | 3309 | CAGCCTGACTATCAACTTCT | 35 | 67 |
| 438539 | 436 | 455 | 10460 | 10479 | GGACTTCCCAATCATTTCCA | 90 | 68 |
| 438540 | 1074 | 1093 | N/A | N/A | GAAAATAGTCTCAGTGAGGA | 70 | 69 |
| 438541 | 1078 | 1097 | N/A | N/A | TTAAGAAAATAGTCTCAGTG | 98 | 70 |
| 438542 | 2275 | 2294 | 56283 | 56302 | CCATGATGCTGTTATTCTGA | 54 | 71 |
| 438543 | 2282 | 2301 | 56290 | 56309 | CATTCAACCATGATGCTGTT | 50 | 72 |
| 438544 | 2361 | 2380 | 61982 | 62001 | GCTCTCTTTCTCACATACCT | 22 | 73 |
| 438545 | 2366 | 2385 | 61987 | 62006 | GGACTGCTCTCTTTCTCACA | 26 | 74 |
| 438546 | 2525 | 2544 | 62146 | 62165 | AATCCTCCAAGGCAAATGCT | 55 | 75 |
| 438547 | 2564 | 2583 | 62185 | 62204 | AAAGGACCAAGCCAAGAAGG | 58 | 76 |
| 438548 | 2571 | 2590 | 62192 | 62211 | TGGAAATAAAGGACCAAGCC | 27 | 77 |
| 438549 | 2759 | 2778 | 65597 | 65616 | ACACTGTCCATAGAAGAGTC | 56 | 78 |
| 438550 | 2764 | 2783 | 65602 | 65621 | CAAACACACTGTCCATAGAA | 44 | 79 |
| 438551 | 3503 | 3522 | 77252 | 77271 | AAAATCTTCAGTTCCTTCAG | 82 | 80 |
| 438552 | 3857 | 3876 | 82202 | 82221 | AGATGCAGTTTCTCTACTCT | 67 | 81 |
| 438553 | 4300 | 4319 | N/A | N/A | CCTCACGACCTGCAAAATCC | 65 | 82 |
| 438554 | 4305 | 4324 | N/A | N/A | GAATTCCTCACGACCTGCAA | 77 | 83 |
| 438555 | 4480 | 4499 | 88581 | 88600 | TCTCATCAGAAACATCCAAA | 77 | 84 |
| 438556 | 4575 | 4594 | 88676 | 88695 | GGTGGCATTCACAAAGTGGT | 52 | 85 |
| 438557 | 4641 | 4660 | N/A | N/A | GATCTTGAAATTAAGGCTCT | 69 | 86 |
| 438558 | 5225 | 5244 | 99231 | 99250 | AATCTTGACCAAAATCCCAT | 79 | 87 |
| 438559 | 5530 | 5549 | 100519 | 100538 | TCTTCAACAGAGTTTCTCCT | 81 | 88 |
| 438560 | 5537 | 5556 | 100526 | 100545 | GCCCATTTCTTCAACAGAGT | 30 | 89 |
| 438561 | 5568 | 5587 | 100557 | 100576 | ATGTTCTTCACCATCATTAA | 98 | 90 |
| 438562 | 5735 | 5754 | 101373 | 101392 | TCAAATTCCAACTCATCATT | 111 | 91 |
| 438563 | 5825 | 5844 | 106516 | 106535 | AAAATCTTCACAGCCACTTC | 109 | 92 |
| 438564 | 5829 | 5848 | 106520 | 106539 | ATTAAAAATCTTCACAGCCA | 136 | 93 |
| 438565 | 6000 | 6019 | 113197 | 113216 | GAGGCTGGCTTTGTCCTGCT | 52 | 94 |
| 438566 | 6074 | 6093 | 118407 | 118426 | ATAATCATGGCTGAGTGGAG | 83 | 95 |
| 438567 | 6135 | 6154 | 118468 | 118487 | GATGGCAGCATTGGGATACA | 90 | 96 |
| 438568 | 6401 | 6420 | 126517 | 126536 | CCATATTCTTTAACTGGATC | 74 | 97 |
| 438569 | 6427 | 6446 | 126543 | 126562 | TCTCAACCATAGGCCATGGG | 47 | 98 |
| 438570 | 6465 | 6484 | 126581 | 126600 | TTCTTGAGGATTTTCTTTCA | 106 | 99 |
| 438571 | 6494 | 6513 | N/A | N/A | ATGTCAAAGACCTGGGCAGA | 107 | 100 |

TABLE 1-continued

Percent control of human LRRK2 RNA with 5-10-5 MOE gapmers with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | LRRK2 % control | SEQ ID NO |
|---|---|---|---|---|---|---|---|
| 438572 | 6572 | 6591 | 129717 | 129736 | GCAACCATGCATTCAACAAT | 76 | 101 |
| 438573 | 6696 | 6715 | 132406 | 132425 | TCTACTATCAGCAACTTCCT | 89 | 102 |
| 438574 | 6845 | 6864 | 132555 | 132574 | AAACAAGTGACAGAATCAGT | 110 | 103 |
| 438575 | 7632 | 7651 | 145801 | 145820 | GTGTTTTTCTAAATTTTGCA | 65 | 104 |
| 438576 | 7640 | 7659 | 145809 | 145828 | ACTTCAATGTGTTTTTCTAA | 105 | 105 |
| 438577 | N/A | N/A | 3658 | 3677 | AAATAACTTGGAGGCTGGAA | 114 | 106 |
| 438578 | N/A | N/A | 4487 | 4506 | GACAAAACTGATTTCAGTTC | 82 | 107 |
| 438579 | N/A | N/A | 77354 | 77373 | CACTTACCAAGAAAATTCAT | 118 | 108 |
| 438580 | N/A | N/A | 116733 | 116752 | ATTATAGAATTTAATCTTAA | 96 | 109 |
| 438581 | N/A | N/A | 142937 | 142956 | ACCTCCCTAGAACCATAAAG | 104 | 110 |
| 438582 | 60 | 79 | 3179 | 3198 | TCCGCTGCTCAGGGAACCGG | 65 | 111 |
| 438583 | 449 | 468 | 10473 | 10492 | TGGTGAACACCAAGGACTTC | 55 | 112 |
| 438584 | 457 | 476 | N/A | N/A | GAATCAATTGGTGAACACCA | 63 | 113 |
| 438585 | 529 | 548 | 13795 | 13814 | GGAGGAGATCTAAGGTCTTC | 90 | 114 |
| 438586 | 550 | 569 | N/A | N/A | AGGTGATTTTACCTGAAGTT | 64 | 115 |
| 438587 | 624 | 643 | 16144 | 16163 | ATCATTGGCTGGAAATGAGT | 51 | 116 |
| 438588 | 883 | 902 | 21714 | 21733 | GGAATGCTTTCATAGCTTCC | 56 | 117 |
| 438589 | 1166 | 1185 | 29427 | 29446 | TTGTAACAGGCTTCCAGCCA | 53 | 118 |
| 438590 | 1300 | 1319 | N/A | N/A | CCCTATGAGCTGGGAAATGG | 79 | 119 |
| 438591 | 1534 | 1553 | N/A | N/A | CCAGGGAAGTGTTGCTTCCT | 77 | 120 |
| 438592 | 1610 | 1629 | 37659 | 37678 | TCCAGCTGCACTGGTAATGA | 90 | 121 |
| 438593 | 1774 | 1793 | N/A | N/A | CAGGATTTCCAATGAACCTG | 72 | 122 |
| 438594 | 1885 | 1904 | 52799 | 52818 | TCTGCAGTGTGTGAAGCACT | 76 | 123 |
| 438595 | 2108 | 2127 | 56042 | 56061 | TGATGCACCAGCAGCTTAGA | 48 | 124 |
| 438596 | 2318 | 2337 | 56326 | 56345 | TTTGCTTGATTGGCATCTGC | 55 | 125 |
| 438597 | 2380 | 2399 | 62001 | 62020 | GTTCCACCAATTTGGGACTG | 34 | 126 |
| 438598 | 2412 | 2431 | 62033 | 62052 | ATCTTGTTCACGAGATCCAC | 70 | 127 |
| 438599 | 2515 | 2534 | 62136 | 62155 | GGCAAATGCTATTGTTGGCC | 63 | 128 |
| 438600 | 3171 | 3190 | 73707 | 73726 | GAGTGCATTCTGGTGAAGCT | 70 | 129 |
| 438601 | 3211 | 3230 | N/A | N/A | AACTCTTCAGAGTTTCACAT | 94 | 130 |
| 438602 | 3475 | 3494 | 77224 | 77243 | GGGAGCATATCCCTGATATT | 42 | 131 |
| 438603 | 3565 | 3584 | 77314 | 77333 | CTTTAGGACAAGCCTCAAGA | 71 | 132 |
| 438604 | 3702 | 3721 | N/A | N/A | AGACCGCAAGTGTGGAAGAT | 17* | 133 |
| 438605 | 3707 | 3726 | N/A | N/A | TCTAAAGACCGCAAGTGTGG | 22* | 134 |
| 438606 | 3930 | 3949 | 83925 | 83944 | ACTGACATCCAGAGATGTCA | 126 | 135 |
| 438607 | 3952 | 3971 | 83947 | 83966 | AGGATCTTAGTTCCAAGTTG | 95 | 136 |

TABLE 1-continued

Percent control of human LRRK2 RNA with 5-10-5 MOE gapmers
with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | LRRK2 % control | SEQ ID NO |
|---|---|---|---|---|---|---|---|
| 438608 | 3957 | 3976 | 83952 | 83971 | GGGAAAGGATCTTAGTTCCA | 70 | 137 |
| 438609 | 3969 | 3988 | 83964 | 83983 | CCCCATTTCATTGGGAAAGG | 77 | 138 |
| 438610 | 4190 | 4209 | 86685 | 86704 | CCAAGATCTGATTTCTTGGT | 104 | 139 |
| 438611 | 4353 | 4372 | 87257 | 87276 | AGCAAGGTACAATGCTCGCT | 69 | 140 |
| 438612 | 4395 | 4414 | 87299 | 87318 | CATGGCATCAACTTCAGCCT | 83 | 141 |
| 438613 | 4413 | 4432 | 87317 | 87336 | ATTGAAGAGCCAAGGCTTCA | 94 | 142 |
| 438614 | 4422 | 4441 | N/A | N/A | AGCCTTTATATTGAAGAGCC | 103 | 143 |
| 438615 | 4428 | 4447 | N/A | N/A | AGCGCGAGCCTTTATATTGA | 91 | 144 |
| 438616 | 4433 | 4452 | N/A | N/A | GAAGAAGCGCGAGCCTTTAT | 66 | 145 |
| 438617 | 4544 | 4563 | 88645 | 88664 | GCAGGGAACCCTCGCTTATT | 97 | 146 |
| 438618 | 4682 | 4701 | 92105 | 92124 | TAGCAGTCTGGAATCAGCTG | 89 | 147 |
| 438619 | 4816 | 4835 | 92239 | 92258 | CGTGAGGAAGCTCATTTTCA | 70 | 148 |
| 438620 | 4963 | 4982 | 98111 | 98130 | GTTTTGGACAACCTTCCACT | 96 | 149 |
| 438621 | 5074 | 5093 | 98222 | 98241 | TCTGGAATTTTTCTAGGAGC | 62 | 150 |
| 438622 | 5116 | 5135 | 98264 | 98283 | TGCTTGGAACCAGCAAATAT | 78 | 151 |
| 438623 | 5451 | 5470 | 100440 | 100459 | GTGGTCCACAACTTGGCCCA | 71 | 152 |
| 438624 | 5745 | 5764 | 101383 | 101402 | TGGAGCTTGTTCAAATTCCA | 104 | 153 |
| 438625 | 5887 | 5906 | 113084 | 113103 | GGTGGAGGTGGCAAAGCACC | 78 | 154 |
| 438626 | 5968 | 5987 | 113165 | 113184 | CCAAGGAACCCTTGGAGGCT | 97 | 155 |
| 438627 | 5986 | 6005 | 113183 | 113202 | CCTGCTGAAGCAGGCGATCC | 75 | 156 |
| 438628 | 5991 | 6010 | 113188 | 113207 | TTTGTCCTGCTGAAGCAGGC | 89 | 157 |
| 438629 | 6058 | 6077 | N/A | N/A | GGAGGTATCTCAAACCATCA | 111 | 158 |
| 438630 | 6149 | 6168 | 118482 | 118501 | GCAATCTTTGCAATGATGGC | 72 | 159 |
| 438631 | 6157 | 6176 | 118490 | 118509 | CGTAGTCAGCAATCTTTGCA | 78 | 160 |
| 438632 | 6581 | 6600 | 129726 | 129745 | TGATGTGTAGCAACCATGCA | 62 | 161 |
| 438633 | 6586 | 6605 | 129731 | 129750 | TGTTGTGATGTGTAGCAACC | 77 | 162 |
| 438634 | 6613 | 6632 | 129758 | 129777 | AGCCCAGCCAAATGCTTGCA | 97 | 163 |
| 438635 | 6624 | 6643 | 129769 | 129788 | GGTGTGCCCACAGCCCAGCC | 70 | 164 |
| 438636 | 6677 | 6696 | 129822 | 129841 | TCAGAAGTGTATCCTTCAGT | 95 | 165 |
| 438637 | 7373 | 7392 | 143021 | 143040 | GCAGTGTTCTTCTGAAGGCA | 100 | 166 |
| 438638 | 7482 | 7501 | 143130 | 143149 | TGTCATCATGACTCTGACCG | 74 | 167 |
| 438639 | 8333 | 8352 | 146502 | 146521 | AGGACTTTGACAGTATGTCA | 66 | 168 |
| 438640 | 8696 | 8715 | 146865 | 146884 | TCCTTCAGCAACTGAAAAGT | 85 | 169 |
| 438641 | 8748 | 8767 | 146917 | 146936 | TGGAAGCCTAGGGTGGCAGA | 62 | 170 |
| 438642 | 8914 | 8933 | 147083 | 147102 | AGTTGTCCTATCACAGGGAA | 90 | 171 |

TABLE 1-continued

Percent control of human LRRK2 RNA with 5-10-5 MOE gapmers with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | LRRK2 % control | SEQ ID NO |
|---|---|---|---|---|---|---|---|
| 438643 | N/A | N/A | 78939 | 78958 | ATCAGATTCCCCTGAGGTAC | 93 | 172 |
| 438644 | N/A | N/A | 78947 | 78966 | CAGTCTGAATCAGATTCCCC | 85 | 173 |
| 438645 | N/A | N/A | 143365 | 143384 | GTTCAGCTGCAGTAATCTGC | 67 | 174 |
| 438646 | N/A | N/A | 143372 | 143391 | ACTGAGTGTTCAGCTGCAGT | 80 | 175 |
| 438647 | N/A | N/A | 143377 | 143396 | CCCAAACTGAGTGTTCAGCT | 99 | 176 |
| 438648 | N/A | N/A | 10479 | 10498 | ACTTACTGGTGAACACCAAG | 121 | 177 |
| 438649 | N/A | N/A | 31012 | 31031 | ATGAGCTGGGAAACTTTCAA | 84 | 178 |
| 438650 | N/A | N/A | 41888 | 41907 | TCTGGCATGCCTAAATGCAC | 101 | 179 |
| 438651 | N/A | N/A | 52827 | 52846 | TTGTACTGACCTTGGTCATC | 126 | 180 |
| 438652 | N/A | N/A | 76342 | 76361 | TCTTCAGAGTCTGAAAAGAC | 83 | 181 |
| 438653 | N/A | N/A | 88530 | 88549 | AAGCGCGAGCCTGGAGGGAA | 89 | 182 |
| 438654 | N/A | N/A | 118392 | 118411 | TGGAGGTATCTGCCAGAAAA | 91 | 183 |
| 438655 | N/A | N/A | 118553 | 118572 | ATCACCTACCTGGTGTGCCC | 122 | 184 |

Example 2: Effect of 5-10-5 MOE Gapmers with Mixed Internucleoside Linkages on Human LRRK2 RNA Expression In Vitro, Single Dose Modified oligonucleotides complementary to a human LRRK2 nucleic acid were designed and tested for their effect on LRRK2 RNA in vitro. The modified oligonucleotides were tested in a series of experiments that had similar culture conditions.

Cultured SH-SY5Y cells at a density of 20,000 cells per well were transfected using electroporation with 5,000 nM concentration of modified oligonucleotide or no modified oligonucleotide for untreated controls. After approximately 24 hours, RNA was isolated from the cells and LRRK2 RNA levels were measured by quantitative real-time PCR Human primer probe sets RTS3132 (forward sequence CAT-CACTCAGGCTGTTAAGACAAGA, designated herein as SEQ ID NO: 14; reverse sequence CAGCTGCCAGCAAA-GATATCAA, designated herein as SEQ ID NO: 15; probe sequence CTTTGCCACCTCCACCACCCCA, designated herein as SEQ ID: 16), RTS3133_MGB (forward sequence TTCCACACTTGCGGTCTTTAGA, designated herein as SEQ ID NO: 11; reverse sequence GCGGGACCTGGTAGGTACTG, designated herein as SEQ ID NO: 12; probe sequence ATGAGCAGCAATGAT, designated herein as SEQ ID: 13), and RTS3146_MGB (forward sequence GAGCTTCCTCACGCAGTTCAC, designated herein as SEQ ID NO: 17; reverse sequence TGCTGGGTCTTGAAAATGAAGA, designated herein as SEQ ID NO: 18; probe sequence TTCTAAATGAATCAG-GAGTCC, designated herein as SEQ ID: 19) were used to measure RNA levels. LRRK2 RNA levels were adjusted according to total RNA content, as measured by RIBOGREEN®. Results are presented in the table below as percent LRRK2 RNA levels relative to untreated control cells. The modified oligonucleotides with percent control values marked with an asterisk (*) target the amplicon region of the primer probe set.

The modified oligonucleotides in Table 2 are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddd-deeeee; wherein 'd' represents a 2'-deoxyribose sugar and 'e' represents a 2'-MOE modified sugar. All cytosine residues throughout each gapmer are 5-methyl cytosines. The internucleoside linkages for each gapmer are mixed phosphodiester and phosphorothioate linkages. The internucleoside linkage motif for the gapmers is (from 5' to 3'): sooosssssssssssooss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 2 below is complementary to human LRRK2 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to the sequence of human LRRK2 RNA reduced the amount of human LRRK2 RNA.

TABLE 2

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control RTS3132 | LRRK2 % control RTS3133_MGB | LRRK2 % control RTS3146_MGB | SEQ ID NO |
|---|---|---|---|---|---|---|---|---|---|
| 693423 | 4064 | 4083 | 84059 | 84078 | AACCTTATGATGTCTTTGGC | 15 | 31 | 18 | 39 |
| 693424 | 4908 | 4927 | 93369 | 93388 | CCACTTGGGTTCCACAAAGT | 24 | 31 | 24 | 43 |
| 693428 | 2361 | 2380 | 61982 | 62001 | GCTCTCTTTCTCACATACCT | 10 | 14 | 11 | 73 |
| 693429 | 2571 | 2590 | 62192 | 62211 | TGGAAATAAAGGACCAAGCC | 26 | 31 | 27 | 77 |
| 780202 | 2368 | 2387 | 61989 | 62008 | TGGGACTGCTCTCTTTCTCA | 19 | 26 | 20 | 185 |
| 780203 | 2371 | 2390 | 61992 | 62011 | ATTTGGGACTGCTCTCTTTC | 28 | 36 | 32 | 186 |
| 780204 | 2406 | 2425 | 62027 | 62046 | TTCACGAGATCCACTATTCA | 48 | 51 | 51 | 187 |
| 780205 | 2451 | 2470 | 62072 | 62091 | GTCACCTTTCCCAATGCTTA | 21 | 35 | 29 | 188 |
| 780206 | 2499 | 2518 | 62120 | 62139 | GGCCACATCCAGGGCCAGCC | 56 | 62 | 45 | 189 |
| 780207 | 2543 | 2562 | 62164 | 62183 | TCAACTTTTCCTATACAAAA | 38 | 42 | 47 | 190 |
| 780208 | 2566 | 2585 | 62187 | 62206 | ATAAAGGACCAAGCCAAGAA | 53 | 56 | 64 | 191 |
| 780209 | 2569 | 2588 | 62190 | 62209 | GAAATAAAGGACCAAGCCAA | 48 | 53 | 54 | 192 |
| 780210 | 2573 | 2592 | 62194 | 62213 | TCTGGAAATAAAGGACCAAG | 21 | 24 | 27 | 193 |
| 780211 | 2576 | 2595 | 62197 | 62216 | TTATCTGGAAATAAAGGACC | 39 | 37 | 41 | 194 |
| 780212 | 2587 | 2606 | 62208 | 62227 | AATTAGAAGTCTTATCTGGA | 59 | 61 | 59 | 195 |
| 780213 | 2632 | 2651 | 65470 | 65489 | TCACCATTCTTGCTAGTGTA | 41 | 42 | 50 | 196 |
| 780214 | 2678 | 2697 | 65516 | 65535 | CCTGAGGCTGTTCCTTCTTC | 37 | 47 | 44 | 197 |
| 780215 | 2722 | 2741 | 65560 | 65579 | CATCAAATTTAGACAGCACA | 41 | 44 | 48 | 198 |
| 780216 | 2759 | 2778 | 65597 | 65616 | ACACTGTCCATAGAAGAGTC | 50 | 48 | 45 | 78 |
| 780217 | 2762 | 2781 | 65600 | 65619 | AACACACTGTCCATAGAAGA | 41 | 47 | 43 | 199 |
| 780218 | 2764 | 2783 | 65602 | 65621 | CAAACACACTGTCCATAGAA | 31 | 39 | 37 | 79 |
| 780219 | 2766 | 2785 | 65604 | 65623 | AGCAAACACACTGTCCATAG | 21 | 27 | 24 | 200 |
| 780220 | 2769 | 2788 | 65607 | 65626 | TTGAGCAAACACACTGTCCA | 34 | 37 | 36 | 201 |
| 780221 | 2810 | 2829 | 71653 | 71672 | AGAAATGAGCCTTCACTTCC | 35 | 49 | 41 | 202 |
| 780222 | 2854 | 2873 | 71697 | 71716 | GGTAAAATTCTCCTACACTA | 37 | 39 | 38 | 203 |
| 780223 | 2898 | 2917 | 71741 | 71760 | ATGTCTTTGCAAATTTGGTG | 41 | 46 | 38 | 204 |
| 780224 | 2942 | 2961 | 72966 | 72985 | TTCAGTAAATCTTCATGATC | 55 | 57 | 64 | 205 |
| 780225 | 2986 | 3005 | N/A | N/A | ATGACCTGAGTGAATCATCT | 51 | 46 | 55 | 206 |
| 780226 | 3031 | 3050 | 73567 | 73586 | GAGAAGAAATGCTGTCTGAA | 54 | 61 | 62 | 207 |
| 780227 | 3075 | 3094 | 73611 | 73630 | TGCTGAAAGGTCTAGTGATG | 34 | 37 | 37 | 208 |
| 780228 | 3120 | 3139 | 73656 | 73675 | TATACAGCATTTCTGGCTTA | 61 | 79 | 59 | 209 |
| 780229 | 3164 | 3183 | 73700 | 73719 | TTCTGGTGAAGCTCCAGCTT | 27 | 32 | 29 | 210 |
| 780230 | 3208 | 3227 | N/A | N/A | TCTTCAGAGTTTCACATAGC | 62 | 70 | 61 | 211 |
| 780231 | 3256 | 3275 | 76390 | 76409 | AAGGAAATGATGTAAATTTA | 65 | 70 | 69 | 212 |
| 780232 | 3300 | 3319 | 76434 | 76453 | AGAGACATCAAGATTAGCAA | 24 | 33 | 35 | 213 |
| 780233 | 3344 | 3363 | 76478 | 76497 | TTCACTGTAGGATCTAAAAC | 46 | 45 | 45 | 214 |

TABLE 2-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control RTS3132 | LRRK2 % control RTS3133_MGB | LRRK2 % control RTS3146_MGB | SEQ ID NO |
|---|---|---|---|---|---|---|---|---|---|
| 780234 | 3389 | 3408 | 76523 | 76542 | GACAGCTGGTTATATGACAG | 30 | 31 | 29 | 215 |
| 780235 | 3433 | 3452 | 76567 | 76586 | GCTCCAGTTTCTCTACCACA | 41 | 40 | 50 | 216 |
| 780236 | 3494 | 3513 | 77243 | 77262 | AGTTCCTTCAGTCTCAAGGG | 16 | 31 | 22 | 217 |
| 780237 | 3538 | 3557 | 77287 | 77306 | CTGATAGGGATGAAATGTGG | 27 | 31 | 28 | 218 |
| 780238 | 3582 | 3601 | 77331 | 77350 | GGCACTGAAACTCTCCACTT | 25 | 37 | 27 | 219 |
| 780239 | 3626 | 3645 | 80906 | 80925 | ATAGAAGGAGGCAAGAAAGG | 47 | 60 | 67 | 220 |
| 780240 | 3670 | 3689 | 80950 | 80969 | CTGGAATACAGGAAAATTTG | 52 | 44 | 51 | 221 |
| 780241 | 3714 | 3733 | 82059 | 82078 | GCTCATATCTAAAGACCGCA | 10 | 3* | 13 | 222 |
| 780242 | 3758 | 3777 | 82103 | 82122 | GATTTCCAGTGTGCGGGACC | 27 | 20* | 33 | 223 |
| 780243 | 3802 | 3821 | 82147 | 82166 | TGCTGATCTGATTATGGCTA | 22 | 36 | 33 | 224 |
| 780244 | 3846 | 3865 | 82191 | 82210 | CTCTACTCTAGACCATAAAT | 25 | 32 | 28 | 225 |
| 780245 | 3891 | 3910 | N/A | N/A | CTCAGGAGGAATCTCTTTCA | 43 | 47 | 51 | 226 |
| 780246 | 3935 | 3954 | 83930 | 83949 | TTGTAACTGACATCCAGAGA | 63 | 75 | 74 | 227 |
| 780247 | 3979 | 3998 | 83974 | 83993 | TGCTTAATTTCCCCATTTCA | 23 | 41 | 37 | 228 |
| 780248 | 4023 | 4042 | 84018 | 84037 | ATCAAAGTTAAGATGCAGTT | 25 | 30 | 29 | 229 |
| 780249 | 4059 | 4078 | 84054 | 84073 | TATGATGTCTTTGGCTTTAC | 33 | 41 | 36 | 230 |
| 780250 | 4062 | 4081 | 84057 | 84076 | CCTTATGATGTCTTTGGCTT | 28 | 34 | 31 | 231 |
| 780251 | 4066 | 4085 | N/A | N/A | GAAACCTTATGATGTCTTTG | 42 | 39 | 41 | 232 |
| 780252 | 4067 | 4086 | N/A | N/A | AGAAACCTTATGATGTCTTT | 34 | 45 | 50 | 233 |
| 780253 | 4069 | 4088 | N/A | N/A | GAAGAAACCTTATGATGTCT | 44 | 61 | 47 | 234 |
| 780254 | 4111 | 4130 | 86606 | 86625 | GTTTCATTCGGTTATAAGGC | 17 | 24 | 14 | 235 |
| 780255 | 4155 | 4174 | 86650 | 86669 | CAATAAGGTGGTTTTACCAC | 35 | 51 | 47 | 236 |
| 780256 | 4199 | 4218 | 86694 | 86713 | CTTTGCATTCCAAGATCTGA | 30 | 33 | 32 | 237 |
| 780257 | 4243 | 4262 | 86738 | 86757 | TTATTTGGATAGGCCAGTCT | 34 | 42 | 50 | 238 |
| 780258 | 4287 | 4306 | 86782 | 86801 | AAAATCCCACACATTTAGGA | 54 | 60 | 57 | 239 |
| 780259 | 4350 | 4369 | 87254 | 87273 | AAGGTACAATGCTCGCTGCG | 51 | 65 | 51 | 240 |
| 780260 | 4394 | 4413 | 87298 | 87317 | ATGGCATCAACTTCAGCCTG | 45 | 41 | 49 | 241 |
| 780261 | 4438 | 4457 | 88539 | 88558 | GGGAAGAAGAAGCGCGAGCC | 29 | 41 | 32 | 242 |
| 780262 | 4483 | 4502 | 88584 | 88603 | GCTTCTCATCAGAAACATCC | 30 | 41 | 35 | 243 |
| 780263 | 4527 | 4546 | 88628 | 88647 | ATTCAGGAGTTCCTTGGTGA | 43 | 85 | 47 | 244 |
| 780264 | 4571 | 4590 | 88672 | 88691 | GCATTCACAAAGTGGTAATC | 35 | 43 | 35 | 245 |
| 780265 | 4615 | 4634 | 88716 | 88735 | TGATGGTTTTCCGAAGTTTT | 43 | 46 | 49 | 246 |
| 780266 | 4659 | 4678 | 92082 | 92101 | AACAACAAGCTGATCTCGGA | 49 | 57 | 56 | 247 |
| 780267 | 4703 | 4722 | 92126 | 92145 | ATGATTTTTTCAAGTTCTAC | 31 | 47 | 45 | 248 |
| 780268 | 4747 | 4766 | 92170 | 92189 | CAATTACGGGAAATTCAATT | 68 | 60 | 57 | 249 |

TABLE 2-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control RTS3132 | LRRK2 % control RTS3133_MGB | LRRK2 % control RTS3146_MGB | SEQ ID NO |
|---|---|---|---|---|---|---|---|---|---|
| 780269 | 4791 | 4810 | 92214 | 92233 | CTGCAGCTGATTTTCTCTCA | 23 | 32 | 27 | 250 |
| 780270 | 4835 | 4854 | 92258 | 92277 | TCATTTAGAAAGTGAACTGC | 40 | 51 | 54* | 251 |
| 780271 | 4883 | 4902 | 93344 | 93363 | TCACTTAACTGCAGTGCTGG | 27 | 38 | 10* | 252 |
| 780272 | 4903 | 4922 | 93364 | 93383 | TGGGTTCCACAAAGTACAAG | 41 | 47 | 42 | 253 |
| 780273 | 4906 | 4925 | 93367 | 93386 | ACTTGGGTTCCACAAAGTAC | 42 | 38 | 38 | 254 |
| 780274 | 4910 | 4929 | 93371 | 93390 | AGCCACTTGGGTTCCACAAA | 28 | 43 | 30 | 255 |
| 780275 | 4913 | 4932 | 93374 | 93393 | CAAAGCCACTTGGGTTCCAC | 31 | 43 | 38 | 256 |

Example 3: Effect of 5-10-5 MOE Gapmers with Mixed Internucleoside Linkages on Human LRRK2 RNA Expression In Vitro, Single Dose Modified oligonucleotides complementary to a human LRRK2 nucleic acid were designed and tested for their effect on LRRK2 RNA in vitro. The modified oligonucleotides were tested in a series of experiments that had similar culture conditions.

Cultured SH-SY5Y cells at a density of 20,000 cells per well were transfected using electroporation with 3,000 nM concentration of modified oligonucleotide or no modified oligonucleotide for untreated controls. After approximately 24 hours, RNA was isolated from the cells and LRRK2 RNA levels were measured by quantitative real-time PCR using human primer probe set RTS3132 as described in Example 2. LRRK2 RNA levels were adjusted according to total RNA content, as measured by RIBOGREEN®. Results are presented in the table below as percent LRRK2 RNA levels relative to untreated control cells. The modified oligonucleotides with percent control values marked with an asterisk (*) target the amplicon region of the primer probe set. Additional assays may be used to measure the potency and efficacy of oligonucleotides targeting the amplicon region.

The modified oligonucleotides in Tables 3-9 are 5-10-5 MOE gapmers. The gapmers are 20 nucleobases in length, wherein the central gap segment comprises ten 2'-deoxy-nucleosides and is flanked by wing segments on both the 5' end and on the 3' end comprising five 2'-MOE nucleosides. The sugar motif for the gapmers is (from 5' to 3'): eeeeedddddddddddeeeee; wherein 'd' represents a 2'-deoxyribose sugar and 'e' represents a 2'-MOE modified sugar. All cytosine residues throughout each gapmer are 5-methyl cytosines. The internucleoside linkages for each gapmer are mixed phosphodiester and phosphorothioate linkages. The internucleoside linkage motif for the gapmers is (from 5' to 3'): sooosssssssssssooss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 3-9 below is complementary to human LRRK2 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to the sequence of human LRRK2 RNA reduced the amount of human LRRK2 RNA.

TABLE 3

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 690092 | 171 | 190 | 3290 | 3309 | CAGCCTGACTATCAACTTCT | 57 | 67 |
| 690093 | 2366 | 2385 | 61987 | 62006 | GGACTGCTCTCTTTCTCACA | 70 | 74 |
| 693420 | 606 | 625 | 16126 | 16145 | GTGCATGGCATCAAAAATTA | 41 | 33 |
| 693421 | 1791 | 1810 | 52705 | 52724 | TCCACATTTCTGAATCCCAG | 48 | 34 |
| 693428 | 2361 | 2380 | 61982 | 62001 | GCTCTCTTTCTCACATACCT | 51 | 73 |
| 693438 | 883 | 902 | 21714 | 21733 | GGAATGCTTTCATAGCTTCC | 43 | 117 |

TABLE 3-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 725607 | 2362 | 2381 | 61983 | 62002 | TGCTCTCTTTCTCACATACC | 35 | 257 |
| 725608 | 2363 | 2382 | 61984 | 62003 | CTGCTCTCTTTCTCACATAC | 40 | 258 |
| 725609 | 2364 | 2383 | 61985 | 62004 | ACTGCTCTCTTTCTCACATA | 62 | 259 |
| 780133 | 1 | 20 | 3120 | 3139 | TCACCGCCCGCAGCCAGCGC | 95 | 260 |
| 780134 | 56 | 75 | 3175 | 3194 | CTGCTCAGGGAACCGGCAGG | 134 | 261 |
| 780135 | 100 | 119 | 3219 | 3238 | TGGCACCTGCTTCCAACCCG | 115 | 262 |
| 780136 | 157 | 176 | 3276 | 3295 | ACTTCTTCAGAGTTTCCTCG | 59 | 263 |
| 780137 | 166 | 185 | 3285 | 3304 | TGACTATCAACTTCTTCAGA | 86 | 264 |
| 780138 | 169 | 188 | 3288 | 3307 | GCCTGACTATCAACTTCTTC | 59 | 265 |
| 780139 | 173 | 192 | 3292 | 3311 | TTCAGCCTGACTATCAACTT | 70 | 266 |
| 780140 | 176 | 195 | 3295 | 3314 | TTGTTCAGCCTGACTATCAA | 87 | 267 |
| 780141 | 203 | 222 | 3322 | 3341 | GTTTCTATCTGTTTTCCTTC | 44 | 268 |
| 780142 | 271 | 290 | N/A | N/A | CTTGAAATAACTTGGAGGCG | 72 | 269 |
| 780143 | 315 | 334 | 3706 | 3725 | ATAGGAGTCCAAGACGATCA | 49 | 270 |
| 780144 | 362 | 381 | 10386 | 10405 | TTGCACAGAAGTGACCAACC | 64 | 271 |
| 780145 | 406 | 425 | 10430 | 10449 | GTCCCATTAAGCTTTGCATT | 48 | 272 |
| 780146 | 451 | 470 | N/A | N/A | ATTGGTGAACACCAAGGACT | 48 | 273 |
| 780147 | 495 | 514 | 13761 | 13780 | CAAGTTTACACTGGCATTAT | 57 | 274 |
| 780148 | 539 | 558 | 13805 | 13824 | CCTGAAGTTAGGAGGAGATC | 32 | 275 |
| 780149 | 585 | 604 | 16105 | 16124 | CATGAAAATATCACTTTCTT | 76 | 276 |
| 780150 | 601 | 620 | 16121 | 16140 | TGGCATCAAAAATTAACATG | 70 | 277 |
| 780151 | 604 | 623 | 16124 | 16143 | GCATGGCATCAAAAATTAAC | 96 | 278 |
| 780152 | 608 | 627 | 16128 | 16147 | GAGTGCATGGCATCAAAAAT | 44 | 279 |
| 780153 | 611 | 630 | 16131 | 16150 | AATGAGTGCATGGCATCAAA | 74 | 280 |
| 780154 | 629 | 648 | 16149 | 16168 | ACTTCATCATTGGCTGGAAA | 57 | 281 |
| 780155 | 673 | 692 | 16193 | 16212 | CTCTCTCAAACAGCACATGT | 74 | 282 |
| 780156 | 717 | 736 | 18616 | 18635 | ATAATCTTTGTTCTCAACAA | 62 | 283 |
| 780157 | 764 | 783 | 18663 | 18682 | ATTTCCTCTTCATCTTTAAA | 134 | 284 |
| 780158 | 808 | 827 | 18707 | 18726 | AAGGAATCGCTAGGGAATGT | 57 | 285 |
| 780159 | 852 | 871 | 21683 | 21702 | ATAACACCTGACATTGCCAC | 48 | 286 |
| 780160 | 878 | 897 | 21709 | 21728 | GCTTTCATAGCTTCCACCAC | 60 | 287 |
| 780161 | 881 | 900 | 21712 | 21731 | AATGCTTTCATAGCTTCCAC | 59 | 288 |
| 780162 | 885 | 904 | 21716 | 21735 | AGGGAATGCTTTCATAGCTT | 34 | 289 |
| 780163 | 888 | 907 | 21719 | 21738 | CATAGGGAATGCTTTCATAG | 99 | 290 |
| 780164 | 896 | 915 | 21727 | 21746 | CTTTCACTCATAGGGAATGC | 34 | 291 |

TABLE 3-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780165 | 940 | 959 | 21771 | 21790 | CTAATGTAAGCCTATGGAGC | 51 | 292 |
| 780166 | 988 | 1007 | 27963 | 27982 | CCACAAACTCATGGACTTCG | 30 | 293 |
| 780167 | 1032 | 1051 | 28007 | 28026 | GATCTGCAATGCTGCATTCT | 58 | 294 |
| 780168 | 1078 | 1097 | N/A | N/A | TTAAGAAATAGTCTCAGTG | 160 | 70 |
| 780169 | 1123 | 1142 | 29384 | 29403 | CATCATCATTCTCTTGATTC | 63 | 295 |
| 780170 | 1167 | 1186 | 29428 | 29447 | TTTGTAACAGGCTTCCAGCC | 46 | 296 |
| 780171 | 1216 | 1235 | N/A | N/A | AGCATGCGGCCTCCTGCACG | 73 | 297 |
| 780172 | 1260 | 1279 | 29611 | 29630 | CTCATGTAAACTGTTTTGGT | 62 | 298 |
| 780173 | 1304 | 1323 | 31020 | 31039 | ACTTCCCTATGAGCTGGGAA | 134 | 299 |
| 780174 | 1348 | 1367 | 31064 | 31083 | GGAAAACTTCCTTTGATGAA | 91 | 300 |
| 780175 | 1417 | 1436 | 35364 | 35383 | TTGATAACAGTATTTTTCTG | 75 | 301 |
| 780176 | 1461 | 1480 | 35408 | 35427 | TATATGCTTCTGCATTAACT | 78 | 302 |
| 780177 | 1505 | 1524 | 35452 | 35471 | TGATTTAGCATTTTACAGCC | 106 | 303 |
| 780178 | 1549 | 1568 | 37598 | 37617 | CTGCTGCCATTATATCCAGG | 56 | 304 |
| 780179 | 1598 | 1617 | 37647 | 37666 | GGTAATGATGTCTCATGACG | 60 | 305 |
| 780180 | 1645 | 1664 | 37694 | 37713 | CAGGCACTATAAAATGTAAA | 93 | 306 |
| 780181 | 1689 | 1708 | 41922 | 41941 | CTTATGATGAAATTCTGTAT | 60 | 307 |
| 780182 | 1734 | 1753 | 41967 | 41986 | TTTGTGAATATCATTCTTGA | 52 | 308 |
| 780183 | 1779 | 1798 | 52693 | 52712 | AATCCCAGGATTTCCAATGA | 78 | 309 |
| 780184 | 1786 | 1805 | 52700 | 52719 | ATTTCTGAATCCCAGGATTT | 119 | 310 |
| 780185 | 1789 | 1808 | 52703 | 52722 | CACATTTCTGAATCCCAGGA | 41 | 311 |
| 780186 | 1793 | 1812 | 52707 | 52726 | AATCCACATTTCTGAATCCC | 70 | 312 |
| 780187 | 1796 | 1815 | 52710 | 52729 | TTTAATCCACATTTCTGAAT | 80 | 313 |
| 780188 | 1826 | 1845 | 52740 | 52759 | TCAGGAAAATGTACAATAGA | 128 | 314 |
| 780189 | 1873 | 1892 | 52787 | 52806 | GAAGCACTGAATCCATAGCA | 34 | 315 |
| 780190 | 1919 | 1938 | N/A | N/A | CCCAGACACTGAATTTCTTG | 56 | 37 |
| 780191 | 1963 | 1982 | 53003 | 53022 | TGAACACATTCTTCTTTGTA | 64 | 316 |
| 780192 | 2009 | 2028 | 53049 | 53068 | TATAAGCTGGAAACCAGAAT | 86 | 317 |
| 780193 | 2053 | 2072 | N/A | N/A | TCTGAAATCCTTTAGTCTGT | 106 | 318 |
| 780194 | 2097 | 2116 | 56031 | 56050 | CAGCTTAGAAAAAGATGCTG | 66 | 319 |
| 780195 | 2141 | 2160 | 56075 | 56094 | GACATTTGATGGAATATTAC | 45 | 320 |
| 780196 | 2185 | 2204 | N/A | N/A | AGAGGTTTAGAAACTGTTGA | 44 | 321 |
| 780197 | 2229 | 2248 | 56237 | 56256 | TTTTAAGTAATCATCCATAG | 70 | 322 |
| 780198 | 2273 | 2292 | 56281 | 56300 | ATGATGCTGTTATTCTGATC | 71 | 323 |
| 780199 | 2317 | 2336 | 56325 | 56344 | TTGCTTGATTGGCATCTGCT | 41 | 324 |
| 780200 | 2356 | 2375 | N/A | N/A | CTTTCTCACATACCTGACAA | 59 | 325 |

TABLE 3-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780201 | 2359 | 2378 | N/A | N/A | TCTCTTTCTCACATACCTGA | 50 | 326 |
| 780254 | 4111 | 4130 | 86606 | 86625 | GTTTCATTCGGTTATAAGGC | 36 | 235 |

TABLE 4

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693428 | 2361 | 2380 | 61982 | 62001 | GCTCTCTTTCTCACATACCT | 28 | 73 |
| 693430 | 5537 | 5556 | 100526 | 100545 | GCCCATTTCTTCAACAGAGT | 25 | 89 |
| 780254 | 4111 | 4130 | 86606 | 86625 | GTTTCATTCGGTTATAAGGC | 23 | 235 |
| 780276 | 4929 | 4948 | 93390 | 93409 | CTGTGCCATGATTTTACAAA | 62 | 327 |
| 780277 | 4973 | 4992 | 98121 | 98140 | CCCTTAGGGTGTTTTGGACA | 65 | 328 |
| 780278 | 5019 | 5038 | 98167 | 98186 | CCTTTTTTTGAAAGAAATT | 154 | 329 |
| 780279 | 5063 | 5082 | 98211 | 98230 | TCTAGGAGCTTAAAATACTG | 112 | 330 |
| 780280 | 5109 | 5128 | 98257 | 98276 | AACCAGCAAATATTCTTCTC | 83 | 331 |
| 780281 | 5169 | 5188 | 99175 | 99194 | TTCAGAGTTCTCACAATGGG | 72 | 332 |
| 780282 | 5217 | 5236 | 99223 | 99242 | CCAAAATCCCATTGGAAAAT | 88 | 333 |
| 780283 | 5261 | 5280 | 99267 | 99286 | AGCATGTAAGGTGAAATCTC | 88 | 334 |
| 780284 | 5305 | 5324 | 100157 | 100176 | GCCAATACATTCTGTTTGGG | 25 | 335 |
| 780285 | 5349 | 5368 | 100201 | 100220 | CAGACAATAAGCTTCAGGAG | 82 | 336 |
| 780286 | 5396 | 5415 | 100248 | 100267 | ATTTTTAAGAAACTCTCTGG | 86 | 337 |
| 780287 | 5440 | 5459 | 100429 | 100448 | CTTGGCCCAAAAGAATACAG | 69 | 338 |
| 780288 | 5488 | 5507 | 100477 | 100496 | GCAACCCAGGAAACCATTCT | 83 | 339 |
| 780289 | 5532 | 5551 | 100521 | 100540 | TTTCTTCAACAGAGTTTCTC | 157 | 340 |
| 780290 | 5535 | 5554 | 100524 | 100543 | CCATTTCTTCAACAGAGTTT | 64 | 341 |
| 780291 | 5539 | 5558 | 100528 | 100547 | ATGCCCATTTCTTCAACAGA | 59 | 342 |
| 780292 | 5542 | 5561 | 100531 | 100550 | ATAATGCCCATTTCTTCAAC | 135 | 343 |
| 780293 | 5577 | 5596 | 100566 | 100585 | GATTTTTGATGTTCTTCAC | 64 | 344 |
| 780294 | 5622 | 5641 | N/A | N/A | TAAGAGATCTCCTTCCTCTG | 77 | 345 |
| 780295 | 5666 | 5685 | 101304 | 101323 | ATCTGAGATATTGGAATGGT | 86 | 346 |
| 780296 | 5710 | 5729 | 101348 | 101367 | ACATAATATTTCTAGGCAGG | 48 | 347 |
| 780297 | 5754 | 5773 | 101392 | 101411 | GAGAAACTCTGGAGCTTGTT | 138 | 348 |
| 780298 | 5798 | 5817 | 106489 | 106508 | TCATAGGCTGCTCGGTAAAC | 109 | 349 |

TABLE 4-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780299 | 5842 | 5861 | 106533 | 106552 | GTGATGTATGTTTATTAAAA | 88* | 350 |
| 780300 | 5886 | 5905 | 113083 | 113102 | GTGGAGGTGGCAAAGCACCA | 50* | 351 |
| 780301 | 5946 | 5965 | 113143 | 113162 | CTCCATCACCAACATCCGGG | 121 | 352 |
| 780302 | 5990 | 6009 | 113187 | 113206 | TTGTCCTGCTGAAGCAGGCG | 136 | 353 |
| 780303 | 6034 | 6053 | 113231 | 113250 | CGTGGAGTGCAATCCTGTGC | 89 | 354 |
| 780304 | 6078 | 6097 | 118411 | 118430 | GTATATAATCATGGCTGAGT | 68 | 355 |
| 780305 | 6122 | 6141 | 118455 | 118474 | GGATACAGTGTGAAAAGCAG | 61 | 356 |
| 780306 | 6166 | 6185 | 118499 | 118518 | GAGCAATGCCGTAGTCAGCA | 61 | 357 |
| 780307 | 6170 | 6189 | 118503 | 118522 | TACTGAGCAATGCCGTAGTC | 75 | 358 |
| 780308 | 6173 | 6192 | 118506 | 118525 | CAGTACTGAGCAATGCCGTA | 61 | 359 |
| 780309 | 6175 | 6194 | 118508 | 118527 | AGCAGTACTGAGCAATGCCG | 58 | 360 |
| 780310 | 6177 | 6196 | 118510 | 118529 | ACAGCAGTACTGAGCAATGC | 70 | 361 |
| 780311 | 6180 | 6199 | 118513 | 118532 | TCTACAGCAGTACTGAGCAA | 88 | 362 |
| 780312 | 6211 | 6230 | 118544 | 118563 | CTGGTGTGCCCTCTGATGTT | 97 | 363 |
| 780313 | 6255 | 6274 | 124886 | 124905 | GTTATAAATGACATTTCCTC | 77 | 364 |
| 780314 | 6299 | 6318 | 124930 | 124949 | ATGTCATAGAGTAGTAAACC | 111 | 365 |
| 780315 | 6345 | 6364 | 124976 | 124995 | ATTTGGAAACTTCAAACCCT | 60 | 366 |
| 780316 | 6389 | 6408 | N/A | N/A | ACTGGATCAGGTAATTTTCC | 62 | 367 |
| 780317 | 6433 | 6452 | 126549 | 126568 | TTAATTTCTCAACCATAGGC | 120 | 368 |
| 780318 | 6477 | 6496 | 126593 | 126612 | AGAAGTAGGCCTTTCTTGAG | 95 | 369 |
| 780319 | 6521 | 6540 | 129666 | 129685 | AGACAGACTAATTCAGCTGA | 78 | 370 |
| 780320 | 6568 | 6587 | 129713 | 129732 | CCATGCATTCAACAATTACG | 57 | 371 |
| 780321 | 6612 | 6631 | 129757 | 129776 | GCCCAGCCAAATGCTTGCAT | 41 | 372 |
| 780322 | 6656 | 6675 | 129801 | 129820 | TTTAAGTCAAGAAATGAGAG | 92 | 373 |
| 780323 | 6700 | 6719 | 132410 | 132429 | ATATTCTACTATCAGCAACT | 97 | 374 |
| 780324 | 6744 | 6763 | 132454 | 132473 | CCAGCTTTCCTTTTCAACAG | 132 | 375 |
| 780325 | 6788 | 6807 | 132498 | 132517 | GTATTGATGACCAGGAGAGT | 92 | 376 |
| 780326 | 6832 | 6851 | 132542 | 132561 | AATCAGTCATCTTTTCTAGG | 98 | 377 |
| 780327 | 6876 | 6895 | N/A | N/A | TTTGCTTTGCTTGGAAAAGG | 85 | 378 |
| 780328 | 6920 | 6939 | 134252 | 134271 | GCTAACTTGCCATCAGCGGT | 84 | 379 |
| 780329 | 6964 | 6983 | 137368 | 137387 | AAGGAGCAGCTCCTTTAAGC | 65 | 380 |
| 780330 | 7008 | 7027 | 137412 | 137431 | ACACATCAATGGAGTACTGA | 51 | 381 |
| 780331 | 7052 | 7071 | 137456 | 137475 | CCCCACATTACATTTCTTTC | 124 | 382 |
| 780332 | 7096 | 7115 | 137500 | 137519 | TGGTGAAATCATTAGAAAAG | 119 | 383 |
| 780333 | 7141 | 7160 | N/A | N/A | CATAAGAAAACAGTTGGCTT | 61 | 384 |
| 780334 | 7185 | 7204 | 141546 | 141565 | AGTGTCTACCACCACTGTTA | 124 | 385 |

TABLE 4-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780335 | 7229 | 7248 | 141590 | 141609 | CACACTTCCACAACAGGGCT | 116 | 386 |
| 780336 | 7273 | 7292 | 141634 | 141653 | GCACGCAGTCTATTAGTCCA | 60 | 387 |
| 780337 | 7318 | 7337 | 142966 | 142985 | GTTTTGATTCCTTGTTTTCT | 92 | 388 |
| 780338 | 7362 | 7381 | 143010 | 143029 | CTGAAGGCAGAGGGTTTTCA | 78 | 389 |
| 780339 | 7406 | 7425 | 143054 | 143073 | AAAATATGGCCTCCTCCAGT | 82 | 390 |
| 780340 | 7457 | 7476 | 143105 | 143124 | CAAAAGTTGTAAATTACACG | 77 | 391 |
| 780341 | 7501 | 7520 | N/A | N/A | TAAGGCTTCCTAGCTGTGCT | 89 | 392 |
| 780342 | 7545 | 7564 | 145148 | 145167 | TTCAGTATTTTTCCGGTTGT | 121 | 393 |
| 780343 | 7589 | 7608 | 145758 | 145777 | CAAACGGTCAAGCAAGATTG | 138 | 394 |
| 780344 | 7636 | 7655 | 145805 | 145824 | CAATGTGTTTTTCTAAATTT | 102 | 395 |
| 780345 | 7688 | 7707 | 145857 | 145876 | TCTTACTCAACAGATGTTCG | 92 | 396 |
| 780346 | 7732 | 7751 | 145901 | 145920 | GAGGAGAGAATAATTTTCCT | 91 | 397 |
| 780347 | 7776 | 7795 | 145945 | 145964 | GAGTACCCTTTCCATGTGAA | 34 | 398 |
| 780348 | 7822 | 7841 | 145991 | 146010 | AAAATAATAACATTCCTTCA | 96 | 399 |
| 780349 | 7867 | 7886 | 146036 | 146055 | AAAATACACATTTACTGGTA | 115 | 400 |
| 780350 | 7912 | 7931 | 146081 | 146100 | CTGGTATTTATAAGAAATAT | 91 | 401 |
| 780351 | 7960 | 7979 | 146129 | 146148 | ATTAGGTACTTCACAGATTT | 140 | 402 |

TABLE 5

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693428 | 2361 | 2380 | 61982 | 62001 | GCTCTCTTTCTCACATACCT | 30 | 73 |
| 780254 | 4111 | 4130 | 86606 | 86625 | GTTTCATTCGGTTATAAGGC | 39 | 235 |
| 780352 | 8004 | 8023 | 146173 | 146192 | AACAAAAAATTATCGGCCTT | 79 | 403 |
| 780353 | 8052 | 8071 | 146221 | 146240 | CTTAAGCACAGAATTTAAAA | 94 | 404 |
| 780354 | 8096 | 8115 | 146265 | 146284 | ATACCGTGCAGATTTCTAGA | 91 | 405 |
| 780355 | 8140 | 8159 | 146309 | 146328 | AAGAAGGAATACATTACATG | 148 | 406 |
| 780356 | 8186 | 8205 | 146355 | 146374 | TTTGAATATTTACAAGCATA | 163 | 407 |
| 780357 | 8201 | 8220 | 146370 | 146389 | ATTAGTGCAAATTCATTTGA | 79 | 408 |
| 780358 | 8206 | 8225 | 146375 | 146394 | ACTTTATTAGTGCAAATTCA | 118 | 409 |
| 780359 | 8211 | 8230 | 146380 | 146399 | AAAGGACTTTATTAGTGCAA | 48 | 410 |
| 780360 | 8216 | 8235 | 146385 | 146404 | CCAACAAAGGACTTTATTAG | 75 | 411 |

TABLE 5-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780361 | 8221 | 8240 | 146390 | 146409 | ACATACCAACAAAGGACTTT | 98 | 412 |
| 780362 | 8231 | 8250 | 146400 | 146419 | AAGAGAATTCACATACCAAC | 164 | 413 |
| 780363 | 8275 | 8294 | 146444 | 146463 | AATTGAGTGAAGTTGTGTAA | 133 | 414 |
| 780364 | 8319 | 8338 | 146488 | 146507 | ATGTCATGTTTTTCATTAG | 157 | 415 |
| 780365 | 8364 | 8383 | 146533 | 146552 | AAAGAGAGTTTCTGTGTCTT | 146 | 416 |
| 780366 | 8408 | 8427 | 146577 | 146596 | ACAACTCTATTATGTCTAGG | 161 | 417 |
| 780367 | 8452 | 8471 | 146621 | 146640 | TATACAAAATTCAGGGTATC | 94 | 418 |
| 780368 | 8515 | 8534 | 146684 | 146703 | TAGTGGTATGAATAAAAAA | 107 | 419 |
| 780369 | 8561 | 8580 | 146730 | 146749 | AGATGAATATAAGCATTAGA | 98 | 420 |
| 780370 | 8605 | 8624 | 146774 | 146793 | TATCTGAATGATGTAGGATC | 118 | 421 |
| 780371 | 8650 | 8669 | 146819 | 146838 | GTAGGAGCTGTGGAATTCTA | 125 | 422 |
| 780372 | 8694 | 8713 | 146863 | 146882 | CTTCAGCAACTGAAAAGTGT | 132 | 423 |
| 780373 | 8741 | 8760 | 146910 | 146929 | CTAGGGTGGCAGATATTTTT | 126 | 424 |
| 780374 | 8785 | 8804 | 146954 | 146973 | TATTGTGGTAAGCTATGTAA | 106 | 425 |
| 780375 | 8829 | 8848 | 146998 | 147017 | AAATGACCTCAAATTATTAC | 84 | 426 |
| 780376 | 8873 | 8892 | 147042 | 147061 | GGTCAGGGCCAAAGAATTTA | 130 | 427 |
| 780377 | 8917 | 8936 | 147086 | 147105 | ACTAGTTGTCCTATCACAGG | 81 | 428 |
| 780378 | 8962 | 8981 | 147131 | 147150 | GTTTTCACATAGTAAAATGC | 47 | 429 |
| 780379 | 9006 | 9025 | 147175 | 147194 | TCATCTTTAAGAATTTGATT | 94 | 430 |
| 780380 | 9050 | 9069 | 147219 | 147238 | ATAACAAGTTAAAGCATAGC | 58 | 431 |
| 780381 | 9094 | 9113 | 147263 | 147282 | CTGGAACAAAGAGCTCTATT | 97 | 432 |
| 780382 | 9143 | 9162 | 147312 | 147331 | CTTTGGTAAAAAAAATTGCA | 125 | 433 |
| 780383 | 9183 | 9202 | 147352 | 147371 | ATTATTCCATTTAAATATGG | 125 | 434 |
| 780384 | 9188 | 9207 | 147357 | 147376 | CCTTTATTATTCCATTTAAA | 77 | 435 |
| 780385 | 9193 | 9212 | 147362 | 147381 | AAAAACCTTTATTATTCCAT | 93 | 436 |
| 780386 | N/A | N/A | 82225 | 82244 | CCTCTTTCAGTTTATTGTGA | 87 | 437 |
| 780387 | N/A | N/A | 82365 | 82384 | ATAGTTGACAGGAATTTATA | 71 | 438 |
| 780388 | N/A | N/A | 82505 | 82524 | GTTTAGTGGAAGTATTAAGG | 51 | 439 |
| 780389 | N/A | N/A | 82645 | 82664 | TATATGATAACATCACACAT | 106 | 440 |
| 780390 | N/A | N/A | 82785 | 82804 | TTCCATAGAACACTCTTTAT | 219 | 441 |
| 780391 | N/A | N/A | 82925 | 82944 | AGGAAATTATGCTGTGTTAC | 108 | 442 |
| 780392 | N/A | N/A | 83065 | 83084 | AGAAAAATGGTTTATTTAAG | 96 | 443 |
| 780394 | N/A | N/A | 79043 | 79062 | ACACTGACCATACACAAGCT | 100 | 444 |
| 780395 | N/A | N/A | 143142 | 143161 | GCCTAGCTGTGCTGTCATCA | 126 | 445 |
| 780396 | N/A | N/A | 143282 | 143301 | TACCAGTCTTATGTTTCACT | 108 | 446 |
| 780397 | N/A | N/A | 143422 | 143441 | ATTTCCCATTTTTGCCTTAG | 62 | 447 |

TABLE 5-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780398 | N/A | N/A | 143565 | 143584 | TGTATTGCTGCAAGAAAAAA | 90 | 448 |
| 780399 | N/A | N/A | 143705 | 143724 | ACGCAAATATATTTATGCAG | 74 | 449 |
| 780400 | N/A | N/A | 143845 | 143864 | ATGTTCAAAACATTCATTAT | 137 | 450 |
| 780401 | N/A | N/A | 143985 | 144004 | TAATAGTTTACAGTCATTAA | 111 | 451 |
| 780402 | N/A | N/A | 144125 | 144144 | TATAACTTCAGTTATAAGCA | 92 | 452 |
| 780403 | N/A | N/A | 144265 | 144284 | AGACAAGCAAGATCTGGTAG | 118 | 453 |
| 780404 | N/A | N/A | 144405 | 144424 | ACAGGAGCTAACATTTCAAA | 123 | 454 |
| 780405 | N/A | N/A | 144553 | 144572 | AACCGTCTTGGAGTTTATAT | 56 | 455 |
| 780406 | N/A | N/A | 144694 | 144713 | TATACTGATACTATGTCAAA | 193 | 456 |
| 780407 | N/A | N/A | 144834 | 144853 | CAGTATTTATACATTACCCT | 150 | 457 |
| 780408 | N/A | N/A | 144974 | 144993 | TTTTCTAGGTGACCCTTCAA | 119 | 458 |
| 780409 | N/A | N/A | 145168 | 145187 | CCTTTCTGCTTTTGTGTACC | 93 | 459 |
| 780410 | N/A | N/A | 145310 | 145329 | AAGTTCTTTACACTATAAAC | 112 | 460 |
| 780411 | N/A | N/A | 145450 | 145469 | GACATTATGTAGATATAGAT | 80 | 461 |
| 780412 | N/A | N/A | 145597 | 145616 | ATTATTATTTATAAAAAACT | 124 | 462 |
| 780413 | N/A | N/A | 145740 | 145759 | TGTATCTCTAGAAAAAGAAA | 111 | 463 |
| 780414 | N/A | N/A | 3862 | 3881 | AATCACAGTCAGAGGTTCCT | 120 | 464 |
| 780415 | N/A | N/A | 4122 | 4141 | CCCTTTTCCAAACTATTCAT | 119 | 465 |
| 780416 | N/A | N/A | 4157 | 4176 | GTGACAAAGTTGCATTTTAT | 108 | 466 |
| 780417 | N/A | N/A | 4174 | 4193 | TCTACAAGAGTTTGCTAGTG | 97 | 467 |
| 780418 | N/A | N/A | 4185 | 4204 | AAGTGCTGAACTCTACAAGA | 134 | 468 |
| 780419 | N/A | N/A | 6986 | 7005 | CTCTCACTTCGCTATGACAG | 116 | 469 |
| 780420 | N/A | N/A | 7557 | 7576 | AACCGTCAATTTTCTAAAGA | 110 | 470 |
| 780421 | N/A | N/A | 7842 | 7861 | CTATTCAATTAAAAGCTTAT | 122 | 471 |
| 780422 | N/A | N/A | 8002 | 8021 | CTCAAGGAAAAAACCTGTTT | 125 | 472 |
| 780423 | N/A | N/A | 8263 | 8282 | AAAGGCGGCAATTTCTGATA | 130 | 473 |
| 780424 | N/A | N/A | 8791 | 8810 | TATACTTGACATGGTCAAAA | 177 | 474 |
| 780425 | N/A | N/A | 8820 | 8839 | CTCCAATTCATTCTATTATA | 89 | 475 |
| 780426 | N/A | N/A | 11028 | 11047 | AACATAGCTGGTAAAATTAC | 143 | 476 |
| 780427 | N/A | N/A | 11977 | 11996 | AAACATTCAATGAATAGAAG | 86 | 477 |
| 780428 | N/A | N/A | 12155 | 12174 | ACGGAAGAAATTTTTCTTCA | 116 | 478 |

TABLE 6

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693428 | 2361 | 2380 | 61982 | 62001 | GCTCTCTTTCTCACATACCT | 38 | 73 |
| 780254 | 4111 | 4130 | 86606 | 86625 | GTTTCATTCGGTTATAAGGC | 18 | 235 |
| 780429 | N/A | N/A | 12244 | 12263 | CCAGTCTTCGATTCTCTGCC | 135 | 479 |
| 780430 | N/A | N/A | 12353 | 12372 | TTGGCTTTACATTATTGGAA | 41 | 480 |
| 780431 | N/A | N/A | 12761 | 12780 | GTGGCCGTTGCTCACGCCTG | 130 | 481 |
| 780432 | N/A | N/A | 12910 | 12929 | TCTTAGACATGTTGATATAT | 136 | 482 |
| 780433 | N/A | N/A | 14791 | 14810 | TCTTAGCAGGACTGATGAGG | 75 | 483 |
| 780434 | N/A | N/A | 15592 | 15611 | CAAATCAATTCATTACCAAG | 91 | 484 |
| 780435 | N/A | N/A | 15874 | 15893 | GCTCTAGATCTTTATAAATG | 102 | 485 |
| 780436 | N/A | N/A | 16258 | 16277 | TACTTTTCCCAGTATAAGCC | 114 | 486 |
| 780437 | N/A | N/A | 16448 | 16467 | CCTTATGCCTTGTTAAGCAA | 84 | 487 |
| 780438 | N/A | N/A | 16899 | 16918 | GAAATTAGACTGGTAAACTG | 113 | 488 |
| 780439 | N/A | N/A | 16920 | 16939 | ATCCCATTCTGGGAACTGCA | 61 | 489 |
| 780440 | N/A | N/A | 17294 | 17313 | TTGTATTCCTTGCAAAATGT | 123 | 490 |
| 780441 | N/A | N/A | 17451 | 17470 | TTAGTTGCAAGATAGAACAT | 82 | 491 |
| 780442 | N/A | N/A | 17796 | 17815 | ATGGTCTAGTTTCCACAGTA | 44 | 492 |
| 780443 | N/A | N/A | 18025 | 18044 | AGTAAGTTCCATTTGGAGTC | 61 | 493 |
| 780444 | N/A | N/A | 18279 | 18298 | GGGAAATTCTAGAGAAAACT | 64 | 494 |
| 780445 | N/A | N/A | 18439 | 18458 | TGTGAAGCAGCCCTTCCTAA | 128 | 495 |
| 780446 | N/A | N/A | 19114 | 19133 | ACTTCAGGTCACACCTTCAT | 66 | 496 |
| 780447 | N/A | N/A | 19502 | 19521 | CACATCAAATTAATTTCTTC | 95 | 497 |
| 780448 | N/A | N/A | 19553 | 19572 | AAACAGAATATGAACCATTA | 129 | 498 |
| 780449 | N/A | N/A | 19583 19556 | 19602 19575 | ACAAAACAGAATATGAACCA | 71 | 499 |
| 780450 | N/A | N/A | 19586 19559 | 19605 19578 | AAAACAAAACAGAATATGAA | 143 | 500 |
| 780451 | N/A | N/A | 19589 19562 | 19608 19581 | TACAAAACAAAACAGAATAT | 190 | 501 |
| 780452 | N/A | N/A | 19592 | 19611 | TGTGGATAAGAAAACATTGT | 119 | 502 |
| 780453 | N/A | N/A | 19953 20195 | 19972 20214 | TCTTGACTTTTGCATTATGA | 76 | 503 |
| 780454 | N/A | N/A | 20454 22583 | 20473 22602 | AAATGTTAACTGTTCTTTTT | 60 | 504 |
| 780455 | N/A | N/A | 20713 | 20732 | TCAGCTATGACCTGTTTCCT | 34 | 505 |
| 780456 | N/A | N/A | 20716 | 20735 | AAATCAGCTATGACCTGTTT | 128 | 506 |
| 780457 | N/A | N/A | 21493 | 21512 | GTAAAAATACTATGCTGTT | 87 | 507 |
| 780458 | N/A | N/A | 22339 | 22358 | CAAACATTAACAATTTTGCT | 118 | 508 |
| 780459 | N/A | N/A | 23396 | 23415 | ACCTCTAATAAATTGTGCTG | 73 | 509 |

TABLE 6-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780460 | N/A | N/A | 23640 | 23659 | GCATGGAATAGTAAAGGCCC | 61 | 510 |
| 780461 | N/A | N/A | 23970 | 23989 | ATTGCTAGGTAGAGAACTTA | 50 | 511 |
| 780462 | N/A | N/A | 24452 | 24471 | TCTAATAAATGACCAAGTTA | 76 | 512 |
| 780463 | N/A | N/A | 24633 | 24652 | GAACTTTATATATAGTTATC | 92 | 513 |
| 780464 | N/A | N/A | 24916 | 24935 | CTTGTGGGAAAGCATGAATC | 67 | 514 |
| 780465 | N/A | N/A | 25082 | 25101 | TCCAACAGTTAACGATCATT | 51 | 515 |
| 780466 | N/A | N/A | 25273 | 25292 | GATATAATCATGATACTAGA | 57 | 516 |
| 780467 | N/A | N/A | 25433 | 25452 | CAGTTTTAGTCATATAACAA | 108 | 517 |
| 780468 | N/A | N/A | 25435 | 25454 | TACAGTTTTAGTCATATAAC | 155 | 518 |
| 780469 | N/A | N/A | 25637 25667 25697 25727 | 25656 25686 25716 25746 | ATATGTATATTTATATACAT | 171 | 519 |
| 780470 | N/A | N/A | 25640 25670 25700 25730 25794 25858 | 25659 25689 25719 25749 25813 25877 | TAAATATGTATATTTATATA | 149 | 520 |
| 780471 | N/A | N/A | 25643 25673 25703 25733 25797 25861 | 25662 25692 25722 25752 25816 25880 | GTATAAATATGTATATTTAT | 163 | 521 |
| 780472 | N/A | N/A | 25646 25676 25706 25736 25800 25864 | 25665 25695 25725 25755 25819 25883 | TGTGTATAAATATGTATATT | 96 | 522 |
| 780473 | N/A | N/A | 25649 25679 25709 25739 25803 25867 | 25668 25698 25728 25758 25822 25886 | ATCTGTGTATAAATATGTAT | 106 | 523 |
| 780474 | N/A | N/A | 25652 25682 25712 25742 25806 25870 | 25671 25701 25731 25761 25825 25889 | TACATCTGTGTATAAATATG | 138 | 524 |
| 780475 | N/A | N/A | 25655 25685 25715 25745 25809 25873 | 25674 25704 25734 25764 25828 25892 | ATATACATCTGTGTATAAAT | 179 | 525 |
| 780476 | N/A | N/A | 25658 25688 25718 25748 | 25677 25707 25737 25767 | TTTATATACATCTGTGTATA | 129 | 526 |

TABLE 6-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| | | | 25812 | 25831 | | | |
| | | | 25876 | 25895 | | | |
| 780477 | N/A | N/A | 25661 | 25680 | ATATTTATATACATCTGTGT | 66 | 527 |
| | | | 25691 | 25710 | | | |
| | | | 25721 | 25740 | | | |
| | | | 25751 | 25770 | | | |
| | | | 25815 | 25834 | | | |
| | | | 25879 | 25898 | | | |
| 780478 | N/A | N/A | 25664 | 25683 | TGTATATTTATATACATCTG | 55 | 528 |
| | | | 25694 | 25713 | | | |
| | | | 25724 | 25743 | | | |
| | | | 25754 | 25773 | | | |
| | | | 25818 | 25837 | | | |
| | | | 25882 | 25901 | | | |
| 780479 | N/A | N/A | 25755 | 25774 | TTGTATATTTATATACATCT | 88 | 529 |
| | | | 25819 | 25838 | | | |
| | | | 25883 | 25902 | | | |
| 780480 | N/A | N/A | 25758 | 25777 | TATTTGTATATTTATATACA | 164 | 530 |
| | | | 25822 | 25841 | | | |
| | | | 25886 | 25905 | | | |
| 780481 | N/A | N/A | 25761 | 25780 | TTATATTTGTATATTTATAT | 156 | 531 |
| | | | 25825 | 25844 | | | |
| | | | 25889 | 25908 | | | |
| 780482 | N/A | N/A | 25764 | 25783 | TATTTATATTTGTATATTTA | 178 | 532 |
| | | | 25828 | 25847 | | | |
| | | | 25892 | 25911 | | | |
| 780483 | N/A | N/A | 25767 | 25786 | ATATATTTATATTTGTATAT | 96 | 533 |
| | | | 25831 | 25850 | | | |
| | | | 25895 | 25914 | | | |
| 780484 | N/A | N/A | 25770 | 25789 | TGTATATATTTATATTTGTA | 110 | 534 |
| | | | 25834 | 25853 | | | |
| | | | 25898 | 25917 | | | |
| 780485 | N/A | N/A | 25773 | 25792 | AAATGTATATATTTATATTT | 102 | 535 |
| | | | 25837 | 25856 | | | |
| | | | 25901 | 25920 | | | |
| 780486 | N/A | N/A | 25776 | 25795 | TATAAATGTATATATTTATA | 144 | 536 |
| | | | 25840 | 25859 | | | |
| | | | 25904 | 25923 | | | |
| 780487 | N/A | N/A | 25779 | 25798 | ATATATAAATGTATATATTT | 122 | 537 |
| | | | 25843 | 25862 | | | |
| | | | 25907 | 25926 | | | |
| 780488 | N/A | N/A | 25782 | 25801 | TTTATATATAAATGTATATA | 106 | 538 |
| | | | 25846 | 25865 | | | |
| | | | 25910 | 25929 | | | |
| 780489 | N/A | N/A | 25785 | 25804 | ATATTTATATATAAATGTAT | 139 | 539 |
| | | | 25849 | 25868 | | | |
| | | | 25913 | 25932 | | | |
| 780490 | N/A | N/A | 25788 | 25807 | TGTATATTTATATATAAATG | 98 | 540 |
| | | | 25852 | 25871 | | | |
| 780491 | N/A | N/A | 25791 | 25810 | ATATGTATATTTATATATAA | 110 | 541 |
| | | | 25855 | 25874 | | | |
| 780492 | N/A | N/A | 26102 | 26121 | CCATGTTTAGAAGAAATACT | 57 | 542 |
| 780493 | N/A | N/A | 26738 | 26757 | ATTACATAGTTTGGCAAAAC | 107 | 543 |

TABLE 6-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780494 | N/A | N/A | 27287 | 27306 | ACTGCAGAAATATGTACCTT | 89 | 544 |
| 780495 | N/A | N/A | 27387 | 27406 | CACCCCAGGAAGAAGTCCCA | 100 | 545 |
| 780496 | N/A | N/A | 27872 | 27891 | GTTAAATTACCTTTAACATA | 174 | 546 |
| 780497 | N/A | N/A | 28186 | 28205 | TCCTTGAAAGTATCCTCTAC | 90 | 547 |
| 780498 | N/A | N/A | 29148 | 29167 | CCATCCTATCCAGATAAATA | 137 | 548 |
| 780499 | N/A | N/A | 29220 | 29239 | AGGTGTGCTTTAGGAGAAGC | 34 | 549 |
| 780500 | N/A | N/A | 32958 | 32977 | TTATTAAGGCAGAACTCCAA | 92 | 550 |
| 780501 | N/A | N/A | 33224 | 33243 | CATCCCAAGTGCCTACAGAC | 146 | 551 |
| 780502 | N/A | N/A | 34124 | 34143 | ACTTTGAAAGTGGCAGAAAA | 125 | 552 |
| 780503 | N/A | N/A | 34685 | 34704 | TTACAGTTATTTTCACAAAG | 89 | 553 |
| 780504 | N/A | N/A | 34756 | 34775 | CAAACATTATAATTTCTATA | 195 | 554 |
| 780505 | N/A | N/A | 34881 | 34900 | TATAAGCATGTGGAGGTATC | 90 | 555 |

TABLE 7

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693428 | 2361 | 2380 | 61982 | 62001 | GCTCTCTTTCTCACATACCT | 49 | 73 |
| 780254 | 4111 | 4130 | 86606 | 86625 | GTTTCATTCGGTTATAAGGC | 33 | 235 |
| 780506 | N/A | N/A | 35751 | 35770 | TGCTATGTGCTATACAATTA | 75 | 556 |
| 780507 | N/A | N/A | 36381 | 36400 | CTTACAAGTCTGCAGTTACG | 72 | 557 |
| 780508 | N/A | N/A | 36600 | 36619 | TGCCCAGAATCTACAGAATC | 99 | 558 |
| 780509 | N/A | N/A | 36661 | 36680 | TCCAGGGCTGCAACTGTACA | 107 | 559 |
| 780510 | N/A | N/A | 36909 | 36928 | GTTCTGTGGACACTGAGATA | 91 | 560 |
| 780511 | N/A | N/A | 36965 | 36984 | GCTTTGCTTGTTAACTGAAA | 66 | 561 |
| 780512 | N/A | N/A | 37065 | 37084 | TTTCTCTCAGGTATTTAAGC | 74 | 562 |
| 780513 | N/A | N/A | 37116 | 37135 | GACTTCTTATAAGGTATTTT | 65 | 563 |
| 780514 | N/A | N/A | 37198 | 37217 | GGCTGGTACCCAAACTTGTC | 91 | 564 |
| 780515 | N/A | N/A | 37201 | 37220 | CAAGGCTGGTACCCAAACTT | 72 | 565 |
| 780516 | N/A | N/A | 37303 | 37322 | ACAATCCCAGCAGGTAGGTG | 57 | 566 |
| 780517 | N/A | N/A | 37333 | 37352 | ATCCTTCTGACCTACGATGG | 72 | 567 |
| 780518 | N/A | N/A | 37398 | 37417 | CTTTGAACTCATAAGATAGA | 83 | 568 |
| 780519 | N/A | N/A | 37548 | 37567 | GCTTATTGAAAGACTGATCT | 88 | 569 |
| 780520 | N/A | N/A | 38071 | 38090 | GAAGGAAGAGAACAGGTATG | 94 | 570 |

TABLE 7-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780521 | N/A | N/A | 38396 | 38415 | CGCCTCTCTCACGCTGCCTG | 92 | 571 |
| 780522 | N/A | N/A | 38720 | 38739 | TGCAAACAATTTTAATAAAC | 96 | 572 |
| 780523 | N/A | N/A | 38837 | 38856 | TGACTACCATGGACCTCCAA | 83 | 573 |
| 780524 | N/A | N/A | 38855 | 38874 | CCTTCACTGGGTCTCACTTG | 91 | 574 |
| 780525 | N/A | N/A | 39213 | 39232 | ACTAAGCTGAAACTATGAAT | 104 | 575 |
| 780526 | N/A | N/A | 39521 | 39540 | CTGATTGATTGTTAACTAAC | 79 | 576 |
| 780527 | N/A | N/A | 40301 | 40320 | TTATAAGTAAGTAGATTTGA | 111 | 577 |
| 780528 | N/A | N/A | 40577 | 40596 | AGATTGTTGCACAAATATTT | 95 | 578 |
| 780529 | N/A | N/A | 40733 | 40752 | TACTATTCAAATGGATATAA | 116 | 579 |
| 780530 | N/A | N/A | 41316 | 41335 | GAACTATGCTAAAAACACTA | 90 | 580 |
| 780531 | N/A | N/A | 41593 | 41612 | TTTTGTGTGAGTAGGCTGTG | 83 | 581 |
| 780532 | N/A | N/A | 42005 | 42024 | TATATTCAACATACCCTGTT | 100 | 582 |
| 780533 | N/A | N/A | 43265 | 43284 | TACAACATAAATTCTTGCCA | 57 | 583 |
| 780534 | N/A | N/A | 45337 | 45356 | AATCTTACTGTCAATATAGT | 101 | 584 |
| 780535 | N/A | N/A | 45380 | 45399 | TTAAAAGGAAGTAACCATGT | 44 | 585 |
| 780536 | N/A | N/A | 45462 | 45481 | TGGTATCCCTCCTAAGTGCT | 55 | 586 |
| 780537 | N/A | N/A | 45650 | 45669 | CTCTCTTGGCTCCCGACTGC | 75 | 587 |
| 780538 | N/A | N/A | 46047 | 46066 | TACCTTATTTGGAACTCTGC | 86 | 588 |
| 780539 | N/A | N/A | 46543 | 46562 | TTACTTATATGTAATTTGTT | 77 | 589 |
| 780540 | N/A | N/A | 46567 | 46586 | CATCCTGTAAACCTTTTTTA | 79 | 590 |
| 780541 | N/A | N/A | 47702 | 47721 | AAAGATTAAATTAAGCTGCA | 121 | 591 |
| 780542 | N/A | N/A | 47812 | 47831 | ACATTAGGAATCTCACCTCA | 71 | 592 |
| 780543 | N/A | N/A | 48404 | 48423 | CTGAATATAAATATTATCTA | 229 | 593 |
| 780544 | N/A | N/A | 48835 | 48854 | ATGTATAGCTAGAATGAGGA | 99 | 594 |
| 780545 | N/A | N/A | 48873 | 48892 | AGATGCAACTCAAGAAAACT | 81 | 595 |
| 780546 | N/A | N/A | 48947 50077 | 48966 50096 | TATTTATAAAGCACCTATCT | 85 | 596 |
| 780547 | N/A | N/A | 50094 | 50113 | AAATTATATCAAATTGATAT | 73 | 597 |
| 780548 | N/A | N/A | 51550 | 51569 | TTTTATAGAGGCTGAGGAGA | 98 | 598 |
| 780549 | N/A | N/A | 52154 | 52173 | GCCAAACTTTAAAGATGCAG | 33 | 599 |
| 780550 | N/A | N/A | 53367 | 53386 | CGAATAAACTCAGCTAGCTG | 87 | 600 |
| 780551 | N/A | N/A | 53543 | 53562 | GACAGTTATTATATATCATG | 42 | 601 |
| 780552 | N/A | N/A | 53603 | 53622 | AAATTTATTCTTAATCTCCC | 79 | 602 |

TABLE 7-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780553 | N/A | N/A | 54774 | 54793 | AAAACAAGTGAATGCTACAG | 92 | 603 |
| 780554 | N/A | N/A | 54886 | 54905 | CTCTTATGATGCTGAGTATC | 108 | 604 |
| 780555 | N/A | N/A | 55333 | 55352 | ATGTTTTAATGAAAGATTGG | 86 | 605 |
| 780556 | N/A | N/A | 55870 | 55889 | TTAACTATAGATATATTGGG | 80 | 606 |
| 780557 | N/A | N/A | 55936 | 55955 | GGCAAAATGAATAAACAGTA | 94 | 607 |
| 780558 | N/A | N/A | 56363 | 56382 | TTGAATATTTACCTGACAAA | 107 | 608 |
| 780559 | N/A | N/A | 56837 | 56856 | AGTGTTACACAACTTTGGCC | 120 | 609 |
| 780560 | N/A | N/A | 56947 | 56966 | GAGGGCTTTAAAGAAAGATA | 97 | 610 |
| 780561 | N/A | N/A | 57738 | 57757 | TGTAGTACAGTTGTATCAGG | 84 | 611 |
| 780562 | N/A | N/A | 57907 | 57926 | TAAACCTAATACATAATCCT | 81 | 612 |
| 780563 | N/A | N/A | 57911 | 57930 | TCTTTAAACCTAATACATAA | 102 | 613 |
| 780564 | N/A | N/A | 59330 | 59349 | ATTAGAACCTACTGGACCTT | 89 | 614 |
| 780565 | N/A | N/A | 60045 | 60064 | TTTTCTCTAAGATATGCCAT | 78 | 615 |
| 780566 | N/A | N/A | 60338 | 60357 | GCTCATAGCAAAATTAAAAG | 109 | 616 |
| 780567 | N/A | N/A | 60503 | 60522 | TTTCATTTAATGTAGCACTG | 101 | 617 |
| 780568 | N/A | N/A | 61046 | 61065 | AGCAACTGAGACTTGGATTT | 91 | 618 |
| 780569 | N/A | N/A | 62829 | 62848 | ACATTTAGTGTGAACAAATG | 77 | 619 |
| 780570 | N/A | N/A | 62985 | 63004 | TGCTAGTGAGTGCATCATAA | 120 | 620 |
| 780571 | N/A | N/A | 63074 | 63093 | TGGATGGGTACTTTTCTCTA | 74 | 621 |
| 780572 | N/A | N/A | 63219 | 63238 | AGGTAGAGAGAGAGTAACAC | 92 | 622 |
| 780573 | N/A | N/A | 63229 | 63248 | ATTTAGAGCTAGGTAGAGAG | 93 | 623 |
| 780574 | N/A | N/A | 63326 | 63345 | TGAGAAATAAAGTGCTATAG | 105 | 624 |
| 780575 | N/A | N/A | 63342 | 63361 | TGAATGGTAGTATATGTGAG | 84 | 625 |
| 780576 | N/A | N/A | 63662 | 63681 | ACATTGTGAGGTCAAAAAAG | 98 | 626 |
| 780577 | N/A | N/A | 64157 | 64176 | TCCCTCTCCAATGGGCCCAC | 74 | 627 |
| 780578 | N/A | N/A | 64433 | 64452 | TTCCAGAGTAATATGTTATG | 134 | 628 |
| 780579 | N/A | N/A | 64500 | 64519 | GATAAACCCCAAGAAGGCAA | 76 | 629 |
| 780580 | N/A | N/A | 64878 | 64897 | TACATTATGTATTAGCTCTA | 76 | 630 |
| 780581 | N/A | N/A | 65152 | 65171 | GTGTTCAAGTCATAGAAATG | 88 | 631 |
| 780582 | N/A | N/A | 65840 | 65859 | AACCAATTAGTATAACATTT | 75 | 632 |

TABLE 8

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693428 | 2361 | 2380 | 61982 | 62001 | GCTCTCTTTCTCACATACCT | 39 | 73 |
| 780254 | 4111 | 4130 | 86606 | 86625 | GTTTCATTCGGTTATAAGGC | 30 | 235 |
| 780583 | N/A | N/A | 66279 | 66298 | CTCATTTTTTGCCCTCTCAA | 55 | 633 |
| 780584 | N/A | N/A | 66413 | 66432 | TAATTTTCAAAGCGCATGAA | 66 | 634 |
| 780585 | N/A | N/A | 66417 | 66436 | ATGTTAATTTTCAAAGCGCA | 39 | 635 |
| 780586 | N/A | N/A | 66480 | 66499 | GAAGAAACTTTTTGGATAA | 72 | 636 |
| 780587 | N/A | N/A | 68762 | 68781 | AATAAATTTGGCAACTTATA | 126 | 637 |
| 780588 | N/A | N/A | 68885 | 68904 | GAGAAAGTAACACAAACAAT | 106 | 638 |
| 780589 | N/A | N/A | 69914 | 69933 | CAAATCCTCAATTACAACTT | 91 | 639 |
| 780590 | N/A | N/A | 69919 | 69938 | ACCAACAAATCCTCAATTAC | 98 | 640 |
| 780591 | N/A | N/A | 70220 | 70239 | GGAGATAGAGATCAACATTT | 55 | 641 |
| 780592 | N/A | N/A | 70279 | 70298 | AATTAAGGGCCATATACATA | 79 | 642 |
| 780593 | N/A | N/A | 72795 | 72814 | ACCCAATTATGAGGATAAAA | 41 | 643 |
| 780594 | N/A | N/A | 72902 | 72921 | TCATTTATTGGAGAAGAGGA | 115 | 644 |
| 780595 | N/A | N/A | 73395 | 73414 | AAACCAAACTATGGAGTTTA | 89 | 645 |
| 780596 | N/A | N/A | 75173 | 75192 | AAGTCCTGTCCTCAAAGAGT | 74 | 646 |
| 780597 | N/A | N/A | 75176 | 75195 | AACAAGTCCTGTCCTCAAAG | 99 | 647 |
| 780598 | N/A | N/A | 75470 | 75489 | AACAAACAAAGTGCCATCTA | 52 | 648 |
| 780599 | N/A | N/A | 75646 | 75665 | ATTATAGAGGCTTATTAACC | 83 | 649 |
| 780600 | N/A | N/A | 76096 | 76115 | TAGAGTTGAAAGCTTCCTTC | 65 | 650 |
| 780601 | N/A | N/A | 76298 | 76317 | CCATCTGAGGAACTTAAGTC | 67 | 651 |
| 780602 | N/A | N/A | 76349 | 76368 | GTCAAACTCTTCAGAGTCTG | 24 | 652 |
| 780603 | N/A | N/A | 76970 76997 | 76989 77016 | TATATAGTATATATATAATA | 138 | 653 |
| 780604 | N/A | N/A | 76973 77000 | 76992 77019 | TTATATATAGTATATATATA | 104 | 654 |
| 780605 | N/A | N/A | 76976 77003 | 76995 77022 | GTATTATATATAGTATATAT | 106 | 655 |
| 780606 | N/A | N/A | 76979 77006 | 76998 77025 | TAAGTATTATATATAGTATA | 105 | 656 |
| 780607 | N/A | N/A | 76982 77009 | 77001 77028 | TAATAAGTATTATATATAGT | 76 | 657 |
| 780608 | N/A | N/A | 76985 77012 | 77004 77031 | ATATAATAAGTATTATATAT | 78 | 658 |
| 780609 | N/A | N/A | 76988 77015 | 77007 77034 | TATATATAATAAGTATTATA | 126 | 659 |
| 780610 | N/A | N/A | 77524 | 77543 | TTTCATAGTTTTATAGCATT | 72 | 660 |
| 780611 | N/A | N/A | 77611 | 77630 | GTCTTATAGTTGGGAACGAA | 43 | 661 |
| 780612 | N/A | N/A | 78065 | 78084 | ACTATCATTTTAACCTCTGA | 71 | 662 |

TABLE 8-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780613 | N/A | N/A | 78080 | 78099 | ACAGTAGGCCAAGTAACTAT | 80 | 663 |
| 780614 | N/A | N/A | 78344 | 78363 | AAGTGATGATAATAATTTGC | 54 | 664 |
| 780615 | N/A | N/A | 78724 | 78743 | TGGCCAATATTCAGGAGGGT | 81 | 665 |
| 780616 | N/A | N/A | 78787 | 78806 | GCTTTGCTTACTAGTGAGTG | 70 | 666 |
| 780617 | N/A | N/A | 81581 87838 | 81600 87857 | GTTTGAAGGAATAGCTGACA | 60 | 667 |
| 780618 | N/A | N/A | 81584 87841 | 81603 87860 | AGTGTTTGAAGGAATAGCTG | 52 | 668 |
| 780619 | N/A | N/A | 81587 87844 | 81606 87863 | CATAGTGTTTGAAGGAATAG | 129 | 669 |
| 780620 | N/A | N/A | 81590 87847 | 81609 87866 | AGCCATAGTGTTTGAAGGAA | 40 | 670 |
| 780621 | N/A | N/A | 81593 87850 | 81612 87869 | AAAGCCATAGTGTTTGAAG | 91 | 671 |
| 780622 | N/A | N/A | 81596 87853 | 81615 87872 | CTAAAAGCCATAGTGTTTG | 85 | 672 |
| 780623 | N/A | N/A | 81599 87856 | 81618 87875 | ATTCTAAAAGCCATAGTGT | 117 | 673 |
| 780624 | N/A | N/A | 81630 87887 | 81649 87906 | GCAGCATCATGCAAGCAGCA | 31 | 674 |
| 780625 | N/A | N/A | 81633 87890 | 81652 87909 | ATTGCAGCATCATGCAAGCA | 81 | 675 |
| 780626 | N/A | N/A | 83145 | 83164 | TGGCGGAATGCAGAAATTTA | 61 | 676 |
| 780627 | N/A | N/A | 83842 | 83861 | GTGGGAAGGAAGAAATGTGC | 70 | 677 |
| 780628 | N/A | N/A | 84184 | 84203 | AGCATATTAATGCCAAATAT | 73 | 678 |
| 780629 | N/A | N/A | 84201 | 84220 | AAAGGCAAATGACACACAGC | 87 | 679 |
| 780630 | N/A | N/A | 84266 | 84285 | ATTAGTCTGGCTAAGAAGAA | 95 | 680 |
| 780631 | N/A | N/A | 84723 | 84742 | ACAGAGCTGAGGTCTGCAAC | 58 | 681 |
| 780632 | N/A | N/A | 84951 | 84970 | AAGCTCAGGAGTTCAGAAAA | 111 | 682 |
| 780633 | N/A | N/A | 86880 | 86899 | GGTTTCTGGATATTAGAACA | 76 | 683 |
| 780634 | N/A | N/A | 87013 | 87032 | TTGTCAGCAACCGATCAAAG | 82 | 684 |
| 780635 | N/A | N/A | 88098 | 88117 | CAATTTGGAGTCTACAATGA | 78 | 685 |
| 780636 | N/A | N/A | 88353 | 88372 | AAATGTAACCTTACGACATT | 77 | 686 |
| 780637 | N/A | N/A | 88867 | 88886 | TAATGCTAACAGCAACAAGG | 85 | 687 |
| 780638 | N/A | N/A | 89084 | 89103 | TCACCTTTACCCTTGTGATT | 57 | 688 |
| 780639 | N/A | N/A | 89635 | 89654 | CAGGCCAAATAGGACTCTAT | 51 | 689 |
| 780640 | N/A | N/A | 89998 | 90017 | AGTCATATTAGTTTCTAATT | 96 | 690 |
| 780641 | N/A | N/A | 90808 | 90827 | CTGCTCTGCTAATGGGCTGG | 54 | 691 |
| 780642 | N/A | N/A | 91043 | 91062 | TTCATGTATCTCTTAACCCA | 42 | 692 |
| 780643 | N/A | N/A | 91084 | 91103 | ACTTCCATATTTACCTGCAA | 105 | 693 |

TABLE 8-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780644 | N/A | N/A | 92608 | 92627 | TGCACTAAACTCATTTGACA | 98 | 694 |
| 780645 | N/A | N/A | 92700 | 92719 | GCATCATCTCAGGGAGCCAT | 45 | 695 |
| 780646 | N/A | N/A | 92957 | 92976 | CAGCATATCTCAGCATACCT | 51 | 696 |
| 780647 | N/A | N/A | 93284 | 93303 | CAAACAGTGAAACATGGAAT | 89 | 697 |
| 780648 | N/A | N/A | 93697 | 93716 | TTCAATTGACTAATTCAGTA | 85 | 698 |
| 780649 | N/A | N/A | 94459 | 94478 | GCTGATTGCAATGTTTCAAT | 33 | 699 |
| 780650 | N/A | N/A | 94553 | 94572 | AAATCACATTATCCATGACA | 78 | 700 |
| 780651 | N/A | N/A | 95499 | 95518 | AATAGCTGTCAGACAAGTTG | 64 | 701 |
| 780652 | N/A | N/A | 95576 | 95595 | TTAGAGCTTCTGCACCATGA | 91 | 702 |
| 780653 | N/A | N/A | 95725 | 95744 | TTCCACCTGATTAATTGAAT | 70 | 703 |
| 780654 | N/A | N/A | 96460 | 96479 | ATTTTTTAAAGAGTTTGTGC | 51 | 704 |
| 780655 | N/A | N/A | 96720 | 96739 | TATAAACTCATAGGCCCTGG | 74 | 705 |
| 780656 | N/A | N/A | 97174 | 97193 | GTTTAAGGAATACTTAAACA | 81 | 706 |
| 780657 | N/A | N/A | 97323 | 97342 | TGCCCTGAGAATGAAATAAC | 73 | 707 |
| 780658 | N/A | N/A | 97591 | 97610 | TTTGATGGATTCTACTTGCA | 83 | 708 |
| 780659 | N/A | N/A | 97610 | 97629 | CTCAAAGTAACTACTGCATT | 46 | 709 |

TABLE 9

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693428 | 2361 | 2380 | 61982 | 62001 | GCTCTCTTTCTCACATACCT | 38 | 73 |
| 780254 | 4111 | 4130 | 86606 | 86625 | GTTTCATTCGGTTATAAGGC | 27 | 235 |
| 780660 | N/A | N/A | 99313 | 99332 | TCTAAAAATCTAATAAGTCT | 89 | 710 |
| 780661 | N/A | N/A | 99451 | 99470 | TACTCCAAGGTTTTATGAGC | 81 | 711 |
| 780662 | N/A | N/A | 99569 | 99588 | AAGAGATAATTACAGTCCCT | 71 | 712 |
| 780663 | N/A | N/A | 99813 | 99832 | CTAAACGCAAAACTTTCTGA | 107 | 713 |
| 780664 | N/A | N/A | 100778 | 100797 | TAGAATACAAGATTTTATTG | 134 | 714 |
| 780665 | N/A | N/A | 102009 | 102028 | TGAGCACCTAAACATGCTAC | 65 | 715 |
| 780666 | N/A | N/A | 102270 | 102289 | ACAGCATCGCAGGTCTTGTA | 50 | 716 |
| 780667 | N/A | N/A | 102579 | 102598 | AATGCATTTCATAGTTGTCC | 60 | 717 |
| 780668 | N/A | N/A | 104248 | 104267 | TTCTCTATTTGAGAATCGCC | 64 | 718 |
| 780669 | N/A | N/A | 104621 | 104640 | AAATTTCAAGTTGGAGTAGG | 85 | 719 |
| 780670 | N/A | N/A | 105660 | 105679 | GTCATATAGTGGCCCCTAAA | 31 | 720 |

TABLE 9-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780671 | N/A | N/A | 106100 | 106119 | CACTGGTATGCCCTTCCAAC | 65 | 721 |
| 780672 | N/A | N/A | 106561 | 106580 | GAATTTCTTACTTGTCTTAA | 95 | 722 |
| 780673 | N/A | N/A | 107953 | 107972 | GCTACATAAAATAAATCACC | 79 | 723 |
| 780674 | N/A | N/A | 109817 | 109836 | AGAGTCTGAAGTATCTAGAA | 98 | 724 |
| 780675 | N/A | N/A | 110040 | 110059 | TGAAGCCTGGAACCAGTTTA | 94 | 725 |
| 780676 | N/A | N/A | 110227 | 110246 | CCTAAAGCCAATTAGCACAA | 101 | 726 |
| 780677 | N/A | N/A | 110637 | 110656 | AGTGTAGCCACTAAGAATTT | 88 | 727 |
| 780678 | N/A | N/A | 110978 | 110997 | CTTATACACTAATTGGCTCT | 66 | 728 |
| 780679 | N/A | N/A | 111011 | 111030 | TTTCTTCCACCATTCCCTTA | 101 | 729 |
| 780680 | N/A | N/A | 111182 | 111201 | CTCACTAATTGCAAAGAAAA | 109 | 730 |
| 780681 | N/A | N/A | 111343 | 111362 | CAAAGCTTCAGACTGTGATC | 70 | 731 |
| 780682 | N/A | N/A | 111843 | 111862 | TCAGAGAGGCCCGCCATGGG | 122 | 732 |
| 780683 | N/A | N/A | 111897 | 111916 | TTCACATGGCTGAAGTCTTG | 115 | 733 |
| 780684 | N/A | N/A | 112310 | 112329 | ATCTACTGAATTCTGGTTAG | 103 | 734 |
| 780685 | N/A | N/A | 112349 | 112368 | GCACACAGTGTAGTCATACT | 44 | 735 |
| 780686 | N/A | N/A | 114870 | 114889 | AACCCAAGATTCCCCCTGGT | 99 | 736 |
| 780687 | N/A | N/A | 115427 | 115446 | TGGAGAAGTAAGCTAACAGT | 109 | 737 |
| 780688 | N/A | N/A | 115958 | 115977 | TAACTGAAAATTCAAGCCTG | 115 | 738 |
| 780689 | N/A | N/A | 116039 | 116058 | CTTAAGGAAAATGAGCTCTC | 106 | 739 |
| 780690 | N/A | N/A | 116174 | 116193 | TATAATATCTAGCTTTCCCT | 95 | 740 |
| 780691 | N/A | N/A | 116253 | 116272 | CAGAGGGAGAAAAACACTGA | 110 | 741 |
| 780692 | N/A | N/A | 116357 | 116376 | CCCTTGAGGGTGTCACAATC | 82 | 742 |
| 780693 | N/A | N/A | 116374 | 116393 | ATCTTTGTATCTCTGCTCCC | 89 | 743 |
| 780694 | N/A | N/A | 116669 | 116688 | TTGAAATAATAAGTAAAGAT | 123 | 744 |
| 780695 | N/A | N/A | 116874 | 116893 | ATAAGACATGCCTCTTTAAG | 74 | 745 |
| 780696 | N/A | N/A | 117178 | 117197 | AGTACATATTATTTAACTGC | 61 | 746 |
| 780697 | N/A | N/A | 117306 | 117325 | ACTGTTGGTTTTGGCTCACA | 66 | 747 |
| 780698 | N/A | N/A | 117646 | 117665 | TCTGGAGACTGACCCACGCA | 73 | 748 |
| 780699 | N/A | N/A | 118398 | 118417 | GCTGAGTGGAGGTATCTGCC | 92 | 749 |
| 780700 | N/A | N/A | 119907 | 119926 | ATATGGTTTAGGAGAGACTA | 41 | 750 |
| 780701 | N/A | N/A | 121039 | 121058 | ATACTTAACTCATGGATAGA | 80 | 751 |
| 780702 | N/A | N/A | 121425 | 121444 | AAAAGTGCAATTGCCATAGG | 57 | 752 |
| 780703 | N/A | N/A | 121530 | 121549 | CCGGTAACATTTTATTTACC | 62 | 753 |
| 780704 | N/A | N/A | 121871 | 121890 | TCAATGTATTGTTGCCAAAT | 45 | 754 |
| 780705 | N/A | N/A | 122553 | 122572 | ATGAGCTACCCACACAGTCA | 78 | 755 |

TABLE 9-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780706 | N/A | N/A | 123081 | 123100 | TTGGAAGGATGGAGACATCG | 28 | 756 |
| 780707 | N/A | N/A | 123885 | 123904 | TGATATGGCATGATGTCTAC | 67 | 757 |
| 780708 | N/A | N/A | 124062 | 124081 | AGATGATATGCTATGACATA | 77 | 758 |
| 780709 | N/A | N/A | 124679 | 124698 | TGTCCTGTCTCATAACATCT | 68 | 759 |
| 780710 | N/A | N/A | 125144 | 125163 | AGAATATTTATGCACTAAAC | 71 | 760 |
| 780711 | N/A | N/A | 125277 | 125296 | GTTCTAACAGCAATTTCCTT | 78 | 761 |
| 780712 | N/A | N/A | 126145 | 126164 | ATCCTTATGTCCTCACAGAT | 89 | 762 |
| 780713 | N/A | N/A | 126446 | 126465 | TATTTCCTCTCAATGTTTAT | 125 | 763 |
| 780714 | N/A | N/A | 127216 | 127235 | TTAAAAAAAGGAATGGGATA | 92 | 764 |
| 780715 | N/A | N/A | 127242 | 127261 | CAACCTGAAAAAATTAGTCT | 79 | 765 |
| 780716 | N/A | N/A | 127360 | 127379 | ATAAATGAGTTGATCAGTGG | 83 | 766 |
| 780717 | N/A | N/A | 127443 | 127462 | TATTCCTGGATGAGAAAAAT | 103 | 767 |
| 780718 | N/A | N/A | 127460 | 127479 | CCTAAGACTGGTTAAAATAT | 91 | 768 |
| 780719 | N/A | N/A | 128188 | 128207 | ATAAGGAAAGTTGTTCTGGG | 108 | 769 |
| 780720 | N/A | N/A | 132660 | 132679 | ATGCAATAACAATTATGCAC | 75 | 770 |
| 780721 | N/A | N/A | 133278 | 133297 | GGAGTTGATATTTCAGGTAC | 81 | 771 |
| 780722 | N/A | N/A | 134443 | 134462 | TTTTCAGAGGATCTACTGTG | 90 | 772 |
| 780723 | N/A | N/A | 136265 | 136284 | TAAATGTGAGGAAATATTTG | 94 | 773 |
| 780724 | N/A | N/A | 137896 | 137915 | CATATGTATAGTCCGTGAAT | 81 | 774 |
| 780725 | N/A | N/A | 138142 | 138161 | TCACTGAGGAATGTGATAAA | 108 | 775 |
| 780726 | N/A | N/A | 138369 | 138388 | TTTATTGACAGCTTACCAGG | 83 | 776 |
| 780727 | N/A | N/A | 138502 | 138521 | AGCAAAAAACAAAGGAGTCA | 94 | 777 |
| 780728 | N/A | N/A | 138562 | 138581 | GAGAACAGTGAGAAGTACAA | 100 | 778 |
| 780729 | N/A | N/A | 138891 | 138910 | TAGAGATCTGAGTCAATTTC | 70 | 779 |
| 780730 | N/A | N/A | 139058 | 139077 | GCTACTGTGAAGGAAAACAT | 66 | 780 |
| 780731 | N/A | N/A | 139370 | 139389 | ATCCAAATGTTAACCACATA | 60 | 781 |
| 780732 | N/A | N/A | 139871 | 139890 | ACAGGAGATACTTGTTCAGA | 62 | 782 |
| 780733 | N/A | N/A | 140263 | 140282 | TAGAAAATAGTTCCAATTAG | 86 | 783 |
| 780734 | N/A | N/A | 140887 | 140906 | CCTTAAAATATTTCCCTTTC | 115 | 784 |
| 780735 | N/A | N/A | 141689 | 141708 | AAAGATAATTCTTTTGGGAA | 129 | 785 |
| 780736 | N/A | N/A | 144735 144754 | 144754 144773 | GTACAAATATGAGTATTTAG | 65 | 786 |

Example 4: Effect of 5-10-5 MOE Gapmers with Mixed Internucleoside Linkages on Human LRRK2 RNA Expression In Vitro, Single Dose Modified oligonucleotides complementary to a human LRRK2 nucleic acid were designed and tested for their effect on LRRK2 RNA in vitro. The modified oligonucleotides were tested in a series of experiments that had similar culture conditions.

Cultured SH-SY5Y cells at a density of 20,000 cells per well were transfected using electroporation with 4,000 nM concentration of modified oligonucleotide or no modified oligonucleotide for untreated controls. After approximately 24 hours, RNA was isolated from the cells and LRRK2 RNA levels were measured by quantitative real-time PCR using human primer probe set RTS3132 as described in Example 2. LRRK2 RNA levels were adjusted according to total RNA content, as measured by RIBOGREEN®. Results are presented in the table below as percent LRRK2 RNA levels relative to untreated control cells. The modified oligonucleotides with percent control values marked with an asterisk (*) target the amplicon region of the primer probe set. Additional assays may be used to measure the potency and efficacy of oligonucleotides targeting the amplicon region.

The modified oligonucleotides in Tables 10-50 are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddddeeeee; wherein 'd' represents a 2'-deoxyribose sugar and 'e' represents a 2'-MOE modified sugar. All cytosine residues throughout each gapmer are 5-methyl cytosines. The internucleoside linkages for each gapmer are mixed phosphodiester and phosphorothioate linkages. The internucleoside linkage motif for the gapmers is (from 5' to 3'): sooosssssssssssooss; wherein 'o' represents a phosphodiester internucleoside linkage and 's' represents a phosphorothioate internucleoside linkage. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 10-50 below is complementary to human LRRK2 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to the sequence of human LRRK2 RNA reduced the amount of human LRRK2 RNA.

TABLE 10

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693426 | 185 | 204 | 3304 | 3323 | TCCTGGACATTGTTCAGCCT | 39 | 55 |
| 780254 | 4111 | 4130 | 86606 | 86625 | GTTTCATTCGGTTATAAGGC | 19 | 235 |
| 780254 | 4111 | 4130 | 86606 | 86625 | GTTTCATTCGGTTATAAGGC | 37 | 235 |
| 802613 | 10 | 29 | 3129 | 3148 | GAGCTCAGCTCACCGCCCGC | 99 | 787 |
| 802614 | 33 | 52 | 3152 | 3171 | GCCGGCCACAGCTCCCCGGG | 138 | 788 |
| 802615 | 80 | 99 | 3199 | 3218 | CCGCCCTCCCAGCATGAACG | 89 | 789 |
| 802616 | 89 | 108 | 3208 | 3227 | TCCAACCCGCCGCCCTCCCA | 122 | 790 |
| 802617 | 109 | 128 | 3228 | 3247 | TAGCCATGGTGGCACCTGCT | 68 | 791 |
| 802618 | 118 | 137 | 3237 | 3256 | AGCTGCCACTAGCCATGGTG | 126 | 792 |
| 802619 | 127 | 146 | 3246 | 3265 | ACCCCTGACAGCTGCCACTA | 83 | 793 |
| 802620 | 136 | 155 | 3255 | 3274 | CCTCTTCGCACCCCTGACAG | 106 | 794 |
| 802621 | 198 | 217 | 3317 | 3336 | TATCTGTTTTCCTTCCTGGA | 67 | 795 |
| 802622 | 199 | 218 | 3318 | 3337 | CTATCTGTTTTCCTTCCTGG | 46 | 796 |
| 802623 | 200 | 219 | 3319 | 3338 | TCTATCTGTTTTCCTTCCTG | 50 | 797 |
| 802624 | 201 | 220 | 3320 | 3339 | TTCTATCTGTTTTCCTTCCT | 42 | 798 |
| 802625 | 202 | 221 | 3321 | 3340 | TTTCTATCTGTTTTCCTTCC | 69 | 799 |
| 802626 | 204 | 223 | 3323 | 3342 | CGTTTCTATCTGTTTTCCTT | 46 | 800 |
| 802627 | 222 | 241 | 3341 | 3360 | CTCCAGGATTTGGACCAGCG | 45 | 801 |
| 802628 | 231 | 250 | 3350 | 3369 | CAGCAGATCCTCCAGGATTT | 91 | 802 |
| 802629 | 240 | 259 | 3359 | 3378 | CGTGAACACCAGCAGATCCT | 68 | 803 |
| 802630 | 280 | 299 | 3671 | 3690 | TATTTTTGCCTTGAAATAAC | 104 | 804 |
| 802631 | 289 | 308 | 3680 | 3699 | GCACATGGATATTTTTGCCT | 38 | 805 |
| 802632 | 298 | 317 | 3689 | 3708 | TCAACAGAGGCACATGGATA | 60 | 806 |

TABLE 10-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802633 | 324 | 343 | 3715 | 3734 | GACTCTCATATAGGAGTCCA | 124 | 807 |
| 802634 | 333 | 352 | 3724 | 3743 | CACACTCGCGACTCTCATAT | 109 | 808 |
| 802635 | 342 | 361 | N/A | N/A | CACCTGCTGCACACTCGCGA | 58 | 809 |
| 802636 | 351 | 370 | N/A | N/A | TGACCAACCCACCTGCTGCA | 101 | 810 |
| 802637 | 371 | 390 | 10395 | 10414 | TCTATTAATTTGCACAGAAG | 104 | 811 |
| 802638 | 380 | 399 | 10404 | 10423 | GGACAGACTTCTATTAATTT | 61 | 812 |
| 802639 | 389 | 408 | 10413 | 10432 | ATTGTACCTGGACAGACTTC | 53 | 813 |
| 802640 | 426 | 445 | 10450 | 10469 | ATCATTTCCAACATCCTGGG | 82 | 814 |
| 802641 | 435 | 454 | 10459 | 10478 | GACTTCCCAATCATTTCCAA | 98 | 815 |
| 802642 | 460 | 479 | N/A | N/A | TAAGAATCAATTGGTGAACA | 62 | 816 |
| 802643 | 469 | 488 | 13735 | 13754 | TTAGCATTTTAAGAATCAAT | 49 | 817 |
| 802644 | 480 | 499 | 13746 | 13765 | ATTATGAACTGTTAGCATTT | 47 | 818 |
| 802645 | 504 | 523 | 13770 | 13789 | AATCACTGACAAGTTTACAC | 74 | 819 |
| 802646 | 513 | 532 | 13779 | 13798 | CTTCAGTCCAATCACTGACA | 54 | 820 |
| 802647 | 522 | 541 | 13788 | 13807 | ATCTAAGGTCTTCAGTCCAA | 80 | 821 |
| 802648 | 534 | 553 | 13800 | 13819 | AGTTAGGAGGAGATCTAAGG | 106 | 822 |
| 802649 | 535 | 554 | 13801 | 13820 | AAGTTAGGAGGAGATCTAAG | 96 | 823 |
| 802650 | 536 | 555 | 13802 | 13821 | GAAGTTAGGAGGAGATCTAA | 87 | 824 |
| 802651 | 537 | 556 | 13803 | 13822 | TGAAGTTAGGAGGAGATCTA | 94 | 825 |
| 802652 | 538 | 557 | 13804 | 13823 | CTGAAGTTAGGAGGAGATCT | 58 | 826 |
| 802653 | 540 | 559 | 13806 | 13825 | ACCTGAAGTTAGGAGGAGAT | 41 | 827 |
| 802654 | 541 | 560 | 13807 | 13826 | TACCTGAAGTTAGGAGGAGA | 53 | 828 |
| 802655 | 542 | 561 | 13808 | 13827 | TTACCTGAAGTTAGGAGGAG | 33 | 829 |
| 802656 | 543 | 562 | N/A | N/A | TTTACCTGAAGTTAGGAGGA | 55 | 830 |
| 802657 | 544 | 563 | N/A | N/A | TTTTACCTGAAGTTAGGAGG | 56 | 831 |
| 802658 | 548 | 567 | N/A | N/A | GTGATTTTACCTGAAGTTAG | 53 | 832 |
| 802659 | 557 | 576 | 16077 | 16096 | ATCAGCAAGGTGATTTTACC | 61 | 833 |
| 802660 | 566 | 585 | 16086 | 16105 | TCATCCAATATCAGCAAGGT | 78 | 834 |
| 802661 | 575 | 594 | 16095 | 16114 | TCACTTTCTTCATCCAATAT | 53 | 835 |
| 802662 | 602 | 621 | 16122 | 16141 | ATGGCATCAAAAATTAACAT | 47 | 836 |
| 802663 | 603 | 622 | 16123 | 16142 | CATGGCATCAAAAATTAACA | 40 | 837 |
| 802664 | 605 | 624 | 16125 | 16144 | TGCATGGCATCAAAAATTAA | 75 | 838 |
| 802665 | 607 | 626 | 16127 | 16146 | AGTGCATGGCATCAAAAATT | 56 | 839 |
| 802666 | 609 | 628 | 16129 | 16148 | TGAGTGCATGGCATCAAAAA | 68 | 840 |
| 802667 | 610 | 629 | 16130 | 16149 | ATGAGTGCATGGCATCAAAA | 62 | 841 |

TABLE 10-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802668 | 612 | 631 | 16132 | 16151 | AAATGAGTGCATGGCATCAA | 54 | 842 |
| 802669 | 613 | 632 | 16133 | 16152 | GAAATGAGTGCATGGCATCA | 49 | 843 |
| 802670 | 620 | 639 | 16140 | 16159 | TTGGCTGGAAATGAGTGCAT | 42 | 844 |
| 802671 | 638 | 657 | 16158 | 16177 | AGTTTCTGGACTTCATCATT | 95 | 845 |
| 802672 | 647 | 666 | 16167 | 16186 | TTGCATCCAAGTTTCTGGAC | 70 | 846 |
| 802673 | 656 | 675 | 16176 | 16195 | TGTAAAGCTTTGCATCCAAG | 73 | 847 |
| 802674 | 682 | 701 | N/A | N/A | CCTCTGAGACTCTCTCAAAC | 41 | 848 |
| 802675 | 691 | 710 | 18590 | 18609 | TCAGTTGCTCCTCTGAGACT | 51 | 849 |
| 802676 | 700 | 719 | 18599 | 18618 | CAAATTCAGTCAGTTGCTCC | 69 | 850 |
| 802677 | 726 | 745 | 18625 | 18644 | CAATATCATATAATCTTTGT | 101 | 851 |
| 802678 | 735 | 754 | 18634 | 18653 | CGCACTTAACAATATCATAT | 34 | 852 |
| 802679 | 744 | 763 | 18643 | 18662 | ATTTGTTAACGCACTTAACA | 63 | 853 |
| 802680 | 753 | 772 | 18652 | 18671 | ATCTTTAAAATTTGTTAACG | 136 | 854 |
| 802681 | 773 | 792 | 18672 | 18691 | TGAAGCACAATTTCCTCTTC | 51 | 855 |
| 802682 | 782 | 801 | 18681 | 18700 | TGCAGCACATGAAGCACAAT | 67 | 856 |
| 802683 | 791 | 810 | 18690 | 18709 | TGTAAACAATGCAGCACATG | 77 | 857 |
| 802684 | 817 | 836 | N/A | N/A | CATTATTGCAAGGAATCGCT | 58 | 858 |
| 802685 | 826 | 845 | N/A | N/A | GGACTTCCACATTATTGCAA | 32 | 859 |
| 802686 | 835 | 854 | 21666 | 21685 | CACTCATGAGGACTTCCACA | 34 | 860 |
| 802687 | 861 | 880 | 21692 | 21711 | CACAATATTATAACACCTGA | 50 | 861 |
| 802688 | 879 | 898 | 21710 | 21729 | TGCTTTCATAGCTTCCACCA | 32 | 862 |

TABLE 11

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 42 | 235 |
| 780254 | 4111 | 4130 | 86606 | 86625 | GTTTCATTCGGTTATAAGGC | 17 | 235 |
| 802689 | 880 | 899 | 21711 | 21730 | ATGCTTTCATAGCTTCCACC | 24 | 863 |
| 802690 | 882 | 901 | 21713 | 21732 | GAATGCTTTCATAGCTTCCA | 36 | 864 |
| 802691 | 884 | 903 | 21715 | 21734 | GGGAATGCTTTCATAGCTT | 30 | 865 |
| 802692 | 886 | 905 | 21717 | 21736 | TAGGGAATGCTTTCATAGCT | 36 | 866 |
| 802693 | 887 | 906 | 21718 | 21737 | ATAGGGAATGCTTTCATAGC | 44 | 867 |
| 802694 | 889 | 908 | 21720 | 21739 | TCATAGGGAATGCTTTCATA | 53 | 868 |

TABLE 11-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802695 | 890 | 909 | 21721 | 21740 | CTCATAGGGAATGCTTTCAT | 44 | 869 |
| 802696 | 891 | 910 | 21722 | 21741 | ACTCATAGGGAATGCTTTCA | 25 | 870 |
| 802697 | 892 | 911 | 21723 | 21742 | CACTCATAGGGAATGCTTTC | 48 | 871 |
| 802698 | 893 | 912 | 21724 | 21743 | TCACTCATAGGGAATGCTTT | 29 | 872 |
| 802699 | 894 | 913 | 21725 | 21744 | TTCACTCATAGGGAATGCTT | 41 | 873 |
| 802700 | 895 | 914 | 21726 | 21745 | TTTCACTCATAGGGAATGCT | 19 | 874 |
| 802701 | 897 | 916 | 21728 | 21747 | TCTTTCACTCATAGGGAATG | 27 | 875 |
| 802702 | 898 | 917 | 21729 | 21748 | TTCTTTCACTCATAGGGAAT | 40 | 876 |
| 802703 | 899 | 918 | 21730 | 21749 | ATTCTTTCACTCATAGGGAA | 35 | 877 |
| 802704 | 900 | 919 | 21731 | 21750 | AATTCTTTCACTCATAGGGA | 40 | 878 |
| 802705 | 901 | 920 | 21732 | 21751 | GAATTCTTTCACTCATAGGG | 30 | 879 |
| 802706 | 905 | 924 | 21736 | 21755 | TCTTGAATTCTTTCACTCAT | 43 | 880 |
| 802707 | 915 | 934 | 21746 | 21765 | GCAACTCACTTCTTGAATTC | 53 | 881 |
| 802708 | 924 | 943 | 21755 | 21774 | GAGCAAACAGCAACTCACTT | 71 | 882 |
| 802709 | 949 | 968 | N/A | N/A | AAAAATTACCTAATGTAAGC | 112 | 883 |
| 802710 | 958 | 977 | 27933 | 27952 | GGATATTGAAAAAATTACCT | 55 | 884 |
| 802711 | 967 | 986 | 27942 | 27961 | TTAATACCAGGATATTGAAA | 88 | 885 |
| 802712 | 989 | 1008 | 27964 | 27983 | ACCACAAACTCATGGACTTC | 42 | 886 |
| 802713 | 990 | 1009 | 27965 | 27984 | CACCACAAACTCATGGACTT | 34 | 887 |
| 802714 | 991 | 1010 | 27966 | 27985 | TCACCACAAACTCATGGACT | 45 | 888 |
| 802715 | 992 | 1011 | 27967 | 27986 | TTCACCACAAACTCATGGAC | 61 | 889 |
| 802716 | 993 | 1012 | 27968 | 27987 | TTTCACCACAAACTCATGGA | 45 | 890 |
| 802717 | 998 | 1017 | 27973 | 27992 | ACAGCTTTCACCACAAACTC | 35 | 891 |
| 802718 | 1007 | 1026 | 27982 | 28001 | TACTGCTGCACAGCTTTCAC | 40 | 892 |
| 802719 | 1016 | 1035 | 27991 | 28010 | TTCTCTGGGTACTGCTGCAC | 47 | 893 |
| 802720 | 1055 | 1074 | 28030 | 28049 | AGGGCCAAACAGCTGAGCGC | 70 | 894 |
| 802721 | 1064 | 1083 | N/A | N/A | TCAGTGAGGAGGGCCAAACA | 83 | 895 |
| 802722 | 1090 | 1109 | 29351 | 29370 | CTAAATCTTGATTTAAGAAA | 134 | 896 |
| 802723 | 1099 | 1118 | 29360 | 29379 | TCTTTTCCTCTAAATCTTGA | 55 | 897 |
| 802724 | 1111 | 1130 | 29372 | 29391 | CTTGATTCTCATTCTTTTCC | 47 | 898 |
| 802725 | 1132 | 1151 | 29393 | 29412 | CTTCCCCCTCATCATCATTC | 58 | 899 |
| 802726 | 1141 | 1160 | 29402 | 29421 | ATTTATCTTCTTCCCCCTCA | 43 | 900 |
| 802727 | 1150 | 1169 | 29411 | 29430 | GCCAAAACAATTTATCTTCT | 44 | 901 |
| 802728 | 1176 | 1195 | 29437 | 29456 | CGTTAATGCTTTGTAACAGG | 26 | 902 |
| 802729 | 1194 | 1213 | 29455 | 29474 | CTTGTTCTTTCTATGCCACG | 64 | 903 |

TABLE 11-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802730 | 1225 | 1244 | 29576 | 29595 | TTAGTGCCCAGCATGCGGCC | 37 | 904 |
| 802731 | 1234 | 1253 | 29585 | 29604 | GGAGATTATTTAGTGCCCAG | 20 | 905 |
| 802732 | 1243 | 1262 | 29594 | 29613 | GGTACATAAGGAGATTATTT | 30 | 906 |
| 802733 | 1269 | 1288 | 29620 | 29639 | TCCAATCTTCTCATGTAAAC | 99 | 907 |
| 802734 | 1278 | 1297 | 29629 | 29648 | ATCTTCATCTCCAATCTTCT | 93 | 908 |
| 802735 | 1287 | 1306 | N/A | N/A | GAAATGGCCATCTTCATCTC | 110 | 909 |
| 802736 | 1313 | 1332 | 31029 | 31048 | GAGAGCATCACTTCCCTATG | 47 | 910 |
| 802737 | 1322 | 1341 | 31038 | 31057 | ATCAGCATGGAGAGCATCAC | 48 | 911 |
| 802738 | 1331 | 1350 | 31047 | 31066 | GAAGAATGCATCAGCATGGA | 58 | 912 |
| 802739 | 1357 | 1376 | 31073 | 31092 | CAGATGCCTGGAAAACTTCC | 51 | 913 |
| 802740 | 1366 | 1385 | 31082 | 31101 | ATGCATTCGCAGATGCCTGG | 43 | 914 |
| 802741 | 1375 | 1394 | 31091 | 31110 | GAGTTGACAATGCATTCGCA | 59 | 915 |
| 802742 | 1385 | 1404 | 31101 | 31120 | TGTTCTAAGAGAGTTGACAA | 85 | 916 |
| 802743 | 1426 | 1445 | 35373 | 35392 | GTATTCCTTTTGATAACAGT | 24 | 917 |
| 802744 | 1435 | 1454 | 35382 | 35401 | CATTCAGGTGTATTCCTTTT | 27 | 918 |
| 802745 | 1444 | 1463 | 35391 | 35410 | ACTCCAAAACATTCAGGTGT | 40 | 919 |
| 802746 | 1470 | 1489 | 35417 | 35436 | AGGAGAATGTATATGCTTCT | 18 | 920 |
| 802747 | 1479 | 1498 | 35426 | 35445 | AGCCACTTCAGGAGAATGTA | 27 | 921 |
| 802748 | 1488 | 1507 | 35435 | 35454 | GCCACTTTCAGCCACTTCAG | 21 | 922 |
| 802749 | 1514 | 1533 | 35461 | 35480 | TCAAAAAGATGATTTAGCAT | 113 | 923 |
| 802750 | 1523 | 1542 | N/A | N/A | TTGCTTCCTTCAAAAAGATG | 78 | 924 |
| 802751 | 1533 | 1552 | N/A | N/A | CAGGGAAGTGTTGCTTCCTT | 53 | 925 |
| 802752 | 1574 | 1593 | 37623 | 37642 | ATAACTGTTAGTATTTTGGG | 34 | 926 |
| 802753 | 1607 | 1626 | 37656 | 37675 | AGCTGCACTGGTAATGATGT | 57 | 927 |
| 802754 | 1631 | 1650 | 37680 | 37699 | TGTAAAATAGCTCGAAGCGC | 90 | 928 |
| 802755 | 1654 | 1673 | N/A | N/A | CTGGCATGCCAGGCACTATA | 62 | 929 |
| 802756 | 1663 | 1682 | N/A | N/A | TGGATTCTTCTGGCATGCCA | 40 | 930 |
| 802757 | 1672 | 1691 | 41905 | 41924 | TATCCTCCCTGGATTCTTCT | 69 | 931 |
| 802758 | 1699 | 1718 | 41932 | 41951 | CCATATTTAGCTTATGATGA | 20 | 932 |
| 802759 | 1708 | 1727 | 41941 | 41960 | GTTTTTTAACCATATTTAGC | 38 | 933 |
| 802760 | 1717 | 1736 | 41950 | 41969 | TGAAACACTGTTTTTTAACC | 48 | 934 |
| 802761 | 1743 | 1762 | 41976 | 41995 | TAGGACCAGTTTGTGAATAT | 72 | 935 |
| 802762 | 1752 | 1771 | 41985 | 42004 | CAAAGCTGCTAGGACCAGTT | 69 | 936 |
| 802763 | 1761 | 1780 | N/A | N/A | GAACCTGTTCAAAGCTGCTA | 47 | 937 |

TABLE 11-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802764 | 1770 | 1789 | N/A | N/A | ATTTCCAATGAACCTGTTCA | 71 | 938 |
| 802765 | 1784 | 1803 | 52698 | 52717 | TTCTGAATCCCAGGATTTCC | 38 | 939 |

TABLE 12

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 42 | 235 |
| 780254 | 4111 | 4130 | 86606 | 86625 | GTTTCATTCGGTTATAAGGC | 50 | 235 |
| 802766 | 1785 | 1804 | 52699 | 52718 | TTTCTGAATCCCAGGATTTC | 140 | 940 |
| 802767 | 1787 | 1806 | 52701 | 52720 | CATTTCTGAATCCCAGGATT | 97 | 941 |
| 802768 | 1788 | 1807 | 52702 | 52721 | ACATTTCTGAATCCCAGGAT | 60 | 942 |
| 802769 | 1790 | 1809 | 52704 | 52723 | CCACATTTCTGAATCCCAGG | 41 | 943 |
| 802770 | 1792 | 1811 | 52706 | 52725 | ATCCACATTTCTGAATCCCA | 57 | 944 |
| 802771 | 1794 | 1813 | 52708 | 52727 | TAATCCACATTTCTGAATCC | 119 | 945 |
| 802772 | 1806 | 1825 | 52720 | 52739 | AGAAATTACTTTTAATCCAC | 97 | 946 |
| 802773 | 1815 | 1834 | 52729 | 52748 | TACAATAGAAGAAATTACTT | 176 | 947 |
| 802774 | 1835 | 1854 | 52749 | 52768 | TCTAATGCATCAGGAAAATG | 145 | 948 |
| 802775 | 1844 | 1863 | 52758 | 52777 | GATAACATCTCTAATGCATC | 56 | 949 |
| 802776 | 1853 | 1872 | 52767 | 52786 | CCTTCCAGGGATAACATCTC | 125 | 950 |
| 802777 | 1862 | 1881 | 52776 | 52795 | TCCATAGCACCTTCCAGGGA | 73 | 951 |
| 802778 | 1868 | 1887 | 52782 | 52801 | ACTGAATCCATAGCACCTTC | 52 | 952 |
| 802779 | 1869 | 1888 | 52783 | 52802 | CACTGAATCCATAGCACCTT | 63 | 953 |
| 802780 | 1870 | 1889 | 52784 | 52803 | GCACTGAATCCATAGCACCT | 44 | 954 |
| 802781 | 1871 | 1890 | 52785 | 52804 | AGCACTGAATCCATAGCACC | 65 | 955 |
| 802782 | 1872 | 1891 | 52786 | 52805 | AAGCACTGAATCCATAGCAC | 70 | 956 |
| 802783 | 1874 | 1893 | 52788 | 52807 | TGAAGCACTGAATCCATAGC | 100 | 957 |
| 802784 | 1875 | 1894 | 52789 | 52808 | GTGAAGCACTGAATCCATAG | 53 | 958 |
| 802785 | 1876 | 1895 | 52790 | 52809 | TGTGAAGCACTGAATCCATA | 107 | 959 |
| 802786 | 1877 | 1896 | 52791 | 52810 | GTGTGAAGCACTGAATCCAT | 62 | 960 |
| 802787 | 1878 | 1897 | 52792 | 52811 | TGTGTGAAGCACTGAATCCA | 73 | 961 |
| 802788 | 1882 | 1901 | 52796 | 52815 | GCAGTGTGTGAAGCACTGAA | 100 | 962 |
| 802789 | 1891 | 1910 | 52805 | 52824 | GATACATCTGCAGTGTGTGA | 116 | 963 |

TABLE 12-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802790 | 1900 | 1919 | 52814 | 52833 | GGTCATCTGGATACATCTGC | 77 | 964 |
| 802791 | 1909 | 1928 | N/A | N/A | GAATTTCTTGGTCATCTGGA | 106 | 965 |
| 802792 | 1928 | 1947 | 52968 | 52987 | AGACTTAAACCCAGACACTG | 78 | 966 |
| 802793 | 1937 | 1956 | 52977 | 52996 | TATCCTATAAGACTTAAACC | 157 | 967 |
| 802794 | 1946 | 1965 | 52986 | 53005 | GTAATCAAGTATCCTATAAG | 105 | 968 |
| 802795 | 1972 | 1991 | 53012 | 53031 | CAGTTCCTATGAACACATTC | 76 | 969 |
| 802796 | 1981 | 2000 | 53021 | 53040 | GCAGATGTCCAGTTCCTATG | 79 | 970 |
| 802797 | 1990 | 2009 | 53030 | 53049 | TTTTTGCCAGCAGATGTCCA | 117 | 971 |
| 802798 | 1999 | 2018 | 53039 | 53058 | AAACCAGAATTTTTGCCAGC | 81 | 972 |
| 802799 | 2018 | 2037 | 53058 | 53077 | TTAAATCGGTATAAGCTGGA | 112 | 973 |
| 802800 | 2027 | 2046 | 53067 | 53086 | GCAACATCCTTAAATCGGTA | 78 | 974 |
| 802801 | 2036 | 2055 | 53076 | 53095 | TGTATTTCAGCAACATCCTT | 145 | 975 |
| 802802 | 2062 | 2081 | N/A | N/A | CTAAGATTGTCTGAAATCCT | 84 | 976 |
| 802803 | 2071 | 2090 | 56005 | 56024 | TGAGGATTGCTAAGATTGTC | 84 | 977 |
| 802804 | 2080 | 2099 | 56014 | 56033 | CTGACAATTTGAGGATTGCT | 58 | 978 |
| 802805 | 2106 | 2125 | 56040 | 56059 | ATGCACCAGCAGCTTAGAAA | 71 | 979 |
| 802806 | 2115 | 2134 | 56049 | 56068 | AAATGAATGATGCACCAGCA | 82 | 980 |
| 802807 | 2124 | 2143 | 56058 | 56077 | TACTAAGTCAAATGAATGAT | 109 | 981 |
| 802808 | 2151 | 2170 | 56085 | 56104 | GATATTGGAAGACATTTGAT | 143 | 982 |
| 802809 | 2160 | 2179 | 56094 | 56113 | TTGTTCCATGATATTGGAAG | 128 | 983 |
| 802810 | 2180 | 2199 | N/A | N/A | TTTAGAAACTGTTGATCCTT | 113 | 984 |
| 802811 | 2181 | 2200 | N/A | N/A | GTTTAGAAACTGTTGATCCT | 128 | 985 |
| 802812 | 2182 | 2201 | N/A | N/A | GGTTTAGAAACTGTTGATCC | 93 | 986 |
| 802813 | 2183 | 2202 | N/A | N/A | AGGTTTAGAAACTGTTGATC | 115 | 987 |
| 802814 | 2184 | 2203 | N/A | N/A | GAGGTTTAGAAACTGTTGAT | 118 | 988 |
| 802815 | 2186 | 2205 | N/A | N/A | CAGAGGTTTAGAAACTGTTG | 63 | 989 |
| 802816 | 2187 | 2206 | N/A | N/A | ACAGAGGTTTAGAAACTGTT | 84 | 990 |
| 802817 | 2188 | 2207 | N/A | N/A | AACAGAGGTTTAGAAACTGT | 119 | 991 |
| 802818 | 2189 | 2208 | N/A | N/A | CAACAGAGGTTTAGAAACTG | 99 | 992 |
| 802819 | 2190 | 2209 | 56198 | 56217 | GCAACAGAGGTTTAGAAACT | 94 | 993 |
| 802820 | 2194 | 2213 | 56202 | 56221 | ACTTGCAACAGAGGTTTAGA | 109 | 994 |
| 802821 | 2203 | 2222 | 56211 | 56230 | TTGCAAAACACTTGCAACAG | 120 | 995 |
| 802822 | 2212 | 2231 | 56220 | 56239 | TAGCTACTTTTGCAAAACAC | 88 | 996 |
| 802823 | 2238 | 2257 | 56246 | 56265 | CATCACATTTTTAAGTAAT | 100 | 997 |
| 802824 | 2247 | 2266 | 56255 | 56274 | TCTCTCTAGCATCACATTTT | 80 | 998 |
| 802825 | 2256 | 2275 | 56264 | 56283 | ATCACACGCTCTCTCTAGCA | 57 | 999 |

TABLE 12-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802826 | 2282 | 2301 | 56290 | 56309 | CATTCAACCATGATGCTGTT | 79 | 72 |
| 802827 | 2291 | 2310 | 56299 | 56318 | AGAAGCAAGCATTCAACCAT | 103 | 1000 |
| 802828 | 2300 | 2319 | 56308 | 56327 | GCTCCCAATAGAAGCAAGCA | 108 | 1001 |
| 802829 | 2312 | 2331 | 56320 | 56339 | TGATTGGCATCTGCTCCCAA | 96 | 1002 |
| 802830 | 2313 | 2332 | 56321 | 56340 | TTGATTGGCATCTGCTCCCA | 67 | 1003 |
| 802831 | 2314 | 2333 | 56322 | 56341 | CTTGATTGGCATCTGCTCCC | 87 | 1004 |
| 802832 | 2315 | 2334 | 56323 | 56342 | GCTTGATTGGCATCTGCTCC | 54 | 1005 |
| 802833 | 2316 | 2335 | 56324 | 56343 | TGCTTGATTGGCATCTGCTC | 83 | 1006 |
| 802834 | 2318 | 2337 | 56326 | 56345 | TTTGCTTGATTGGCATCTGC | 82 | 125 |
| 802835 | 2319 | 2338 | 56327 | 56346 | CTTTGCTTGATTGGCATCTG | 80 | 1007 |
| 802836 | 2320 | 2339 | 56328 | 56347 | CCTTTGCTTGATTGGCATCT | 70 | 1008 |
| 802837 | 2321 | 2340 | 56329 | 56348 | TCCTTTGCTTGATTGGCATC | 94 | 1009 |
| 802838 | 2322 | 2341 | 56330 | 56349 | CTCCTTTGCTTGATTGGCAT | 75 | 1010 |
| 802839 | 2326 | 2345 | 56334 | 56353 | ATCCCTCCTTTGCTTGATTG | 124 | 1011 |
| 802840 | 2335 | 2354 | 56343 | 56362 | TTAAAGAAGATCCCTCCTTT | 186 | 1012 |
| 802841 | 2344 | 2363 | 56352 | 56371 | CCTGACAAATTAAAGAAGAT | 148 | 1013 |
| 802842 | 2357 | 2376 | N/A | N/A | TCTTTCTCACATACCTGACA | 69 | 1014 |

TABLE 13

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 693433 | 2380 | 2399 | 62001 | 62020 | GTTCCACCAATTTGGGACTG | 41 | 126 |
| 780254 | 4111 | 4130 | 86606 | 86625 | GTTTCATTCGGTTATAAGGC | 30 | 235 |
| 780254 | 4111 | 4130 | 86606 | 86625 | GTTTCATTCGGTTATAAGGC | 22 | 235 |
| 802843 | 2358 | 2377 | N/A | N/A | CTCTTTCTCACATACCTGAC | 74 | 1015 |
| 802844 | 2360 | 2379 | N/A | N/A | CTCTCTTTCTCACATACCTG | 53 | 1016 |
| 802845 | 2365 | 2384 | 61986 | 62005 | GACTGCTCTCTTTCTCACAT | 34 | 1017 |
| 802846 | 2367 | 2386 | 61988 | 62007 | GGGACTGCTCTCTTTCTCAC | 39 | 1018 |
| 802847 | 2369 | 2388 | 61990 | 62009 | TTGGGACTGCTCTCTTTCTC | 53 | 1019 |
| 802848 | 2370 | 2389 | 61991 | 62010 | TTTGGGACTGCTCTCTTTCT | 59 | 1020 |
| 802849 | 2372 | 2391 | 61993 | 62012 | AATTGGGACTGCTCTCTTT | 99 | 1021 |
| 802850 | 2373 | 2392 | 61994 | 62013 | CAATTGGGACTGCTCTCTT | 83 | 1022 |

TABLE 13-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802851 | 2389 | 2408 | 62010 | 62029 | TCAGTAAGAGTTCCACCAAT | 65 | 1023 |
| 802852 | 2415 | 2434 | 62036 | 62055 | TACATCTTGTTCACGAGATC | 92 | 1024 |
| 802853 | 2460 | 2479 | 62081 | 62100 | GATCTGGCTGTCACCTTTCC | 65 | 1025 |
| 802854 | 2469 | 2488 | 62090 | 62109 | CAAGCTGATGATCTGGCTGT | 98 | 1026 |
| 802855 | 2478 | 2497 | 62099 | 62118 | CCTTAAGAGCAAGCTGATGA | 58 | 1027 |
| 802856 | 2487 | 2506 | 62108 | 62127 | GGCCAGCCTCCTTAAGAGCA | 74 | 1028 |
| 802857 | 2508 | 2527 | 62129 | 62148 | GCTATTGTTGGCCACATCCA | 44 | 1029 |
| 802858 | 2517 | 2536 | 62138 | 62157 | AAGGCAAATGCTATTGTTGG | 90 | 1030 |
| 802859 | 2526 | 2545 | 62147 | 62166 | AAATCCTCCAAGGCAAATGC | 92 | 1031 |
| 802860 | 2552 | 2571 | 62173 | 62192 | CAAGAAGGTTCAACTTTTCC | 87 | 1032 |
| 802861 | 2596 | 2615 | 62217 | 62236 | GTTTCCTTAAATTAGAAGTC | 169 | 1033 |
| 802862 | 2606 | 2625 | N/A | N/A | ATATTTGTTTGTTTCCTTAA | 81 | 1034 |
| 802863 | 2615 | 2634 | N/A | N/A | GTAGATGCTATATTTGTTTG | 82 | 1035 |
| 802864 | 2641 | 2660 | 65479 | 65498 | GATATCTGATCACCATTCTT | 78 | 1036 |
| 802865 | 2650 | 2669 | 65488 | 65507 | TTTTCATCTGATATCTGATC | 121 | 1037 |
| 802866 | 2659 | 2678 | 65497 | 65516 | CCACAGCACTTTTCATCTGA | 116 | 1038 |
| 802867 | 2668 | 2687 | 65506 | 65525 | TTCCTTCTTCCACAGCACTT | 115 | 1039 |
| 802868 | 2687 | 2706 | 65525 | 65544 | CCATCGCTGCCTGAGGCTGT | 69 | 1040 |
| 802869 | 2696 | 2715 | 65534 | 65553 | GAAAAATTTCCATCGCTGCC | 149 | 1041 |
| 802870 | 2705 | 2724 | 65543 | 65562 | ACATCTTCAGAAAAATTTCC | 86 | 1042 |
| 802871 | 2731 | 2750 | 65569 | 65588 | AGGTCCATTCATCAAATTTA | 77 | 1043 |
| 802872 | 2740 | 2759 | 65578 | 65597 | CAGGAATAAAGGTCCATTCA | 68 | 1044 |
| 802873 | 2749 | 2768 | 65587 | 65606 | TAGAAGAGTCAGGAATAAAG | 119 | 1045 |
| 802874 | 2761 | 2780 | 65599 | 65618 | ACACACTGTCCATAGAAGAG | 53 | 1046 |
| 802875 | 2763 | 2782 | 65601 | 65620 | AAACACACTGTCCATAGAAG | 102 | 1047 |
| 802876 | 2765 | 2784 | 65603 | 65622 | GCAAACACACTGTCCATAGA | 43 | 1048 |
| 802877 | 2767 | 2786 | 65605 | 65624 | GAGCAAACACACTGTCCATA | 42 | 1049 |
| 802878 | 2768 | 2787 | 65606 | 65625 | TGAGCAAACACACTGTCCAT | 70 | 1050 |
| 802879 | 2770 | 2789 | 65608 | 65627 | TTTGAGCAAACACACTGTCC | 124 | 1051 |
| 802880 | 2771 | 2790 | 65609 | 65628 | CTTTGAGCAAACACACTGTC | 141 | 1052 |
| 802881 | 2778 | 2797 | 65616 | 65635 | GTCATCACTTTGAGCAAACA | 90 | 1053 |
| 802882 | 2787 | 2806 | 65625 | 65644 | ACTATCCAGGTCATCACTTT | 121 | 1054 |
| 802883 | 2796 | 2815 | N/A | N/A | ACTTCCTTCACTATCCAGGT | 53 | 1055 |
| 802884 | 2819 | 2838 | 71662 | 71681 | TTTTTCACAAGAAATGAGCC | 96 | 1056 |
| 802885 | 2828 | 2847 | 71671 | 71690 | TTAGATTTCTTTTCACAAG | 116 | 1057 |
| 802886 | 2837 | 2856 | 71680 | 71699 | CTAATTGAATTAGATTTCTT | 106 | 1058 |

TABLE 13-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802887 | 2863 | 2882 | 71706 | 71725 | CGGCATCTCGGTAAAATTCT | 48 | 1059 |
| 802888 | 2872 | 2891 | 71715 | 71734 | GCTGTAATACGGCATCTCGG | 27 | 1060 |
| 802889 | 2907 | 2926 | 71750 | 71769 | GGAATTGGAATGTCTTTGCA | 76 | 1061 |
| 802890 | 2916 | 2935 | N/A | N/A | GGGCCCCAAGGAATTGGAAT | 102 | 1062 |
| 802891 | 2925 | 2944 | N/A | N/A | ATCAAAAATGGGCCCCAAGG | 87 | 1063 |
| 802892 | 2951 | 2970 | 72975 | 72994 | CTTTTTCGCTTCAGTAAATC | 79 | 1064 |
| 802893 | 2962 | 2981 | 72986 | 73005 | ATAATATTTTCTTTTTCGC | 109 | 1065 |
| 802894 | 2971 | 2990 | 72995 | 73014 | CATCTGAAGATAATATTTTT | 141 | 1066 |
| 802895 | 2995 | 3014 | N/A | N/A | GAAGTTTTGATGACCTGAGT | 108 | 1067 |
| 802896 | 3004 | 3023 | 73540 | 73559 | TATGGGATTGAAGTTTTGAT | 56 | 1068 |
| 802897 | 3013 | 3032 | 73549 | 73568 | AATGCCTCATATGGGATTGA | 93 | 1069 |
| 802898 | 3022 | 3041 | 73558 | 73577 | TGCTGTCTGAATGCCTCATA | 60 | 1070 |
| 802899 | 3040 | 3059 | 73576 | 73595 | CAGAAGCCAGAGAAGAAATG | 135 | 1071 |
| 802900 | 3049 | 3068 | 73585 | 73604 | ATTCTCTCTCAGAAGCCAGA | 53 | 1072 |
| 802901 | 3058 | 3077 | 73594 | 73613 | ATGTAATATATTCTCTCTCA | 52 | 1073 |
| 802902 | 3084 | 3103 | 73620 | 73639 | TAGTTCATTTGCTGAAAGGT | 66 | 1074 |
| 802903 | 3093 | 3112 | 73629 | 73648 | AATATCTCTTAGTTCATTTG | 146 | 1075 |
| 802904 | 3102 | 3121 | 73638 | 73657 | TAGGGCATCAATATCTCTTA | 40 | 1076 |
| 802905 | 3111 | 3130 | 73647 | 73666 | TTTCTGGCTTAGGGCATCAA | 133 | 1077 |
| 802906 | 3129 | 3148 | 73665 | 73684 | ATGAACACTTATACAGCATT | 114 | 1078 |
| 802907 | 3138 | 3157 | 73674 | 73693 | ATGCTCCAAATGAACACTTA | 124 | 1079 |
| 802908 | 3147 | 3166 | 73683 | 73702 | CTTTTCAAGATGCTCCAAAT | 170 | 1080 |
| 802909 | 3173 | 3192 | 73709 | 73728 | GTGAGTGCATTCTGGTGAAG | 72 | 1081 |
| 802910 | 3192 | 3211 | 73728 | 73747 | TAGCTGTTGTGGAAAGCTCG | 114 | 1082 |
| 802911 | 3217 | 3236 | N/A | N/A | GTGTCAAACTCTTCAGAGTT | 34 | 1083 |
| 802912 | 3218 | 3237 | 76352 | 76371 | TGTGTCAAACTCTTCAGAGT | 60 | 1084 |
| 802913 | 3219 | 3238 | 76353 | 76372 | ATGTGTCAAACTCTTCAGAG | 63 | 1085 |
| 802914 | 3220 | 3239 | 76354 | 76373 | AATGTGTCAAACTCTTCAGA | 99 | 1086 |
| 802915 | 3226 | 3245 | 76360 | 76379 | AGTCCAAATGTGTCAAACTC | 23 | 1087 |
| 802916 | 3235 | 3254 | 76369 | 76388 | TACTGTGCAAGTCCAAATGT | 119 | 1088 |
| 802917 | 3244 | 3263 | 76378 | 76397 | TAAATTTATTACTGTGCAAG | 55 | 1089 |
| 802918 | 3265 | 3284 | 76399 | 76418 | ACAAATAAGAAGGAAATGAT | 196 | 1090 |

TABLE 14

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 22 | 235 |
| 780254 | 4111 | 4130 | 86606 | 86625 | GTTTCATTCGGTTATAAGGC | 29 | 235 |
| 802919 | 3274 | 3293 | 76408 | 76427 | TCATTTTCAACAAATAAGAA | 110 | 1091 |
| 802920 | 3283 | 3302 | 76417 | 76436 | CAATACAACTCATTTTCAAC | 63 | 1092 |
| 802921 | 3309 | 3328 | 76443 | 76462 | GTCATTTCGAGAGACATCAA | 36 | 1093 |
| 802922 | 3318 | 3337 | 76452 | 76471 | GGGTCCAATGTCATTTCGAG | 38 | 1094 |
| 802923 | 3327 | 3346 | 76461 | 76480 | AACCACTGAGGGTCCAATGT | 51 | 1095 |
| 802924 | 3353 | 3372 | 76487 | 76506 | GTTGGACATTTCACTGTAGG | 20 | 1096 |
| 802925 | 3362 | 3381 | 76496 | 76515 | TGTTTCAGAGTTGGACATTT | 77 | 1097 |
| 802926 | 3371 | 3390 | 76505 | 76524 | AGGTTAAACTGTTTCAGAGT | 36 | 1098 |
| 802927 | 3380 | 3399 | 76514 | 76533 | TTATATGACAGGTTAAACTG | 103 | 1099 |
| 802928 | 3398 | 3417 | 76532 | 76551 | GGTACAAAAGACAGCTGGTT | 34 | 1100 |
| 802929 | 3407 | 3426 | 76541 | 76560 | AGGTTCTCAGGTACAAAAGA | 47 | 1101 |
| 802930 | 3416 | 3435 | 76550 | 76569 | ACATCAGTGAGGTTCTCAGG | 37 | 1102 |
| 802931 | 3442 | 3461 | 76576 | 76595 | AAATGAGCTGCTCCAGTTTC | 75 | 1103 |
| 802932 | 3451 | 3470 | N/A | N/A | TTCCTTCTAAAATGAGCTGC | 53 | 1104 |
| 802933 | 3463 | 3482 | N/A | N/A | CTGATATTTTATTTCCTTCT | 69 | 1105 |
| 802934 | 3472 | 3491 | 77221 | 77240 | AGCATATCCCTGATATTTTA | 29 | 1106 |
| 802935 | 3495 | 3514 | 77244 | 77263 | CAGTTCCTTCAGTCTCAAGG | 32 | 1107 |
| 802936 | 3496 | 3515 | 77245 | 77264 | TCAGTTCCTTCAGTCTCAAG | 49 | 1108 |
| 802937 | 3497 | 3516 | 77246 | 77265 | TTCAGTTCCTTCAGTCTCAA | 80 | 1109 |
| 802938 | 3498 | 3517 | 77247 | 77266 | CTTCAGTTCCTTCAGTCTCA | 37 | 1110 |
| 802939 | 3499 | 3518 | 77248 | 77267 | TCTTCAGTTCCTTCAGTCTC | 56 | 1111 |
| 802940 | 3505 | 3524 | 77254 | 77273 | TTAAAATCTTCAGTTCCTTC | 59 | 1112 |
| 802941 | 3514 | 3533 | 77263 | 77282 | TACTAAGGTTTAAAATCTTC | 105 | 1113 |
| 802942 | 3523 | 3542 | 77272 | 77291 | TGTGGTTCTTACTAAGGTTT | 38 | 1114 |
| 802943 | 3547 | 3566 | 77296 | 77315 | GAAAGTTCTCTGATAGGGAT | 59 | 1115 |
| 802944 | 3556 | 3575 | 77305 | 77324 | AAGCCTCAAGAAAGTTCTCT | 59 | 1116 |
| 802945 | 3565 | 3584 | 77314 | 77333 | CTTTAGGACAAGCCTCAAGA | 65 | 132 |
| 802946 | 3591 | 3610 | 77340 | 77359 | ATTCATTCTGGCACTGAAAC | 136 | 1117 |
| 802947 | 3600 | 3619 | N/A | N/A | AGCAAGAAAATTCATTCTGG | 75 | 1118 |
| 802948 | 3609 | 3628 | N/A | N/A | AGGCATAGCAGCAAGAAAAT | 57 | 1119 |
| 802949 | 3635 | 3654 | 80915 | 80934 | AGGATTGTCATAGAAGGAGG | 19 | 1120 |
| 802950 | 3644 | 3663 | 80924 | 80943 | GATAATTTTAGGATTGTCAT | 58 | 1121 |
| 802951 | 3654 | 3673 | 80934 | 80953 | TTTGTTCTGAGATAATTTTA | 32 | 1122 |
| 802952 | 3679 | 3698 | 80959 | 80978 | AAATTGCTTCTGGAATACAG | 75 | 1123 |

TABLE 14-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802953 | 3688 | 3707 | 80968 | 80987 | GAAGATTTAAAATTGCTTCT | 115 | 1124 |
| 802954 | 3697 | 3716 | N/A | N/A | GCAAGTGTGGAAGATTTAAA | 50 | 1125 |
| 802955 | 3709 | 3728 | N/A | N/A | TATCTAAAGACCGCAAGTGT | 51 | 1126 |
| 802956 | 3710 | 3729 | N/A | N/A | ATATCTAAAGACCGCAAGTG | 62 | 1127 |
| 802957 | 3711 | 3730 | N/A | N/A | CATATCTAAAGACCGCAAGT | 63 | 1128 |
| 802958 | 3712 | 3731 | 82057 | 82076 | TCATATCTAAAGACCGCAAG | 71 | 1129 |
| 802959 | 3713 | 3732 | 82058 | 82077 | CTCATATCTAAAGACCGCAA | 47 | 1130 |
| 802960 | 3715 | 3734 | 82060 | 82079 | TGCTCATATCTAAAGACCGC | 35 | 1131 |
| 802961 | 3716 | 3735 | 82061 | 82080 | CTGCTCATATCTAAAGACCG | 43 | 1132 |
| 802962 | 3717 | 3736 | 82062 | 82081 | GCTGCTCATATCTAAAGACC | 28 | 1133 |
| 802963 | 3718 | 3737 | 82063 | 82082 | TGCTGCTCATATCTAAAGAC | 64 | 1134 |
| 802964 | 3719 | 3738 | 82064 | 82083 | TTGCTGCTCATATCTAAAGA | 79 | 1135 |
| 802965 | 3723 | 3742 | 82068 | 82087 | ATCATTGCTGCTCATATCTA | 82 | 1136 |
| 802966 | 3732 | 3751 | 82077 | 82096 | GTACTGAATATCATTGCTGC | 31 | 1137 |
| 802967 | 3741 | 3760 | 82086 | 82105 | ACCTGGTAGGTACTGAATAT | 50 | 1138 |
| 802968 | 3767 | 3786 | 82112 | 82131 | AAGTTCAAAGATTTCCAGTG | 50 | 1139 |
| 802969 | 3776 | 3795 | 82121 | 82140 | AGTTCCCTTAAGTTCAAAGA | 78 | 1140 |
| 802970 | 3785 | 3804 | 82130 | 82149 | CTAAATAAGAGTTCCCTTAA | 75 | 1141 |
| 802971 | 3811 | 3830 | 82156 | 82175 | AGTCCAAGATGCTGATCTGA | 49 | 1142 |
| 802972 | 3820 | 3839 | 82165 | 82184 | TTTCACTCAAGTCCAAGATG | 52 | 1143 |
| 802973 | 3829 | 3848 | 82174 | 82193 | AATATGCTTTTTCACTCAAG | 64 | 1144 |
| 802974 | 3855 | 3874 | 82200 | 82219 | ATGCAGTTTCTCTACTCTAG | 31 | 1145 |
| 802975 | 3864 | 3883 | 82209 | 82228 | GTGAGAAAGATGCAGTTTCT | 47 | 1146 |
| 802976 | 3873 | 3892 | 82218 | 82237 | CAGTTTATTGTGAGAAAGAT | 89 | 1147 |
| 802977 | 3882 | 3901 | N/A | N/A | AATCTCTTTCAGTTTATTGT | 65 | 1148 |
| 802978 | 3900 | 3919 | 83895 | 83914 | ACAGCCAATCTCAGGAGGAA | 56 | 1149 |
| 802979 | 3909 | 3928 | 83904 | 83923 | ATTTTCAAGACAGCCAATCT | 72 | 1150 |
| 802980 | 3918 | 3937 | 83913 | 83932 | AGATGTCAGATTTTCAAGAC | 141 | 1151 |
| 802981 | 3944 | 3963 | 83939 | 83958 | AGTTCCAAGTTGTAACTGAC | 59 | 57 |
| 802982 | 3953 | 3972 | 83948 | 83967 | AAGGATCTTAGTTCCAAGTT | 89 | 1152 |
| 802983 | 3962 | 3981 | 83957 | 83976 | TCATTGGGAAAGGATCTTAG | 107 | 1153 |
| 802984 | 3988 | 4007 | 83983 | 84002 | CCCATATTTTGCTTAATTTC | 54 | 1154 |
| 802985 | 3997 | 4016 | 83992 | 84011 | AAGGAAGATCCCATATTTTG | 72 | 1155 |
| 802986 | 4006 | 4025 | 84001 | 84020 | GTTCATCCAAAGGAAGATCC | 40 | 1156 |
| 802987 | 4033 | 4052 | 84028 | 84047 | TATGTTTAAAATCAAGTTA | 128 | 1157 |

TABLE 14-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 802988 | 4042 | 4061 | 84037 | 84056 | TACATCCTATATGTTTAAAA | 101 | 1158 |
| 802989 | 4060 | 4079 | 84055 | 84074 | TTATGATGTCTTTGGCTTTA | 41 | 1159 |
| 802990 | 4061 | 4080 | 84056 | 84075 | CTTATGATGTCTTTGGCTTT | 53 | 1160 |
| 802991 | 4063 | 4082 | 84058 | 84077 | ACCTTATGATGTCTTTGGCT | 36 | 1161 |
| 802992 | 4065 | 4084 | N/A | N/A | AAACCTTATGATGTCTTTGG | 41 | 1162 |
| 802993 | 4068 | 4087 | N/A | N/A | AAGAAACCTTATGATGTCTT | 80 | 1163 |
| 802994 | 4078 | 4097 | N/A | N/A | ATCGCTGTTGAAGAAACCTT | 38 | 1164 |
| 802995 | 4087 | 4106 | 86582 | 86601 | CCTTTTTTAATCGCTGTTGA | 69 | 1165 |

TABLE 15

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 31 | 235 |
| 780254 | 4111 | 4130 | 86606 | 86625 | GTTTCATTCGGTTATAAGGC | 51 | 235 |
| 802996 | 4096 | 4115 | 86591 | 86610 | AAGGCACAGCCTTTTTTAAT | 88 | 1166 |
| 802997 | 4106 | 4125 | 86601 | 86620 | ATTCGGTTATAAGGCACAGC | 39 | 1167 |
| 802998 | 4107 | 4126 | 86602 | 86621 | CATTCGGTTATAAGGCACAG | 54 | 1168 |
| 802999 | 4108 | 4127 | 86603 | 86622 | TCATTCGGTTATAAGGCACA | 51 | 1169 |
| 803000 | 4109 | 4128 | 86604 | 86623 | TTCATTCGGTTATAAGGCAC | 34 | 1170 |
| 803001 | 4110 | 4129 | 86605 | 86624 | TTTCATTCGGTTATAAGGCA | 47 | 1171 |
| 803002 | 4112 | 4131 | 86607 | 86626 | AGTTTCATTCGGTTATAAGG | 57 | 1172 |
| 803003 | 4113 | 4132 | 86608 | 86627 | AAGTTTCATTCGGTTATAAG | 72 | 1173 |
| 803004 | 4114 | 4133 | 86609 | 86628 | TAAGTTTCATTCGGTTATAA | 89 | 1174 |
| 803005 | 4115 | 4134 | 86610 | 86629 | ATAAGTTTCATTCGGTTATA | 44 | 1175 |
| 803006 | 4116 | 4135 | 86611 | 86630 | CATAAGTTTCATTCGGTTAT | 45 | 1176 |
| 803007 | 4120 | 4139 | 86615 | 86634 | CAATCATAAGTTTCATTCGG | 51 | 1177 |
| 803008 | 4129 | 4148 | 86624 | 86643 | TATTTCCCACAATCATAAGT | 98 | 1178 |
| 803009 | 4138 | 4157 | 86633 | 86652 | CACTCCCAGTATTTCCCACA | 69 | 1179 |
| 803010 | 4164 | 4183 | 86659 | 86678 | TAATTGCTGCAATAAGGTGG | 51 | 1180 |
| 803011 | 4173 | 4192 | 86668 | 86687 | GGTTTTCATTAATTGCTGCA | 40 | 1181 |
| 803012 | 4184 | 4203 | 86679 | 86698 | TCTGATTTCTTGGTTTTCAT | 58 | 1182 |
| 803013 | 4208 | 4227 | 86703 | 86722 | ACTGTGGCACTTTGCATTCC | 80 | 1183 |
| 803014 | 4217 | 4236 | 86712 | 86731 | TCTATGCCAACTGTGGCACT | 79 | 1184 |

TABLE 15-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803015 | 4226 | 4245 | 86721 | 86740 | TCTTTCACATCTATGCCAAC | 79 | 1185 |
| 803016 | 4252 | 4271 | 86747 | 86766 | TTTTGTCTCTTATTTGGATA | 44 | 1186 |
| 803017 | 4267 | 4286 | 86762 | 86781 | CGAGATCTCTCTTTCTTTTG | 56 | 1187 |
| 803018 | 4276 | 4295 | 86771 | 86790 | CATTTAGGACGAGATCTCTC | 92 | 1188 |
| 803019 | 4296 | 4315 | N/A | N/A | ACGACCTGCAAAATCCCACA | 65 | 1189 |
| 803020 | 4305 | 4324 | N/A | N/A | GAATTCCTCACGACCTGCAA | 90 | 83 |
| 803021 | 4314 | 4333 | 87218 | 87237 | AGTACTATAGAATTCCTCAC | 35 | 1190 |
| 803022 | 4359 | 4378 | 87263 | 87282 | ATAGACAGCAAGGTACAATG | 101 | 1191 |
| 803023 | 4368 | 4387 | 87272 | 87291 | GCTGAGGTCATAGACAGCAA | 101 | 1192 |
| 803024 | 4377 | 4396 | 87281 | 87300 | CTGTCCCTTGCTGAGGTCAT | 89 | 1193 |
| 803025 | 4403 | 4422 | 87307 | 87326 | CAAGGCTTCATGGCATCAAC | 85 | 1194 |
| 803026 | 4412 | 4431 | 87316 | 87335 | TTGAAGAGCCAAGGCTTCAT | 96 | 1195 |
| 803027 | 4421 | 4440 | N/A | N/A | GCCTTTATATTGAAGAGCCA | 62 | 1196 |
| 803028 | 4456 | 4475 | 88557 | 88576 | TGCCAACGAGAATCACAGGG | 45 | 1197 |
| 803029 | 4465 | 4484 | 88566 | 88585 | CCAAATGTGTGCCAACGAGA | 70 | 1198 |
| 803030 | 4474 | 4493 | 88575 | 88594 | CAGAAACATCCAAATGTGTG | 69 | 1199 |
| 803031 | 4505 | 4524 | 88606 | 88625 | TTACTCATGCAGGCTTTGCG | 44 | 1200 |
| 803032 | 4514 | 4533 | 88615 | 88634 | TTGGTGATTTTACTCATGCA | 43 | 1201 |
| 803033 | 4536 | 4555 | 88637 | 88656 | CCCTCGCTTATTCAGGAGTT | 98 | 1202 |
| 803034 | 4545 | 4564 | 88646 | 88665 | GGCAGGGAACCCTCGCTTAT | 61 | 1203 |
| 803035 | 4580 | 4599 | 88681 | 88700 | TCCTCGGTGGCATTCACAAA | 60 | 42 |
| 803036 | 4589 | 4608 | 88690 | 88709 | GCATCAGATTCCTCGGTGGC | 39 | 1204 |
| 803037 | 4598 | 4617 | 88699 | 88718 | TTTGCCAAAGCATCAGATTC | 67 | 1205 |
| 803038 | 4639 | 4658 | N/A | N/A | TCTTGAAATTAAGGCTCTCG | 91 | 1206 |
| 803039 | 4648 | 4667 | N/A | N/A | GATCTCGGATCTTGAAATTA | 125 | 1207 |
| 803040 | 4668 | 4687 | 92091 | 92110 | CAGCTGTCCAACAACAAGCT | 81 | 1208 |
| 803041 | 4677 | 4696 | 92100 | 92119 | GTCTGGAATCAGCTGTCCAA | 55 | 1209 |
| 803042 | 4686 | 4705 | 92109 | 92128 | TACATAGCAGTCTGGAATCA | 75 | 1210 |
| 803043 | 4712 | 4731 | 92135 | 92154 | TCCGATAAAATGATTTTTTC | 60 | 1211 |
| 803044 | 4721 | 4740 | 92144 | 92163 | TTTTTACGCTCCGATAAAAT | 132 | 1212 |
| 803045 | 4730 | 4749 | 92153 | 92172 | ATTGGCACATTTTTACGCTC | 24 | 1213 |
| 803046 | 4756 | 4775 | 92179 | 92198 | GTTTCCGGTCAATTACGGGA | 21 | 1214 |
| 803047 | 4775 | 4794 | 92198 | 92217 | CTCACTAGTTGTAATAATCG | 63 | 1215 |
| 803048 | 4800 | 4819 | 92223 | 92242 | TTCATCTAACTGCAGCTGAT | 59 | 1216 |
| 803049 | 4810 | 4829 | 92233 | 92252 | GAAGCTCATTTTCATCTAAC | 49 | 1217 |

TABLE 15-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803050 | 4844 | 4863 | N/A | N/A | ACTCCTGATTCATTTAGAAA | 88 | 1218 |
| 803051 | 4853 | 4872 | N/A | N/A | TGAAGAAGGACTCCTGATTC | 99 | 1219 |
| 803052 | 4862 | 4881 | 93323 | 93342 | TCTTGAAAATGAAGAAGGAC | 100 | 1220 |
| 803053 | 4871 | 4890 | 93332 | 93351 | AGTGCTGGGTCTTGAAAATG | 55 | 1221 |
| 803054 | 4892 | 4911 | 93353 | 93372 | AAGTACAAGTCACTTAACTG | 38 | 1222 |
| 803055 | 4938 | 4957 | N/A | N/A | TGTCAAAATCTGTGCCATGA | 70 | 1223 |
| 803056 | 4947 | 4966 | 98095 | 98114 | CACTTTCACTGTCAAAATCT | 76 | 1224 |
| 803057 | 4956 | 4975 | 98104 | 98123 | ACAACCTTCCACTTTCACTG | 65 | 1225 |
| 803058 | 4982 | 5001 | 98130 | 98149 | GAAATAATGCCCTTAGGGTG | 98 | 1226 |
| 803059 | 4991 | 5010 | 98139 | 98158 | TCTCTACGCGAAATAATGCC | 58 | 1227 |
| 803060 | 5000 | 5019 | 98148 | 98167 | TTTTCCACATCTCTACGCGA | 49 | 1228 |
| 803061 | 5009 | 5028 | 98157 | 98176 | GAAAGAAATTTTTCCACATC | 65 | 1229 |
| 803062 | 5028 | 5047 | 98176 | 98195 | TGGAAATTTCCTTTTTTTTG | 81 | 1230 |
| 803063 | 5038 | 5057 | 98186 | 98205 | TGTAGTTCTTTGGAAATTTC | 45 | 1231 |
| 803064 | 5047 | 5066 | 98195 | 98214 | ACTGTGACATGTAGTTCTTT | 29 | 1232 |
| 803065 | 5072 | 5091 | 98220 | 98239 | TGGAATTTTTCTAGGAGCTT | 23 | 1233 |
| 803066 | 5082 | 5101 | 98230 | 98249 | CAAAGCAATCTGGAATTTTT | 104 | 1234 |
| 803067 | 5091 | 5110 | 98239 | 98258 | TCCTATTGGCAAAGCAATCT | 79 | 1235 |
| 803068 | 5100 | 5119 | 98248 | 98267 | ATATTCTTCTCCTATTGGCA | 84 | 1236 |
| 803069 | 5118 | 5137 | N/A | N/A | ACTGCTTGGAACCAGCAAAT | 72 | 1237 |
| 803070 | 5127 | 5146 | N/A | N/A | GTCAGACAAACTGCTTGGAA | 84 | 1238 |
| 803071 | 5136 | 5155 | 99142 | 99161 | AGGCCTGTGGTCAGACAAAC | 87 | 1239 |
| 803072 | 5145 | 5164 | 99151 | 99170 | CTCTATCACAGGCCTGTGGT | 73 | 1240 |

TABLE 16

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 11 | 235 |
| 780254 | 4111 | 4130 | 86606 | 86625 | GTTTCATTCGGTTATAAGGC | 26 | 235 |
| 803073 | 5178 | 5197 | 99184 | 99203 | GATGATAATTTCAGAGTTCT | 49 | 1241 |
| 803074 | 5187 | 5206 | 99193 | 99212 | ATATAGTCGGATGATAATTT | 53 | 1242 |
| 803075 | 5196 | 5215 | 99202 | 99221 | AGGCATTTCATATAGTCGGA | 11 | 1243 |
| 803076 | 5206 | 5225 | 99212 | 99231 | TTGGAAAATAAGGCATTTCA | 48 | 1244 |

TABLE 16-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803077 | 5227 | 5246 | 99233 | 99252 | TTAATCTTGACCAAAATCCC | 76 | 1245 |
| 803078 | 5236 | 5255 | 99242 | 99261 | ATCGATTGATTAATCTTGAC | 48 | 1246 |
| 803079 | 5245 | 5264 | 99251 | 99270 | TCTCAAGTAATCGATTGATT | 34 | 1247 |
| 803080 | 5270 | 5289 | 99276 | 99295 | CTCCCTGAAAGCATGTAAGG | 64 | 1248 |
| 803081 | 5294 | 5313 | 100146 | 100165 | CTGTTTGGGCGAAGTGCTCG | 45 | 1249 |
| 803082 | 5300 | 5319 | 100152 | 100171 | TACATTCTGTTTGGGCGAAG | 52 | 1250 |
| 803083 | 5301 | 5320 | 100153 | 100172 | ATACATTCTGTTTGGGCGAA | 40 | 1251 |
| 803084 | 5302 | 5321 | 100154 | 100173 | AATACATTCTGTTTGGGCGA | 33 | 1252 |
| 803085 | 5303 | 5322 | 100155 | 100174 | CAATACATTCTGTTTGGGCG | 39 | 1253 |
| 803086 | 5304 | 5323 | 100156 | 100175 | CCAATACATTCTGTTTGGGC | 48 | 1254 |
| 803087 | 5306 | 5325 | 100158 | 100177 | CGCCAATACATTCTGTTTGG | 36 | 1255 |
| 803088 | 5307 | 5326 | 100159 | 100178 | TCGCCAATACATTCTGTTTG | 44 | 1256 |
| 803089 | 5308 | 5327 | 100160 | 100179 | GTCGCCAATACATTCTGTTT | 57 | 1257 |
| 803090 | 5309 | 5328 | 100161 | 100180 | TGTCGCCAATACATTCTGTT | 55 | 1258 |
| 803091 | 5310 | 5329 | 100162 | 100181 | TTGTCGCCAATACATTCTGT | 62 | 1259 |
| 803092 | 5314 | 5333 | 100166 | 100185 | TGCCTTGTCGCCAATACATT | 46 | 1260 |
| 803093 | 5323 | 5342 | 100175 | 100194 | TTAAGTAAATGCCTTGTCGC | 61 | 1261 |
| 803094 | 5332 | 5351 | 100184 | 100203 | GAGACCAATTTAAGTAAATG | 63 | 1262 |
| 803095 | 5358 | 5377 | 100210 | 100229 | AGATCCTACCAGACAATAAG | 83 | 1263 |
| 803096 | 5367 | 5386 | 100219 | 100238 | TAAGACTTCAGATCCTACCA | 49 | 1264 |
| 803097 | 5376 | 5395 | 100228 | 100247 | ATGATTGTCTAAGACTTCAG | 38 | 1265 |
| 803098 | 5385 | 5404 | 100237 | 100256 | ACTCTCTGGATGATTGTCTA | 36 | 1266 |
| 803099 | 5405 | 5424 | 100257 | 100276 | GGAACTGTAATTTTTAAGAA | 98 | 1267 |
| 803100 | 5414 | 5433 | 100266 | 100285 | CTACAAGAAGGAACTGTAAT | 98 | 1268 |
| 803101 | 5423 | 5442 | N/A | N/A | CAGCCTTTTCTACAAGAAGG | 40 | 1269 |
| 803102 | 5449 | 5468 | 100438 | 100457 | GGTCCACAACTTGGCCCAAA | 28 | 1270 |
| 803103 | 5458 | 5477 | 100447 | 100466 | AATCAATGTGGTCCACAACT | 70 | 1271 |
| 803104 | 5467 | 5486 | 100456 | 100475 | CCATGAGAGAATCAATGTGG | 35 | 1272 |
| 803105 | 5476 | 5495 | 100465 | 100484 | ACCATTCTTCCATGAGAGAA | 36 | 1273 |
| 803106 | 5497 | 5516 | 100486 | 100505 | CAATCTCCAGCAACCCAGGA | 69 | 1274 |
| 803107 | 5507 | 5526 | 100496 | 100515 | CCACAAATATCAATCTCCAG | 45 | 1275 |
| 803108 | 5516 | 5535 | 100505 | 100524 | TCTCCTTCACCACAAATATC | 46 | 1276 |
| 803109 | 5533 | 5552 | 100522 | 100541 | ATTTCTTCAACAGAGTTTCT | 103 | 1277 |
| 803110 | 5534 | 5553 | 100523 | 100542 | CATTTCTTCAACAGAGTTTC | 64 | 1278 |
| 803111 | 5536 | 5555 | 100525 | 100544 | CCCATTTCTTCAACAGAGTT | 36 | 1279 |

TABLE 16-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803112 | 5538 | 5557 | 100527 | 100546 | TGCCCATTTCTTCAACAGAG | 22 | 1280 |
| 803113 | 5540 | 5559 | 100529 | 100548 | AATGCCCATTTCTTCAACAG | 53 | 1281 |
| 803114 | 5541 | 5560 | 100530 | 100549 | TAATGCCCATTTCTTCAACA | 67 | 1282 |
| 803115 | 5551 | 5570 | 100540 | 100559 | TAAAACTATATAATGCCCAT | 49 | 1283 |
| 803116 | 5560 | 5579 | 100549 | 100568 | CACCATCATTAAAACTATAT | 72 | 1284 |
| 803117 | 5586 | 5605 | 100575 | 100594 | ATCAAGTAAGATTTTTTGAT | 84 | 1285 |
| 803118 | 5595 | 5614 | 100584 | 100603 | CATCAAGTCATCAAGTAAGA | 70 | 1286 |
| 803119 | 5604 | 5623 | 100593 | 100612 | TGCTTTCTTCATCAAGTCAT | 80 | 1287 |
| 803120 | 5631 | 5650 | 101269 | 101288 | TGGATTTACTAAGAGATCTC | 36 | 1288 |
| 803121 | 5640 | 5659 | 101278 | 101297 | TGGTTGATCTGGATTTACTA | 49 | 1289 |
| 803122 | 5649 | 5668 | 101287 | 101306 | GGTGAGCCTTGGTTGATCTG | 28 | 1290 |
| 803123 | 5689 | 5708 | 101327 | 101346 | CAGCCAAAATCAAGTCAGGG | 29 | 1291 |
| 803124 | 5698 | 5717 | 101336 | 101355 | TAGGCAGGTCAGCCAAAATC | 47 | 1292 |
| 803125 | 5721 | 5740 | 101359 | 101378 | ATCATTATTCAACATAATAT | 78 | 1293 |
| 803126 | 5730 | 5749 | 101368 | 101387 | TTCCAACTCATCATTATTCA | 37 | 1294 |
| 803127 | 5739 | 5758 | 101377 | 101396 | TTGTTCAAATTCCAACTCAT | 79 | 1295 |
| 803128 | 5763 | 5782 | N/A | N/A | ATCACCTAGGAGAAACTCTG | 52 | 1296 |
| 803129 | 5772 | 5791 | N/A | N/A | AAAACTGCCATCACCTAGGA | 60 | 1297 |
| 803130 | 5781 | 5800 | 106472 | 106491 | AACTGATCCAAAACTGCCAT | 51 | 1298 |
| 803131 | 5807 | 5826 | 106498 | 106517 | TCTTCTCCTTCATAGGCTGC | 55 | 1299 |
| 803132 | 5816 | 5835 | 106507 | 106526 | ACAGCCACTTCTTCTCCTTC | 80 | 1300 |
| 803133 | 5825 | 5844 | 106516 | 106535 | AAAATCTTCACAGCCACTTC | 102 | 92 |
| 803134 | 5851 | 5870 | 106542 | 106561 | ACAGCCTGAGTGATGTATGT | 32* | 1301 |
| 803135 | 5860 | 5879 | 106551 | 106570 | CTTGTCTTAACAGCCTGAGT | 28* | 1302 |
| 803136 | 5869 | 5888 | N/A | N/A | CCACAAGCTCTTGTCTTAAC | 34* | 1303 |
| 803137 | 5909 | 5928 | 113106 | 113125 | AGCAAAGATATCAAACTGGG | 51* | 1304 |
| 803138 | 5918 | 5937 | 113115 | 113134 | CCAGCTGCCAGCAAAGATAT | 44* | 1305 |
| 803139 | 5927 | 5946 | 113124 | 113143 | GGACGAATCCCAGCTGCCAG | 42* | 1306 |
| 803140 | 5955 | 5974 | 113152 | 113171 | GGAGGCTAACTCCATCACCA | 35 | 1307 |
| 803141 | 5964 | 5983 | 113161 | 113180 | GGAACCCTTGGAGGCTAACT | 89 | 1308 |
| 803142 | 5973 | 5992 | 113170 | 113189 | GCGATCCAAGGAACCCTTGG | 91 | 1309 |
| 803143 | 5999 | 6018 | 113196 | 113215 | AGGCTGGCTTTGTCCTGCTG | 110 | 1310 |
| 803144 | 6008 | 6027 | 113205 | 113224 | GTTCTAGTGAGGCTGGCTTT | 75 | 1311 |
| 803145 | 6017 | 6036 | 113214 | 113233 | TGCTGTAGGGTTCTAGTGAG | 93 | 1312 |
| 803146 | 6052 | 6071 | N/A | N/A | ATCTCAAACCATCAGCTACG | 76 | 1313 |
| 803147 | 6061 | 6080 | N/A | N/A | AGTGGAGGTATCTCAAACCA | 85 | 1314 |

TABLE 16-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803148 | 6087 | 6106 | 118420 | 118439 | CAGGTCTCGGTATATAATCA | 69 | 1315 |
| 803149 | 6111 | 6130 | 118444 | 118463 | GAAAAGCAGCACATTGTGGG | 47 | 1316 |

TABLE 17

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 12 | 235 |
| 780254 | 4111 | 4130 | 86606 | 86625 | GTTTCATTCGGTTATAAGGC | 24 | 235 |
| 803150 | 6131 | 6150 | 118464 | 118483 | GCAGCATTGGGATACAGTGT | 53 | 1317 |
| 803151 | 6140 | 6159 | 118473 | 118492 | GCAATGATGGCAGCATTGGG | 59 | 1318 |
| 803152 | 6149 | 6168 | 118482 | 118501 | GCAATCTTTGCAATGATGGC | 56 | 159 |
| 803153 | 6189 | 6208 | 118522 | 118541 | TATCCCCATTCTACAGCAGT | 81 | 1319 |
| 803154 | 6198 | 6217 | 118531 | 118550 | TGATGTTTTATCCCCATTC | 98 | 1320 |
| 803155 | 6220 | 6239 | N/A | N/A | CACGAAACCCTGGTGTGCCC | 58 | 1321 |
| 803156 | 6229 | 6248 | 124860 | 124879 | CTTCAGGTGCACGAAACCCT | 101 | 1322 |
| 803157 | 6238 | 6257 | 124869 | 124888 | CTCTGGCAACTTCAGGTGCA | 65 | 1323 |
| 803158 | 6264 | 6283 | 124895 | 124914 | AGCCTGTTGGTTATAAATGA | 64 | 1324 |
| 803159 | 6273 | 6292 | 124904 | 124923 | ATAAACATCAGCCTGTTGGT | 83 | 1325 |
| 803160 | 6282 | 6301 | 124913 | 124932 | ACCAAATGAATAAACATCAG | 60 | 1326 |
| 803161 | 6308 | 6327 | 124939 | 124958 | GTTGTCAAAATGTCATAGAG | 57 | 1327 |
| 803162 | 6317 | 6336 | 124948 | 124967 | CTACCTCCAGTTGTCAAAAT | 72 | 1328 |
| 803163 | 6326 | 6345 | 124957 | 124976 | TCTACTATTCTACCTCCAGT | 57 | 1329 |
| 803164 | 6335 | 6354 | 124966 | 124985 | TTCAAACCCTCTACTATTCT | 85 | 1330 |
| 803165 | 6354 | 6373 | 124985 | 125004 | ATCAAACTCATTTGGAAACT | 71 | 1331 |
| 803166 | 6363 | 6382 | 124994 | 125013 | TTCTAATTCATCAAACTCAT | 90 | 1332 |
| 803167 | 6372 | 6391 | 125003 | 125022 | TCCTTGTATTTCTAATTCAT | 93 | 1333 |
| 803168 | 6398 | 6417 | N/A | N/A | TATTCTTTAACTGGATCAGG | 81 | 1334 |
| 803169 | 6407 | 6426 | 126523 | 126542 | GCACAACCATATTCTTTAAC | 70 | 1335 |
| 803170 | 6442 | 6461 | 126558 | 126577 | ACTGTTTAATTAATTTCTCA | 60 | 1336 |
| 803171 | 6451 | 6470 | 126567 | 126586 | CTTTCAAACACTGTTTAATT | 68 | 1337 |
| 803172 | 6460 | 6479 | 126576 | 126595 | GAGGATTTTCTTTCAAACAC | 39 | 1338 |
| 803173 | 6486 | 6505 | N/A | N/A | GACCTGGGCAGAAGTAGGCC | 62 | 1339 |

TABLE 17-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803174 | 6495 | 6514 | N/A | N/A | AATGTCAAAGACCTGGGCAG | 94 | 1340 |
| 803175 | 6504 | 6523 | 129649 | 129668 | TGAATTCAAAATGTCAAAGA | 113 | 1341 |
| 803176 | 6548 | 6567 | 129693 | 129712 | TTTTTAGGTAATAAAATGCG | 112 | 1342 |
| 803177 | 6577 | 6596 | 129722 | 129741 | GTGTAGCAACCATGCATTCA | 32 | 1343 |
| 803178 | 6586 | 6605 | 129731 | 129750 | TGTTGTGATGTGTAGCAACC | 54 | 162 |
| 803179 | 6595 | 6614 | 129740 | 129759 | CATTCCTGCTGTTGTGATGT | 66 | 1344 |
| 803180 | 6607 | 6626 | 129752 | 129771 | GCCAAATGCTTGCATTCCTG | 42 | 1345 |
| 803181 | 6608 | 6627 | 129753 | 129772 | AGCCAAATGCTTGCATTCCT | 38 | 1346 |
| 803182 | 6609 | 6628 | 129754 | 129773 | CAGCCAAATGCTTGCATTCC | 64 | 1347 |
| 803183 | 6610 | 6629 | 129755 | 129774 | CCAGCCAAATGCTTGCATTC | 53 | 1348 |
| 803184 | 6611 | 6630 | 129756 | 129775 | CCCAGCCAAATGCTTGCATT | 59 | 1349 |
| 803185 | 6613 | 6632 | 129758 | 129777 | AGCCCAGCCAAATGCTTGCA | 43 | 163 |
| 803186 | 6614 | 6633 | 129759 | 129778 | CAGCCCAGCCAAATGCTTGC | 73 | 1350 |
| 803187 | 6615 | 6634 | 129760 | 129779 | ACAGCCCAGCCAAATGCTTG | 97 | 1351 |
| 803188 | 6616 | 6635 | 129761 | 129780 | CACAGCCCAGCCAAATGCTT | 90 | 1352 |
| 803189 | 6617 | 6636 | 129762 | 129781 | CCACAGCCCAGCCAAATGCT | 104 | 1353 |
| 803190 | 6621 | 6640 | 129766 | 129785 | GTGCCCACAGCCCAGCCAAA | 60 | 1354 |
| 803191 | 6630 | 6649 | 129775 | 129794 | TCTGTCGGTGTGCCCACAGC | 77 | 1355 |
| 803192 | 6639 | 6658 | 129784 | 129803 | GAGCTGTCCTCTGTCGGTGT | 71 | 1356 |
| 803193 | 6665 | 6684 | 129810 | 129829 | CCTTCAGTATTTAAGTCAAG | 75 | 1357 |
| 803194 | 6674 | 6693 | 129819 | 129838 | GAAGTGTATCCTTCAGTATT | 76 | 1358 |
| 803195 | 6683 | 6702 | N/A | N/A | ACTTCCTCAGAAGTGTATCC | 89 | 1359 |
| 803196 | 6709 | 6728 | 132419 | 132438 | CTAAGCACAATATTCTACTA | 65 | 1360 |
| 803197 | 6718 | 6737 | 132428 | 132447 | GCACCAAGGCTAAGCACAAT | 54 | 1361 |
| 803198 | 6727 | 6746 | 132437 | 132456 | CAGGAAGATGCACCAAGGCT | 53 | 1362 |
| 803199 | 6753 | 6772 | 132463 | 132482 | AGACACAATCCAGCTTTCCT | 113 | 1363 |
| 803200 | 6762 | 6781 | 132472 | 132491 | CTGTGTCCCAGACACAATCC | 91 | 1364 |
| 803201 | 6771 | 6790 | 132481 | 132500 | AGTACCAGACTGTGTCCCAG | 74 | 1365 |
| 803202 | 6797 | 6816 | 132507 | 132526 | CCATCTTCGGTATTGATGAC | 57 | 1366 |
| 803203 | 6806 | 6825 | 132516 | 132535 | CTCTTTTTCCCATCTTCGGT | 61 | 1367 |
| 803204 | 6815 | 6834 | 132525 | 132544 | AGGGTATGTCTCTTTTTCCC | 42 | 1368 |
| 803205 | 6841 | 6860 | 132551 | 132570 | AAGTGACAGAATCAGTCATC | 71 | 52 |
| 803206 | 6850 | 6869 | 132560 | 132579 | AATACAAACAAGTGACAGAA | 98 | 1369 |
| 803207 | 6864 | 6883 | 132574 | 132593 | GGAAAAGGAATTGCAATACA | 76 | 1370 |
| 803208 | 6902 | 6921 | 134234 | 134253 | GTTCCAACCAAAAGAAAATT | 86 | 1371 |
| 803209 | 6911 | 6930 | 134243 | 134262 | CCATCAGCGGTTCCAACCAA | 55 | 1372 |

TABLE 17-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803210 | 6929 | 6948 | 134261 | 134280 | TCAAAAATTGCTAACTTGCC | 111 | 1373 |
| 803211 | 6938 | 6957 | 134270 | 134289 | GTCTTATCTTCAAAATTGC | 92 | 1374 |
| 803212 | 6947 | 6966 | N/A | N/A | AGCTTAACAGTCTTATCTTC | 94 | 1375 |
| 803213 | 6973 | 6992 | 137377 | 137396 | GTATCTTCAAAGGAGCAGCT | 72 | 1376 |
| 803214 | 6983 | 7002 | 137387 | 137406 | CCTATATTTAGTATCTTCAA | 54 | 1377 |
| 803215 | 6992 | 7011 | 137396 | 137415 | CTGACATTTCCTATATTTAG | 73 | 1378 |
| 803216 | 7017 | 7036 | 137421 | 137440 | TTCACTCAAACACATCAATG | 68 | 1379 |
| 803217 | 7026 | 7045 | 137430 | 137449 | ATTTGTGGATTCACTCAAAC | 72 | 1380 |
| 803218 | 7035 | 7054 | 137439 | 137458 | TTCCGTTGAATTTGTGGATT | 85 | 1381 |
| 803219 | 7061 | 7080 | 137465 | 137484 | CCACATCCTCCCCACATTAC | 62 | 1382 |
| 803220 | 7070 | 7089 | 137474 | 137493 | ATCTTTGTGCCACATCCTCC | 77 | 1383 |
| 803221 | 7087 | 7106 | 137491 | 137510 | CATTAGAAAAGGAGAAAATC | 85 | 1384 |
| 803222 | 7105 | 7124 | 137509 | 137528 | GTTTCTGAATGGTGAAATCA | 76 | 1385 |
| 803223 | 7114 | 7133 | 137518 | 137537 | TCTCAATGAGTTTCTGAATG | 74 | 1386 |
| 803224 | 7123 | 7142 | 137527 | 137546 | TTGTTCTTGTCTCAATGAGT | 100 | 1387 |
| 803225 | 7132 | 7151 | 137536 | 137555 | ACAGTTGGCTTGTTCTTGTC | 104 | 1388 |
| 803226 | 7150 | 7169 | 141511 | 141530 | TGAAAGCTGCATAAGAAAAC | 116 | 1389 |

TABLE 18

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 25 | 235 |
| 780254 | 4111 | 4130 | 86606 | 86625 | GTTTCATTCGGTTATAAGGC | 20 | 235 |
| 803227 | 7159 | 7178 | 141520 | 141539 | TGGAATCACTGAAAGCTGCA | 65 | 1390 |
| 803228 | 7168 | 7187 | 141529 | 141548 | TTATGATGTTGGAATCACTG | 60 | 1391 |
| 803229 | 7194 | 7213 | 141555 | 141574 | ATAGAGAGCAGTGTCTACCA | 66 | 1392 |
| 803230 | 7203 | 7222 | 141564 | 141583 | CTTAGCAATATAGAGAGCAG | 97 | 1393 |
| 803231 | 7212 | 7231 | 141573 | 141592 | GCTATTTTGCTTAGCAATAT | 46 | 1394 |
| 803232 | 7238 | 7257 | 141599 | 141618 | TTCTTATCCCACACTTCCAC | 89 | 1395 |
| 803233 | 7248 | 7267 | 141609 | 141628 | TTTTTCAGTTTTCTTATCCC | 75 | 1396 |
| 803234 | 7257 | 7276 | 141618 | 141637 | TCCACAGAGTTTTTCAGTTT | 64 | 1397 |
| 803235 | 7282 | 7301 | 141643 | 141662 | TTAAAAGTGCACGCAGTCT | 108 | 1398 |

TABLE 18-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803236 | 7291 | 7310 | N/A | N/A | TTACCTCCCTTAAAAAGTGC | 95 | 1399 |
| 803237 | 7300 | 7319 | N/A | N/A | CTTTTACCATTACCTCCCTT | 80 | 1400 |
| 803238 | 7309 | 7328 | 142957 | 142976 | CCTTGTTTTCTTTTACCATT | 65 | 1401 |
| 803239 | 7339 | 7358 | 142987 | 143006 | TCCCAGAATAAGACATTTTG | 68 | 1402 |
| 803240 | 7348 | 7367 | 142996 | 143015 | TTTTCACTCTCCCAGAATAA | 62 | 1403 |
| 803241 | 7371 | 7390 | 143019 | 143038 | AGTGTTCTTCTGAAGGCAGA | 60 | 1404 |
| 803242 | 7380 | 7399 | 143028 | 143047 | CCAAAGAGCAGTGTTCTTCT | 86 | 1405 |
| 803243 | 7389 | 7408 | 143037 | 143056 | AGTTCCTATCCAAAGAGCAG | 87 | 1406 |
| 803244 | 7415 | 7434 | 143063 | 143082 | TCCAGGAGTAAAATATGGCC | 51 | 1407 |
| 803245 | 7424 | 7443 | 143072 | 143091 | GTTGAAAGATCCAGGAGTAA | 106 | 1408 |
| 803246 | 7433 | 7452 | 143081 | 143100 | AGTCGACGAGTTGAAAGATC | 106 | 1409 |
| 803247 | 7466 | 7485 | 143114 | 143133 | ACCGAATTACAAAAGTTGTA | 71 | 1410 |
| 803248 | 7475 | 7494 | 143123 | 143142 | ATGACTCTGACCGAATTACA | 82 | 1411 |
| 803249 | 7484 | 7503 | 143132 | 143151 | GCTGTCATCATGACTCTGAC | 65 | 1412 |
| 803250 | 7510 | 7529 | 145113 | 145132 | TGACATTTTTAAGGCTTCCT | 58 | 1413 |
| 803251 | 7522 | 7541 | 145125 | 145144 | CCAATACCAGCATGACATTT | 75 | 1414 |
| 803252 | 7531 | 7550 | 145134 | 145153 | GGTTGTAGCCCAATACCAGC | 74 | 1415 |
| 803253 | 7554 | 7573 | 145157 | 145176 | TTGTGTACCTTCAGTATTTT | 61 | 1416 |
| 803254 | 7564 | 7583 | 145167 | 145186 | CTTTCTGCTTTTGTGTACCT | 92 | 1417 |
| 803255 | 7573 | 7592 | N/A | N/A | ATTGTATCTCTTTCTGCTTT | 104 | 1418 |
| 803256 | 7598 | 7617 | 145767 | 145786 | TTGATGTCCCAAACGGTCAA | 49 | 1419 |
| 803257 | 7607 | 7626 | 145776 | 145795 | TGTGGAAGATTGATGTCCCA | 96 | 1420 |
| 803258 | 7616 | 7635 | 145785 | 145804 | TGCACTTCATGTGGAAGATT | 74 | 1421 |
| 803259 | 7625 | 7644 | 145794 | 145813 | TCTAAATTTTGCACTTCATG | 71 | 1422 |
| 803260 | 7645 | 7664 | 145814 | 145833 | TTCTCACTTCAATGTGTTTT | 48 | 1423 |
| 803261 | 7654 | 7673 | 145823 | 145842 | CTAATTCTTTTCTCACTTCA | 93 | 1424 |
| 803262 | 7666 | 7685 | 145835 | 145854 | TCATTTTTTCAGCTAATTCT | 95 | 1425 |
| 803263 | 7697 | 7716 | 145866 | 145885 | CTATTTCTCTCTTACTCAAC | 77 | 1426 |
| 803264 | 7706 | 7725 | 145875 | 145894 | AGACAATTCCTATTTCTCTC | 45 | 1427 |
| 803265 | 7717 | 7736 | 145886 | 145905 | TTCCTATCCAAAGACAATTC | 83 | 1428 |
| 803266 | 7741 | 7760 | 145910 | 145929 | TATTTACAAGAGGAGAGAAT | 75 | 1429 |
| 803267 | 7771 | 7790 | 145940 | 145959 | CCCTTTCCATGTGAACATTT | 65 | 1430 |
| 803268 | 7772 | 7791 | 145941 | 145960 | ACCCTTTCCATGTGAACATT | 49 | 1431 |
| 803269 | 7773 | 7792 | 145942 | 145961 | TACCCTTTCCATGTGAACAT | 49 | 1432 |
| 803270 | 7774 | 7793 | 145943 | 145962 | GTACCCTTTCCATGTGAACA | 41 | 1433 |
| 803271 | 7775 | 7794 | 145944 | 145963 | AGTACCCTTTCCATGTGAAC | 54 | 1434 |

TABLE 18-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803272 | 7777 | 7796 | 145946 | 145965 | TGAGTACCCTTTCCATGTGA | 43 | 1435 |
| 803273 | 7778 | 7797 | 145947 | 145966 | GTGAGTACCCTTTCCATGTG | 44 | 1436 |
| 803274 | 7779 | 7798 | 145948 | 145967 | TGTGAGTACCCTTTCCATGT | 66 | 1437 |
| 803275 | 7780 | 7799 | 145949 | 145968 | ATGTGAGTACCCTTTCCATG | 37 | 1438 |
| 803276 | 7781 | 7800 | 145950 | 145969 | AATGTGAGTACCCTTTCCAT | 57 | 1439 |
| 803277 | 7785 | 7804 | 145954 | 145973 | AAAAAATGTGAGTACCCTTT | 68 | 1440 |
| 803278 | 7794 | 7813 | 145963 | 145982 | AGCTATTTCAAAAAATGTGA | 89 | 1441 |
| 803279 | 7803 | 7822 | 145972 | 145991 | ATACACACGAGCTATTTCAA | 76 | 1442 |
| 803280 | 7812 | 7831 | 145981 | 146000 | CATTCCTTCATACACACGAG | 57 | 1443 |
| 803281 | 7850 | 7869 | 146019 | 146038 | GTAAGTATTTTACATATAT | 69 | 1444 |
| 803282 | 7876 | 7895 | 146045 | 146064 | TAGTTCTTTAAAATACACAT | 58 | 1445 |
| 803283 | 7888 | 7907 | 146057 | 146076 | TTGTGTTTTAAATAGTTCTT | 56 | 1446 |
| 803284 | 7897 | 7916 | 146066 | 146085 | AATATAACATTGTGTTTTAA | 95 | 1447 |
| 803285 | 7921 | 7940 | 146090 | 146109 | CGAAAGTAACTGGTATTTAT | 40 | 1448 |
| 803286 | 7930 | 7949 | 146099 | 146118 | ATTAATGAACGAAAGTAACT | 125 | 1449 |
| 803287 | 7939 | 7958 | 146108 | 146127 | TTTTCATTAATTAATGAACG | 99 | 1450 |
| 803288 | 7948 | 7967 | 146117 | 146136 | ACAGATTTATTTTCATTAAT | 82 | 1451 |
| 803289 | 7969 | 7988 | 146138 | 146157 | AGTACTTAAATTAGGTACTT | 126 | 1452 |
| 803290 | 7978 | 7997 | 146147 | 146166 | TTTAGTATGAGTACTTAAAT | 102 | 1453 |
| 803291 | 7987 | 8006 | 146156 | 146175 | CTTATAAATTTTAGTATGAG | 98 | 1454 |
| 803292 | 8019 | 8038 | 146188 | 146207 | CATTACAGACAAGAAAACAA | 109 | 1455 |
| 803293 | 8028 | 8047 | 146197 | 146216 | GTTTACCTCCATTACAGACA | 61 | 1456 |
| 803294 | 8037 | 8056 | 146206 | 146225 | TAAAATAAAGTTTACCTCCA | 59 | 1457 |
| 803295 | 8061 | 8080 | 146230 | 146249 | TAGTCCTGTCTTAAGCACAG | 74 | 1458 |
| 803296 | 8070 | 8089 | 146239 | 146258 | GACAAGCAATAGTCCTGTCT | 66 | 1459 |
| 803297 | 8079 | 8098 | 146248 | 146267 | AGAAAAATCGACAAGCAATA | 89 | 1460 |
| 803298 | 8105 | 8124 | 146274 | 146293 | ATTTTCATTATACCGTGCAG | 55 | 1461 |
| 803299 | 8116 | 8135 | 146285 | 146304 | ACTGTCTTAATATTTTCATT | 53 | 1462 |
| 803300 | 8125 | 8144 | 146294 | 146313 | ACATGGGAAACTGTCTTAAT | 56 | 1463 |
| 803301 | 8149 | 8168 | 146318 | 146337 | ATGCAATCTAAGAAGGAATA | 67 | 1464 |
| 803302 | 8158 | 8177 | 146327 | 146346 | TGCATTTCGATGCAATCTAA | 36 | 1465 |
| 803303 | 8167 | 8186 | 146336 | 146355 | ATATGATAGTGCATTTCGAT | 69 | 1466 |

TABLE 19

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 27 | 235 |
| 780254 | 4111 | 4130 | 86606 | 86625 | GTTTCATTCGGTTATAAGGC | 12 | 235 |
| 803304 | 8176 | 8195 | 146345 | 146364 | TACAAGCATATATGATAGTG | 83 | 1467 |
| 803305 | 8207 | 8226 | 146376 | 146395 | GACTTTATTAGTGCAAATTC | 54 | 1468 |
| 803306 | 8208 | 8227 | 146377 | 146396 | GGACTTTATTAGTGCAAATT | 45 | 1469 |
| 803307 | 8209 | 8228 | 146378 | 146397 | AGGACTTTATTAGTGCAAAT | 54 | 1470 |
| 803308 | 8210 | 8229 | 146379 | 146398 | AAGGACTTTATTAGTGCAAA | 56 | 1471 |
| 803309 | 8212 | 8231 | 146381 | 146400 | CAAAGGACTTTATTAGTGCA | 59 | 1472 |
| 803310 | 8213 | 8232 | 146382 | 146401 | ACAAAGGACTTTATTAGTGC | 58 | 1473 |
| 803311 | 8214 | 8233 | 146383 | 146402 | AACAAAGGACTTTATTAGTG | 63 | 1474 |
| 803312 | 8215 | 8234 | 146384 | 146403 | CAACAAAGGACTTTATTAGT | 101 | 1475 |
| 803313 | 8240 | 8259 | 146409 | 146428 | ACAGCAACAAAGAGAATTCA | 88 | 1476 |
| 803314 | 8252 | 8271 | 146421 | 146440 | GCACTGTTTGCAACAGCAAC | 91 | 1477 |
| 803315 | 8261 | 8280 | 146430 | 146449 | GTGTAAGATGCACTGTTTGC | 74 | 1478 |
| 803316 | 8284 | 8303 | 146453 | 146472 | TTTCTTTTGAATTGAGTGAA | 92 | 1479 |
| 803317 | 8293 | 8312 | 146462 | 146481 | TAATGGAGTTTCTTTTGAA | 87 | 1480 |
| 803318 | 8302 | 8321 | 146471 | 146490 | TAGTACTTTTAATGGAGTTT | 115 | 1481 |
| 803319 | 8328 | 8347 | 146497 | 146516 | TTTGACAGTATGTCATGTTT | 118 | 1482 |
| 803320 | 8337 | 8356 | 146506 | 146525 | TATGAGGACTTTGACAGTAT | 101 | 1483 |
| 803321 | 8346 | 8365 | 146515 | 146534 | TTTCCTAGATATGAGGACTT | 121 | 1484 |
| 803322 | 8355 | 8374 | 146524 | 146543 | TTCTGTGTCTTTCCTAGATA | 125 | 1485 |
| 803323 | 8373 | 8392 | 146542 | 146561 | TTCTGTGACAAAGAGAGTTT | 73 | 1486 |
| 803324 | 8382 | 8401 | 146551 | 146570 | ACAGAGAGTTTCTGTGACAA | 85 | 1487 |
| 803325 | 8391 | 8410 | 146560 | 146579 | AGGAAAGACACAGAGAGTTT | 100 | 1488 |
| 803326 | 8418 | 8437 | 146587 | 146606 | GAGTTGAAAAACAACTCTAT | 129 | 1489 |
| 803327 | 8427 | 8446 | 146596 | 146615 | TCAAACATAGAGTTGAAAAA | 116 | 1490 |
| 803328 | 8436 | 8455 | 146605 | 146624 | TATCCACATTCAAACATAGA | 116 | 1491 |
| 803329 | 8461 | 8480 | 146630 | 146649 | TACACTAATTATACAAAATT | 114 | 1492 |
| 803330 | 8470 | 8489 | 146639 | 146658 | CACTGTATTTACACTAATTA | 73 | 1493 |
| 803331 | 8479 | 8498 | 146648 | 146667 | AGGACTGAACACTGTATTTA | 56 | 1494 |
| 803332 | 8488 | 8507 | 146657 | 146676 | ATCACTTGAAGGACTGAACA | 73 | 1495 |
| 803333 | 8524 | 8543 | 146693 | 146712 | ACAAGTAGCTAGTGGTATGA | 85 | 1496 |
| 803334 | 8533 | 8552 | 146702 | 146721 | GATTAGAAAACAAGTAGCTA | 69 | 1497 |
| 803335 | 8545 | 8564 | 146714 | 146733 | TAGAATGAAGCAGATTAGAA | 116 | 1498 |
| 803336 | 8570 | 8589 | 146739 | 146758 | TTAGGGAAAGATGAATATA | 93 | 1499 |
| 803337 | 8579 | 8598 | 146748 | 146767 | ATCACAAATTTAGGGAAAAG | 72 | 1500 |

TABLE 19-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803338 | 8588 | 8607 | 146757 | 146776 | ATCTGCAGCATCACAAATTT | 77 | 1501 |
| 803339 | 8614 | 8633 | 146783 | 146802 | AAAGGTTTCTATCTGAATGA | 107 | 1502 |
| 803340 | 8639 | 8658 | 146808 | 146827 | GGAATTCTATAATTCTGAAA | 80 | 1503 |
| 803341 | 8659 | 8678 | 146828 | 146847 | ATGGTCTTGGTAGGAGCTGT | 77 | 1504 |
| 803342 | 8668 | 8687 | 146837 | 146856 | TTTATCCTCATGGTCTTGGT | 56 | 1505 |
| 803343 | 8677 | 8696 | 146846 | 146865 | TGTTAGATATTTATCCTCAT | 66 | 1506 |
| 803344 | 8705 | 8724 | 146874 | 146893 | GCTCCTTTCTCCTTCAGCAA | 58 | 1507 |
| 803345 | 8714 | 8733 | 146883 | 146902 | ATAACTAAAGCTCCTTTCTC | 111 | 1508 |
| 803346 | 8723 | 8742 | 146892 | 146911 | TTATCCATCATAACTAAAGC | 112 | 1509 |
| 803347 | 8732 | 8751 | 146901 | 146920 | CAGATATTTTATCCATCAT | 57 | 1510 |
| 803348 | 8750 | 8769 | 146919 | 146938 | TTTGGAAGCCTAGGGTGGCA | 80 | 1511 |
| 803349 | 8759 | 8778 | 146928 | 146947 | TAAGTATAATTTGGAAGCCT | 69 | 1512 |
| 803350 | 8768 | 8787 | 146937 | 146956 | TAAACAATTTAAGTATAATT | 121 | 1513 |
| 803351 | 8794 | 8813 | 146963 | 146982 | TGATACTCCTATTGTGGTAA | 89 | 1514 |
| 803352 | 8803 | 8822 | 146972 | 146991 | ATTTGGCCCTGATACTCCTA | 71 | 1515 |
| 803353 | 8812 | 8831 | 146981 | 147000 | TACATAGGTATTTGGCCCTG | 111 | 1516 |
| 803354 | 8838 | 8857 | 147007 | 147026 | CTAAAGCAGAAATGACCTCA | 61 | 1517 |
| 803355 | 8847 | 8866 | 147016 | 147035 | GTACTTTTCCTAAAGCAGAA | 74 | 1518 |
| 803356 | 8856 | 8875 | 147025 | 147044 | TTACCGAAAGTACTTTTCCT | 89 | 1519 |
| 803357 | 8882 | 8901 | 147051 | 147070 | ATGAATACTGGTCAGGGCCA | 102 | 61 |
| 803358 | 8891 | 8910 | 147060 | 147079 | TCTGAAATAATGAATACTGG | 85 | 1520 |
| 803359 | 8900 | 8919 | 147069 | 147088 | AGGGAATTATCTGAAATAAT | 46 | 1521 |
| 803360 | 8926 | 8945 | 147095 | 147114 | ATTAAATGTACTAGTTGTCC | 90 | 1522 |
| 803361 | 8935 | 8954 | 147104 | 147123 | TCTGAGAATATTAAATGTAC | 66 | 1523 |
| 803362 | 8944 | 8963 | 147113 | 147132 | GCCATAAGTTCTGAGAATAT | 53 | 1524 |
| 803363 | 8953 | 8972 | 147122 | 147141 | TAGTAAAATGCCATAAGTTC | 79 | 1525 |
| 803364 | 8957 | 8976 | 147126 | 147145 | CACATAGTAAAATGCCATAA | 51 | 1526 |
| 803365 | 8958 | 8977 | 147127 | 147146 | TCACATAGTAAAATGCCATA | 63 | 1527 |
| 803366 | 8959 | 8978 | 147128 | 147147 | TTCACATAGTAAAATGCCAT | 43 | 1528 |
| 803367 | 8960 | 8979 | 147129 | 147148 | TTTCACATAGTAAAATGCCA | 55 | 1529 |
| 803368 | 8961 | 8980 | 147130 | 147149 | TTTTCACATAGTAAAATGCC | 80 | 1530 |
| 803369 | 8963 | 8982 | 147132 | 147151 | AGTTTTCACATAGTAAAATG | 101 | 1531 |
| 803370 | 8964 | 8983 | 147133 | 147152 | AAGTTTTCACATAGTAAAAT | 133 | 1532 |
| 803371 | 8965 | 8984 | 147134 | 147153 | AAAGTTTTCACATAGTAAAA | 77 | 1533 |
| 803372 | 8966 | 8985 | 147135 | 147154 | TAAAGTTTTCACATAGTAAA | 88 | 1534 |

TABLE 19-continued

Percent control of human LRRK RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803373 | 8967 | 8986 | 147136 | 147155 | TTAAAGTTTTCACATAGTAA | 97 | 1535 |
| 803374 | 8972 | 8991 | 147141 | 147160 | TAAATTTAAAGTTTTCACAT | 104 | 1536 |
| 803375 | 8988 | 9007 | 147157 | 147176 | TTACCCTTAATATAAATAAA | 113 | 1537 |
| 803376 | 8997 | 9016 | 147166 | 147185 | AGAATTTGATTACCCTTAAT | 82 | 1538 |
| 803377 | 9015 | 9034 | 147184 | 147203 | GAAAATCTTTCATCTTTAAG | 116 | 1539 |
| 803378 | 9028 | 9047 | 147197 | 147216 | CCTTTAAAATACAGAAAATC | 110 | 1540 |
| 803379 | 9037 | 9056 | 147206 | 147225 | GCATAGCTTCCTTTAAAATA | 70 | 1541 |
| 803380 | 9059 | 9078 | 147228 | 147247 | GTTAATTACATAACAAGTTA | 76 | 1542 |

TABLE 20

Percent control of human LRRK RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 25 | 235 |
| 780254 | 4111 | 4130 | 86606 | 86625 | GTTTCATTCGGTTATAAGGC | 20 | 235 |
| 803381 | 9078 | 9097 | 147247 | 147266 | TATTATATATGATTTTTTTG | 96 | 1543 |
| 803382 | 9103 | 9122 | 147272 | 147291 | GAGATAACACTGGAACAAAG | 79 | 1544 |
| 803383 | 9112 | 9131 | 147281 | 147300 | ACAATGAAAGAGATAACACT | 96 | 1545 |
| 803384 | 9125 | 9144 | 147294 | 147313 | CAAATACAAAGTAACAATGA | 119 | 1546 |
| 803385 | 9164 | 9183 | 147333 | 147352 | GTATTCATTTTTTTAATTTG | 95 | 1547 |
| 803386 | N/A | N/A | 3733 | 3752 | TACCTGCTGCACACTCGCGA | 32 | 1548 |
| 803387 | N/A | N/A | 4361 | 4380 | ATCCAAGATACATAGCAAAT | 61 | 1549 |
| 803388 | N/A | N/A | 4768 | 4787 | TAATAGTCAGATGGAAAATA | 92 | 1550 |
| 803389 | N/A | N/A | 5023 | 5042 | TATCAAGCAGGAGTGACTCT | 81 | 1551 |
| 803390 | N/A | N/A | 5210 | 5229 | CTCTCTAGGCAGAAATACTA | 87 | 1552 |
| 803391 | N/A | N/A | 5227 | 5246 | ATACTTTGCCTCTGGTACTC | 80 | 1553 |
| 803392 | N/A | N/A | 5291 | 5310 | CAACTATGATATATCCAAAA | 139 | 1554 |
| 803393 | N/A | N/A | 7598 | 7617 | AAAAGATAGGCAGGAAAAGA | 185 | 1555 |
| 803394 | N/A | N/A | 8034 | 8053 | TGCCAAACTCATCTCTGTAC | 76 | 1556 |
| 803395 | N/A | N/A | 8402 | 8421 | GTAAACAACGGCTATTTTAG | 65 | 1557 |
| 803396 | N/A | N/A | 10211 | 10230 | CCCAGAAACAAAAGCAAGCC | 70 | 1558 |
| 803397 | N/A | N/A | 11602 | 11621 | GTACTGAAAACAAGAAGAGC | 96 | 1559 |
| 803398 | N/A | N/A | 11762 | 11781 | GGACATTTAAAGTTACAATT | 66 | 1560 |
| 803399 | N/A | N/A | 12023 | 12042 | TCTTCTTCACAACTGCATGG | 71 | 1561 |

TABLE 20-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803400 | N/A | N/A | 12348 | 12367 | TTTACATTATTGGAAGAAGA | 84 | 1562 |
| 803401 | N/A | N/A | 12349 | 12368 | CTTTACATTATTGGAAGAAG | 96 | 1563 |
| 803402 | N/A | N/A | 12350 | 12369 | GCTTTACATTATTGGAAGAA | 64 | 1564 |
| 803403 | N/A | N/A | 12351 | 12370 | GGCTTTACATTATTGGAAGA | 46 | 1565 |
| 803404 | N/A | N/A | 12352 | 12371 | TGGCTTTACATTATTGGAAG | 52 | 1566 |
| 803405 | N/A | N/A | 12354 | 12373 | TTTGGCTTTACATTATTGGA | 69 | 1567 |
| 803406 | N/A | N/A | 12355 | 12374 | GTTTGGCTTTACATTATTGG | 40 | 1568 |
| 803407 | N/A | N/A | 12356 | 12375 | TGTTTGGCTTTACATTATTG | 68 | 1569 |
| 803408 | N/A | N/A | 12357 | 12376 | TTGTTTGGCTTTACATTATT | 85 | 1570 |
| 803409 | N/A | N/A | 12358 | 12377 | ATTGTTTGGCTTTACATTAT | 57 | 1571 |
| 803410 | N/A | N/A | 13200 | 13219 | GAATAATTCACAATGTACAC | 64 | 1572 |
| 803411 | N/A | N/A | 13280 | 13299 | CATGTGTGTTTGTTCTTTC | 70 | 1573 |
| 803412 | N/A | N/A | 14768 | 14787 | ATTCAAACCTTCCCAATCAC | 131 | 1574 |
| 803413 | N/A | N/A | 14988 | 15007 | TCCATCGCCAAATGGAGAAT | 102 | 1575 |
| 803414 | N/A | N/A | 15083 | 15102 | AATACTGGAATAGGAGTAGT | 98 | 1576 |
| 803415 | N/A | N/A | 15343 | 15362 | TCTCATGATCCTTAGTATGA | 72 | 1577 |
| 803416 | N/A | N/A | 15717 | 15736 | ACCTGGCCTACTCCTGTTCC | 95 | 1578 |
| 803417 | N/A | N/A | 16619 | 16638 | ATGCATATTAGTCTTTTTCC | 61 | 1579 |
| 803418 | N/A | N/A | 18995 | 19014 | CTGCCACTGTAATCACCTCT | 54 | 1580 |
| 803419 | N/A | N/A | 19777 | 19796 | TACATATTGTCTAATAATCC | 114 | 1581 |
| 803420 | N/A | N/A | 20043 | 20062 | TTTGTTGGCAGTGATGTCTC | 49 | 1582 |
| 803421 | N/A | N/A | 20233 | 20252 | TTAAAAACTTTTGATTTCTT | 131 | 1583 |
| 803422 | N/A | N/A | 20684 | 20703 | AAGGGCAACCAATGTACAAG | 43 | 1584 |
| 803423 | N/A | N/A | 20708 | 20727 | TATGACCTGTTTCCTCCATT | 60 | 1585 |
| 803424 | N/A | N/A | 20709 | 20728 | CTATGACCTGTTTCCTCCAT | 82 | 1586 |
| 803425 | N/A | N/A | 20710 | 20729 | GCTATGACCTGTTTCCTCCA | 37 | 1587 |
| 803426 | N/A | N/A | 20711 | 20730 | AGCTATGACCTGTTTCCTCC | 43 | 1588 |
| 803427 | N/A | N/A | 20712 | 20731 | CAGCTATGACCTGTTTCCTC | 35 | 1589 |
| 803428 | N/A | N/A | 20714 | 20733 | ATCAGCTATGACCTGTTTCC | 69 | 1590 |
| 803429 | N/A | N/A | 20715 | 20734 | AATCAGCTATGACCTGTTTC | 70 | 1591 |
| 803430 | N/A | N/A | 20717 | 20736 | AAAATCAGCTATGACCTGTT | 72 | 1592 |
| 803431 | N/A | N/A | 20718 | 20737 | TAAAATCAGCTATGACCTGT | 88 | 1593 |
| 803432 | N/A | N/A | 21079 | 21098 | ATGTGGTGAATATTATAGAA | 38 | 1594 |
| 803433 | N/A | N/A | 21236 | 21255 | CTTTATTGAAAATTGCCACA | 43 | 1595 |
| 803434 | N/A | N/A | 22179 | 22198 | CATTTAAGTTGGATAGTGAG | 80 | 1596 |

TABLE 20-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803435 | N/A | N/A | 23283 | 23302 | GGAATAAAATATACAATATA | 86 | 1597 |
| 803436 | N/A | N/A | 23734 | 23753 | AGTTCTTCTTAAAATGATCC | 34 | 1598 |
| 803437 | N/A | N/A | 24259 | 24278 | AAGCCCACATTGAAAAACA | 80 | 1599 |
| 803438 | N/A | N/A | 24494 | 24513 | TGAAAATAAACAGAGAAGAT | 93 | 1600 |
| 803439 | N/A | N/A | 24497 | 24516 | ATGTGAAAATAAACAGAGAA | 97 | 1601 |
| 803440 | N/A | N/A | 24663 | 24682 | AGCCTAGAAGCAGTTGGTTT | 88 | 1602 |
| 803441 | N/A | N/A | 25966 | 25985 | AATAATAACAATATCCCATC | 83 | 1603 |
| 803442 | N/A | N/A | 26005 | 26024 | AAGATTGATGAACCACAGGA | 51 | 1604 |
| 803443 | N/A | N/A | 26046 | 26065 | ATTTCATCCCTTACTGCTTA | 123 | 1605 |
| 803444 | N/A | N/A | 26583 | 26602 | AGAGATAATCAAGAGAAAAA | 104 | 1606 |
| 803445 | N/A | N/A | 27062 | 27081 | AGTATGGAGCTCCTTTACCA | 66 | 1607 |
| 803446 | N/A | N/A | 28223 | 28242 | TACATTGAGATGTGTATATT | 111 | 1608 |
| 803447 | N/A | N/A | 29215 | 29234 | TGCTTTAGGAGAAGCCTTGG | 62 | 1609 |
| 803448 | N/A | N/A | 29216 | 29235 | GTGCTTTAGGAGAAGCCTTG | 41 | 1610 |
| 803449 | N/A | N/A | 29217 | 29236 | TGTGCTTTAGGAGAAGCCTT | 36 | 1611 |
| 803450 | N/A | N/A | 29218 | 29237 | GTGTGCTTTAGGAGAAGCCT | 34 | 1612 |
| 803451 | N/A | N/A | 29219 | 29238 | GGTGTGCTTTAGGAGAAGCC | 40 | 1613 |
| 803452 | N/A | N/A | 29221 | 29240 | GAGGTGTGCTTTAGGAGAAG | 58 | 1614 |
| 803453 | N/A | N/A | 29222 | 29241 | TGAGGTGTGCTTTAGGAGAA | 56 | 1615 |
| 803454 | N/A | N/A | 29223 | 29242 | ATGAGGTGTGCTTTAGGAGA | 80 | 1616 |
| 803455 | N/A | N/A | 29224 | 29243 | AATGAGGTGTGCTTTAGGAG | 68 | 1617 |
| 803456 | N/A | N/A | 29225 | 29244 | GAATGAGGTGTGCTTTAGGA | 63 | 1618 |
| 803457 | N/A | N/A | 29927 | 29946 | ATTTTAAAACGATCAGCCAG | 87 | 1619 |

TABLE 21

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 16 | 235 |
| 780254 | 4111 | 4130 | 86606 | 86625 | GTTTCATTCGGTTATAAGGC | 28 | 235 |
| 803458 | N/A | N/A | 30062 | 30081 | AGTTGGGAACTCATCATAGG | 79 | 1620 |
| 803459 | N/A | N/A | 30238 | 30257 | AGGCTCACGGATATGAAACA | 59 | 1621 |
| 803460 | N/A | N/A | 30698 | 30717 | AAGAGAGGAAAAACTGAAAA | 83 | 1622 |
| 803461 | N/A | N/A | 31335 | 31354 | GTTTACACATAGAAGTCCGG | 46 | 1623 |

TABLE 21-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803462 | N/A | N/A | 32129 | 32148 | TAAAGGGATACAAGCCATTT | 74 | 1624 |
| 803463 | N/A | N/A | 32534 | 32553 | TCCTTGAGAGCAGCCCCTGT | 76 | 1625 |
| 803464 | N/A | N/A | 32577 | 32596 | ATTCGAGAACAGCGATTCCC | 100 | 1626 |
| 803465 | N/A | N/A | 32857 | 32876 | ACTGAACAAAGACATCAGGG | 36 | 1627 |
| 803466 | N/A | N/A | 32987 | 33006 | ATGAACGAGCTACTCAAGTT | 79 | 1628 |
| 803467 | N/A | N/A | 32997 | 33016 | AAGAAAGTTGATGAACGAGC | 48 | 1629 |
| 803468 | N/A | N/A | 33091 | 33110 | CCTGCCAATGTAGCCATTTT | 40 | 1630 |
| 803469 | N/A | N/A | 33163 | 33182 | GAATAGGAAAATGTCACAC | 39 | 1631 |
| 803470 | N/A | N/A | 33422 | 33441 | GTCTTACTCAATAGTCACCT | 25 | 1632 |
| 803471 | N/A | N/A | 33499 | 33518 | TCTTGATCTCATCCACTCCA | 44 | 1633 |
| 803472 | N/A | N/A | 35580 | 35599 | CAAGTGTCTTATGTTTTTCT | 42 | 1634 |
| 803473 | N/A | N/A | 35803 | 35822 | GATTTTATCTTTTATAACTT | 75 | 1635 |
| 803474 | N/A | N/A | 36736 | 36755 | TCTGTTTACTTATCAGTCTC | 77 | 1636 |
| 803475 | N/A | N/A | 37002 | 37021 | GCAGTAGGTACTATGAACTT | 36 | 1637 |
| 803476 | N/A | N/A | 38011 | 38030 | CTTGAACTCAGGTCATGGCA | 69 | 1638 |
| 803477 | N/A | N/A | 38572 | 38591 | CTCACCCCCGACCATGTGCA | 71 | 1639 |
| 803478 | N/A | N/A | 38768 | 38787 | CACAATGCTATTGTCTTTAG | 72 | 1640 |
| 803479 | N/A | N/A | 39901 | 39920 | CATAATGTACATCTTTGCCA | 59 | 1641 |
| 803480 | N/A | N/A | 40030 | 40049 | AATGTCTATATAACAAGTTA | 80 | 1642 |
| 803481 | N/A | N/A | 40156 | 40175 | TATATCCCTTCTTAAAGAAT | 94 | 1643 |
| 803482 | N/A | N/A | 40684 | 40703 | CGTGTGGACTGTAAATTTTT | 91 | 1644 |
| 803483 | N/A | N/A | 40840 | 40859 | CATCATGCTACATGTAATGG | 59 | 1645 |
| 803484 | N/A | N/A | 41078 | 41097 | TGCTGGGAATACTATGGTAA | 64 | 1646 |
| 803485 | N/A | N/A | 41108 | 41127 | ATTCCAATTACATGCCAAGG | 49 | 1647 |
| 803486 | N/A | N/A | 41173 | 41192 | ATCTGCATTAATGCAAACTG | 71 | 1648 |
| 803487 | N/A | N/A | 41893 | 41912 | ATTCTTCTGGCATGCCTAAA | 75 | 1649 |
| 803488 | N/A | N/A | 42134 | 42153 | TCATCTTATGTCTCTAACCA | 68 | 1650 |
| 803489 | N/A | N/A | 44968 | 44987 | TACTTTGCTGAGTACCATCC | 54 | 1651 |
| 803490 | N/A | N/A | 45375 | 45394 | AGGAAGTAACCATGTCCTCA | 38 | 1652 |
| 803491 | N/A | N/A | 45376 | 45395 | AAGGAAGTAACCATGTCCTC | 58 | 1653 |
| 803492 | N/A | N/A | 45377 | 45396 | AAAGGAAGTAACCATGTCCT | 57 | 1654 |
| 803493 | N/A | N/A | 45378 | 45397 | AAAAGGAAGTAACCATGTCC | 93 | 1655 |
| 803494 | N/A | N/A | 45379 | 45398 | TAAAAGGAAGTAACCATGTC | 92 | 1656 |
| 803495 | N/A | N/A | 45381 | 45400 | ATTAAAAGGAAGTAACCATG | 78 | 1657 |
| 803496 | N/A | N/A | 45382 | 45401 | TATTAAAAGGAAGTAACCAT | 90 | 1658 |

TABLE 21-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803497 | N/A | N/A | 45383 | 45402 | GTATTAAAAGGAAGTAACCA | 86 | 1659 |
| 803498 | N/A | N/A | 45384 | 45403 | GGTATTAAAAGGAAGTAACC | 34 | 1660 |
| 803499 | N/A | N/A | 45385 | 45404 | AGGTATTAAAAGGAAGTAAC | 50 | 1661 |
| 803500 | N/A | N/A | 46126 | 46145 | TATGTATCCAAACATGGATT | 71 | 1662 |
| 803501 | N/A | N/A | 46232 | 46251 | GGTGACAAAGTCTTCATCTG | 58 | 1663 |
| 803502 | N/A | N/A | 46931 | 46950 | TTTATTTGAGTCTATTTCCT | 79 | 1664 |
| 803503 | N/A | N/A | 48097 | 48116 | GGGTGCATAGTCTGTAGGTA | 32 | 1665 |
| 803504 | N/A | N/A | 48768 | 48787 | GGATTTCAAGAGAAAAAATC | 93 | 1666 |
| 803505 | N/A | N/A | 48918 | 48937 | ATATCTTTACCATGTATATG | 88 | 1667 |
| 803506 | N/A | N/A | 49003 | 49022 | TCCAAACTCAGAATGCACCA | 42 | 1668 |
| 803507 | N/A | N/A | 49316 | 49335 | GTCTATGAGTAATGGCATGG | 47 | 1669 |
| 803508 | N/A | N/A | 49674 | 49693 | GGATTAAAATCAATTTATCA | 80 | 1670 |
| 803509 | N/A | N/A | 50436 | 50455 | AATTTCTTTTGGCTTGATAC | 89 | 1671 |
| 803510 | N/A | N/A | 51368 | 51387 | TTCAAATTATGCGAATCTGA | 66 | 1672 |
| 803511 | N/A | N/A | 51478 | 51497 | TTGGACATCATTTCATTTAT | 48 | 1673 |
| 803512 | N/A | N/A | 52070 | 52089 | ACCTTAAAAGCCCAGGATCT | 85 | 1674 |
| 803513 | N/A | N/A | 52149 | 52168 | ACTTTAAAGATGCAGAAATA | 80 | 1675 |
| 803514 | N/A | N/A | 52150 | 52169 | AACTTTAAAGATGCAGAAAT | 92 | 1676 |
| 803515 | N/A | N/A | 52151 | 52170 | AAACTTTAAAGATGCAGAAA | 111 | 1677 |
| 803516 | N/A | N/A | 52152 | 52171 | CAAACTTTAAAGATGCAGAA | 63 | 1678 |
| 803517 | N/A | N/A | 52153 | 52172 | CCAAACTTTAAAGATGCAGA | 28 | 1679 |
| 803518 | N/A | N/A | 52155 | 52174 | TGCCAAACTTTAAAGATGCA | 40 | 1680 |
| 803519 | N/A | N/A | 52156 | 52175 | TTGCCAAACTTTAAAGATGC | 30 | 1681 |
| 803520 | N/A | N/A | 52157 | 52176 | TTTGCCAAACTTTAAAGATG | 63 | 1682 |
| 803521 | N/A | N/A | 52158 | 52177 | GTTTGCCAAACTTTAAAGAT | 50 | 1683 |
| 803522 | N/A | N/A | 52159 | 52178 | GGTTTGCCAAACTTTAAAGA | 39 | 1684 |
| 803523 | N/A | N/A | 52305 | 52324 | CCAAATATGTTTCACCCCAG | 78 | 1685 |
| 803524 | N/A | N/A | 52501 | 52520 | AGCATTTTTACAATTAAGGA | 59 | 1686 |
| 803525 | N/A | N/A | 53088 | 53107 | CATACTTTAGTCTGTATTTC | 69 | 1687 |
| 803526 | N/A | N/A | 53538 | 53557 | TTATTATATATCATGTTTTA | 83 | 1688 |
| 803527 | N/A | N/A | 53539 | 53558 | GTTATTATATATCATGTTTT | 62 | 1689 |
| 803528 | N/A | N/A | 53540 | 53559 | AGTTATTATATATCATGTTT | 55 | 1690 |
| 803529 | N/A | N/A | 53541 | 53560 | CAGTTATTATATATCATGTT | 55 | 1691 |
| 803530 | N/A | N/A | 53542 | 53561 | ACAGTTATTATATATCATGT | 33 | 1692 |
| 803531 | N/A | N/A | 53544 | 53563 | AGACAGTTATTATATATCAT | 49 | 1693 |
| 803532 | N/A | N/A | 53545 | 53564 | AAGACAGTTATTATATATCA | 64 | 1694 |

TABLE 21-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803533 | N/A | N/A | 53546 | 53565 | AAAGACAGTTATTATATATC | 80 | 1695 |
| 803534 | N/A | N/A | 53547 | 53566 | CAAAGACAGTTATTATATAT | 100 | 1696 |

TABLE 22

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 20 | 235 |
| 780254 | 4111 | 4130 | 86606 | 86625 | GTTTCATTCGGTTATAAGGC | 19 | 235 |
| 803535 | N/A | N/A | 53548 | 53567 | ACAAAGACAGTTATTATATA | 107 | 1697 |
| 803536 | N/A | N/A | 54011 | 54030 | TTCCTGAGTCAGCTGGGCAC | 74 | 1698 |
| 803537 | N/A | N/A | 55467 | 55486 | GTTGAGTGTAGTTGAGAAGC | 49 | 1699 |
| 803538 | N/A | N/A | 55699 | 55718 | AAAGATGCTTGTCTAAAGCC | 51 | 1700 |
| 803539 | N/A | N/A | 55823 | 55842 | AATAAATACTCCCTCTCTCT | 89 | 1701 |
| 803540 | N/A | N/A | 56181 | 56200 | ACTAAAAAGAGTGGAAATGA | 98 | 1702 |
| 803541 | N/A | N/A | 57300 | 57319 | GGCAAACATAGTACTTTATT | 27 | 1703 |
| 803542 | N/A | N/A | 57536 | 57555 | TGTTGCTTGCTTAAAAGAAA | 87 | 1704 |
| 803543 | N/A | N/A | 59667 | 59686 | TACTGCTCACAGATATTTAT | 82 | 1705 |
| 803544 | N/A | N/A | 59986 | 60005 | CTCTTGTCAATGCCCTACAC | 64 | 1706 |
| 803545 | N/A | N/A | 60613 | 60632 | GCAAAAAGGTGTTCATTCTT | 71 | 1707 |
| 803546 | N/A | N/A | 60625 | 60644 | ACTTTTCACCCAGCAAAAG | 106 | 1708 |
| 803547 | N/A | N/A | 60658 | 60677 | ATGCTATTTCTATTACCCCA | 58 | 1709 |
| 803548 | N/A | N/A | 61404 | 61423 | ACCTTCCTCTAAATGTTATG | 87 | 1710 |
| 803549 | N/A | N/A | 61573 | 61592 | CTGTCCTGCCTTTATTTGTG | 86 | 1711 |
| 803550 | N/A | N/A | 62233 | 62252 | TGTTACTTACTTGTTTGTTT | 108 | 1712 |
| 803551 | N/A | N/A | 63413 | 63432 | TTGACTTCATGGTACTAACA | 76 | 1713 |
| 803552 | N/A | N/A | 63832 | 63851 | CAAAGCATTCCACAACATGT | 65 | 1714 |
| 803553 | N/A | N/A | 63953 | 63972 | TGCATTTTCATCAACATTAG | 59 | 1715 |
| 803554 | N/A | N/A | 64097 | 64116 | TTTTTGGCATAAGACTAGTT | 79 | 1716 |
| 803555 | N/A | N/A | 64246 | 64265 | TCTATGTTTTTTTAACTGGG | 40 | 1717 |
| 803556 | N/A | N/A | 64593 | 64612 | CAACAGTAGGAATAGCAATA | 98 | 1718 |
| 803557 | N/A | N/A | 64954 | 64973 | GTTTGCTGAGTGATTCATTA | 59 | 1719 |
| 803558 | N/A | N/A | 66316 | 66335 | AATGGTTTGACTTGAGACAC | 52 | 1720 |

TABLE 22-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803559 | N/A | N/A | 66412 | 66431 | AATTTTCAAAGCGCATGAAA | 92 | 1721 |
| 803560 | N/A | N/A | 66414 | 66433 | TTAATTTTCAAAGCGCATGA | 45 | 1722 |
| 803561 | N/A | N/A | 66415 | 66434 | GTTAATTTTCAAAGCGCATG | 29 | 1723 |
| 803562 | N/A | N/A | 66416 | 66435 | TGTTAATTTTCAAAGCGCAT | 29 | 1724 |
| 803563 | N/A | N/A | 66418 | 66437 | TATGTTAATTTTCAAAGCGC | 32 | 1725 |
| 803564 | N/A | N/A | 66419 | 66438 | ATATGTTAATTTTCAAAGCG | 96 | 1726 |
| 803565 | N/A | N/A | 66420 | 66439 | AATATGTTAATTTTCAAAGC | 90 | 1727 |
| 803566 | N/A | N/A | 66421 | 66440 | GAATATGTTAATTTTCAAAG | 100 | 1728 |
| 803567 | N/A | N/A | 66422 | 66441 | TGAATATGTTAATTTTCAAA | 112 | 1729 |
| 803568 | N/A | N/A | 66672 | 66691 | AGAATGCTCATGTACTGCTG | 43 | 1730 |
| 803569 | N/A | N/A | 66673 | 66692 | CAGAATGCTCATGTACTGCT | 55 | 1731 |
| 803570 | N/A | N/A | 66911 | 66930 | CTGTCACAACTTCTATCTAG | 69 | 1732 |
| 803571 | N/A | N/A | 67066 | 67085 | GTTTCTTAAGTGGGATACAA | 25 | 1733 |
| 803572 | N/A | N/A | 67163 | 67182 | ACTTAAAATGTTTTAGACCT | 88 | 1734 |
| 803573 | N/A | N/A | 68270 | 68289 | AATACCTCAGCAGATGCTGA | 81 | 1735 |
| 803574 | N/A | N/A | 68715 | 68734 | CACATTACTAAAACTGACTT | 78 | 1736 |
| 803575 | N/A | N/A | 68989 | 69008 | AAACCAGTGTTCTAAGCTTC | 64 | 1737 |
| 803576 | N/A | N/A | 70079 | 70098 | AAATGATACTAACTGCAAAC | 85 | 1738 |
| 803577 | N/A | N/A | 70083 | 70102 | AAGAAAATGATACTAACTGC | 78 | 1739 |
| 803578 | N/A | N/A | 70146 | 70165 | TAATCTGCATATGGGTTTCT | 36 | 1740 |
| 803579 | N/A | N/A | 70615 | 70634 | AGATTATTAAATTATCATAA | 112 | 1741 |
| 803580 | N/A | N/A | 71056 | 71075 | TATTTGAATTTCATGTTTCA | 54 | 1742 |
| 803581 | N/A | N/A | 71205 | 71224 | TTTTTATGGAGACCGCTGGA | 77 | 1743 |
| 803582 | N/A | N/A | 71512 | 71531 | GTCCATTCCCTTTGTAAAAT | 53 | 1744 |
| 803583 | N/A | N/A | 71525 | 71544 | TGGAAATTTCACAGTCCATT | 30 | 1745 |
| 803584 | N/A | N/A | 72654 | 72673 | TCATTAACCAAACTACTTTT | 106 | 1746 |
| 803585 | N/A | N/A | 72790 | 72809 | ATTATGAGGATAAAAGAAAA | 125 | 1747 |
| 803586 | N/A | N/A | 72791 | 72810 | AATTATGAGGATAAAAGAAA | 121 | 1748 |
| 803587 | N/A | N/A | 72792 | 72811 | CAATTATGAGGATAAAAGAA | 117 | 1749 |
| 803588 | N/A | N/A | 72793 | 72812 | CCAATTATGAGGATAAAAGA | 92 | 1750 |
| 803589 | N/A | N/A | 72794 | 72813 | CCCAATTATGAGGATAAAAG | 49 | 1751 |
| 803590 | N/A | N/A | 72796 | 72815 | AACCCAATTATGAGGATAAA | 81 | 1752 |
| 803591 | N/A | N/A | 72797 | 72816 | GAACCCAATTATGAGGATAA | 60 | 1753 |
| 803592 | N/A | N/A | 72798 | 72817 | AGAACCCAATTATGAGGATA | 85 | 1754 |
| 803593 | N/A | N/A | 72799 | 72818 | AAGAACCCAATTATGAGGAT | 99 | 1755 |
| 803594 | N/A | N/A | 72800 | 72819 | TAAGAACCCAATTATGAGGA | 89 | 1756 |

TABLE 22-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803595 | N/A | N/A | 73940 | 73959 | AGATCTGTTTCCATTGCCTG | 24 | 1757 |
| 803596 | N/A | N/A | 74241 | 74260 | CTTTAAGTTACACATTATTT | 44 | 1758 |
| 803597 | N/A | N/A | 74300 | 74319 | CAAACTATGTTATACTTTAA | 92 | 1759 |
| 803598 | N/A | N/A | 76344 | 76363 | ACTCTTCAGAGTCTGAAAAG | 79 | 1760 |
| 803599 | N/A | N/A | 76345 | 76364 | AACTCTTCAGAGTCTGAAAA | 71 | 1761 |
| 803600 | N/A | N/A | 76346 | 76365 | AAACTCTTCAGAGTCTGAAA | 71 | 1762 |
| 803601 | N/A | N/A | 76347 | 76366 | CAAACTCTTCAGAGTCTGAA | 67 | 1763 |
| 803602 | N/A | N/A | 76348 | 76367 | TCAAACTCTTCAGAGTCTGA | 62 | 1764 |
| 803603 | N/A | N/A | 76350 | 76369 | TGTCAAACTCTTCAGAGTCT | 20 | 1765 |
| 803604 | N/A | N/A | 76351 | 76370 | GTGTCAAACTCTTCAGAGTC | 16 | 1766 |
| 803605 | N/A | N/A | 77606 | 77625 | ATAGTTGGGAACGAATAGTA | 61 | 1767 |
| 803606 | N/A | N/A | 77607 | 77626 | TATAGTTGGGAACGAATAGT | 89 | 1768 |
| 803607 | N/A | N/A | 77608 | 77627 | TTATAGTTGGGAACGAATAG | 94 | 1769 |
| 803608 | N/A | N/A | 77609 | 77628 | CTTATAGTTGGGAACGAATA | 72 | 1770 |
| 803609 | N/A | N/A | 77610 | 77629 | TCTTATAGTTGGGAACGAAT | 65 | 1771 |
| 803610 | N/A | N/A | 77612 | 77631 | TGTCTTATAGTTGGGAACGA | 36 | 1772 |
| 803611 | N/A | N/A | 77613 | 77632 | ATGTCTTATAGTTGGGAACG | 32 | 1773 |

TABLE 23

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 12 | 235 |
| 780254 | 4111 | 4130 | 86606 | 86625 | GTTTCATTCGGTTATAAGGC | 11 | 235 |
| 780617 | N/A | N/A | 81581 87838 | 81600 87857 | GTTTGAAGGAATAGCTGACA | 35 | 667 |
| 780618 | N/A | N/A | 81584 87841 | 81603 87860 | AGTGTTTGAAGGAATAGCTG | 25 | 668 |
| 780619 | N/A | N/A | 81587 87844 | 81606 87863 | CATAGTGTTTGAAGGAATAG | 62 | 669 |
| 780620 | N/A | N/A | 81590 87847 | 81609 87866 | AGCCATAGTGTTTGAAGGAA | 11 | 670 |
| 780621 | N/A | N/A | 81593 87850 | 81612 87869 | AAAAGCCATAGTGTTTGAAG | 55 | 671 |
| 780622 | N/A | N/A | 81596 87853 | 81615 87872 | CTAAAAGCCATAGTGTTTG | 69 | 672 |

TABLE 23-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780623 | N/A | N/A | 81599 87856 | 81618 87875 | ATTCTAAAAGCCATAGTGT | 45 12 | 673 674 |
| 780624 | N/A | N/A | 81630 87887 | 81649 87906 | GCAGCATCATGCAAGCAGCA | | |
| 780625 | N/A | N/A | 81633 87890 | 81652 87909 | ATTGCAGCATCATGCAAGCA | 40 | 675 |
| 803612 | N/A | N/A | 77614 | 77633 | AATGTCTTATAGTTGGGAAC | 36 | 1774 |
| 803613 | N/A | N/A | 77615 | 77634 | GAATGTCTTATAGTTGGGAA | 45 | 1775 |
| 803614 | N/A | N/A | 77616 | 77635 | AGAATGTCTTATAGTTGGGA | 30 | 1776 |
| 803615 | N/A | N/A | 78807 | 78826 | TAAGGACAGAGACCGAGTTT | 58 | 1777 |
| 803616 | N/A | N/A | 79332 | 79351 | CATTTACATGGGATTATTTT | 56 | 1778 |
| 803617 | N/A | N/A | 79675 | 79694 | ATAGCTATTATACCTCACCT | 52 | 1779 |
| 803618 | N/A | N/A | 79976 | 79995 | ATTGTTAAGAAGGAAATGCA | 70 | 1780 |
| 803619 | N/A | N/A | 80327 | 80346 | ACTCTGGTATATTTTATGAT | N/A | 1781 |
| 803620 | N/A | N/A | 80378 | 80397 | AGAGATTGGGAAACATTCAG | 38 | 1782 |
| 803621 | N/A | N/A | 80523 | 80542 | TATAGCAAAACAACTATGAA | 84 | 1783 |
| 803622 | N/A | N/A | 81353 | 81372 | CCCCAAAATTTCACTCAAAC | 55 | 1784 |
| 803623 | N/A | N/A | 81582 87839 | 81601 87858 | TGTTTGAAGGAATAGCTGAC | 50 | 1785 |
| 803624 | N/A | N/A | 81583 87840 | 81602 87859 | GTGTTTGAAGGAATAGCTGA | 39 | 1786 |
| 803625 | N/A | N/A | 81585 87842 | 81604 87861 | TAGTGTTTGAAGGAATAGCT | 48 | 1787 |
| 803626 | N/A | N/A | 81586 87843 | 81605 87862 | ATAGTGTTTGAAGGAATAGC | 48 | 1788 |
| 803627 | N/A | N/A | 81588 87845 | 81607 87864 | CCATAGTGTTTGAAGGAATA | 26 | 1789 |
| 803628 | N/A | N/A | 81589 87846 | 81608 87865 | GCCATAGTGTTTGAAGGAAT | 12 | 1790 |
| 803629 | N/A | N/A | 81591 87848 | 81610 87867 | AAGCCATAGTGTTTGAAGGA | 19 | 1791 |
| 803630 | N/A | N/A | 81592 87849 | 81611 87868 | AAAGCCATAGTGTTTGAAGG | 34 | 1792 |
| 803631 | N/A | N/A | 81594 87851 | 81613 87870 | AAAAAGCCATAGTGTTTGAA | 56 | 1793 |
| 803632 | N/A | N/A | 81595 87852 | 81614 87871 | TAAAAGCCATAGTGTTTGA | 76 | 1794 |
| 803633 | N/A | N/A | 81597 87854 | 81616 87873 | TCTAAAAGCCATAGTGTTT | 58 | 1795 |
| 803634 | N/A | N/A | 81598 87855 | 81617 87874 | TTCTAAAAGCCATAGTGTT | 71 | 1796 |
| 803635 | N/A | N/A | 81625 | 81644 | ATCATGCAAGCAGCATTTTA | 63 | 1797 |
| 803636 | N/A | N/A | 81626 | 81645 | CATCATGCAAGCAGCATTTT | 82 | 1798 |

TABLE 23-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803637 | N/A | N/A | 81627 | 81646 | GCATCATGCAAGCAGCATTT | 23 | 1799 |
| 803638 | N/A | N/A | 81628 | 81647 | AGCATCATGCAAGCAGCATT | 25 | 1800 |
| 803639 | N/A | N/A | 81629 | 81648 | CAGCATCATGCAAGCAGCAT | 34 | 1801 |
| 803640 | N/A | N/A | 81631 | 81650 | TGCAGCATCATGCAAGCAGC | 16 | 1802 |
| 803641 | N/A | N/A | 81632 87888 | 81651 87907 | TTGCAGCATCATGCAAGCAG | 31 | 1803 |
| 803642 | N/A | N/A | 81634 87889 | 81653 87908 | CATTGCAGCATCATGCAAGC | 44 | 1804 |
| 803643 | N/A | N/A | 81635 87891 | 81654 87910 | TCATTGCAGCATCATGCAAG | 43 | 1805 |
| | | | 87892 | 87911 | | | |
| 803644 | N/A | N/A | 81822 | 81841 | GGAGATAATAACAGTGGCTA | 48 | 1806 |
| 803645 | N/A | N/A | 82500 | 82519 | GTGGAAGTATTAAGGCTACT | 14 | 1807 |
| 803646 | N/A | N/A | 82501 | 82520 | AGTGGAAGTATTAAGGCTAC | 23 | 1808 |
| 803647 | N/A | N/A | 82502 | 82521 | TAGTGGAAGTATTAAGGCTA | 20 | 1809 |
| 803648 | N/A | N/A | 82503 | 82522 | TTAGTGGAAGTATTAAGGCT | 36 | 1810 |
| 803649 | N/A | N/A | 82504 | 82523 | TTTAGTGGAAGTATTAAGGC | 43 | 1811 |
| 803650 | N/A | N/A | 82506 | 82525 | TGTTTAGTGGAAGTATTAAG | 32 | 1812 |
| 803651 | N/A | N/A | 82507 | 82526 | TTGTTTAGTGGAAGTATTAA | 81 | 1813 |
| 803652 | N/A | N/A | 82508 | 82527 | ATTGTTTAGTGGAAGTATTA | 60 | 1814 |
| 803653 | N/A | N/A | 82509 | 82528 | TATTGTTTAGTGGAAGTATT | 62 | 1815 |
| 803654 | N/A | N/A | 82510 | 82529 | TTATTGTTTAGTGGAAGTAT | 36 | 1816 |
| 803655 | N/A | N/A | 82697 | 82716 | TTGTCATAGTTAAGTAACAG | 20 | 1817 |
| 803656 | N/A | N/A | 83102 | 83121 | AAACAAGTAATACAGTATAC | 83 | 1818 |
| 803657 | N/A | N/A | 83213 | 83232 | ATTTCAGATTTACAACAGAG | 70 | 1819 |
| 803658 | N/A | N/A | 85777 | 85796 | TGTTAAAGCTTGATAATAGG | 49 | 1820 |
| 803659 | N/A | N/A | 86988 | 87007 | AGCACCAAATTGTTCCTAAC | 62 | 1821 |
| 803660 | N/A | N/A | 89783 | 89802 | AGCACACATAATCTATATAA | 34 | 1822 |
| 803661 | N/A | N/A | 89916 | 89935 | TACCATCTATCATCAATAAA | 26 | 1823 |
| 803662 | N/A | N/A | 90146 | 90165 | TTCTCTGACAACAATGACAA | 62 | 1824 |
| 803663 | N/A | N/A | 90678 | 90697 | TGTCTGCACAGACACCTGTT | 87 | 1825 |
| 803664 | N/A | N/A | 91038 | 91057 | GTATCTCTTAACCCAGAGAA | 37 | 1826 |
| 803665 | N/A | N/A | 91039 | 91058 | TGTATCTCTTAACCCAGAGA | 17 | 1827 |
| 803666 | N/A | N/A | 91040 | 91059 | ATGTATCTCTTAACCCAGAG | 24 | 1828 |
| 803667 | N/A | N/A | 91041 | 91060 | CATGTATCTCTTAACCCAGA | 36 | 1829 |
| 803668 | N/A | N/A | 91042 | 91061 | TCATGTATCTCTTAACCCAG | 37 | 1830 |
| 803669 | N/A | N/A | 91044 | 91063 | TTTCATGTATCTCTTAACCC | 26 | 1831 |
| 803670 | N/A | N/A | 91045 | 91064 | TTTTCATGTATCTCTTAACC | 58 | 1832 |
| 803671 | N/A | N/A | 91046 | 91065 | GTTTTCATGTATCTCTTAAC | 20 | 1833 |
| 803672 | N/A | N/A | 91047 | 91066 | TGTTTTCATGTATCTCTTAA | 36 | 1834 |

TABLE 23-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803673 | N/A | N/A | 91048 | 91067 | CTGTTTTCATGTATCTCTTA | 21 | 1835 |
| 803674 | N/A | N/A | 91144 | 91163 | AAATTAACTTGGTCTTTTTC | 68 | 1836 |
| 803675 | N/A | N/A | 91456 | 91475 | TCTGTTGCTCTTAGAATCTA | 23 | 1837 |
| 803676 | N/A | N/A | 91530 | 91549 | ATGGAACCTTGAACTTGGGA | 25 | 1838 |
| 803677 | N/A | N/A | 92329 | 92348 | GATTCAGAAACACTTTTATA | 59 | 1839 |
| 803678 | N/A | N/A | 92773 | 92792 | AAGTTGCTTTGAGAATTTTC | 48 | 1840 |
| 803679 | N/A | N/A | 93235 | 93254 | AAATCTAGTCCAACTTCCTC | 78 | 1841 |

TABLE 24

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 18 | 235 |
| 780254 | 4111 | 4130 | 86606 | 86625 | GTTTCATTCGGTTATAAGGC | 20 | 235 |
| 803680 | N/A | N/A | 93932 | 93951 | ACTCATTGGTAATGGATTAT | 24 | 1842 |
| 803681 | N/A | N/A | 94454 | 94473 | TTGCAATGTTTCAATATGCT | 53 | 1843 |
| 803682 | N/A | N/A | 94455 | 94474 | ATTGCAATGTTTCAATATGC | 26 | 1844 |
| 803683 | N/A | N/A | 94456 | 94475 | GATTGCAATGTTTCAATATG | 58 | 1845 |
| 803684 | N/A | N/A | 94457 | 94476 | TGATTGCAATGTTTCAATAT | 65 | 1846 |
| 803685 | N/A | N/A | 94458 | 94477 | CTGATTGCAATGTTTCAATA | 53 | 1847 |
| 803686 | N/A | N/A | 94460 | 94479 | TGCTGATTGCAATGTTTCAA | 24 | 1848 |
| 803687 | N/A | N/A | 94461 | 94480 | TTGCTGATTGCAATGTTTCA | 57 | 1849 |
| 803688 | N/A | N/A | 94462 | 94481 | ATTGCTGATTGCAATGTTTC | 59 | 1850 |
| 803689 | N/A | N/A | 94463 | 94482 | AATTGCTGATTGCAATGTTT | 54 | 1851 |
| 803690 | N/A | N/A | 94464 | 94483 | TAATTGCTGATTGCAATGTT | 75 | 1852 |
| 803691 | N/A | N/A | 95362 | 95381 | AATCGGAAATTTAAATTATC | 104 | 1853 |
| 803692 | N/A | N/A | 95619 | 95638 | TTAGTGACCTAACAGCTCGG | 64 | 1854 |
| 803693 | N/A | N/A | 97048 | 97067 | GTACAGTATTTATTGAATCA | 27 | 1855 |
| 803694 | N/A | N/A | 97142 | 97161 | ATTTATGCTATCATGTAGTT | 71 | 1856 |
| 803695 | N/A | N/A | 97748 | 97767 | AATAATATATTCCCAGGAAA | 90 | 1857 |
| 803696 | N/A | N/A | 97935 | 97954 | TAGCAACCATGTGGCCTAGA | 59 | 1858 |
| 803697 | N/A | N/A | 98088 | 98107 | ACTGTCAAAATCTGAAAGAT | 92 | 1859 |
| 803698 | N/A | N/A | 98337 | 98356 | AGTTAGTTTGACAATTAAAA | 72 | 1860 |

TABLE 24-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803699 | N/A | N/A | 98486 | 98505 | AGTAACTATACACATAAAGT | 99 | 1861 |
| 803700 | N/A | N/A | 99619 | 99638 | CACCGGATTTGCTCTTTTTT | 30 | 1862 |
| 803701 | N/A | N/A | 100073 | 100092 | AATCTACTGCACACAACACA | 89 | 1863 |
| 803702 | N/A | N/A | 100118 | 100137 | AATGGAGCCATTAATTATTA | 95 | 1864 |
| 803703 | N/A | N/A | 100281 | 100300 | ATTTCCTTACCTTTTCTACA | 103 | 1865 |
| 803704 | N/A | N/A | 100353 | 100372 | GCTTTAAGGTAAAGTTTTTT | 33 | 1866 |
| 803705 | N/A | N/A | 100816 | 100835 | GCCAGCATTCAAACCCTCAA | 39 | 1867 |
| 803706 | N/A | N/A | 102479 | 102498 | ATGAGAGTAGATTTTAATAG | 85 | 1868 |
| 803707 | N/A | N/A | 102841 | 102860 | CTGAGTTCCAAAGCATTTAA | 80 | 1869 |
| 803708 | N/A | N/A | 103029 | 103048 | CACATTTTAATGCAGGAAAA | 97 | 1870 |
| 803709 | N/A | N/A | 105168 | 105187 | TGGATATAAGTGAATACACA | 71 | 1871 |
| 803710 | N/A | N/A | 105655 | 105674 | ATAGTGGCCCCTAAATCCTT | 83 | 1872 |
| 803711 | N/A | N/A | 105656 | 105675 | TATAGTGGCCCCTAAATCCT | 79 | 1873 |
| 803712 | N/A | N/A | 105657 | 105676 | ATATAGTGGCCCCTAAATCC | 73 | 1874 |
| 803713 | N/A | N/A | 105658 | 105677 | CATATAGTGGCCCCTAAATC | 88 | 1875 |
| 803714 | N/A | N/A | 105659 | 105678 | TCATATAGTGGCCCCTAAAT | 80 | 1876 |
| 803715 | N/A | N/A | 105661 | 105680 | AGTCATATAGTGGCCCCTAA | 46 | 1877 |
| 803716 | N/A | N/A | 105662 | 105681 | TAGTCATATAGTGGCCCCTA | 58 | 1878 |
| 803717 | N/A | N/A | 105663 | 105682 | ATAGTCATATAGTGGCCCCT | 57 | 1879 |
| 803718 | N/A | N/A | 105664 | 105683 | CATAGTCATATAGTGGCCCC | 49 | 1880 |
| 803719 | N/A | N/A | 105665 | 105684 | CCATAGTCATATAGTGGCCC | 35 | 1881 |
| 803720 | N/A | N/A | 105789 | 105808 | CTTCCAACTCATTCTCTCTC | 75 | 1882 |
| 803721 | N/A | N/A | 105839 | 105858 | GTGGCCTCAGAGCTTTCTGC | 62 | 1883 |
| 803722 | N/A | N/A | 105902 | 105921 | TCCACTGTGTAGCCTCATTT | 103 | 1884 |
| 803723 | N/A | N/A | 106062 | 106081 | AAGCCACATTTATTACCTTT | 49 | 1885 |
| 803724 | N/A | N/A | 106724 | 106743 | GAGAAATAACACAAAACTTT | 101 | 1886 |
| 803725 | N/A | N/A | 106922 | 106941 | GGCACTGAAAAGTCCCAAGT | 28 | 1887 |
| 803726 | N/A | N/A | 107295 | 107314 | AGTAGGAAATAGGATAAGCA | 79 | 1888 |
| 803727 | N/A | N/A | 108334 | 108353 | TTAACATGTAAGGACTGAAA | 97 | 1889 |
| 803728 | N/A | N/A | 108377 | 108396 | TGATGACATATCCACCACAT | 84 | 1890 |
| 803729 | N/A | N/A | 108774 | 108793 | TTTAGCTTACTACTATATAT | 91 | 1891 |
| 803730 | N/A | N/A | 109150 | 109169 | TAATGCAAGTAATACAAAAA | 102 | 1892 |
| 803731 | N/A | N/A | 109281 | 109300 | TTCTTTAACAATCAATAGAG | 79 | 1893 |
| 803732 | N/A | N/A | 109893 | 109912 | TATGGATGAAAAGTGAACAT | 91 | 1894 |
| 803733 | N/A | N/A | 110855 | 110874 | GAAATTACCTACACATTAAA | 103 | 1895 |
| 803734 | N/A | N/A | 110955 | 110974 | GACATTTTAATGTACTAAT | 63 | 1896 |

TABLE 24-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803735 | N/A | N/A | 111205 | 111224 | AATTTTCTATCCTGGAAAAG | 95 | 1897 |
| 803736 | N/A | N/A | 111262 | 111281 | AGAAGGAGTTAAGTTAGCTC | 51 | 1898 |
| 803737 | N/A | N/A | 112344 | 112363 | CAGTGTAGTCATACTAACAG | 58 | 1899 |
| 803738 | N/A | N/A | 112345 | 112364 | ACAGTGTAGTCATACTAACA | 54 | 1900 |
| 803739 | N/A | N/A | 112346 | 112365 | CACAGTGTAGTCATACTAAC | 58 | 1901 |
| 803740 | N/A | N/A | 112347 | 112366 | ACACAGTGTAGTCATACTAA | 31 | 1902 |
| 803741 | N/A | N/A | 112348 | 112367 | CACACAGTGTAGTCATACTA | 38 | 1903 |
| 803742 | N/A | N/A | 112350 | 112369 | TGCACACAGTGTAGTCATAC | 35 | 1904 |
| 803743 | N/A | N/A | 112351 | 112370 | GTGCACACAGTGTAGTCATA | 30 | 1905 |
| 803744 | N/A | N/A | 112352 | 112371 | AGTGCACACAGTGTAGTCAT | 27 | 1906 |
| 803745 | N/A | N/A | 112353 | 112372 | CAGTGCACACAGTGTAGTCA | 19 | 1907 |
| 803746 | N/A | N/A | 112354 | 112373 | ACAGTGCACACAGTGTAGTC | 45 | 1908 |
| 803747 | N/A | N/A | 112629 | 112648 | CTTGCTTTATGGTAAGAATG | 46 | 1909 |
| 803748 | N/A | N/A | 113302 | 113321 | CAAGTCTGGATCACACTTGT | 71 | 1910 |
| 803749 | N/A | N/A | 113398 | 113417 | AAAATTTGATCAGGGAAATG | 102 | 1911 |
| 803750 | N/A | N/A | 113772 | 113791 | GTGGAATAGTGATGAATCCC | 35 | 1912 |
| 803751 | N/A | N/A | 113824 | 113843 | AGACTATTTAAAAAATGGGA | 77 | 1913 |
| 803752 | N/A | N/A | 114604 | 114623 | CACAGTAATTCTGAAGGCTT | 64 | 1914 |
| 803753 | N/A | N/A | 114621 | 114640 | CCTTCCCCTACTGTCAACAC | 80 | 1915 |
| 803754 | N/A | N/A | 114658 | 114677 | CCCCAGGCACTGTTTTCCTT | 92 | 1916 |
| 803755 | N/A | N/A | 115071 | 115090 | GTTTCAGAGAACTAGAATAA | 65 | 1917 |
| 803756 | N/A | N/A | 115110 | 115129 | ACTTCATCAGAAACTGCTGG | 48 | 1918 |

TABLE 25

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780254 | 4111 | 4130 | 86606 | 86625 | GTTTCATTCGGTTATAAGGC | 24 | 235 |
| 780254 | 4111 | 4130 | 86606 | 86625 | GTTTCATTCGGTTATAAGGC | 26 | 235 |
| 803757 | N/A | N/A | 117459 | 117478 | AAAATTCTGATTTCCAACTC | 94 | 1919 |
| 803758 | N/A | N/A | 118016 | 118035 | GTATGTTAAATAAGAATTGA | 99 | 1920 |
| 803759 | N/A | N/A | 118692 | 118711 | CAATGTGATGCTTGCATTTT | 87 | 1921 |
| 803760 | N/A | N/A | 118987 | 119006 | TGACACCAAATTAGTCATTT | 55 | 1922 |

TABLE 25-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803761 | N/A | N/A | 119091 | 119110 | TGTACTCAAACATGTATATA | 75 | 1923 |
| 803762 | N/A | N/A | 119108 | 119127 | GGTCACGGCCAGCCCCTGT | 95 | 1924 |
| 803763 | N/A | N/A | 119608 | 119627 | AACATACACTTTGAAGTGTT | 62 | 1925 |
| 803764 | N/A | N/A | 119902 | 119921 | GTTTAGGAGAGACTATAGAA | 73 | 1926 |
| 803765 | N/A | N/A | 119903 | 119922 | GGTTTAGGAGAGACTATAGA | 42 | 1927 |
| 803766 | N/A | N/A | 119904 | 119923 | TGGTTTAGGAGAGACTATAG | 43 | 1928 |
| 803767 | N/A | N/A | 119905 | 119924 | ATGGTTTAGGAGAGACTATA | 43 | 1929 |
| 803768 | N/A | N/A | 119906 | 119925 | TATGGTTTAGGAGAGACTAT | 49 | 1930 |
| 803769 | N/A | N/A | 119908 | 119927 | CATATGGTTTAGGAGAGACT | 28 | 1931 |
| 803770 | N/A | N/A | 119909 | 119928 | GCATATGGTTTAGGAGAGAC | 8 | 1932 |
| 803771 | N/A | N/A | 119910 | 119929 | TGCATATGGTTTAGGAGAGA | 14 | 1933 |
| 803772 | N/A | N/A | 119911 | 119930 | TTGCATATGGTTTAGGAGAG | 40 | 1934 |
| 803773 | N/A | N/A | 119912 | 119931 | GTTGCATATGGTTTAGGAGA | 21 | 1935 |
| 803774 | N/A | N/A | 120040 | 120059 | TCTATGGAATTTCATCCTTT | 62 | 1936 |
| 803775 | N/A | N/A | 120380 | 120399 | CAGCAAAACCAGGAAGTCAG | 75 | 1937 |
| 803776 | N/A | N/A | 121866 | 121885 | GTATTGTTGCCAAATGAATG | 50 | 1938 |
| 803777 | N/A | N/A | 121867 | 121886 | TGTATTGTTGCCAAATGAAT | 64 | 1939 |
| 803778 | N/A | N/A | 121868 | 121887 | ATGTATTGTTGCCAAATGAA | 66 | 1940 |
| 803779 | N/A | N/A | 121869 | 121888 | AATGTATTGTTGCCAAATGA | 77 | 1941 |
| 803780 | N/A | N/A | 121870 | 121889 | CAATGTATTGTTGCCAAATG | 56 | 1942 |
| 803781 | N/A | N/A | 121872 | 121891 | TTCAATGTATTGTTGCCAAA | 49 | 1943 |
| 803782 | N/A | N/A | 121873 | 121892 | GTTCAATGTATTGTTGCCAA | 21 | 1944 |
| 803783 | N/A | N/A | 121874 | 121893 | TGTTCAATGTATTGTTGCCA | 43 | 1945 |
| 803784 | N/A | N/A | 121875 | 121894 | ATGTTCAATGTATTGTTGCC | 38 | 1946 |
| 803785 | N/A | N/A | 121876 | 121895 | AATGTTCAATGTATTGTTGC | 57 | 1947 |
| 803786 | N/A | N/A | 122268 | 122287 | CACATCCTTTTACAATAGTT | 46 | 1948 |
| 803787 | N/A | N/A | 123076 | 123095 | AGGATGGAGACATCGAATTT | 67 | 1949 |
| 803788 | N/A | N/A | 123077 | 123096 | AAGGATGGAGACATCGAATT | 78 | 1950 |
| 803789 | N/A | N/A | 123078 | 123097 | GAAGGATGGAGACATCGAAT | 45 | 1951 |
| 803790 | N/A | N/A | 123079 | 123098 | GGAAGGATGGAGACATCGAA | 46 | 1952 |
| 803791 | N/A | N/A | 123080 | 123099 | TGGAAGGATGGAGACATCGA | 67 | 1953 |
| 803792 | N/A | N/A | 123082 | 123101 | GTTGGAAGGATGGAGACATC | 65 | 1954 |
| 803793 | N/A | N/A | 123083 | 123102 | AGTTGGAAGGATGGAGACAT | 54 | 1955 |
| 803794 | N/A | N/A | 123084 | 123103 | GAGTTGGAAGGATGGAGACA | 67 | 1956 |
| 803795 | N/A | N/A | 123085 | 123104 | AGAGTTGGAAGGATGGAGAC | 82 | 1957 |
| 803796 | N/A | N/A | 123086 | 123105 | AAGAGTTGGAAGGATGGAGA | 99 | 1958 |

TABLE 25-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803797 | N/A | N/A | 124014 | 124033 | TGGATAGACAGAAAGTTATC | 89 | 1959 |
| 803798 | N/A | N/A | 124460 | 124479 | TCCAGGACAGTGTTTTAAAA | 57 | 1960 |
| 803799 | N/A | N/A | 125043 | 125062 | AATCTTCATTGTAGAGAAAA | 96 | 1961 |
| 803800 | N/A | N/A | 125214 | 125233 | GCGGATTTTTAAAAAGCCT | 44 | 1962 |
| 803801 | N/A | N/A | 126287 | 126306 | TAAAAAGAGACCCAAATAAC | 108 | 1963 |
| 803802 | N/A | N/A | 126714 | 126733 | TTTAATTCTGTCTCTGTGTG | 88 | 1964 |
| 803803 | N/A | N/A | 127951 | 127970 | GCTTGAGAAGACCTAAGTAA | 72 | 1965 |
| 803804 | N/A | N/A | 128819 | 128838 | GATGGTAACCTAAATTAAAA | 87 | 1966 |
| 803805 | N/A | N/A | 129120 | 129139 | AGAGCTGTGACATGGCCACC | 74 | 1967 |
| 803806 | N/A | N/A | 129202 | 129221 | TCTCTAGATTCTGTTTTTGA | 97 | 1968 |
| 803807 | N/A | N/A | 129512 | 129531 | CTGGAACCCAACTAGATCAC | 78 | 1969 |
| 803808 | N/A | N/A | 129985 | 130004 | TGATTCTAAAGCAAAACACA | 96 | 1970 |
| 803809 | N/A | N/A | 130212 | 130231 | CTTGCCTGGCAGTGGGAAAA | 120 | 1971 |
| 803810 | N/A | N/A | 130229 | 130248 | AATGAAAGACTGGCTCCCTT | 103 | 1972 |
| 803811 | N/A | N/A | 130358 | 130377 | GTTCAGAGATGTGCTATTTA | 61 | 1973 |
| 803812 | N/A | N/A | 130530 | 130549 | GCACAATATTTATCTTCAGG | 44 | 1974 |
| 803813 | N/A | N/A | 130540 | 130559 | TAATGTTGAGGCACAATATT | 121 | 1975 |
| 803814 | N/A | N/A | 132624 | 132643 | AAAGATCTGTAATTTCCCCA | 59 | 1976 |
| 803815 | N/A | N/A | 134408 | 134427 | AGCAATACAAATACAGCATA | 55 | 1977 |
| 803816 | N/A | N/A | 136673 | 136692 | GTAGGTAGACCAATGTAGAG | 73 | 1978 |
| 803817 | N/A | N/A | 137059 | 137078 | ATTAATAAAATACCTAGGAG | 110 | 1979 |
| 803818 | N/A | N/A | 137783 | 137802 | TACTAAGATTACAATGAGTT | 82 | 1980 |
| 803819 | N/A | N/A | 137934 | 137953 | TTCCTACAATCAATACTTAA | 86 | 1981 |
| 803820 | N/A | N/A | 138184 | 138203 | GAACTATGATTTATGCTCTT | 47 | 1982 |
| 803821 | N/A | N/A | 138715 | 138734 | ATTGCATCAGATTGATGTAC | 82 | 1983 |
| 803822 | N/A | N/A | 139321 | 139340 | AAAAATCCTCATTCATGGGA | 66 | 1984 |
| 803823 | N/A | N/A | 139750 | 139769 | TAAAGCATCTATGCTCCAAA | 47 | 1985 |
| 803824 | N/A | N/A | 140044 | 140063 | GCAGACCTAGAACTCCAAAA | 39 | 1986 |
| 803825 | N/A | N/A | 140485 | 140504 | AACAACGAGGAATATGTAAA | 91 | 1987 |
| 803826 | N/A | N/A | 140731 | 140750 | CAAAATAGACCAACCAGTCC | 87 | 1988 |
| 803827 | N/A | N/A | 140958 | 140977 | CATCCAAACATAAACAGAAA | 85 | 1989 |
| 803828 | N/A | N/A | 141091 | 141110 | GTTAGCCTTTTATACCTAGA | 29 | 1990 |
| 803829 | N/A | N/A | 141151 | 141170 | ATCTGTAACTTTTGAATGTT | 77 | 1991 |
| 803830 | N/A | N/A | 142094 | 142113 | GGTCTTGATCCCCACTCCTT | 110 | 1992 |
| 803831 | N/A | N/A | 142406 | 142425 | TATCAAGGAGACCTGTTGGC | 114 | 1993 |

TABLE 25-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 803832 | N/A | N/A | 142595 | 142614 | AAGTTTTACATGAAGTCTCA | 92 | 1994 |
| 803833 | N/A | N/A | 144471 | 144490 | AGCTGTTATGGGAACCCAAA | 60 | 1995 |

TABLE 26

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 24 | 222 |
| 803625 | N/A | N/A | 81585 87842 | 81604 87861 | TAGTGTTTGAAGGAATAGCT | 69 | 1787 |
| 876008 | 62 | 81 | 3181 | 3200 | CGTCCGCTGCTCAGGGAACC | 39 | 1996 |
| 876032 | 737 | 756 | 18636 | 18655 | AACGCACTTAACAATATCAT | 33 | 1997 |
| 876056 | 872 | 891 | 21703 | 21722 | ATAGCTTCCACCACAATATT | 71 | 1998 |
| 876080 | 1337 | 1356 | 31053 | 31072 | TTTGATGAAGAATGCATCAG | 83 | 1999 |
| 876104 | 1486 | 1505 | 35433 | 35452 | CACTTTCAGCCACTTCAGGA | 47 | 2000 |
| 876128 | 1728 | 1747 | 41961 | 41980 | AATATCATTCTTGAAACACT | 44 | 2001 |
| 876152 | 2493 | 2512 | 62114 | 62133 | ATCCAGGGCCAGCCTCCTTA | 76 | 2002 |
| 876176 | 3158 | 3177 | 73694 | 73713 | TGAAGCTCCAGCTTTTCAAG | 45 | 2003 |
| 876200 | 3571 | 3590 | 77320 | 77339 | TCTCCACTTTAGGACAAGCC | 35 | 2004 |
| 876224 | 3856 | 3875 | 82201 | 82220 | GATGCAGTTTCTCTACTCTA | 24 | 2005 |
| 876248 | 4319 | 4338 | 87223 | 87242 | GGATGAGTACTATAGAATTC | 41 | 2006 |
| 876272 | 4754 | 4773 | 92177 | 92196 | TTCCGGTCAATTACGGGAAA | 63 | 2007 |
| 876296 | 5075 | 5094 | 98223 | 98242 | ATCTGGAATTTTTCTAGGAG | 49 | 2008 |
| 876320 | 5482 | 5501 | 100471 | 100490 | CAGGAAACCATTCTTCCATG | 44 | 2009 |
| 876344 | 5833 | 5852 | 106524 | 106543 | GTTTATTAAAAATCTTCACA | 76 | 2010 |
| 876368 | 6603 | 6622 | 129748 | 129767 | AATGCTTGCATTCCTGCTGT | 70 | 2011 |
| 876392 | 7223 | 7242 | 141584 | 141603 | TCCACAACAGGGCTATTTTG | 75 | 2012 |
| 876416 | 8192 | 8211 | 146361 | 146380 | AATTCATTTGAATATTTACA | 89 | 2013 |
| 876440 | 9043 | 9062 | 147212 | 147231 | GTTAAAGCATAGCTTCCTTT | 63 | 2014 |
| 876464 | N/A | N/A | 4983 | 5002 | AATGAAGGTGGCCAGAATCA | 125 | 2015 |
| 876488 | N/A | N/A | 7242 | 7261 | AAGTGAGTATTAAAATGTCA | 112 | 2016 |
| 876512 | N/A | N/A | 9238 | 9257 | CAAAATGTAAGTTATCAGAA | 138 | 2017 |
| 876536 | N/A | N/A | 12445 | 12464 | TCAATAATGTTTAGTTAGTT | 85 | 2018 |
| 876560 | N/A | N/A | 15299 | 15318 | ACTATAGTACATGTATCTCA | 68 | 2019 |

TABLE 26-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876584 | N/A | N/A | 17431 | 17450 | TTATACATGACAGCCTGAAG | 121 | 2020 |
| 876608 | N/A | N/A | 19744 | 19763 | AGAACACTTATTACATACCA | 56 | 2021 |
| 876632 | N/A | N/A | 21991 | 22010 | TTTTTGACACTCCTTTTAAA | 93 | 2022 |
| 876656 | N/A | N/A | 25071 | 25090 | ACGATCATTCCTTATTATTC | 52 | 2023 |
| 876680 | N/A | N/A | 27616 | 27635 | GGCACGACAATATTCATTGT | 68 | 2024 |
| 876704 | N/A | N/A | 30008 | 30027 | CAACCTGCTGGCTAGTCACC | 40 | 2025 |
| 876728 | N/A | N/A | 32100 | 32119 | TAATTATACAAAGCTATAAG | 126 | 2026 |
| 876752 | N/A | N/A | 33547 | 33566 | ATAGAACATTTTACACACTA | 63 | 2027 |
| 876776 | N/A | N/A | 35959 | 35978 | AACCGCCAGCTATATAATCT | 73 | 2028 |
| 876800 | N/A | N/A | 38194 | 38213 | AGGTGATAACAGATGTCAGT | 104 | 2029 |
| 876824 | N/A | N/A | 39985 | 40004 | AGTAATAGATTGAAAGAAAC | 90 | 2030 |
| 876848 | N/A | N/A | 42029 | 42048 | TTAATAGTATAAATACAGAA | 119 | 2031 |
| 876872 | N/A | N/A | 45638 | 45657 | CCGACTGCTGAGGTTACACC | 64 | 2032 |
| 876896 | N/A | N/A | 47955 | 47974 | GTGAGGGAGAGGACATAAAG | 99 | 2033 |
| 876920 | N/A | N/A | 49786 | 49805 | TGTATTACATAGGTATGACT | 52 | 2034 |
| 876944 | N/A | N/A | 52148 | 52167 | CTTTAAAGATGCAGAAATAA | 100 | 2035 |
| 876968 | N/A | N/A | 55095 | 55114 | TTACCCGTGCATGCACCTGT | 119 | 2036 |
| 876992 | N/A | N/A | 57336 | 57355 | ATATTAAATACAGTAAGGTT | 115 | 2037 |
| 877016 | N/A | N/A | 60029 | 60048 | CCATTCACTCCTTACTTTGT | 66 | 2038 |
| 877040 | N/A | N/A | 62799 | 62818 | AAAGATAAAAATAGTGTCAG | 91 | 2039 |
| 877064 | N/A | N/A | 65735 | 65754 | CTCAAGTTTTTCCAGATGAT | 55 | 2040 |
| 877088 | N/A | N/A | 67068 | 67087 | AGGTTTCTTAAGTGGGATAC | 40 | 2041 |
| 877112 | N/A | N/A | 70290 | 70309 | GCTTAGAGACAAATTAAGGG | 37 | 2042 |
| 877136 | N/A | N/A | 72623 | 72642 | TTATATATAAATTCGAAAGA | 158 | 2043 |
| 877160 | N/A | N/A | 73942 | 73961 | TCAGATCTGTTTCCATTGCC | 31 | 2044 |
| 877184 | N/A | N/A | 75823 | 75842 | CAATTTCTAATTTTATAATG | 111 | 2045 |
| 877208 | N/A | N/A | 78402 | 78421 | ATTTCCTCTATTATTTCATA | 47 | 2046 |
| 877239 | N/A | N/A | 83094 | 83113 | AATACAGTATACAGGCCAGT | 32 | 2047 |
| 877263 | N/A | N/A | 85311 | 85330 | CATTACCTTTCTTGATTTAT | 85 | 2048 |
| 877287 | N/A | N/A | 88256 | 88275 | TTTCCTTTCCCATCTTCATG | 92 | 2049 |
| 877311 | N/A | N/A | 90591 | 90610 | GAGGACAAAAAATGATCTCT | 70 | 2050 |
| 877335 | N/A | N/A | 92465 | 92484 | CTAAATTTGTTTTCTTATGA | 129 | 2051 |
| 877359 | N/A | N/A | 94743 | 94762 | ACCAGGGAGGCAATATAGAA | 62 | 2052 |
| 877383 | N/A | N/A | 96119 | 96138 | CCACATGGAGAAGCACCAAT | 62 | 2053 |
| 877407 | N/A | N/A | 99047 | 99066 | AAAGTCAATGAAGGTAATCA | 56 | 2054 |
| 877431 | N/A | N/A | 101670 | 101689 | ATTAAGGCAAATACAAAGAT | 127 | 2055 |

TABLE 26-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
| --- | --- | --- | --- | --- | --- | --- | --- |
| 877455 | N/A | N/A | 104228 | 104247 | GCTGCATTAATATGGAGTAT | 47 | 2056 |
| 877479 | N/A | N/A | 106092 | 106111 | TGCCCTTCCAACTCAATCAC | 82 | 2057 |
| 877503 | N/A | N/A | 108922 | 108941 | TTATAGATAAAACTTGAAGA | 126 | 2058 |
| 877527 | N/A | N/A | 111504 | 111523 | ATGCTTTAAACTGTGATTGC | 72 | 2059 |
| 877551 | N/A | N/A | 113499 | 113518 | TTAAGATGATGGGTTCTAGA | 77 | 2060 |
| 877575 | N/A | N/A | 116118 | 116137 | TGCAAGAAACACAAGTTGGA | 102 | 2061 |
| 877599 | N/A | N/A | 118373 | 118392 | ATGCACAGGAAATCTTATTC | 96 | 2062 |
| 877623 | N/A | N/A | 120463 | 120482 | ATATTGGAGATTAAAAGGGA | 121 | 2063 |
| 877647 | N/A | N/A | 122643 | 122662 | TTTACAAACGACATAATCCT | 117 | 2064 |
| 877671 | N/A | N/A | 126280 | 126299 | AGACCCAAATAACGATTTAA | 55 | 2065 |
| 877695 | N/A | N/A | 128683 | 128702 | CCAAATCAAGAGCTCACAAC | 91 | 2066 |
| 877719 | N/A | N/A | 133235 | 133254 | TAGTACTTTTTTCCAATAC | 65 | 2067 |
| 877743 | N/A | N/A | 136955 | 136974 | AGATATTCATGCTCACAGAC | 142 | 2068 |
| 877767 | N/A | N/A | 140322 | 140341 | TGTTGTCAGAGAGCCACTAC | 71 | 2069 |
| 877791 | N/A | N/A | 141782 | 141801 | GAAGCATTACAAATTTTTT | 105 | 2070 |
| 877815 | N/A | N/A | 144092 | 144111 | CCAAAGTACATACAATTCAA | 61 | 2071 |

TABLE 27

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
| --- | --- | --- | --- | --- | --- | --- | --- |
| 780241 | 3714 | 3733 | 82059 | 82078 | GCTCATATCTAAAGACCGCA | 29 | 222 |
| 803626 | N/A | N/A | 81586 87843 | 81605 87862 | ATAGTGTTTGAAGGAATAGC | 50 | 1788 |
| 876009 | 191 | 210 | 3310 | 3329 | TTTCCTTCCTGGACATTGTT | 50 | 2072 |
| 876033 | 738 | 757 | 18637 | 18656 | TAACGCACTTAACAATATCA | 31 | 2073 |
| 876057 | 874 | 893 | 21705 | 21724 | TCATAGCTTCCACCACAATA | 74 | 2074 |
| 876081 | 1342 | 1361 | 31058 | 31077 | CTTCCTTTGATGAAGAATGC | 39 | 2075 |
| 876105 | 1487 | 1506 | 35434 | 35453 | CCACTTTCAGCCACTTCAGG | 55 | 2076 |
| 876129 | 1865 | 1884 | 52779 | 52798 | GAATCCATAGCACCTTCCAG | 62 | 2077 |
| 876153 | 2532 | 2551 | 62153 | 62172 | TATACAAAATCCTCCAAGGC | 71 | 2078 |
| 876177 | 3198 | 3217 | 73734 | 73753 | TTCACATAGCTGTTGTGGAA | 76 | 2079 |
| 876201 | 3576 | 3595 | 77325 | 77344 | GAAACTCTCCACTTTAGGAC | 30 | 2080 |
| 876225 | 3857 | 3876 | 82202 | 82221 | AGATGCAGTTTCTCTACTCT | 43 | 81 |

TABLE 27-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876249 | 4320 | 4339 | 87224 | 87243 | GGGATGAGTACTATAGAATT | 44 | 2081 |
| 876273 | 4755 | 4774 | 92178 | 92197 | TTTCCGGTCAATTACGGGAA | 48 | 2082 |
| 876297 | 5077 | 5096 | 98225 | 98244 | CAATCTGGAATTTTTCTAGG | 67 | 2083 |
| 876321 | 5522 | 5541 | 100511 | 100530 | AGAGTTTCTCCTTCACCACA | 42 | 2084 |
| 876345 | 5875 | 5894 | N/A | N/A | AAAGCACCACAAGCTCTTGT | 18* | 2085 |
| 876369 | 6605 | 6624 | 129750 | 129769 | CAAATGCTTGCATTCCTGCT | 61 | 2086 |
| 876393 | 7263 | 7282 | 141624 | 141643 | TATTAGTCCACAGAGTTTTT | 108 | 2087 |
| 876417 | 8267 | 8286 | 146436 | 146455 | GAAGTTGTGTAAGATGCACT | 83 | 2088 |
| 876441 | 9084 | 9103 | 147253 | 147272 | GAGCTCTATTATATATGATT | 68 | 2089 |
| 876465 | N/A | N/A | 5078 | 5097 | TTATCTAGACCCTGCAGACC | 105 | 2090 |
| 876489 | N/A | N/A | 7262 | 7281 | GAAGGAAAAATACTACTTTT | 92 | 2091 |
| 876513 | N/A | N/A | 9756 | 9775 | AGTTTTAGAGGTTGTACCAA | 62 | 2092 |
| 876537 | N/A | N/A | 12772 | 12791 | GTAGTGGGCCGGTGGCCGTT | 77 | 2093 |
| 876561 | N/A | N/A | 15455 | 15474 | GCTTAATTGCTCTACAGTCC | 48 | 2094 |
| 876585 | N/A | N/A | 17472 | 17491 | ATCCTAATTGTCATCGAAAG | 99 | 2095 |
| 876609 | N/A | N/A | 19783 | 19802 | ATAAAATACATATTGTCTAA | 97 | 2096 |
| 876633 | N/A | N/A | 22053 | 22072 | TATAGAACTACATCTATAAA | 103 | 2097 |
| 876657 | N/A | N/A | 25245 | 25264 | TACAAGTTGCTACAATGGAG | 69 | 2098 |
| 876681 | N/A | N/A | 27636 | 27655 | ATGTCATGTCTGTGACACAC | 65 | 2099 |
| 876705 | N/A | N/A | 30159 | 30178 | TTATGATGTTTGAATGGCAC | 108 | 2100 |
| 876729 | N/A | N/A | 32279 | 32298 | ATTTTTTGCCCTCTAAAAAT | 109 | 2101 |
| 876753 | N/A | N/A | 33681 | 33700 | CCCAGCAAATGCTGCTGGTC | 96 | 2102 |
| 876777 | N/A | N/A | 36087 | 36106 | TGTGCCAATTATTTTTTTTA | 84 | 2103 |
| 876801 | N/A | N/A | 38237 | 38256 | AATACAGACATAGGTGTTTT | 86 | 2104 |
| 876825 | N/A | N/A | 40148 | 40167 | TTCTTAAAGAATTTCACATT | 111 | 2105 |
| 876849 | N/A | N/A | 42157 | 42176 | TTTCACTTCCCACATCCCCA | 91 | 2106 |
| 876873 | N/A | N/A | 45665 | 45684 | CACAGCACTTACTTGCTCTC | 45 | 2107 |
| 876897 | N/A | N/A | 48048 | 48067 | AATTCCAGGAACCACAAACT | 98 | 2108 |
| 876921 | N/A | N/A | 49975 | 49994 | TCAGTACAGGTTAATGATGA | 63 | 2109 |
| 876945 | N/A | N/A | 52174 | 52193 | CAGCTTCATGTAATAGGTTT | 44 | 2110 |
| 876969 | N/A | N/A | 55241 | 55260 | CCTCTAATATTACATATTAA | 111 | 2111 |
| 876993 | N/A | N/A | 57372 | 57391 | AATCCATAGGCAAGTGGGAT | 63 | 2112 |
| 877017 | N/A | N/A | 60530 | 60549 | ACCATTTCTCCTCCCGGCTC | 83 | 2113 |
| 877041 | N/A | N/A | 62800 | 62819 | AAAAGATAAAAATAGTGTCA | 136 | 2114 |
| 877065 | N/A | N/A | 65802 | 65821 | TTCCTTGACCCATCACTTTA | 87 | 2115 |

TABLE 27-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877089 | N/A | N/A | 67069 | 67088 | AAGGTTTCTTAAGTGGGATA | 60 | 2116 |
| 877113 | N/A | N/A | 70299 | 70318 | TGGCCTTCTGCTTAGAGACA | 36 | 2117 |
| 877137 | N/A | N/A | 72643 | 72662 | ACTACTTTTTATAACTAAAT | 150 | 2118 |
| 877161 | N/A | N/A | 73943 | 73962 | ATCAGATCTGTTTCCATTGC | 36 | 2119 |
| 877185 | N/A | N/A | 76014 | 76033 | TTTGAATTAATGATTTAACA | 128 | 2120 |
| 877209 | N/A | N/A | 78477 | 78496 | GAATTCCTGTTTATTGTCAT | 64 | 2121 |
| 877240 | N/A | N/A | 83109 | 83128 | AGCTGAAAAACAAGTAATAC | 112 | 2122 |
| 877264 | N/A | N/A | 85425 | 85444 | AATTAGAGAAAAAGACTAAA | 117 | 2123 |
| 877288 | N/A | N/A | 88395 | 88414 | AAGAAAAGAACAACTGTCCT | 75 | 2124 |
| 877312 | N/A | N/A | 90592 | 90611 | AGAGGACAAAAAATGATCTC | 86 | 2125 |
| 877336 | N/A | N/A | 92591 | 92610 | ACATTATGAATGTCATTTGA | 111 | 2126 |
| 877360 | N/A | N/A | 94819 | 94838 | TCCTGATTAACATTCTTTAA | 76 | 2127 |
| 877384 | N/A | N/A | 96218 | 96237 | ATCTGCTTCATTTCTCTTGG | 60 | 2128 |
| 877408 | N/A | N/A | 99066 | 99085 | GCAAATGATTTTACTGCTTA | 52 | 2129 |
| 877432 | N/A | N/A | 101696 | 101715 | CTTATTTGCCTCCCATATCC | 112 | 2130 |
| 877456 | N/A | N/A | 104260 | 104279 | TTTTTAAAGCCCTTCTCTAT | 110 | 2131 |
| 877480 | N/A | N/A | 106129 | 106148 | CTACACTTCCAACTTTGTGT | 97 | 2132 |
| 877504 | N/A | N/A | 108958 | 108977 | GAAACCTGTAAGAGACAGTC | 111 | 2133 |
| 877528 | N/A | N/A | 111524 | 111543 | GTGTGATGTTAAATTGATTC | 58 | 2134 |
| 877552 | N/A | N/A | 113529 | 113548 | CATTTTTATAGAAGGCAGAT | 68 | 2135 |
| 877576 | N/A | N/A | 116214 | 116233 | ACTCTCCTACTAGACTGTAA | 69 | 2136 |
| 877600 | N/A | N/A | 118773 | 118792 | ATTCTCTTCTTTTTATTCAG | 64 | 2137 |
| 877624 | N/A | N/A | 120519 | 120538 | ATTAGGCCCTGGGTTTCTGA | 87 | 2138 |
| 877648 | N/A | N/A | 122804 | 122823 | AAGATAAAACATATCCCTAA | 83 | 2139 |
| 877672 | N/A | N/A | 126378 | 126397 | TTTATGTAAATTTACTTGTC | 108 | 2140 |
| 877696 | N/A | N/A | 128758 | 128777 | TAAAGTCATTATAGTTGTAC | 83 | 2141 |
| 877720 | N/A | N/A | 133258 | 133277 | AAAAAACAGGCTTCACATTT | 127 | 2142 |
| 877744 | N/A | N/A | 137015 | 137034 | ATCTCTATAAGGAAACCTGA | 120 | 2143 |
| 877768 | N/A | N/A | 140412 | 140431 | TTTAACAATCATTAGTATAT | 88 | 2144 |
| 877792 | N/A | N/A | 141884 | 141903 | GAGAACATTCTTTGTAATAC | 66 | 2145 |
| 877816 | N/A | N/A | 144288 | 144307 | TGAGAAGAACTGGATGTTCA | 65 | 2146 |

TABLE 28

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 38 | 222 |
| 780619 | N/A | N/A | 81587 87844 | 81606 87863 | CATAGTGTTTGAAGGAATAG | 91 | 669 |
| 876010 | 304 | 323 | 3695 | 3714 | AGACGATCAACAGAGGCACA | 56 | 2147 |
| 876034 | 740 | 759 | 18639 | 18658 | GTTAACGCACTTAACAATAT | 46 | 2148 |
| 876058 | 875 | 894 | 21706 | 21725 | TTCATAGCTTCCACCACAAT | 72 | 2149 |
| 876082 | 1403 | 1422 | N/A | N/A | TTTCTGAAATTAACATTTTG | 88 | 2150 |
| 876106 | 1489 | 1508 | 35436 | 35455 | AGCCACTTTCAGCCACTTCA | 41 | 2151 |
| 876130 | 1867 | 1886 | 52781 | 52800 | CTGAATCCATAGCACCTTCC | 55 | 2152 |
| 876154 | 2537 | 2556 | 62158 | 62177 | TTTCCTATACAAAATCCTCC | 55 | 2153 |
| 876178 | 3212 | 3231 | N/A | N/A | AAACTCTTCAGAGTTTCACA | 108 | 2154 |
| 876202 | 3615 | 3634 | N/A | N/A | CAAGAAAGGCATAGCAGCAA | 77 | 2155 |
| 876226 | 3858 | 3877 | 82203 | 82222 | AAGATGCAGTTTCTCTACTC | 105 | 2156 |
| 876250 | 4383 | 4402 | 87287 | 87306 | TTCAGCCTGTCCCTTGCTGA | 91 | 2157 |
| 876274 | 4757 | 4776 | 92180 | 92199 | CGTTTCCGGTCAATTACGGG | 32 | 2158 |
| 876298 | 5151 | 5170 | 99157 | 99176 | GGGAAGCTCTATCACAGGCC | 31 | 2159 |
| 876322 | 5543 | 5562 | 100532 | 100551 | TATAATGCCCATTTCTTCAA | 99 | 2160 |
| 876346 | 5880 | 5899 | 113077 | 113096 | GTGGCAAAGCACCACAAGCT | 35 | 2161 |
| 876370 | 6606 | 6625 | 129751 | 129770 | CCAAATGCTTGCATTCCTGC | 73 | 2162 |
| 876394 | 7324 | 7343 | 142972 | 142991 | TTTTGTGTTTTGATTCCTTG | 65 | 2163 |
| 876418 | 8308 | 8327 | 146477 | 146496 | TTTCATTAGTACTTTTAATG | 120 | 2164 |
| 876442 | 9131 | 9150 | 147300 | 147319 | AAATTGCAAATACAAAGTAA | 137 | 2165 |
| 876466 | N/A | N/A | 5103 | 5122 | CTGGGTTGTCAAGTATAGCA | 81 | 2166 |
| 876490 | N/A | N/A | 7469 | 7488 | TATCATGTTAAATGGCATCT | 56 | 2167 |
| 876514 | N/A | N/A | 9834 | 9853 | CATATAATTTCTAAATTATG | 126 | 2168 |
| 876538 | N/A | N/A | 12900 | 12919 | GTTGATATATTAAAATATAG | 101 | 2169 |
| 876562 | N/A | N/A | 15482 | 15501 | ATTCTCATCTAGAATGCAAA | 93 | 2170 |
| 876586 | N/A | N/A | 17692 | 17711 | TACTCTACATTTATAGTCAT | 117 | 2171 |
| 876610 | N/A | N/A | 19865 | 19884 | GAAGGCTCACACCTTCAGAT | 72 | 2172 |
| 876634 | N/A | N/A | 22186 25650 25680 | 22205 25669 25699 | TATACAACATTTAAGTTGGA | 95 | 2173 |
| 876658 | N/A | N/A | 25710 25740 25804 25868 | 25729 25759 25823 25887 | CATCTGTGTATAAATATGTA | 85 | 2174 |
| 876682 | N/A | N/A | 27649 | 27668 | CTGATTCCCTCTCATGTCAT | 63 | 2175 |
| 876706 | N/A | N/A | 30201 | 30220 | ACTCCTTGCTACAGCTTGTA | 40 | 2176 |
| 876730 | N/A | N/A | 32460 | 32479 | GGTGAGATGAAAAGGAGGA | 64 | 2177 |

TABLE 28-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876754 | N/A | N/A | 33697 | 33716 | CTGTTTATCAAGTTCCCCCA | 61 | 2178 |
| 876778 | N/A | N/A | 36104 | 36123 | GTTTTCACTGCAACTTCTGT | 73 | 2179 |
| 876802 | N/A | N/A | 38252 | 38271 | TAAATGTGTTGGATGAATAC | 104 | 2180 |
| 876826 | N/A | N/A | 40280 | 40299 | TAGAGTTTCATATCCCTTTG | 58 | 2181 |
| 876850 | N/A | N/A | 42247 | 42266 | GAGTGGATTTATGTTACTGG | 35 | 2182 |
| 876874 | N/A | N/A | 45671 | 45690 | CCACATCACAGCACTTACTT | 60 | 2183 |
| 876898 | N/A | N/A | 48092 | 48111 | CATAGTCTGTAGGTAGTAGT | 54 | 2184 |
| 876922 | N/A | N/A | 50209 | 50228 | CGTTAATAATTTTCAAACAA | 145 | 2185 |
| 876946 | N/A | N/A | 52275 | 52294 | CTTGACCAGTAAAACGCAAT | 72 | 2186 |
| 876970 | N/A | N/A | 55359 | 55378 | CAGAGTCTGTCCTCTTCACT | 79 | 2187 |
| 876994 | N/A | N/A | 57490 | 57509 | GTTTATGTGATTTTAATTCA | 60 | 2188 |
| 877018 | N/A | N/A | 60774 | 60793 | AAGCACTACAGAGCTCTGAT | 75 | 2189 |
| 877042 | N/A | N/A | 63004 | 63023 | CTGACCAAAACTGGTGTTTT | 131 | 2190 |
| 877066 | N/A | N/A | 65861 | 65880 | TTTCCTGGAATATTAACCAT | 57 | 2191 |
| 877090 | N/A | N/A | 67071 | 67090 | AAAAGGTTTCTTAAGTGGGA | 70 | 2192 |
| 877114 | N/A | N/A | 70300 | 70319 | CTGGCCTTCTGCTTAGAGAC | 55 | 2193 |
| 877138 | N/A | N/A | 72664 | 72683 | ATATAATTTCTCATTAACCA | 79 | 2194 |
| 877162 | N/A | N/A | 73945 | 73964 | TAATCAGATCTGTTTCCATT | 52 | 2195 |
| 877186 | N/A | N/A | 76016 | 76035 | TATTTGAATTAATGATTTAA | 155 | 2196 |
| 877210 | N/A | N/A | 78507 | 78526 | TATTCTCTATGAAGGAAGAT | 72 | 2197 |
| 877241 | N/A | N/A | 83229 | 83248 | GACAAACAAATTATCAATTT | 70 | 2198 |
| 877265 | N/A | N/A | 86490 | 86509 | TCTTTTACATGTCACACTAT | 116 | 2199 |
| 877289 | N/A | N/A | 88459 | 88478 | TGTTGATATTTGCTTTCCGT | 45 | 2200 |
| 877313 | N/A | N/A | 90605 | 90624 | TGAAAATAAATGAGAGGAC | 107 | 2201 |
| 877337 | N/A | N/A | 92763 | 92782 | GAGAATTTTCATCTTTGAGA | 42 | 2202 |
| 877361 | N/A | N/A | 94894 | 94913 | TTATTTGTCCCCATACATGA | 102 | 2203 |
| 877385 | N/A | N/A | 96275 | 96294 | GTAGCAGAATTAATATTTTT | 59 | 2204 |
| 877409 | N/A | N/A | 99079 | 99098 | CCAACCTTGTTGAGCAAATG | 109 | 2205 |
| 877433 | N/A | N/A | 101710 | 101729 | CACCTGAAAACTGTCTTATT | 123 | 2206 |
| 877457 | N/A | N/A | 104825 | 104844 | ACTGGAATCAGAAATAGAAT | 119 | 2207 |
| 877481 | N/A | N/A | 106421 | 106440 | AATTAAGCTGTCCAAGCGAA | 150 | 2208 |
| 877505 | N/A | N/A | 109331 | 109350 | TGAATGTGAAGAATGCCCAT | 97 | 2209 |
| 877529 | N/A | N/A | 111530 | 111549 | TAGCTTGTGTGATGTTAAAT | 56 | 2210 |
| 877553 | N/A | N/A | 113596 | 113615 | GACTCATCTTTCCTCATTGG | 52 | 2211 |
| 877577 | N/A | N/A | 116216 | 116235 | TGACTCTCCTACTAGACTGT | 66 | 2212 |

TABLE 28-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877601 | N/A | N/A | 118774 | 118793 | CATTCTCTTCTTTTTATTCA | 60 | 2213 |
| 877625 | N/A | N/A | 120524 | 120543 | AAAAGATTAGGCCCTGGGTT | 71 | 2214 |
| 877649 | N/A | N/A | 122888 | 122907 | ATTATACATTTCCTTAGAAT | 142 | 2215 |
| 877673 | N/A | N/A | 126380 | 126399 | TATTTATGTAAATTTACTTG | 115 | 2216 |
| 877697 | N/A | N/A | 128864 | 128883 | ATTTTTACTGTGGACATAAA | 96 | 2217 |
| 877721 | N/A | N/A | 133263 | 133282 | GGTACAAAAAACAGGCTTCA | 55 | 2218 |
| 877745 | N/A | N/A | 137032 | 137051 | AACAAAGATGATGAACGATC | 134 | 2219 |
| 877769 | N/A | N/A | 140492 | 140511 | ATGAATGAACAACGAGGAAT | 145 | 2220 |
| 877793 | N/A | N/A | 141955 | 141974 | TGTGACAGAACTATGTCAAA | 87 | 2221 |
| 877817 | N/A | N/A | 144304 | 144323 | AATATAGCATAGTAATTGAG | 109 | 2222 |

TABLE 29

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 32 | 222 |
| 803627 | N/A | N/A | 81588 87845 | 81607 87864 | CCATAGTGTTTGAAGGAATA | 47 | 1789 |
| 876011 | 309 | 328 | 3700 | 3719 | GTCCAAGACGATCAACAGAG | 47 | 2223 |
| 876035 | 797 | 816 | 18696 | 18715 | AGGGAATGTAAACAATGCAG | 41 | 2224 |
| 876059 | 876 | 895 | 21707 | 21726 | TTTCATAGCTTCCACCACAA | 59 | 2225 |
| 876083 | 1408 | 1427 | N/A | N/A | GTATTTTTCTGAAATTAACA | 87 | 2226 |
| 876107 | 1490 | 1509 | 35437 | 35456 | CAGCCACTTTCAGCCACTTC | 49 | 2227 |
| 876131 | 1952 | 1971 | 52992 | 53011 | TTCTTTGTAATCAAGTATCC | 110 | 2228 |
| 876155 | 2558 | 2577 | 62179 | 62198 | CCAAGCCAAGAAGGTTCAAC | 51 | 2229 |
| 876179 | 3214 | 3233 | N/A | N/A | TCAAACTCTTCAGAGTTTCA | 97 | 2230 |
| 876203 | 3620 | 3639 | 80900 | 80919 | GGAGGCAAGAAAGGCATAGC | 46 | 2231 |
| 876227 | 3860 | 3879 | 82205 | 82224 | GAAAGATGCAGTTTCTCTAC | 59 | 2232 |
| 876251 | 4388 | 4407 | 87292 | 87311 | TCAACTTCAGCCTGTCCCTT | 105 | 2233 |
| 876275 | 4781 | 4800 | 92204 | 92223 | TTTTCTCTCACTAGTTGTAA | 48 | 2234 |
| 876299 | 5191 | 5210 | 99197 | 99216 | TTTCATATAGTCGGATGATA | 72 | 2235 |
| 876323 | 5566 | 5585 | 100555 | 100574 | GTTCTTCACCATCATTAAAA | 61 | 2236 |
| 876347 | 5979 | 5998 | 113176 | 113195 | AAGCAGGCGATCCAAGGAAC | 112 | 2237 |
| 876371 | 6645 | 6664 | 129790 | 129809 | AAATGAGAGCTGTCCTCTGT | 71 | 2238 |

TABLE 29-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876395 | 7354 | 7373 | 143002 | 143021 | AGAGGGTTTTCACTCTCCCA | 60 | 2239 |
| 876419 | 8313 | 8332 | 146482 | 146501 | TGTTTTTTCATTAGTACTTT | 91 | 2240 |
| 876443 | 9170 | 9189 | 147339 | 147358 | AATATGGTATTCATTTTTTT | 100 | 2241 |
| 876467 | N/A | N/A | 5161 | 5180 | ATGCTCAGGCTTGGGCAATT | 64 | 2242 |
| 876491 | N/A | N/A | 7474 | 7493 | TGGAATATCATGTTAAATGG | 65 | 2243 |
| 876515 | N/A | N/A | 10519 | 10538 | AAATAAATACTCAAGGCCAT | 88 | 2244 |
| 876539 | N/A | N/A | 13003 | 13022 | TATTTTCACCCAACTCCATA | 126 | 2245 |
| 876563 | N/A | N/A | 15487 | 15506 | TTTGCATTCTCATCTAGAAT | 108 | 2246 |
| 876587 | N/A | N/A | 17742 | 17761 | CCCCTGAGTCCTGGAGAACC | 99 | 2247 |
| 876611 | N/A | N/A | 19889 | 19908 | ATTGGGTTTTACTCTGCCTA | 41 | 2248 |
| 876635 | N/A | N/A | 22443 25651 25681 | 22462 25670 25700 | CCACATGCAAAAATATTTCT | 57 | 2249 |
| 876659 | N/A | N/A | 25711 25741 25805 25869 | 25730 25760 25824 25888 | ACATCTGTGTATAAATATGT | 61 | 2250 |
| 876683 | N/A | N/A | 27820 | 27839 | GATGAATATTCAATGGCATT | 36 | 2251 |
| 876707 | N/A | N/A | 30247 | 30266 | AAAACACAAAGGCTCACGGA | 73 | 2252 |
| 876731 | N/A | N/A | 32510 | 32529 | CTGTCAGTGCCCTGGCCACT | 42 | 2253 |
| 876755 | N/A | N/A | 33873 | 33892 | GTGGCTAGCTTCTAGCCAAG | 110 | 2254 |
| 876779 | N/A | N/A | 36197 | 36216 | TGTTATTATCATTCCTCTTT | 95 | 2255 |
| 876803 | N/A | N/A | 38423 | 38442 | AAAGCCTTTTATATATGCAT | 57 | 2256 |
| 876827 | N/A | N/A | 40345 | 40364 | CTTTTTAAGTCCTCCATATT | 65 | 2257 |
| 876851 | N/A | N/A | 42335 | 42354 | AGAAAACAGCAGCCATAGTA | 113 | 2258 |
| 876875 | N/A | N/A | 45683 | 45702 | AAGTGATTTCTCCACATCA | 62 | 2259 |
| 876899 | N/A | N/A | 48094 | 48113 | TGCATAGTCTGTAGGTAGTA | 23 | 2260 |
| 876923 | N/A | N/A | 50229 | 50248 | TGTTGTCACCCTTGTAAAAT | 85 | 2261 |
| 876947 | N/A | N/A | 52382 | 52401 | AATTCACTGAGGGTTAGAAT | 82 | 2262 |
| 876971 | N/A | N/A | 55369 | 55388 | AGCACATCCCCAGAGTCTGT | 76 | 2263 |
| 876995 | N/A | N/A | 57777 | 57796 | TAAATTGAAAGAATAGTAGA | 147 | 2264 |
| 877019 | N/A | N/A | 60820 | 60839 | AAATGCCCACCAGTCTCCAA | 93 | 2265 |
| 877043 | N/A | N/A | 63105 | 63124 | AAACCTTGATGTATAAAGGC | 115 | 2266 |
| 877067 | N/A | N/A | 65930 | 65949 | TACACAAGCCACGAAAGGAT | 72 | 2267 |
| 877091 | N/A | N/A | 67193 | 67212 | TCTTCATTGACACACCACAC | 52 | 2268 |

TABLE 29-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877115 | N/A | N/A | 70305 | 70324 | TCACTCTGGCCTTCTGCTTA | 76 | 2269 |
| 877139 | N/A | N/A | 72670 | 72689 | ATATCCATATAATTTCTCAT | 97 | 2270 |
| 877163 | N/A | N/A | 74025 | 74044 | GAATTAAATGATTAAAGTAT | 91 | 2271 |
| 877187 | N/A | N/A | 76071 | 76090 | TTTTGTAAATTATTTCCAGA | 80 | 2272 |
| 877211 | N/A | N/A | 78563 | 78582 | AAAAATTATTTTACTGAGTC | 158 | 2273 |
| 877242 | N/A | N/A | 83232 | 83251 | TGAGACAAACAAATTATCAA | 55 | 2274 |
| 877266 | N/A | N/A | 86571 | 86590 | CGCTGTTGAAGAAACCTAGT | 62 | 2275 |
| 877290 | N/A | N/A | 88524 | 88543 | GAGCCTGGAGGGAAAGACAC | 99 | 2276 |
| 877314 | N/A | N/A | 90620 | 90639 | GATCAAAGGCAAATATGAAA | 81 | 2277 |
| 877338 | N/A | N/A | 92815 | 92834 | ATTTCTAGCAAGGTAATATG | 82 | 2278 |
| 877362 | N/A | N/A | 94924 | 94943 | GTACAGGATGCAGCTACCTA | 56 | 2279 |
| 877386 | N/A | N/A | 96286 | 96305 | GTTACTAGAATGTAGCAGAA | 74 | 2280 |
| 877410 | N/A | N/A | 99359 | 99378 | CATCTCCCTAATTTCTCTAA | 92 | 2281 |
| 877434 | N/A | N/A | 101744 | 101763 | GTCATTTTATAAAATATGGC | 95 | 2282 |
| 877458 | N/A | N/A | 104836 | 104855 | AACTGTTACATACTGGAATC | 109 | 2283 |
| 877482 | N/A | N/A | 106589 | 106608 | ATGTGCAATTTAATATAATT | 89 | 2284 |
| 877506 | N/A | N/A | 109785 | 109804 | ACTTGTGGCCCACAGGTCGC | 87 | 2285 |
| 877530 | N/A | N/A | 111542 | 111561 | TGTTGAAATGTATAGCTTGT | 57 | 2286 |
| 877554 | N/A | N/A | 113660 | 113679 | GACATGTGAGATGGTCATGC | 55 | 2287 |
| 877578 | N/A | N/A | 116500 | 116519 | TCTTCATAGCTTAAAGTAAA | 79 | 2288 |
| 877602 | N/A | N/A | 118817 | 118836 | GAATCTACAAATCTAACTTT | 118 | 2289 |
| 877626 | N/A | N/A | 120677 | 120696 | AAAATTGGAGGCAGAGTTTA | 94 | 2290 |
| 877650 | N/A | N/A | 122924 | 122943 | ATATTGTTACAGATACAATG | 90 | 2291 |
| 877674 | N/A | N/A | 126393 | 126412 | CTCCATAATCCTATATTTAT | 83 | 2292 |
| 877698 | N/A | N/A | 128986 | 129005 | AAGTATGTCTAAGCTTTTTA | 59 | 2293 |
| 877722 | N/A | N/A | 133331 | 133350 | TTGAAATTTTCTTTGACCA | 36 | 2294 |
| 877746 | N/A | N/A | 137262 | 137281 | TTTCCATCTTAAATGATTAG | 86 | 2295 |
| 877770 | N/A | N/A | 140513 | 140532 | AATAGAAGAAGGCACTACAG | 111 | 2296 |
| 877794 | N/A | N/A | 142230 | 142249 | AAATAAAAATATAAAGTGGC | 154 | 2297 |
| 877818 | N/A | N/A | 144312 | 144331 | TGAGGCAAAATATAGCATAG | 93 | 2298 |

TABLE 30

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 43 | 222 |
| 780620 | N/A | N/A | 81590<br>87847 | 81609<br>87866 | AGCCATAGTGTTTGAAGGAA | 28 | 670 |
| 876013 | 339 | 358 | 3730 | 3749 | CTGCTGCACACTCGCGACTC | 55 | 2299 |
| 876037 | 821 | 840 | N/A | N/A | TCCACATTATTGCAAGGAAT | 51 | 2300 |
| 876061 | 930 | 949 | 21761 | 21780 | CCTATGGAGCAAACAGCAAC | 89 | 2301 |
| 876085 | 1455 | 1474 | 35402 | 35421 | CTTCTGCATTAACTCCAAAA | 49 | 2302 |
| 876109 | 1493 | 1512 | 35440 | 35459 | TTACAGCCACTTTCAGCCAC | 33 | 2303 |
| 876133 | 2042 | 2061 | 53082 | 53101 | TTAGTCTGTATTTCAGCAAC | 81 | 2304 |
| 876157 | 2626 | 2645 | 65464 | 65483 | TTCTTGCTAGTGTAGATGCT | 48 | 2305 |
| 876181 | 3216 | 3235 | N/A | N/A | TGTCAAACTCTTCAGAGTTT | 40 | 2306 |
| 876205 | 3703 | 3722 | N/A | N/A | AAGACCGCAAGTGTGGAAGA | 56 | 2307 |
| 876229 | 3929 | 3948 | 83924 | 83943 | CTGACATCCAGAGATGTCAG | 89 | 2308 |
| 876253 | 4432 | 4451 | N/A | N/A | AAGAAGCGCGAGCCTTTATA | 103 | 2309 |
| 876277 | 4877 | 4896 | 93338 | 93357 | AACTGCAGTGCTGGGTCTTG | 49 | 2310 |
| 876301 | 5194 | 5213 | 99200 | 99219 | GCATTTCATATAGTCGGATG | 22 | 2311 |
| 876325 | 5610 | 5629 | 100599 | 100618 | TTCCTCTGCTTTCTTCATCA | 56 | 2312 |
| 876349 | 6023 | 6042 | 113220 | 113239 | ATCCTGTGCTGTAGGGTTCT | 58 | 2313 |
| 876373 | 6689 | 6708 | N/A | N/A | TCAGCAACTTCCTCAGAAGT | 97 | 2314 |
| 876397 | 7400 | 7419 | 143048 | 143067 | TGGCCTCCTCCAGTTCCTAT | 73 | 2315 |
| 876421 | 8402 | 8421 | 146571 | 146590 | CTATTATGTCTAGGAAAGAC | 138 | 2316 |
| 876445 | N/A | N/A | 3487 | 3506 | CTCCTTAAGAGTCCGGGTTT | 103 | 2317 |
| 876469 | N/A | N/A | 5188 | 5207 | TGACACTCATAACTACTCCG | 68 | 2318 |
| 876493 | N/A | N/A | 7785 | 7804 | AATACAATTAAATTGGTAGT | 97 | 2319 |
| 876517 | N/A | N/A | 10746 | 10765 | AAAATCTACAACTTAACCAG | 107 | 2320 |
| 876541 | N/A | N/A | 13064 | 13083 | AAAAAGTTAAAAGCACTACT | 90 | 2321 |
| 876565 | N/A | N/A | 15570 | 15589 | CTTTAAGAATATCTCCTACA | 97 | 2322 |
| 876589 | N/A | N/A | 17908 | 17927 | AGTGATCAACATTCATTTTT | 58 | 2323 |
| 876613 | N/A | N/A | 19993 | 20012 | TTATTGTTCAGCCCCACCCA | 92 | 2324 |
| 876637 | N/A | N/A | 22715<br>25662<br>25692 | 22734<br>25681<br>25711 | CTATCCTGTGAACAATATTG | 74 | 2325 |
| 876661 | N/A | N/A | 25722<br>25752<br>25816<br>25880 | 25741<br>25771<br>25835<br>25899 | TATATTTATATACATCTGTG | 60 | 2326 |
| 876685 | N/A | N/A | 27910 | 27929 | AGTTAAGTGAAACATTAGCT | 98 | 2327 |
| 876709 | N/A | N/A | 30373 | 30392 | AACAAATAGACGGTCAAGAT | 58 | 2328 |
| 876733 | N/A | N/A | 32619 | 32638 | TCCCTGTCCAGACCTCTTTA | 83 | 2329 |

TABLE 30-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876757 | N/A | N/A | 33996 | 34015 | ATACTGCCAGAGCCTGAAAA | 81 | 2330 |
| 876781 | N/A | N/A | 36419 | 36438 | TTAGTTAGACTGATGTTAAA | 96 | 2331 |
| 876805 | N/A | N/A | 38456 | 38475 | GAAGAAATTATTTGTGCCTC | 56 | 2332 |
| 876829 | N/A | N/A | 40740 | 40759 | GAGGTCCTACTATTCAAATG | 49 | 2333 |
| 876853 | N/A | N/A | 42906 | 42925 | CTTCTCTTTTTCATACTCAG | 47 | 2334 |
| 876877 | N/A | N/A | 46382 | 46401 | AGAAGACTGGTTTTACTTTA | 78 | 2335 |
| 876901 | N/A | N/A | 48096 | 48115 | GGTGCATAGTCTGTAGGTAG | 28 | 2336 |
| 876925 | N/A | N/A | 50288 | 50307 | TTCACAGGTGTGTATTTCAC | 62 | 2337 |
| 876949 | N/A | N/A | 52569 | 52588 | AAATCAGTATCCTTGATTTT | 92 | 2338 |
| 876973 | N/A | N/A | 55733 | 55752 | GGAAAAAGAACTAATACCCT | 97 | 2339 |
| 876997 | N/A | N/A | 57805 | 57824 | AAAATCCTGTTGGGTAGAAA | 84 | 2340 |
| 877021 | N/A | N/A | 61061 | 61080 | CCCTTACAGCTAGCAAGCAA | 75 | 2341 |
| 877045 | N/A | N/A | 63132 | 63151 | AACTTTTGGAGCCTACTGAG | 79 | 2342 |
| 877069 | N/A | N/A | 66149 | 66168 | TCATTATATATTTCACCATA | 47 | 2343 |
| 877093 | N/A | N/A | 67368 | 67387 | TAAGAATAAGGTATAAATCA | 114 | 2344 |
| 877117 | N/A | N/A | 70856 | 70875 | ATTTTAAATTCCCCTACTCT | 87 | 2345 |
| 877141 | N/A | N/A | 72684 | 72703 | TGAGTGAAAAGCTATATCC | 52 | 2346 |
| 877165 | N/A | N/A | 74316 | 74335 | AGAGCTATCCTATCAACAAA | 83 | 2347 |
| 877189 | N/A | N/A | 76262 | 76281 | CTTACACACCTCTGGTAACT | 47 | 2348 |
| 877213 | N/A | N/A | 78841 | 78860 | TTTGTCTGTGCTCTGAACTT | 69 | 2349 |
| 877244 | N/A | N/A | 83428 | 83447 | CCTAATTGGAGTAATTTCTT | 89 | 2350 |
| 877268 | N/A | N/A | 86896 | 86915 | TCCATACAGTCTACCAGGTT | 50 | 2351 |
| 877292 | N/A | N/A | 89032 | 89051 | GGCATCAAAAACATTTTCTC | 23 | 2352 |
| 877316 | N/A | N/A | 90814 | 90833 | AGATGCCTGCTCTGCTAATG | 83 | 2353 |
| 877340 | N/A | N/A | 93050 | 93069 | TTCACACATAAGTAGAAATT | 106 | 2354 |
| 877364 | N/A | N/A | 95117 | 95136 | CTGTATAAGATATACCCATC | 35 | 2355 |
| 877388 | N/A | N/A | 96349 | 96368 | TGCTATTCATATAGAGTCTC | 27 | 2356 |
| 877412 | N/A | N/A | 99735 | 99754 | ATTTTGGAAACCAGTAACAC | 94 | 2357 |
| 877436 | N/A | N/A | 101885 | 101904 | TTTGAGTATGTCACCATGTA | 59 | 2358 |
| 877460 | N/A | N/A | 104875 | 104894 | ATTAGTTAGGATTGTTGGTA | 62 | 2359 |
| 877484 | N/A | N/A | 106759 | 106778 | AGGATTCTCAGATACAGTGT | 99 | 2360 |
| 877508 | N/A | N/A | 109926 | 109945 | AATCCTATGGTGAGTACCTC | 94 | 2361 |
| 877532 | N/A | N/A | 111674 | 111693 | GATCCAATGGCAACAACCCT | 97 | 2362 |
| 877556 | N/A | N/A | 113970 | 113989 | GGAATGTAAGGTGACTCTCA | 80 | 2363 |
| 877580 | N/A | N/A | 116687 | 116706 | AGACTAGCAAAATAGCTTTT | 97 | 2364 |

TABLE 30-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877604 | N/A | N/A | 118908 | 118927 | GTGGACCTGAATTTGATTTG | 58 | 2365 |
| 877628 | N/A | N/A | 120831 | 120850 | AGGAAGATTCATTAAACGGA | 76 | 2366 |
| 877652 | N/A | N/A | 123128 | 123147 | AAAGATGGAGCTCAGCAGTC | 89 | 2367 |
| 877676 | N/A | N/A | 126731 | 126750 | TTTGCCTTATAACTATTTTT | 92 | 2368 |
| 877700 | N/A | N/A | 129195 | 129214 | ATTCTGTTTTTGATCTGGAG | 78 | 2369 |
| 877724 | N/A | N/A | 133350 | 133369 | CCTTGCCCAATTCCATCCAT | 49 | 2370 |
| 877748 | N/A | N/A | 138041 | 138060 | TATTCTTGTTTGAAACTGGT | 46 | 2371 |
| 877772 | N/A | N/A | 140642 | 140661 | CCCTCACACTAGATTATGAG | 72 | 2372 |
| 877796 | N/A | N/A | 142347 | 142366 | AGAAAAACTGTCAGATGAAT | 116 | 2373 |
| 877820 | N/A | N/A | 144537 | 144556 | ATATTCTAGTGAAGAGACTA | 164 | 2374 |

TABLE 31

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 19 | 222 |
| 780621 | N/A | N/A | 81593 87850 | 81612 87869 | AAAAGCCATAGTGTTTGAAG | 35 | 671 |
| 876016 | 395 | 414 | 10419 | 10438 | CTTTGCATTGTACCTGGACA | 37 | 2375 |
| 876040 | 825 | 844 | N/A | N/A | GACTTCCACATTATTGCAAG | 36 | 2376 |
| 876064 | 1070 | 1089 | N/A | N/A | ATAGTCTCAGTGAGGAGGGC | 50 | 2377 |
| 876088 | 1468 | 1487 | 35415 | 35434 | GAGAATGTATATGCTTCTGC | 15 | 2378 |
| 876112 | 1539 | 1558 | 37588 | 37607 | TATATCCAGGGAAGTGTTGC | 71 | 2379 |
| 876136 | 2091 | 2110 | 56025 | 56044 | AGAAAAAGATGCTGACAATT | 86 | 2380 |
| 876160 | 2802 | 2821 | N/A | N/A | GCCTTCACTTCCTTCACTAT | 59 | 2381 |
| 876184 | 3223 | 3242 | 76357 | 76376 | CCAAATGTGTCAAACTCTTC | 39 | 2382 |
| 876208 | 3791 | 3810 | 82136 | 82155 | TTATGGCTAAATAAGAGTTC | 69 | 2383 |
| 876232 | 4012 | 4031 | 84007 | 84026 | GATGCAGTTCATCCAAAGGA | 35 | 2384 |
| 876256 | 4609 | 4628 | 88710 | 88729 | TTTTCCGAAGTTTTGCCAAA | 73 | 2385 |
| 876280 | 4967 | 4986 | 98115 | 98134 | GGGTGTTTTGGACAACCTTC | 37 | 2386 |
| 876304 | 5198 | 5217 | 99204 | 99223 | TAAGGCATTTCATATAGTCG | 48 | 2387 |
| 876328 | 5647 | 5666 | 101285 | 101304 | TGAGCCTTGGTTGATCTGGA | 21 | 2388 |
| 876352 | 6072 | 6091 | 118405 | 118424 | AATCATGGCTGAGTGGAGGT | 80 | 2389 |
| 876376 | 6738 | 6757 | 132448 | 132467 | TTCCTTTTCAACAGGAAGAT | 68 | 2390 |

TABLE 31-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876400 | 7495 | 7514 | N/A | N/A | TTCCTAGCTGTGCTGTCATC | 91 | 2391 |
| 876424 | 8539 | 8558 | 146708 | 146727 | GAAGCAGATTAGAAAACAAG | 86 | 2392 |
| 876448 | N/A | N/A | 3736 | 3755 | CTTTACCTGCTGCACACTCG | 63 | 2393 |
| 876472 | N/A | N/A | 5572 | 5591 | CCAGAGACTGGAAATGAAAG | 95 | 2394 |
| 876496 | N/A | N/A | 7851 | 7870 | TCCATTAATCTATTCAATTA | 78 | 2395 |
| 876520 | N/A | N/A | 10808 | 10827 | GTATCGATTCTATTATTAAA | 71 | 2396 |
| 876544 | N/A | N/A | 13929 | 13948 | AATCAAGCTACCCTAATCCT | 95 | 2397 |
| 876568 | N/A | N/A | 15860 | 15879 | TAAATGAGATAAACTCCCAG | 96 | 2398 |
| 876592 | N/A | N/A | 18000 | 18019 | TATTGGGCAACAACCTGAAA | 95 | 2399 |
| 876616 | N/A | N/A | 20210 | 20229 | TTTTAGCTGCTACTTTCTTG | 84 | 2400 |
| 876640 | N/A | N/A | 23220 | 23239 | GATACATAAAAAAGAGTAAA | 135 | 2401 |
| 876664 | N/A | N/A | 26207 | 26226 | AGATTAAAACATTATCAGAT | 84 | 2402 |
| 876688 | N/A | N/A | 28199 | 28218 | ACAACTGTTAGTTTCCTTGA | 55 | 2403 |
| 876712 | N/A | N/A | 30796 | 30815 | TTTCAAAAGCATATGCAGCA | 51 | 2404 |
| 876736 | N/A | N/A | 32794 | 32813 | CAGTCGAAATTTCACAAAGT | 66 | 2405 |
| 876760 | N/A | N/A | 34084 | 34103 | CTTAAGTACTGCTTTTAAAA | 69 | 2406 |
| 876784 | N/A | N/A | 36835 | 36854 | CCTCCCCTCCTTGGGTAACC | 93 | 2407 |
| 876808 | N/A | N/A | 38630 | 38649 | TCAGCCTTTCCTTCCACACT | 74 | 2408 |
| 876832 | N/A | N/A | 40891 | 40910 | TATTACACCTTAAGAAGATG | 106 | 2409 |
| 876856 | N/A | N/A | 42932 | 42951 | TTACACAATTTAAATGTAAT | 104 | 2410 |
| 876880 | N/A | N/A | 46724 | 46743 | TTAGTTCCAGAAAATACTAT | 71 | 2411 |
| 876904 | N/A | N/A | 48100 | 48119 | CCAGGGTGCATAGTCTGTAG | 44 | 2412 |
| 876928 | N/A | N/A | 50374 | 50393 | CTTCTACAAAAAAAAGTCAG | 87 | 2413 |
| 876952 | N/A | N/A | 52953 | 52972 | CACTGAATTTCTAGGAAAAT | 117 | 2414 |
| 876976 | N/A | N/A | 56393 | 56412 | AGAATACTGAGCAAAGACAA | 88 | 2415 |
| 877000 | N/A | N/A | 58100 | 58119 | GTCTAACACAACTCCACCCT | 95 | 2416 |
| 877024 | N/A | N/A | 61215 | 61234 | CCAAGATAACAGGTAATAGA | 60 | 2417 |
| 877048 | N/A | N/A | 63290 | 63309 | CTTCCAGACTGGTGATAGCA | 97 | 2418 |
| 877072 | N/A | N/A | 66302 | 66321 | AGACACAATATTTTGGAACA | 53 | 2419 |
| 877096 | N/A | N/A | 67753 | 67772 | GTTAGAAATTTTAAAAGACT | 86 | 2420 |
| 877120 | N/A | N/A | 71190 | 71209 | CTGGAATAGGGTCTAGCAGC | 37 | 2421 |
| 877144 | N/A | N/A | 72946 | 72965 | AAAAATGGGCCCCTATTAAA | 102 | 2422 |
| 877168 | N/A | N/A | 74838 | 74857 | TCCCTTAAATATACTTAAAA | 101 | 2423 |
| 877192 | N/A | N/A | 76677 | 76696 | GTTGTTAAAACTCATTGCTA | 38 | 2424 |
| 877216 | N/A | N/A | 79254 | 79273 | GACCACTTCTCAAACTATTA | 64 | 2425 |
| 877247 | N/A | N/A | 83670 | 83689 | CTCCCAAACAATCTATGTCA | 41 | 2426 |

TABLE 31-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877271 | N/A | N/A | 87005 | 87024 | AACCGATCAAAGTACCTAGC | 36 | 2427 |
| 877295 | N/A | N/A | 89220 | 89239 | CACAGTGACAAAATTCATGA | 50 | 2428 |
| 877319 | N/A | N/A | 91037 | 91056 | TATCTCTTAACCCAGAGAAT | 79 | 2429 |
| 877343 | N/A | N/A | 93174 | 93193 | CTGGGACTAGAAGCTGTGCA | 37 | 2430 |
| 877367 | N/A | N/A | 95220 | 95239 | ACTTAATTACTCCACAGAAT | 91 | 2431 |
| 877391 | N/A | N/A | 96751 | 96770 | TTCTCTCATTTGAATATCAG | 63 | 2432 |
| 877415 | N/A | N/A | 99949 | 99968 | TAAAAAGAGTTAAATCCCCT | 88 | 2433 |
| 877439 | N/A | N/A | 102322 | 102341 | TGTACAAAGTATATCTTTTT | 45 | 2434 |
| 877463 | N/A | N/A | 104975 | 104994 | ATTAGATTGTAAATATGTTA | 147 | 2435 |
| 877487 | N/A | N/A | 106908 | 106927 | CCAAGTTTCTACATTTCTAA | 64 | 2436 |
| 877511 | N/A | N/A | 110185 | 110204 | TTGTTGAGAAAAGCACAGAT | 94 | 2437 |
| 877535 | N/A | N/A | 111992 | 112011 | CATTGGCATTCATTCAATCC | 73 | 2438 |
| 877559 | N/A | N/A | 114281 | 114300 | GGTATCTGCAAGGAACCTCA | 87 | 2439 |
| 877583 | N/A | N/A | 117201 | 117220 | TTCAATTGTATGAGGGCCTG | 102 | 2440 |
| 877607 | N/A | N/A | 119250 | 119269 | TTACTTCCTGCTCAAACTGA | 99 | 2441 |
| 877631 | N/A | N/A | 121200 | 121219 | CAGGAGCTCTGCTCTCAGGC | 67 | 2442 |
| 877655 | N/A | N/A | 123752 | 123771 | GTACTACTCTTTCTTTCTTT | 62 | 2443 |
| 877679 | N/A | N/A | 126891 | 126910 | TTTTTTCTGATTTGATTTGT | 81 | 2444 |
| 877703 | N/A | N/A | 129329 | 129348 | GCATGCAATTCTATATTGCA | 100 | 2445 |
| 877727 | N/A | N/A | 133490 | 133509 | CCCACTTCCTTCCAACAAGG | 77 | 2446 |
| 877751 | N/A | N/A | 138235 | 138254 | GAAAGGTTATTGCCCAAGTT | 45 | 2447 |
| 877775 | N/A | N/A | 140814 | 140833 | GCCACATCAGCATGGCAAAC | 50 | 2448 |
| 877799 | N/A | N/A | 142668 | 142687 | TACCAAAGCTATCTAATTCA | 99 | 2449 |
| 877823 | N/A | N/A | 144798 | 144817 | TTAAACGAGGTAATGTGTGT | 60 | 2450 |

TABLE 32

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 37 | 222 |
| 803631 | N/A | N/A | 81594 87851 | 81613 87870 | AAAAAGCCATAGTGTTTGAA | 80 | 1793 |
| 876017 | 400 | 419 | 10424 | 10443 | TTAAGCTTTGCATTGTACCT | 40 | 2451 |
| 876041 | 827 | 846 | N/A | N/A | AGGACTTCCACATTATTGCA | 37 | 2452 |

TABLE 32-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876065 | 1084 | 1103 | 29345 | 29364 | CTTGATTTAAGAAAATAGTC | 83 | 2453 |
| 876089 | 1469 | 1488 | 35416 | 35435 | GGAGAATGTATATGCTTCTG | 27 | 2454 |
| 876113 | 1555 | 1574 | 37604 | 37623 | GGACCACTGCTGCCATTATA | 43 | 2455 |
| 876137 | 2130 | 2149 | 56064 | 56083 | GAATATTACTAAGTCAAATG | 84 | 2456 |
| 876161 | 2843 | 2862 | 71686 | 71705 | CCTACACTAATTGAATTAGA | 52 | 2457 |
| 876185 | 3224 | 3243 | 76358 | 76377 | TCCAAATGTGTCAAACTCTT | 31 | 2458 |
| 876209 | 3796 | 3815 | 82141 | 82160 | TCTGATTATGGCTAAATAAG | 41 | 2459 |
| 876233 | 4017 | 4036 | 84012 | 84031 | GTTAAGATGCAGTTCATCCA | 55 | 2460 |
| 876257 | 4621 | 4640 | 88722 | 88741 | CGTTTATGATGGTTTTCCGA | 79 | 2461 |
| 876281 | 5042 | 5061 | 98190 | 98209 | GACATGTAGTTCTTTGGAAA | 44 | 2462 |
| 876305 | 5199 | 5218 | 99205 | 99224 | ATAAGGCATTTCATATAGTC | 74 | 2463 |
| 876329 | 5648 | 5667 | 101286 | 101305 | GTGAGCCTTGGTTGATCTGG | 55 | 2464 |
| 876353 | 6093 | 6112 | 118426 | 118445 | GGGTTTCAGGTCTCGGTATA | 72 | 2465 |
| 876377 | 6777 | 6796 | 132487 | 132506 | CAGGAGAGTACCAGACTGTG | 71 | 2466 |
| 876401 | 7516 | 7535 | 145119 | 145138 | CCAGCATGACATTTTTAAGG | 37 | 2467 |
| 876425 | 8551 | 8570 | 146720 | 146739 | AAGCATTAGAATGAAGCAGA | 56 | 2468 |
| 876449 | N/A | N/A | 3738 | 3757 | GCCTTTACCTGCTGCACACT | 69 | 2469 |
| 876473 | N/A | N/A | 5806 | 5825 | CTCTAAATTAATTACTTAAC | 97 | 2470 |
| 876497 | N/A | N/A | 7895 | 7914 | TGATTAAATAGAATCTCTGG | 89 | 2471 |
| 876521 | N/A | N/A | 10905 | 10924 | AAATGTACTATTTAAAGACA | 84 | 2472 |
| 876545 | N/A | N/A | 13978 | 13997 | GGCTGTCCCATCACTAGGTC | 40 | 2473 |
| 876569 | N/A | N/A | 15888 | 15907 | GTTAGACTTATCAAGCTCTA | 41 | 2474 |
| 876593 | N/A | N/A | 18037 | 18056 | TTTGATCAAGCCAGTAAGTT | 47 | 2475 |
| 876617 | N/A | N/A | 20433 | 20452 | TGTTTAAAAAAGGCTGTTT | 88 | 2476 |
| 876641 | N/A | N/A | 23260 | 23279 | ATTATCTTAGGGAAAGGACA | 83 | 2477 |
| 876665 | N/A | N/A | 26250 | 26269 | TGTGCTACTCTGACACCTGG | 41 | 2478 |
| 876689 | N/A | N/A | 28210 | 28229 | GTATATTTGTCACAACTGTT | 52 | 2479 |
| 876713 | N/A | N/A | 30800 | 30819 | GCTTTTTCAAAAGCATATGC | 35 | 2480 |
| 876737 | N/A | N/A | 32826 | 32845 | TGTAACCAGTCCTCAGACAC | 73 | 2481 |
| 876761 | N/A | N/A | 34100 | 34119 | ACATAAAAAGTTTAACTTA | 105 | 2482 |
| 876785 | N/A | N/A | 36869 | 36888 | AAAGTCCCAGTTTAAACACA | 73 | 2483 |
| 876809 | N/A | N/A | 38643 | 38662 | TTTTCTTTGGGCCTCAGCCT | 110 | 2484 |
| 876833 | N/A | N/A | 40900 | 40919 | GAGGCTGCCTATTACACCTT | 60 | 2485 |
| 876857 | N/A | N/A | 42939 | 42958 | TTTTGCATTACACAATTTAA | 74 | 2486 |
| 876881 | N/A | N/A | 46818 | 46837 | TGGAGTTAGGCCATATGAAT | 45 | 2487 |

TABLE 32-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876905 | N/A | N/A | 48102 | 48121 | GTCCAGGGTGCATAGTCTGT | 28 | 2488 |
| 876929 | N/A | N/A | 50419 | 50438 | TACCAGTATCTTAAATTCAG | 93 | 2489 |
| 876953 | N/A | N/A | 53117 | 53136 | AGTTCCCAAATTCTTTCCAA | 86 | 2490 |
| 876977 | N/A | N/A | 56418 | 56437 | AATGGCAGGGCTCTTACATT | 45 | 2491 |
| 877001 | N/A | N/A | 58449 | 58468 | GAGCCACCCTGCATGAAGCT | 74 | 2492 |
| 877025 | N/A | N/A | 61291 | 61310 | GCACTGCATGCTGGCCCTAC | 122 | 2493 |
| 877049 | N/A | N/A | 63355 | 63374 | TTATATAATGTGGTGAATGG | 124 | 2494 |
| 877073 | N/A | N/A | 66309 | 66328 | TGACTTGAGACACAATATTT | 52 | 2495 |
| 877097 | N/A | N/A | 67953 | 67972 | ATTGTGAACAAAGAAAATCC | 110 | 2496 |
| 877121 | N/A | N/A | 71306 | 71325 | CAAATCAATCAACGGTTACA | 60 | 2497 |
| 877145 | N/A | N/A | 73081 | 73100 | TAATTGGAGGAAATTCAACC | 113 | 2498 |
| 877169 | N/A | N/A | 74847 | 74866 | GAAAAAACATCCCTTAAATA | 119 | 2499 |
| 877193 | N/A | N/A | 77052 | 77071 | TAAAGTTGTAATATTCATT | 88 | 2500 |
| 877217 | N/A | N/A | 79613 | 79632 | TTCAGAGTCTTGAGTTTCAT | 51 | 2501 |
| 877248 | N/A | N/A | 84372 | 84391 | TCTTTAGATTGTGTAATTGG | 43 | 2502 |
| 877272 | N/A | N/A | 87027 | 87046 | CACTTTTAGCATATTTGTCA | 80 | 2503 |
| 877296 | N/A | N/A | 89765 | 89784 | AAATGGAACAGAACTAAGCT | 100 | 2504 |
| 877320 | N/A | N/A | 91067 | 91086 | CAAATGGTTACTCAAGAGAC | 68 | 2505 |
| 877344 | N/A | N/A | 93198 | 93217 | ATTTCAGCATAGCTAGTGAC | 102 | 2506 |
| 877368 | N/A | N/A | 95236 | 95255 | CTTTCATGGAGTTTCAACTT | 100 | 2507 |
| 877392 | N/A | N/A | 96941 | 96960 | TCCCATGTTGTGTACTTTAT | 36 | 2508 |
| 877416 | N/A | N/A | 100066 | 100085 | TGCACACAACACAAGTGATT | 64 | 2509 |
| 877440 | N/A | N/A | 102409 | 102428 | TCTCCATTCCACAACATATA | 98 | 2510 |
| 877464 | N/A | N/A | 105094 | 105113 | ATGGAAAGCCTCTACCTATT | 111 | 2511 |
| 877488 | N/A | N/A | 106972 | 106991 | TGGAGGCAGCTAGGAGTCTG | 100 | 2512 |
| 877512 | N/A | N/A | 110233 | 110252 | CAAAGGCCTAAAGCCAATTA | 128 | 2513 |
| 877536 | N/A | N/A | 112047 | 112066 | AGGCCTTCCAGACCTTCTCG | 108 | 2514 |
| 877560 | N/A | N/A | 114295 | 114314 | GATATAAAGCCTCTGGTATC | 98 | 2515 |
| 877584 | N/A | N/A | 117209 | 117228 | CCTGAACTTTCAATTGTATG | 73 | 2516 |
| 877608 | N/A | N/A | 119259 | 119278 | CTAAATGATTTACTTCCTGC | 77 | 2517 |
| 877632 | N/A | N/A | 121414 | 121433 | TGCCATAGGACCCAGAATTA | 146 | 2518 |
| 877656 | N/A | N/A | 124006 | 124025 | CAGAAAGTTATCAAATATGT | 90 | 2519 |
| 877680 | N/A | N/A | 126954 | 126973 | AGCTCGAAAAAGAAATTGCA | 80 | 2520 |
| 877704 | N/A | N/A | 129393 | 129412 | TAACTTGAAAAGAAAATCTC | 105 | 2521 |
| 877728 | N/A | N/A | 133512 | 133531 | CCTAATCACATTGACAACTG | 101 | 2522 |
| 877752 | N/A | N/A | 138252 | 138271 | GAGATGACTGAAGATGTGAA | 73 | 2523 |

TABLE 32-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877776 | N/A | N/A | 140877 | 140896 | TTTCCCTTTCAACCTAAGAC | 99 | 2524 |
| 877800 | N/A | N/A | 142754 | 142773 | CTTTACTTGAAGCATAAATT | 93 | 2525 |
| 877824 | N/A | N/A | 144813 | 144832 | CCCAAAGTTACAATGTTAAA | 72 | 2526 |

TABLE 33

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 38 | 222 |
| 780622 | N/A | N/A | 81596 87853 | 81615 87872 | CTAAAAGCCATAGTGTTTG | 53 | 672 |
| 876019 | 486 | 505 | 13752 | 13771 | ACTGGCATTATGAACTGTTA | 37 | 2527 |
| 876043 | 829 | 848 | 21660 | 21679 | TGAGGACTTCCACATTATTG | 47 | 2528 |
| 876067 | 1156 | 1175 | 29417 | 29436 | CTTCCAGCCAAAACAATTTA | 99 | 2529 |
| 876091 | 1472 | 1491 | 35419 | 35438 | TCAGGAGAATGTATATGCTT | 47 | 2530 |
| 876115 | 1613 | 1632 | 37662 | 37681 | GCCTCCAGCTGCACTGGTAA | 58 | 2531 |
| 876139 | 2223 | 2242 | 56231 | 56250 | GTAATCATCCATAGCTACTT | 31 | 2532 |
| 876163 | 2867 | 2886 | 71710 | 71729 | AATACGGCATCTCGGTAAAA | 77 | 2533 |
| 876187 | 3227 | 3246 | 76361 | 76380 | AAGTCCAAATGTGTCAAACT | 44 | 2534 |
| 876211 | 3799 | 3818 | 82144 | 82163 | TGATCTGATTATGGCTAAAT | 49 | 2535 |
| 876235 | 4053 | 4072 | 84048 | 84067 | GTCTTTGGCTTTACATCCTA | 48 | 2536 |
| 876259 | 4697 | 4716 | 92120 | 92139 | TTTTCAAGTTCTACATAGCA | 59 | 2537 |
| 876283 | 5045 | 5064 | 98193 | 98212 | TGTGACATGTAGTTCTTTGG | 38 | 2538 |
| 876307 | 5251 | 5270 | 99257 | 99276 | GTGAAATCTCAAGTAATCGA | 74 | 2539 |
| 876331 | 5651 | 5670 | 101289 | 101308 | ATGGTGAGCCTTGGTTGATC | 57 | 2540 |
| 876355 | 6160 | 6179 | 118493 | 118512 | TGCCGTAGTCAGCAATCTTT | 86 | 2541 |
| 876379 | 6821 | 6840 | 132531 | 132550 | TTTTCTAGGGTATGTCTCTT | 88 | 2542 |
| 876403 | 7579 | 7598 | N/A | N/A | AGCAAGATTGTATCTCTTTC | 78 | 2543 |
| 876427 | 8599 | 8618 | 146768 | 146787 | AATGATGTAGGATCTGCAGC | 65 | 2544 |
| 876451 | N/A | N/A | 3760 | 3779 | AATGAGTTGAAGTGAAAACA | 130 | 2545 |
| 876475 | N/A | N/A | 6080 | 6099 | TATCAACAGATTAACAAAGA | 111 | 2546 |
| 876499 | N/A | N/A | 7975 | 7994 | TTGGTGAAGCAACAGTATCA | 42 | 2547 |
| 876523 | N/A | N/A | 10994 | 11013 | TACAGATGTGCTGAAAGTTA | 112 | 2548 |
| 876547 | N/A | N/A | 14093 | 14112 | TAAAACCAATGTATTGAATG | 84 | 2549 |

TABLE 33-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876571 | N/A | N/A | 16270 | 16289 | ATAACTGTGTTCTACTTTTC | 82 | 2550 |
| 876595 | N/A | N/A | 18575 | 18594 | AGACTTAAAAATGAAAGACA | 106 | 2551 |
| 876619 | N/A | N/A | 20584 | 20603 | AAAATATAAGTCTTAGGGAC | 89 | 2552 |
| 876643 | N/A | N/A | 23603 | 23622 | GTGCCTAAAAAGAATGTAT | 49 | 2553 |
| 876667 | N/A | N/A | 26400 | 26419 | AGTAGCATTTCCCTGATCAC | 49 | 2554 |
| 876691 | N/A | N/A | 29101 | 29120 | AAAAAAAACCTAATAGACG | 118 | 2555 |
| 876715 | N/A | N/A | 30926 | 30945 | AAATATCTCTAACAACAATT | 88 | 2556 |
| 876739 | N/A | N/A | 33082 | 33101 | GTAGCCATTTTTTCTAAAAA | 51 | 2557 |
| 876763 | N/A | N/A | 34583 | 34602 | TAATGATTAAGGAATAATTT | 124 | 2558 |
| 876787 | N/A | N/A | 36936 | 36955 | ATCAGAACCATGTTCTCACT | 95 | 2559 |
| 876811 | N/A | N/A | 38784 | 38803 | CTATCATCCTCTGCACCACA | 96 | 2560 |
| 876835 | N/A | N/A | 41037 | 41056 | CCCTCCTCCAACTTTCAGTC | 89 | 2561 |
| 876859 | N/A | N/A | 43022 | 43041 | TATGTCTTTATTCTTAACAT | 67 | 2562 |
| 876883 | N/A | N/A | 47044 | 47063 | TATTCAGCTTTCTTTGCTTT | 93 | 2563 |
| 876907 | N/A | N/A | 48276 | 48295 | GATACTTTTAAATCTAATAG | 116 | 2564 |
| 876931 | N/A | N/A | 50755 | 50774 | CTTCTTTTACCTCCAAACCC | 81 | 2565 |
| 876955 | N/A | N/A | 53306 | 53325 | AATGGTGAATAACCATGCTG | 76 | 2566 |
| 876979 | N/A | N/A | 56534 | 56553 | CCTAAAGGACCCTATTACTT | 99 | 2567 |
| 877003 | N/A | N/A | 59266 | 59285 | CAGTGCCCAGGTGGTAATGA | 73 | 2568 |
| 877027 | N/A | N/A | 61418 | 61437 | TCTCTCAGTCTTCAACCTTC | 93 | 2569 |
| 877051 | N/A | N/A | 63467 | 63486 | ATGTGCAAAACACTAGTATC | 74 | 2570 |
| 877075 | N/A | N/A | 66552 | 66571 | ATTGTCAGGAAGCAAATGAT | 60 | 2571 |
| 877099 | N/A | N/A | 68281 | 68300 | TGAAAATATGAATACCTCA | 100 | 2572 |
| 877123 | N/A | N/A | 71767 | 71786 | ACAATTTAACTTACCAAGGA | 152 | 2573 |
| 877147 | N/A | N/A | 73109 | 73128 | GATGAAACTGGCACCAAGAA | 100 | 2574 |
| 877171 | N/A | N/A | 74897 | 74916 | GTGGGTCACCTTTCTTTCTT | 43 | 2575 |
| 877195 | N/A | N/A | 77106 | 77125 | ATCAAAGAGGACTCATTAAT | 116 | 2576 |
| 877219 | N/A | N/A | 79825 | 79844 | CAAATCTACCGTTTCTAGGA | 84 | 2577 |
| 877250 | N/A | N/A | 84428 | 84447 | GTTAACTAGTTGCTATATGA | 54 | 2578 |
| 877274 | N/A | N/A | 87487 | 87506 | ACTCGGAAAGTTTCCCAATT | 63 | 2579 |
| 877298 | N/A | N/A | 89963 | 89982 | GAATAGGAAAGTCTACAAAT | 72 | 2580 |
| 877322 | N/A | N/A | 91301 | 91320 | TAATATCCAGAGTGCCGTTA | 52 | 2581 |
| 877346 | N/A | N/A | 93489 | 93508 | CTTAACTAAACCCAAATTCT | 116 | 2582 |
| 877370 | N/A | N/A | 95491 | 95510 | TCAGACAAGTTGCTCTTGGT | 31 | 2583 |
| 877394 | N/A | N/A | 97213 | 97232 | AAGAGGTTTGTATTTAATTT | 68 | 2584 |

TABLE 33-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877418 | N/A | N/A | 100658 | 100677 | CACTTCATAAGTATTGAAGG | 53 | 2585 |
| 877442 | N/A | N/A | 102464 | 102483 | AATAGTTCTCACCACATAAA | 101 | 2586 |
| 877466 | N/A | N/A | 105201 | 105220 | TCTCATATAGTGCCTTGAAA | 65 | 2587 |
| 877490 | N/A | N/A | 107094 | 107113 | AGTCATGTTCAATAAAAATA | 124 | 2588 |
| 877514 | N/A | N/A | 110289 | 110308 | AGGTGGGAATATTCTAAGTA | 48 | 2589 |
| 877538 | N/A | N/A | 112191 | 112210 | CTACAAAAGTTTACCGAGGA | 67 | 2590 |
| 877562 | N/A | N/A | 114372 | 114391 | GAAAGATTCAGATAATCCTT | 130 | 2591 |
| 877586 | N/A | N/A | 117360 | 117379 | ATAATTTCTCACAAGACTTA | 85 | 2592 |
| 877610 | N/A | N/A | 119341 | 119360 | GTAATTTTACTTACAAATAA | 101 | 2593 |
| 877634 | N/A | N/A | 121663 | 121682 | TAAGAGAAATTTATGAATTA | 108 | 2594 |
| 877658 | N/A | N/A | 124138 | 124157 | AACCTAAAGACATCCAATCA | 86 | 2595 |
| 877682 | N/A | N/A | 127082 | 127101 | CAACAGGACCAAATAGGAAT | 78 | 2596 |
| 877706 | N/A | N/A | 130011 | 130030 | GGGACCCTGAGCTAAGACAT | 99 | 2597 |
| 877730 | N/A | N/A | 134153 | 134172 | AAATGGCCTTAATGTTCTCC | 71 | 2598 |
| 877754 | N/A | N/A | 138408 | 138427 | TTTGTGACTCAAAGCTAATA | 76 | 2599 |
| 877778 | N/A | N/A | 140926 | 140945 | CCATTTTCCCCTTTTAAACA | 79 | 2600 |
| 877802 | N/A | N/A | 143250 | 143269 | AAGACCATCCATATGACACT | 89 | 2601 |
| 877826 | N/A | N/A | 144863 | 144882 | AACAGCTTAACCTTTCTATA | 88 | 2602 |

TABLE 34

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 44 | 222 |
| 876020 | 528 | 547 | 13794 | 13813 | GAGGAGATCTAAGGTCTTCA | 37 | 2603 |
| 876044 | 830 | 849 | 21661 | 21680 | ATGAGGACTTCCACATTATT | 110 | 2604 |
| 876068 | 1161 | 1180 | 29422 | 29441 | ACAGGCTTCCAGCCAAAACA | 15 | 2605 |
| 876092 | 1473 | 1492 | 35420 | 35439 | TTCAGGAGAATGTATATGCT | 93 | 2606 |
| 876116 | 1637 | 1656 | 37686 | 37705 | ATAAAATGTAAAATAGCTCG | 56 | 2607 |
| 876140 | 2262 | 2281 | 56270 | 56289 | ATTCTGATCACACGCTCTCT | 46 | 2608 |
| 876164 | 2869 | 2888 | 71712 | 71731 | GTAATACGGCATCTCGGTAA | 84 | 2609 |
| 876188 | 3228 | 3247 | 76362 | 76381 | CAAGTCCAAATGTGTCAAAC | 97 | 2610 |
| 876212 | 3800 | 3819 | 82145 | 82164 | CTGATCTGATTATGGCTAAA | 66 | 2611 |
| 876236 | 4144 | 4163 | 86639 | 86658 | TTTTACCACTCCCAGTATTT | 76 | 2612 |

TABLE 34-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876260 | 4725 | 4744 | 92148 | 92167 | CACATTTTTACGCTCCGATA | 49 | 2613 |
| 876284 | 5046 | 5065 | 98194 | 98213 | CTGTGACATGTAGTTCTTTG | 65 | 2614 |
| 876308 | 5338 | 5357 | 100190 | 100209 | CTTCAGGAGACCAATTTAAG | 75 | 2615 |
| 876332 | 5652 | 5671 | 101290 | 101309 | AATGGTGAGCCTTGGTTGAT | 126 | 2616 |
| 876356 | 6204 | 6223 | 118537 | 118556 | GCCCTCTGATGTTTTTATCC | 31 | 2617 |
| 876380 | 6826 | 6845 | 132536 | 132555 | TCATCTTTTCTAGGGTATGT | 38 | 2618 |
| 876404 | 7660 | 7679 | 145829 | 145848 | TTTCAGCTAATTCTTTTCTC | 100 | 2619 |
| 876428 | 8683 | 8702 | 146852 | 146871 | GAAAAGTGTTAGATATTTAT | 34 | 2620 |
| 876452 | N/A | N/A | 3761 | 3780 | GAATGAGTTGAAGTGAAAAC | 53 | 2621 |
| 876476 | N/A | N/A | 6208 | 6227 | ATCCAGTAATCTCATCGCTG | 50 | 2622 |
| 876500 | N/A | N/A | 8095 | 8114 | ATTCTGAACAGCTTCTGGTG | 102 | 2623 |
| 876524 | N/A | N/A | 11128 | 11147 | TTTTCCTGGAAACACATTCT | 71 | 2624 |
| 876548 | N/A | N/A | 14203 | 14222 | AAGGGCAGGAATGACCACTA | 127 | 2625 |
| 876572 | N/A | N/A | 16432 | 16451 | GCAATTGAAGAAAGTCTACT | 81 | 2626 |
| 876596 | N/A | N/A | 18903 | 18922 | GTTTCTCCAGCACCAAGCCC | 126 | 2627 |
| 876620 | N/A | N/A | 20690 | 20709 | TTCCAGAAGGGCAACCAATG | 89 | 2628 |
| 876644 | N/A | N/A | 23667 | 23686 | GAACTGGACAAGTTAATCCT | 57 | 2629 |
| 876668 | N/A | N/A | 26426 | 26445 | TGCTGTTCTAGACAATTTGG | 73 | 2630 |
| 876692 | N/A | N/A | 29204 | 29223 | AAGCCTTGGTCAATTATAAA | 131 | 2631 |
| 876716 | N/A | N/A | 30940 | 30959 | CACTTGCCATTATCAAATAT | 100 | 2632 |
| 876740 | N/A | N/A | 33139 | 33158 | TGTATGCAACCTTGGGACCT | 56 | 2633 |
| 876764 | N/A | N/A | 34714 | 34733 | TGGAAAGCATTTACATAGAA | 97 | 2634 |
| 876788 | N/A | N/A | 36957 | 36976 | TGTTAACTGAAACTTGTGCA | 44 | 2635 |
| 876812 | N/A | N/A | 38785 | 38804 | TCTATCATCCTCTGCACCAC | 52 | 2636 |
| 876836 | N/A | N/A | 41061 | 41080 | TAAGGAAGGCAGCCTTGATA | 42 | 2637 |
| 876860 | N/A | N/A | 43045 | 43064 | TTTATAAAAATGTTCACACT | 31 | 2638 |
| 876884 | N/A | N/A | 47090 | 47109 | AATCTCATCCATCTGTAATT | 80 | 2639 |
| 876908 | N/A | N/A | 48315 | 48334 | TACTCTGATTTCCTCATCTT | 66 | 2640 |
| 876932 | N/A | N/A | 50766 | 50785 | CTTTACAATGTCTTCTTTTA | 103 | 2641 |
| 876956 | N/A | N/A | 53309 | 53328 | ATAAATGGTGAATAACCATG | 140 | 2642 |
| 876980 | N/A | N/A | 56543 | 56562 | TGGATAACACCTAAAGGACC | 39 | 2643 |
| 877004 | N/A | N/A | 59276 | 59295 | GTATTTGGAGCAGTGCCCAG | 52 | 2644 |
| 877028 | N/A | N/A | 61596 | 61615 | GTACCTTAACACAGTAAATA | 104 | 2645 |
| 877052 | N/A | N/A | 63476 | 63495 | TAATCTACTATGTGCAAAAC | 53 | 2646 |
| 877076 | N/A | N/A | 66557 | 66576 | TCTACATTGTCAGGAAGCAA | 51 | 2647 |

TABLE 34-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877100 | N/A | N/A | 68445 | 68464 | ATCTCTCACAGATGCAAAAT | 74 | 2648 |
| 877124 | N/A | N/A | 71781 | 71800 | ATAATCACAATTGCACAATT | 107 | 2649 |
| 877148 | N/A | N/A | 73144 | 73163 | GAATCATTAGGTAAATATAT | 107 | 2650 |
| 877172 | N/A | N/A | 74948 | 74967 | AGTGGAGAAGAGAGAAAGAC | 63 | 2651 |
| 877196 | N/A | N/A | 77137 | 77156 | TATCAAAAACAATTTGCTTT | 143 | 2652 |
| 877220 | N/A | N/A | 79895 | 79914 | ACAGTCTCTTTTCTTATCTG | 74 | 2653 |
| 877232 | N/A | N/A | 81609 | 81628 | TTTAGTGTCAATTCTAAAAA | 101 | 2654 |
| 877251 | N/A | N/A | 84464 | 84483 | CAGTAGCTATAATGCTTTAA | 66 | 2655 |
| 877275 | N/A | N/A | 87627 | 87646 | TTTAGATTTCATTTAAGAAA | 69 | 2656 |
| 877299 | N/A | N/A | 89982 | 90001 | AATTACATGTCCAACAAGAG | 35 | 2657 |
| 877323 | N/A | N/A | 91362 | 91381 | AATAAAAGTATCTTCCAAAC | 76 | 2658 |
| 877347 | N/A | N/A | 93509 | 93528 | AAATTCACAAAAGTTTCTGC | 90 | 2659 |
| 877371 | N/A | N/A | 95698 | 95717 | TTTCATATCTCTTTTATCAT | 77 | 2660 |
| 877395 | N/A | N/A | 97239 | 97258 | TTTTGCTTTGTCAAATTCAC | 41 | 2661 |
| 877419 | N/A | N/A | 100725 | 100744 | CTATAATTGAATATACTATT | 33 | 2662 |
| 877443 | N/A | N/A | 102592 | 102611 | ATTAAATCAATCTAATGCAT | 122 | 2663 |
| 877467 | N/A | N/A | 105313 | 105332 | CTCAATCCCCAAGGAGTTTG | 61 | 2664 |
| 877491 | N/A | N/A | 107115 | 107134 | CTTTCACCCTGAACACACAG | 72 | 2665 |
| 877515 | N/A | N/A | 110361 | 110380 | CTCAACCCTCACCCATGCAG | 100 | 2666 |
| 877539 | N/A | N/A | 112217 | 112236 | CCTGCTTATAATCTCTGGTT | 57 | 2667 |
| 877563 | N/A | N/A | 114595 | 114614 | TCTGAAGGCTTACTATTTTA | 72 | 2668 |
| 877587 | N/A | N/A | 117410 | 117429 | ACTACAGCATTTCATGTGAT | 51 | 2669 |
| 877611 | N/A | N/A | 119355 | 119374 | ATGTATAGCCACCTGTAATT | 47 | 2670 |
| 877635 | N/A | N/A | 121814 | 121833 | CTTGGATAATTATCATAATG | 70 | 2671 |
| 877659 | N/A | N/A | 124271 | 124290 | TCTCTTGGGTTCATGCCTGA | 49 | 2672 |
| 877683 | N/A | N/A | 127120 | 127139 | TAAATATTTTGTAGCTCTA | 47 | 2673 |
| 877707 | N/A | N/A | 130019 | 130038 | TGTTTCTAGGGACCCTGAGC | 66 | 2674 |
| 877731 | N/A | N/A | 134194 | 134213 | AAATGTTGAAATTGTTACAA | 68 | 2675 |
| 877755 | N/A | N/A | 138536 | 138555 | AAATGACAATTAGGAGGGTC | 61 | 2676 |
| 877779 | N/A | N/A | 141131 | 141150 | CTTGCAAAACTTTGTTTCAT | 38 | 2677 |
| 877803 | N/A | N/A | 143288 | 143307 | AATTTATACCAGTCTTATGT | 147 | 2678 |
| 877827 | N/A | N/A | 144888 | 144907 | ATTCTTAATTATGTGAGTCT | 75 | 2679 |

TABLE 35

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 17 | 222 |
| 780624 | N/A | N/A | 81630 87887 | 81649 87906 | GCAGCATCATGCAAGCAGCA | 33 | 674 |
| 876021 | 545 | 564 | N/A | N/A | ATTTTACCTGAAGTTAGGAG | 71 | 2680 |
| 876045 | 831 | 850 | 21662 | 21681 | CATGAGGACTTCCACATTAT | 56 | 2681 |
| 876069 | 1229 | 1248 | 29580 | 29599 | TTATTTAGTGCCCAGCATGC | 61 | 2682 |
| 876093 | 1474 | 1493 | 35421 | 35440 | CTTCAGGAGAATGTATATGC | 41 | 2683 |
| 876117 | 1678 | 1697 | 41911 | 41930 | ATTCTGTATCCTCCCTGGAT | 49 | 2684 |
| 876141 | 2267 | 2286 | 56275 | 56294 | CTGTTATTCTGATCACACGC | 25 | 2685 |
| 876165 | 2870 | 2889 | 71713 | 71732 | TGTAATACGGCATCTCGGTA | 24 | 2686 |
| 876189 | 3229 | 3248 | 76363 | 76382 | GCAAGTCCAAATGTGTCAAA | 30 | 2687 |
| 876213 | 3801 | 3820 | 82146 | 82165 | GCTGATCTGATTATGGCTAA | 24 | 2688 |
| 876237 | 4149 | 4168 | 86644 | 86663 | GGTGGTTTTACCACTCCCAG | 31 | 2689 |
| 876261 | 4727 | 4746 | 92150 | 92169 | GGCACATTTTTACGCTCCGA | 10 | 2690 |
| 876285 | 5048 | 5067 | 98196 | 98215 | TACTGTGACATGTAGTTCTT | 18 | 2691 |
| 876309 | 5343 | 5362 | 100195 | 100214 | ATAAGCTTCAGGAGACCAAT | 51 | 2692 |
| 876333 | 5654 | 5673 | 101292 | 101311 | GGAATGGTGAGCCTTGGTTG | 42 | 2693 |
| 876357 | 6244 | 6263 | 124875 | 124894 | CATTTCCTCTGGCAACTTCA | 55 | 2694 |
| 876381 | 6856 | 6875 | 132566 | 132585 | AATTGCAATACAAACAAGTG | 115 | 2695 |
| 876405 | 7723 | 7742 | 145892 | 145911 | ATAATTTTCCTATCCAAAGA | 108 | 2696 |
| 876429 | 8688 | 8707 | 146857 | 146876 | CAACTGAAAAGTGTTAGATA | 67 | 2697 |
| 876453 | N/A | N/A | 4066 | 4085 | ATACTTGGAATAGTCAAGTC | 73 | 2698 |
| 876477 | N/A | N/A | 6274 | 6293 | TAGCACAGCCATGATGAAAC | 74 | 2699 |
| 876501 | N/A | N/A | 8339 | 8358 | TTGGATCTTTTCCAGATTAA | 48 | 2700 |
| 876525 | N/A | N/A | 11354 | 11373 | AAAAGATTTAAAGTTAATGA | 101 | 2701 |
| 876549 | N/A | N/A | 14435 | 14454 | ACTTCAGTGTTTGTCACTTA | 62 | 2702 |
| 876573 | N/A | N/A | 16563 | 16582 | AATTTCTATGATTTCTGGTG | 57 | 2703 |
| 876597 | N/A | N/A | 19215 | 19234 | ACTGAGCTACTTTGTCTTC | 65 | 2704 |
| 876621 | N/A | N/A | 20798 | 20817 | TTGGAGAATGACTTTTGCAT | 77 | 2705 |
| 876645 | N/A | N/A | 23873 | 23892 | TGCATTTCTTTATGAAAACA | 26 | 2706 |
| 876669 | N/A | N/A | 26498 | 26517 | AAAGTTACATATGACATGAC | 99 | 2707 |
| 876693 | N/A | N/A | 29206 | 29225 | AGAAGCCTTGGTCAATTATA | 45 | 2708 |
| 876717 | N/A | N/A | 30957 | 30976 | TAACTATCTCAAATTCTCAC | 64 | 2709 |
| 876741 | N/A | N/A | 33365 | 33384 | GATGTCTAACATATCATATT | 39 | 2710 |
| 876765 | N/A | N/A | 34855 | 34874 | TCACTCAGCTTTTGGGAGT | 60 | 2711 |
| 876789 | N/A | N/A | 37013 | 37032 | TTGACTAGAATGCAGTAGGT | 43 | 2712 |

TABLE 35-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876813 | N/A | N/A | 38806 | 38825 | TGTATCTAGTCTCTCTCCCT | 70 | 2713 |
| 876837 | N/A | N/A | 41246 | 41265 | ATAATGTTTTCCAAACCTAA | 85 | 2714 |
| 876861 | N/A | N/A | 43074 | 43093 | CCATTAATTATTTTAAATAG | 125 | 2715 |
| 876885 | N/A | N/A | 47190 | 47209 | AAATTTCCCTCCAACAAGGT | 78 | 2716 |
| 876909 | N/A | N/A | 48331 | 48350 | ATATTAGAAGTGCAAATACT | 102 | 2717 |
| 876933 | N/A | N/A | 50793 | 50812 | CTTTAAAATCATTCCTTTAC | 143 | 2718 |
| 876957 | N/A | N/A | 53340 | 53359 | TTAGCACATTCTCTGAACTT | 76 | 2719 |
| 876981 | N/A | N/A | 56553 | 56572 | AAGATTAGACTGGATAACAC | 79 | 2720 |
| 877005 | N/A | N/A | 59643 | 59662 | ACATTTAAATAATAATGAAG | 126 | 2721 |
| 877029 | N/A | N/A | 61788 | 61807 | ATCAATGTCAGAATAGCATG | 87 | 2722 |
| 877053 | N/A | N/A | 63610 | 63629 | TGCCAAATTGTCCTCAAAAG | 142 | 2723 |
| 877077 | N/A | N/A | 66573 | 66592 | CTAGAGAAAACATTAATCTA | 125 | 2724 |
| 877101 | N/A | N/A | 68563 | 68582 | AAAATACCTTTACACAAATT | 116 | 2725 |
| 877125 | N/A | N/A | 71841 | 71860 | TTGTTCCTAGCTTTGGCATA | 93 | 2726 |
| 877149 | N/A | N/A | 73151 | 73170 | ATGGAAGGAATCATTAGGTA | 47 | 2727 |
| 877173 | N/A | N/A | 74967 | 74986 | GTATTTAGCAAGGCAAAGAA | 92 | 2728 |
| 877197 | N/A | N/A | 77171 | 77190 | AAATTGCATAAATTCATATG | 114 | 2729 |
| 877221 | N/A | N/A | 79928 | 79947 | CTGTGAAACACAATTTGGGA | 60 | 2730 |
| 877252 | N/A | N/A | 84473 | 84492 | ACATGATGTCAGTAGCTATA | 41 | 2731 |
| 877276 | N/A | N/A | 87718 | 87737 | TTCACACTAAATGGCCCCTG | 81 | 2732 |
| 877300 | N/A | N/A | 90037 | 90056 | TAATTGGATGAATAAATTTT | 132 | 2733 |
| 877324 | N/A | N/A | 91380 | 91399 | TAAGAGGATAGTTTCTACAA | 57 | 2734 |
| 877348 | N/A | N/A | 93609 | 93628 | TGGCTTGAAAACCAAGTCAT | 86 | 2735 |
| 877372 | N/A | N/A | 95700 | 95719 | TCTTTCATATCTCTTTTATC | 68 | 2736 |
| 877396 | N/A | N/A | 97476 | 97495 | TGATCCTTGTCATGGCAGTT | 36 | 2737 |
| 877420 | N/A | N/A | 100797 | 100816 | AATCAACATTTTCTGAATCT | 84 | 2738 |
| 877444 | N/A | N/A | 102597 | 102616 | TTTATATTAAATCAATCTAA | 120 | 2739 |
| 877468 | N/A | N/A | 105335 | 105354 | AAGAGCTCTGCTACTCCATC | 131 | 2740 |
| 877492 | N/A | N/A | 107501 | 107520 | TAAAGAACTTGAGAAGGTGA | 94 | 2741 |
| 877516 | N/A | N/A | 110418 | 110437 | CCACTGTTAACTAACAGTGT | 144 | 2742 |
| 877540 | N/A | N/A | 112261 | 112280 | CTATAGCCACTACTAATCAG | 109 | 2743 |
| 877564 | N/A | N/A | 114597 | 114616 | ATTCTGAAGGCTTACTATTT | 89 | 2744 |
| 877588 | N/A | N/A | 117435 | 117454 | TTCTCTGCCCCATGATGTCA | 75 | 2745 |
| 877612 | N/A | N/A | 119387 | 119406 | GGTGATTTAATTGAGTTGCA | 45 | 2746 |
| 877636 | N/A | N/A | 121878 | 121897 | TAAATGTTCAATGTATTGTT | 70 | 2747 |
| 877660 | N/A | N/A | 124436 | 124455 | GAGAGATGAGTAGAAAGGAG | 92 | 2748 |

TABLE 35-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877684 | N/A | N/A | 127318 | 127337 | GCACATTATCTTTAATAAAT | 84 | 2749 |
| 877708 | N/A | N/A | 130037 | 130056 | ATAACCCATCTCAGGCTCTG | 62 | 2750 |
| 877732 | N/A | N/A | 134431 | 134450 | CTACTGTGTTCAAGATTTTA | 66 | 2751 |
| 877756 | N/A | N/A | 138860 | 138879 | AGCACAGATGGCAAAAAGCT | 77 | 2752 |
| 877780 | N/A | N/A | 141161 | 141180 | GAAATATTATATCTGTAACT | 85 | 2753 |
| 877804 | N/A | N/A | 143352 | 143371 | AATCTGCTTCTCTTGTGGGA | 68 | 2754 |
| 877828 | N/A | N/A | 145005 | 145024 | CAAATACCTTGGAACTGAAT | 109 | 2755 |

TABLE 36

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 49 | 222 |
| 803643 | N/A | N/A | 81635 87892 | 81654 87911 | TCATTGCAGCATCATGCAAG | 53 | 1805 |
| 876025 | 706 | 725 | 18605 | 18624 | TCTCAACAAATTCAGTCAGT | 55 | 2756 |
| 876049 | 836 | 855 | 21667 | 21686 | CCACTCATGAGGACTTCCAC | 55 | 2757 |
| 876073 | 1235 | 1254 | 29586 | 29605 | AGGAGATTATTTAGTGCCCA | 35 | 2758 |
| 876097 | 1478 | 1497 | 35425 | 35444 | GCCACTTCAGGAGAATGTAT | 39 | 2759 |
| 876121 | 1697 | 1716 | 41930 | 41949 | ATATTTAGCTTATGATGAAA | 93 | 2760 |
| 876145 | 2448 | 2467 | 62069 | 62088 | ACCTTTCCCAATGCTTATCG | 57 | 2761 |
| 876169 | 2890 | 2909 | 71733 | 71752 | GCAAATTTGGTGAGCAACGC | 50 | 2762 |
| 876193 | 3294 | 3313 | 76428 | 76447 | ATCAAGATTAGCAATACAAC | 105 | 2763 |
| 876217 | 3807 | 3826 | 82152 | 82171 | CAAGATGCTGATCTGATTAT | 64 | 2764 |
| 876241 | 4309 | 4328 | 87213 | 87232 | TATAGAATTCCTCACGACCT | 85 | 2765 |
| 876265 | 4732 | 4751 | 92155 | 92174 | CAATTGGCACATTTTTACGC | 79 | 2766 |
| 876289 | 5053 | 5072 | 98201 | 98220 | TAAAATACTGTGACATGTAG | 39 | 2767 |
| 876313 | 5446 | 5465 | 100435 | 100454 | CCACAACTTGGCCCAAAAGA | 68 | 2768 |
| 876337 | 5691 | 5710 | 101329 | 101348 | GTCAGCCAAAATCAAGTCAG | 48 | 2769 |
| 876361 | 6380 | 6399 | 125011 | 125030 | GGTAATTTTCCTTGTATTTC | 57 | 2770 |
| 876385 | 6998 | 7017 | 137402 | 137421 | GGAGTACTGACATTTCCTAT | 46 | 2771 |
| 876409 | 7903 | 7922 | 146072 | 146091 | ATAAGAAATATAACATTGTG | 99 | 2772 |
| 876433 | 8823 | 8842 | 146992 | 147011 | CCTCAAATTATTACATAGGT | 60 | 2773 |
| 876457 | N/A | N/A | 4255 | 4274 | TAAGACATCACTTTCTTTAG | 58 | 2774 |

TABLE 36-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876481 | N/A | N/A | 6920 | 6939 | GAATCAAATATTGGCTGTGC | 115 | 2775 |
| 876505 | N/A | N/A | 8749 | 8768 | CATATATGTACCCTCTAGAG | 88 | 2776 |
| 876529 | N/A | N/A | 11687 | 11706 | CTGATACATAGAATTACAGA | 70 | 2777 |
| 876553 | N/A | N/A | 14518 | 14537 | GCCAAAGTTTTCTCAGGGAA | 54 | 2778 |
| 876577 | N/A | N/A | 16867 | 16886 | GGGCCCACATAAATCATTCT | 113 | 2779 |
| 876601 | N/A | N/A | 19369 | 19388 | CTCTCCACTCCATGTCTCTG | 75 | 2780 |
| 876625 | N/A | N/A | 21104 | 21123 | ACAATAATGTAACATATTTT | 94 | 2781 |
| 876649 | N/A | N/A | 24272 | 24291 | AGCAAACATTTAAAAGCCCA | 52 | 2782 |
| 876673 | N/A | N/A | 26747 | 26766 | CATAATTAGATTACATAGTT | 110 | 2783 |
| 876697 | N/A | N/A | 29480 | 29499 | TTTATGAGAGTCCTACCTGC | 131 | 2784 |
| 876721 | N/A | N/A | 31326 | 31345 | TAGAAGTCCGGAAAAATATA | 106 | 2785 |
| 876745 | N/A | N/A | 33421 | 33440 | TCTTACTCAATAGTCACCTT | 72 | 2786 |
| 876769 | N/A | N/A | 35273 | 35292 | TTAGAATATTAATATAGTCC | 44 | 2787 |
| 876793 | N/A | N/A | 37536 | 37555 | ACTGATCTGATTCAATGGTA | 96 | 2788 |
| 876817 | N/A | N/A | 38963 | 38982 | CAGAACAAAGTATCATCCCT | 88 | 2789 |
| 876841 | N/A | N/A | 41339 | 41358 | CTTTATTAAGCTACACTGTA | 82 | 2790 |
| 876865 | N/A | N/A | 43282 | 43301 | AGATAAATTTAACCCATTAC | 95 | 2791 |
| 876889 | N/A | N/A | 47322 | 47341 | ACGAATCATGCCACAGTGAA | 95 | 2792 |
| 876913 | N/A | N/A | 48676 | 48695 | TACTAGAACACAGTGAAATG | 119 | 2793 |
| 876937 | N/A | N/A | 51449 | 51468 | AATACATAGTCTCCCTTGAC | 95 | 2794 |
| 876961 | N/A | N/A | 53597 | 53616 | ATTCTTAATCTCCCGTGAAC | 74 | 2795 |
| 876985 | N/A | N/A | 56874 | 56893 | CATGGTTCAGGAGGGAAGAG | 107 | 2796 |
| 877009 | N/A | N/A | 59869 | 59888 | TCCTTGGAGGATCCAAACTA | 99 | 2797 |
| 877033 | N/A | N/A | 62406 | 62425 | TCATAAAGAACTTAAATGTC | 135 | 2798 |
| 877057 | N/A | N/A | 64411 | 64430 | ATGGGAAATTATCCCGAAGC | 133 | 2799 |
| 877081 | N/A | N/A | 66847 | 66866 | CAAAATACTTCAACACTTCA | 119 | 2800 |
| 877105 | N/A | N/A | 68855 | 68874 | AATATAACAAAAATCTGATT | 126 | 2801 |
| 877129 | N/A | N/A | 72099 | 72118 | AACCCACACCATTAGGTAGA | 90 | 2802 |
| 877153 | N/A | N/A | 73877 | 73896 | TGCAAAACCAGAGGCACGG | 78 | 2803 |
| 877177 | N/A | N/A | 75128 | 75147 | TTTTAAATCAAATTGGATGA | 143 | 2804 |
| 877201 | N/A | N/A | 77744 | 77763 | CCCCTCTATAGTATACAAAA | 94 | 2805 |
| 877225 | N/A | N/A | 80668 | 80687 | TTAACCTGGAAGCTAAACAG | 149 | 2806 |
| 877256 | N/A | N/A | 84735 | 84754 | TGAGAGGTGATGACAGAGCT | 99 | 2807 |
| 877280 | N/A | N/A | 87905 | 87924 | TGCACAGAAGAGTTCATTGC | 86 | 2808 |
| 877304 | N/A | N/A | 90343 | 90362 | TAAAAGTTGTCTTCAAAGG | 87 | 2809 |

TABLE 36-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877328 | N/A | N/A | 91620 | 91639 | CTTGGTTATTTGTAAAATGT | 37 | 2810 |
| 877352 | N/A | N/A | 93973 | 93992 | TTATGTCAAAGCTACAGAGA | 60 | 2811 |
| 877376 | N/A | N/A | 95796 | 95815 | TTTTCCAAATTCCTTTGTAT | 58 | 2812 |
| 877400 | N/A | N/A | 97827 | 97846 | GAAACAATGAACATCAGTAT | 80 | 2813 |
| 877424 | N/A | N/A | 101020 | 101039 | AACTGCTGCAGACTACCAGA | 82 | 2814 |
| 877448 | N/A | N/A | 102830 | 102849 | AGCATTTAAATTCAACCTAA | 133 | 2815 |
| 877472 | N/A | N/A | 105422 | 105441 | GTAAGGTTGAGAACAAGTGC | 80 | 2816 |
| 877496 | N/A | N/A | 108081 | 108100 | AGTAGATTCTGTTATACAAA | 53 | 2817 |
| 877520 | N/A | N/A | 110838 | 110857 | AAAAGAGATTATGTCAGATT | 86 | 2818 |
| 877544 | N/A | N/A | 112426 | 112445 | GTACTGTCAGAATTAAATTT | 76 | 2819 |
| 877568 | N/A | N/A | 115091 | 115110 | GATTTGTTATTTAAAGTAAG | 166 | 2820 |
| 877592 | N/A | N/A | 117565 | 117584 | ACAGTGTAAAGTTTTCATCT | 58 | 2821 |
| 877616 | N/A | N/A | 119914 | 119933 | GAGTTGCATATGGTTTAGGA | 36 | 2822 |
| 877640 | N/A | N/A | 122283 | 122302 | TTCTCATCCAGTGCACACAT | 81 | 2823 |
| 877664 | N/A | N/A | 124843 | 124862 | CCTGAAAGTAAGCAGATAAA | 141 | 2824 |
| 877688 | N/A | N/A | 127923 | 127942 | AATTCATGCCATTCCAGAAT | 143 | 2825 |
| 877712 | N/A | N/A | 132134 | 132153 | ATAAGAAGATTGTTCCTCTC | 84 | 2826 |
| 877736 | N/A | N/A | 135027 | 135046 | AGAGAAATAAATGCTCATGG | 82 | 2827 |
| 877760 | N/A | N/A | 139725 | 139744 | TATGGAACTTTAAAGAGTTA | 93 | 2828 |
| 877784 | N/A | N/A | 141305 | 141324 | ACTTTACTTACTTTTGGTTA | 81 | 2829 |
| 877808 | N/A | N/A | 143492 | 143511 | AGACTATGATTAAAACAAAC | 88 | 2830 |
| 877832 | N/A | N/A | 145211 | 145230 | ACATCATTGCCCTGTTTGGA | 55 | 2831 |

TABLE 37

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 34 | 222 |
| 876026 | 711 | 730 | 18610 | 18629 | TTTGTTCTCAACAAATTCAG | 45 | 2832 |
| 876050 | 837 | 856 | 21668 | 21687 | GCCACTCATGAGGACTTCCA | 25 | 2833 |
| 876074 | 1236 | 1255 | 29587 | 29606 | AAGGAGATTATTTAGTGCCC | 41 | 2834 |
| 876098 | 1480 | 1499 | 35427 | 35446 | CAGCCACTTCAGGAGAATGT | 33 | 2835 |
| 876122 | 1698 | 1717 | 41931 | 41950 | CATATTTAGCTTATGATGAA | 66 | 2836 |
| 876146 | 2449 | 2468 | 62070 | 62089 | CACCTTTCCCAATGCTTATC | 44 | 2837 |

TABLE 37-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876170 | 2931 | 2950 | 72955 | 72974 | TTCATGATCAAAAATGGGCC | 44 | 2838 |
| 876194 | 3333 | 3352 | 76467 | 76486 | ATCTAAAACCACTGAGGGTC | 59 | 2839 |
| 876218 | 3835 | 3854 | 82180 | 82199 | ACCATAAATATGCTTTTTCA | 36 | 2840 |
| 876242 | 4311 | 4330 | 87215 | 87234 | ACTATAGAATTCCTCACGAC | 45 | 2841 |
| 876266 | 4733 | 4752 | 92156 | 92175 | TCAATTGGCACATTTTTACG | 71 | 2842 |
| 876290 | 5067 | 5086 | 98215 | 98234 | TTTTTCTAGGAGCTTAAAAT | 90 | 2843 |
| 876314 | 5447 | 5466 | 100436 | 100455 | TCCACAACTTGGCCCAAAAG | 75 | 2844 |
| 876338 | 5692 | 5711 | 101330 | 101349 | GGTCAGCCAAAATCAAGTCA | 76 | 2845 |
| 876362 | 6427 | 6446 | 126543 | 126562 | TCTCAACCATAGGCCATGGG | 36 | 89 |
| 876386 | 7041 | 7060 | 137445 | 137464 | ATTTCTTTCCGTTGAATTTG | 71 | 2846 |
| 876410 | 7993 | 8012 | 146162 | 146181 | ATCGGCCTTATAAATTTTAG | 56 | 2847 |
| 876434 | 8862 | 8881 | 147031 | 147050 | AAGAATTTACCGAAAGTACT | 88 | 2848 |
| 876458 | N/A | N/A | 4345 | 4364 | AAATTTCTGGGTTTCCTATG | 78 | 2849 |
| 876482 | N/A | N/A | 7014 | 7033 | AGCTCTTTGATCCTCAGTGA | 43 | 2850 |
| 876506 | N/A | N/A | 8763 | 8782 | AAAAAGAGAAAGTGCATATA | 97 | 2851 |
| 876530 | N/A | N/A | 11858 | 11877 | TGTACAGGAATATGACTAGA | 73 | 2852 |
| 876554 | N/A | N/A | 14745 | 14764 | TCCAGCCTCTCTCATGCTAT | 94 | 2853 |
| 876578 | N/A | N/A | 16881 | 16900 | TGATAACTGACACAGGGCCC | 91 | 2854 |
| 876602 | N/A | N/A | 19380 | 19399 | GGCCCTTCATGCTCTCCACT | 81 | 2855 |
| 876626 | N/A | N/A | 21285 | 21304 | AGATAAATAAATTGGAGGGT | 76 | 2856 |
| 876650 | N/A | N/A | 24302 | 24321 | ATATTTTTAAGCCCACATTG | 83 | 2857 |
| 876674 | N/A | N/A | 27099 | 27118 | TCATCAACGGCCTCACAATC | 114 | 2858 |
| 876698 | N/A | N/A | 29500 | 29519 | AATTTTGAATAACTCTAATA | 115 | 2859 |
| 876722 | N/A | N/A | 31348 | 31367 | ATGTCATGTGTGAGTTTACA | 46 | 2860 |
| 876746 | N/A | N/A | 33423 | 33442 | GGTCTTACTCAATAGTCACC | 55 | 2861 |
| 876770 | N/A | N/A | 35317 | 35336 | ACTTATAGATATGAAAGCAT | 86 | 2862 |
| 876794 | N/A | N/A | 37818 | 37837 | AAAGATTTACATTTAGTCGA | 67 | 2863 |
| 876818 | N/A | N/A | 39048 | 39067 | ATATAACTAGAGAAAATGAT | 118 | 2864 |
| 876842 | N/A | N/A | 41389 | 41408 | AAGTTCTGTAAAGGCTATAT | 65 | 2865 |
| 876866 | N/A | N/A | 43424 | 43443 | AAAGAAAAGAACCAAGGTTT | 67 | 2866 |
| 876890 | N/A | N/A | 47351 | 47370 | GCATTTAGTTTGTTGCCACA | 30 | 2867 |
| 876914 | N/A | N/A | 48782 | 48801 | CTAATAAAGTGGATGGATTT | 117 | 2868 |
| 876938 | N/A | N/A | 51461 | 51480 | TATCATCTTAATAATACATA | 66 | 2869 |
| 876962 | N/A | N/A | 53654 | 53673 | CTCTTGAAGAAAAACTATTT | 96 | 2870 |
| 876986 | N/A | N/A | 56900 | 56919 | AGAACAATCAGATAGATATA | 105 | 2871 |

TABLE 37-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877010 | N/A | N/A | 59885 | 59904 | TTTGTGGAAGGAATTTTCCT | 73 | 2872 |
| 877034 | N/A | N/A | 62466 | 62485 | GTACCCCTTCAAAAAGCTTC | 97 | 2873 |
| 877058 | N/A | N/A | 64464 | 64483 | CACTATACCCATATACCCAA | 84 | 2874 |
| 877082 | N/A | N/A | 67017 | 67036 | GAAAACTGCATTTCACCAAG | 67 | 2875 |
| 877106 | N/A | N/A | 69629 | 69648 | TTATCCAGAAAATCTCCAAA | 99 | 2876 |
| 877130 | N/A | N/A | 72373 | 72392 | TCCATAGTTCCAAAACAGAC | 76 | 2877 |
| 877154 | N/A | N/A | 73916 | 73935 | CAAAGATGCTCCTGAACATC | 87 | 2878 |
| 877178 | N/A | N/A | 75204 | 75223 | CACTGGGAATAGACAGAAAC | 68 | 2879 |
| 877202 | N/A | N/A | 77774 | 77793 | GGTTTTGACAAGTGTACCAT | 57 | 2880 |
| 877226 | N/A | N/A | 80802 | 80821 | ACCAATAGTGTGTCACTTAA | 48 | 2881 |
| 877233 | N/A | N/A | 81930 | 81949 | ACTAGCATTATTGACATATG | 98 | 2882 |
| 877257 | N/A | N/A | 84787 | 84806 | TAGTGAGTGAACACAGCCAT | 48 | 2883 |
| 877281 | N/A | N/A | 87933 | 87952 | TCCTGACACAAGCTTTTTAA | 64 | 2884 |
| 877305 | N/A | N/A | 90378 | 90397 | CTGGTATTTCTCAAAGCATT | 40 | 2885 |
| 877329 | N/A | N/A | 91655 | 91674 | TTTTAAATATTCAAGGTAAA | 96 | 2886 |
| 877353 | N/A | N/A | 94061 | 94080 | AATGTGCAACAAAGAATTAT | 74 | 2887 |
| 877377 | N/A | N/A | 95892 | 95911 | CATTATCTTGACTTTATCAC | 78 | 2888 |
| 877401 | N/A | N/A | 98295 | 98314 | TAGCAATTAATTTTTTAAGG | 95 | 2889 |
| 877425 | N/A | N/A | 101246 | 101265 | AGAAGTAATAAAACATTTTT | 140 | 2890 |
| 877449 | N/A | N/A | 103447 | 103466 | GGGAGAGTAATCACAAACAT | 76 | 2891 |
| 877473 | N/A | N/A | 105724 | 105743 | TCTCCTGTTCAGAAACAAAT | 103 | 2892 |
| 877497 | N/A | N/A | 108130 | 108149 | GTTAGAGCAGTAAGTCATG | 65 | 2893 |
| 877521 | N/A | N/A | 110906 | 110925 | TAAAATTTGAAATGCATGCT | 118 | 2894 |
| 877545 | N/A | N/A | 112696 | 112715 | TACTTAACGAAGATTAAATA | 106 | 2895 |
| 877569 | N/A | N/A | 115659 | 115678 | CAAATGCATACTTGCTTTCG | 71 | 2896 |
| 877593 | N/A | N/A | 117566 | 117585 | AACAGTGTAAAGTTTTCATC | 65 | 2897 |
| 877617 | N/A | N/A | 119915 | 119934 | AGAGTTGCATATGGTTTAGG | 39 | 2898 |
| 877641 | N/A | N/A | 122290 | 122309 | TTCTAAATTCTCATCCAGTG | 61 | 2899 |
| 877665 | N/A | N/A | 125117 | 125136 | ATGATCATCTGTTTAAGGAA | 74 | 2900 |
| 877689 | N/A | N/A | 128242 | 128261 | AGCATAAACAAGAAGGAGAA | 80 | 2901 |
| 877713 | N/A | N/A | 132213 | 132232 | AGTTTTGCCTATCAAGATGA | 82 | 2902 |
| 877737 | N/A | N/A | 135443 | 135462 | CCTAAGCACCCATGAATGAA | 79 | 2903 |
| 877761 | N/A | N/A | 139807 | 139826 | AATCTCTTTTGGGAGATGAG | 81 | 2904 |
| 877785 | N/A | N/A | 141341 | 141360 | TAACCATTCTGAATTGAATA | 86 | 2905 |

TABLE 37-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877809 | N/A | N/A | 143723 | 143742 | AATTATTATCAAAGGAAGAC | 126 | 2906 |
| 877833 | N/A | N/A | 145245 | 145264 | AATTTATGAAACACATAATA | 101 | 2907 |

TABLE 38

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 15 | 222 |
| 803630 | N/A | N/A | 81592 87849 | 81611 87868 | AAAGCCATAGTGTTTGAAGG | 66 | 1792 |
| 876015 | 341 | 360 | 3732 | 3751 | ACCTGCTGCACACTCGCGAC | 39 | 2908 |
| 876039 | 824 | 843 | N/A | N/A | ACTTCCACATTATTGCAAGG | 38 | 2909 |
| 876063 | 1038 | 1057 | 28013 | 28032 | CGCTGAGATCTGCAATGCTG | 66 | 2910 |
| 876087 | 1467 | 1486 | 35414 | 35433 | AGAATGTATATGCTTCTGCA | 75 | 2911 |
| 876111 | 1499 | 1518 | 35446 | 35465 | AGCATTTTACAGCCACTTTC | 50 | 2912 |
| 876135 | 2086 | 2105 | 56020 | 56039 | AAGATGCTGACAATTTGAGG | 66 | 2913 |
| 876159 | 2716 | 2735 | 65554 | 65573 | ATTTAGACAGCACATCTTCA | 76 | 2914 |
| 876183 | 3222 | 3241 | 76356 | 76375 | CAAATGTGTCAAACTCTTCA | 42 | 2915 |
| 876207 | 3752 | 3771 | 82097 | 82116 | CAGTGTGCGGGACCTGGTAG | 52 | 2916 |
| 876231 | 3973 | 3992 | 83968 | 83987 | ATTTCCCCATTTCATTGGGA | 74 | 2917 |
| 876255 | 4604 | 4623 | 88705 | 88724 | CGAAGTTTTGCCAAAGCATC | 37 | 2918 |
| 876279 | 4962 | 4981 | 98110 | 98129 | TTTTGGACAACCTTCCACTT | 51 | 2919 |
| 876303 | 5197 | 5216 | 99203 | 99222 | AAGGCATTTCATATAGTCGG | 31 | 2920 |
| 876327 | 5646 | 5665 | 101284 | 101303 | GAGCCTTGGTTGATCTGGAT | 41 | 2921 |
| 876351 | 6067 | 6086 | N/A | N/A | TGGCTGAGTGGAGGTATCTC | 100 | 2922 |
| 876375 | 6733 | 6752 | 132443 | 132462 | TTTCAACAGGAAGATGCACC | 68 | 2923 |
| 876399 | 7490 | 7509 | 143138 | 143157 | AGCTGTGCTGTCATCATGAC | 77 | 2924 |
| 876423 | 8494 | 8513 | 146663 | 146682 | AAAAATATCACTTGAAGGAC | 76 | 2925 |
| 876447 | N/A | N/A | 3735 | 3754 | TTTACCTGCTGCACACTCGC | 44 | 2926 |
| 876471 | N/A | N/A | 5332 | 5351 | TATACATGTATCAAATAGCA | 56 | 2927 |
| 876495 | N/A | N/A | 7824 | 7843 | ATCTCTCTAAGAGAGAAGGT | 110 | 2928 |
| 876519 | N/A | N/A | 10780 | 10799 | TCTCTTCATGGTTTGAATTC | 72 | 2929 |
| 876543 | N/A | N/A | 13667 | 13686 | AAGTTTGCTTATTTGCATTT | 75 | 2930 |
| 876567 | N/A | N/A | 15828 | 15847 | TAATTTCATGAGTCTCAATC | 89 | 2931 |

TABLE 38-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876591 | N/A | N/A | 17978 | 17997 | CATGTATAAAATTATAGTTT | 72 | 2932 |
| 876615 | N/A | N/A | 20147 | 20166 | CAATGTGGGTGGAAAACAAT | 107 | 2933 |
| 876639 | N/A | N/A | 23039 | 23058 | ATAGACAATGACCCTTGCTC | 38 | 2934 |
| 876663 | N/A | N/A | 26161 | 26180 | TTCTCATGAAAAATAATGAA | 80 | 2935 |
| 876687 | N/A | N/A | 28159 | 28178 | TGAGCTACACAGGACAGAAA | 90 | 2936 |
| 876711 | N/A | N/A | 30793 | 30812 | CAAAAGCATATGCAGCAGAG | 47 | 2937 |
| 876735 | N/A | N/A | 32754 | 32773 | ATCAAAGGAGATTTCCAGGT | 33 | 2938 |
| 876759 | N/A | N/A | 34066 | 34085 | AATAAGTAGTCTATCTTAAG | 101 | 2939 |
| 876783 | N/A | N/A | 36564 | 36583 | TCCGCTGTGTTTTGCCTCA | 65 | 2940 |
| 876807 | N/A | N/A | 38580 | 38599 | ATGCCTCACTCACCCCCGAC | 70 | 2941 |
| 876831 | N/A | N/A | 40880 | 40899 | AAGAAGATGTGACCACTAAA | 122 | 2942 |
| 876855 | N/A | N/A | 42917 | 42936 | GTAATTCCCTTCTTCTCTTT | 47 | 2943 |
| 876879 | N/A | N/A | 46712 | 46731 | AATACTATTGTTATTTTTAC | 126 | 2944 |
| 876903 | N/A | N/A | 48099 | 48118 | CAGGGTGCATAGTCTGTAGG | 49 | 2945 |
| 876927 | N/A | N/A | 50346 | 50365 | TCTGAACTTTCTGTTTGATT | 35 | 2946 |
| 876951 | N/A | N/A | 52863 | 52882 | GCCCTACAAAAATCTATTCT | 53 | 2947 |
| 876975 | N/A | N/A | 56130 | 56149 | GGATGCAAGTGAAAAACACT | 103 | 2948 |
| 876999 | N/A | N/A | 57946 | 57965 | CTAGATATAAATAACCTCTG | 52 | 2949 |
| 877023 | N/A | N/A | 61194 | 61213 | ATAATATCCATCAGTTACTG | 97 | 2950 |
| 877047 | N/A | N/A | 63254 | 63273 | GAAGAGACAGCCAGGTGAAG | 126 | 2951 |
| 877071 | N/A | N/A | 66298 | 66317 | ACAATATTTTGGAACAACTC | 51 | 2952 |
| 877095 | N/A | N/A | 67597 | 67616 | ATAGGTAATATGATTTAATT | 127 | 2953 |
| 877119 | N/A | N/A | 71046 | 71065 | TCATGTTTCATGGTTTCTTT | 31 | 2954 |
| 877143 | N/A | N/A | 72871 | 72890 | GGAAGGAACCATGAAATTTT | 74 | 2955 |
| 877167 | N/A | N/A | 74441 | 74460 | CCTTGAGAATTTAACAATTT | 44 | 2956 |
| 877191 | N/A | N/A | 76594 | 76613 | CTCTTTCTTACCCTTCTAAA | 143 | 2957 |
| 877215 | N/A | N/A | 79222 | 79241 | GCAAAGCAAACAGATTTTGA | 49 | 2958 |
| 877246 | N/A | N/A | 83653 | 83672 | TCACTCATCTGTAATATTAA | 34 | 2959 |
| 877270 | N/A | N/A | 86973 | 86992 | CTAACATATCCCTCCATGTT | 69 | 2960 |
| 877294 | N/A | N/A | 89174 | 89193 | CCATAAAACAGGAATTCCAA | 84 | 2961 |
| 877318 | N/A | N/A | 91036 | 91055 | ATCTCTTAACCCAGAGAATT | 93 | 2962 |
| 877342 | N/A | N/A | 93085 | 93104 | ATATTTGAGACACTGACATG | 107 | 2963 |
| 877366 | N/A | N/A | 95216 | 95235 | AATTACTCCACAGAATCTTC | 104 | 2964 |
| 877390 | N/A | N/A | 96680 | 96699 | AATTCTAACTCTACCTCTTC | 140 | 2965 |
| 877414 | N/A | N/A | 99835 | 99854 | TAAAAGAAGTTTTTGATCA | 100 | 2966 |

TABLE 38-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877438 | N/A | N/A | 102077 | 102096 | ATGTGCAGGAAGTCAAGATA | 63 | 2967 |
| 877462 | N/A | N/A | 104952 | 104971 | GTATTATTTGCATCTTATCA | 57 | 2968 |
| 877486 | N/A | N/A | 106807 | 106826 | AGTGAGTCTTACAAAAAGTT | 73 | 2969 |
| 877510 | N/A | N/A | 110180 | 110199 | GAGAAAAGCACAGATGACTC | 46 | 2970 |
| 877534 | N/A | N/A | 111786 | 111805 | CTCTGCAATTCAAAAAAAGT | 100 | 2971 |
| 877558 | N/A | N/A | 114104 | 114123 | TAGGCAATGAGAGATGATAC | 147 | 2972 |
| 877582 | N/A | N/A | 117147 | 117166 | CAGCTGAAGATTCTCTCTCT | 66 | 2973 |
| 877606 | N/A | N/A | 119182 | 119201 | TCAGGATTGGGAACTAAGAA | 56 | 2974 |
| 877630 | N/A | N/A | 121116 | 121135 | TTCTCTAAACTTTAGTCTCT | 53 | 2975 |
| 877654 | N/A | N/A | 123425 | 123444 | TACTCTTTCAACTGTTCTTT | 61 | 2976 |
| 877678 | N/A | N/A | 126753 | 126772 | GGATGGTGAAAATTATAGGA | 61 | 2977 |
| 877702 | N/A | N/A | 129321 | 129340 | TTCTATATTGCAGAGCCACC | 131 | 2978 |
| 877726 | N/A | N/A | 133413 | 133432 | TTCAGTGGAGTTTAGTTCAG | 81 | 2979 |
| 877750 | N/A | N/A | 138222 | 138241 | CCAAGTTCACAAAACCAATA | 57 | 2980 |
| 877774 | N/A | N/A | 140803 | 140822 | ATGGCAAACTCCTACTTGGC | 97 | 2981 |
| 877798 | N/A | N/A | 142508 | 142527 | TTTTCCCAGAACCAGTGAAT | 102 | 2982 |
| 877822 | N/A | N/A | 144769 | 144788 | TTTGGATATGGTAAGGTACA | 71 | 2983 |

TABLE 39

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 18 | 222 |
| 803628 | N/A | N/A | 81589 87846 | 81608 87865 | GCCATAGTGTTTGAAGGAAT | 43 | 1790 |
| 876012 | 338 | 357 | 3729 | 3748 | TGCTGCACACTCGCGACTCT | 71 | 2984 |
| 876036 | 802 | 821 | 18701 | 18720 | TCGCTAGGGAATGTAAACAA | 63 | 2985 |
| 876060 | 877 | 896 | 21708 | 21727 | CTTTCATAGCTTCCACCACA | 56 | 2986 |
| 876084 | 1450 | 1469 | 35397 | 35416 | GCATTAACTCCAAAACATTC | 32 | 2987 |
| 876108 | 1491 | 1510 | 35438 | 35457 | ACAGCCACTTTCAGCCACTT | 63 | 2988 |
| 876132 | 1957 | 1976 | 52997 | 53016 | CATTCTTCTTTGTAATCAAG | 53 | 2989 |
| 876156 | 2621 | 2640 | N/A | N/A | GCTAGTGTAGATGCTATATT | 26 | 2990 |
| 876180 | 3215 | 3234 | N/A | N/A | GTCAAACTCTTCAGAGTTTC | 21 | 2991 |
| 876204 | 3660 | 3679 | 80940 | 80959 | GGAAAATTTGTTCTGAGATA | 20 | 2992 |

TABLE 39-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876228 | 3924 | 3943 | 83919 | 83938 | ATCCAGAGATGTCAGATTTT | 131 | 2993 |
| 876252 | 4427 | 4446 | N/A | N/A | GCGCGAGCCTTTATATTGAA | 95 | 2994 |
| 876276 | 4816 | 4835 | 92239 | 92258 | CGTGAGGAAGCTCATTTTCA | 30 | 148 |
| 876300 | 5193 | 5212 | 99199 | 99218 | CATTTCATATAGTCGGATGA | 46 | 2995 |
| 876324 | 5571 | 5590 | 100560 | 100579 | TTGATGTTCTTCACCATCAT | 57 | 2996 |
| 876348 | 5984 | 6003 | 113181 | 113200 | TGCTGAAGCAGGCGATCCAA | 97 | 2997 |
| 876372 | 6650 | 6669 | 129795 | 129814 | TCAAGAAATGAGAGCTGTCC | 87 | 2998 |
| 876396 | 7395 | 7414 | 143043 | 143062 | TCCTCCAGTTCCTATCCAAA | 87 | 2999 |
| 876420 | 8397 | 8416 | 146566 | 146585 | ATGTCTAGGAAAGACACAGA | 119 | 3000 |
| 876444 | 9175 | 9194 | 147344 | 147363 | ATTTAAATATGGTATTCATT | 145 | 3001 |
| 876468 | N/A | N/A | 5184 | 5203 | ACTCATAACTACTCCGGACA | 101 | 3002 |
| 876492 | N/A | N/A | 7482 | 7501 | TGGCAGTCTGGAATATCATG | 62 | 3003 |
| 876516 | N/A | N/A | 10656 | 10675 | AATCAAACTTCTGAGTTTAA | 78 | 3004 |
| 876540 | N/A | N/A | 13053 | 13072 | AGCACTACTTATTTTCCAAT | 34 | 3005 |
| 876564 | N/A | N/A | 15510 | 15529 | AGGCACCTTCATTCCTATTG | 63 | 3006 |
| 876588 | N/A | N/A | 17889 | 17908 | TTTTAATTTTATGCCAGAGT | 42 | 3007 |
| 876612 | N/A | N/A | 19937 | 19956 | TTGTGATTTTATAAACATCA | 72 | 3008 |
| 876636 | N/A | N/A | 22628 | 22647 | TTAACCCTTATTTATATATG | 104 | 3009 |
| 876660 | N/A | N/A | 25657<br>25687<br>25717<br>25747<br>25811<br>25875 | 25676<br>25706<br>25736<br>25766<br>25830<br>25894 | TTATATACATCTGTGTATAA | 85 | 3010 |
| 876684 | N/A | N/A | 27860 | 27879 | TTAACATATAACACTATTTA | 119 | 3011 |
| 876708 | N/A | N/A | 30296 | 30315 | CAGAGGATACCCATTGCAAA | 60 | 3012 |
| 876732 | N/A | N/A | 32607 | 32626 | CCTCTTTAACTGCACAGTAG | 38 | 3013 |
| 876756 | N/A | N/A | 33886 | 33905 | AACCTTTCCCAAAGTGGCTA | 56 | 3014 |
| 876780 | N/A | N/A | 36392 | 36411 | TAACCCTACTTCTTACAAGT | 109 | 3015 |
| 876804 | N/A | N/A | 38436 | 38455 | CATCGATATTCTCAAAGCCT | 45 | 3016 |
| 876828 | N/A | N/A | 40375 | 40394 | TACTTAAAATACTTCAAACA | 110 | 3017 |
| 876852 | N/A | N/A | 42387 | 42406 | ACCATATACTATGAGACCAG | 40 | 3018 |
| 876876 | N/A | N/A | 45845 | 45864 | GGAATTACAGTGGAGAGGTT | 107 | 3019 |
| 876900 | N/A | N/A | 48095 | 48114 | GTGCATAGTCTGTAGGTAGT | 28 | 3020 |
| 876924 | N/A | N/A | 50233 | 50252 | GCTCTGTTGTCACCCTTGTA | 62 | 3021 |
| 876948 | N/A | N/A | 52394 | 52413 | CATTAGAAGATGAATTCACT | 104 | 3022 |
| 876972 | N/A | N/A | 55581 | 55600 | ATAATATTGAACAGTAGGTT | 84 | 3023 |
| 876996 | N/A | N/A | 57799 | 57818 | CTGTTGGGTAGAAAGATTTG | 85 | 3024 |

TABLE 39-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877020 | N/A | N/A | 60838 | 60857 | GGTTGGAAGGCACCAATTAA | 76 | 3025 |
| 877044 | N/A | N/A | 63123 | 63142 | AGCCTACTGAGCGGTTGGAA | 82 | 3026 |
| 877068 | N/A | N/A | 66018 | 66037 | GTTGCAGACATTTTACATAC | 32 | 3027 |
| 877092 | N/A | N/A | 67322 | 67341 | TAGAACCATACCTAAATAGT | 97 | 3028 |
| 877116 | N/A | N/A | 70348 | 70367 | GTAATACCCGAAAGAAGGGA | 53 | 3029 |
| 877140 | N/A | N/A | 72680 | 72699 | TGAAAAGCTATATCCATAT | 120 | 3030 |
| 877164 | N/A | N/A | 74213 | 74232 | AAAAAAACTTTCAGTAATC | 142 | 3031 |
| 877188 | N/A | N/A | 76212 | 76231 | AACACAATCCACAACAGAAT | 89 | 3032 |
| 877212 | N/A | N/A | 78681 | 78700 | AGGAGGAAAATACTATCCAA | 59 | 3033 |
| 877243 | N/A | N/A | 83326 | 83345 | TATATGCACAGTTTTGCTGA | 71 | 3034 |
| 877267 | N/A | N/A | 86866 | 86885 | AGAACAGAAAGCTCAGTTTT | 80 | 3035 |
| 877291 | N/A | N/A | 89005 | 89024 | CTCTCAGAAACATTTTCTCA | 66 | 3036 |
| 877315 | N/A | N/A | 90693 | 90712 | AACAAAACTTAAAAGTGTCT | 166 | 3037 |
| 877339 | N/A | N/A | 92828 | 92847 | AAACAACTCACACATTTCTA | 84 | 3038 |
| 877363 | N/A | N/A | 95003 | 95022 | AGTTGAGTTACCTCCTGATA | 72 | 3039 |
| 877387 | N/A | N/A | 96290 | 96309 | TCTGGTTACTAGAATGTAGC | 104 | 3040 |
| 877411 | N/A | N/A | 99458 | 99477 | GATTGCCTACTCCAAGGTTT | 56 | 3041 |
| 877435 | N/A | N/A | 101844 | 101863 | AGGCTTTTAATGAATATTTC | 80 | 3042 |
| 877459 | N/A | N/A | 104859 | 104878 | GGTATTGAGAGAGCTTCAGA | 51 | 3043 |
| 877483 | N/A | N/A | 106692 | 106711 | GAAAAGACAAACTAGGATTG | 70 | 3044 |
| 877507 | N/A | N/A | 109824 | 109843 | GTAGAACAGAGTCTGAAGTA | 67 | 3045 |
| 877531 | N/A | N/A | 111551 | 111570 | CTGTAACTCTGTTGAAATGT | 96 | 3046 |
| 877555 | N/A | N/A | 113739 | 113758 | TCAAAGACCACAGCCTTTCC | 116 | 3047 |
| 877579 | N/A | N/A | 116515 | 116534 | GCTAAGAGACTTCTTTCTTC | 48 | 3048 |
| 877603 | N/A | N/A | 118863 | 118882 | ACTAAAGTTTTTGCTGTTAC | 51 | 3049 |
| 877627 | N/A | N/A | 120815 | 120834 | CGGAAAAGACAAGAAGATAA | 82 | 3050 |
| 877651 | N/A | N/A | 122955 | 122974 | TTATCATGTGAATTAGCATA | 47 | 3051 |
| 877675 | N/A | N/A | 126419 | 126438 | CCAGACATTGCAAAGAAAAA | 65 | 3052 |
| 877699 | N/A | N/A | 129171 | 129190 | AGTGTGAAGGCACCGTAAGA | 73 | 3053 |
| 877723 | N/A | N/A | 133344 | 133363 | CCAATTCCATCCATTGAAAT | 69 | 3054 |
| 877747 | N/A | N/A | 137747 | 137766 | AAAAGTGATTAGGTTGAGTG | 62 | 3055 |
| 877771 | N/A | N/A | 140595 | 140614 | TATTTTCTACATACCCCTCG | 93 | 3056 |
| 877795 | N/A | N/A | 142281 | 142300 | ATCTAAAATGTTCTCAAGAG | 136 | 3057 |
| 877819 | N/A | N/A | 144428 | 144447 | GTTGGCTTCTCAGAGGTTTT | 50 | 3058 |

TABLE 40

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 24 | 222 |
| 803632 | N/A | N/A | 81595 87852 | 81614 87871 | TAAAAAGCCATAGTGTTTGA | 91 | 1794 |
| 876018 | 441 | 460 | 10465 | 10484 | ACCAAGGACTTCCCAATCAT | 69 | 32 |
| 876042 | 828 | 847 | 21659 | 21678 | GAGGACTTCCACATTATTGC | 19 | 3059 |
| 876066 | 1105 | 1124 | 29366 | 29385 | TCTCATTCTTTTCCTCTAAA | 30 | 3060 |
| 876090 | 1471 | 1490 | 35418 | 35437 | CAGGAGAATGTATATGCTTC | 25 | 3061 |
| 876114 | 1580 | 1599 | 37629 | 37648 | CGTTTCATAACTGTTAGTAT | 46 | 3062 |
| 876138 | 2218 | 2237 | 56226 | 56245 | CATCCATAGCTACTTTTGCA | 54 | 3063 |
| 876162 | 2848 | 2867 | 71691 | 71710 | ATTCTCCTACACTAATTGAA | 64 | 3064 |
| 876186 | 3225 | 3244 | 76359 | 76378 | GTCCAAATGTGTCAAACTCT | 20 | 3065 |
| 876210 | 3797 | 3816 | 82142 | 82161 | ATCTGATTATGGCTAAATAA | 48 | 3066 |
| 876234 | 4048 | 4067 | 84043 | 84062 | TGGCTTTACATCCTATATGT | 43 | 3067 |
| 876258 | 4692 | 4711 | 92115 | 92134 | AAGTTCTACATAGCAGTCTG | 34 | 3068 |
| 876282 | 5044 | 5063 | 98192 | 98211 | GTGACATGTAGTTCTTTGGA | 11 | 3069 |
| 876306 | 5201 | 5220 | 99207 | 99226 | AAATAAGGCATTTCATATAG | 56 | 3070 |
| 876330 | 5650 | 5669 | 101288 | 101307 | TGGTGAGCCTTGGTTGATCT | 42 | 3071 |
| 876354 | 6155 | 6174 | 118488 | 118507 | TAGTCAGCAATCTTTGCAAT | 96 | 3072 |
| 876378 | 6782 | 6801 | 132492 | 132511 | ATGACCAGGAGAGTACCAGA | 69 | 3073 |
| 876402 | 7537 | 7556 | 145140 | 145159 | TTTTCCGGTTGTAGCCCAAT | 70 | 3074 |
| 876426 | 8594 | 8613 | 146763 | 146782 | TGTAGGATCTGCAGCATCAC | 60 | 3075 |
| 876450 | N/A | N/A | 3743 | 3762 | ACAATGCCTTTACCTGCTGC | 98 | 3076 |
| 876474 | N/A | N/A | 5889 | 5908 | TACTTCAGCCCAGGATTGCA | 70 | 3077 |
| 876498 | N/A | N/A | 7911 | 7930 | CTACATGGAACTTCTGTGAT | 71 | 3078 |
| 876522 | N/A | N/A | 10992 | 11011 | CAGATGTGCTGAAAGTTAAT | 62 | 3079 |
| 876546 | N/A | N/A | 14076 | 14095 | ATGAGATTTTGAGAGGCAA | 107 | 3080 |
| 876570 | N/A | N/A | 15984 | 16003 | AATTTTTACATGAAGACTGT | 83 | 3081 |
| 876594 | N/A | N/A | 18271 | 18290 | CTAGAGAAAACTGACAGTGA | 80 | 3082 |
| 876618 | N/A | N/A | 20538 | 20557 | AAAGACTCTACCAGAAAAAG | 106 | 3083 |
| 876642 | N/A | N/A | 23590 | 23609 | AATGTATGGTGACTTGACCT | 97 | 3084 |
| 876666 | N/A | N/A | 26378 | 26397 | AACAAAACCACTTCTTCTTC | 69 | 3085 |
| 876690 | N/A | N/A | 28864 | 28883 | TGAAGAGAAAACCACACACT | 50 | 3086 |
| 876714 | N/A | N/A | 30858 | 30877 | TTATAGTTCATTTTTTAAGA | 159 | 3087 |
| 876738 | N/A | N/A | 32945 | 32964 | ACTCCAAAGACAATACAAAA | 102 | 3088 |
| 876762 | N/A | N/A | 34263 | 34282 | CAACTGGCCAATTTTCCTCT | 60 | 3089 |
| 876786 | N/A | N/A | 36893 | 36912 | GATACATTCCTTCTTTTCCA | 50 | 3090 |

TABLE 40-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876810 | N/A | N/A | 38645 | 38664 | CCTTTTCTTTGGGCCTCAGC | 55 | 3091 |
| 876834 | N/A | N/A | 40906 | 40925 | ACTTCTGAGGCTGCCTATTA | 102 | 3092 |
| 876858 | N/A | N/A | 42989 | 43008 | CCAATTCATCTTATGCAAAA | 50 | 3093 |
| 876882 | N/A | N/A | 46918 | 46937 | ATTTCCTGAGCCACCCTTCT | 62 | 3094 |
| 876906 | N/A | N/A | 48113 | 48132 | ATTAAGTACTTGTCCAGGGT | 41 | 3095 |
| 876930 | N/A | N/A | 50500 | 50519 | GACACAGAGAGCTGTGAGCA | 73 | 3096 |
| 876954 | N/A | N/A | 53300 | 53319 | GAATAACCATGCTGACTTTA | 66 | 3097 |
| 876978 | N/A | N/A | 56491 | 56510 | AAGACACAAACAATTGCAAT | 98 | 3098 |
| 877002 | N/A | N/A | 59243 | 59262 | TGATAGAAGTGTTTGGTTTT | 60 | 3099 |
| 877026 | N/A | N/A | 61360 | 61379 | GGTTAGCATGTGAGGTGCCA | 83 | 3100 |
| 877050 | N/A | N/A | 63441 | 63460 | AAGGTTACAACCATGAACAA | 158 | 3101 |
| 877074 | N/A | N/A | 66455 | 66474 | ATATTGCATAACTTAATAGC | 106 | 3102 |
| 877098 | N/A | N/A | 68250 | 68269 | AGAGCATTTTCAACACCTA | 13 | 3103 |
| 877122 | N/A | N/A | 71326 | 71345 | ATAGTCCAGCAGGAAAAAGC | 81 | 3104 |
| 877146 | N/A | N/A | 73085 | 73104 | TGAATAATTGGAGGAAATTC | 98 | 3105 |
| 877170 | N/A | N/A | 74875 | 74894 | CTCTGTCTCCAGATATAAAA | 27 | 3106 |
| 877194 | N/A | N/A | 77081 | 77100 | AATTAGTTGTAAAAATGTAA | 118 | 3107 |
| 877218 | N/A | N/A | 79715 | 79734 | CAGGACACTCCTAGAAGCTG | 44 | 3108 |
| 877249 | N/A | N/A | 84418 | 84437 | TGCTATATGAAATACAGTGT | 58 | 3109 |
| 877273 | N/A | N/A | 87070 | 87089 | GACCATGTTTAGAGAACTAT | 48 | 3110 |
| 877297 | N/A | N/A | 89927 | 89946 | TTACATGACATTACCATCTA | 50 | 3111 |
| 877321 | N/A | N/A | 91204 | 91223 | CAGAATTTCTGCTTAAATTC | 56 | 3112 |
| 877345 | N/A | N/A | 93276 | 93295 | GAAACATGGAATCTAGAACA | 150 | 3113 |
| 877369 | N/A | N/A | 95294 | 95313 | CAAATTAACTTAATTTTTAC | 125 | 3114 |
| 877393 | N/A | N/A | 97092 | 97111 | GCCCAAGGACTTGTCTTACC | 52 | 3115 |
| 877417 | N/A | N/A | 100614 | 100633 | GTATCAAAACATACCTTCCT | 108 | 3116 |
| 877441 | N/A | N/A | 102459 | 102478 | TTCTCACCACATAAATATTT | 67 | 3117 |
| 877465 | N/A | N/A | 105189 | 105208 | CCTTGAAATGTAGTCACTTG | 61 | 3118 |
| 877489 | N/A | N/A | 107021 | 107040 | ACAGAAGGCGAAGTCAGGAG | 90 | 3119 |
| 877513 | N/A | N/A | 110256 | 110275 | GGCCACAGTGATCAGTTTGG | 56 | 3120 |
| 877537 | N/A | N/A | 112156 | 112175 | AAAAAATACATATCATCCCC | 124 | 3121 |
| 877561 | N/A | N/A | 114361 | 114380 | ATAATCCTTTATAATAAGTA | 118 | 3122 |
| 877585 | N/A | N/A | 117351 | 117370 | CACAAGACTTAATGGAGTTA | 61 | 3123 |
| 877609 | N/A | N/A | 119274 | 119293 | AACAAATGCCAACCCCTAAA | 103 | 3124 |
| 877633 | N/A | N/A | 121503 | 121522 | TATAGTATTTATATGGGTGT | 50 | 3125 |
| 877657 | N/A | N/A | 124119 | 124138 | ACAAAGGGAAATGGTTAAAC | 40 | 3126 |

TABLE 40-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877681 | N/A | N/A | 126991 | 127010 | ACGGGCACCCTACAAGAAAT | 117 | 3127 |
| 877705 | N/A | N/A | 129885 | 129904 | AGTAACTTTCCAAATGGTAT | 69 | 3128 |
| 877729 | N/A | N/A | 134033 | 134052 | CTCTGCCCCTTTTCCCAGAC | 83 | 3129 |
| 877753 | N/A | N/A | 138357 | 138376 | TTACCAGGTGCTGGTCATTA | 24 | 3130 |
| 877777 | N/A | N/A | 140907 | 140926 | ATAAAGAAAAATTACGAACA | 79 | 3131 |
| 877801 | N/A | N/A | 142946 | 142965 | TTTACCATTACCTCCCTAGA | 61 | 3132 |
| 877825 | N/A | N/A | 144861 | 144880 | CAGCTTAACCTTTCTATAAA | 60 | 3133 |

TABLE 41

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 16 | 222 |
| 876020 | 528 | 547 | 13794 | 13813 | GAGGAGATCTAAGGTCTTCA | 35 | 2603 |
| 876044 | 830 | 849 | 21661 | 21680 | ATGAGGACTTCCACATTATT | 47 | 2604 |
| 876068 | 1161 | 1180 | 29422 | 29441 | ACAGGCTTCCAGCCAAAACA | 63 | 2605 |
| 876092 | 1473 | 1492 | 35420 | 35439 | TTCAGGAGAATGTATATGCT | 46 | 2606 |
| 876116 | 1637 | 1656 | 37686 | 37705 | ATAAAATGTAAAATAGCTCG | 112 | 2607 |
| 876140 | 2262 | 2281 | 56270 | 56289 | ATTCTGATCACACGCTCTCT | 42 | 2608 |
| 876164 | 2869 | 2888 | 71712 | 71731 | GTAATACGGCATCTCGGTAA | 66 | 2609 |
| 876188 | 3228 | 3247 | 76362 | 76381 | CAAGTCCAAATGTGTCAAAC | 58 | 2610 |
| 876212 | 3800 | 3819 | 82145 | 82164 | CTGATCTGATTATGGCTAAA | 59 | 2611 |
| 876236 | 4144 | 4163 | 86639 | 86658 | TTTTACCACTCCCAGTATTT | 114 | 2612 |
| 876260 | 4725 | 4744 | 92148 | 92167 | CACATTTTACGCTCCGATA | 31 | 2613 |
| 876284 | 5046 | 5065 | 98194 | 98213 | CTGTGACATGTAGTTCTTTG | 39 | 2614 |
| 876308 | 5338 | 5357 | 100190 | 100209 | CTTCAGGAGACCAATTTAAG | 48 | 2615 |
| 876332 | 5652 | 5671 | 101290 | 101309 | AATGGTGAGCCTTGGTTGAT | 57 | 2616 |
| 876356 | 6204 | 6223 | 118537 | 118556 | GCCCTCTGATGTTTTTATCC | 98 | 2617 |
| 876380 | 6826 | 6845 | 132536 | 132555 | TCATCTTTTCTAGGGTATGT | 43 | 2618 |
| 876404 | 7660 | 7679 | 145829 | 145848 | TTTCAGCTAATTCTTTTCTC | 56 | 2619 |
| 876428 | 8683 | 8702 | 146852 | 146871 | GAAAAGTGTTAGATATTTAT | 135 | 2620 |
| 876452 | N/A | N/A | 3761 | 3780 | GAATGAGTTGAAGTGAAAAC | 120 | 2621 |
| 876476 | N/A | N/A | 6208 | 6227 | ATCCAGTAATCTCATCGCTG | 47 | 2622 |

TABLE 41-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876500 | N/A | N/A | 8095 | 8114 | ATTCTGAACAGCTTCTGGTG | 136 | 2623 |
| 876524 | N/A | N/A | 11128 | 11147 | TTTTCCTGGAAACACATTCT | 114 | 2624 |
| 876548 | N/A | N/A | 14203 | 14222 | AAGGGCAGGAATGACCACTA | 72 | 2625 |
| 876572 | N/A | N/A | 16432 | 16451 | GCAATTGAAGAAAGTCTACT | 56 | 2626 |
| 876596 | N/A | N/A | 18903 | 18922 | GTTTCTCCAGCACCAAGCCC | 49 | 2627 |
| 876620 | N/A | N/A | 20690 | 20709 | TTCCAGAAGGGCAACCAATG | 100 | 2628 |
| 876644 | N/A | N/A | 23667 | 23686 | GAACTGGACAAGTTAATCCT | 47 | 2629 |
| 876668 | N/A | N/A | 26426 | 26445 | TGCTGTTCTAGACAATTTGG | 46 | 2630 |
| 876692 | N/A | N/A | 29204 | 29223 | AAGCCTTGGTCAATTATAAA | 91 | 2631 |
| 876716 | N/A | N/A | 30940 | 30959 | CACTTGCCATTATCAAATAT | 84 | 2632 |
| 876740 | N/A | N/A | 33139 | 33158 | TGTATGCAACCTTGGGACCT | 57 | 2633 |
| 876764 | N/A | N/A | 34714 | 34733 | TGGAAAGCATTTACATAGAA | 47 | 2634 |
| 876788 | N/A | N/A | 36957 | 36976 | TGTTAACTGAAACTTGTGCA | 70 | 2635 |
| 876812 | N/A | N/A | 38785 | 38804 | TCTATCATCCTCTGCACCAC | 69 | 2636 |
| 876836 | N/A | N/A | 41061 | 41080 | TAAGGAAGGCAGCCTTGATA | 54 | 2637 |
| 876860 | N/A | N/A | 43045 | 43064 | TTTATAAAATGTTCACACT | 112 | 2638 |
| 876884 | N/A | N/A | 47090 | 47109 | AATCTCATCCATCTGTAATT | 50 | 2639 |
| 876908 | N/A | N/A | 48315 | 48334 | TACTCTGATTTCCTCATCTT | 58 | 2640 |
| 876932 | N/A | N/A | 50766 | 50785 | CTTTACAATGTCTTCTTTTA | 139 | 2641 |
| 876956 | N/A | N/A | 53309 | 53328 | ATAAATGGTGAATAACCATG | 60 | 2642 |
| 876980 | N/A | N/A | 56543 | 56562 | TGGATAACACCTAAAGGACC | 122 | 2643 |
| 877004 | N/A | N/A | 59276 | 59295 | GTATTTGGAGCAGTGCCCAG | 110 | 2644 |
| 877028 | N/A | N/A | 61596 | 61615 | GTACCTTAACACAGTAAATA | 82 | 2645 |
| 877052 | N/A | N/A | 63476 | 63495 | TAATCTACTATGTGCAAAAC | 100 | 2646 |
| 877076 | N/A | N/A | 66557 | 66576 | TCTACATTGTCAGGAAGCAA | 66 | 2647 |
| 877100 | N/A | N/A | 68445 | 68464 | ATCTCTCACAGATGCAAAAT | 82 | 2648 |
| 877124 | N/A | N/A | 71781 | 71800 | ATAATCACAATTGCACAATT | 109 | 2649 |
| 877148 | N/A | N/A | 73144 | 73163 | GAATCATTAGGTAAATATAT | 99 | 2650 |
| 877172 | N/A | N/A | 74948 | 74967 | AGTGGAGAAGAGAGAAAGAC | 92 | 2651 |
| 877196 | N/A | N/A | 77137 | 77156 | TATCAAAAACAATTTGCTTT | 136 | 2652 |
| 877220 | N/A | N/A | 79895 | 79914 | ACAGTCTCTTTTCTTATCTG | 76 | 2653 |
| 877232 | N/A | N/A | 81609 | 81628 | TTTAGTGTCAATTCTAAAAA | 119 | 2654 |
| 877251 | N/A | N/A | 84464 | 84483 | CAGTAGCTATAATGCTTTAA | 80 | 2655 |
| 877275 | N/A | N/A | 87627 | 87646 | TTTAGATTTCATTTAAGAAA | 105 | 2656 |
| 877299 | N/A | N/A | 89982 | 90001 | AATTACATGTCCAACAAGAG | 92 | 2657 |
| 877323 | N/A | N/A | 91362 | 91381 | AATAAAGTATCTTCCAAAC | 91 | 2658 |

TABLE 41-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877347 | N/A | N/A | 93509 | 93528 | AAATTCACAAAAGTTTCTGC | 80 | 2659 |
| 877371 | N/A | N/A | 95698 | 95717 | TTTCATATCTCTTTTATCAT | 97 | 2660 |
| 877395 | N/A | N/A | 97239 | 97258 | TTTTGCTTTGTCAAATTCAC | 45 | 2661 |
| 877419 | N/A | N/A | 100725 | 100744 | CTATAATTGAATATACTATT | 108 | 2662 |
| 877443 | N/A | N/A | 102592 | 102611 | ATTAAATCAATCTAATGCAT | 105 | 2663 |
| 877467 | N/A | N/A | 105313 | 105332 | CTCAATCCCCAAGGAGTTTG | 60 | 2664 |
| 877491 | N/A | N/A | 107115 | 107134 | CTTTCACCCTGAACACACAG | 68 | 2665 |
| 877515 | N/A | N/A | 110361 | 110380 | CTCAACCCTCACCCATGCAG | 93 | 2666 |
| 877539 | N/A | N/A | 112217 | 112236 | CCTGCTTATAATCTCTGGTT | 87 | 2667 |
| 877563 | N/A | N/A | 114595 | 114614 | TCTGAAGGCTTACTATTTTA | 71 | 2668 |
| 877587 | N/A | N/A | 117410 | 117429 | ACTACAGCATTTCATGTGAT | 46 | 2669 |
| 877611 | N/A | N/A | 119355 | 119374 | ATGTATAGCCACCTGTAATT | 93 | 2670 |
| 877635 | N/A | N/A | 121814 | 121833 | CTTGGATAATTATCATAATG | 41 | 2671 |
| 877659 | N/A | N/A | 124271 | 124290 | TCTCTTGGGTTCATGCCTGA | 67 | 2672 |
| 877683 | N/A | N/A | 127120 | 127139 | TAAATATTTTGTAGCTCTA | 83 | 2673 |
| 877707 | N/A | N/A | 130019 | 130038 | TGTTTCTAGGGACCCTGAGC | 58 | 2674 |
| 877731 | N/A | N/A | 134194 | 134213 | AAATGTTGAAATTGTTACAA | 150 | 2675 |
| 877755 | N/A | N/A | 138536 | 138555 | AAATGACAATTAGGAGGGTC | 78 | 2676 |
| 877779 | N/A | N/A | 141131 | 141150 | CTTGCAAAACTTTGTTTCAT | 66 | 2677 |
| 877803 | N/A | N/A | 143288 | 143307 | AATTTATACCAGTCTTATGT | 126 | 2678 |
| 877827 | N/A | N/A | 144888 | 144907 | ATTCTTAATTATGTGAGTCT | 77 | 2679 |

TABLE 42

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 35 | 222 |
| 803640 | N/A | N/A | 81631 87888 | 81650 87907 | TGCAGCATCATGCAAGCAGC | 22 | 1802 |
| 876022 | 547 | 566 | N/A | N/A | TGATTTTACCTGAAGTTAGG | 82 | 3134 |
| 876046 | 832 | 851 | 21663 | 21682 | TCATGAGGACTTCCACATTA | 50 | 3135 |
| 876070 | 1231 | 1250 | 29582 | 29601 | GATTATTTAGTGCCCAGCAT | 47 | 3136 |
| 876094 | 1475 | 1494 | 35422 | 35441 | ACTTCAGGAGAATGTATATG | 58 | 3137 |
| 876118 | 1683 | 1702 | 41916 | 41935 | ATGAAATTCTGTATCCTCCC | 70 | 3138 |

TABLE 42 -continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876142 | 2306 | 2325 | 56314 | 56333 | GCATCTGCTCCCAATAGAAG | 48 | 3139 |
| 876166 | 2871 | 2890 | 71714 | 71733 | CTGTAATACGGCATCTCGGT | 25 | 3140 |
| 876190 | 3231 | 3250 | 76365 | 76384 | GTGCAAGTCCAAATGTGTCA | 15 | 3141 |
| 876214 | 3803 | 3822 | 82148 | 82167 | ATGCTGATCTGATTATGGCT | 76 | 3142 |
| 876238 | 4190 | 4209 | 86685 | 86704 | CCAAGATCTGATTTCTTGGT | 72 | 139 |
| 876262 | 4728 | 4747 | 92151 | 92170 | TGGCACATTTTTACGCTCCG | 26 | 3143 |
| 876286 | 5049 | 5068 | 98197 | 98216 | ATACTGTGACATGTAGTTCT | 24 | 3144 |
| 876310 | 5429 | 5448 | N/A | N/A | AGAATACAGCCTTTTCTACA | 53 | 3145 |
| 876334 | 5655 | 5674 | 101293 | 101312 | TGGAATGGTGAGCCTTGGTT | 41 | 3146 |
| 876358 | 6249 | 6268 | 124880 | 124899 | AATGACATTTCCTCTGGCAA | 69 | 3147 |
| 876382 | 6870 | 6889 | 132580 | 132599 | TTGCTTGGAAAAGGAATTGC | 63 | 3148 |
| 876406 | 7747 | 7766 | 145916 | 145935 | AATAAATATTTACAAGAGGA | 165 | 3149 |
| 876430 | 8774 | 8793 | 146943 | 146962 | GCTATGTAAACAATTTAAGT | 96 | 3150 |
| 876454 | N/A | N/A | 4075 | 4094 | ATTGGGAAGATACTTGGAAT | 86 | 3151 |
| 876478 | N/A | N/A | 6864 | 6883 | ACACAAATCATTTCAAAATG | 80 | 3152 |
| 876502 | N/A | N/A | 8430 | 8449 | GGCACAAGTTTCTTACTCGC | 56 | 3153 |
| 876526 | N/A | N/A | 11515 | 11534 | TCTAATTTGTCTAAATTTAT | 120 | 3154 |
| 876550 | N/A | N/A | 14441 | 14460 | CTCTGCACTTCAGTGTTTGT | 55 | 3155 |
| 876574 | N/A | N/A | 16653 | 16672 | ATCTCAGTTATCAATCTCAG | 51 | 3156 |
| 876598 | N/A | N/A | 19231 | 19250 | ATAACCCCACACCTTTACTG | 239 | 3157 |
| 876622 | N/A | N/A | 20813 | 20832 | CGAGGCTCAACCCCATTGGA | 58 | 3158 |
| 876646 | N/A | N/A | 23976 | 23995 | TATATAATTGCTAGGTAGAG | 52 | 3159 |
| 876670 | N/A | N/A | 26660 | 26679 | TCATTCAGCTACTTTTGAAA | 55 | 3160 |
| 876694 | N/A | N/A | 29232 | 29251 | ACCAACAGAATGAGGTGTGC | 36 | 3161 |
| 876718 | N/A | N/A | 30990 | 31009 | ATTCAAACAAAATGTTAGTA | 125 | 3162 |
| 876742 | N/A | N/A | 33417 | 33436 | ACTCAATAGTCACCTTCTTT | 60 | 3163 |
| 876766 | N/A | N/A | 34874 | 34893 | ATGTGGAGGTATCGACCATT | 32 | 3164 |
| 876790 | N/A | N/A | 37365 | 37384 | CGGGAATTATTTCACTTCAT | 21 | 3165 |
| 876814 | N/A | N/A | 38809 | 38828 | CCTTGTATCTAGTCTCTCTC | 49 | 3166 |
| 876838 | N/A | N/A | 41299 | 41318 | CTACAAGTCAAAAATGTGGT | 71 | 3167 |
| 876862 | N/A | N/A | 43081 | 43100 | ATCATTTCCATTAATTATTT | 72 | 3168 |
| 876886 | N/A | N/A | 47247 | 47266 | CTTAGAATGAAATTGCTGAT | 48 | 3169 |
| 876910 | N/A | N/A | 48381 | 48400 | TGCCAATGTGGAGTTAATTT | 103 | 3170 |
| 876934 | N/A | N/A | 50807 | 50826 | TAATTATTCTCAGTCTTTAA | 110 | 3171 |
| 876958 | N/A | N/A | 53342 | 53361 | TCTTAGCACATTCTCTGAAC | 61 | 3172 |

TABLE 42 -continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876982 | N/A | N/A | 56609 | 56628 | GACACATTTGAAAAGTTATT | 45 | 3173 |
| 877006 | N/A | N/A | 59726 | 59745 | TCTTTAGAATATTCACACAT | 112 | 3174 |
| 877030 | N/A | N/A | 61906 | 61925 | ACTGGCAAATCAAACTTCAT | 104 | 3175 |
| 877054 | N/A | N/A | 63890 | 63909 | AATGTAATCTTTATCAGGAC | 65 | 3176 |
| 877078 | N/A | N/A | 66625 | 66644 | TTGGAAAACAGACACAAAAG | 61 | 3177 |
| 877102 | N/A | N/A | 68600 | 68619 | GGCCTTTGCTGGTGAAGTCT | 39 | 3178 |
| 877126 | N/A | N/A | 71855 | 71874 | GAAATCCCTACCAATTGTTC | 119 | 3179 |
| 877150 | N/A | N/A | 73433 | 73452 | CAATCAGGCTTTCTTCAAGG | 88 | 3180 |
| 877174 | N/A | N/A | 75007 | 75026 | TGATGAAGTGACAGTTAAAT | 116 | 3181 |
| 877198 | N/A | N/A | 77396 | 77415 | GTACAACTTAGAGGGCCTGG | 38 | 3182 |
| 877222 | N/A | N/A | 80337 | 80356 | AGTTCTCAATACTCTGGTAT | 35 | 3183 |
| 877253 | N/A | N/A | 84478 | 84497 | ATTTCACATGATGTCAGTAG | 61 | 3184 |
| 877277 | N/A | N/A | 87800 | 87819 | AGATAGAAAAGCAACAAAAG | 153 | 3185 |
| 877301 | N/A | N/A | 90174 | 90193 | CAACAAGTCTTTTAAAGAT | 74 | 3186 |
| 877325 | N/A | N/A | 91493 | 91512 | AACATCAGTGATTCTGATAG | 136 | 3187 |
| 877349 | N/A | N/A | 93656 | 93675 | GGATCTAGTAAAGCAGCATG | 39 | 3188 |
| 877373 | N/A | N/A | 95702 | 95721 | TCTCTTTCATATCTCTTTTA | 42 | 3189 |
| 877397 | N/A | N/A | 97648 | 97667 | GAATAGGAAGACAGACTGTG | 69 | 3190 |
| 877421 | N/A | N/A | 100889 | 100908 | TCTTTATAACAGTTCTATGA | 99 | 3191 |
| 877445 | N/A | N/A | 102737 | 102756 | GACAACTTTTTGCTAATAAT | 70 | 3192 |
| 877469 | N/A | N/A | 105355 | 105374 | TTCAGGCCTCCATACCCTTG | 184 | 3193 |
| 877493 | N/A | N/A | 107755 | 107774 | AGAGAATCCATTTGACTTTG | 37 | 3194 |
| 877517 | N/A | N/A | 110432 | 110451 | GAATACAGGAATAACCACTG | 61 | 3195 |
| 877541 | N/A | N/A | 112355 | 112374 | AACAGTGCACACAGTGTAGT | 46 | 3196 |
| 877565 | N/A | N/A | 114614 | 114633 | CTACTGTCAACACAGTAATT | 72 | 3197 |
| 877589 | N/A | N/A | 117436 | 117455 | CTTCTCTGCCCCATGATGTC | 56 | 3198 |
| 877613 | N/A | N/A | 119406 | 119425 | TTTCTTCTGTGCCAGGCACG | 47 | 3199 |
| 877637 | N/A | N/A | 121914 | 121933 | GCCACTATTAAGTGGTAGAG | 52 | 3200 |
| 877661 | N/A | N/A | 124653 | 124672 | CCAAGGTTGACCACACAGGA | 66 | 3201 |
| 877685 | N/A | N/A | 127508 | 127527 | TCATAAGATTTGACAGCATG | 48 | 3202 |
| 877709 | N/A | N/A | 130133 | 130152 | TTCAGAAACCACATTTCTGC | 123 | 3203 |
| 877733 | N/A | N/A | 134456 | 134475 | CAATCAGCAAGTATTTTCAG | 113 | 3204 |
| 877757 | N/A | N/A | 138991 | 139010 | GTGGTGCTTGGACTGAAATA | 85 | 3205 |
| 877781 | N/A | N/A | 141186 | 141205 | TTGTACTATATCTAAATTTC | 89 | 3206 |

TABLE 42-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877805 | N/A | N/A | 143353 | 143372 | TAATCTGCTTCTCTTGTGGG | 71 | 3207 |
| 877829 | N/A | N/A | 145054 | 145073 | ATATTAAACTGGCCTGAAAA | 145 | 3208 |

TABLE 43

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 49 | 222 |
| 803641 | N/A | N/A | 81632 87889 | 81651 87908 | TTGCAGCATCATGCAAGCAG | 57 | 1803 |
| 876023 | 662 | 681 | 16182 | 16201 | AGCACATGTAAAGCTTTGCA | 51 | 3209 |
| 876047 | 833 | 852 | 21664 | 21683 | CTCATGAGGACTTCCACATT | 60 | 3210 |
| 876071 | 1232 | 1251 | 29583 | 29602 | AGATTATTTAGTGCCCAGCA | 43 | 3211 |
| 876095 | 1476 | 1495 | 35423 | 35442 | CACTTCAGGAGAATGTATAT | 35 | 3212 |
| 876119 | 1694 | 1713 | 41927 | 41946 | TTTAGCTTATGATGAAATTC | 36 | 3213 |
| 876143 | 2395 | 2414 | 62016 | 62035 | CACTATTCAGTAAGAGTTCC | 19 | 3214 |
| 876167 | 2873 | 2892 | 71716 | 71735 | CGCTGTAATACGGCATCTCG | 58 | 3215 |
| 876191 | 3250 | 3269 | 76384 | 76403 | ATGATGTAAATTTATTACTG | 75 | 3216 |
| 876215 | 3804 | 3823 | 82149 | 82168 | GATGCTGATCTGATTATGGC | 33 | 3217 |
| 876239 | 4232 | 4251 | 86727 | 86746 | GGCCAGTCTTTCACATCTAT | 39 | 3218 |
| 876263 | 4729 | 4748 | 92152 | 92171 | TTGGCACATTTTTACGCTCC | 21 | 3219 |
| 876287 | 5050 | 5069 | 98198 | 98217 | AATACTGTGACATGTAGTTC | 38 | 3220 |
| 876311 | 5434 | 5453 | N/A | N/A | CCAAAAGAATACAGCCTTTT | 52 | 3221 |
| 876335 | 5660 | 5679 | 101298 | 101317 | GATATTGGAATGGTGAGCCT | 28 | 3222 |
| 876359 | 6288 | 6307 | 124919 | 124938 | TAGTAAACCAAATGAATAAA | 78 | 3223 |
| 876383 | 6953 | 6972 | N/A | N/A | CCTTTAAGCTTAACAGTCTT | 125 | 3224 |
| 876407 | 7856 | 7875 | 146025 | 146044 | TTACTGGTAAGTATTTTTAC | 57 | 3225 |
| 876431 | 8779 | 8798 | 146948 | 146967 | GGTAAGCTATGTAAACAATT | 105 | 3226 |
| 876455 | N/A | N/A | 4112 | 4131 | AACTATTCATAATCTTCTCA | 93 | 3227 |
| 876479 | N/A | N/A | 6910 | 6929 | TTGGCTGTGCAAAAGAAGGA | 112 | 3228 |
| 876503 | N/A | N/A | 8563 | 8582 | CTGCTACATGATAAGGAAGC | 62 | 3229 |
| 876527 | N/A | N/A | 11614 | 11633 | CACACCCTTTATGTACTGAA | 33 | 3230 |
| 876551 | N/A | N/A | 14462 | 14481 | TCTTAGTGGCCAAAGCAACT | 80 | 3231 |
| 876575 | N/A | N/A | 16768 | 16787 | TCACAAGCTCTGTGTCCTCA | 45 | 3232 |

TABLE 43-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876599 | N/A | N/A | 19233 | 19252 | TCATAACCCCACACCTTTAC | 91 | 3233 |
| 876623 | N/A | N/A | 20902 | 20921 | TTTTTTTTGATGTGGAGAAA | 161 | 3234 |
| 876647 | N/A | N/A | 24058 | 24077 | GACTCATGTAAGAAGACAAG | 48 | 3235 |
| 876671 | N/A | N/A | 26694 | 26713 | TTTAATTTTAACTATGAAGA | 101 | 3236 |
| 876695 | N/A | N/A | 29272 | 29291 | TAACAGTTTGACCAACTCTA | 76 | 3237 |
| 876719 | N/A | N/A | 30991 | 31010 | AATTCAAACAAAATGTTAGT | 180 | 3238 |
| 876743 | N/A | N/A | 33419 | 33438 | TTACTCAATAGTCACCTTCT | 62 | 3239 |
| 876767 | N/A | N/A | 34973 | 34992 | TTCCAATACTTAAAACAAGT | 76 | 3240 |
| 876791 | N/A | N/A | 37386 | 37405 | AAGATAGAATTCATAGTAAT | 108 | 3241 |
| 876815 | N/A | N/A | 38831 | 38850 | CCATGGACCTCCAACCCAAT | 86 | 3242 |
| 876839 | N/A | N/A | 41301 | 41320 | CACTACAAGTCAAAATGTG | 62 | 3243 |
| 876863 | N/A | N/A | 43157 | 43176 | ATTTTTAAGGGAGATCTCTC | 56 | 3244 |
| 876887 | N/A | N/A | 47300 | 47319 | TTCATGTCTAATAATCTTTA | 64 | 3245 |
| 876911 | N/A | N/A | 48530 | 48549 | TCTAAAGAAATTCAGACAAC | 115 | 3246 |
| 876935 | N/A | N/A | 50878 | 50897 | CAAAGAAAAAGTCCAATAA | 168 | 3247 |
| 876959 | N/A | N/A | 53439 | 53458 | GCAACCTGCAATAAAACCCA | 43 | 3248 |
| 876983 | N/A | N/A | 56638 | 56657 | AGACTAAGTTGTAGAGATGC | 79 | 3249 |
| 877007 | N/A | N/A | 59787 | 59806 | TAAAATAAATAAATGCCAGC | 125 | 3250 |
| 877031 | N/A | N/A | 62296 | 62315 | ACTAAAAGACTAGTGACTTA | 69 | 3251 |
| 877055 | N/A | N/A | 64013 | 64032 | GAACCCATTTCTGGAGGGTT | 180 | 3252 |
| 877079 | N/A | N/A | 66732 | 66751 | CACTAGAACAGCTAAAAGTA | 172 | 3253 |
| 877103 | N/A | N/A | 68807 | 68826 | TCACTAACAGGATAATTAAA | 103 | 3254 |
| 877127 | N/A | N/A | 72021 | 72040 | TGAAGTGTACTGTAAGTATA | 46 | 3255 |
| 877151 | N/A | N/A | 73765 | 73784 | CTTGAAAGTTACAAGGATAA | 60 | 3256 |
| 877175 | N/A | N/A | 75058 | 75077 | GGTGGGTAGGTTGGCTGGAG | 88 | 3257 |
| 877199 | N/A | N/A | 77450 | 77469 | ACTGAAATGCCACTTTTAAA | 74 | 3258 |
| 877223 | N/A | N/A | 80422 | 80441 | ATGGGTGTTATTTAATAAAA | 65 | 3259 |
| 877254 | N/A | N/A | 84582 | 84601 | AAGTGTAAAGACCAGAAACA | 169 | 3260 |
| 877278 | N/A | N/A | 87864 | 87883 | TAGTCTCCATTCTAAAAAGC | 64 | 3261 |
| 877302 | N/A | N/A | 90291 | 90310 | GACTTATTGGTAATGATATC | 57 | 3262 |
| 877326 | N/A | N/A | 91566 | 91585 | GCAGAGACATAAAATCCCAC | 36 | 3263 |
| 877350 | N/A | N/A | 93891 | 93910 | TTCCATGTGAAATATAAGAA | 79 | 3264 |
| 877374 | N/A | N/A | 95756 | 95775 | AAGGTTAAATTGCCATGTAA | 45 | 3265 |
| 877398 | N/A | N/A | 97666 | 97685 | CTAGGAGAGGACTTCCATGA | 52 | 3266 |
| 877422 | N/A | N/A | 100940 | 100959 | ATTATATGGCAGACATGTTG | 73 | 3267 |

TABLE 43-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877446 | N/A | N/A | 102740 | 102759 | TTGGACAACTTTTTGCTAAT | 72 | 3268 |
| 877470 | N/A | N/A | 105358 | 105377 | ACCTTCAGGCCTCCATACCC | 95 | 3269 |
| 877494 | N/A | N/A | 107793 | 107812 | CCTTTATTTTTATAAATTGA | 51 | 3270 |
| 877518 | N/A | N/A | 110571 | 110590 | TACAGTTGAGTTCTGGTATA | 100 | 3271 |
| 877542 | N/A | N/A | 112357 | 112376 | GAAACAGTGCACACAGTGTA | 56 | 3272 |
| 877566 | N/A | N/A | 114956 | 114975 | AAAAACTAGAACCTAGAGTT | 90 | 3273 |
| 877590 | N/A | N/A | 117469 | 117488 | AGATGTCTATAAAATTCTGA | 77 | 3274 |
| 877614 | N/A | N/A | 119511 | 119530 | AACCAGGCATTGGAATCTGG | 65 | 3275 |
| 877638 | N/A | N/A | 121934 | 121953 | AATTTCTTGATGAACATCAT | 69 | 3276 |
| 877662 | N/A | N/A | 124733 | 124752 | CTAAACCAGGCTGTGTTATT | 75 | 3277 |
| 877686 | N/A | N/A | 127511 | 127530 | TTTTCATAAGATTTGACAGC | 83 | 3278 |
| 877710 | N/A | N/A | 130554 | 130573 | TTTAACCTCAGAACTAATGT | 152 | 3279 |
| 877734 | N/A | N/A | 134509 | 134528 | ATCAGATGTCATTTATCATT | 67 | 3280 |
| 877758 | N/A | N/A | 139025 | 139044 | AGCACAAAGTCACCTAACCT | 50 | 3281 |
| 877782 | N/A | N/A | 141209 | 141228 | TCTATGTGGCTCTTTGTAGA | 50 | 3282 |
| 877806 | N/A | N/A | 143361 | 143380 | AGCTGCAGTAATCTGCTTCT | 33 | 3283 |
| 877830 | N/A | N/A | 145056 | 145075 | ATATATTAAACTGGCCTGAA | 152 | 3284 |

TABLE 44

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 23 | 222 |
| 780625 | N/A | N/A | 81633 87890 | 81652 87909 | ATTGCAGCATCATGCAAGCA | 56 | 675 |
| 876024 | 667 | 686 | 16187 | 16206 | CAAACAGCACATGTAAAGCT | 75 | 3285 |
| 876048 | 834 | 853 | 21665 | 21684 | ACTCATGAGGACTTCCACAT | 42 | 3286 |
| 876072 | 1233 | 1252 | 29584 | 29603 | GAGATTATTTAGTGCCCAGC | 30 | 3287 |
| 876096 | 1477 | 1496 | 35424 | 35443 | CCACTTCAGGAGAATGTATA | 48 | 3288 |
| 876120 | 1696 | 1715 | 41929 | 41948 | TATTTAGCTTATGATGAAAT | 58 | 3289 |
| 876144 | 2400 | 2419 | 62021 | 62040 | AGATCCACTATTCAGTAAGA | 42 | 3290 |
| 876168 | 2874 | 2893 | 71717 | 71736 | ACGCTGTAATACGGCATCTC | 26 | 3291 |
| 876192 | 3289 | 3308 | 76423 | 76442 | GATTAGCAATACAACTCATT | 41 | 3292 |
| 876216 | 3805 | 3824 | 82150 | 82169 | AGATGCTGATCTGATTATGG | 46 | 3293 |

TABLE 44-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876240 | 4237 | 4256 | 86732 | 86751 | GGATAGGCCAGTCTTTCACA | 43 | 3294 |
| 876264 | 4731 | 4750 | 92154 | 92173 | AATTGGCACATTTTTACGCT | 41 | 3295 |
| 876288 | 5052 | 5071 | 98200 | 98219 | AAAATACTGTGACATGTAGT | 26 | 3296 |
| 876312 | 5444 | 5463 | 100433 | 100452 | ACAACTTGGCCCAAAAGAAT | 101 | 3297 |
| 876336 | 5690 | 5709 | 101328 | 101347 | TCAGCCAAAATCAAGTCAGG | 50 | 3298 |
| 876360 | 6293 | 6312 | 124924 | 124943 | TAGAGTAGTAAACCAAATGA | 82 | 3299 |
| 876384 | 6958 | 6977 | N/A | N/A | CAGCTCCTTTAAGCTTAACA | 73 | 3300 |
| 876408 | 7861 | 7880 | 146030 | 146049 | CACATTTACTGGTAAGTATT | 52 | 3301 |
| 876432 | 8818 | 8837 | 146987 | 147006 | AATTATTACATAGGTATTTG | 97 | 3302 |
| 876456 | N/A | N/A | 4226 | 4245 | GGTATACTACAACTAAAGGC | 45 | 3303 |
| 876480 | N/A | N/A | 6916 | 6935 | CAAATATTGGCTGTGCAAAA | 50 | 3304 |
| 876504 | N/A | N/A | 8607 | 8626 | TAAGCCAGATTGTATAAGAA | 91 | 3305 |
| 876528 | N/A | N/A | 11615 | 11634 | ACACACCCTTTATGTACTGA | 35 | 3306 |
| 876552 | N/A | N/A | 14467 | 14486 | CTACCTCTTAGTGGCCAAAG | 58 | 3307 |
| 876576 | N/A | N/A | 16784 | 16803 | TAATTGAACTGTACTGTCAC | 77 | 3308 |
| 876600 | N/A | N/A | 19236 | 19255 | CACTCATAACCCCACACCTT | 68 | 3309 |
| 876624 | N/A | N/A | 20923 | 20942 | TGTTATATTGCTTACCTTTT | 69 | 3310 |
| 876648 | N/A | N/A | 24093 | 24112 | TCAATGGCTCTATTTAACAC | 74 | 3311 |
| 876672 | N/A | N/A | 26696 | 26715 | GTTTTAATTTTAACTATGAA | 63 | 3312 |
| 876696 | N/A | N/A | 29292 | 29311 | CATTATATATATTATCTACT | 94 | 3313 |
| 876720 | N/A | N/A | 30992 | 31011 | AAATTCAAACAAAATGTTAG | 77 | 3314 |
| 876744 | N/A | N/A | 33420 | 33439 | CTTACTCAATAGTCACCTTC | 51 | 3315 |
| 876768 | N/A | N/A | 35168 | 35187 | ACACATGTCATTTCCAATTT | 38 | 3316 |
| 876792 | N/A | N/A | 37410 | 37429 | TAATTGTCTAAACTTTGAAC | 72 | 3317 |
| 876816 | N/A | N/A | 38923 | 38942 | TCACATCAAACAGATCTCCC | 68 | 3318 |
| 876840 | N/A | N/A | 41323 | 41342 | TGTAGCTGAACTATGCTAAA | 118 | 3319 |
| 876864 | N/A | N/A | 43234 | 43253 | TGTATTAAAGTTTGAGTATA | 77 | 3320 |
| 876888 | N/A | N/A | 47312 | 47331 | CCACAGTGAACATTCATGTC | 39 | 3321 |
| 876912 | N/A | N/A | 48595 | 48614 | GTCCAAATATAAAGGCAAAA | 36 | 3322 |
| 876936 | N/A | N/A | 51297 | 51316 | AGAAGTGGTAAGTTAAAAG | 101 | 3323 |
| 876960 | N/A | N/A | 53567 | 53586 | CCAGTATCTTGAATTCCTTA | 38 | 3324 |
| 876984 | N/A | N/A | 56680 | 56699 | TATCAAAACATTAGAACTAT | 86 | 3325 |
| 877008 | N/A | N/A | 59803 | 59822 | GAGAAAGTGAATCTGATAAA | 48 | 3326 |
| 877032 | N/A | N/A | 62335 | 62354 | ATCTTTGGCTTAAGGTCCCT | 54 | 3327 |
| 877056 | N/A | N/A | 64117 | 64136 | TGAAGATTAAAGTAAGCAGG | 46 | 3328 |
| 877080 | N/A | N/A | 66821 | 66840 | AATAAGAATGGCCAATAAGA | 97 | 3329 |

TABLE 44-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877104 | N/A | N/A | 68820 | 68839 | CAGGATAATTAAATCACTAA | 89 | 3330 |
| 877128 | N/A | N/A | 72024 | 72043 | TCTTGAAGTGTACTGTAAGT | 36 | 3331 |
| 877152 | N/A | N/A | 73771 | 73790 | AAATGTCTTGAAAGTTACAA | 58 | 3332 |
| 877176 | N/A | N/A | 75109 | 75128 | ACCGAATGAGAATTAGGTGG | 22 | 3333 |
| 877200 | N/A | N/A | 77633 | 77652 | ATAATTTTGTCTCTTCCAGA | 61 | 3334 |
| 877224 | N/A | N/A | 80461 | 80480 | TATGGTACTAGCTCATAAAG | 87 | 3335 |
| 877255 | N/A | N/A | 84665 | 84684 | TATGAGAAAGTAATAAGACC | 103 | 3336 |
| 877279 | N/A | N/A | 87867 | 87886 | GTTTAGTCTCCATTCTAAAA | 58 | 3337 |
| 877303 | N/A | N/A | 90326 | 90345 | AGGTGATTTATAAGTGCCAA | 28 | 3338 |
| 877327 | N/A | N/A | 91617 | 91636 | GGTTATTTGTAAAATGTTAT | 33 | 3339 |
| 877351 | N/A | N/A | 93895 | 93914 | CATTTTCCATGTGAAATATA | 50 | 3340 |
| 877375 | N/A | N/A | 95790 | 95809 | AAATTCCTTTGTATTTCTCC | 31 | 3341 |
| 877399 | N/A | N/A | 97756 | 97775 | GTCTCATCAATAATATATTC | 46 | 3342 |
| 877423 | N/A | N/A | 100944 | 100963 | TGTTATTATATGGCAGACAT | 66 | 3343 |
| 877447 | N/A | N/A | 102748 | 102767 | CTCAAATTTTGGACAACTTT | 66 | 3344 |
| 877471 | N/A | N/A | 105367 | 105386 | ATGCTTTGTACCTTCAGGCC | 39 | 3345 |
| 877495 | N/A | N/A | 108045 | 108064 | TTAGAAACACTTGAAGTCAT | 61 | 3346 |
| 877519 | N/A | N/A | 110743 | 110762 | AATTAAAATGCCCCCAGGAT | 74 | 3347 |
| 877543 | N/A | N/A | 112384 | 112403 | CTCTGTTTTTATCAGACATT | 49 | 3348 |
| 877567 | N/A | N/A | 115086 | 115105 | GTTATTTAAAGTAAGGTTTC | 52 | 3349 |
| 877591 | N/A | N/A | 117552 | 117571 | TTCATCTCAACCAGGTCTTA | 67 | 3350 |
| 877615 | N/A | N/A | 119913 | 119932 | AGTTGCATATGGTTTAGGAG | 29 | 3351 |
| 877639 | N/A | N/A | 122135 | 122154 | AATATTTACTTCAATATGGA | 68 | 3352 |
| 877663 | N/A | N/A | 124792 | 124811 | CATCCAAGGAGGCATACACT | 78 | 3353 |
| 877687 | N/A | N/A | 127780 | 127799 | TTAAAGGAAAAGTTAACCAG | 75 | 3354 |
| 877711 | N/A | N/A | 132127 | 132146 | GATTGTTCCTCTCCCTCTCC | 57 | 3355 |
| 877735 | N/A | N/A | 134694 | 134713 | TAATGACTAAATAGGAATCT | 89 | 3356 |
| 877759 | N/A | N/A | 139104 | 139123 | GTAGATTTAGTGGTATTGAG | 54 | 3357 |
| 877783 | N/A | N/A | 141286 | 141305 | ACTTTATATTAATTTCTTGT | 67 | 3358 |
| 877807 | N/A | N/A | 143430 | 143449 | TACCATGTATTTCCCATTTT | 61 | 3359 |
| 877831 | N/A | N/A | 145069 | 145088 | TTCTGTTAAAACTATATATT | 128 | 3360 |

TABLE 45

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 16 | 222 |
| 876028 | 732 | 751 | 18631 | 18650 | ACTTAACAATATCATATAAT | 116 | 3361 |
| 876052 | 840 | 859 | 21671 | 21690 | ATTGCCACTCATGAGGACTT | 23 | 3362 |
| 876076 | 1239 | 1258 | 29590 | 29609 | CATAAGGAGATTATTTAGTG | 51 | 3363 |
| 876100 | 1482 | 1501 | 35429 | 35448 | TTCAGCCACTTCAGGAGAAT | 36 | 3364 |
| 876124 | 1701 | 1720 | 41934 | 41953 | AACCATATTTAGCTTATGAT | 35 | 3365 |
| 876148 | 2452 | 2471 | 62073 | 62092 | TGTCACCTTTCCCAATGCTT | 37 | 3366 |
| 876172 | 2977 | 2996 | 73001 | 73020 | GTGAATCATCTGAAGATAAT | 79 | 3367 |
| 876196 | 3422 | 3441 | 76556 | 76575 | TCTACCACATCAGTGAGGTT | 46 | 3368 |
| 876220 | 3850 | 3869 | 82195 | 82214 | GTTTCTCTACTCTAGACCAT | 29 | 3369 |
| 876244 | 4313 | 4332 | 87217 | 87236 | GTACTATAGAATTCCTCACG | 33 | 3370 |
| 876268 | 4736 | 4755 | 92159 | 92178 | AATTCAATTGGCACATTTTT | 80 | 3371 |
| 876292 | 5070 | 5089 | 98218 | 98237 | GAATTTTCTAGGAGCTTAA | 47 | 3372 |
| 876316 | 5450 | 5469 | 100439 | 100458 | TGGTCCACAACTTGGCCCAA | 45 | 3373 |
| 876340 | 5704 | 5723 | 101342 | 101361 | TATTTCTAGGCAGGTCAGCC | 62 | 3374 |
| 876364 | 6471 | 6490 | 126587 | 126606 | AGGCCTTTCTTGAGGATTTT | 56 | 3375 |
| 876388 | 7076 | 7095 | 137480 | 137499 | GAGAAAATCTTTGTGCCACA | 66 | 3376 |
| 876412 | 8045 | 8064 | 146214 | 146233 | ACAGAATTTAAAATAAAGTT | 64 | 3377 |
| 876436 | 8906 | 8925 | 147075 | 147094 | TATCACAGGGAATTATCTGA | 113 | 3378 |
| 876460 | N/A | N/A | 4437 | 4456 | ATCACCTTGGCCTATAATTT | 73 | 3379 |
| 876484 | N/A | N/A | 7124 | 7143 | TTGCTTTTTACTAGCTTGCA | 38 | 3380 |
| 876508 | N/A | N/A | 9022 | 9041 | GGCTCTTTCACATTTCGAAA | 63 | 3381 |
| 876532 | N/A | N/A | 11902 | 11921 | TTTCCTACATAAACTTTTAT | 137 | 3382 |
| 876556 | N/A | N/A | 14858 | 14877 | GTTGAGTACCTTCTTGTTTT | 43 | 3383 |
| 876580 | N/A | N/A | 17001 | 17020 | TCTTGTGTATTATAATTATC | 55 | 3384 |
| 876604 | N/A | N/A | 19521 | 19540 | AGCAATCATTGGTAGCATAC | 17 | 3385 |
| 876628 | N/A | N/A | 21334 | 21353 | GTACTGAAAATGAAAGTCTG | 79 | 3386 |
| 876652 | N/A | N/A | 24857 | 24876 | AAGGTAAGGTCTCAACCAGA | 41 | 3387 |
| 876676 | N/A | N/A | 27470 | 27489 | TCATTGGCATGTTTACCATT | 46 | 3388 |
| 876700 | N/A | N/A | 29725 | 29744 | CTAACAATAAAAGTTACGGT | 49 | 3389 |
| 876724 | N/A | N/A | 31409 | 31428 | AATTTGGTTATAAAAGAGTA | 94 | 3390 |
| 876748 | N/A | N/A | 33425 | 33444 | CAGGTCTTACTCAATAGTCA | 32 | 3391 |
| 876772 | N/A | N/A | 35704 | 35723 | AGCATCAGGTTCAAAAGCAA | 43 | 3392 |
| 876796 | N/A | N/A | 37927 | 37946 | CATTGTAGTTACTTTGTATA | 100 | 3393 |
| 876820 | N/A | N/A | 39204 | 39223 | AAACTATGAATAGGACACCA | 49 | 3394 |
| 876844 | N/A | N/A | 41563 | 41582 | CTGGAAGATTTTTATGCAAC | 66 | 3395 |

TABLE 45-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876868 | N/A | N/A | 45405 | 45424 | CTCTCACAATGAGACAGGAT | 48 | 3396 |
| 876892 | N/A | N/A | 47401 | 47420 | GGTGGAGAAATAAAAATATC | 153 | 3397 |
| 876916 | N/A | N/A | 49326 | 49345 | GATGTCCCTTGTCTATGAGT | 80 | 3398 |
| 876940 | N/A | N/A | 51672 | 51691 | GTCTTTGACCAAAATCTTCT | 53 | 3399 |
| 876964 | N/A | N/A | 54224 | 54243 | CTATCTTGGTTTAATCAGCC | 51 | 3400 |
| 876988 | N/A | N/A | 57012 | 57031 | ATATATTTTCATAGACTGAC | 73 | 3401 |
| 877012 | N/A | N/A | 59950 | 59969 | CATCTTGAAACAGGAAACCC | 90 | 3402 |
| 877036 | N/A | N/A | 62729 | 62748 | GCTTGAAAGTATAAAGAAAA | 92 | 3403 |
| 877060 | N/A | N/A | 64985 | 65004 | GCTAAATAAAGGATCTTGTT | 61 | 3404 |
| 877084 | N/A | N/A | 67063 | 67082 | TCTTAAGTGGGATACAAAAA | 77 | 3405 |
| 877108 | N/A | N/A | 69905 | 69924 | AATTACAACTTCAATATTTC | 117 | 3406 |
| 877132 | N/A | N/A | 72455 | 72474 | CAAAGTGAACCTGAGAATAA | 86 | 3407 |
| 877156 | N/A | N/A | 73937 | 73956 | TCTGTTTCCATTGCCTGCCC | 24 | 3408 |
| 877180 | N/A | N/A | 75325 | 75344 | ATTATTTTGCTTGCTCATTT | 62 | 3409 |
| 877204 | N/A | N/A | 78164 | 78183 | TATCTCAGTATCAGGATGCC | 36 | 3410 |
| 877228 | N/A | N/A | 81375 | 81394 | TACATAAACTTGCCTAATCT | 120 | 3411 |
| 877235 | N/A | N/A | 82381 | 82400 | ATGGAAATCTGGATTTATAG | 48 | 3412 |
| 877259 | N/A | N/A | 84939 | 84958 | TCAGAAAACAAAATCCTTCC | 70 | 3413 |
| 877283 | N/A | N/A | 87993 | 88012 | CATTAAAAAATACCCAAATT | 142 | 3414 |
| 877307 | N/A | N/A | 90438 | 90457 | TCAAACCATTATGCCAGAAT | 34 | 3415 |
| 877331 | N/A | N/A | 91722 | 91741 | AATGTGAAACAGACACGCTA | 53 | 3416 |
| 877355 | N/A | N/A | 94450 | 94469 | AATGTTTCAATATGCTCTTG | 22 | 3417 |
| 877379 | N/A | N/A | 95946 | 95965 | ATTTTAAGCCTCCAAGTTTC | 110 | 3418 |
| 877403 | N/A | N/A | 98420 | 98439 | CAAAATAAATGATACATGTC | 104 | 3419 |
| 877427 | N/A | N/A | 101435 | 101454 | CATCCTAATTTTTATTCTCA | 94 | 3420 |
| 877451 | N/A | N/A | 103549 | 103568 | AGCCAAAATGGCAACAGCTC | 52 | 3421 |
| 877475 | N/A | N/A | 105747 | 105766 | TCATTCCACTTTGATTGTGT | 40 | 3422 |
| 877499 | N/A | N/A | 108438 | 108457 | GGAATTTCTTCAAATTTTG | 102 | 3423 |
| 877523 | N/A | N/A | 111233 | 111252 | TCATAGGCACAGACAGAGGT | 68 | 3424 |
| 877547 | N/A | N/A | 112873 | 112892 | ACTACAGTTGACCTATGGAC | 74 | 3425 |
| 877571 | N/A | N/A | 115802 | 115821 | ATTGCAAGCATAAACAGATT | 98 | 3426 |
| 877595 | N/A | N/A | 118045 | 118064 | ATGAATATTTAACTATTTC | 65 | 3427 |
| 877619 | N/A | N/A | 119984 | 120003 | GCTATTCATGGCTCTGTTGT | 66 | 3428 |
| 877643 | N/A | N/A | 122352 | 122371 | GTTAGAATTTGGAATCACAG | 42 | 3429 |
| 877667 | N/A | N/A | 125287 | 125306 | CAAATGTGGAGTTCTAACAG | 106 | 3430 |

TABLE 45-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877691 | N/A | N/A | 128589 | 128608 | TGGACAAGGTTACTTGGGCA | 55 | 3431 |
| 877715 | N/A | N/A | 132782 | 132801 | TTTATAAATGTCTCAGCTAG | 72 | 3432 |
| 877739 | N/A | N/A | 135635 | 135654 | ATTGCTATAGCCACTACGGA | 102 | 3433 |
| 877763 | N/A | N/A | 140038 | 140057 | CTAGAACTCCAAAAGTCCTA | 76 | 3434 |
| 877787 | N/A | N/A | 141378 | 141397 | ACAAGCTAGACTATTGCAAT | 55 | 3435 |
| 877811 | N/A | N/A | 143863 | 143882 | GAATATATTTTCTTCACCAT | 62 | 3436 |
| 877835 | N/A | N/A | 145294 | 145313 | AAACTACCAATTAAAATTCC | 80 | 3437 |

TABLE 46

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 42 | 222 |
| 876029 | 733 | 752 | 18632 | 18651 | CACTTAACAATATCATATAA | 73 | 3438 |
| 876053 | 841 | 860 | 21672 | 21691 | CATTGCCACTCATGAGGACT | 29 | 3439 |
| 876077 | 1249 | 1268 | 29600 | 29619 | TGTTTTGGTACATAAGGAGA | 60 | 3440 |
| 876101 | 1483 | 1502 | 35430 | 35449 | TTTCAGCCACTTCAGGAGAA | 50 | 3441 |
| 876125 | 1702 | 1721 | 41935 | 41954 | TAACCATATTTAGCTTATGA | 56 | 3442 |
| 876149 | 2453 | 2472 | 62074 | 62093 | CTGTCACCTTTCCCAATGCT | 26 | 3443 |
| 876173 | 3064 | 3083 | 73600 | 73619 | CTAGTGATGTAATATATTCT | 32 | 3444 |
| 876197 | 3427 | 3446 | 76561 | 76580 | GTTTCTCTACCACATCAGTG | 38 | 3445 |
| 876221 | 3852 | 3871 | 82197 | 82216 | CAGTTTCTCTACTCTAGACC | 28 | 3446 |
| 876245 | 4315 | 4334 | 87219 | 87238 | GAGTACTATAGAATTCCTCA | 81 | 3447 |
| 876269 | 4741 | 4760 | 92164 | 92183 | CGGGAAATTCAATTGGCACA | 44 | 3448 |
| 876293 | 5071 | 5090 | 98219 | 98238 | GGAATTTTTCTAGGAGCTTA | 27 | 3449 |
| 876317 | 5451 | 5470 | 100440 | 100459 | GTGGTCCACAACTTGGCCCA | 72 | 152 |
| 876341 | 5745 | 5764 | 101383 | 101402 | TGGAGCTTGTTCAAATTCCA | 52 | 153 |
| 876365 | 6510 | 6529 | 129655 | 129674 | TTCAGCTGAATTCAAAATGT | 82 | 3450 |
| 876389 | 7174 | 7193 | 141535 | 141554 | CCACTGTTATGATGTTGGAA | 65 | 3451 |
| 876413 | 8085 | 8104 | 146254 | 146273 | ATTTCTAGAAAAATCGACAA | 115 | 3452 |
| 876437 | 8911 | 8930 | 147080 | 147099 | TGTCCTATCACAGGGAATTA | 81 | 3453 |
| 876461 | N/A | N/A | 4590 | 4609 | GTCTGTCAAGCCTCTCAACC | 79 | 3454 |
| 876485 | N/A | N/A | 7136 | 7155 | TATCAAACCATTTTGCTTTT | 79 | 3455 |
| 876509 | N/A | N/A | 9076 | 9095 | CAGATTTCTCTAGAATGAAT | 67 | 3456 |

TABLE 46-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876533 | N/A | N/A | 12031 | 12050 | TGTGTCTATCTTCTTCACAA | 119 | 3457 |
| 876557 | N/A | N/A | 14909 | 14928 | AGACTCTTAGTGCATGCCAT | 46 | 3458 |
| 876581 | N/A | N/A | 17076 | 17095 | CCTTAGAAACACAGTAAACT | 72 | 3459 |
| 876605 | N/A | N/A | 19554 19584 | 19573 19603 | AAAACAGAATATGAACCATT | 48 | 3460 |
| 876629 | N/A | N/A | 21340 | 21359 | GGAAAAGTACTGAAAATGAA | 134 | 3461 |
| 876653 | N/A | N/A | 24869 | 24888 | CAGACTCTCTGCAAGGTAAG | 88 | 3462 |
| 876677 | N/A | N/A | 27495 | 27514 | CTTAAAGGAATAGTGCTTAG | 71 | 3463 |
| 876701 | N/A | N/A | 29875 | 29894 | AATTACCAAATGACCCTTGA | 73 | 3464 |
| 876725 | N/A | N/A | 31897 | 31916 | TGGTGTTTACTATGGGTTCC | 28 | 3465 |
| 876749 | N/A | N/A | 33427 | 33446 | TGCAGGTCTTACTCAATAGT | 75 | 3466 |
| 876773 | N/A | N/A | 35778 | 35797 | CACACAATAATTAGAAAAAC | 106 | 3467 |
| 876797 | N/A | N/A | 37999 | 38018 | TCATGGCAACAAAAATAGAA | 129 | 3468 |
| 876821 | N/A | N/A | 39337 | 39356 | TGTCAACTTTAAGGATAATC | 35 | 3469 |
| 876845 | N/A | N/A | 41680 | 41699 | TAAATATAATGTGTAAGAAT | 117 | 3470 |
| 876869 | N/A | N/A | 45530 | 45549 | CACCAACACTCACCATGAAT | 62 | 3471 |
| 876893 | N/A | N/A | 47579 | 47598 | CCCTCAGGGACCTCTACTGA | 59 | 3472 |
| 876917 | N/A | N/A | 49662 | 49681 | ATTTATCAGTGTCTACTTAG | 68 | 3473 |
| 876941 | N/A | N/A | 51782 | 51801 | TTCATTTAGATGATGTTTTG | 95 | 3474 |
| 876965 | N/A | N/A | 54337 | 54356 | ACTCTACTATAGAGATTCTA | 95 | 3475 |
| 876989 | N/A | N/A | 57276 | 57295 | ATTTAATAATGTGTATTAAA | 129 | 3476 |
| 877013 | N/A | N/A | 59957 | 59976 | TACAAACCATCTTGAAACAG | 98 | 3477 |
| 877037 | N/A | N/A | 62733 | 62752 | ATGAGCTTGAAAGTATAAAG | 83 | 3478 |
| 877061 | N/A | N/A | 65104 | 65123 | GTATCAGTGTCCTCACCTGG | 84 | 3479 |
| 877085 | N/A | N/A | 67064 | 67083 | TTCTTAAGTGGGATACAAAA | 81 | 3480 |
| 877109 | N/A | N/A | 69996 | 70015 | ATAGTCCTTAATGTTTGCAC | 46 | 3481 |
| 877133 | N/A | N/A | 72458 | 72477 | TTTCAAAGTGAACCTGAGAA | 83 | 3482 |
| 877157 | N/A | N/A | 73938 | 73957 | ATCTGTTTCCATTGCCTGCC | 69 | 3483 |
| 877181 | N/A | N/A | 75378 | 75397 | CCTTGTCACAGTCTCTTCCA | 56 | 3484 |
| 877205 | N/A | N/A | 78262 | 78281 | AAAACCATTAAATGATTAAT | 148 | 3485 |
| 877229 | N/A | N/A | 81468 | 81487 | AACACACTCAAGATCCAATT | 94 | 3486 |
| 877236 | N/A | N/A | 82634 | 82653 | ATCACACATAATTTGAAATG | 91 | 3487 |
| 877260 | N/A | N/A | 85112 | 85131 | AGTATAATACACTGAAAGCT | 86 | 3488 |
| 877284 | N/A | N/A | 88019 | 88038 | AGCTGTAAAAAAGTTAATAA | 80 | 3489 |
| 877308 | N/A | N/A | 90441 | 90460 | TTTTCAAACCATTATGCCAG | 77 | 3490 |
| 877332 | N/A | N/A | 91728 | 91747 | AAACTTAATGTGAAACAGAC | 77 | 3491 |

TABLE 46-continued

Percent control of human LRRK RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877356 | N/A | N/A | 94452 | 94471 | GCAATGTTTCAATATGCTCT | 13 | 3492 |
| 877380 | N/A | N/A | 96049 | 96068 | GAATGAAGCCAAGTGAATAA | 82 | 3493 |
| 877404 | N/A | N/A | 98444 | 98463 | AGTGTCAGATGCAATGTTTT | 92 | 3494 |
| 877428 | N/A | N/A | 101447 | 101466 | AGGAGAAAATTACATCCTAA | 81 | 3495 |
| 877452 | N/A | N/A | 104028 | 104047 | AAGAGGAAATGTACCCTGTG | 77 | 3496 |
| 877476 | N/A | N/A | 105776 | 105795 | CTCTCTCTCTTGCAAAATTA | 74 | 3497 |
| 877500 | N/A | N/A | 108554 | 108573 | AATTCAAAAGGTCAAATTTT | 105 | 3498 |
| 877524 | N/A | N/A | 111239 | 111258 | TTGTTTTCATAGGCACAGAC | 35 | 3499 |
| 877548 | N/A | N/A | 112899 | 112918 | TTCAGTAATAAAAAGCTGGT | 63 | 3500 |
| 877572 | N/A | N/A | 115808 | 115827 | CAAGGAATTGCAAGCATAAA | 69 | 3501 |
| 877596 | N/A | N/A | 118216 | 118235 | GTCTAATATTACACAGCAAA | 55 | 3502 |
| 877620 | N/A | N/A | 119990 | 120009 | ATATTTGCTATTCATGGCTC | 54 | 3503 |
| 877644 | N/A | N/A | 122379 | 122398 | AGCATATTTTTCTTGATAA | 40 | 3504 |
| 877668 | N/A | N/A | 125297 | 125316 | TAAAAATCACCAAATGTGGA | 85 | 3505 |
| 877692 | N/A | N/A | 128599 | 128618 | GATAATATGGTGGACAAGGT | 38 | 3506 |
| 877716 | N/A | N/A | 132876 | 132895 | GATTCATTGATCTGAGGAGA | 55 | 3507 |
| 877740 | N/A | N/A | 135638 | 135657 | TAAATTGCTATAGCCACTAC | 72 | 3508 |
| 877764 | N/A | N/A | 140071 | 140090 | TTGCCGACCTAGGACTAAAA | 53 | 3509 |
| 877788 | N/A | N/A | 141480 | 141499 | AAAAAATAGAAAGTCATCAC | 128 | 3510 |
| 877812 | N/A | N/A | 143888 | 143907 | TTCCTCTTTCACATATACTT | 77 | 3511 |
| 877836 | N/A | N/A | 145295 | 145314 | TAAACTACCAATTAAAATTC | 139 | 3512 |

TABLE 47

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 31 | 222 |
| 876030 | 734 | 753 | 18633 | 18652 | GCACTTAACAATATCATATA | 34 | 3513 |
| 876054 | 846 | 865 | 21677 | 21696 | CCTGACATTGCCACTCATGA | 38 | 3514 |
| 876078 | 1293 | 1312 | N/A | N/A | AGCTGGGAAATGGCCATCTT | 64 | 3515 |
| 876102 | 1484 | 1503 | 35431 | 35450 | CTTTCAGCCACTTCAGGAGA | 62 | 3516 |
| 876126 | 1704 | 1723 | 41937 | 41956 | TTTAACCATATTTAGCTTAT | 58 | 3517 |
| 876150 | 2454 | 2473 | 62075 | 62094 | GCTGTCACCTTTCCCAATGC | 31 | 3518 |

TABLE 47-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876174 | 3069 | 3088 | 73605 | 73624 | AAGGTCTAGTGATGTAATAT | 43 | 3519 |
| 876198 | 3457 | 3476 | N/A | N/A | TTTTATTTCCTTCTAAAATG | 113 | 3520 |
| 876222 | 3853 | 3872 | 82198 | 82217 | GCAGTTTCTCTACTCTAGAC | 25 | 3521 |
| 876246 | 4316 | 4335 | 87220 | 87239 | TGAGTACTATAGAATTCCTC | 46 | 3522 |
| 876270 | 4751 | 4770 | 92174 | 92193 | CGGTCAATTACGGGAAATTC | 45 | 3523 |
| 876294 | 5073 | 5092 | 98221 | 98240 | CTGGAATTTTTCTAGGAGCT | 13 | 3524 |
| 876318 | 5452 | 5471 | 100441 | 100460 | TGTGGTCCACAACTTGGCCC | 43 | 3525 |
| 876342 | 5787 | 5806 | 106478 | 106497 | TCGGTAAACTGATCCAAAAC | 63 | 3526 |
| 876366 | 6515 | 6534 | 129660 | 129679 | ACTAATTCAGCTGAATTCAA | 67 | 3527 |
| 876390 | 7179 | 7198 | 141540 | 141559 | TACCACCACTGTTATGATGT | 45 | 3528 |
| 876414 | 8090 | 8109 | 146259 | 146278 | TGCAGATTTCTAGAAAAATC | 43 | 3529 |
| 876438 | 8978 | 8997 | 147147 | 147166 | TATAAATAAATTTAAAGTTT | 96 | 3530 |
| 876462 | N/A | N/A | 4609 | 4628 | AAAGATTGAGATGCCTCATG | 73 | 3531 |
| 876486 | N/A | N/A | 7222 | 7241 | GTAGGAGACCCCTTTCTACA | 67 | 3532 |
| 876510 | N/A | N/A | 9202 | 9221 | AATGAAGCTAGAATAATAGA | 118 | 3533 |
| 876534 | N/A | N/A | 12064 | 12083 | GAGTGATCTAATACACTCCA | 93 | 3534 |
| 876558 | N/A | N/A | 14962 | 14981 | CCGTCAAAAAAAAAATACCT | 129 | 3535 |
| 876582 | N/A | N/A | 17310 | 17329 | CTCGCTGCAATACACTTTGT | 66 | 3536 |
| 876606 | N/A | N/A | 19555 19585 | 19574 19604 | CAAAACAGAATATGAACCAT | 84 | 3537 |
| 876630 | N/A | N/A | 21645 | 21664 | TATTGCCTGAATTTAAAGAG | 81 | 3538 |
| 876654 | N/A | N/A | 25038 | 25057 | ACTTTTAAATGCATTGTTGT | 72 | 3539 |
| 876678 | N/A | N/A | 27571 | 27590 | TTTAAAGTTGAAACTCTTAA | 124 | 3540 |
| 876702 | N/A | N/A | 29941 | 29960 | TGAATTAATATGGCATTTTA | 86 | 3541 |
| 876726 | N/A | N/A | 31920 | 31939 | AAACAGAGGAGGAAAGTGAT | 126 | 3542 |
| 876750 | N/A | N/A | 33456 | 33475 | TCAGAGGCAAAAAACAATAT | 67 | 3543 |
| 876774 | N/A | N/A | 35835 | 35854 | CGTTGTGAAAGAGCAAAATT | 50 | 3544 |
| 876798 | N/A | N/A | 38037 | 38056 | GTACAATTCAAACAAGAGAA | 100 | 3545 |
| 876822 | N/A | N/A | 39461 | 39480 | GAAATACTGTATTCAAAACT | 73 | 3546 |
| 876846 | N/A | N/A | 41819 | 41838 | GACTGTTACTTTCTAGAAAT | 93 | 3547 |
| 876870 | N/A | N/A | 45583 | 45602 | GGCTAACTGGAACCAGTTAT | 48 | 3548 |
| 876894 | N/A | N/A | 47597 | 47616 | GACTCTGCTTGTTGTAGTCC | 68 | 3549 |
| 876918 | N/A | N/A | 49701 | 49720 | TAATGTATTGCATTGGTGCT | 62 | 3550 |
| 876942 | N/A | N/A | 51819 | 51838 | TAAAAATTATAGTGCCATCC | 51 | 3551 |
| 876966 | N/A | N/A | 54764 | 54783 | AATGCTACAGCAGAGCAGGC | 45 | 3552 |
| 876990 | N/A | N/A | 57307 | 57326 | AACTATTGGCAAACATAGTA | 76 | 3553 |

TABLE 47-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877014 | N/A | N/A | 59967 | 59986 | CATACAGACCTACAAACCAT | 69 | 3554 |
| 877038 | N/A | N/A | 62754 | 62773 | CATAATATGTACAAAATACA | 100 | 3555 |
| 877062 | N/A | N/A | 65304 | 65323 | AGTGATCCTGAATAATTAAC | 94 | 3556 |
| 877086 | N/A | N/A | 67065 | 67084 | TTTCTTAAGTGGGATACAAA | 66 | 3557 |
| 877110 | N/A | N/A | 70097 | 70116 | AATTCTTCCAGAGGAAGAAA | 123 | 3558 |
| 877134 | N/A | N/A | 72483 | 72502 | ATTGGAGAATAGGTTAGAAC | 64 | 3559 |
| 877158 | N/A | N/A | 73939 | 73958 | GATCTGTTTCCATTGCCTGC | 44 | 3560 |
| 877182 | N/A | N/A | 75408 | 75427 | TGTCCAGTCATTGAATGCCG | 30 | 3561 |
| 877206 | N/A | N/A | 78354 | 78373 | CTTTTAATAAAAGTGATGAT | 115 | 3562 |
| 877230 | N/A | N/A | 81470 | 81489 | ACAACACACTCAAGATCCAA | 68 | 3563 |
| 877237 | N/A | N/A | 82682 | 82701 | AACAGTTAAGAATAATTTGA | 122 | 3564 |
| 877261 | N/A | N/A | 85276 | 85295 | CACTATTTGAAAAAATGTCT | 81 | 3565 |
| 877285 | N/A | N/A | 88051 | 88070 | GACTGCCACTGTACTATTTG | 45 | 3566 |
| 877309 | N/A | N/A | 90454 | 90473 | GCAATCAAATGAGTTTTCAA | 66 | 3567 |
| 877333 | N/A | N/A | 92392 | 92411 | ATCAGTGGCCTATTAAAGAA | 98 | 3568 |
| 877357 | N/A | N/A | 94453 | 94472 | TGCAATGTTTCAATATGCTC | 34 | 3569 |
| 877381 | N/A | N/A | 96103 | 96122 | CAATACTCCAAAAACATGCA | 52 | 3570 |
| 877405 | N/A | N/A | 98870 | 98889 | TTAGTTATGCATAGACAAAT | 49 | 3571 |
| 877429 | N/A | N/A | 101479 | 101498 | ATATAATTATGAAATCTATT | 95 | 3572 |
| 877453 | N/A | N/A | 104214 | 104233 | GAGTATGGATTGTCATGTCT | 63 | 3573 |
| 877477 | N/A | N/A | 105993 | 106012 | ACAAAAGTCTTTTTGAGGC | 48 | 3574 |
| 877501 | N/A | N/A | 108768 | 108787 | TTACTACTATATATATATCA | 72 | 3575 |
| 877525 | N/A | N/A | 111286 | 111305 | CATGTCAGTTGGTTAGAACT | 62 | 3576 |
| 877549 | N/A | N/A | 113456 | 113475 | TATTACTACTTGCTATGAGG | 55 | 3577 |
| 877573 | N/A | N/A | 116029 | 116048 | ATGAGCTCTCTAGGCAGACA | 40 | 3578 |
| 877597 | N/A | N/A | 118217 | 118236 | AGTCTAATATTACACAGCAA | 41 | 3579 |
| 877621 | N/A | N/A | 120065 | 120084 | TTTTTCCAGGTGGAAATATA | 120 | 3580 |
| 877645 | N/A | N/A | 122402 | 122421 | ATTCAAAACTATTTAAATG | 118 | 3581 |
| 877669 | N/A | N/A | 125328 | 125347 | TAATGAGTACACAGTAATTC | 54 | 3582 |
| 877693 | N/A | N/A | 128602 | 128621 | TCAGATAATATGGTGGACAA | 53 | 3583 |
| 877717 | N/A | N/A | 132890 | 132909 | AGAGGCCCTACAAAGATTCA | 92 | 3584 |
| 877741 | N/A | N/A | 136288 | 136307 | TCAACAATATAGAGAGGATC | 113 | 3585 |
| 877765 | N/A | N/A | 140272 | 140291 | TGTATTTAATAGAAAATAGT | 114 | 3586 |
| 877789 | N/A | N/A | 141697 | 141716 | TGAAGTGCAAAGATAATTCT | 129 | 3587 |

TABLE 47-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877813 | N/A | N/A | 144037 | 144056 | CTGAGACAACCTATTGAGAG | 67 | 3588 |
| 877837 | N/A | N/A | 145342 | 145361 | CATATCACTTGTAATTTTGA | 43 | 3589 |

TABLE 48

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 18 | 222 |
| 876031 | 736 | 755 | 18635 | 18654 | ACGCACTTAACAATATCATA | 22 | 3590 |
| 876055 | 867 | 886 | 21698 | 21717 | TTCCACCACAATATTATAAC | 42 | 3591 |
| 876079 | 1298 | 1317 | N/A | N/A | CTATGAGCTGGGAAATGGCC | 62 | 3592 |
| 876103 | 1485 | 1504 | 35432 | 35451 | ACTTTCAGCCACTTCAGGAG | 38 | 3593 |
| 876127 | 1723 | 1742 | 41956 | 41975 | CATTCTTGAAACACTGTTTT | 39 | 3594 |
| 876151 | 2456 | 2475 | 62077 | 62096 | TGGCTGTCACCTTTCCCAAT | 33 | 3595 |
| 876175 | 3153 | 3172 | 73689 | 73708 | CTCCAGCTTTTCAAGATGCT | 33 | 3596 |
| 876199 | 3529 | 3548 | 77278 | 77297 | ATGAAATGTGGTTCTTACTA | 35 | 3597 |
| 876223 | 3854 | 3873 | 82199 | 82218 | TGCAGTTTCTCTACTCTAGA | 23 | 3598 |
| 876247 | 4317 | 4336 | 87221 | 87240 | ATGAGTACTATAGAATTCCT | 48 | 3599 |
| 876271 | 4753 | 4772 | 92176 | 92195 | TCCGGTCAATTACGGGAAAT | 36 | 3600 |
| 876295 | 5074 | 5093 | 98222 | 98241 | TCTGGAATTTTTCTAGGAGC | 26 | 150 |
| 876319 | 5454 | 5473 | 100443 | 100462 | AATGTGGTCCACAACTTGGC | 49 | 3601 |
| 876343 | 5792 | 5811 | 106483 | 106502 | GCTGCTCGGTAAACTGATCC | 46 | 3602 |
| 876367 | 6601 | 6620 | 129746 | 129765 | TGCTTGCATTCCTGCTGTTG | 43 | 3603 |
| 876391 | 7218 | 7237 | 141579 | 141598 | AACAGGGCTATTTTGCTTAG | 54 | 3604 |
| 876415 | 8131 | 8150 | 146300 | 146319 | TACATTACATGGGAAACTGT | 43 | 3605 |
| 876439 | 9021 | 9040 | 147190 | 147209 | AATACAGAAAATCTTTCATC | 120 | 3606 |
| 876463 | N/A | N/A | 4967 | 4986 | ATCAGGCACTTCTGAACACC | 51 | 3607 |
| 876487 | N/A | N/A | 7241 | 7260 | AGTGAGTATTAAAATGTCAG | 47 | 3608 |
| 876511 | N/A | N/A | 9214 | 9233 | TGCTCCCCAAGTAATGAAGC | 65 | 3609 |
| 876535 | N/A | N/A | 12417 | 12436 | GATTTTAATCCCTATGTTAT | 115 | 3610 |
| 876559 | N/A | N/A | 15046 | 15065 | ACTTCAATATATTCCAGTGT | 54 | 3611 |
| 876583 | N/A | N/A | 17338 | 17357 | TGCTATTCTGACTTTTGACA | 87 | 3612 |
| 876607 | N/A | N/A | 19605 | 19624 | GTTAATGGTCACTTACAAAA | 32 | 3613 |

TABLE 48-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876631 | N/A | N/A | 21986 | 22005 | GACACTCCTTTTAAAAGTCC | 33 | 3614 |
| 876655 | N/A | N/A | 25054 | 25073 | TTCAGCAACCACTCTCACTT | 60 | 3615 |
| 876679 | N/A | N/A | 27604 | 27623 | TTCATTGTGTAAAATAACTT | 95 | 3616 |
| 876703 | N/A | N/A | 29976 | 29995 | ATCACAGATGGCTCTGCAAT | 56 | 3617 |
| 876727 | N/A | N/A | 32024 | 32043 | ATAATAGACAATTTTACCAG | 33 | 3618 |
| 876751 | N/A | N/A | 33545 | 33564 | AGAACATTTTACACACTATC | 52 | 3619 |
| 876775 | N/A | N/A | 35950 | 35969 | CTATATAATCTTAGCATCTC | 86 | 3620 |
| 876799 | N/A | N/A | 38144 | 38163 | CATTGAGGTAAATGAGTACA | 83 | 3621 |
| 876823 | N/A | N/A | 39741 | 39760 | TTGATACCTAGAATGATACG | 71 | 3622 |
| 876847 | N/A | N/A | 42026 | 42045 | ATAGTATAAATACAGAAAAC | 84 | 3623 |
| 876871 | N/A | N/A | 45585 | 45604 | TTGGCTAACTGGAACCAGTT | 63 | 3624 |
| 876895 | N/A | N/A | 47882 | 47901 | GGAAGGAAAAAACGAATACC | 61 | 3625 |
| 876919 | N/A | N/A | 49713 | 49732 | ATCTTGAAATAGTAATGTAT | 67 | 3626 |
| 876943 | N/A | N/A | 52094 | 52113 | TGGGACTTGAATATAAATGT | 97 | 3627 |
| 876967 | N/A | N/A | 54851 | 54870 | TTGATAAGCAAAGTAGCCTT | 34 | 3628 |
| 876991 | N/A | N/A | 57309 | 57328 | TAAACTATTGGCAAACATAG | 79 | 3629 |
| 877015 | N/A | N/A | 60005 | 60024 | AGGTGATTTATGTTTTACTC | 56 | 3630 |
| 877039 | N/A | N/A | 62783 | 62802 | TCAGAAGATGGTAACTTACC | 85 | 3631 |
| 877063 | N/A | N/A | 65433 | 65452 | TAAGAGATACACCAGCAACT | 91 | 3632 |
| 877087 | N/A | N/A | 67067 | 67086 | GGTTTCTTAAGTGGGATACA | 45 | 3633 |
| 877111 | N/A | N/A | 70265 | 70284 | TACATAAGAAGAAATTTAAA | 105 | 3634 |
| 877135 | N/A | N/A | 72531 | 72550 | ATTAACACAAAACAACCCTC | 63 | 3635 |
| 877159 | N/A | N/A | 73941 | 73960 | CAGATCTGTTTCCATTGCCT | 23 | 3636 |
| 877183 | N/A | N/A | 75798 | 75817 | AGCAAACCCCTACTTACACA | 37 | 3637 |
| 877207 | N/A | N/A | 78361 | 78380 | TCTACAACTTTTAATAAAAG | 85 | 3638 |
| 877231 | N/A | N/A | 81545 | 81564 | AAAGATAAATTTACACATAT | 76 | 3639 |
| 877238 | N/A | N/A | 82750 | 82769 | AGAATTTTATCCTTATACT | 77 | 3640 |
| 877262 | N/A | N/A | 85277 | 85296 | CCACTATTTGAAAAAATGTC | 41 | 3641 |
| 877286 | N/A | N/A | 88222 | 88241 | ATTCACTCCTAAATAAAATA | 95 | 3642 |
| 877310 | N/A | N/A | 90580 | 90599 | ATGATCTCTAATAGATTAAA | 76 | 3643 |
| 877334 | N/A | N/A | 92439 | 92458 | ACATGATTGTCATGAACAC | 19 | 3644 |
| 877358 | N/A | N/A | 94604 | 94623 | TAAGTGCTCTGGGTCACACT | 53 | 3645 |
| 877382 | N/A | N/A | 96108 | 96127 | AGCACCAATACTCCAAAAAC | 67 | 3646 |
| 877406 | N/A | N/A | 98871 | 98890 | ATTAGTTATGCATAGACAAA | 83 | 3647 |
| 877430 | N/A | N/A | 101490 | 101509 | AATCTATGACAATATAATTA | 102 | 3648 |
| 877454 | N/A | N/A | 104219 | 104238 | ATATGGAGTATGGATTGTCA | 46 | 3649 |

TABLE 48-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877478 | N/A | N/A | 106035 | 106054 | ACTAGTTTTTATTCTACCTT | 90 | 3650 |
| 877502 | N/A | N/A | 108861 | 108880 | CTAACATATACTCTTGGAGC | 44 | 3651 |
| 877526 | N/A | N/A | 111304 | 111323 | AATCTTTTTTTAATGCCCA | 61 | 3652 |
| 877550 | N/A | N/A | 113493 | 113512 | TGATGGGTTCTAGAGCAGAA | 38 | 3653 |
| 877574 | N/A | N/A | 116095 | 116114 | GCTAACACTTCATGACACAC | 49 | 3654 |
| 877598 | N/A | N/A | 118289 | 118308 | AGCATCAAAAATTCTGTGCT | 51 | 3655 |
| 877622 | N/A | N/A | 120141 | 120160 | GTGGTCCAGTCCACCTTCAT | 61 | 3656 |
| 877646 | N/A | N/A | 122515 | 122534 | TTATGCTTCCCTTCTTAGAA | 63 | 3657 |
| 877670 | N/A | N/A | 125342 | 125361 | AAAACATTCCAGGATAATGA | 52 | 3658 |
| 877694 | N/A | N/A | 128625 | 128644 | TAAAACATGACAAGAGTTCT | 124 | 3659 |
| 877718 | N/A | N/A | 133009 | 133028 | TCTTAATTTGGTAGTTAGAT | 28 | 3660 |
| 877742 | N/A | N/A | 136525 | 136544 | GATGAAAGTAGGCCCCACTC | 70 | 3661 |
| 877766 | N/A | N/A | 140319 | 140338 | TGTCAGAGAGCCACTACGCT | 57 | 3662 |
| 877790 | N/A | N/A | 141746 | 141765 | TTCTCTATTCAGAGGCAGAA | 61 | 3663 |
| 877814 | N/A | N/A | 144077 | 144096 | TTCAACTAGAGAATGCAACA | 58 | 3664 |
| 877838 | N/A | N/A | 145702 | 145721 | AAAGATCCATCATAAAACAT | 111 | 3665 |

TABLE 49

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 28 | 222 |
| 876027 | 730 | 749 | 18629 | 18648 | TTAACAATATCATATAATCT | 6 | 3666 |
| 876051 | 838 | 857 | 21669 | 21688 | TGCCACTCATGAGGACTTCC | 39 | 3667 |
| 876075 | 1237 | 1256 | 29588 | 29607 | TAAGGAGATTATTTAGTGCC | 61 | 3668 |
| 876099 | 1481 | 1500 | 35428 | 35447 | TCAGCCACTTCAGGAGAATG | 53 | 3669 |
| 876123 | 1700 | 1719 | 41933 | 41952 | ACCATATTTAGCTTATGATG | 25 | 3670 |
| 876147 | 2450 | 2469 | 62071 | 62090 | TCACCTTTCCCAATGCTTAT | 77 | 3671 |
| 876171 | 2936 | 2955 | 72960 | 72979 | AAATCTTCATGATCAAAAAT | 85 | 3672 |
| 876195 | 3338 | 3357 | 76472 | 76491 | GTAGGATCTAAAACCACTGA | 22 | 3673 |
| 876219 | 3840 | 3859 | 82185 | 82204 | TCTAGACCATAAATATGCTT | 29 | 3674 |
| 876243 | 4312 | 4331 | 87216 | 87235 | TACTATAGAATTCCTCACGA | 58 | 3675 |
| 876267 | 4735 | 4754 | 92158 | 92177 | ATTCAATTGGCACATTTTTA | 49 | 3676 |

TABLE 49-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876291 | 5069 | 5088 | 98217 | 98236 | AATTTTTCTAGGAGCTTAAA | 107 | 3677 |
| 876315 | 5448 | 5467 | 100437 | 100456 | GTCCACAACTTGGCCCAAAA | 30 | 3678 |
| 876339 | 5694 | 5713 | 101332 | 101351 | CAGGTCAGCCAAAATCAAGT | 37 | 3679 |
| 876363 | 6466 | 6485 | 126582 | 126601 | TTTCTTGAGGATTTTCTTTC | 75 | 3680 |
| 876387 | 7046 | 7065 | 137450 | 137469 | ATTACATTTCTTTCCGTTGA | 53 | 3681 |
| 876411 | 7998 | 8017 | 146167 | 146186 | AAATTATCGGCCTTATAAAT | 96 | 3682 |
| 876435 | 8867 | 8886 | 147036 | 147055 | GGCCAAAGAATTTACCGAAA | 48 | 3683 |
| 876459 | N/A | N/A | 4386 | 4405 | TTTTTAAGGCCCCCTTTAAA | 95 | 3684 |
| 876483 | N/A | N/A | 7028 | 7047 | TTAGGTCTGTCACAAGCTCT | 50 | 3685 |
| 876507 | N/A | N/A | 8960 | 8979 | CAGTCTGTTTACAAGATGCC | 36 | 3686 |
| 876531 | N/A | N/A | 11871 | 11890 | TGAACAGTTGGTTTGTACAG | 67 | 3687 |
| 876555 | N/A | N/A | 14783 | 14802 | GGACTGATGAGGACAATTCA | 88 | 3688 |
| 876579 | N/A | N/A | 16929 | 16948 | AGGTGATCTATCCCATTCTG | 67 | 3689 |
| 876603 | N/A | N/A | 19458 | 19477 | GTGGCTAAATTTCAAAGCCT | 70 | 3690 |
| 876627 | N/A | N/A | 21316 | 21335 | TGGAAATGTAATGTATTGGT | 56 | 3691 |
| 876651 | N/A | N/A | 24654 | 24673 | GCAGTTGGTTTAGACTCCCC | 44 | 3692 |
| 876675 | N/A | N/A | 27306 | 27325 | AGGAAAAACTTTACCTGATA | 83 | 3693 |
| 876699 | N/A | N/A | 29666 | 29685 | ATTTTCTATCATATAAAATC | 93 | 3694 |
| 876723 | N/A | N/A | 31361 | 31380 | TAAAATTTTGTATATGTCAT | 146 | 3695 |
| 876747 | N/A | N/A | 33424 | 33443 | AGGTCTTACTCAATAGTCAC | 34 | 3696 |
| 876771 | N/A | N/A | 35347 | 35366 | CTGAAATTAACTGAGATTTT | 84 | 3697 |
| 876795 | N/A | N/A | 37878 | 37897 | TATAAAATTAATCTAAGTG | 85 | 3698 |
| 876819 | N/A | N/A | 39165 | 39184 | CTGATTGAATAGCCACCAGA | 110 | 3699 |
| 876843 | N/A | N/A | 41526 | 41545 | AAGCTCAGAGTTACTTGGAC | 52 | 3700 |
| 876867 | N/A | N/A | 45354 | 45373 | GACGCGGCAACTGTGGCAAT | 34 | 3701 |
| 876891 | N/A | N/A | 47370 | 47389 | ATGAATGATTACCATGTAAG | 87 | 3702 |
| 876915 | N/A | N/A | 49237 | 49256 | TCCAACATCATATGACTGAT | 62 | 3703 |
| 876939 | N/A | N/A | 51525 | 51544 | CAGTTTCTCACCCTGTGTCC | 50 | 3704 |
| 876963 | N/A | N/A | 54026 | 54045 | AGTTACAAAAAATATTTCCT | 79 | 3705 |
| 876987 | N/A | N/A | 56923 | 56942 | GAATTATATTTTGAAGGGAG | 66 | 3706 |
| 877011 | N/A | N/A | 59932 | 59951 | CCATTTTATATTCTCTATTA | 85 | 3707 |
| 877035 | N/A | N/A | 62618 | 62637 | TACATGTAAGCATATAAAAA | 116 | 3708 |
| 877059 | N/A | N/A | 64920 | 64939 | CCTGATGGAATTTCAAAGTT | 89 | 3709 |
| 877083 | N/A | N/A | 67061 | 67080 | TTAAGTGGGATACAAAAAGC | 65 | 3710 |
| 877107 | N/A | N/A | 69892 | 69911 | ATATTTCTCTATCAAATACA | 79 | 3711 |
| 877131 | N/A | N/A | 72432 | 72451 | GGCTCCCAATTTCCTCAACT | 25 | 3712 |

TABLE 49-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877155 | N/A | N/A | 73935 | 73954 | TGTTTCCATTGCCTGCCCTC | 62 | 3713 |
| 877179 | N/A | N/A | 75295 | 75314 | AATTGAAGGATTACCAAGTT | 67 | 3714 |
| 877203 | N/A | N/A | 78122 | 78141 | TGCATGTTTAGTTTAAGACT | 65 | 3715 |
| 877227 | N/A | N/A | 81187 | 81206 | GTTTTTACACAATGATCCAC | 57 | 3716 |
| 877234 | N/A | N/A | 82324 | 82343 | TCATGAAATTGGTATTTAGA | 73 | 3717 |
| 877258 | N/A | N/A | 84886 | 84905 | AGAGATTTTAGGCAGAAGAG | 68 | 3718 |
| 877282 | N/A | N/A | 87961 | 87980 | TGTATGCAGCCAATTACATG | 81 | 3719 |
| 877306 | N/A | N/A | 90436 | 90455 | AAACCATTATGCCAGAATGC | 54 | 3720 |
| 877330 | N/A | N/A | 91673 | 91692 | CTTTTGGATATTATTATATT | 76 | 3721 |
| 877354 | N/A | N/A | 94268 | 94287 | AATAATTTTAGGAACTCGGG | 85 | 3722 |
| 877378 | N/A | N/A | 95893 | 95912 | ACATTATCTTGACTTTATCA | 41 | 3723 |
| 877402 | N/A | N/A | 98345 | 98364 | TAGACTACAGTTAGTTTGAC | 49 | 3724 |
| 877426 | N/A | N/A | 101401 | 101420 | ATTACCTAGGAGAAACTCTG | 66 | 3725 |
| 877450 | N/A | N/A | 103499 | 103518 | TTCTGTAAATGAACATGGGA | 62 | 3726 |
| 877474 | N/A | N/A | 105725 | 105744 | CTCTCCTGTTCAGAAACAAA | 114 | 3727 |
| 877498 | N/A | N/A | 108194 | 108213 | GAGGGCGAGGAAACTAACTC | 66 | 3728 |
| 877522 | N/A | N/A | 111004 | 111023 | CACCATTCCCTTAGTTTGCC | 38 | 3729 |
| 877546 | N/A | N/A | 112841 | 112860 | AAGTGCATGAGTCCACATAT | 81 | 3730 |
| 877570 | N/A | N/A | 115680 | 115699 | TAGAGTCAAGGACCTGGTGG | 62 | 3731 |
| 877594 | N/A | N/A | 117784 | 117803 | CTTCTGTTTGAGTATATAAT | 83 | 3732 |
| 877618 | N/A | N/A | 119917 | 119936 | TTAGAGTTGCATATGGTTTA | 41 | 3733 |
| 877642 | N/A | N/A | 122346 | 122365 | ATTTGGAATCACAGGCTCTT | 66 | 3734 |
| 877666 | N/A | N/A | 125137 | 125156 | TTATGCACTAAACAAAAAAA | 106 | 3735 |
| 877690 | N/A | N/A | 128267 | 128286 | TGGGACCCCAAAGGACTGCA | 54 | 3736 |
| 877714 | N/A | N/A | 132254 | 132273 | TTTATTTAATTTTCAGCAAT | 78 | 3737 |
| 877738 | N/A | N/A | 135518 | 135537 | ATATCAAAGGGATTCCTATA | 113 | 3738 |
| 877762 | N/A | N/A | 139971 | 139990 | CCTCTCAGTCGGTGTGTACT | 102 | 3739 |
| 877786 | N/A | N/A | 141372 | 141391 | TAGACTATTGCAATTATTTC | 87 | 3740 |
| 877810 | N/A | N/A | 143858 | 143877 | TATTTCTTCACCATGTTCA | 97 | 3741 |
| 877834 | N/A | N/A | 145268 | 145287 | TACCATATGTAATATTTTCT | 57 | 3742 |

TABLE 50

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 780241 | 3714 | 3733 | 82059 | 82078 | GCTCATATCTAAAGACCGCA | 24 | 222 |
| 803629 | N/A | N/A | 81591 | 81610 | AAGCCATAGTGTTTGAAGGA | 34 | 1791 |
| 876014 | 340 | 359 | 87848 | 87867 | CCTGCTGCACACTCGCGACT | 48 | 3743 |
| 876038 | 823 | 842 | 3731 | 3750 | CTTCCACATTATTGCAAGGA | 41 | 3744 |
| 876062 | 1022 | 1041 | 27997 | 28016 | GCTGCATTCTCTGGGTACTG | 28 | 3745 |
| 876086 | 1465 | 1484 | 35412 | 35431 | AATGTATATGCTTCTGCATT | 77 | 3746 |
| 876110 | 1494 | 1513 | 35441 | 35460 | TTTACAGCCACTTTCAGCCA | 63 | 3747 |
| 876134 | 2047 | 2066 | N/A | N/A | ATCCTTTAGTCTGTATTTCA | 83 | 3748 |
| 876158 | 2711 | 2730 | 65549 | 65568 | GACAGCACATCTTCAGAAAA | 64 | 3749 |
| 876182 | 3221 | 3240 | 76355 | 76374 | AAATGTGTCAAACTCTTCAG | 52 | 3750 |
| 876206 | 3747 | 3766 | 82092 | 82111 | TGCGGGACCTGGTAGGTACT | 57 | 3751 |
| 876230 | 3968 | 3987 | 83963 | 83982 | CCCATTTCATTGGGAAAGGA | 45 | 3752 |
| 876254 | 4520 | 4539 | 88621 | 88640 | AGTTCCTTGGTGATTTTACT | 45 | 3753 |
| 876278 | 4919 | 4938 | 93380 | 93399 | ATTTTACAAAGCCACTTGGG | 74 | 3754 |
| 876302 | 5195 | 5214 | 99201 | 99220 | GGCATTTCATATAGTCGGAT | 26 | 3755 |
| 876326 | 5644 | 5663 | 101282 | 101301 | GCCTTGGTTGATCTGGATTT | 32 | 3756 |
| 876350 | 6028 | 6047 | 113225 | 113244 | GTGCAATCCTGTGCTGTAGG | 42 | 3757 |
| 876374 | 6694 | 6713 | N/A | N/A | TACTATCAGCAACTTCCTCA | 100 | 3758 |
| 876398 | 7439 | 7458 | 143087 | 143106 | CGTATAAGTCGACGAGTTGA | 98 | 3759 |
| 876422 | 8442 | 8461 | 146611 | 146630 | TCAGGGTATCCACATTCAAA | 69 | 3760 |
| 876446 | N/A | N/A | 3734 | 3753 | TTACCTGCTGCACACTCGCG | 63 | 3761 |
| 876470 | N/A | N/A | 5242 | 5261 | TCCTTATTTTCCAGCATACT | 57 | 3762 |
| 876494 | N/A | N/A | 7823 | 7842 | TCTCTCTAAGAGAGAAGGTT | 64 | 3763 |
| 876518 | N/A | N/A | 10777 | 10796 | CTTCATGGTTTGAATTCAAA | 38 | 3764 |
| 876542 | N/A | N/A | 13175 | 13194 | AAATCATCAATTGTATACCT | 70 | 3765 |
| 876566 | N/A | N/A | 15815 | 15834 | CTCAATCAGTACTTCTAGCC | 79 | 3766 |
| 876590 | N/A | N/A | 17963 | 17982 | AGTTTATCTAGCTTGAGAAT | 67 | 3767 |
| 876614 | N/A | N/A | 20012 | 20031 | AAACCATGGCCTTTCTCTAT | 65 | 3768 |
| 876638 | N/A | N/A | 22763 | 22782 | CCAAAACATTATTATCCAGA | 58 | 3769 |
| 876662 | N/A | N/A | 26068 | 26087 | AGAAATTTGGGTTCTCAGCC | 64 | 3770 |
| 876686 | N/A | N/A | 28077 | 28096 | AAATGCCTCTGTAAGAATCC | 81 | 3771 |
| 876710 | N/A | N/A | 30722 | 30741 | AAGTGAGGAGAAGAGAATGG | 96 | 3772 |
| 876734 | N/A | N/A | 32675 | 32694 | TCTAAAGGTGCCCCAACAGA | 71 | 3773 |
| 876758 | N/A | N/A | 34015 | 34034 | ATCACATACACATTCTAAAA | 68 | 3774 |
| 876782 | N/A | N/A | 36424 | 36443 | ATAGATTAGTTAGACTGATG | 48 | 3775 |
| 876806 | N/A | N/A | 38547 | 38566 | TTCTGCTTGAAATGTCTTCC | 78 | 3776 |

TABLE 50-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 876830 | N/A | N/A | 40757 | 40776 | TCTTTGTTCTATCACTTGAG | 72 | 3777 |
| 876854 | N/A | N/A | 42910 | 42929 | CCTTCTTCTCTTTTTCATAC | 42 | 3778 |
| 876878 | N/A | N/A | 46658 | 46677 | TAAAAATTTAGTCCTTCATC | 115 | 3779 |
| 876902 | N/A | N/A | 48098 | 48117 | AGGGTGCATAGTCTGTAGGT | 52 | 3780 |
| 876926 | N/A | N/A | 50310 | 50329 | CTGTTTGGCAGGCAAGGCCA | 114 | 3781 |
| 876950 | N/A | N/A | 52848 | 52867 | ATTCTAAATCCTGAATTCAA | 102 | 3782 |
| 876974 | N/A | N/A | 55881 | 55900 | AGGATGTTCATTTAACTATA | 53 | 3783 |
| 876998 | N/A | N/A | 57829 | 57848 | GAATATGGAAAGAGGAATAA | 94 | 3784 |
| 877022 | N/A | N/A | 61188 | 61207 | TCCATCAGTTACTGTGCTAA | 58 | 3785 |
| 877046 | N/A | N/A | 63238 | 63257 | GAAGAGAGAATTTAGAGCTA | 81 | 3786 |
| 877070 | N/A | N/A | 66210 | 66229 | AAAGCCCCTCACTCCATTTT | 60 | 3787 |
| 877094 | N/A | N/A | 67516 | 67535 | AAGTTAGTTGATTAAAAATT | 120 | 3788 |
| 877118 | N/A | N/A | 71000 | 71019 | ATAAATTTGGCTGGCAATAA | 76 | 3789 |
| 877142 | N/A | N/A | 72845 | 72864 | GTTAATGGTATTTATAATTA | 86 | 3790 |
| 877166 | N/A | N/A | 74324 | 74343 | ATTTTCAGAGAGCTATCCTA | 103 | 3791 |
| 877190 | N/A | N/A | 76592 | 76611 | CTTTCTTACCCTTCTAAAAT | 71 | 3792 |
| 877214 | N/A | N/A | 79053 | 79072 | CTGAGATGACACACTGACCA | 50 | 3793 |
| 877245 | N/A | N/A | 83601 | 83620 | CTCTTCAAGACATTGAAAGT | 81 | 3794 |
| 877269 | N/A | N/A | 86919 | 86938 | GAAATGAAGGGCTTTGGAAT | 76 | 3795 |
| 877293 | N/A | N/A | 89053 | 89072 | ATAAGAAGTTGAATCAGAAA | 99 | 3796 |
| 877317 | N/A | N/A | 91034 | 91053 | CTCTTAACCCAGAGAATTAG | 82 | 3797 |
| 877341 | N/A | N/A | 93061 | 93080 | ACAGAGCATATTTCACACAT | 42 | 3798 |
| 877365 | N/A | N/A | 95209 | 95228 | CCACAGAATCTTCAGGAATT | 45 | 3799 |
| 877389 | N/A | N/A | 96646 | 96665 | TTGGATAAATTATTCAACCT | 70 | 3800 |
| 877413 | N/A | N/A | 99821 | 99840 | TGATCATGCTAAACGCAAAA | 90 | 3801 |
| 877437 | N/A | N/A | 102050 | 102069 | GAATATTGAAACATGGTTAC | 48 | 3802 |
| 877461 | N/A | N/A | 104931 | 104950 | TCTTGGTATTCTCTCATTCT | 46 | 3803 |
| 877485 | N/A | N/A | 106787 | 106806 | TTACAACACACTATGTATCA | 86 | 3804 |
| 877509 | N/A | N/A | 109992 | 110011 | ATTAAACCAATATACCAAGG | 60 | 3805 |
| 877533 | N/A | N/A | 111782 | 111801 | GCAATTCAAAAAAGTCCGA | 58 | 3806 |
| 877557 | N/A | N/A | 114063 | 114082 | TGAGAGAAATTGTTAGAAGC | 85 | 3807 |
| 877581 | N/A | N/A | 116850 | 116869 | TTTATAGAACACAGACTCTT | 88 | 3808 |
| 877605 | N/A | N/A | 119162 | 119181 | AGGGAGGTAAGATTCCACAG | 62 | 3809 |
| 877629 | N/A | N/A | 121067 | 121086 | CATATGTCAGAGGGTCCTAA | 63 | 3810 |
| 877653 | N/A | N/A | 123315 | 123334 | TTTGCTAAAATTATCTGTGC | 65 | 3811 |
| 877677 | N/A | N/A | 126752 | 126771 | GATGGTGAAAATTATAGGAG | 50 | 3812 |

TABLE 50-continued

Percent control of human LRRK2 RNA with 5-10-5 MOE gapmers with mixed internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | LRRK2 % control | SEQ ID NO |
|---|---|---|---|---|---|---|---|
| 877701 | N/A | N/A | 129290 | 129309 | AAAAACCCTTGGGCCAACAA | 71 | 3813 |
| 877725 | N/A | N/A | 133380 | 133399 | CCCTGCTGTGATAGGCTTGA | 51 | 3814 |
| 877749 | N/A | N/A | 138071 | 138090 | TTGAAAGAGGTTTATATTAA | 95 | 3815 |
| 877773 | N/A | N/A | 140699 | 140718 | GGTGTCACTGTCATATTATA | 60 | 3816 |
| 877797 | N/A | N/A | 142490 | 142509 | ATAGTCTAATTCATGACAAA | 102 | 3817 |
| 877821 | N/A | N/A | 144612 | 144631 | CTATGTAGGCCCTAGGCTAG | 73 | 3818 |

Example 5: Effect of 5-10-5 MOE Gapmers with Phosphorothioate Internucleoside Linkages on Human LRRK2 RNA Expression In Vitro, Multiple Doses Modified oligonucleotides selected from Example 1 above were tested at various doses in SH-SY5Y cells. Cells were plated at a density of 20,000 cells per well and transfected using electroporation with 1.125 µM, 2.250 µM, 4.500 µM, 9.000 µM, and 18.000 µM concentrations of modified oligonucleotide, as specified in the tables below. After a treatment period of approximately 24 hours, total RNA was isolated from the cells and LRRK2 RNA levels were measured by quantitative real-time PCR. Human LRRK2 primer probe set RTS3133_MGB (described herein in Example 1) was used to measure RNA levels. LRRK2 RNA levels were adjusted according to total RNA content, as measured by RIBOGREEN®. Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 51

Dose-dependent reduction of human LRRK2 RNA expression in SH-SY5Y cells

| | LRRK2 expression (% control) | | | | | |
|---|---|---|---|---|---|---|
| Compound Number | 1.125 µM | 2.250 µM | 4.500 µM | 9.000 µM | 18.000 µM | IC$_{50}$ (µM) |
| 438387 | 81 | 43 | 30 | 18 | 14 | 2 |
| 438429 | 119 | 109 | 116 | 89 | 81 | 31 |
| 438432 | 110 | 78 | 64 | 42 | 15 | 7 |
| 438543 | 94 | 85 | 69 | 44 | 42 | 10 |
| 438565 | 92 | 80 | 80 | 66 | 53 | 22 |
| 438569 | 94 | 79 | 65 | 51 | 47 | 12 |
| 438586 | 98 | 85 | 52 | 38 | 27 | 6 |
| 438587 | 91 | 80 | 58 | 43 | 32 | 7 |
| 438595 | 86 | 66 | 41 | 35 | 25 | 4 |
| 438597 | 45 | 39 | 37 | 32 | 18 | n/a* |
| 438602 | 59 | 73 | 50 | 30 | 33 | 4 |
| 438622 | 109 | 115 | 100 | 92 | 85 | 40 |
| 438625 | 110 | 108 | 96 | 94 | 81 | 36 |
| 422428 | 75 | 57 | 35 | 27 | 20 | 3 |
| 422433 | 75 | 56 | 32 | 18 | 15 | 3 |
| 422450 | 81 | 97 | 87 | 71 | 66 | 51 |
| 422451 | 74 | 52 | 40 | 29 | 26 | 3 |
| 422461 | 89 | 65 | 44 | 30 | 25 | 4 |
| 438538 | 72 | 54 | 33 | 20 | 16 | 3 |
| 438544 | 65 | 39 | 28 | 18 | 12 | 2 |
| 438545 | 90 | 60 | 37 | 15 | 13 | 3 |
| 438548 | 89 | 65 | 38 | 20 | 16 | 4 |
| 438550 | 95 | 78 | 59 | 34 | 15 | 6 |
| 438560 | 56 | 41 | 30 | 22 | 23 | 1 |
| 438588 | 65 | 57 | 49 | 26 | 17 | 3 |
| 438652 | 109 | 94 | 74 | 54 | 53 | 15 |

*IC$_{50}$ value could not be calculated

Example 6: Effect of 5-10-5 MOE Gapmers with Mixed Internucleoside Linkages on Human LRRK2 RNA Expression In Vitro, Multiple Doses Modified oligonucleotides selected from Examples 2 and 3 above were tested at various doses in SH-SY5Y cells. Cells were plated at a density of 20,000 cells per well and transfected using electroporation with 0.333 µM, 1.000 µM, 3.000 µM, and 9.000 µM concentrations of modified oligonucleotide, as specified in the tables below. After a treatment period of approximately 24 hours, total RNA was isolated from the cells and LRRK2 RNA levels were measured by quantitative real-time PCR. Human LRRK2 primer probe set RTS3132 (described hereinabove in Example 2) was used to measure RNA levels. LRRK2 RNA levels were adjusted according to total RNA content, as measured by RIBOGREEN®. Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 52

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.333 μM | 1.000 μM | 3.000 μM | 9.000 μM | |
| 693423 | 62 | 46 | 45 | 13 | 0.9 |
| 693428 | 58 | 45 | 34 | 13 | 0.7 |
| 693430 | 68 | 28 | 32 | 26 | 0.6 |
| 725607 | 66 | 42 | 30 | 21 | 0.8 |
| 725608 | 54 | 44 | 36 | 40 | 0.4 |
| 780148 | 80 | 67 | 51 | 19 | 2.2 |
| 780162 | 56 | 35 | 29 | 19 | 0.4 |
| 780164 | 43 | 24 | 21 | 24 | 0.07 |
| 780166 | 60 | 51 | 26 | 18 | 0.8 |
| 780189 | 60 | 37 | 22 | 31 | 0.5 |
| 780202 | 70 | 42 | 36 | 20 | 0.9 |
| 780205 | 68 | 44 | 32 | 25 | 0.9 |
| 780210 | 62 | 56 | 31 | 25 | 1.0 |
| 780219 | 75 | 52 | 24 | 31 | 1.2 |
| 780236 | 42 | 34 | 29 | 19 | 0.1 |
| 780241 | 67 | 47 | 18 | 5 | 0.8 |
| 780243 | 37 | 41 | 26 | 25 | n/a* |
| 780254 | 68 | 37 | 35 | 19 | 0.8 |
| 780284 | 66 | 44 | 26 | 19 | 0.8 |

*$IC_{50}$ value cannot be calculated

TABLE 53

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.333 μM | 1.000 μM | 3.000 μM | 9.000 μM | |
| 780254 | 61 | 45 | 23 | 17 | 0.7 |
| 780321 | 66 | 59 | 46 | 25 | 1.6 |
| 780347 | 55 | 47 | 43 | 47 | 0.8 |
| 780430 | 82 | 70 | 55 | 33 | 3.5 |
| 780442 | 80 | 81 | 43 | 31 | 3.0 |
| 780455 | 92 | 61 | 47 | 21 | 2.2 |
| 780461 | 74 | 90 | 72 | 40 | 7.3 |
| 780499 | 74 | 67 | 36 | 36 | 2.2 |
| 780535 | 86 | 71 | 75 | 63 | >60 |
| 780549 | 56 | 31 | 19 | 2 | 0.4 |
| 780551 | 93 | 65 | 26 | 35 | 1.9 |
| 780602 | 52 | 41 | 27 | 17 | 0.4 |
| 780624 | 71 | 52 | 37 | 27 | 1.3 |
| 780649 | 67 | 40 | 29 | 12 | 0.7 |
| 780670 | 85 | 71 | 55 | 31 | 3.4 |
| 780685 | 73 | 43 | 29 | 15 | 0.9 |
| 780700 | 96 | 61 | 36 | 24 | 2.0 |
| 780704 | 84 | 86 | 45 | 37 | 3.8 |
| 780706 | 94 | 72 | 66 | 42 | 6.1 |

Example 7: Effect of 5-10-5 MOE Gapmers with Mixed Internucleoside Linkages on Human LRRK2 RNA Expression In Vitro, Multiple Doses Modified oligonucleotides selected from Example 4 above were tested at various doses in SH-SY5Y cells. Cells were plated at a density of 20,000 cells per well and transfected using electroporation with 0.296, 0.888, 2.666, and 8.000 μM concentrations of modified oligonucleotide, as specified in the tables below. After a treatment period of approximately 24 hours, total RNA was isolated from the cells and LRRK2 RNA levels were measured by quantitative real-time PCR. Human LRRK2 primer probe set RTS3132 (described herein in Example 2) was used to measure RNA levels. LRRK2 RNA levels were adjusted according to total RNA content, as measured by RIBOGREEN®. Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 54

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.296 μM | 0.888 μM | 2.666 μM | 8.000 μM | |
| 780254 | 58 | 36 | 30 | 15 | 0.5 |
| 802655 | 103 | 90 | 87 | 20 | 5.0 |
| 802678 | 51 | 68 | 25 | 5 | 0.7 |
| 802685 | 110 | 82 | 43 | 13 | 2.3 |
| 802686 | 147 | 115 | 70 | 29 | 4.8 |
| 802688 | 87 | 67 | 40 | 15 | 1.7 |
| 802689 | 85 | 69 | 52 | 6 | 2.0 |
| 802700 | 163 | 84 | 29 | 29 | 2.0 |
| 802731 | 155 | 89 | 43 | 40 | 3.7 |
| 802746 | 120 | 78 | 65 | 18 | 3.5 |
| 802748 | 116 | 82 | 36 | 12 | 2.1 |
| 802758 | 119 | 71 | 31 | 5 | 1.7 |
| 802769 | 87 | 81 | 39 | 38 | 2.9 |
| 802778 | 97 | 53 | 56 | 30 | 2.6 |
| 802780 | 92 | 53 | 34 | 22 | 1.4 |
| 802784 | 84 | 82 | 42 | 26 | 2.5 |
| 802832 | 116 | 62 | 94 | 31 | 6.0 |
| 802888 | 58 | 54 | 26 | 10 | 0.7 |
| 802915 | 80 | 50 | 28 | 10 | 1.0 |

TABLE 55

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.296 μM | 0.888 μM | 2.666 μM | 8.000 μM | |
| 780254 | 76 | 56 | 26 | 12 | 1.0 |
| 802845 | 127 | 100 | 43 | 13 | 1.0 |
| 802911 | 77 | 44 | 27 | 11 | 0.8 |
| 802924 | 184 | 159 | 59 | 18 | n/a* |
| 802934 | 158 | 108 | 93 | 47 | 7.6 |
| 802949 | 113 | 69 | 33 | No signal | 1.7 |
| 802962 | 128 | 150 | 93 | 27 | 6.1 |
| 802966 | 171 | 130 | 17 | 31 | n/a* |
| 802974 | 120 | 71 | 36 | 13 | 1.9 |
| 803000 | 106 | 158 | 57 | 36 | 4.9 |
| 803021 | 80 | 112 | 75 | 70 | 22.1 |
| 803045 | 87 | 68 | 54 | 32 | 3.0 |
| 803046 | 70 | 69 | 28 | 14 | 1.2 |
| 803054 | 104 | 114 | 116 | 45 | n/a* |
| 803064 | 60 | 80 | 62 | 26 | 3.1 |
| 803065 | 101 | 89 | 27 | 55 | 4.0 |
| 803075 | 94 | 56 | 53 | 10 | 1.8 |
| 803112 | 90 | 37 | 27 | 11 | 0.9 |
| 803122 | 74 | 63 | 26 | 27 | 1.3 |

*$IC_{50}$ value cannot be calculated

TABLE 56

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.296 μM | 0.888 μM | 2.666 μM | 8.000 μM | |
| 780254 | 57 | 43 | 30 | 10 | 0.5 |
| 803102 | 76 | 76 | 46 | 28 | 2.4 |
| 803123 | 103 | 110 | 60 | 30 | 4.2 |
| 803172 | 104 | 87 | 82 | 46 | 7.3 |
| 803177 | 138 | 98 | 72 | 41 | 5.9 |
| 803181 | 142 | 84 | 86 | 50 | 8.0 |
| 803272 | 105 | 94 | 68 | 47 | 6.6 |
| 803285 | 87 | 80 | 56 | 38 | 4.1 |
| 803359 | 102 | 81 | 105 | 69 | n/a* |
| 803386 | 81 | 65 | 28 | 24 | 1.4 |
| 803436 | 116 | 97 | 59 | 81 | n/a* |
| 803470 | 60 | 61 | 25 | 44 | 1.1 |
| 803503 | 71 | 50 | 61 | 50 | 8.4 |
| 803517 | 75 | 48 | 58 | 22 | 1.7 |
| 803519 | 80 | 59 | 43 | 52 | 3.9 |
| 803571 | 65 | 57 | 36 | 26 | 1.1 |
| 803595 | 66 | 62 | 34 | 25 | 1.2 |
| 803603 | 86 | 65 | 59 | 29 | 3.0 |
| 803604 | 50 | 32 | 52 | 22 | 0.2 |

*$IC_{50}$ value cannot be calculated

TABLE 57

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.296 μM | 0.888 μM | 2.666 μM | 8.000 μM | |
| 780254 | 54 | 45 | 18 | 22 | 0.4 |
| 780620 | 120 | 87 | 77 | 37 | 5.7 |
| 780624 | 133 | 66 | 38 | 62 | 5.5 |
| 803541 | 110 | 86 | 40 | 16 | 2.3 |
| 803628 | 140 | 77 | 57 | 15 | 3.0 |
| 803629 | 78 | 31 | 40 | 15 | 0.8 |
| 803640 | 116 | 125 | 81 | 39 | 6.4 |
| 803645 | 123 | 117 | 59 | 33 | 4.5 |
| 803665 | 154 | 121 | 68 | 48 | 6.8 |
| 803680 | 87 | 71 | 39 | 27 | 2.1 |
| 803682 | 94 | 64 | 31 | 17 | 1.5 |
| 803686 | 79 | 69 | 54 | 21 | 2.3 |
| 803744 | 85 | 50 | 29 | 20 | 1.1 |
| 803745 | 91 | 75 | 55 | 24 | 2.9 |
| 803769 | 60 | 79 | 48 | 19 | 1.9 |
| 803770 | 43 | 38 | 25 | 5 | 0.2 |
| 803771 | 49 | 47 | 20 | 11 | 0.4 |
| 803773 | 73 | 54 | 28 | 28 | 1.1 |
| 803782 | 75 | 61 | 22 | 16 | 1.1 |

Example 8: Effect of 5-10-5 MOE Gapmers with Mixed Internucleoside Linkages on Human LRRK2 RNA Expression In Vitro, Multiple Doses Modified oligonucleotides selected from Example 4 above were tested at various doses in SH-SY5Y cells. Cells were plated at a density of 20,000 cells per well and transfected using electroporation with 0.444, 1.333, 4.000, and 12.000 μM concentrations of modified oligonucleotide, as specified in the tables below. After a treatment period of approximately 24 hours, total RNA was isolated from the cells and LRRK2 RNA levels were measured by quantitative real-time PCR. Human LRRK2 primer probe set RTS3132 (described herein in Example 2) was used to measure RNA levels. LRRK2 RNA levels were adjusted according to total RNA content, as measured by RIBOGREEN®. Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 58

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.444 μM | 1.333 μM | 4.000 μM | 12.000 μM | |
| 780241 | 57 | 29 | 9 | 3 | 0.6 |
| 876032 | 80 | 56 | 25 | 12 | 1.6 |
| 876033 | 65 | 45 | 45 | 8 | 1.3 |
| 876035 | 65 | 59 | 35 | 17 | 1.6 |
| 876200 | 105 | 49 | 29 | 17 | 1.9 |
| 876201 | 83 | 84 | 45 | 22 | 3.8 |
| 876204 | 58 | 38 | 22 | 14 | 0.7 |
| 876224 | 74 | 48 | 41 | 15 | 1.6 |
| 876274 | 70 | 48 | 26 | 16 | 1.2 |
| 876298 | 60 | 47 | 42 | 28 | 1.2 |
| 876611 | 71 | 52 | 27 | 16 | 1.4 |
| 876683 | 79 | 58 | 23 | 27 | 1.8 |
| 876706 | 80 | 57 | 43 | 17 | 2.2 |
| 876850 | 89 | 64 | 37 | 16 | 2.4 |
| 876899 | 42 | 29 | 18 | 9 | 0.3 |
| 877113 | 53 | 44 | 34 | 10 | 0.7 |
| 877160 | 88 | 57 | 29 | 14 | 1.9 |
| 877239 | 115 | 93 | 59 | 31 | 6.1 |
| 877722 | 72 | 43 | 38 | 28 | 1.5 |

TABLE 59

Dose-dependent reduction of human LRRK2 expression in SH-SY5Y cells

| Compound Number | LRRK2 expression (% control) | | | | $IC_{50}$ (μM) |
|---|---|---|---|---|---|
| | 0.444 μM | 1.333 μM | 4.000 μM | 12.000 μM | |
| 780241 | 54 | 37 | 41 | 19 | n/a* |
| 803629 | 90 | 60 | 31 | 31 | 2.5 |
| 876062 | 62 | 38 | 16 | 7 | 0.8 |
| 876084 | 114 | 89 | 42 | 18 | 3.7 |
| 876109 | 84 | 58 | 59 | 40 | 5.6 |
| 876156 | 80 | 68 | 28 | 31 | 2.5 |
| 876180 | 79 | 53 | 41 | 15 | 1.9 |
| 876181 | 73 | 51 | 31 | 33 | 1.7 |
| 876276 | 93 | 51 | 19 | 11 | 1.5 |
| 876301 | 55 | 41 | 32 | 7 | 0.7 |
| 876302 | 47 | 25 | 21 | 7 | 0.3 |
| 876326 | 66 | 50 | 35 | 12 | 1.3 |
| 876900 | 63 | 42 | 21 | 13 | 0.9 |
| 876901 | 63 | 56 | 36 | 29 | 1.6 |
| 877068 | 66 | 42 | 17 | 5 | 0.9 |
| 877292 | 53 | 34 | 16 | 28 | 0.4 |
| 877364 | 71 | 53 | 28 | 31 | 1.6 |
| 877388 | 57 | 56 | 34 | 37 | 1.3 |
| 877748 | 71 | 58 | 40 | 24 | 2.0 |

*$IC_{50}$ value cannot be calculated

TABLE 60

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 87 | 35 | 22 | 14 | 1.2 |
| 876038 | 68 | 39 | 40 | 32 | 1.3 |
| 876041 | 78 | 60 | 31 | 23 | 2.0 |
| 876042 | 52 | 34 | 25 | 12 | 0.5 |
| 876088 | 77 | 61 | 56 | 20 | 3.1 |
| 876089 | 80 | 76 | 48 | 15 | 3.2 |
| 876090 | 73 | 53 | 38 | 22 | 1.8 |
| 876185 | 55 | 52 | 32 | 15 | 0.9 |
| 876186 | 52 | 33 | 23 | 11 | 0.5 |
| 876282 | 53 | 35 | 25 | 11 | 0.5 |
| 876328 | 79 | 60 | 25 | 15 | 1.7 |
| 876401 | 83 | 60 | 52 | 42 | 5.1 |
| 876518 | 75 | 75 | 39 | 22 | 2.8 |
| 876713 | 61 | 59 | 50 | 19 | 1.9 |
| 876905 | 75 | 58 | 42 | 25 | 2.3 |
| 877098 | 82 | 54 | 34 | 24 | 2.0 |
| 877170 | 71 | 60 | 35 | 24 | 1.9 |
| 877392 | 68 | 48 | 31 | 23 | 1.3 |
| 877753 | 67 | 55 | 26 | 22 | 1.4 |

TABLE 61

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 70 | 44 | 39 | 18 | 1.4 |
| 876019 | 67 | 45 | 28 | 11 | 1.1 |
| 876020 | 67 | 55 | 49 | 25 | 2.2 |
| 876066 | 60 | 62 | 36 | 19 | 1.5 |
| 876139 | 78 | 37 | 39 | 10 | 1.3 |
| 876140 | 80 | 47 | 36 | 14 | 1.6 |
| 876255 | 72 | 39 | 33 | 27 | 1.2 |
| 876260 | 70 | 46 | 22 | 29 | 1.2 |
| 876261 | 33 | 25 | 18 | 4 | n/a* |
| 876283 | 75 | 60 | 29 | 13 | 1.7 |
| 876284 | 48 | 35 | 35 | 18 | n/a* |
| 876303 | 48 | 21 | 32 | 2 | 0.3 |
| 876499 | 66 | 72 | 42 | 26 | 2.7 |
| 876735 | 67 | 43 | 28 | 7 | 1.0 |
| 876927 | 63 | 42 | 37 | 41 | 1.2 |
| 877119 | 61 | 31 | 35 | 4 | 0.7 |
| 877246 | 78 | 58 | 43 | 34 | 2.9 |
| 877370 | 69 | 58 | 46 | 40 | 3.3 |
| 877635 | 77 | 82 | 46 | 24 | 3.7 |

*IC$_{50}$ value cannot be calculated

TABLE 62

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 62 | 42 | 16 | 23 | 0.8 |
| 780624 | 70 | 37 | 21 | 6 | 0.9 |
| 803640 | 80 | 34 | 53 | 43 | 3.0 |
| 876141 | 66 | 50 | 30 | 17 | 1.2 |
| 876143 | 70 | 55 | 38 | 29 | 1.9 |
| 876165 | 110 | 74 | 54 | 18 | 4.1 |
| 876166 | 64 | 53 | 34 | 27 | 1.4 |
| 876189 | 62 | 33 | 24 | 22 | 0.7 |
| 876190 | 44 | 27 | 34 | 10 | 0.2 |
| 876213 | 71 | 50 | 37 | 12 | 1.5 |
| 876237 | 52 | 41 | 20 | 15 | 0.6 |
| 876262 | 59 | 37 | 21 | 13 | 0.7 |
| 876263 | 61 | 36 | 36 | 23 | 0.8 |
| 876285 | 68 | 62 | 31 | 23 | 1.8 |
| 876286 | 69 | 67 | 33 | 21 | 2.0 |
| 876645 | 94 | 59 | 47 | 17 | 2.8 |
| 876766 | 67 | 37 | 26 | 13 | 0.9 |
| 876790 | 58 | 41 | 33 | 13 | 0.8 |
| 877222 | 68 | 48 | 32 | 20 | 1.3 |

TABLE 63

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 71 | 54 | 41 | 27 | 2.0 |
| 876072 | 73 | 57 | 40 | 29 | 2.2 |
| 876073 | 72 | 52 | 24 | 25 | 1.4 |
| 876095 | 101 | 80 | 61 | 31 | 5.8 |
| 876097 | 55 | 44 | 42 | 24 | n/a* |
| 876168 | 64 | 45 | 21 | 9 | 0.9 |
| 876215 | 88 | 62 | 37 | 13 | 2.3 |
| 876288 | 75 | 62 | 28 | 6 | 1.7 |
| 876289 | 73 | 65 | 41 | 20 | 2.3 |
| 876335 | 77 | 75 | 43 | 25 | 3.2 |
| 876527 | 90 | 73 | 41 | 21 | 3.1 |
| 876769 | 78 | 67 | 41 | 31 | 1.5 |
| 877176 | 75 | 55 | 41 | 7 | 1.8 |
| 877303 | 61 | 45 | 23 | 19 | 0.8 |
| 877328 | 64 | 38 | 27 | 12 | 0.9 |
| 877375 | 82 | 68 | 47 | 28 | 3.5 |
| 877615 | 58 | 61 | 33 | 21 | 1.4 |
| 877616 | 75 | 50 | 25 | 19 | 1.4 |
| 877806 | 83 | 76 | 50 | 26 | 4.0 |

*IC$_{50}$ value can't be calculated

TABLE 64

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 66 | 53 | 29 | 24 | 1.4 |
| 876050 | 83 | 58 | 52 | 17 | 2.8 |
| 876052 | 72 | 48 | 53 | 17 | 2.0 |
| 876053 | 75 | 47 | 36 | 20 | 1.6 |
| 876098 | 95 | 59 | 38 | 16 | 2.4 |
| 876149 | 71 | 52 | 28 | 20 | 1.4 |
| 876218 | 79 | 61 | 44 | 17 | 2.4 |
| 876220 | 68 | 43 | 39 | 18 | 1.3 |
| 876221 | 48 | 29 | 16 | 9 | 0.4 |
| 876293 | 72 | 54 | 21 | 17 | 1.3 |
| 876337 | 85 | 90 | 59 | 19 | 4.9 |
| 876362 | 86 | 73 | 54 | 26 | 4.2 |

TABLE 64-continued

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 876385 | 81 | 62 | 36 | 20 | 2.3 |
| 876604 | 48 | 27 | 23 | 16 | 0.3 |
| 876725 | 66 | 50 | 39 | 35 | 1.7 |
| 876890 | 76 | 57 | 37 | 21 | 2.0 |
| 877156 | 80 | 58 | 44 | 28 | 2.7 |
| 877355 | 71 | 46 | 42 | 14 | 1.5 |
| 877356 | 49 | 41 | 24 | 29 | 0.3 |

TABLE 65

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 75 | 62 | 42 | 15 | 2.2 |
| 876027 | 87 | 76 | 74 | 54 | n/a* |
| 876030 | 75 | 60 | 44 | 18 | 2.3 |
| 876031 | 69 | 44 | 43 | 13 | 1.4 |
| 876123 | 68 | 48 | 28 | 27 | 1.3 |
| 876150 | 82 | 55 | 48 | 27 | 2.8 |
| 876195 | 77 | 51 | 31 | 45 | 2.4 |
| 876219 | 77 | 65 | 46 | 24 | 2.9 |
| 876222 | 102 | 68 | 54 | 21 | 3.9 |
| 876223 | 74 | 58 | 41 | 16 | 2.0 |
| 876294 | 44 | 25 | 16 | 10 | 0.3 |
| 876295 | 71 | 48 | 51 | 36 | 2.7 |
| 876315 | 75 | 58 | 46 | 41 | 3.7 |
| 877131 | 83 | 67 | 43 | 23 | 2.9 |
| 877159 | 68 | 59 | 41 | 24 | 2.0 |
| 877182 | 104 | 88 | 70 | 19 | 5.9 |
| 877334 | 93 | 87 | 51 | 22 | 4.4 |
| 877357 | 97 | 84 | 51 | 25 | 4.5 |
| 877718 | 73 | 57 | 51 | 32 | 3.0 |

*IC$_{50}$ value cannot be calculated

TABLE 66

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 63 | 36 | 24 | 23 | 0.8 |
| 803627 | 76 | 52 | 30 | 10 | 1.4 |
| 876008 | 59 | 56 | 33 | 31 | 1.3 |
| 876011 | 90 | 66 | 45 | 29 | 3.4 |
| 876034 | 102 | 67 | 39 | 28 | 3.2 |
| 876081 | 80 | 69 | 56 | 29 | 4.2 |
| 876106 | 64 | 43 | 31 | 23 | 1.0 |
| 876203 | 60 | 40 | 23 | 7 | 0.8 |
| 876225 | 77 | 54 | 41 | 32 | 2.4 |
| 876249 | 81 | 69 | 37 | 33 | 3.1 |
| 876321 | 74 | 63 | 43 | 21 | 2.4 |
| 876540 | 90 | 69 | 44 | 22 | 3.1 |
| 876704 | 83 | 73 | 49 | 47 | 6.8 |
| 876731 | 70 | 49 | 39 | 40 | 2.1 |
| 877088 | 77 | 61 | 38 | 31 | 2.6 |
| 877112 | 65 | 52 | 28 | 17 | 1.2 |
| 877161 | 91 | 61 | 62 | 19 | 3.8 |
| 877289 | 73 | 55 | 34 | 20 | 1.7 |
| 877337 | 71 | 57 | 31 | 22 | 1.7 |

TABLE 67

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 50 | 107 | 20 | 6 | n/a* |
| 876015 | 89 | 63 | 46 | 35 | 3.8 |
| 876039 | 64 | 52 | 30 | 29 | 1.3 |
| 876043 | 56 | 41 | 20 | 6 | 0.7 |
| 876091 | 90 | 59 | 30 | 20 | 2.1 |
| 876092 | 72 | 49 | 33 | 21 | 1.5 |
| 876093 | 58 | 97 | 31 | 27 | 3.1 |
| 876187 | 75 | 55 | 47 | 21 | 2.2 |
| 876235 | 72 | 51 | 28 | 20 | 1.4 |
| 876380 | 86 | 57 | 41 | 27 | 2.6 |
| 876639 | 76 | 62 | 42 | 35 | 3.0 |
| 876668 | 75 | 54 | 31 | 22 | 1.7 |
| 876732 | 77 | 52 | 44 | 24 | 2.2 |
| 876741 | 75 | 113 | 46 | 51 | 9.0 |
| 876852 | 70 | 53 | 38 | 28 | 1.8 |
| 877171 | 57 | 39 | 32 | 26 | 0.7 |
| 877395 | 62 | 35 | 22 | 26 | 0.7 |
| 877396 | 77 | 42 | 32 | 7 | 1.2 |
| 877587 | 108 | 83 | 48 | 46 | 6.7 |

*IC$_{50}$ value cannot be calculated

TABLE 68

Dose-dependent reduction of human LRRK2 expression in SH-SY5Y cells

| Compound Number | LRRK2 expression (% control) | | | | IC$_{50}$ (μM) |
|---|---|---|---|---|---|
| | 0.444 μM | 1.333 μM | 4.000 μM | 12.000 μM | |
| 780241 | 52 | 36 | 33 | 11 | 0.5 |
| 876119 | 80 | 67 | 42 | 22 | 2.8 |
| 876169 | 64 | 50 | 34 | 26 | 1.3 |
| 876239 | 71 | 44 | 29 | 23 | 1.2 |
| 876287 | 55 | 41 | 29 | 23 | 0.6 |
| 876334 | 64 | 51 | 44 | 37 | 2.0 |
| 876528 | 83 | 49 | 31 | 19 | 1.7 |
| 876649 | 78 | 60 | 37 | 32 | 2.5 |
| 876694 | 66 | 48 | 32 | 26 | 1.3 |
| 876912 | 68 | 48 | 25 | 30 | 1.2 |
| 876960 | 52 | 32 | 26 | 8 | 0.5 |
| 877102 | 67 | 48 | 30 | 32 | 1.3 |
| 877128 | 66 | 53 | 35 | 30 | 1.6 |
| 877198 | 73 | 52 | 35 | 17 | 1.6 |
| 877252 | 75 | 73 | 34 | 31 | 2.9 |
| 877326 | 50 | 40 | 33 | 12 | 0.5 |
| 877327 | 78 | 53 | 27 | 25 | 1.7 |
| 877349 | 47 | 41 | 33 | 24 | 0.3 |
| 877493 | 88 | 75 | 44 | 37 | 0.4 |

TABLE 69

Dose-dependent reduction of human LRRK2 expression in SH-SY5Y cells

| Compound Number | LRRK2 expression (% control) | | | | IC$_{50}$ (μM) |
| --- | --- | --- | --- | --- | --- |
| | 0.444 μM | 1.333 μM | 4.000 μM | 12.000 μM | |
| 780241 | 63 | 34 | 25 | 9 | 0.8 |
| 803643 | 49 | 59 | 54 | 32 | 1.7 |
| 876049 | 72 | 49 | 46 | 20 | 1.8 |
| 876074 | 54 | 32 | 28 | 7 | 0.5 |
| 876100 | 91 | 50 | 32 | 17 | 1.9 |
| 876124 | 61 | 37 | 17 | 23 | 0.7 |
| 876146 | 52 | 36 | 30 | 26 | 0.4 |
| 876170 | 78 | 48 | 41 | 25 | 1.9 |
| 876173 | 65 | 51 | 23 | 30 | 1.2 |
| 876244 | 71 | 52 | 29 | 31 | 1.6 |
| 876482 | 84 | 83 | 48 | 23 | 4.0 |
| 876553 | 79 | 54 | 32 | 23 | 1.8 |
| 876748 | 75 | 45 | 25 | 14 | 1.2 |
| 876821 | 83 | 64 | 40 | 26 | 2.8 |
| 877204 | 101 | 76 | 45 | 29 | 4.1 |
| 877305 | 63 | 41 | 28 | 17 | 0.9 |
| 877307 | 72 | 50 | 31 | 25 | 1.5 |
| 877496 | 71 | 59 | 34 | 24 | 1.9 |
| 877617 | 62 | 71 | 31 | 20 | 1.8 |

TABLE 70

Dose-dependent reduction of human LRRK2 expression in SH-SY5Y cells

| Compound Number | LRRK2 expression (% control) | | | | IC$_{50}$ (μM) |
| --- | --- | --- | --- | --- | --- |
| | 0.444 μM | 1.333 μM | 4.000 μM | 12.000 μM | |
| 780241 | 62 | 39 | 34 | 7 | 0.9 |
| 876054 | 72 | 74 | 42 | 27 | 3.0 |
| 876151 | 66 | 62 | 53 | 34 | 3.5 |
| 876175 | 95 | 48 | 36 | 29 | 2.3 |
| 876197 | 75 | 64 | 37 | 29 | 2.5 |
| 876318 | 68 | 58 | 39 | 16 | 1.7 |
| 876339 | 91 | 77 | 43 | 25 | 3.6 |
| 876414 | 77 | 52 | 48 | 25 | 2.4 |
| 876507 | 103 | 80 | 66 | 46 | 9.2 |
| 876607 | 79 | 57 | 43 | 25 | 2.4 |
| 876631 | 68 | 43 | 25 | 25 | 1.1 |
| 876727 | 93 | 79 | 59 | 32 | 5.6 |
| 876747 | 75 | 54 | 35 | 19 | 1.8 |
| 876867 | 71 | 54 | 25 | 13 | 1.3 |
| 877524 | 106 | 106 | 71 | 42 | 9.0 |
| 877573 | 75 | 59 | 36 | 28 | 2.1 |
| 877597 | 88 | 79 | 45 | 33 | 4.3 |
| 877644 | 94 | 67 | 41 | 45 | 4.8 |
| 877692 | 78 | 67 | 53 | 25 | 3.5 |

Example 9: Design of Gapmers with Mixed Internucleoside Linkages Complementary to Human LRRK2 RNA Modified oligonucleotides complementary to a human LRRK2 nucleic acid were designed. The modified oligonucleotides in Table 71 are gapmers. The gapmers have a central gap segment that comprises 2'-deoxynucleosides and is flanked by wing segments on both the 5' end on the 3' end comprising and cEt nucleosides and/or 2'-MOE nucleosides. All cytosine residues throughout each gapmer are 5'-methyl cytosines. The internucleoside linkages are mixed phosphodiester internucleoside linkages and phosphorothioate internucleoside linkages. The sequence and chemical notation column specifies the sequence, including 5'-methyl cytosines, sugar chemistry, and the internucleoside linkage chemistry, wherein subscript 'd' represents a 2'-deoxyribose sugar; subscript 'e' represents a 2'-MOE modified sugar; subscript 'k' represents a cEt modified sugar; subscript 'o' represents a phosphodiester internucleoside linkage; subscript 's' represents a phosphorothioate internucleoside linkage; and a 'm' superscript before the cytosine residue indicates a 5-methyl cytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in the table below is complementary to human LRRK2 nucleic acid sequence SEQ ID NO: 1 or SEQ ID NO: 2, as indicated. 'N/A' indicates that the modified oligonucleotide is not complementary to that particular nucleic acid with 100% complementarity.

TABLE 71

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
| --- | --- | --- | --- | --- | --- | --- |
| 872246 | 3714 | 3733 | 82059 | 82078 | $G_{es}{}^mC_{eo}T_{eo}{}^mC_{es}A_{es}T_{ds}A_{ds}T_{ds}{}^mC_{ds}T_{ds}A_{ds}A_{ds}A_{ds}$ $G_{ds}A_{ds}{}^mC_{eo}{}^mC_{eo}G_{es}{}^mC_{es}A_{e}$ | 222 |
| 872247 | N/A | N/A | 52154 | 52173 | $G_{es}{}^mC_{eo}{}^mC_{eo}A_{es}A_{es}A_{ds}{}^mC_{ds}T_{ds}T_{ds}T_{ds}A_{ds}A_{ds}A_{ds}$ $G_{ds}A_{ds}T_{eo}G_{eo}{}^mC_{es}A_{es}G_{e}$ | 599 |
| 872248 | 3494 | 3513 | 77243 | 77262 | $A_{es}G_{eo}T_{eo}T_{es}{}^mC_{es}{}^mC_{ds}T_{ds}T_{ds}{}^mC_{ds}A_{ds}G_{ds}T_{ds}{}^m$ ${}^mC_{ds}T_{ds}{}^mC_{ds}A_{eo}A_{eo}G_{es}G_{es}G_{e}$ | 217 |
| 872249 | 7776 | 7795 | 145945 | 145964 | $G_{es}A_{eo}G_{eo}T_{es}A_{es}{}^mC_{ds}{}^mC_{ds}{}^mC_{ds}T_{ds}T_{ds}T_{ds}{}^mC_{ds}{}^m$ ${}^mC_{ds}A_{ds}T_{ds}G_{eo}T_{eo}G_{es}A_{es}A_{e}$ | 398 |
| 872250 | 988 | 1007 | 27963 | 27982 | ${}^mC_{es}{}^mC_{eo}A_{eo}{}^mC_{es}A_{es}A_{ds}A_{ds}{}^mC_{ds}T_{ds}T_{ds}{}^mC_{ds}A_{ds}$ $T_{ds}G_{ds}G_{ds}A_{ds}{}^mC_{eo}T_{eo}T_{es}{}^mC_{es}G_{e}$ | 293 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 872251 | 3714 | 3733 | 82059 | 82078 | $G_{es}{}^mC_{eo}T_{es}{}^mC_{es}A_{es}T_{ds}A_{ds}T_{ds}{}^mC_{ds}T_{ds}A_{ds}A_{ds}A_{ds}G_{ds}A_{ds}{}^mC_{eo}{}^mC_{eo}G_{es}{}^mC_{es}A_e$ | 222 |
| 872252 | N/A | N/A | 52154 | 52173 | $G_{es}{}^mC_{eo}{}^mC_{es}A_{es}A_{es}A_{ds}{}^mC_{ds}T_{ds}T_{ds}T_{ds}A_{ds}A_{ds}A_{ds}G_{ds}A_{ds}T_{eo}G_{eo}{}^mC_{es}A_{es}G_e$ | 599 |
| 872253 | 3494 | 3513 | 77243 | 77262 | $A_{es}G_{eo}T_{es}T_{es}{}^mC_{es}{}^mC_{ds}T_{ds}T_{ds}{}^mC_{ds}A_{ds}G_{ds}T_{ds}{}^mC_{ds}T_{ds}{}^mC_{ds}A_{eo}A_{eo}G_{es}G_{es}G_e$ | 217 |
| 872254 | 7776 | 7795 | 145945 | 145964 | $G_{es}A_{eo}G_{es}T_{es}A_{es}{}^mC_{ds}{}^mC_{ds}{}^mC_{ds}T_{ds}T_{ds}T_{ds}{}^mC_{ds}{}^mC_{ds}A_{ds}T_{ds}G_{eo}T_{eo}G_{es}A_{es}A_e$ | 398 |
| 872255 | 988 | 1007 | 27963 | 27982 | ${}^mC_{es}{}^mC_{eo}A_{es}{}^mC_{es}A_{es}A_{ds}A_{ds}{}^mC_{ds}T_{ds}{}^mC_{ds}A_{ds}T_{ds}G_{ds}G_{ds}A_{ds}{}^mC_{eo}T_{eo}T_{es}{}^mC_{es}G_e$ | 293 |
| 872256 | 3714 | 3733 | 82059 | 82078 | $G_{es}{}^mC_{eo}T_{es}{}^mC_{es}A_{es}T_{ds}A_{ds}T_{ds}{}^mC_{ds}T_{ds}A_{ds}A_{ds}A_{ds}A_{ds}G_{ds}A_{ds}{}^mC_{es}{}^mC_{eo}G_{es}{}^mC_{es}A_e$ | 222 |
| 872257 | N/A | N/A | 52154 | 52173 | $G_{es}{}^mC_{eo}{}^mC_{es}A_{es}A_{es}A_{ds}{}^mC_{ds}T_{ds}T_{ds}T_{ds}A_{ds}A_{ds}A_{ds}G_{ds}A_{ds}T_{es}G_{eo}{}^mC_{es}A_{es}G_e$ | 599 |
| 872258 | 3494 | 3513 | 77243 | 77262 | $A_{es}G_{eo}T_{es}T_{es}{}^mC_{es}{}^mC_{ds}T_{ds}T_{ds}{}^mC_{ds}A_{ds}G_{ds}T_{ds}{}^mC_{ds}T_{ds}{}^mC_{ds}A_{es}A_{eo}G_{es}G_{es}G_e$ | 217 |
| 872259 | 7776 | 7795 | 145945 | 145964 | $G_{es}A_{eo}G_{es}T_{es}A_{es}{}^mC_{ds}{}^mC_{ds}{}^mC_{ds}T_{ds}T_{ds}T_{ds}{}^mC_{ds}{}^mC_{ds}A_{ds}T_{ds}G_{es}T_{eo}G_{es}A_{es}A_e$ | 398 |
| 872260 | 988 | 1007 | 27963 | 27982 | ${}^mC_{es}{}^mC_{eo}A_{es}{}^mC_{es}A_{es}A_{ds}A_{ds}{}^mC_{ds}T_{ds}{}^mC_{ds}A_{ds}T_{ds}G_{ds}G_{ds}A_{ds}{}^mC_{es}T_{eo}T_{es}{}^mC_{es}G_e$ | 293 |
| 872261 | 3714 | 3733 | 82059 | 82078 | $G_{es}{}^mC_{es}T_{es}{}^mC_{es}A_{es}T_{ds}A_{ds}T_{ds}{}^mC_{ds}T_{ds}A_{ds}A_{ds}A_{ds}G_{ds}A_{ds}{}^mC_{es}{}^mC_{eo}G_{es}{}^mC_{es}A_e$ | 222 |
| 872262 | N/A | N/A | 52154 | 52173 | $G_{es}{}^mC_{es}{}^mC_{es}A_{es}A_{es}A_{ds}{}^mC_{ds}T_{ds}T_{ds}T_{ds}A_{ds}A_{ds}A_{ds}G_{ds}A_{ds}T_{es}G_{eo}{}^mC_{es}A_{es}G_e$ | 599 |
| 872263 | 3494 | 3513 | 77243 | 77262 | $A_{es}G_{es}T_{es}T_{es}{}^mC_{es}{}^mC_{ds}T_{ds}T_{ds}{}^mC_{ds}A_{ds}G_{ds}T_{ds}{}^mC_{ds}T_{ds}{}^mC_{ds}A_{es}A_{eo}G_{es}G_{es}G_e$ | 217 |
| 872264 | 7776 | 7795 | 145945 | 145964 | $G_{es}A_{es}G_{es}T_{es}A_{es}{}^mC_{ds}{}^mC_{ds}{}^mC_{ds}T_{ds}T_{ds}T_{ds}{}^mC_{ds}{}^mC_{ds}A_{ds}T_{ds}G_{es}T_{eo}G_{es}A_{es}A_e$ | 398 |
| 872265 | 988 | 1007 | 27963 | 27982 | ${}^mC_{es}{}^mC_{es}A_{es}{}^mC_{es}A_{es}A_{ds}A_{ds}{}^mC_{ds}T_{ds}{}^mC_{ds}A_{ds}T_{ds}G_{ds}G_{ds}A_{ds}{}^mC_{es}T_{eo}T_{es}{}^mC_{es}G_e$ | 293 |
| 872266 | 3712 | 3731 | 82057 | 82076 | $T_{es}{}^mC_{es}A_{es}T_{es}A_{es}T_{ds}{}^mC_{ds}T_{ds}A_{ds}A_{ds}A_{ds}G_{ds}A_{ds}{}^mC_{ds}{}^mC_{ds}G_{es}{}^mC_{eo}A_{es}A_{es}G_e$ | 1129 |
| 872267 | 3713 | 3732 | 82058 | 82077 | ${}^mC_{es}T_{eo}{}^mC_{es}A_{es}T_{es}A_{ds}T_{ds}{}^mC_{ds}T_{ds}A_{ds}A_{ds}A_{ds}G_{ds}A_{ds}{}^mC_{ds}{}^mC_{es}G_{eo}{}^mC_{es}A_{es}A_e$ | 1130 |
| 872268 | 3715 | 3734 | 82060 | 82079 | $T_{es}G_{eo}{}^mC_{es}T_{es}{}^mC_{es}A_{ds}T_{ds}A_{ds}T_{ds}{}^mC_{ds}T_{ds}A_{ds}A_{ds}A_{ds}G_{ds}A_{es}{}^mC_{eo}{}^mC_{es}G_{es}{}^mC_e$ | 1131 |
| 872269 | 3716 | 3735 | 82061 | 82080 | ${}^mC_{es}T_{eo}G_{es}{}^mC_{es}T_{es}{}^mC_{ds}A_{ds}T_{ds}A_{ds}T_{ds}{}^mC_{ds}T_{ds}A_{ds}A_{ds}A_{ds}G_{es}A_{eo}{}^mC_{es}{}^mC_{es}G_e$ | 1132 |
| 872270 | 3717 | 3736 | 82062 | 82081 | $G_{es}{}^mC_{eo}T_{es}G_{es}{}^mC_{es}T_{ds}{}^mC_{ds}A_{ds}T_{ds}A_{ds}T_{ds}{}^mC_{ds}T_{ds}A_{ds}A_{ds}A_{es}G_{eo}A_{es}{}^mC_{es}{}^mC_e$ | 1133 |
| 872271 | N/A | N/A | 52151 | 52170 | $A_{es}A_{eo}A_{es}{}^mC_{es}T_{es}T_{ds}T_{ds}A_{ds}A_{ds}A_{ds}G_{ds}A_{ds}T_{ds}G_{ds}{}^mC_{ds}A_{es}G_{eo}A_{es}A_{es}A_e$ | 1677 |
| 872272 | N/A | N/A | 52152 | 52171 | ${}^mC_{es}A_{eo}A_{es}A_{es}{}^mC_{es}T_{ds}T_{ds}T_{ds}A_{ds}A_{ds}A_{ds}G_{ds}A_{ds}T_{ds}G_{ds}{}^mC_{es}A_{eo}G_{es}A_{es}A_e$ | 1678 |
| 872273 | N/A | N/A | 52153 | 52172 | ${}^mC_{es}{}^mC_{eo}A_{es}A_{es}A_{es}{}^mC_{ds}T_{ds}T_{ds}T_{ds}A_{ds}A_{ds}G_{ds}A_{ds}T_{ds}G_{es}{}^mC_{eo}A_{es}G_{es}A_e$ | 1679 |
| 872274 | N/A | N/A | 52155 | 52174 | $T_{es}G_{eo}{}^mC_{es}{}^mC_{es}A_{es}A_{ds}A_{ds}{}^mC_{ds}T_{ds}T_{ds}T_{ds}A_{ds}A_{ds}A_{ds}G_{ds}A_{es}T_{eo}G_{es}{}^mC_{es}A_e$ | 1680 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 872275 | N/A | N/A | 52156 | 52175 | $T_{es}T_{eo}G_{es}{}^mC_{es}{}^mC_{es}A_{ds}A_{ds}A_{ds}{}^mC_{ds}T_{ds}T_{ds}T_{ds}A_{ds}A_{ds}A_{ds}G_{es}A_{eo}T_{es}G_{es}{}^mC_e$ | 1681 |
| 872276 | N/A | N/A | 52157 | 52176 | $T_{es}T_{eo}T_{es}G_{es}{}^mC_{es}{}^mC_{ds}A_{ds}A_{ds}A_{ds}{}^mC_{ds}T_{ds}T_{ds}T_{ds}A_{ds}A_{ds}A_{es}G_{eo}A_{es}T_{es}G_e$ | 1682 |
| 872277 | 3495 | 3514 | 77244 | 77263 | ${}^mC_{es}A_{eo}G_{es}T_{es}T_{es}{}^mC_{ds}{}^mC_{ds}T_{ds}T_{ds}{}^mC_{ds}A_{ds}G_{ds}T_{ds}{}^mC_{ds}T_{ds}{}^mC_{es}A_{eo}A_{es}G_{es}G_e$ | 1107 |
| 872278 | 3496 | 3515 | 77245 | 77264 | $T_{es}{}^mC_{eo}A_{es}G_{es}T_{es}T_{ds}{}^mC_{ds}{}^mC_{ds}T_{ds}T_{ds}{}^mC_{ds}A_{ds}G_{ds}T_{ds}{}^mC_{ds}T_{es}{}^mC_{eo}A_{es}A_{es}G_e$ | 1108 |
| 872279 | 3497 | 3516 | 77246 | 77265 | $T_{es}T_{eo}{}^mC_{es}A_{es}G_{es}T_{ds}T_{ds}{}^mC_{ds}{}^mC_{ds}T_{ds}T_{ds}{}^mC_{ds}A_{ds}G_{ds}T_{ds}{}^mC_{es}T_{eo}{}^mC_{es}A_{es}A_e$ | 1109 |
| 872280 | 7773 | 7792 | 145942 | 145961 | $T_{es}A_{eo}{}^mC_{es}{}^mC_{es}{}^mC_{es}T_{ds}T_{ds}T_{ds}{}^mC_{ds}{}^mC_{ds}A_{ds}T_{ds}G_{ds}T_{ds}G_{ds}A_{es}A_{eo}{}^mC_{es}A_{es}T_e$ | 1432 |
| 872281 | 7774 | 7793 | 145943 | 145962 | $G_{es}T_{eo}A_{es}{}^mC_{es}{}^mC_{es}{}^mC_{ds}T_{ds}T_{ds}T_{ds}{}^mC_{ds}{}^mC_{ds}A_{ds}T_{ds}G_{ds}T_{ds}G_{es}A_{eo}A_{es}{}^mC_{es}A_e$ | 1433 |
| 872282 | 7775 | 7794 | 145944 | 145963 | $A_{es}G_{eo}T_{es}A_{es}{}^mC_{es}{}^mC_{ds}{}^mC_{ds}T_{ds}T_{ds}T_{ds}{}^mC_{ds}{}^mC_{ds}A_{ds}T_{ds}G_{ds}T_{es}G_{eo}A_{es}A_{es}{}^mC_e$ | 1434 |
| 872283 | 7777 | 7796 | 145946 | 145965 | $T_{es}G_{eo}A_{es}G_{es}T_{es}A_{ds}{}^mC_{ds}{}^mC_{ds}{}^mC_{ds}T_{ds}T_{ds}T_{ds}{}^mC_{ds}{}^mC_{ds}A_{ds}T_{es}G_{eo}T_{es}G_{es}A_e$ | 1435 |
| 872284 | 7778 | 7797 | 145947 | 145966 | $G_{es}T_{eo}G_{es}A_{es}G_{es}T_{ds}A_{ds}{}^mC_{ds}{}^mC_{ds}{}^mC_{ds}T_{ds}T_{ds}T_{ds}{}^mC_{ds}{}^mC_{ds}A_{es}T_{eo}G_{es}T_{es}G_e$ | 1436 |
| 872285 | 7779 | 7798 | 145948 | 145967 | $T_{es}G_{eo}T_{es}G_{es}A_{es}G_{ds}T_{ds}A_{ds}{}^mC_{ds}{}^mC_{ds}{}^mC_{ds}T_{ds}T_{ds}T_{ds}{}^mC_{ds}{}^mC_{es}A_{eo}T_{es}G_{es}T_e$ | 1437 |
| 874144 | N/A | N/A | 82056 | 82075 | ${}^mC_{es}A_{eo}T_{eo}A_{eo}T_{es}{}^mC_{ds}T_{ds}A_{ds}A_{ds}A_{ds}G_{ds}A_{ds}{}^mC_{ds}{}^mC_{ds}G_{ds}{}^mC_{es}A_{eo}A_{es}G_{es}{}^mC_e$ | 3820 |
| 874145 | 3493 | 3512 | 77242 | 77261 | $G_{es}T_{eo}T_{eo}{}^mC_{eo}{}^mC_{es}T_{ds}T_{ds}{}^mC_{ds}A_{ds}G_{ds}T_{ds}{}^mC_{ds}T_{ds}{}^mC_{ds}A_{ds}A_{eo}G_{es}G_{es}G_e$ | 3821 |
| 874146 | 3492 | 3511 | 77241 | 77260 | $T_{es}T_{eo}{}^mC_{eo}{}^mC_{eo}T_{es}T_{ds}{}^mC_{ds}A_{ds}G_{ds}T_{ds}{}^mC_{ds}T_{ds}{}^mC_{ds}A_{ds}A_{ds}G_{eo}G_{eo}G_{es}G_e$ | 3822 |
| 874147 | 3491 | 3510 | 77240 | 77259 | $T_{es}{}^mC_{eo}{}^mC_{eo}T_{eo}T_{es}{}^mC_{ds}A_{ds}G_{ds}T_{ds}{}^mC_{ds}T_{ds}{}^mC_{ds}A_{ds}A_{ds}G_{ds}G_{eo}G_{eo}G_{es}A_e$ | 3823 |
| 874148 | 4117 | 4136 | 86612 | 86631 | $T_{es}{}^mC_{eo}A_{eo}T_{eo}A_{es}A_{ds}G_{ds}T_{ds}T_{ds}T_{ds}{}^mC_{ds}A_{ds}T_{ds}{}^mC_{ds}G_{eo}G_{eo}T_{es}T_{es}A_e$ | 3824 |
| 874149 | N/A | N/A | 82056 | 82075 | ${}^mC_{es}A_{eo}T_{es}A_{es}T_{es}{}^mC_{ds}T_{ds}A_{ds}A_{ds}A_{ds}G_{ds}A_{ds}{}^mC_{ds}{}^mC_{ds}G_{ds}{}^mC_{es}A_{eo}A_{es}G_{es}{}^mC_e$ | 3820 |
| 874150 | 3493 | 3512 | 77242 | 77261 | $G_{es}T_{eo}T_{es}{}^mC_{es}{}^mC_{es}T_{ds}T_{ds}{}^mC_{ds}A_{ds}G_{ds}T_{ds}{}^mC_{ds}T_{ds}{}^mC_{ds}A_{ds}A_{es}G_{eo}G_{es}G_{es}G_e$ | 3821 |
| 874151 | 3492 | 3511 | 77241 | 77260 | $T_{es}T_{eo}{}^mC_{es}{}^mC_{es}T_{es}T_{ds}{}^mC_{ds}A_{ds}G_{ds}T_{ds}{}^mC_{ds}T_{ds}{}^mC_{ds}A_{ds}A_{ds}G_{es}G_{eo}G_{es}G_e$ | 3822 |
| 890206 | N/A | N/A | 61977 | 61996 | ${}^mC_{es}T_{eo}T_{eo}T_{eo}{}^mC_{es}T_{ds}{}^mC_{ds}A_{ds}{}^mC_{ds}A_{ds}T_{ds}A_{ds}{}^mC_{ds}{}^mC_{ds}T_{ds}A_{eo}T_{eo}T_{es}A_{es}A_e$ | 3825 |
| 890207 | N/A | N/A | 61978 | 61997 | $T_{es}{}^mC_{eo}T_{eo}T_{eo}T_{es}{}^mC_{ds}T_{ds}{}^mC_{ds}A_{ds}{}^mC_{ds}A_{ds}T_{ds}A_{ds}{}^mC_{ds}{}^mC_{ds}T_{eo}A_{eo}T_{es}T_{es}A_e$ | 3826 |
| 890208 | N/A | N/A | 61979 | 61998 | ${}^mC_{es}T_{eo}{}^mC_{eo}T_{eo}T_{es}T_{ds}{}^mC_{ds}T_{ds}{}^mC_{ds}A_{ds}{}^mC_{ds}A_{ds}T_{ds}A_{ds}{}^mC_{ds}{}^mC_{eo}T_{eo}A_{es}T_{es}T_e$ | 3827 |
| 890209 | N/A | N/A | 61980 | 61999 | $T_{es}{}^mC_{eo}T_{eo}{}^mC_{eo}T_{es}T_{ds}T_{ds}{}^mC_{ds}T_{ds}{}^mC_{ds}A_{ds}{}^mC_{ds}A_{ds}T_{ds}A_{ds}{}^mC_{eo}{}^mC_{eo}T_{es}A_{es}T_e$ | 3828 |
| 934514 | 879 | 898 | 21710 | 21729 | $T_{es}G_{eo}{}^mC_{es}T_{es}T_{es}T_{ds}{}^mC_{ds}A_{ds}T_{ds}A_{ds}G_{ds}{}^mC_{ds}T_{ds}T_{ds}{}^mC_{ds}{}^mC_{es}A_{eo}{}^mC_{es}{}^mC_{es}A_e$ | 862 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 934515 | 880 | 899 | 21711 | 21730 | $A_{es}T_{eo}G_{es}{}^mC_{es}T_{es}T_{ds}T_{ds}{}^mC_{ds}A_{ds}T_{ds}A_{ds}G_{ds}{}^mC_{ds}T_{ds}T_{ds}{}^mC_{es}{}^mC_{eo}A_{es}{}^mC_{es}{}^mC_e$ | 863 |
| 934516 | 837 | 856 | 21668 | 21687 | $G_{es}{}^mC_{eo}{}^mC_{es}A_{es}{}^mC_{es}T_{ds}{}^mC_{ds}A_{ds}T_{ds}G_{ds}A_{ds}G_{ds}G_{ds}A_{ds}{}^mC_{ds}T_{es}T_{eo}{}^mC_{es}{}^mC_{es}A_e$ | 2833 |
| 934517 | 840 | 859 | 21671 | 21690 | $A_{es}T_{eo}T_{es}G_{es}{}^mC_{es}{}^mC_{ds}A_{ds}{}^mC_{ds}T_{ds}{}^mC_{ds}A_{ds}T_{ds}G_{ds}A_{ds}G_{ds}G_{es}A_{eo}{}^mC_{es}T_{es}T_e$ | 3362 |
| 934517 | 840 | 859 | 21671 | 21690 | $A_{es}T_{eo}T_{es}G_{es}{}^mC_{es}{}^mC_{ds}A_{ds}{}^mC_{ds}T_{ds}{}^mC_{ds}A_{ds}T_{ds}G_{ds}A_{ds}G_{ds}G_{es}A_{eo}{}^mC_{es}T_{es}T_e$ | 3362 |
| 934518 | 846 | 865 | 21677 | 21696 | ${}^mC_{es}{}^mC_{eo}T_{es}G_{es}A_{es}{}^mC_{ds}A_{ds}T_{ds}G_{ds}{}^mC_{ds}{}^mC_{ds}A_{ds}{}^mC_{ds}T_{ds}{}^mC_{es}A_{eo}T_{es}G_{es}A_e$ | 3514 |
| 934518 | 846 | 865 | 21677 | 21696 | ${}^mC_{es}{}^mC_{eo}T_{es}G_{es}A_{es}{}^mC_{ds}A_{ds}T_{ds}G_{ds}{}^mC_{ds}{}^mC_{ds}A_{ds}{}^mC_{ds}T_{ds}{}^mC_{es}A_{eo}T_{es}G_{es}A_e$ | 3514 |
| 934519 | N/A | N/A | 23873 | 23892 | $T_{es}G_{eo}{}^mC_{es}A_{es}T_{es}T_{ds}T_{ds}{}^mC_{ds}T_{ds}T_{ds}A_{ds}T_{ds}G_{ds}A_{ds}A_{es}A_{eo}A_{es}{}^mC_{es}A_e$ | 2706 |
| 934520 | 1233 | 1252 | 29584 | 29603 | $G_{es}A_{eo}G_{es}A_{es}T_{es}T_{ds}A_{ds}T_{ds}T_{ds}T_{ds}A_{ds}G_{ds}T_{ds}G_{ds}{}^mC_{ds}{}^mC_{es}{}^mC_{eo}A_{es}G_{es}{}^mC_e$ | 3287 |
| 934521 | 1426 | 1445 | 35373 | 35392 | $G_{es}T_{eo}A_{es}T_{es}T_{es}{}^mC_{ds}{}^mC_{ds}T_{ds}T_{ds}T_{ds}T_{ds}G_{ds}A_{ds}T_{ds}A_{ds}A_{es}{}^mC_{es}A_{es}G_{es}T_e$ | 917 |
| 934522 | 1435 | 1454 | 35382 | 35401 | ${}^mC_{es}A_{eo}T_{es}T_{es}{}^mC_{es}A_{ds}G_{ds}G_{ds}T_{ds}G_{ds}T_{ds}A_{ds}T_{ds}T_{ds}{}^mC_{ds}{}^mC_{es}T_{eo}T_{es}T_{es}T_e$ | 918 |
| 934523 | 1488 | 1507 | 35435 | 35454 | $G_{es}{}^mC_{eo}{}^mC_{es}A_{es}{}^mC_{es}T_{ds}T_{ds}T_{ds}{}^mC_{ds}A_{ds}G_{ds}{}^mC_{ds}{}^mC_{ds}A_{ds}{}^mC_{ds}T_{es}T_{eo}{}^mC_{es}A_{es}G_e$ | 922 |
| 934524 | 1700 | 1719 | 41933 | 41952 | $A_{es}{}^mC_{eo}{}^mC_{es}A_{es}T_{es}A_{ds}T_{ds}T_{ds}T_{ds}A_{ds}G_{ds}{}^mC_{ds}T_{ds}T_{ds}A_{ds}T_{es}G_{eo}A_{es}T_{es}G_e$ | 3670 |
| 934525 | 1701 | 1720 | 41934 | 41953 | $A_{es}A_{eo}{}^mC_{es}{}^mC_{es}A_{es}T_{ds}A_{ds}T_{ds}T_{ds}T_{ds}A_{ds}G_{ds}{}^mC_{ds}T_{ds}T_{ds}A_{es}T_{eo}G_{es}A_{es}T_e$ | 3365 |
| 934526 | N/A | N/A | 48094 | 48113 | $T_{es}G_{eo}{}^mC_{es}A_{es}T_{es}A_{ds}G_{ds}T_{ds}{}^mC_{ds}T_{ds}G_{ds}T_{ds}A_{ds}G_{ds}G_{ds}T_{es}A_{eo}G_{es}T_{es}A_e$ | 2260 |
| 934528 | 2267 | 2286 | 56275 | 56294 | ${}^mC_{es}T_{eo}G_{es}T_{es}T_{es}A_{ds}T_{ds}T_{ds}{}^mC_{ds}T_{ds}G_{ds}A_{ds}T_{ds}{}^mC_{ds}A_{ds}{}^mC_{es}A_{eo}{}^mC_{es}G_{es}{}^mC_e$ | 2685 |
| 934529 | 2452 | 2471 | 62073 | 62092 | $T_{es}G_{eo}T_{es}{}^mC_{es}A_{es}{}^mC_{ds}A_{ds}T_{ds}T_{ds}T_{ds}{}^mC_{ds}{}^mC_{ds}{}^mC_{ds}A_{ds}A_{ds}T_{es}G_{eo}{}^mC_{es}T_{es}T_e$ | 3366 |
| 934530 | 2453 | 2472 | 62074 | 62093 | ${}^mC_{es}T_{eo}G_{es}T_{es}{}^mC_{es}A_{ds}{}^mC_{ds}A_{ds}T_{ds}T_{ds}T_{ds}{}^mC_{ds}{}^mC_{ds}{}^mC_{ds}A_{ds}A_{es}T_{eo}G_{es}{}^mC_{es}T_e$ | 3443 |
| 934531 | 2454 | 2473 | 62075 | 62094 | $G_{es}{}^mC_{eo}T_{es}G_{es}T_{es}{}^mC_{ds}A_{ds}{}^mC_{ds}A_{ds}{}^mC_{ds}T_{ds}T_{ds}T_{ds}{}^mC_{ds}{}^mC_{ds}{}^mC_{ds}A_{es}A_{eo}T_{es}G_{es}{}^mC_e$ | 3518 |
| 934532 | 2456 | 2475 | 62077 | 62096 | $T_{es}G_{eo}G_{es}{}^mC_{es}T_{es}G_{ds}T_{ds}{}^mC_{ds}A_{ds}{}^mC_{ds}{}^mC_{ds}T_{ds}T_{ds}T_{ds}{}^mC_{ds}{}^mC_{ds}{}^mC_{es}{}^mC_{eo}A_{es}A_{es}T_e$ | 3595 |
| 934533 | 2363 | 2382 | 61984 | 62003 | ${}^mC_{es}T_{eo}G_{es}{}^mC_{es}T_{es}{}^mC_{ds}T_{ds}{}^mC_{ds}T_{ds}T_{ds}T_{ds}{}^mC_{ds}T_{ds}{}^mC_{ds}A_{ds}{}^mC_{es}A_{eo}T_{es}A_{es}{}^mC_e$ | 258 |
| 934534 | 2871 | 2890 | 71714 | 71733 | ${}^mC_{es}T_{eo}G_{es}T_{es}A_{es}A_{ds}T_{ds}A_{ds}{}^mC_{ds}G_{ds}G_{ds}{}^mC_{ds}A_{ds}T_{ds}{}^mC_{ds}T_{es}{}^mC_{es}{}^mC_{eo}G_{es}G_{es}T_e$ | 3140 |
| 934535 | N/A | N/A | 73941 | 73960 | ${}^mC_{es}A_{eo}G_{es}A_{es}T_{es}{}^mC_{ds}T_{ds}G_{ds}T_{ds}T_{ds}T_{ds}{}^mC_{ds}{}^mC_{ds}A_{ds}T_{ds}T_{es}G_{eo}{}^mC_{es}{}^mC_{es}T_e$ | 3636 |
| 934536 | 3582 | 3601 | 77331 | 77350 | $G_{es}G_{eo}{}^mC_{es}A_{es}{}^mC_{es}T_{ds}G_{ds}A_{ds}A_{ds}A_{ds}{}^mC_{ds}T_{ds}{}^mC_{ds}T_{ds}{}^mC_{ds}{}^mC_{es}A_{eo}{}^mC_{es}T_{es}T_e$ | 219 |
| 934537 | 3850 | 3869 | 82195 | 82214 | $G_{es}T_{eo}T_{es}T_{es}{}^mC_{es}T_{es}{}^mC_{ds}T_{ds}A_{ds}{}^mC_{ds}T_{ds}{}^mC_{ds}T_{ds}A_{ds}G_{ds}A_{es}{}^mC_{eo}{}^mC_{es}A_{es}T_e$ | 3369 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 934538 | 3852 | 3871 | 82197 | 82216 | $^mC_{es}A_{eo}G_{es}T_{es}T_{es}T_{es}{}^mC_{ds}T_{ds}{}^mC_{ds}T_{ds}A_{ds}{}^mC_{ds}T_{ds}{}^mC_{ds}T_{ds}A_{es}G_{eo}A_{es}{}^mC_{es}{}^mC_e$ | 3446 |
| 934540 | N/A | N/A | 91040 | 91059 | $A_{es}T_{eo}G_{es}T_{es}A_{es}T_{ds}{}^mC_{ds}T_{ds}{}^mC_{ds}T_{ds}T_{ds}A_{ds}A_{ds}{}^mC_{ds}{}^mC_{ds}{}^mC_{es}A_{eo}G_{es}A_{es}G_e$ | 1828 |
| 934541 | N/A | N/A | 91041 | 91060 | $^mC_{es}A_{eo}T_{es}G_{es}T_{es}A_{ds}T_{ds}{}^mC_{ds}T_{ds}{}^mC_{ds}T_{ds}T_{ds}A_{ds}A_{ds}{}^mC_{ds}{}^mC_{es}{}^mC_{eo}A_{es}G_{es}A_e$ | 1829 |
| 934542 | N/A | N/A | 91046 | 91065 | $G_{es}T_{eo}T_{es}T_{es}T_{es}{}^mC_{ds}A_{ds}T_{ds}G_{ds}T_{ds}A_{ds}T_{ds}{}^mC_{ds}T_{ds}{}^mC_{ds}T_{es}T_{eo}A_{es}A_{es}{}^mC_e$ | 1833 |
| 934543 | N/A | N/A | 91047 | 91066 | $T_{es}G_{eo}T_{es}T_{es}T_{es}T_{ds}{}^mC_{ds}A_{ds}T_{ds}G_{ds}T_{ds}A_{ds}T_{ds}{}^mC_{ds}T_{ds}{}^mC_{es}T_{eo}T_{es}A_{es}A_e$ | 1834 |
| 934544 | N/A | N/A | 91048 | 91067 | $^mC_{es}T_{eo}G_{es}T_{es}T_{es}T_{ds}T_{ds}{}^mC_{ds}A_{ds}T_{ds}G_{ds}T_{ds}A_{ds}T_{ds}{}^mC_{ds}T_{es}{}^mC_{eo}T_{es}T_{es}A_e$ | 1835 |
| 934545 | 4727 | 4746 | 92150 | 92169 | $G_{es}G_{eo}{}^mC_{es}A_{es}T_{ds}T_{ds}T_{ds}T_{ds}T_{ds}A_{ds}{}^mC_{ds}G_{ds}{}^mC_{ds}T_{es}{}^mC_{eo}{}^mC_{es}G_{es}A_e$ | 2690 |
| 934546 | 5073 | 5092 | 98221 | 98240 | $^mC_{es}T_{eo}G_{es}G_{es}A_{es}A_{ds}T_{ds}T_{ds}T_{ds}T_{ds}T_{ds}{}^mC_{ds}T_{ds}A_{ds}G_{ds}G_{es}A_{eo}G_{es}{}^mC_{es}T_e$ | 3524 |
| 934547 | N/A | N/A | 91042 | 91061 | $T_{es}{}^mC_{eo}A_{es}T_{es}G_{es}T_{ds}A_{ds}T_{ds}{}^mC_{ds}T_{ds}{}^mC_{ds}T_{ds}T_{ds}A_{ds}A_{ds}{}^mC_{es}{}^mC_{eo}{}^mC_{es}A_{es}G_e$ | 1830 |
| 934548 | 541 | 560 | 13807 | 13826 | $T_{es}A_{eo}{}^mC_{es}{}^mC_{es}T_{es}G_{ds}A_{ds}A_{ds}G_{ds}T_{ds}T_{ds}A_{ds}G_{ds}G_{ds}A_{ds}G_{es}G_{eo}G_{es}G_{es}A_e$ | 828 |
| 934549 | 540 | 559 | 13806 | 13825 | $A_{es}{}^mC_{eo}{}^mC_{es}T_{es}G_{es}A_{ds}A_{ds}G_{ds}T_{ds}T_{ds}A_{ds}G_{ds}G_{ds}A_{ds}G_{ds}G_{es}A_{eo}G_{es}A_{es}T_e$ | 827 |
| 934552 | 734 | 753 | 18633 | 18652 | $G_{es}{}^mC_{eo}A_{es}{}^mC_{es}T_{es}T_{ds}A_{ds}A_{ds}{}^mC_{ds}A_{ds}A_{ds}T_{ds}A_{ds}T_{ds}{}^mC_{ds}A_{es}T_{eo}A_{es}T_{es}A_e$ | 3513 |
| 934553 | 737 | 756 | 18636 | 18655 | $A_{es}A_{eo}{}^mC_{es}G_{es}{}^mC_{es}A_{ds}{}^mC_{ds}T_{ds}T_{ds}A_{ds}A_{ds}{}^mC_{ds}A_{ds}A_{ds}T_{ds}A_{es}T_{eo}{}^mC_{es}A_{es}T_e$ | 1997 |
| 934554 | 738 | 757 | 18637 | 18656 | $T_{es}A_{eo}A_{es}{}^mC_{es}G_{es}{}^mC_{ds}A_{ds}{}^mC_{ds}T_{ds}T_{ds}A_{ds}A_{ds}{}^mC_{ds}A_{ds}A_{ds}T_{es}A_{eo}T_{es}{}^mC_{es}A_e$ | 2073 |
| 934555 | 740 | 759 | 18639 | 18658 | $G_{es}T_{eo}T_{es}A_{es}A_{es}{}^mC_{ds}G_{ds}{}^mC_{ds}A_{ds}{}^mC_{ds}T_{ds}T_{ds}A_{ds}A_{ds}{}^mC_{ds}A_{es}A_{eo}T_{es}A_{es}T_e$ | 2148 |
| 934556 | 735 | 754 | 18634 | 18653 | $^mC_{es}G_{eo}{}^mC_{es}A_{es}{}^mC_{es}T_{ds}T_{ds}A_{ds}A_{ds}{}^mC_{ds}A_{ds}A_{ds}T_{ds}A_{ds}T_{ds}{}^mC_{es}A_{eo}T_{es}A_{es}T_e$ | 852 |
| 934557 | 736 | 755 | 18635 | 18654 | $A_{es}{}^mC_{eo}G_{es}{}^mC_{es}A_{es}{}^mC_{ds}T_{ds}T_{ds}A_{ds}A_{ds}{}^mC_{ds}A_{ds}A_{ds}T_{ds}A_{ds}T_{es}{}^mC_{eo}A_{es}T_{es}A_e$ | 3590 |
| 934558 | N/A | N/A | 19521 | 19540 | $A_{es}G_{eo}{}^mC_{es}A_{es}A_{es}T_{ds}{}^mC_{ds}A_{ds}T_{ds}T_{ds}G_{ds}G_{ds}T_{ds}A_{ds}G_{ds}{}^mC_{es}A_{eo}T_{es}A_{es}{}^mC_e$ | 3385 |
| 934584 | 7772 | 7791 | 145941 | 145960 | $A_{es}{}^mC_{eo}{}^mC_{es}{}^mC_{es}T_{es}T_{ds}T_{ds}{}^mC_{ds}mC_{ds}A_{ds}T_{ds}G_{ds}T_{ds}G_{ds}A_{ds}A_{es}{}^mC_{eo}A_{es}T_{es}T_e$ | 1431 |
| 934585 | 7780 | 7799 | 145949 | 145968 | $A_{es}T_{eo}G_{es}T_{es}G_{es}A_{ds}G_{ds}T_{ds}A_{ds}{}^mC_{ds}{}^mC_{ds}{}^mC_{ds}T_{ds}T_{ds}T_{ds}{}^mC_{es}{}^mC_{eo}A_{es}T_{es}G_e$ | 1438 |
| 934586 | 732 | 751 | 18631 | 18650 | $A_{es}{}^mC_{eo}T_{es}T_{es}A_{es}A_{ds}{}^mC_{ds}A_{ds}A_{ds}T_{ds}A_{ds}T_{ds}{}^mC_{ds}A_{ds}T_{ds}A_{es}T_{eo}A_{es}A_{es}T_e$ | 3361 |
| 934587 | 733 | 752 | 18632 | 18651 | $^mC_{es}A_{eo}{}^mC_{es}T_{es}T_{es}A_{ds}A_{ds}{}^mC_{ds}A_{ds}A_{ds}T_{ds}A_{ds}T_{ds}{}^mC_{ds}A_{ds}T_{es}A_{eo}T_{es}A_{es}A_e$ | 3438 |
| 934588 | 2451 | 2470 | 62072 | 62091 | $G_{es}T_{eo}{}^mC_{es}A_{es}{}^mC_{es}{}^mC_{ds}T_{ds}T_{ds}T_{ds}{}^mC_{ds}{}^mC_{ds}{}^mC_{ds}A_{ds}A_{ds}T_{ds}G_{es}{}^mC_{eo}T_{es}T_{es}A_e$ | 188 |
| 934589 | 835 | 854 | 21666 | 21685 | $^mC_{es}A_{eo}{}^mC_{es}T_{es}{}^mC_{es}A_{ds}T_{ds}G_{ds}A_{ds}G_{ds}G_{ds}A_{ds}{}^mC_{ds}T_{ds}T_{ds}{}^mC_{es}{}^mC_{eo}A_{es}{}^mC_{es}A_e$ | 860 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 934590 | 836 | 855 | 21667 | 21686 | $^mC_{es}{}^mC_{eo}A_{es}{}^mC_{es}T_{es}{}^mC_{ds}A_{ds}T_{ds}G_{ds}A_{ds}G_{ds}G_{ds}A_{ds}{}^mC_{ds}T_{ds}T_{es}{}^mC_{eo}{}^mC_{es}A_{es}{}^mC_e$ | 2757 |
| 934591 | 834 | 853 | 21665 | 21684 | $A_{es}{}^mC_{eo}T_{es}{}^mC_{es}A_{es}T_{ds}G_{ds}A_{ds}G_{ds}G_{ds}A_{ds}{}^mC_{ds}T_{ds}T_{ds}{}^mC_{ds}{}^mC_{es}A_{eo}{}^mC_{es}A_{es}T_e$ | 3286 |
| 934592 | 2362 | 2381 | 61983 | 62002 | $T_{es}G_{eo}{}^mC_{es}T_{es}{}^mC_{es}T_{ds}{}^mC_{ds}T_{ds}T_{ds}{}^mC_{ds}T_{ds}{}^mC_{ds}A_{ds}{}^mC_{ds}A_{es}T_{eo}A_{es}{}^mC_{es}{}^mC_e$ | 257 |
| 934593 | 896 | 915 | 21727 | 21746 | $^mC_{es}T_{eo}T_{es}T_{es}{}^mC_{es}A_{ds}{}^mC_{ds}T_{ds}{}^mC_{ds}A_{ds}T_{ds}A_{ds}G_{ds}G_{ds}A_{es}A_{eo}T_{es}G_{es}{}^mC_e$ | 291 |
| 934594 | 2365 | 2384 | 61986 | 62005 | $G_{es}A_{eo}{}^mC_{es}T_{es}G_{es}{}^mC_{ds}T_{ds}{}^mC_{ds}T_{ds}{}^mC_{ds}T_{ds}T_{ds}{}^mC_{ds}T_{ds}{}^mC_{es}A_{eo}{}^mC_{es}A_{es}T_e$ | 1017 |
| 934595 | 2364 | 2383 | 61985 | 62004 | $A_{es}{}^mC_{eo}T_{es}G_{es}{}^mC_{es}T_{ds}{}^mC_{ds}T_{ds}{}^mC_{ds}T_{ds}T_{ds}T_{ds}{}^mC_{ds}T_{ds}{}^mC_{ds}A_{es}{}^mC_{eo}A_{es}T_{es}A_e$ | 259 |
| 934596 | 542 | 561 | 13808 | 13827 | $T_{es}T_{eo}A_{es}{}^mC_{es}{}^mC_{es}T_{ds}G_{ds}A_{ds}A_{ds}G_{ds}T_{ds}T_{ds}A_{ds}G_{ds}G_{ds}A_{es}G_{eo}G_{es}A_{es}G_e$ | 829 |
| 934597 | 4112 | 4131 | 86607 | 86626 | $A_{es}G_{eo}T_{es}T_{es}{}^mC_{ds}A_{ds}T_{ds}T_{ds}{}^mC_{ds}G_{ds}G_{ds}T_{ds}T_{ds}A_{ds}T_{es}A_{eo}A_{es}G_{es}G_e$ | 1172 |
| 934599 | 2368 | 2387 | 61989 | 62008 | $T_{es}G_{eo}G_{es}G_{es}A_{es}{}^mC_{ds}T_{ds}G_{ds}{}^mC_{ds}T_{ds}{}^mC_{ds}T_{ds}{}^mC_{ds}T_{ds}T_{ds}T_{es}{}^mC_{eo}T_{es}{}^mC_{es}A_e$ | 185 |
| 934600 | 2369 | 2388 | 61990 | 62009 | $T_{es}T_{eo}G_{es}G_{es}G_{es}A_{ds}{}^mC_{ds}T_{ds}G_{ds}{}^mC_{ds}T_{ds}{}^mC_{ds}T_{ds}{}^mC_{ds}T_{ds}T_{es}T_{eo}{}^mC_{es}T_{es}{}^mC_e$ | 1019 |
| 952334 | 607 | 626 | 16127 | 16146 | $A_{es}G_{eo}T_{es}G_{es}{}^mC_{es}A_{ds}T_{ds}G_{ds}G_{ds}{}^mC_{ds}A_{ds}T_{ds}{}^mC_{ds}A_{ds}A_{ds}A_{es}A_{eo}A_{es}T_{es}T_e$ | 839 |
| 952335 | 730 | 749 | 18629 | 18648 | $T_{es}T_{eo}A_{es}A_{es}{}^mC_{es}A_{ds}A_{ds}T_{ds}A_{ds}A_{ds}T_{ds}{}^mC_{ds}A_{ds}T_{ds}A_{ds}A_{es}A_{eo}T_{es}{}^mC_{es}T_e$ | 3666 |
| 952336 | 872 | 891 | 21703 | 21722 | $A_{es}T_{eo}A_{es}G_{es}{}^mC_{es}T_{ds}T_{ds}{}^mC_{ds}{}^mC_{ds}A_{ds}{}^mC_{ds}{}^mC_{ds}A_{ds}{}^mC_{ds}A_{ds}A_{es}T_{eo}A_{es}T_{es}T_e$ | 1998 |
| 952338 | 875 | 894 | 21706 | 21725 | $T_{es}T_{eo}{}^mC_{es}A_{es}T_{es}A_{ds}G_{ds}{}^mC_{ds}T_{ds}T_{ds}{}^mC_{ds}{}^mC_{ds}A_{ds}{}^mC_{ds}{}^mC_{ds}A_{es}{}^mC_{eo}A_{es}A_{es}T_e$ | 2149 |
| 952340 | 877 | 896 | 21708 | 21727 | $^mC_{es}T_{eo}T_{es}T_{es}{}^mC_{es}A_{ds}T_{ds}A_{ds}G_{ds}{}^mC_{ds}T_{ds}T_{ds}{}^mC_{ds}{}^mC_{ds}A_{ds}{}^mC_{es}{}^mC_{eo}A_{es}{}^mC_{es}A_e$ | 2986 |
| 952358 | 3227 | 3246 | 76361 | 76380 | $A_{es}A_{eo}G_{es}T_{es}{}^mC_{es}{}^mC_{ds}A_{ds}A_{ds}A_{ds}T_{ds}G_{ds}T_{ds}G_{ds}T_{ds}{}^mC_{ds}A_{es}A_{eo}A_{es}{}^mC_{es}T_e$ | 2534 |
| 952359 | 3228 | 3247 | 76362 | 76381 | $^mC_{es}A_{eo}A_{es}G_{es}T_{es}{}^mC_{ds}{}^mC_{ds}A_{ds}A_{ds}A_{ds}T_{ds}G_{ds}T_{ds}G_{ds}T_{ds}{}^mC_{es}A_{eo}A_{es}A_{es}{}^mC_e$ | 2610 |
| 952360 | 3229 | 3248 | 76363 | 76382 | $G_{es}{}^mC_{eo}A_{es}A_{es}G_{es}T_{ds}{}^mC_{ds}{}^mC_{ds}A_{ds}A_{ds}A_{ds}T_{ds}G_{ds}T_{ds}G_{ds}T_{es}{}^mC_{eo}A_{es}A_{es}A_e$ | 2687 |
| 952361 | 3231 | 3250 | 76365 | 76384 | $G_{es}T_{eo}G_{es}{}^mC_{es}A_{es}A_{ds}G_{ds}T_{ds}{}^mC_{ds}{}^mC_{ds}A_{ds}A_{ds}A_{ds}T_{ds}G_{as}T_{es}G_{eo}T_{es}{}^mC_{es}A_e$ | 3141 |
| 952362 | 3498 | 3517 | 77247 | 77266 | $^mC_{es}T_{eo}T_{es}{}^mC_{es}A_{es}G_{ds}T_{ds}T_{ds}{}^mC_{ds}{}^mC_{ds}T_{ds}T_{ds}{}^mC_{ds}A_{ds}G_{ds}T_{es}{}^mC_{eo}T_{es}{}^mC_{es}A_e$ | 1110 |
| 952363 | 3499 | 3518 | 77248 | 77267 | $T_{es}{}^mC_{eo}T_{es}T_{es}{}^mC_{es}A_{ds}G_{ds}T_{ds}T_{ds}{}^mC_{ds}{}^mC_{ds}T_{ds}T_{ds}{}^mC_{ds}A_{ds}G_{es}T_{eo}{}^mC_{es}T_{es}{}^mC_e$ | 1111 |
| 952364 | 3505 | 3524 | 77254 | 77273 | $T_{es}T_{eo}A_{es}A_{es}A_{es}A_{ds}T_{ds}{}^mC_{ds}T_{ds}T_{ds}{}^mC_{ds}A_{ds}G_{ds}T_{ds}T_{ds}{}^mC_{es}{}^mC_{eo}T_{es}T_{es}{}^mC_e$ | 1112 |
| 952365 | 3718 | 3737 | 82063 | 82082 | $T_{es}G_{eo}{}^mC_{es}T_{es}G_{es}{}^mC_{ds}T_{ds}{}^mC_{ds}A_{ds}A_{ds}T_{ds}{}^mC_{ds}T_{ds}A_{ds}A_{es}A_{eo}G_{es}A_{es}{}^mC_e$ | 1134 |
| 952366 | 3719 | 3738 | 82064 | 82083 | $T_{es}T_{eo}G_{es}{}^mC_{es}T_{es}G_{ds}{}^mC_{ds}T_{ds}{}^mC_{ds}A_{ds}A_{ds}T_{ds}A_{ds}T_{ds}{}^mC_{ds}T_{ds}A_{es}A_{eo}A_{es}G_{es}A_e$ | 1135 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 952367 | 3723 | 3742 | 82068 | 82087 | $A_{es}T_{eo}{}^mC_{es}A_{es}T_{es}T_{ds}G_{ds}{}^mC_{ds}T_{ds}G_{ds}{}^mC_{ds}T_{ds}{}^mC_{ds}A_{ds}T_{ds}A_{es}T_{eo}{}^mC_{es}T_{es}A_e$ | 1136 |
| 952368 | 4106 | 4125 | 86601 | 86620 | $A_{es}T_{eo}T_{es}{}^mC_{es}G_{es}G_{ds}T_{ds}T_{ds}A_{ds}T_{ds}A_{ds}A_{ds}G_{ds}G_{ds}{}^mC_{ds}A_{es}{}^mC_{eo}A_{es}G_{es}{}^mC_e$ | 1167 |
| 952369 | 4107 | 4126 | 86602 | 86621 | ${}^mC_{es}A_{eo}T_{es}T_{es}{}^mC_{es}G_{ds}G_{ds}T_{ds}T_{ds}A_{ds}T_{ds}A_{ds}A_{ds}G_{ds}G_{ds}{}^mC_{es}A_{eo}{}^mC_{es}A_{es}G_e$ | 1168 |
| 952370 | 4108 | 4127 | 86603 | 86622 | $T_{es}{}^mC_{eo}A_{es}T_{es}T_{es}{}^mC_{ds}G_{ds}G_{ds}T_{ds}T_{ds}A_{ds}T_{ds}A_{ds}A_{ds}G_{ds}G_{es}{}^mC_{eo}A_{es}{}^mC_{es}A_e$ | 1169 |
| 952371 | 4109 | 4128 | 86604 | 86623 | $T_{es}T_{eo}{}^mC_{es}A_{es}T_{es}T_{ds}{}^mC_{ds}G_{ds}G_{ds}T_{ds}T_{ds}A_{ds}T_{ds}A_{ds}A_{ds}G_{es}G_{eo}{}^mC_{es}A_{es}{}^mC_e$ | 1170 |
| 952372 | 4110 | 4129 | 86605 | 86624 | $T_{es}T_{eo}T_{es}{}^mC_{es}A_{es}T_{ds}T_{ds}{}^mC_{ds}G_{ds}G_{ds}T_{ds}T_{ds}A_{ds}T_{ds}A_{ds}A_{es}G_{eo}G_{es}{}^mC_{es}A_e$ | 1171 |
| 952373 | 4111 | 4130 | 86606 | 86625 | $G_{es}T_{eo}T_{es}T_{es}{}^mC_{es}A_{ds}T_{ds}T_{ds}{}^mC_{ds}G_{ds}G_{ds}T_{ds}T_{ds}A_{ds}T_{ds}A_{es}A_{eo}G_{es}G_{es}{}^mC_e$ | 235 |
| 952374 | 4115 | 4134 | 86610 | 86629 | $A_{es}T_{eo}A_{es}A_{es}G_{es}T_{ds}T_{ds}T_{ds}{}^mC_{ds}A_{ds}T_{ds}T_{ds}{}^mC_{ds}G_{ds}G_{ds}T_{es}T_{eo}A_{es}T_{es}A_e$ | 1175 |
| 952375 | 608 | 627 | 16128 | 16147 | $G_{es}A_{eo}G_{es}T_{es}G_{es}{}^mC_{ds}A_{ds}T_{ds}G_{ds}G_{ds}{}^mC_{ds}A_{ds}T_{ds}{}^mC_{ds}A_{ds}A_{es}{}^mC_{eo}A_{es}A_{es}T_e$ | 279 |
| 952376 | 609 | 628 | 16129 | 16148 | $T_{es}G_{eo}A_{es}G_{es}T_{es}G_{ds}{}^mC_{ds}A_{ds}T_{ds}G_{ds}G_{ds}{}^mC_{ds}A_{ds}T_{ds}{}^mC_{ds}A_{ds}A_{es}{}^mC_{eo}A_{es}A_{es}A_e$ | 840 |
| 952377 | 610 | 629 | 16130 | 16149 | $A_{es}T_{eo}G_{es}A_{es}G_{es}T_{ds}G_{ds}{}^mC_{ds}A_{ds}T_{ds}G_{ds}G_{ds}{}^mC_{ds}A_{ds}T_{ds}{}^mC_{es}A_{eo}A_{es}A_{es}A_e$ | 841 |
| 952378 | 611 | 630 | 16131 | 16150 | $A_{es}A_{eo}T_{es}G_{es}A_{es}G_{ds}T_{ds}G_{ds}{}^mC_{ds}A_{ds}T_{ds}G_{ds}G_{ds}{}^mC_{ds}A_{ds}T_{es}{}^mC_{eo}A_{es}A_{es}A_e$ | 280 |
| 952379 | 612 | 631 | 16132 | 16151 | $A_{es}A_{eo}A_{es}T_{es}G_{es}A_{ds}G_{ds}T_{ds}G_{ds}{}^mC_{ds}A_{ds}T_{ds}G_{ds}G_{ds}{}^mC_{ds}A_{es}T_{eo}{}^mC_{es}A_{es}A_e$ | 842 |
| 952380 | 613 | 632 | 16133 | 16152 | $G_{es}A_{eo}A_{es}A_{es}T_{es}G_{ds}A_{ds}G_{ds}T_{ds}G_{ds}{}^mC_{ds}A_{ds}T_{ds}G_{ds}G_{ds}{}^mC_{es}A_{eo}T_{es}{}^mC_{es}A_e$ | 843 |
| 952381 | 620 | 639 | 16140 | 16159 | $T_{es}T_{eo}G_{es}G_{es}{}^mC_{es}T_{ds}G_{ds}G_{ds}A_{ds}A_{ds}A_{ds}T_{ds}G_{ds}A_{ds}G_{ds}T_{es}G_{eo}{}^mC_{es}A_{es}T_e$ | 844 |
| 953599 | 732 | 748 | 18631 | 18647 | $T_{es}A_{eo}A_{eo}{}^mC_{es}A_{ds}A_{ds}T_{ds}A_{ds}T_{ds}{}^mC_{ds}A_{ds}T_{ds}A_{ds}Tk_oA_{es}A_{es}T_e$ | 3829 |
| 953600 | 733 | 749 | 18632 | 18648 | $T_{es}T_{eo}A_{eo}A_{es}{}^mC_{ds}A_{ds}A_{ds}T_{ds}A_{ds}T_{ds}{}^mC_{ds}A_{ds}T_{ds}Ak_oT_{es}A_{es}A_e$ | 3830 |
| 953601 | 734 | 750 | 18633 | 18649 | ${}^mC_{es}T_{eo}T_{eo}A_{es}A_{ds}{}^mC_{ds}A_{ds}A_{ds}T_{ds}A_{ds}T_{ds}{}^mC_{ds}A_{ds}Tk_oA_{es}T_{es}A_e$ | 3831 |
| 953602 | 735 | 751 | 18634 | 18650 | $A_{es}{}^mC_{eo}T_{eo}T_{es}A_{ds}A_{ds}{}^mC_{ds}A_{ds}A_{ds}T_{ds}A_{ds}T_{ds}{}^mC_{ds}Ak_oT_{es}A_{es}T_e$ | 3832 |
| 953603 | 736 | 752 | 18635 | 18651 | ${}^mC_{es}A_{eo}{}^mC_{eo}T_{es}T_{ds}A_{ds}A_{ds}{}^mC_{ds}A_{ds}A_{ds}T_{ds}A_{ds}T_{ds}Ck_oA_{es}T_{es}A_e$ | 3833 |
| 953604 | 1874 | 1890 | 52788 | 52804 | $A_{es}G_{eo}{}^mC_{eo}A_{es}{}^mC_{ds}T_{ds}G_{ds}A_{ds}A_{ds}T_{ds}{}^mC_{ds}{}^mC_{ds}A_{ds}Tk_oA_{es}G_{es}{}^mC_e$ | 3834 |
| 953605 | 1791 | 1807 | 52705 | 52721 | $A_{es}{}^mC_{eo}A_{eo}T_{es}T_{ds}T_{ds}{}^mC_{ds}T_{ds}G_{ds}A_{ds}A_{ds}T_{ds}{}^mC_{ds}Ck_{om}C_{es}A_{es}G_e$ | 3835 |
| 953606 | 3493 | 3509 | 77242 | 77258 | ${}^mC_{es}{}^mC_{eo}T_{eo}T_{es}{}^mC_{ds}A_{ds}G_{ds}T_{ds}{}^mC_{ds}T_{ds}{}^mC_{ds}A_{ds}A_{ds}Gk_oG_{es}G_{es}G_e$ | 3836 |
| 953607 | 3713 | 3729 | 82058 | 82074 | $A_{es}T_{eo}A_{eo}T_{es}{}^mC_{ds}T_{ds}A_{ds}A_{ds}A_{ds}G_{ds}A_{ds}{}^mC_{ds}{}^mC_{ds}Gk_o{}^mC_{es}A_{es}A_e$ | 3837 |

TABLE 71-continued

Modified oligonucleotides complementary to human LRRK2 RNA

| Compound Number | SEQ ID NO: 1 Start Site | SEQ ID NO: 1 Stop Site | SEQ ID NO: 2 Start Site | SEQ ID NO: 2 Stop Site | Sequence and chemistry notation (5' to 3') | SEQ ID NO |
|---|---|---|---|---|---|---|
| 953608 | 987 | 1003 | 27962 | 27978 | $A_{es}A_{eo}A_{eo}{}^mC_{es}T_{ds}{}^mC_{ds}A_{ds}T_{ds}G_{ds}G_{ds}A_{ds}{}^mC_{ds}T_{ds}Tk_o{}^mC_{es}G_{es}T_e$ | 3838 |
| 953609 | 4110 | 4126 | 86605 | 86621 | ${}^mC_{es}A_{eo}T_{eo}T_{es}{}^mC_{ds}G_{ds}G_{ds}T_{ds}T_{ds}A_{ds}T_{ds}A_{ds}A_{ds}Gk_oG_{es}{}^mC_{es}A_e$ | 3839 |
| 953610 | 7775 | 7791 | 145944 | 145960 | $A_{es}{}^mC_{eo}{}^mC_{eo}{}^mC_{es}T_{ds}T_{ds}T_{ds}{}^mC_{ds}{}^mC_{ds}A_{ds}T_{ds}G_{ds}T_{ds}Gk_oA_{es}A_{es}{}^mC_e$ | 3840 |
| 953611 | 879 | 895 | 21710 | 21726 | $T_{es}T_{eo}T_{eo}{}^mC_{es}A_{ds}T_{ds}A_{ds}G_{as}{}^mC_{ds}T_{as}T_{as}{}^mC_{ds}{}^mC_{ds}Ak_o{}^mC_{es}{}^mC_{es}A_e$ | 3841 |
| 953612 | 834 | 850 | 21665 | 21681 | ${}^mC_{es}A_{eo}T_{eo}G_{es}A_{ds}G_{ds}G_{ds}A_{ds}{}^mC_{ds}T_{ds}T_{ds}{}^mC_{ds}{}^mC_{ds}Ak_o{}^mC_{es}A_{es}T_e$ | 3842 |
| 953613 | 606 | 622 | 16126 | 16142 | ${}^mC_{es}A_{eo}T_{eo}G_{es}G_{ds}{}^mC_{ds}A_{ds}T_{as}{}^mC_{ds}A_{ds}A_{ds}A_{ds}A_{ds}Ak_oT_{es}T_{es}A_e$ | 3843 |
| 953614 | 990 | 1006 | 27965 | 27981 | ${}^mC_{es}A_{eo}{}^mC_{eo}A_{es}A_{ds}A_{ds}{}^mC_{ds}T_{ds}{}^mC_{ds}A_{ds}T_{ds}G_{ds}G_{ds}Ak_o{}^mC_{es}T_{es}T_e$ | 3844 |
| 953615 | 3497 | 3513 | 77246 | 77262 | $A_{es}G_{eo}T_{eo}T_{es}{}^mC_{ds}{}^mC_{ds}T_{ds}T_{ds}{}^mC_{ds}A_{ds}G_{ds}T_{ds}{}^mC_{ds}Tk_o{}^mC_{es}A_{es}A_e$ | 3845 |
| 953616 | 4108 | 4124 | 86603 | 86619 | $T_{es}T_{eo}{}^mC_{eo}G_{es}G_{as}T_{ds}T_{ds}A_{ds}T_{as}A_{ds}A_{ds}G_{ds}G_{as}{}^mCk_oA_{es}{}^mC_{es}A_e$ | 3846 |
| 953617 | 1698 | 1714 | 41931 | 41947 | $A_{es}T_{eo}T_{eo}T_{es}A_{ds}G_{ds}{}^mC_{ds}T_{ds}T_{ds}A_{ds}T_{ds}G_{ds}A_{ds}Tk_oG_{es}A_{es}A_e$ | 3847 |

Example 10: Effect of 5-10-5 MOE Gapmers with Mixed Internucleoside Linkages on Human LRRK2 RNA Expression In Vitro Via Free Uptake Modified oligonucleotides selected from the examples above were tested at various doses in A431 cells by free uptake. Cells were plated at a density of 10,000 cells per well with 0.039, 0.156, 0.625, 2.500 and 10.000 µM concentrations of modified oligonucleotide, as specified in the tables below. After a treatment period of approximately 24 hours, total RNA was isolated from the cells and LRRK2 RNA levels were measured by quantitative real-time PCR. Human LRRK2 primer probe set RTS3132 (described herein in Example 2) was used to measure RNA levels. LRRK2 RNA levels were adjusted according to total RNA content, as measured by RIBOGREEN®. Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 72

Dose-dependent reduction of human LRRK2 expression in A431 cells by free uptake

| Compound Number | LRRK2 expression (% control) | | | | | IC$_{50}$ (µM) |
|---|---|---|---|---|---|---|
| | 0.039 µM | 0.156 µM | 0.625 µM | 2.500 µM | 10.000 µM | |
| 780160 | 101 | 86 | 56 | 55 | 48 | 4.5 |
| 780161 | 102 | 85 | 58 | 31 | 45 | 1.9 |
| 780164 | 95 | 75 | 63 | 52 | 40 | 3.1 |
| 780166 | 94 | 42 | 42 | 31 | 32 | 0.4 |
| 780241 | 70 | 70 | 46 | 35 | 50 | 1.3 |
| 802655 | 81 | 76 | 58 | 52 | 36 | 2.3 |
| 802665 | 78 | 73 | 62 | 59 | 53 | 14.3 |
| 802678 | 77 | 44 | 28 | 24 | 26 | 0.2 |
| 802714 | 84 | 84 | 64 | 47 | 40 | 2.8 |
| 802758 | 84 | 51 | 25 | 23 | 29 | 0.2 |
| 802770 | 74 | 68 | 44 | 28 | 31 | 0.5 |
| 802784 | 88 | 70 | 37 | 20 | 25 | 0.5 |
| 802938 | 109 | 53 | 50 | 38 | 34 | 1.0 |
| 802939 | 96 | 80 | 63 | 44 | 31 | 1.9 |
| 802963 | 92 | 102 | 88 | 78 | 64 | 26.0 |
| 803000 | 85 | 84 | 60 | 30 | 33 | 1.3 |
| 803006 | 89 | 77 | 53 | 43 | 37 | 1.7 |
| 803268 | 90 | 93 | 55 | 46 | 27 | 1.7 |
| 803270 | 86 | 80 | 52 | 44 | 43 | 2.2 |
| 872255 | 96 | 67 | 36 | 29 | 22 | 0.5 |
| 872260 | 52 | 55 | 33 | 23 | 29 | 0.1 |
| 876031 | 96 | 60 | 33 | 21 | 20 | 0.4 |
| 876180 | 101 | 94 | 90 | 90 | 80 | >300 |
| 876190 | 81 | 68 | 36 | 24 | 23 | 0.4 |
| 876604 | 91 | 71 | 46 | 28 | 41 | 0.0 |
| 934517 | 80 | 86 | 43 | 38 | 48 | 0.9 |
| 934518 | 82 | 54 | 28 | 25 | 31 | 1.8 |
| 934523 | 71 | 49 | 30 | 15 | 23 | 0.3 |
| 934528 | 71 | 57 | 50 | 26 | 34 | 0.2 |
| 934529 | 76 | 43 | 24 | 27 | 29 | 0.4 |
| 934530 | 89 | 68 | 40 | 28 | 25 | 0.2 |

TABLE 72-continued

Dose-dependent reduction of human LRRK2 expression in A431 cells by free uptake

| Compound Number | LRRK2 expression (% control) | | | | | IC$_{50}$ (µM) |
|---|---|---|---|---|---|---|
| | 0.039 µM | 0.156 µM | 0.625 µM | 2.500 µM | 10.000 µM | |
| 934553 | 99 | 73 | 51 | 33 | 31 | 0.6 |
| 934554 | 95 | 73 | 72 | 40 | 35 | 1.0 |
| 934556 | 63 | 59 | 41 | 26 | 28 | 2.1 |
| 934557 | 107 | 63 | 51 | 33 | 33 | 0.3 |

Example 11: Effect of Modified Oligonucleotides on Rhesus Monkey LRRK2 RNA In Vitro, Multiple Doses Modified oligonucleotides selected from the examples above, which are also complementary to rhesus monkey LRRK2 were tested at various doses in LLC-MK2 monkey cells. Cells were plated at a density of 20,000 cells per well and transfected using electroporation with 0.011, 0.034, 0.103, 0.309, 0.926, 2.778, 8.333, and 25.000 µM concentrations of modified oligonucleotide, as specified in the tables below. Also tested were control oligonucleotides, 676630, a 5-10-5 MOE gapmer with mixed phosphodiester and phosphorothioate backbone with no known target and the sequence CCTATAGGACTATCCAGGAA (SEQ ID NO: 3848). After a treatment period of approximately 24 hours, total RNA was isolated from the cells and LRRK2 RNA levels were measured by quantitative real-time PCR. Human LRRK2 primer probe set hLRRK2 LTS35700 (forward sequence CCAGGTACAATGCAAAGCTTAAT, designated herein as SEQ ID NO: 20; reverse sequence TCAGTCCAATCACTGACAAGTT, designated herein as SEQ ID NO: 21; probe sequence TTGG-GAAGTCCTTGGTGTTCACCA, designated herein as SEQ ID NO: 22) was used to measure RNA levels. LRRK2 RNA levels were adjusted according to total RNA content, as measured by RIBOGREEN Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 73

Dose-dependent reduction of human LRRK2 expression in LLC-MK2 rhesus monkey cells

| Compound Number | LRRK2 expression (% control) | | | | | | | | IC$_{50}$ (µM) |
|---|---|---|---|---|---|---|---|---|---|
| | 0.011 µM | 0.034 µM | 0.103 µM | 0.309 µM | 0.926 µM | 2.778 µM | 8.333 µM | 25.000 µM | |
| 676630 | 118 | 114 | 124 | 128 | 123 | 134 | 125 | 125 | n/a# |
| 780241 | 114 | 118 | 116 | 92 | 67 | 51 | 46 | 41 | 6.4 |
| 802714** | 122 | 116 | 130 | 131 | 112 | 80 | 41 | 20 | 7.4 |
| 803268* | 101 | 109 | 105 | 112 | 108 | 89 | 76 | 69 | 50.4 |
| 876031 | 122 | 113 | 106 | 84 | 46 | 14 | 8 | 1 | 0.9 |
| 876604** | 97 | 95 | 99 | 97 | 107 | 107 | 105 | 77 | n/a# |
| 934556 | 88 | 84 | 71 | 55 | 30 | 12 | 11 | 6 | 0.3 |

IC$_{50}$ value cannot be calculated
*This modified oligonucleotide is complementary to and contains one mismatch to rhesus monkey LRRK2 nucleic acid SEQ ID NO: 3
**These modified oligonucleotides are complementary to and contain two mismatches to rhesus monkey LRRK2 nucleic acid SEQ ID NO: 3

Example 12: Effect of Modified Oligonucleotides on Human LRRK2 RNA Expression In Vitro, Multiple Doses Modified oligonucleotides described above were tested at various doses in SH-SY5Y cells. Cells were plated at a density of 20,000 cells per well and transfected using electroporation with 0.011, 0.034, 0.103, 0.309, 0.926, 2.778, 8.333, and 25.000 µM of modified oligonucleotide, as specified in the tables below. Also tested was control oligonucleotide, 676630, a 5-10-5 MOE gapmer with mixed phosphodiester and phosphorothioate backbone with no known target. After a treatment period of approximately 24 hours, total RNA was isolated from the cells and LRRK2 RNA levels were measured by quantitative real-time PCR. Human LRRK2 primer probe set LTS35700 (described herein in Example 11) was used to measure RNA levels. LRRK2 RNA levels were adjusted according to total RNA content, as measured by RIBOGREEN Results are presented in the table below as percent LRRK2 RNA levels relative to untreated control cells. As illustrated in the tables below, LRRK2 RNA levels were reduced in a dose-dependent manner in modified oligonucleotide-treated cells. IC50 was calculated using the "log(inhibitor) vs. response—variable slope (4 parameters)" formula using Prism6 software.

TABLE 74

Dose-dependent reduction of human LRRK2 expression in SH-SY5Y Cells

| Compound Number | LRRK2 expression (% control) | | | | | | | | IC$_{50}$ (µM) |
|---|---|---|---|---|---|---|---|---|---|
| | 0.011 µM | 0.034 µM | 0.103 µM | 0.309 µM | 0.926 µM | 2.778 µM | 8.333 µM | 25.000 µM | |
| Control 676630 | 129 | 113 | 108 | 133 | 109 | 131 | 122 | 133 | n/a* |
| 780241 | 117 | 104 | 92 | 93 | 76 | 59 | 58 | 58 | n/a* |
| 802714 | 100 | 123 | 98 | 93 | 75 | 56 | 44 | 36 | 6.3 |
| 803268 | 99 | 121 | 96 | 83 | 77 | 84 | 73 | 68 | 105.6 |
| 876031 | 96 | 99 | 93 | 73 | 49 | 22 | 18 | 15 | 1.0 |
| 876604 | 97 | 91 | 78 | 65 | 43 | 20 | 15 | 15 | 0.6 |
| 934556 | 97 | 90 | 77 | 55 | 42 | 27 | 20 | 15 | 0.6 |

*IC$_{50}$ value cannot be calculated

Example 13: Activity of Modified Oligonucleotides Complementary to Human LRRK2 in Transgenic Mice, Two Week Assessment Modified oligonucleotides described above were tested in the human BAC wild type LRRK2 transgenic mouse model (B6; SJL-Tg(LRRK2)66Mjff/J; Stock No: 013725, The Jackson Laboratory) to assess activity after two weeks. Mice hemizygous for the BAC LRRK2-Wt transgene are viable and fertile. These mice express a wild-type human leucine-rich repeat kinase 2 (LRRK2) gene directed by the human LRRK2 promoter/enhancer regions on the BAC transgene (Ouyang Y et al., 2011). Mice from this model express human LRRK2 in a variety of tissues, including the spinal cord and brain.

Treatment

LRRK2 transgenic mice each received a single intracerebroventricular (ICV) dose of 300 µg of modified oligonucleotides listed in the table below. Each treatment group consisted of 4 mice. A group of 4 mice received PBS as a negative control.

RNA Analysis

After two weeks, mice were sacrificed and RNA was extracted from cortical brain tissue and spinal cord for real-time PCR analysis of measurement of RNA expression of LRRK2 using primer probe set hLRRK2 LTS35700 (described herein above in Example 11). Results are presented in the table below as percent LRRK2 RNA levels relative to relative to PBS control, normalized with cyclophilin A As shown in the table below, treatment with modified oligonucleotides resulted in reduction of human LRRK2 RNA in comparison to the PBS control.

TABLE 75

Reduction of human LRRK2 RNA in transgenic mice

| Compound Number | LRRK2 Expression (% control) | |
|---|---|---|
| | Cortex | Spinal Cord |
| PBS | 100 | 100 |
| 693430 | 46 | 37 |
| 725607 | 24 | 50 |
| 725608 | 19 | 33 |
| 725609 | 30 | 37 |
| 780162 | 59 | 76 |
| 780164 | 27 | 62 |
| 780166 | 14 | 26 |
| 780189 | 58 | 49 |
| 780202 | 42 | 36 |
| 780203 | 65 | 66 |
| 780205 | 13 | 29 |
| 780219 | 34 | 43 |
| 780236 | 19 | 29 |
| 780241 | 23 | 38 |
| 780243 | 54 | 47 |
| 780254 | 42 | 41 |
| 780284 | 61 | 53 |
| 780321 | 39 | 64 |
| 780347 | 42 | 51 |
| 780549 | 63 | 53 |
| 780602 | 93 | 103 |
| 780620 | 47 | 45 |
| 780624 | 63 | 75 |
| 780649 | 52 | 48 |
| 780685 | 42 | 37 |
| 802655 | 30 | 48 |
| 802678 | 7 | 26 |
| 802685 | 38 | 32 |
| 802686 | 17 | 40 |
| 802688 | 18 | 27 |
| 802689 | 16 | 36 |
| 802731 | 42 | 44 |
| 802746 | 42 | 64 |
| 802747 | 56 | 44 |
| 802748 | 32 | 25 |
| 802845 | 30 | 26 |
| 802846 | 35 | 41 |
| 802848 | 68 | 72 |

TABLE 76

Reduction of human LRRK2 RNA in transgenic mice

| Compound Number | LRRK2 Expression (% control) | |
|---|---|---|
| | Cortex | Spinal Cord |
| PBS | 100 | 100 |
| 802849 | 78 | 77 |
| 802850 | 73 | 92 |
| 802888 | 49 | 63 |
| 802911 | 80 | 92 |
| 802915 | 54 | 68 |
| 802935 | 69 | 61 |
| 802936 | 40 | 52 |
| 802937 | 43 | 40 |
| 802958 | 57 | 78 |
| 802960 | 54 | 48 |
| 802961 | 34 | 44 |

TABLE 76-continued

Reduction of human LRRK2 RNA in transgenic mice

| Compound Number | LRRK2 Expression (% control) Cortex | Spinal Cord |
|---|---|---|
| 802962 | 40 | 51 |
| 802974 | 50 | 55 |
| 803002 | 30 | 44 |
| 803003 | 67 | 85 |
| 803004 | 73 | 86 |
| 803005 | 66 | 65 |
| 803046 | 95 | 65 |
| 803065 | 55 | 52 |
| 802959 | 41 | 62 |
| 803075 | 38 | 54 |
| 803102 | 89 | 89 |
| 803112 | 40 | 51 |
| 803122 | 52 | 71 |
| 803386 | 73 | 80 |
| 803515 | 81 | 104 |
| 803516 | 63 | 81 |
| 803517 | 55 | 67 |
| 803518 | 60 | 85 |
| 803519 | 70 | 79 |
| 803520 | 50 | 80 |
| 803571 | 66 | 71 |
| 803595 | 80 | 71 |
| 803604 | 65 | 67 |
| 803629 | 57 | 72 |
| 803682 | 47 | 46 |
| 803744 | 47 | 53 |
| 803770 | 73 | 54 |
| 803771 | 53 | 46 |
| 803773 | 40 | 50 |
| 803782 | 80 | 96 |

TABLE 77

Reduction of human LRRK2 RNA in transgenic mice

| Compound Number | LRRK2 Expression (% control) Cortex | Spinal Cord |
|---|---|---|
| PBS | 100 | 100 |
| 780160 | 13 | 15 |
| 780161 | 24 | 30 |
| 802665 | 17 | 35 |
| 802678 | 27 | 35 |
| 802690 | 33 | 40 |
| 802714 | 21 | 47 |
| 802758 | 23 | 42 |
| 802770 | 11 | 22 |
| 802781 | 32 | 49 |
| 802784 | 16 | 30 |
| 802938 | 21 | 32 |
| 802939 | 13 | 41 |
| 802963 | 26 | 51 |
| 803000 | 22 | 42 |
| 803001 | 36 | 50 |
| 803006 | 29 | 39 |
| 803268 | 31 | 52 |
| 803269 | 38 | 49 |
| 803270 | 24 | 75 |
| 803271 | 31 | 48 |
| 803272 | 76 | 75 |
| 803273 | 77 | 70 |
| 803274 | 50 | 65 |

TABLE 78

Reduction of human LRRK2 RNA in transgenic mice

| Compound Number | LRRK2 Expression (% control) Cortex | Spinal Cord |
|---|---|---|
| PBS | 100 | 100 |
| 802678 | 24 | 19 |
| 803275 | 52 | 77 |
| 872246 | 44 | 49 |
| 872247 | 57 | 63 |
| 872248 | 24 | 44 |
| 872249 | 61 | 73 |
| 872250 | 34 | 28 |
| 872251 | 37 | 51 |
| 872252 | 54 | 62 |
| 872253 | 29 | 43 |
| 872254 | 94 | 71 |
| 872256 | 34 | 44 |
| 872257 | 70 | 72 |
| 872258 | 55 | 42 |
| 872259 | 82 | 72 |
| 872260 | 10 | 30 |
| 872261 | 37 | 55 |
| 872262 | 50 | 71 |
| 872263 | 28 | 49 |
| 872264 | 43 | 67 |
| 872265 | 36 | 35 |
| 872266 | 92 | 88 |
| 872267 | 68 | 74 |

TABLE 79

Reduction of human LRRK2 RNA in transgenic mice

| Compound Number | LRRK2 Expression (% control) Cortex | Spinal Cord |
|---|---|---|
| PBS | 100 | 100 |
| 802678 | 9 | 19 |
| 802780 | 42 | 49 |
| 802847 | 54 | 64 |
| 803021 | 67 | 70 |
| 803045 | 36 | 60 |
| 803064 | 42 | 67 |
| 803123 | 56 | 76 |
| 803181 | 41 | 74 |
| 803470 | 34 | 52 |
| 803503 | 67 | 72 |
| 803665 | 58 | 84 |
| 803769 | 71 | 90 |
| 872255 | 23 | 42 |
| 872268 | 52 | 66 |
| 872269 | 37 | 54 |
| 872270 | 39 | 61 |
| 872271 | 94 | 101 |
| 872272 | 76 | 77 |
| 872273 | 31 | 38 |
| 872274 | 54 | 85 |
| 872275 | 84 | 84 |
| 872276 | 73 | 97 |
| 872277 | 47 | 67 |
| 872278 | 36 | 68 |
| 872279 | 39 | 69 |
| 874144 | 81 | 86 |
| 874145 | 64 | 67 |
| 874146 | 67 | 64 |
| 874147 | 78 | 79 |
| 874148 | 57 | 58 |
| 874149 | 55 | 69 |
| 874150 | 57 | 44 |
| 874151 | 102 | 84 |

TABLE 80

Reduction of human LRRK2 RNA in transgenic mice

| Compound Number | LRRK2 Expression (% control) | |
|---|---|---|
| | Cortex | Spinal Cord |
| PBS | 100 | 100 |
| 802678 | 30 | 41 |
| 803426 | 70 | 63 |
| 872280 | 83 | 64 |
| 872281 | 49 | 64 |
| 872282 | 48 | 64 |
| 872283 | 61 | 60 |
| 872285 | 26 | 41 |
| 876019 | 58 | 72 |
| 876097 | 47 | 46 |
| 876141 | 47 | 50 |
| 876168 | 103 | 89 |
| 876180 | 21 | 27 |
| 934558 | 54 | 49 |
| 934584 | 45 | 55 |
| 934585 | 162 | 95 |
| 934586 | 174 | 102 |
| 934587 | 35 | 238 |
| 934588 | 30 | 42 |
| 934589 | 19 | 30 |
| 934590 | 24 | 50 |
| 934591 | 42 | 52 |
| 934592 | 38 | 49 |
| 934593 | 31 | 35 |
| 934594 | 22 | 45 |
| 934595 | 59 | 61 |
| 934596 | n.d. | n.d. |
| 934597 | 48 | 59 |
| 934600 | 15 | 33 |

TABLE 81

Reduction of human LRRK2 RNA in transgenic mice

| Compound Number | LRRK2 Expression (% control) | |
|---|---|---|
| | Cortex | Spinal Cord |
| PBS | 100 | 100 |
| 780241 | 55 | 57 |
| 802678 | 12 | 20 |
| 876185 | 59 | 56 |
| 876190 | 25 | 38 |
| 876223 | 46 | 70 |
| 876326 | 36 | 57 |
| 876345 | 77 | 79 |
| 876735 | 64 | 57 |
| 876766 | 67 | 75 |
| 876900 | 41 | 46 |
| 877068 | 44 | 52 |
| 877159 | 52 | 61 |
| 877305 | 52 | 57 |
| 877328 | 68 | 76 |
| 890207 | 42 | 60 |
| 890208 | 32 | 45 |
| 890209 | 40 | 58 |
| 934599 | 29 | 37 |

TABLE 82

Reduction of human LRRK2 RNA in transgenic mice

| Compound Number | LRRK2 Expression (% control) | |
|---|---|---|
| | Cortex | Spinal Cord |
| PBS | 100 | 100 |
| 802678 | 15 | 21 |
| 803427 | 34 | 32 |

TABLE 82-continued

Reduction of human LRRK2 RNA in transgenic mice

| Compound Number | LRRK2 Expression (% control) | |
|---|---|---|
| | Cortex | Spinal Cord |
| 876028 | 99 | 61 |
| 876029 | 106 | 69 |
| 876043 | 55 | 36 |
| 876062 | 39 | 26 |
| 876074 | 70 | 35 |
| 876146 | 82 | 42 |
| 876189 | 54 | 34 |
| 876203 | 90 | 46 |
| 876221 | 60 | 31 |
| 876237 | 80 | 35 |
| 876262 | 58 | 31 |
| 876284 | 74 | 41 |
| 876287 | 129 | 57 |
| 876302 | 81 | 34 |
| 876303 | 76 | 46 |
| 876899 | 60 | 34 |
| 876960 | 93 | 41 |
| 877119 | 62 | 36 |
| 877171 | 67 | 66 |
| 877292 | 68 | 58 |
| 877326 | 74 | 58 |
| 877349 | 106 | 81 |
| 877395 | 69 | 75 |

TABLE 83

Reduction of human LRRK2 RNA in transgenic mice

| Compound Number | LRRK2 Expression (% control) | |
|---|---|---|
| | Cortex | Spinal Cord |
| PBS | 100 | 100 |
| 802678 | 13 | 13 |
| 876027 | 166 | 94 |
| 876031 | 23 | 18 |
| 876042 | 85 | 60 |
| 876068 | 80 | 54 |
| 876088 | 48 | 60 |
| 876143 | 79 | 70 |
| 876186 | 60 | 45 |
| 876195 | 54 | 48 |
| 876261 | 32 | 35 |
| 876263 | 46 | 42 |
| 876282 | 64 | 45 |
| 876285 | 89 | 59 |
| 876294 | 37 | 39 |
| 876301 | 51 | 55 |
| 876328 | 63 | 53 |
| 876604 | 26 | 22 |
| 876790 | 87 | 54 |
| 877098 | 65 | 41 |
| 877176 | 175 | 74 |

TABLE 84

Reduction of human LRRK2 RNA in transgenic mice

| Compound Number | LRRK2 Expression (% control) | |
|---|---|---|
| | Cortex | Spinal Cord |
| PBS | 100 | 100 |
| 802678 | 31 | 40 |
| 872284 | 69 | 57 |
| 876274 | 65 | 60 |
| 877113 | 76 | 98 |
| 877303 | 67 | 68 |
| 890206 | 41 | 77 |

TABLE 84-continued

Reduction of human LRRK2 RNA in transgenic mice

| Compound Number | LRRK2 Expression (% control) Cortex | Spinal Cord |
|---|---|---|
| 934538 | 49 | 49 |
| 934540 | 80 | 67 |
| 934541 | 43 | 54 |
| 934542 | 44 | 63 |
| 934543 | 58 | 60 |
| 934544 | 46 | 52 |
| 934545 | 39 | 35 |
| 934546 | 37 | 44 |
| 934547 | 45 | 51 |
| 934548 | 37 | 43 |
| 934549 | 34 | 42 |
| 934552 | 37 | 35 |
| 934553 | 27 | 36 |
| 934554 | 23 | 36 |
| 934555 | 38 | 43 |
| 934556 | 10 | 17 |
| 934557 | 17 | 29 |
| 934558 | 46 | 51 |

TABLE 85

Reduction of human LRRK2 RNA in transgenic mice

| Compound Number | LRRK2 Expression (% control) Cortex | Spinal Cord |
|---|---|---|
| PBS | 100 | 100 |
| 802678 | 10 | 17 |
| 934514 | 17 | 28 |
| 934515 | 16 | 21 |
| 934516 | 9 | 26 |
| 934517 | 16 | 36 |
| 934518 | 25 | 23 |
| 934519 | 71 | 70 |
| 934520 | 47 | 27 |
| 934521 | 52 | 50 |
| 934522 | 45 | 58 |
| 934523 | 29 | 30 |
| 934524 | 35 | 38 |
| 934525 | 50 | 56 |
| 934526 | 41 | 43 |
| 934528 | 28 | 33 |
| 934529 | 30 | 33 |
| 934530 | 31 | 35 |
| 934531 | 33 | 37 |
| 934532 | 33 | 37 |
| 934533 | 37 | 32 |
| 934534 | 38 | 44 |
| 934535 | 80 | 55 |
| 934536 | 57 | 61 |
| 934537 | 45 | 45 |

TABLE 86

Reduction of human LRRK2 RNA in transgenic mice

| Compound Number | LRRK2 Expression (% control) Cortex | Spinal Cord |
|---|---|---|
| PBS | 100 | 100 |
| 802678 | 11 | 22 |
| 952334 | 43 | 27 |
| 952335 | 86 | 96 |
| 952336 | 34 | 53 |
| 952338 | 68 | 62 |
| 952340 | 36 | 36 |
| 953599 | 123 | 87 |

TABLE 86-continued

Reduction of human LRRK2 RNA in transgenic mice

| Compound Number | LRRK2 Expression (% control) Cortex | Spinal Cord |
|---|---|---|
| 953600 | 105 | 83 |
| 953601 | 103 | 87 |
| 953602 | 70 | 89 |
| 953603 | 48 | 74 |
| 953604 | 36 | 46 |
| 953605 | 69 | 51 |
| 953606 | 93 | 74 |
| 953607 | 53 | 65 |
| 953608 | 41 | 36 |
| 953609 | 84 | 69 |
| 953610 | 59 | 61 |
| 953611 | 42 | 61 |
| 953612 | 47 | 85 |
| 953613 | 81 | 74 |
| 953614 | 61 | 62 |
| 953615 | 41 | 42 |
| 953616 | 79 | 57 |
| 953617 | 107 | 67 |

TABLE 87

Reduction of human LRRK2 RNA in transgenic mice

| Compound Number | LRRK2 Expression (% control) Cortex | Spinal Cord |
|---|---|---|
| PBS | 100 | 100 |
| 802678 | 16 | 18 |
| 952358 | 80 | 84 |
| 952359 | 54 | 66 |
| 952360 | 34 | 39 |
| 952361 | 51 | 47 |
| 952362 | 42 | 41 |
| 952363 | 45 | 42 |
| 952364 | 45 | 57 |
| 952365 | 39 | 63 |
| 952366 | 38 | 56 |
| 952367 | 61 | 50 |
| 952368 | 33 | 52 |
| 952369 | 56 | 59 |
| 952370 | 37 | 62 |
| 952371 | 34 | 56 |
| 952372 | 27 | 65 |
| 952373 | 43 | 55 |
| 952374 | 58 | 72 |
| 952375 | 20 | 42 |
| 952376 | 29 | 41 |
| 952377 | 20 | 34 |
| 952378 | 28 | 41 |
| 952379 | 35 | 49 |
| 952380 | 22 | 51 |
| 952381 | 22 | 40 |

Example 14: Activity of Modified Oligonucleotides Complementary to Human LRRK2 in Transgenic Mice, Eight Week Assessment Modified oligonucleotides described above were tested in the human BAC wild type LRRK2 transgenic mouse model (described herein above) to assess activity after eight weeks. Mice hemizygous for the BAC LRRK2-Wt transgene are viable and fertile. These mice express a wild-type human leucine-rich repeat kinase 2 (LRRK2) gene directed by the human LRRK2 promoter/enhancer regions on the BAC transgene (Ouyang Y et al., 2011). Mice from this model express human LRRK2 in a variety of tissues, including the spinal cord and brain.

Treatment

LRRK2 transgenic mice each received a single ICV dose of 300 ng of modified oligonucleotides listed in the table below. Each treatment group consisted of 4 mice. A group of 4 mice received PBS as a negative control.

RNA Analysis

After eight weeks, mice were sacrificed and RNA was extracted from cortical brain tissue and spinal cord for real-time PCR analysis of measurement of RNA expression of LRRK2 using primer probe set hLRRK2 LTS35700 (described herein above in Example 11). Results are presented in the table below as percent LRRK2 RNA levels relative to relative to PBS control, normalized with cyclophilin A As shown in the table below, treatment with modified oligonucleotides resulted in reduction of human LRRK2 RNA in comparison to the PBS control.

TABLE 88

Reduction of human LRRK2 RNA in transgenic mice

| Compound Number | LRRK2 Expression in Cortex (% control) |
|---|---|
| PBS | 100 |
| 802665 | 44 |
| 934556 | 16 |
| 934517 | 26 |
| 802678 | 19 |
| 876031 | 33 |
| 934553 | 34 |
| 934554 | 34 |
| 780166 | 28 |
| 802714 | 27 |
| 802770 | 16 |
| 802938 | 23 |
| 803270 | 33 |
| 780161 | 39 |
| 780241 | 44 |
| 934557 | 18 |

TABLE 89

Reduction of human LRRK2 RNA in transgenic mice

| Compound Number | LRRK2 Expression in Cortex (% control) |
|---|---|
| PBS | 100 |
| 780164 | 54 |
| 803000 | 39 |
| 803268 | 66 |
| 876604 | 78 |
| 934518 | 21 |

Example 15: Activity of Modified Oligonucleotides Complementary to Human LRRK2 in Transgenic Rats Modified oligonucleotides described above were tested in the human BAC G2019S mutant LRRK2 transgenic rat (NTac:SD-Tg(LRRK*G2019S)571Cjli; Taconic) model to assess activity. The model was created through pronuclear injection of the entire human LRRK2 gene with the G2019S mutation into NTac:SD zygotes. Rats from this model express human LRRK2 in a variety of tissues, including the spinal cord and brain (West A B et al., *J. Comp. Neurology*, 2014, 522(11):2465-2480).

Treatment

LRRK2 transgenic rats each received a single ICV dose of 1,000 µg of modified oligonucleotides listed in the table below. Each treatment group consisted of 4-5 rats. A group of 4 rats received PBS as a negative control.

RNA Analysis

After two weeks, rats were sacrificed and RNA was extracted from brainstem, cortical brain tissue, spinal cord, lung and kidney for real-time PCR analysis of measurement of RNA expression of LRRK2 using primer probe set hLRRK2 LTS35700 (described herein above in Example 11). Results are presented in the table below as percent LRRK2 RNA levels relative to relative to PBS control, normalized with cyclophilin A As shown in the table below, treatment with modified oligonucleotides resulted in reduction of human LRRK2 RNA in comparison to the PBS control.

TABLE 90

Reduction of human LRRK2 RNA in transgenic rats

| Compound Number | LRRK2 Expression (% control) | | |
|---|---|---|---|
| | Brainstem | Cortex | Spinal Cord |
| PBS | 100 | 100 | 100 |
| 780241 | 60 | 42 | 54 |
| 802714 | 43 | 33 | 53 |
| 803268 | 66 | 58 | 73 |
| 876031 | 33 | 9 | 33 |
| 876604 | 38 | 19 | 39 |
| 934556 | 31 | 9 | 35 |

Example 16: Potency of Modified Oligonucleotides Complementary to Human LRRK2 in Transgenic Rats Modified oligonucleotides described above were tested in the human BAC G2019S mutant LRRK2 transgenic rat (NTac:SD-Tg(LRRK*G2019S)571Cjli) model, described herein above, to test the potency of oligonucleotides.

Treatment

LRRK2 transgenic rats each received a single intracerebroventricular (ICV) dose of 10, 30, 100, 300, 700, 1,000, or 3,000 µg of modified oligonucleotides listed in the table below. Each treatment group consisted of 5 rats. A group of 5 rats received PBS as a negative control for each dosage group.

RNA Analysis

After two weeks, rats were sacrificed and RNA was extracted from cortex for real-time PCR analysis of measurement of RNA expression of LRRK2 using primer probe set hLRRK2 LTS35700 (described herein above in Example 11). Results are presented in the table below as percent LRRK2 RNA levels relative to relative to PBS control, normalized with cyclophilin A.

As shown in the table below, treatment with modified oligonucleotides resulted in reduction of human LRRK2 RNA in comparison to the PBS control. Dose response data was analyzed using GraphPad Prism 6 software (San Diego, Calif.). $ED_{50}$ values were calculated from log transformed dose or concentrations and individual animal LRRK2 RNA levels using the built in GraphPad formula "log(agonist) vs. response—Find ECanything", with the following constraints: bottom >0, top=100, F=50 for $ED_{50}$

TABLE 91

Dose-dependent percent reduction of human LRRK2 RNA in transgenic rats, cortex

| Compound Number | LRRK2 expression (% control) in cortex | | | | | | $ED_{50}$ (µg/g) |
|---|---|---|---|---|---|---|---|
| | 10 µg | 30 µg | 100 µg | 300 µg | 1000 µg | 3000 µg | |
| 780241 | 107.4 | 96.4 | 75.9 | 41.9 | 33.1 | 34.9 | 129 |
| 876031 | 102.0 | 94.6 | 67.6 | 18.7 | 5.9 | 4.6 | 135 |
| 934556 | 105.9 | 94.2 | 56.6 | 17.3 | 7.1 | 3.7 | 111 |

Example 17: Tolerability of Modified Oligonucleotides Complementary to LRRK2 in Wild-Type Mice, 3 Hour FOB Assessment Modified oligonucleotides described above were tested in wild-type female C57/Bl6 mice to assess the tolerability of the oligonucleotides. Wild-type female C57/Bl6 mice each received a single ICV dose of 700 µg of modified oligonucleotide listed in the table below. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the tables below.

TABLE 92

Tolerability scores in mice at 700 µg dose

| Compound Number | 3 hr FOB |
|---|---|
| PBS | 0 |
| 802678 | 0 |
| 693430 | 0 |
| 725607 | 0 |
| 780164 | 0 |
| 780166 | 6 |
| 780205 | 0 |
| 780254 | 7 |
| 780321 | 0 |
| 780685 | 2 |
| 802685 | 0 |
| 802688 | 0 |
| 802689 | 0 |
| 802731 | 6 |
| 802746 | 6 |
| 802888 | 6 |
| 802936 | 4 |
| 802937 | 4 |
| 802959 | 1 |
| 802962 | 0 |
| 802974 | 0 |
| 803002 | 7 |
| 803075 | 4 |
| 803682 | 1 |

TABLE 93

Tolerability scores in mice at 700 µg dose

| Compound Number | 3 hr FOB |
|---|---|
| PBS | 0 |
| 780160 | 0 |
| 802784 | 6 |
| 802939 | 3 |
| 803006 | 5 |
| 872248 | 7 |
| 872253 | 7 |
| 872260 | 7 |
| 872263 | 7 |
| 876190 | 2 |
| 934552 | 2 |
| 934553 | 0 |
| 934554 | 2 |
| 934555 | 2 |
| 934556 | 1 |
| 934557 | 1 |

TABLE 94

Tolerability scores in mice at 700 µg dose

| Compound Number | 3 hr FOB |
|---|---|
| PBS | 0 |
| 872255 | 5 |
| 934514 | 4 |
| 934515 | 2 |
| 934516 | 6 |
| 934518 | 4 |
| 934523 | 7 |
| 934528 | 5 |
| 934529 | 5 |
| 934530 | 3 |
| 934517 | 4 |
| 802758 | 7 |
| 876180 | 0 |

TABLE 95

Tolerability scores in mice at 700 µg dose

| Compound Number | 3 hr FOB |
|---|---|
| PBS | 0 |
| 780161 | 1 |
| 780164 | 5 |
| 780166 | 6 |
| 802665 | 1 |
| 802714 | 3 |
| 802770 | 4 |
| 802938 | 4 |
| 802963 | 0 |
| 803000 | 4 |
| 803268 | 4 |
| 803270 | 1 |

TABLE 96

Tolerability scores in mice at 700 µg dose

| Compound Number | 3 hr FOB |
|---|---|
| PBS | 0 |
| 876031 | 0 |
| 876604 | 5 |

TABLE 97

Tolerability scores in mice at 700 µg dose

| Compound Number | 3 hr FOB |
|---|---|
| PBS | 0 |
| 952334 | 2 |
| 952335 | 0 |
| 952336 | 2 |
| 952338 | 5 |
| 952340 | 3 |
| 952358 | 5 |
| 952359 | 7 |
| 952360 | 6 |
| 952361 | 4 |
| 952362 | 6 |
| 952363 | 3 |

TABLE 98

Tolerability scores in mice at 700 µg dose

| Compound Number | 3 hr FOB |
|---|---|
| PBS | 0 |
| 952364 | 0 |
| 952365 | 0 |
| 952366 | 3 |
| 952367 | 6 |
| 952368 | 5 |
| 952369 | 7 |
| 952370 | 7 |
| 952371 | 6 |
| 952372 | 7 |
| 952373 | 7 |
| 952374 | 4 |
| 952375 | 2 |
| 952376 | 5 |
| 952377 | 6 |
| 952378 | 3 |
| 952379 | 4 |
| 952380 | 7 |
| 952381 | 6 |
| 953599 | 0 |
| 953600 | 0 |
| 953601 | 0 |
| 953602 | 0 |
| 953603 | 0 |
| 953604 | 4 |
| 953605 | 5 |
| 953606 | 6 |
| 953607 | 3 |
| 953608 | 6 |
| 953609 | 6 |
| 953610 | 3 |
| 953611 | 3 |
| 953612 | 1 |
| 953613 | 0 |
| 953614 | 2 |
| 953615 | 4 |
| 953616 | 5 |
| 953617 | 5 |

Example 18: Tolerability of Modified Oligonucleotides Complementary to Human LRRK2 in Rats, 3 Hour FOB Assessment Modified oligonucleotides described abovere were tested in Sprague Dawley rats to assess the tolerability of the oligonucleotides. Sprague Dawley rats each received a single intrathecal (IT) dose of 3 mg of oligonucleotide listed in the table below. Each treatment group consisted of 3-4 rats. A group of 4 rats received PBS as a negative control for each experiment (identified in separate tables below). At 3 hours post-injection, movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was not moving. For each of the 7 criteria, a rat was given a subscore of 0 if it met the criteria and 1 if it did not (the functional observational battery score or FOB). After all 7 criteria were evaluated, the scores were summed for each rat and averaged within each treatment group. The results are presented in the tables below.

TABLE 99

Tolerability scores in rats at 3 mg dose

| Compound Number | 3 hr FOB |
|---|---|
| PBS | n.d. |
| 780164 | 2 |
| 780166 | 2 |
| 780189 | 1 |
| 780236 | 4 |
| 780241 | 1 |
| 780243 | 3 |
| 780254 | 3 |
| 780347 | 0 |
| 780549 | 0 |

TABLE 100

Tolerability scores in rats at 3 mg dose

| Compound Number | 3 hr FOB |
|---|---|
| PBS | 0.25 |
| 780236 | 5 |
| 802678 | 2 |
| 802688 | 2 |
| 802748 | 6 |
| 872259 | 3 |
| 872261 | 4 |
| 872269 | 4 |
| 872279 | 3 |

TABLE 101

Tolerability scores in rats at 3 mg dose

| Compound Number | 3 hr FOB |
|---|---|
| PBS | 0 |
| 725607 | 1 |
| 780620 | 6 |
| 802888 | 5 |
| 802936 | 5 |
| 802937 | 5 |
| 802959 | 4 |
| 802961 | 2 |
| 802962 | 2 |
| 802974 | 3 |
| 803520 | 5 |

TABLE 102

Tolerability scores in rats at 3 mg dose

| Compound Number | 3 hr FOB |
|---|---|
| PBS | 0 |
| 725609 | 0 |
| 780164 | 3 |
| 780166 | 6 |
| 780205 | 3 |
| 802689 | 2 |
| 802731 | 7 |
| 802746 | 5 |
| 802845 | 2 |
| 802846 | 4 |
| 876088 | 1 |

TABLE 103

Tolerability scores in rats at 3 mg dose

| Compound Number | 3 hr FOB |
|---|---|
| PBS | 0 |
| 802655 | 5 |
| 802686 | 2 |
| 802688 | 2 |
| 803075 | 5 |
| 803682 | 1 |
| 876031 | 0 |
| 876261 | 4 |
| 876263 | 2 |
| 876294 | 2 |

TABLE 104

Tolerability scores in rats at 3 mg dose

| Compound Number | 3 hr FOB |
|---|---|
| PBS | 0 |
| 693430 | 3 |
| 780219 | 5 |
| 780254 | 2 |
| 780321 | 3 |
| 780347 | 1 |

TABLE 105

Tolerability scoes in rats at 3 mg dose

| Compound Number | 3 hr FOB |
|---|---|
| PBS | 0 |
| 780160 | 1 |
| 780161 | 2 |
| 802784 | 5 |
| 802938 | 1 |
| 802939 | 3 |
| 802963 | 2 |
| 803000 | 5 |
| 803006 | 4 |
| 803270 | 1 |
| 872248 | 3 |
| 872253 | 6 |

TABLE 106

Tolerability scores in rats at 3 mg dose

| Compound Number | 3 hr FOB |
|---|---|
| PBS | 0 |
| 872260 | 5 |
| 872263 | 7 |
| 934553 | 0 |
| 934554 | 0 |
| 934555 | 2 |
| 934556 | 0 |
| 934557 | 0 |

TABLE 107

Tolerability scores in rats at 3 mg dose

| Compound Number | 3 hr FOB |
|---|---|
| PBS | 0 |
| 934517 | 2 |
| 934523 | 6 |
| 934528 | 4 |
| 934529 | 1 |
| 934530 | 0 |

TABLE 108

Tolerability scores in rats at 3 mg dose

| Compound Number | 3 hr FOB |
|---|---|
| PBS | 0 |
| 802678 | 0.5 |
| 802758 | 3.25 |
| 876604 | 5 |

TABLE 109

Tolerability scores in rats at 3 mg dose

| Compound Number | 3 hr FOB |
|---|---|
| PBS | 0 |
| 802665 | 1 |
| 802714 | 2 |
| 802770 | 2 |
| 803268 | 3 |
| 872255 | 5 |
| 934516 | 3 |
| 934518 | 4 |

TABLE 110

Tolerability scores in rats at 3 mg dose

| Compound Number | 3 hr FOB |
|---|---|
| PBS | 0 |
| 693421 | 2.5 |
| 690093 | 3.0 |

TABLE 111

Tolerability scores in rats at 3 mg dose

| Compound Number | 3 hr FOB |
|---|---|
| PBS | 0 |
| 952334 | 4 |
| 952335 | 2 |
| 952336 | 3 |
| 952338 | 2 |
| 952358 | 3 |
| 952359 | 2 |

TABLE 112

Tolerability scores in rats at 3 mg dose

| Compound Number | 3 hr FOB |
|---|---|
| PBS | 0 |
| 952378 | 5 |
| 952379 | 5 |
| 952380 | 3 |
| 952381 | 4 |
| 953599 | 1 |
| 953600 | 1 |
| 953601 | 0 |
| 953602 | 2 |
| 953603 | 0 |
| 953604 | 3 |
| 953605 | 5 |
| 953606 | 5 |

TABLE 113

Tolerability scores in rats at 3 mg dose

| Compound Number | 3 hr FOB |
|---|---|
| PBS | 0 |
| 953607 | 3 |
| 953608 | 4 |
| 953609 | 5 |
| 953610 | 3 |
| 953611 | 4 |
| 953612 | 3 |
| 953613 | 1 |
| 953614 | 4 |
| 953615 | 1 |
| 953616 | 4 |
| 953617 | 4 |

TABLE 114

Tolerability scores in rats at 3 mg dose

| Compound Number | 3 hr FOB |
|---|---|
| PBS | 0 |
| 952371 | 4 |
| 952372 | 4 |
| 952373 | 4 |
| 952374 | 2 |
| 952375 | 5 |
| 952376 | 4 |
| 952377 | 5 |

TABLE 115

Tolerability scores in rats at 3 mg dose

| Compound Number | 3 hr FOB |
|---|---|
| PBS | 0 |
| 952340 | 1 |
| 952360 | 4 |
| 952361 | 3 |
| 952362 | 5 |
| 952363 | 4 |
| 952364 | 5 |
| 952365 | 2 |
| 952366 | 5 |
| 952367 | 5 |
| 952368 | 6 |
| 952369 | 4 |
| 952370 | 5 |

Example 19: Prophylactic Reduction of LRRK2 with Modified Oligonucleotides in PFF Model Wild type mice received a single ICV injection of 700 μg of an oligonucleotide listed in the table below or PBS vehicle alone. Each treatment group consisted of eleven or twelve mice. Two weeks after oligonucleotide treatment, preformed fibrils (PFFs) of α-synuclein were injected into the striatum, resulting in formation of α-synuclein aggregates in several brain regions and motor deficits, as described (see Luk et al., *Science*, 2012, 338, 949-953). One control group did not receive injection of PFFs. Fifty-five days after the oligonucleotide treatment, motor function was tested in a wire hang test. The results are presented in the table below as the average length of time the mice of each treatment group remained on the wire.

One day after the wire hang test, all of the mice in each treatment group were sacrificed except for the group that received no oligonucleotide and no PFF injection; only four mice in that group were sacrificed Animals were perfused with ice-cold PBS. Ipsilateral hemispheres were fixed and processed for immunochemistry. Contralateral midbrain and striatum were dissected and frozen until RNA analysis, while entire contralateral cortex was dissected and frozen until protein analysis. LRRK2 RNA expression was analyzed by quantitative real-time PCR using the murine primer probe set RTS3043 (forward sequence GGCGAGTTATCCGCACCAT, designated herein as SEQ ID NO: 23; reverse sequence CCAAAACCAGCATGACATTCTTAA, designated herein as SEQ ID NO: 24; probe sequence TGAGAGCCATGGCCACAGCACAA, designated herein as SEQ ID NO: 25). LRRK2 RNA levels were adjusted according to total RNA content, as measured by RIBOGREEN. The results are shown in the table below as average percent inhibition relative to the wild type control group that received neither oligonucleotide treatment nor PFF injection.

LRRK2, α-synuclein, and hyperphosphorylated α-synuclein (p-α-syn) protein levels in the cortex were analyzed by western blot. Contralateral cortex tissue was first homogenized in RIPA buffer and centrifuged at 13,300×g. The supernatant was subjected to western blot for LRRK2 protein level, and β-tubulin was used as a loading control. The results indicated that LRRK2 protein levels in the cortex were significantly lower in the oligonucleotide treated animals than in the animals that did not receive oligonucleotide treatment. The pellet was resuspended in RIPA buffer, centrifuged at 100,000×g, and the resulting insoluble material was further suspended in 2% SDS buffer, followed by an additional 100,000×g spin. The resulting supernatant was analyzed by western blot for α-synuclein and p-α-syn. The results showed that PFF injection resulted in recruitment of endogenous mouse α-synuclein into insoluble aggregates, as reported in Luk et al. The aggregates were also hyperphosphorylated. Oligonucleotide treatments reduced formation of the aggregates, as evidenced by a reduction of insoluble mouse α-synuclein and p-α-syn in the western blots. p-α-syn aggregates in the substantia nigra were visualized by immunohistochemistry. The average number of aggregates observed for samples of equal size from each treatment group is shown in the table below. One-way ANOVA test of the results showed that the differences between the PBS treated and oligonucleotide treated animals were significant.

TABLE 116

Prophylactic treatment of PFF mice with LRKK2 modified oligonucleotides

| Compound Number | PFF injected | Time in wirehang test (sec) | Inhibition of LRRK2 RNA (%) | | No. of p-α-syn aggregates |
|---|---|---|---|---|---|
| | | | Midbrain | Striatum | |
| PBS | No | 193 | 0 | 4.0 | 0 |
| PBS | Yes | 94 | 0 | 0 | 42 |
| 693421 | Yes | 187 | 52.0 | 49.0 | 12 |
| 690093 | Yes | 175 | 43.0 | 24.8 | 21 |

Example 20: Reduction of LRRK2 with Modified Oligonucleotide in PFF Model

The effects of oligonucleotide reduction in wild type mice after the injection of PFFs was evaluated using 690093. Mice were treated as described in Example 19 except that oligonucleotide treatment occurred two weeks after PFF injection instead of two weeks before PFF injection. Each treatment group consisted of ten animals Fifty-five days after PFF injection, the mice were assessed in a wire hang test, as described in Example 19. One day after the wire hang test, the mice were sacrificed, the midbrain, striatum, and substantia nigra were collected, and LRRK2 RNA and p-α-syn aggregates were measured, as described in Example 19. The results are shown in the table below as the averages for each treatment group. An entry of "nd" indicates that data was not collected for that treatment group. The results show that even when the modified oligonucleotide was administered after the onset of the PFF model, motor function was improved and the number of pathological aggregates was reduced.

TABLE 117

Treatment of PFF mice with LRKK2 modified oligonucleotides

| Oligo ID | PFF injected | Time in wirehang test (sec) | Inhibition of LRRK2 RNA (%) | | No. of p-α-syn aggregates |
|---|---|---|---|---|---|
| | | | Midbrain | Striatum | |
| PBS | No | 227 | 0 | 0 | nd |
| PBS | Yes | 58 | 0 | 0 | 49 |
| 690093 | Yes | 141 | 62.3 | 43.6 | 38 |

Example 21: Prophylactic Reduction of LRRK2 with Modified Oligonucleotides in PFF Model in a Long Term Study Modified oligonucleotides were tested in a long term study to determine if long term treatment with modified oligonucleotides is protective of dopaminergic neurons. Accumulation of α-syn aggregates in the substantia nigra pars compacta compromises survival of dopaminergic neurons over time (Luk 2012, Tran 2014).

The effects of oligonucleotide reduction in wild type mice after the injection of PFFs was evaluated using 690093 or control oligonucleotide 676630, a 5-10-5 MOE gapmer with mixed phosphodiester and phosphorothioate backbone with no known target. Mice were treated as described in Example 19 except mice received a second ICV dose of 690093 at 90 days, and were sacrificed at 180 days post first ICV treatment. Each treatment group consisted of 12 animals. At sacrifice, midbrain, striatum, and substantia nigra were collected, and LRRK2 RNA and p-α-syn aggregates were measured, as described in Example 19, and dopaminergic cells were quantified by immunohistochemistry using anti-tyrosine hydroxylase (TH) antibody. The results are shown in the table below as the averages for each treatment group. The results show that in the group treated with modified oligonucleotide complementary to LRRK2, the number of pathological aggregates was reduced over a long treatment course. Additionally, quantification of TH-positive neurons showed that 690093-mediated LRRK2 suppression rescued TH-positive cells in the ipsilateral substantia nigra pars compacta as compared to control treated cells.

TABLE 118

Prophylactic treatment of PFF mice with LRKK2 modified oligonucleotides in long term study

| Compound Number | PFF injected | Inhibition of LRRK2 RNA (%) Midbrain | Striatum | No. of p-α-syn aggregates | No. of dopaminergic cells |
|---|---|---|---|---|---|
| 676630 | Yes | 0 | 0 | 160 | 5880 |
| 690093 | Yes | 61.7 | 0 | 48 | 7522 |

Example 22: Tolerability of Modified Oligonucleotides Complementary to Human LRRK2 in Rats, Long-Term Assessment In separate studies run under the same conditions, modified oligonucleotides described above were tested in Sprague Dawley rats to assess the long-term tolerability of the oligonucleotides. Sprague Dawley rats each received a single intrathecal (IT) delivered dose of 3 mg of oligonucleotide or PBS. For 6 weeks beginning 1 week post-treatment, each animal was weighed and evaluated weekly by a trained observer for adverse events. Adverse events were defined as neurological dysfunction not typical in PBS-treated control animals, including, but not limited to: abnormal limb splay, abnormal gait, tremors, abnormal respiration, paralysis, and spasticity. The onset of the adverse event is defined as the week post-dosing when the dysfunction was first recorded. If no adverse event was achieved, there is no onset (–). The onset of adverse events typically correlates with a failure to thrive as defined by a lack of body weight gain/maintenance similar to PBS-treated animals Similar tolerability assessments were described in Ostergaard et al., Nucleic Acids Res. 2013 November; 41(21): 9634-9650 and Southwell et al., Mol Ther. 2014 December; 22(12): 2093-2106. As shown in the table below, 876031, 780241, 802714, 803268, 876604, and 934556 were well-tolerated in the long-term tolerability assessment.

TABLE 119

Long-term tolerability in rats at 3 mg dose

| Compound Number | Adverse event onset, weeks post-treatment, individual animals |
|---|---|
| 690093 | 2, 3, 4, 4 |
| 693421 | 4, —, —, — |
| 876031 | —, —, —, — |
| 780241 | —, —, —, — |
| 802714 | —, —, —, — |
| 803268 | —, —, —, — |
| 876604 | —, —, —, — |
| 934556 | —, —, —, — |
| PBS | —, —, —, — |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11332746B1). An electronic copy of the "Sequence Listing" will also be available from the USPTO upon request and payment of the fee set forth in 37 CFR 1.19(b)(3).

The invention claimed is:
1. A modified oligonucleotide according to the following chemical structure:

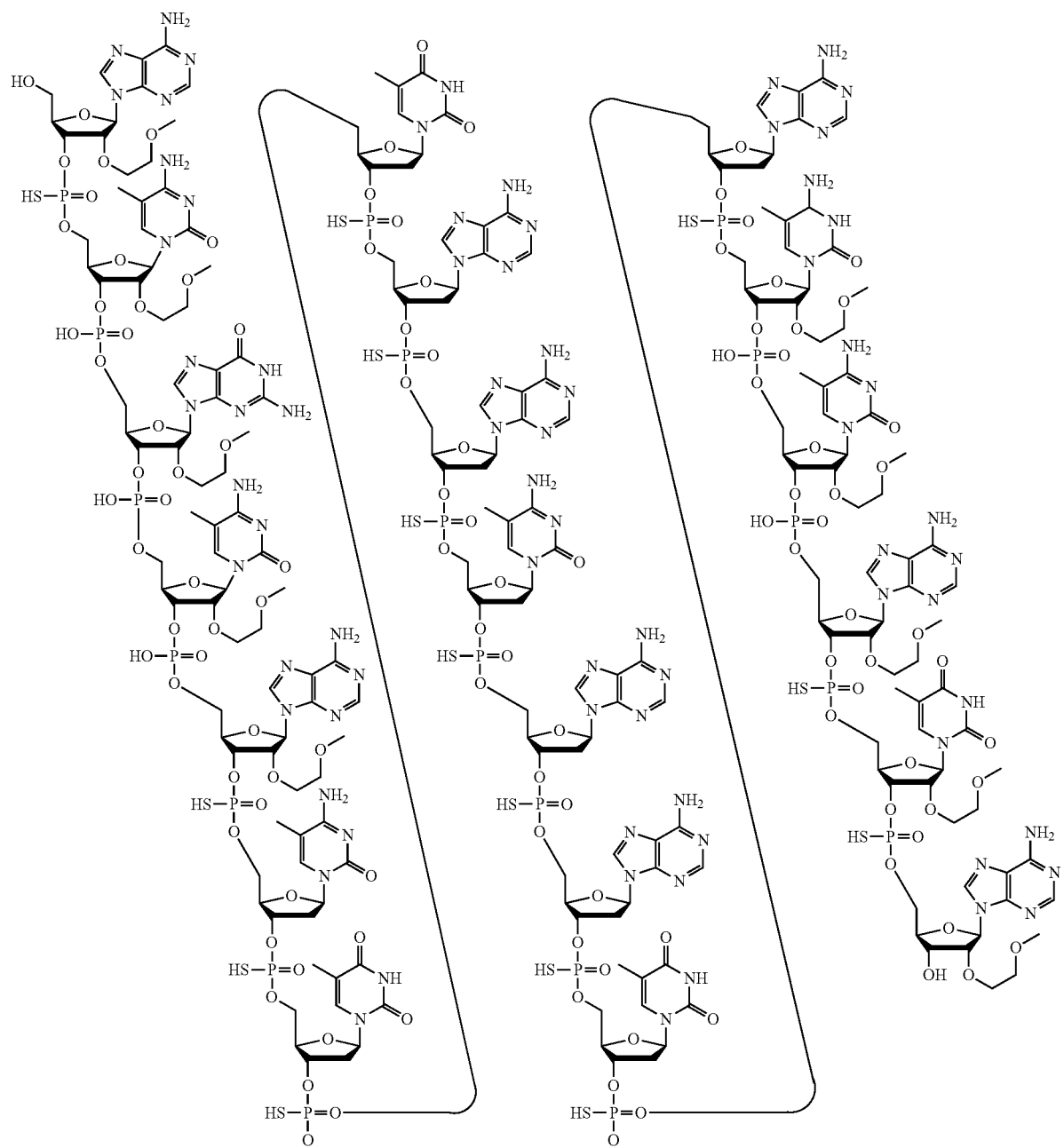

(SEQ ID NO: 3590)
or a salt thereof.

2. The modified oligonucleotide of claim 1, which is the sodium salt or the potassium salt.

3. A modified oligonucleotide according to the following chemical structure:

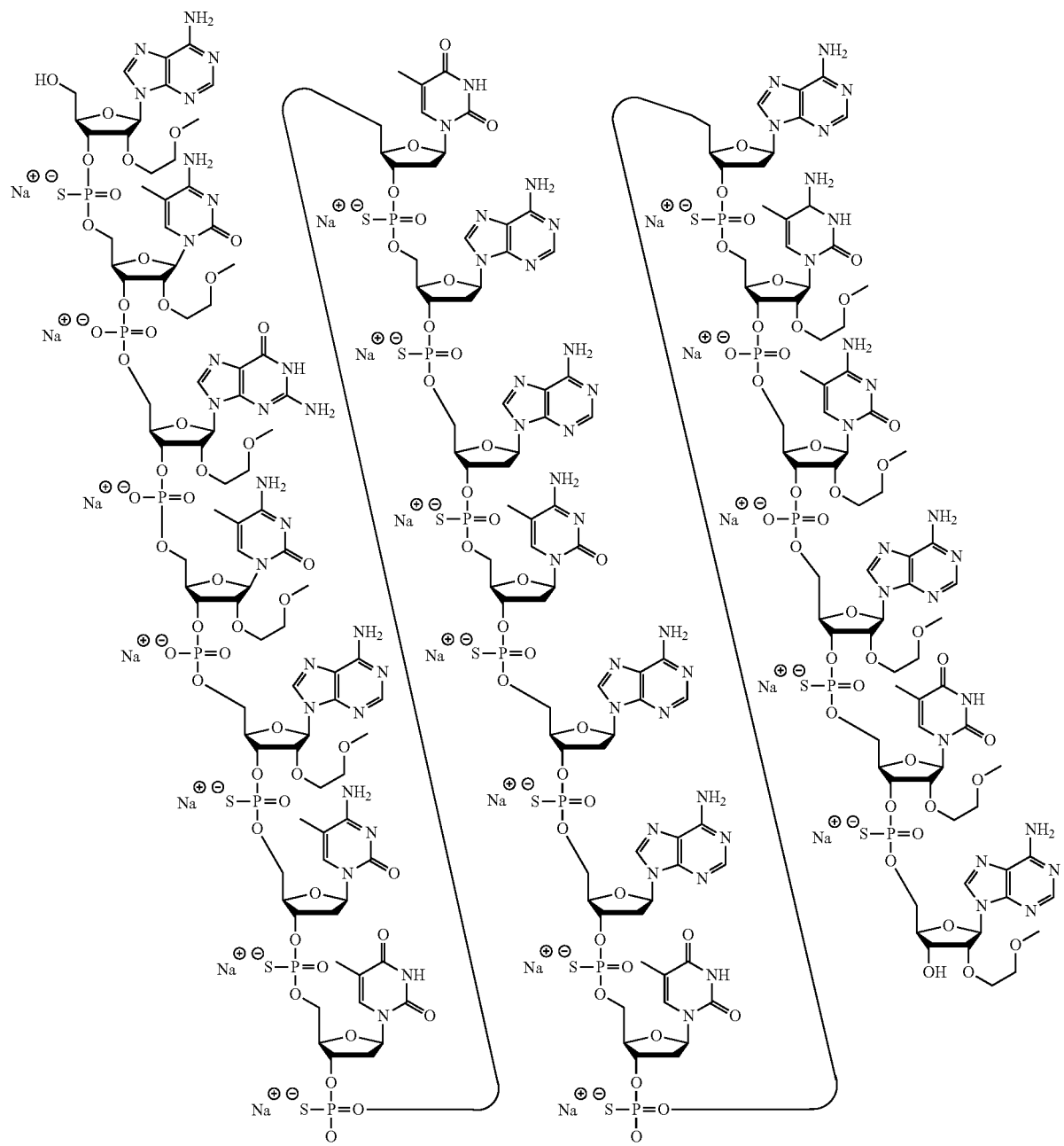

(SEQ ID NO: 3590).

4. An oligomeric compound comprising a modified oligonucleotide according to the following chemical notation:

Aes mCeo Geo mCeo Aes mCds Tds Tds Ads Ads
mCds Ads Ads Tds Ads Teo mCeo Aes Tes Ae
(SEQ ID NO: 3590); wherein, A=an adenine nucleobase,
mC=a 5-methyl cytosine nucleobase,
G=a guanine nucleobase,
T=a thymine nucleobase,
e=a 2'-OCH$_2$CH$_2$OCH$_3$ ribosyl sugar moiety,
d=a 2'-deoxyribosyl sugar moiety,
s=a phosphorothioate internucleoside linkage, and
o=a phosphodiester internucleoside linkage.

5. A population of modified oligonucleotides of claim 1, wherein all of the phosphorothioate internucleoside linkages of the modified oligonucleotides are stereorandom.

6. A pharmaceutical composition comprising a modified oligonucleotide of claim 1 and a pharmaceutically acceptable diluent.

7. The pharmaceutical composition of claim 6, wherein the pharmaceutically acceptable diluent is phosphate-buffered saline (PBS) or artificial cerebrospinal fluid.

8. The pharmaceutical composition of claim 7, wherein the pharmaceutical composition consists essentially of the modified oligonucleotide and artificial cerebrospinal fluid.

9. The pharmaceutical composition of claim 7, wherein the pharmaceutical composition consists essentially of the modified oligonucleotide and PBS.

10. A population of modified oligonucleotides of claim 3, wherein all of the phosphorothioate internucleoside linkages of the modified oligonucleotides are stereorandom.

11. A pharmaceutical composition comprising a modified oligonucleotide of claim 3 and a pharmaceutically acceptable diluent.

12. The pharmaceutical composition of claim 11, wherein the pharmaceutically acceptable diluent is phosphate-buffered saline (PBS) or artificial cerebrospinal fluid.

13. The pharmaceutical composition of claim 12, wherein the pharmaceutical composition consists essentially of the modified oligonucleotide and artificial cerebrospinal fluid.

14. The pharmaceutical composition of claim 12, wherein the pharmaceutical composition consists essentially of the modified oligonucleotide and PBS.

15. A population of oligomeric compounds of claim 4, wherein all of the phosphorothioate internucleoside linkages of the modified oligonucleotide are stereorandom.

16. A pharmaceutical composition comprising the oligomeric compound of claim 4 and a pharmaceutically acceptable diluent.

17. The pharmaceutical composition of claim 16, wherein the pharmaceutically acceptable diluent is phosphate-buffered saline (PBS) or artificial cerebrospinal fluid.

18. The pharmaceutical composition of claim 17, wherein the pharmaceutical composition consists essentially of the oligomeric compund and artificial cerebrospinal fluid.

19. The pharmaceutical composition of claim 17, wherein the pharmaceutical composition consists essentially of the oligomeric compund and PBS.

20. A method comprising administering to a subject a pharmaceutical composition of claim 6.

21. A method of treating Parkinson's disease comprising administering to a subject having or at risk for developing Parkinson's disease a therapeutically effective amount of a pharmaceutical composition according to claim 6 and thereby treating Parkinson's disease.

22. The method of claim 21, wherein at least one symptom or hallmark of Parkinson's disease is ameliorated.

23. The method of claim 22, wherein the symptom or hallmark is any of ataxia, neuropathy, and aggregate formation.

24. A method of reducing expression of LRRK2 in a cell comprising contacting the cell with a modified oligonucleotide of claim 1.

25. The method of claim 21, wherein the subject is human.

26. The method of claim 24, wherein the cell is a human cell.

\* \* \* \* \*